US012590169B2

(12) United States Patent
Timmer et al.

(10) Patent No.: US 12,590,169 B2
(45) Date of Patent: Mar. 31, 2026

(54) 5T4 SINGLE DOMAIN ANTIBODIES AND THERAPEUTIC COMPOSITIONS THEREOF

(71) Applicant: Inhibrx Biosciences, Inc., La Jolla, CA (US)

(72) Inventors: John C. Timmer, La Jolla, CA (US); Michael D. Kaplan, La Jolla, CA (US); Katelyn M. Willis, La Jolla, CA (US); Rajay A. Pandit, La Jolla, CA (US); Angelica N. Sanabria, La Jolla, CA (US); Sydney A. Barnes, La Jolla, CA (US); Margaret E. Haerr, La Jolla, CA (US); Brendan P. Eckelman, La Jolla, CA (US); Rutger H. Jackson, La Jolla, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 1212 days.

(21) Appl. No.: 17/283,830

(22) PCT Filed: Oct. 9, 2019

(86) PCT No.: PCT/US2019/055454
§ 371 (c)(1),
(2) Date: Apr. 8, 2021

(87) PCT Pub. No.: WO2020/076992
PCT Pub. Date: Apr. 16, 2020

(65) Prior Publication Data
US 2021/0340273 A1     Nov. 4, 2021

Related U.S. Application Data

(60) Provisional application No. 62/877,824, filed on Jul. 23, 2019, provisional application No. 62/744,631, filed on Oct. 11, 2018.

(51) Int. Cl.
| | |
|---|---|
| *C07K 16/30* | (2006.01) |
| *A61P 35/00* | (2006.01) |
| *C07K 14/56* | (2006.01) |
| *C07K 14/565* | (2006.01) |
| *C07K 14/57* | (2006.01) |
| *C07K 16/28* | (2006.01) |

(52) U.S. Cl.
CPC .............. *C07K 16/30* (2013.01); *A61P 35/00* (2018.01); *C07K 14/56* (2013.01); *C07K 14/565* (2013.01); *C07K 14/57* (2013.01); *C07K 16/2809* (2013.01); *C07K 16/2818* (2013.01); *C07K 16/283* (2013.01); *C07K 2317/21* (2013.01); *C07K 2317/24* (2013.01); *C07K 2317/31* (2013.01); *C07K 2317/33* (2013.01); *C07K 2317/35* (2013.01); *C07K 2317/565* (2013.01); *C07K 2317/569* (2013.01); *C07K 2317/624* (2013.01); *C07K 2317/71* (2013.01); *C07K 2317/72* (2013.01);

*C07K 2317/76* (2013.01); *C07K 2317/92* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 4,816,567 | A | 3/1989 | Cabilly et al. |
| 4,832,959 | A | 5/1989 | Engels et al. |
| 5,258,498 | A | 11/1993 | Huston et al. |
| 5,500,362 | A | 3/1996 | Robinson et al. |
| 5,525,491 | A | 6/1996 | Huston et al. |
| 5,731,168 | A | 3/1998 | Carter et al. |
| 5,821,337 | A | 10/1998 | Carter et al. |
| 5,834,597 | A | 11/1998 | Tso et al. |
| 6,054,297 | A | 4/2000 | Carter et al. |
| 6,120,762 | A | 9/2000 | Johnson et al. |
| 6,132,992 | A | 10/2000 | Ledbetter et al. |
| 6,982,321 | B2 | 1/2006 | Winter |
| 7,087,409 | B2 | 8/2006 | Barbas et al. |
| 7,183,076 | B2 | 2/2007 | Arathoon et al. |
| 7,381,803 | B1 | 6/2008 | Weiner et al. |
| 7,527,791 | B2 | 5/2009 | Adams et al. |

(Continued)

FOREIGN PATENT DOCUMENTS

| | | |
|---|---|---|
| CA | 2477192 | 11/2001 |
| CA | 2441653 | 3/2005 |

(Continued)

OTHER PUBLICATIONS

Skolnick et al (Trends Biotechnol. Jan. 2000;18(1):34-9) (Year: 2000).*

(Continued)

*Primary Examiner* — Brian Gangle
*Assistant Examiner* — Andrea K McCollum
(74) *Attorney, Agent, or Firm* — Wilson Sonsini Goodrich & Rosati

(57) ABSTRACT

Provided herein are binding polypeptides that specifically bind 5T4. More specifically, provided herein are fusion proteins, including multivalent and/or multispecific constructs and chimeric antigen receptors, that bind 5T4. Also provided are pharmaceutical compositions containing the polypeptides, nucleic acid molecules encoding the polypeptides and vectors and cells thereof, and methods of use and uses of the provided 5T4 binding polypeptides for treating diseases and conditions, such as cancer.

23 Claims, 53 Drawing Sheets

Specification includes a Sequence Listing.

(56) References Cited

U.S. PATENT DOCUMENTS

| | | |
|---|---|---|
| 7,635,475 B2 | 12/2009 | Kumagai et al. |
| 7,728,114 B2 | 6/2010 | Mach et al. |
| 7,959,925 B2 | 6/2011 | Weinberg et al. |
| 7,994,289 B2 | 8/2011 | Waldmann et al. |
| 7,998,469 B2 | 8/2011 | Gantier et al. |
| 8,052,964 B2 | 11/2011 | Gantier et al. |
| 9,006,399 B2 | 4/2015 | Liu et al. |
| 9,035,026 B2 | 5/2015 | Hoffmann et al. |
| 9,605,084 B2 | 3/2017 | Moore et al. |
| 9,644,016 B2 | 5/2017 | Stagliano et al. |
| 9,650,446 B2 | 5/2017 | Moore et al. |
| 9,701,750 B2 | 7/2017 | Hoffmann et al. |
| 9,701,759 B2 | 7/2017 | Desjarlais et al. |
| 9,803,021 B2 | 10/2017 | Morrison |
| 10,010,626 B2 | 7/2018 | Chang et al. |
| 10,066,015 B2 | 9/2018 | Zhukovsky et al. |
| 10,087,250 B2 | 10/2018 | Bruenker et al. |
| 10,131,710 B2 | 11/2018 | Moore et al. |
| 10,858,417 B2 | 12/2020 | Moore et al. |
| 11,866,507 B2 * | 1/2024 | Eckelman ............... A61P 35/00 |
| 2006/0270045 A1 | 11/2006 | Cregg et al. |
| 2008/0279851 A1 | 11/2008 | Coyle et al. |
| 2009/0025106 A1 | 1/2009 | Reini et al. |
| 2009/0162380 A1 | 6/2009 | Glaser et al. |
| 2010/0254998 A1 | 10/2010 | Bossenmaier et al. |
| 2011/0274685 A1 | 11/2011 | Keler et al. |
| 2011/0275787 A1 | 11/2011 | Kufer et al. |
| 2012/0149876 A1 | 6/2012 | Von Kreudenstein et al. |
| 2012/0237498 A1 | 9/2012 | Ahrens et al. |
| 2013/0183321 A1 | 7/2013 | Smith et al. |
| 2013/0273054 A1 | 10/2013 | Bossenmaier et al. |
| 2014/0072581 A1 | 3/2014 | Dixit et al. |
| 2014/0154253 A1 | 6/2014 | Ng et al. |
| 2014/0288275 A1 | 9/2014 | Moore et al. |
| 2014/0294823 A1 | 10/2014 | Moore et al. |
| 2014/0322129 A1 | 10/2014 | Leong et al. |
| 2014/0348841 A1 | 11/2014 | Schebye et al. |
| 2014/0363426 A1 | 12/2014 | Moore et al. |
| 2015/0064204 A1 | 3/2015 | Beers et al. |
| 2015/0079088 A1 | 3/2015 | Lowman et al. |
| 2015/0087810 A1 | 3/2015 | Moore et al. |
| 2015/0239991 A1 | 8/2015 | Blein et al. |
| 2015/0307617 A1 | 10/2015 | Du et al. |
| 2015/0307628 A1 | 10/2015 | Kim et al. |
| 2016/0039942 A1 | 2/2016 | Cobbold et al. |
| 2016/0122425 A1 | 5/2016 | Daugherty et al. |
| 2016/0194399 A1 | 7/2016 | Irving et al. |
| 2016/0207981 A1 | 7/2016 | Eckelman et al. |
| 2016/0280795 A1 | 9/2016 | Wang |
| 2016/0289324 A1 | 10/2016 | Moore et al. |
| 2017/0022284 A1 | 1/2017 | Timmer et al. |
| 2017/0081397 A1 | 3/2017 | Stagliano et al. |
| 2017/0198050 A1 | 7/2017 | Eckelman et al. |
| 2017/0204139 A1 | 7/2017 | Moore et al. |
| 2017/0226215 A1 | 8/2017 | Gray et al. |
| 2017/0369563 A1 | 12/2017 | Dubridge et al. |
| 2018/0011883 A1 | 1/2018 | Goldbrenner et al. |
| 2018/0016354 A1 | 1/2018 | Wozniak-Knopp et al. |
| 2018/0194842 A1 | 7/2018 | Mach et al. |
| 2018/0230225 A1 | 8/2018 | Fan et al. |
| 2018/0355038 A1 | 12/2018 | Smith et al. |
| 2019/0010242 A1 | 1/2019 | Eckelman et al. |
| 2019/0218515 A1 | 7/2019 | Ballesteros Nobell et al. |
| 2019/0330366 A1 | 10/2019 | Eckelman et al. |
| 2020/0048350 A1 | 2/2020 | Eckelman et al. |
| 2020/0190193 A1 | 6/2020 | Pandit et al. |
| 2021/0340273 A1 | 11/2021 | Timmer et al. |
| 2021/0380679 A1 | 12/2021 | Eckelman et al. |
| 2023/0295336 A1 | 9/2023 | Eckelman et al. |
| 2024/0101704 A1 | 3/2024 | Eckelman et al. |

FOREIGN PATENT DOCUMENTS

| | | |
|---|---|---|
| CN | 101583376 | 11/2009 |
| CN | 108084265 | 5/2018 |
| EP | 0219781 | 4/1987 |
| EP | 1391213 | 2/2004 |
| EP | 2920209 | 9/2015 |
| EP | 3502140 | 6/2019 |
| WO | WO-1992/008737 | 5/1992 |
| WO | WO-1994/004679 | 3/1994 |
| WO | WO-1998/050431 | 11/1998 |
| WO | WO-2000/024884 | 5/2000 |
| WO | WO-2000/041474 | 7/2000 |
| WO | WO 2002/059264 | 8/2002 |
| WO | WO-2002/079249 | 10/2002 |
| WO | WO-2002/083733 | 10/2002 |
| WO | WO-2002/086156 | 10/2002 |
| WO | WO-2002/095067 | 11/2002 |
| WO | WO-2002/101048 | 12/2002 |
| WO | WO-2003/000896 | 3/2003 |
| WO | WO-2003/023032 | 3/2003 |
| WO | WO-2004/022593 | 3/2004 |
| WO | WO-2004/022747 | 3/2004 |
| WO | WO-2004/092219 | 10/2004 |
| WO | WO-2005/035584 | 4/2005 |
| WO | WO-2005/040220 | 5/2005 |
| WO | WO-2005/063816 | 7/2005 |
| WO | WO-2005/100402 | 10/2005 |
| WO | WO-2006/029879 | 3/2006 |
| WO | WO-2007/033230 | 3/2007 |
| WO | WO-2008/119567 | 10/2008 |
| WO | WO 2009/018386 | 2/2009 |
| WO | WO-2009/067800 | 6/2009 |
| WO | WO-2009/089004 | 7/2009 |
| WO | WO 2010/037836 | 4/2010 |
| WO | WO-2010/151792 | 12/2010 |
| WO | WO-2011/056983 | 5/2011 |
| WO | WO-2011/133886 | 10/2011 |
| WO | WO-2011/143545 | 11/2011 |
| WO | WO 2012/025525 | 3/2012 |
| WO | WO-2012/058768 | 5/2012 |
| WO | WO-2013/026837 | 2/2013 |
| WO | WO-2013/041687 | 3/2013 |
| WO | WO-2013/101909 | 7/2013 |
| WO | WO 2013/128194 | 9/2013 |
| WO | WO-2014/067011 | 5/2014 |
| WO | WO-2014/099997 | 6/2014 |
| WO | WO-2014/145806 | 9/2014 |
| WO | WO-2014/194100 | 12/2014 |
| WO | WO-2015/001085 | 1/2015 |
| WO | WO 2015/026894 | 2/2015 |
| WO | WO-2015/168469 | 11/2015 |
| WO | WO 2015/187793 | 12/2015 |
| WO | WO 2015/197598 | 12/2015 |
| WO | WO-2015/197789 | 12/2015 |
| WO | WO-2016/020309 | 2/2016 |
| WO | WO-2016/034666 | 3/2016 |
| WO | WO 2016/046778 | 3/2016 |
| WO | WO-2016/055593 | 4/2016 |
| WO | WO-2015/095392 | 6/2016 |
| WO | WO-2016/086189 | 6/2016 |
| WO | WO-2016/087416 | 6/2016 |
| WO | WO-2016/097408 | 6/2016 |
| WO | WO-2016/105450 | 6/2016 |
| WO | WO-2016097408 A1 * | 6/2016 | ............. A61P 35/00 |
| WO | WO-2016/177762 | 11/2016 |
| WO | WO-2016/179517 | 11/2016 |
| WO | WO-2016/180982 | 11/2016 |
| WO | WO-2016/204966 | 12/2016 |
| WO | WO-2017/015623 | 1/2017 |
| WO | WO-2017/055398 | 4/2017 |
| WO | WO-2017/060144 | 4/2017 |
| WO | WO-2017/123650 | 7/2017 |
| WO | WO-2017/123673 | 7/2017 |
| WO | WO-2017/134440 | 8/2017 |
| WO | WO-2017/167672 | 10/2017 |
| WO | WO-2017/182672 | 10/2017 |
| WO | WO-2018/027025 | 2/2018 |
| WO | WO-2018/068695 | 4/2018 |
| WO | WO-2018/127473 | 7/2018 |
| WO | WO-2018/167486 | 9/2018 |
| WO | WO-2018/185045 | 10/2018 |
| WO | WO-2018/191438 | 10/2018 |

(56) References Cited

FOREIGN PATENT DOCUMENTS

| | | | | | |
|---|---|---|---|---|---|
| WO | WO-2018191438 A1 | * | 10/2018 | .............. | A61P 35/00 |
| WO | WO-2019/133761 | | 7/2019 | | |
| WO | WO-2019/200022 | | 10/2019 | | |
| WO | WO-2020/023553 | | 1/2020 | | |
| WO | WO-2020023553 A1 | * | 1/2020 | ............ | C07K 16/28 |
| WO | WO-2020/076970 | | 4/2020 | | |
| WO | WO-2020/076977 | | 4/2020 | | |
| WO | WO-2021/155071 | | 8/2021 | | |

OTHER PUBLICATIONS

Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000,10:398-400) (Year: 2000).*
Kulmanov et al (Bioinformatics, 34(4), 2018, 660-668) (Year: 2018).*
Vajdos et al. (J Mol Biol. Jul. 5, 2002;320(2):415-28) (Year: 2002).*
Brown et al. (J Immunol. May 1996;156(9):3285-91) (Year: 1996).*
Vattekatte, (PeerJ. Mar. 6, 2020:8:e8408. doi: 10.7717/peerj.8408. eCollection 2020.) (Year: 2020).*
Lloyd et al. (Protein Eng Des Sel. Mar. 2009;22(3):159-68. Epub Oct. 29, 2008.) (Year: 2009).*
Goel et al. (J Immunol. Dec. 15, 2004;173(12):7358-67) (Year: 2004).*
Khan et al. (J Immunol (2014) 192 (11): 5398-5405) (Year: 2014).*
Poosarla et al. (Biotechnol Bioeng. Jun. 2017 ; 114(6): 1331-1342) (Year: 2017).*
Rabia, et al. (Biochem Eng J. Sep. 15, 2018:137:365-374. Epub Jun. 5, 2018) (Year: 2018).*
Asano et al. "Domain order of a bispecific diabody dramatically enhances its antitumor activity beyond structural format conversion: the case of the hEx3 diabody." *Protein Engineering, Design & Selection* 26.5 (2013): 359-367.
Barthelemy et al. "Comprehensive analysis of the factors contributing to the stability and solubility of autonomous human VH domains." *Journal of Biological Chemistry* 283.6 (2008): 3639-3654.
Beiboer et al. "Guided selection of a pan carcinoma specific antibody reveals similar binding characteristics yet structural divergence between the original murine antibody and its human equivalent." *Journal of Molecular Biology* 296.3 (2000): 833-849.
Choi et al. "Predicting antibody complementarity determining region structures without classification." *Molecular BioSystems* 7.12 (2011): 3327-3334.
De Genst et al. "Antibody repertoire development in camelids." *Developmental & Comparative Immunology* 30.1-2 (2006): 187-198.
Driessens et al. "Costimulatory and coinhibitory receptors in anti-tumor immunity." *Immunological reviews* (2009) 229.1: 126-144.
Griffiths et al. "Human anti-self antibodies with high specificity from phage display libraries." *The EMBO journal* 12.2 (1993): 725-734.
Kuo et al., "Engineering a CD123xCD3 bispecific scFv immunofusion for the treatment of leukemia and elimination of leukemia stem cells," Protein Eng Des Sel. (2012) 25(10): 561-9.
Maeda et al., "Engineering of functional chimeric protein G-Vargula luciferase," Anal Biochem. (1997) 249(2):147-52.
Malia et al. "Epitope mapping and structural basis for the recognition of phosphorylated tau by the anti-tau antibody AT8." *Proteins: Structure, Function, and Bioinformatics* 84.4 (2016): 427-434.
Schmiedel e tal. "Expression of a bispecific dsFv-dsFv' antibody fragment in *Escherichia coli*." Protein Engineering 13.10 (2000): 725-734.
Weidle et al. "The intriguing options of multispecific antibody formats for treatment of cancer." *Cancer genomics & proteomics* 10.1 (2013): 1-18.

Xing et al., "BiHC, a T-Cell-Engaging Bispecific Recombinant Antibody, Has Potent Cytotoxic Activity Against Her2 Tumor Cells," Transl Oncol (2017) 10(5):780-785.
Zhang et al., "Amplification Ex Vivo and Cytocidal Activity of Leukemia Tumor-Associated Antigen-Specific Cytotoic T Lympohcytes," Chinese Journal of Experimental Hematology, (2015) 23(3); 814-820; (Article in Chinese; English abstract provided).
Kumar et al., "Molecular cloning and expression of the Fabs of human autoantibodies in *Escherichia coli*," J. Biol. Chem. (2000) 275:35129-36.
Miyazaki, "Studies on Alpaca VHH antibodies for industrial applications," Kagoshima. University Repository, Jun. 1, 2015, 102 pages. https://ir.kagoshima-u.ac.jp/records/9025 (Machine translation provided).
Smith-Gill et al., "Contributions of immunoglobulin heavy and light chains to antibody specificity for lysozyme and two haptens," J. Immunol. (1987) 139:4135-44.
Song et al., "Light chain of natural antibody plays a dominant role in protein antigen binding," Biochem. Biophys. Res. Comm. (2000) 268:390-94.
Ackerman et al., "Biologic activity in a fragment of recombinant human interferon alpha," Proc Natl Acad Sci U S A. (1984) 81(4): 1045-1047.
Al-Lazikani et al., "Standard Conformations for the Canonical Structures of Immunoglobulins," J. Mol. Biol. (1997) 273: 927-948.
Alegre et al., "Effect of a single amino acid mutation on the activating and immunosuppressive properties of a "humanized" OKT3 monoclonal antibody," J Immunol (1992) 148(11):3461-3468.
Almagro et al., "Humanization of Antibodies," Frontiers in Bioscience. (2008) 13:1619-1633.
Anasetti et al., "Treatment of acute graft-versus-host disease with a nonmitogenic anti-CD3 monoclonal antibody," Transplantation. (1992) 54(5): 844-51.
Anderson et al., "Fc gamma receptor type III (CD16) is included in the zeta NK receptor complex expressed by human natural killer cells.," Proc Natl Acad Sci USA. (1990) 87(6): 2274-2278.
Arndt et al., "A bispecific diabody that mediates natural killer cell cytotoxicity against xenotransplantated human Hodgkin's tumors," Blood. (1999) 94(8): 2562-2568.
Baca et al., "Antibody Humanization Using Monovalent Phage Display," J. Biol. Chem. (1997) 272(16): 10678-10684.
Bacac et al., "CD20 Tcb (RG6026), a Novel "2:1" T Cell Bispecific Antibody for the Treatment of B Cell Malignancies," Blood (2016) 128:1836.
Behar et al., "Isolation and characterization of anti-FcgammaRIII (CD16) llama single-domain antibodies that activate natural killer cells," Protein Eng Des Sel. (2008) 21(1): 1-10.
Beliveau et al., "Probing the substrate specificities of matriptase, matriptase-2, hepsin and DESC1 with internally quenched fluorescent peptides," FEBS J (2009) 276(8):2213-2226.
Brinkmann et al., "The making of bispecific antibodies," MABS (2017) 9(2):182-212.
Bruggemann et al., "Comparison of the effector functions of human immunoglobulins using a matched set of chimeric antibodies," J Exp Med (1987) 166(5):1351-1361.
Capel et al., "Heterogeneity of Human IgG Fc Receptors," Immunomethods (1994) 4(1): 25-34.
Carsberg et al., "Metastasis-associated 5T4 antigen disrupts cell-cell contacts and induces cellular motility in epithelial cells," Int J Cancer. (1996) 68(1): 84-92.
Carter et al., "Bispecific human IgG by design," J Immunol Methods (2001) 248(1-2):7-15.
Carter et al., "Humanization of an Anti-p185HER2 Antibody For Human Cancer Therapy," Proc. Natl. Acad. Sci. USA (1992) 89: 4285-4289.
Chen et al., "Fusion protein linkers: property, design and functionality," Adv Drug Deliv Rev (2013) 65(10):1357-1369.
Clackson et al., "Making Antibody Fragments Using Phage Display Libraries," Nature (1991) 352: 624-628.
Clynes et al., "Fc receptors are required in passive and active immunity to melanoma," Proc Natl Acad Sci USA (1998) 95(2):652-656.

(56)            References Cited

OTHER PUBLICATIONS

Cragg et al., "Antibody specificity controls in vivo effector mechanisms of anti-CD20 reagents," Blood (2004) 103:2738-2743.

Cragg et al., "Complement-mediated lysis by anti-CD20 mAb correlates with segregation into lipid rafts," Blood (2003) 101(3):1045-1052.

Daeron, "Fc receptor biology," Annu Rev Immunol. (1997) 15: 203-34.

Dall'Acqua et al., "Properties of Human IgG1s Engineered for Enhanced Binding to the Neonatal Fc Receptor (FcRn)," J Biol Chem (2006) 281(33):23514-23524.

Dall'Acqua et al., "Antibody Humanization by Framework Shuffling," Methods (2005) 36:43-60.

Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel (2010) 23(4):195-202.

De Haas, M. et al. "Fc Gamma receptors of Phagocytes," J. Lab. Clin. Med. (1995) 126:330-341.

Deer et al., "High-Level Expression Of Proteins In Mammalian Cells Using Transcription Regulatory Sequences From The Chinese Hamster EF-1Alpha Gene," Biotechnol. Prog. (2004) 20(3): 880-889.

Deisenhofer, "Crystallographic refinement and atomic models of a human Fc fragment and its complex with fragment B of protein A from Staphylococcus aureus at 2.9- and 2.8-.ANG. resolution," Biochemistry (1981) 20(9):2361-2370.

Diaz et al., "Structure of the human type-I interferon gene cluster determined from a YAC clone contig," Genomics. (1994) 22(3): 540-552.

Dotti et al., "Design and development of therapies using chimeric antigen receptor-expressing T cells," Immunol Rev. (2014) 257(1); 35 pages.

Endo et al., "High-Throughput, Genome-Scale Protein Production Method Based On The Wheat Germ Cell-Free Expression System," Biotechnol. Adv. (2003) 21; 695-713.

Gazzano-Santoro et al., "A non-radioactive complement-dependent cytotoxicity assay for anti-CD20 monoclonal antibody," J Immunol Methods (1997) 202(2):163-171.

Ghetie et al,. "FcRn: the MHC Class I-related Receptor That Is More Than An IgG Transporter," Immunol. Today (1997) 18(12): 592-598.

Ghetie et al., "Increasing the Serum Persistence of an IgG Fragment by Random Mutagenesis," Nat Biotech (1997) 15:637-640.

Golovleva et al., "Polymorphism in the interferon-alpha gene family," Am J Hum Genet. (1996) 59(3): 570-8.

Gunasekaran et al., "Enhancing antibody Fc heterodimer formation through electrostatic steering effects: applications to bispecific molecules and monovalent IgG," J Biol Chem (2010) 285(25):19637-19646.

Guyer et al., "Immunoglobulin binding by mouse intestinal epithelial cell receptors," J Immunol. (1976) 117(2): 587-593.

Ha et al., "Immunoglobulin Fc Heterodimer Platform Technology: From Design to Applications in Therapeutic Antibodies and Proteins," Front Immunol (2016) 7:394.

Harwood et al., "ATTACK, a novel bispecific T cell-recruiting antibody with trivalent EGFR binding and monovalent CD3 binding for cancer immunotherapy," Oncoimmunology (2018) 7(1):e1377874.

Hawkins et al., "Phase I evaluation of a synthetic mutant of beta-interferon," Cancer Res. (1985) 45; 5914-20.

Hayward et al., "Lysis of CD3 hybridoma targets by cloned human CD4 lymphocytes," Immunology. (1988) 64(1): 87-92.

Hellstrom et al., "Antitumor effects of L6, an IgG2a antibody that reacts with most human carcinomas," Proc Natl Acad Sci USA (1986) 83(18):7059-7063.

Hellstrom et al., "Strong antitumor activities of IgG3 antibodies to a human melanoma-associated ganglioside," Proc Natl Acad Sci USA (1985) 82(5):1499-1502.

Henry et al., "Stability-Diversity tradeoffs impose fundamental constraints on selection of synthetic human VH/VL single-domain antibodies from in vitro display libraries," Frontiers in Immunology (2017) 8:1-15.

Hernandez-Hoyos et al., "MOR209/ES414, a Novel Bispecific Antibody Targeting PSMA for the Treatment of Metastatic Castration-Resistant Prostate Cancer," Mol Cancer Ther (2016) 15(9):2155-2165.

Hinman et al. "Preparation and characterization of monoclonal antibody conjugates of the calicheamicins: a novel and potent family of antitumor antibiotics," Cancer Res. (1993) 53(14): 3336-3342.

Hinton et al., "Engineered Human IgG Antibodies with Longer Serum Half-lives in Primates," J. Biol. Chem. (2004) 279(8): 6213-6216.

Hole et al., "A 72 kD trophoblast glycoprotein defined by a monoclonal antibody," Br J Cancer. (1988) 57(3): 239-246.

Holliger et al., "Specific killing of lymphoma cells by cytotoxic T-cells mediated by a bispecific diabody," Protein Engineering Design and Selection (1996) 9(3):299-305.

Honegger et al., "Yet Another Numbering Scheme for Immunoglobulin Variable Domains: An Automatic Modeling and Analysis Tool," J Mol Biol. (2001) 309(3): 657-670.

Hussain et al., "IFN-alpha1a gene is the major variant in the North American population," J Interferon Cytokine Res. (2000) 20(9): 763-768.

Idusogie et al., "Engineered antibodies with increased activity to recruit complement," J Immunol (2001) 166(4):2571-2575.

Jaitin et al., "Inquiring into the differential action of interferons (IFNs): an IFN-alpha2 mutant with enhanced affinity to IFNAR1 is functionally similar to IFN-beta," Mol Cell Biol. (2006) 26(5): 1888-1897.

Jendeberg et al., "Engineering of Fc(1) and Fc(3) from human immunoglobulin G to analyse subclass specificity for staphylococcal protein A," J Immnuol Methods (1997) 201(1):25-34.

Jones et al., "Investigation of expression of 5T4 antigen in cervical cancer," Br J Cancer. (1990) 61(1): 96-100.

Kalie et al., "An interferon alpha2 mutant optimized by phage display for IFNAR1 binding confers specifically enhanced antitumor activities," J Biol Chem. (2007) 282(15): 11602-11611.

Kaneko et al., "Optimizing Therapeutic Antibody Function," Biodrugs (2011) 25(1):1-11.

Kashmiri et al., "SDR grafting—A New Approach to Antibody Humanization," Methods. (2005) 36: 25-34.

Kerk et al., "5T4-Targeted Therapy Ablates Cancer Stem Cells and Prevents Recurrence of Head and Neck Squamous Cell Carcinoma," Clin Cancer Res. (2017) 23(10): 2516-2527.

Kim et al., "Mutational approaches to improve the biophysical properties of human single-domain antibodies," Biochimica et Biophysica Acta (2014) 1844:1983-2001.

Kim et al., "Localization of the Site of the Murine IgGI Molecule That is Involved in Binding to the Murine Intestinal Fc Receptor," Eur. J. Immunol. (1994) 24:2429-2434.

Kindt, T.J .et al. (2007). "Antigens And Antibodies," Chapter 4 In Kuby Immunology 6th Ed., W.H. Freeman And Co., p. 91.

Kipriyanov et al., "Bispecific tandem diabody for tumor therapy with improved antigen binding and pharmacokinetics," J Mol Biol (1999) 293(1):41-56.

Klimka et al., "Human Anti-CD30 Recombinant Antibodies by Guided Phage Antibody Selection Using Cell Panning," Br. J. Cancer (2000) 83(2):252-260.

Kohler et al., "Continuous Culture of Fused Cells Secreting Antibody of Predefined Specificity," Nature (1975) 256:495-497.

Krause et al., "Signaling by covalent heterodimers of interferon-gamma. Evidence for one-sided signaling in the active tetrameric receptor complex," J Biol Chem. (2000) 275(30); 22995-3004.

La Rocca et al., "Zymographic detection and clinical correlations of MMP-2 and MMP-9 in breast cancer sera," British Journal of Cancer (2004) 90:1414-1421.

Lazar et al., "Engineered antibody Fc variants with enhanced effector function," Proc Natl Acad Sci USA (2006) 103(11):4005-4010.

(56)            References Cited

OTHER PUBLICATIONS

Leaver-Fay et al., "Computationally Designed Bispecific Antibodies using Negative State Repertoires," Structure (2016) 24(4):641-651.

Lefranc et al., "IMGT unique numbering for immunoglobulin and T cell receptor variable domains and Ig superfamily V-like domains," Dev Comp Immunol (2003) 27(1):55-77.

Liu et al., "Eradication of Large Colon Tumor Xenografts by Targeted Delivery of Maytansinoids," Proc. Natl. Acad. Sci. USA (1996) 93: 8618-8623.

Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58:2925-2928.

MacCallum et al., "Antibody-antigen interactions: Contact analysis and binding site topography," J. Mol. Biol. (1996) 262, 732-745.

Mandler et al., "Synthesis and evaluation of antiproliferative activity of a geldanamycin-Herceptin immunoconjugate," Bioorg Med Chem Lett. (2000) 10(10): 1025-1028.

Mandler et al., "Modifications in Synthesis Strategy Improve the Yield and Efficacy of Geldanamycin-Herceptin Immunoconjugates," Bioconjugate Chem. (2002)13:786-791.

Mandler et al., "Immunoconjugates of Geldanan1ycin and Anti-HER2 Monoclonal Antibodies: Antiproliferative Activity on Human Breast Carcinoma Cell Lines," J. Nat. Cancer Inst. (2000) 92(19): 1573-1581.

Martin et al., "Modeling antibody hypervariable loops: a combined algorithm," Proc Natl Acad Sci U S A. (1989) 86(23): 9268-9272.

McCafferty et al., "Phage antibodies: filamentous phage displaying antibody variable domains," Nature (1990) 348:552-554.

McGinn et al., "Targeting the 5T4 oncofetal glycoprotein with an antibody drug conjugate (A1mcMMAF) improves survival in patient-derived xenograft models of acute lymphoblastic leukemia," Haematologica. (2017) 102(6): 1075-1084.

Merchant et al., "An efficient route to human bispecific IgG," Nat Biotechnol (1998) 16(7):677-681.

Miller, "Protein-protein recognition and the association of immunoglobulin constant domains," JMB (1990) 216(4):965-973.

Moore et al., "A novel bispecific antibody format enables simultaneous bivalent and monovalent co-engagement of distinct target antigens," MAbs (2011) 3(6):546-557.

Moore et al., "Engineered Fc variant antibodies with enhanced ability to recruit complement and mediate effector functions," MAbs (2010) 2(2):181-189.

Nagorsen et al., "Immunomodulatory therapy of cancer with T cell-engaging BiTE antibody blinatumomab," Exp Cell Res. (2011) 317(9): 1255-60.

Natsume et al., "Engineered Antibodies of IgG1/IgG3 Mixed Isotype with Enhanced Cytotoxic Activities," Cancer Res (2008) 68(10):3863-3872.

Nyman et al., "Structural characterisation of N-linked and O-linked oligosaccharides derived from interferon-alpha2b and interferon-alpha14c produced by Sendai-virus-induced human peripheral blood leukocytes," Eur J Biochem. (1998) 253(2): 485-93.

Ohannesian et al., "Carcinoembryonic antigen and other glycoconjugates act as ligands for galectin-3 in human colon carcinoma cells," Cancer Res. (1995) 55(10): 2191-2199.

Osbourn, et al., "From Rodent Regents to Human Therapeutics Using Antibody Guided Selection," Methods. (2005) 36:61-68.

Padlan, "A possible procedure for reducing the immunogenicity of antibody variable domains while preserving their ligand-binding properties," Mol Immunol (1991) 28(4-5):489-498.

Pan et al., "Structural characterization of human interferon gamma. Heterogeneity of the carboxyl terminus," Eur J Biochem. (1987) 166(1): 145-149.

Pan et al., "Site-specific PEGylation of an anti-CEA/CD3 bispecific antibody improves its antitumor efficacy," Int J Nanomedicine. (2018)13: 3189-3201.

Pessano, S. et al., "The T3/T Cell Receptor Complex: Antigenic Distinction Between The Two 20-kd T3 (T3-δand T3-ε) Subunits," The EMBO Journal (1985) 4(2):337-344.

Petkova et al., "Enhanced half-life of genetically engineered human IgG1 antibodies in a humanized FcRn mouse model: potential application in humorally mediated autoimmune disease," Int Immunol (2006) 18(12):1759-1769.

Pollard et al., "Fixation, processing, and immunochemical reagent effects on preservation of T-lymphocyte surface membrane antigens in paraffin-embedded tissue," J Histochem Cytochem. (1987)35(11): 1329-38.

Portolano et al., "Lack of promiscuity in autoantigen-specific H and L chain combinations as revealed by human H and L chain "roulette"," J. Immunol. (1993) 150:880-887.

Presta et al., "Humanization of an Antibody Directed Against IgE," J. Immunol. (1993) 151(2): 2623-2632.

Queen et al., "A humanized antibody that binds to the interleukin 2 receptor," Proc Natl Acad Sci USA (1989) 86:10029-10033.

Ravetch et al., "Fc receptors," Annu Rev Immunol. (1991) 9:457-92.

Reusch et al., "A Novel Tetravalent Bispecific T and Ab (CD30/CD 16A) Efficiently Recruits NK Cells For The Lysis Of CD30+ Tumor Cells," mABs (2014) 6(SUPPL 3): 727-738.

Ridgway et al., "'Knobs-into-holes' engineering of antibody CH3 domains for heavy chain heterodimerization," Protein engineering (1996) 9(7):617-621.

Riechmann et al., "Reshaping Human Antibodies for Therapy," Nature (1988) 332: 323-327.

Rosenberg et al., "Use Of Tumor-Infiltrating Lymphocytes And Interleukin-2 In The Immunotherapy Of Patients With Metastatic Melanoma. A Preliminary Report," N Engl J Med. (1988) 319(25): 1676-1680.

Rosok et al., "A Combinatorial Library Strategy for the Rapid Humanization of Anticarcinoma BR96 Fab," J. Biol. Chem. (1996) 271(37): 22611-22618.

Rowland et al., "Drug Localisation And Growth Inhibition Studies of Vindesine-Monoclonal Anti-CEA Conjugates in a Human Tumour Xenograft," Cancer Immunol. Immunother. (1996) 21:183-187.

Sadelain et al., "The basic principles of chimeric antigen receptor design," Cancer Discov. (2013) 3(4): 388-398.

Sadelain et al., "The promise and potential pitfalls of chimeric antigen receptors," Curr Opin Immunol. (2009) 21(2): 215-23.

Seimetz et al., "Development and approval of the trifunctional antibody catumaxomab (anti-EpCAM x anti-CD3) as a targeted cancer immunotherapy," Cancer Treat Rev (2010) 36:458-467.

Shields et al., "High Resolution Mapping of the Binding Site on Human IgG1 for FcγRI, FcγRII, FcγRIII, and FcRn and Design of IgG1 Variants with Improved Binding to the FcγR*," JBC (2001) 276(9):6591-6604.

Sims et al., "A Humanized CD18 Antibody Can Block Function Without Cell Destruction," J. Immunol. (1993) 151(4): 2296-2308.

Sitaraman et al., "High-throughput protein expression using cell-free system," Methods Mol. Biol. (2009) 498: 229-44.

Southall et al., "Immunohistological distribution of 5T4 antigen in normal and malignant tissues," Br J Cancer. (1990) 61(1): 89-95.

Southgate et al., "CXCR4 mediated chemotaxis is regulated by 5T4 oncofetal glycoprotein in mouse embryonic cells," PLoS One. (2010) 5(4): e9982.

Spirin, "High-Throughput Cell-Free Systems For Synthesis Of Functionally Active Proteins," Trends Biotechnol. (2004) 22(10): 538-545.

Starzynska et al., "The expression of 5T4 antigen in colorectal and gastric carcinoma," Br J Cancer. (1992) 66(5): 867-869.

Stavenhagen et al., "Enhancing the potency of therapeutic monoclonal antibodies via Fc optimization," Adv Enzyme Regul (2008) 48:152-164.

Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.

Taylor et al., "Nanocell targeting using engineered bispecific antibodies," mAbs (2015) 7(1):53-65.

(56)                    References Cited

OTHER PUBLICATIONS

Uhlmann et al., "Antisense oligonucleotides: a new therapeutic principle," Chem Rev (1990) 90(4):543-584.

Von Kreudenstein et al., "Improving biophysical properties of a bispecific antibody scaffold to aid developability: quality by molecular design," MAbs (2013) 5(5):646-654.

Wang, "Lyophilization and development of solid protein pharmaceuticals," Int J Pharm (2000) 203(1-2):1-60.

Ward et al., "Binding activities of a repertoire of single immunoglobulin variable domains secreted from *Escherichia coli*," Nature (1989) 341:544-56.

Wirthmueller et al., "Signal transduction by Fc gamma RIII (CD16) is mediated through the gamma chain," J Exp Med. (1992) 175(5):1381-90.

Yang et al., "A Common Pathway For T Lymphocyte Activation Involving Both The CD3-Ti Complex And CD2 Sheep Erythrocyte Receptor Determinants," J. Immunol. (1986) 137(4): 1097-1100.

Young et al., "Antibody-Cytokine Fusion Proteins For Treatment Of Cancer: Engineering Cytokines For Improved Efficacy and Safety," Seminars In Oncology. (2014) 41(5):623-636, 19 pages.

Zalevsky et al., "Enhanced antibody half-life improves in vivo activity," Nat Biotechnol (2010) 28(2):157-159.

Golovleva et al., "Ethnic differences in interferon-alpha allele frequencies," Hum Hered. (1997) 47(4): 185-188.

Golovleva et al., "Novel variants of human IFN-alpha detected in tumor cell lines and biopsy specimens," J Interferon Cytokine Res. (1997) 17(10): 637-645.

Hussain et al., "Interferon-alpha 8b is the only variant of interferon-alpha 8 identified in a large human population," J Interferon Cytokine Res. (1996) 16(7): 523-529.

Hussain et al., "Both variant forms of interferon-alpha4 gene (IFNA4a and IFNA4b) are present in the human population," J Interferon Cytokine Res. (1997) 17(9): 559-566.

Hussain et al., "A new allele of interferon-alpha17 gene encoding IFN-alpha17b is the major variant in human population," J Interferon Cytokine Res. (1998) 18(7): 469-77.

Kim et al., "Interferon, alpha 17 (IFNA17) IIe184Arg polymorphism and cervical cancer risk," Cancer Lett. (2003) 189(2); 183-188.

Kita et al., "Determination of interferon-alpha2 allele composition in the genomic DNA from healthy volunteers and leukemic patients in Japan," J Interferon Cytokine Res. (1997) 17(3); 135-140.

Ledbetter et al., "Valency of CD3 binding and internalization of the CD3 cell-surface complex control T cell responses to second signals: distinction between effects on protein kinase C, cytoplasmic free calcium, and proliferation," J Immunol. (1986) 136(11); 3945-3952.

Linge et al., "Transcription of interferon-alpha 2 alleles from virus-induced human leucocytes and lymphoblastoid cells of African origin," Biochim Biophys Acta. (1995) 1264(3):363-8.

Lundell et al., "The carboxyl-terminal region of human interferon gamma is important for biological activity: mutagenic and NMR analysis," Protein Eng. (1991) 4(3): 335-341.

McCall et al., "Isolation and characterization of an anti-CD16 single-chain Fv fragment and construction of an anti-HER2/neu/anti-CD16 bispecific scFv that triggers CD16-dependent tumor cytolysis," Mol. Immunol. (1999) 36:433-45.

Nicolaou et al., "Calicheamicin θ: A Rationally Designed Molecule with Extremely Potent and Selective DNA Cleaving Properties and Apoptosis Inducing Activity," Angew Chem Int Edit (1994) 33(2):183-186.

Pestka et al., The human interferons—from protein purification and sequence to cloning and expression in bacteria: before, between, and beyond, Arch Biochem Biophys. (1983) 221(1): 1-37.

Pestka, vol. 119. Interferons (Part C) (1986) Meth. Enzymol, 199: 3-4.

Rodrigues et al., "Engineering a humanized bispecific F(ab')2 fragment for improved binding to T cells," Int J Cancer Suppl. (1992) 7:45-50.

Starzynska et al., "5T4 oncofetal antigen in gastric carcinoma and its clinical significance," Eur J Gastroenterol Hepatol. (1998) 10(6): 479-484.

Valedkarimi et al., "Antibody-cytokine fusion proteins for improving efficacy and safety of cancer therapy," Biomed Pharmacother. (2017) 95: 731-742.

Van De Winkel et al., "Human IgG Fc receptor heterogeneity: molecular aspects and clinical implications," Immunol Today. (1993) 14(5): 215-21.

Wrigley et al., "5T4 oncofetal antigen expression in ovarian carcinoma.," Int J Gynecol Cancer. (1995) 5(4): 269-274.

Yamamoto et al., "Creation of interferon-alpha8 mutants with amino acid substitutions against interferon-alpha receptor-2 binding sites using phage display system and evaluation of their biologic properties," J Interferon Cytokine Res. (2009) 29(3): 161-70.

* cited by examiner

Chain 1        Chain 2

5T4 sdAb #1

Fc-Knob

Anti-CD3 VH

5T4 sdAb #2

5T4 sdAb #3

Fc-Hole

Anti-CD3-VL

41BB sdAb

5T4 sdAb #1

Fc -Heterodimer

5T4 sdAb #3

Anti-CD3-FV

5T4 sdAb #2

41BB sdAb

Chain 1          Chain 2

OVCAR5 cells                    T cells cx3547

Anti-CD3

2° only cx3547

● Binding to OVCAR5 cells

■ Binding to T cells cx3546

Anti-CD3

2° only cx4913

Anti-CD3

2° only cx4913

Binding to OVCAR5 cells

Binding to T cells

OVCAR5 cells                    T cells cx3265

Anti-CD3

2° only

APC-A ∷ APC - Area          APC-A ∷ APC - Area cx3265

—●— Binding to OVCAR5 cells
—▼— Binding to T cells cx4911

Anti-CD3

2° only cx4911

—●— Binding to OVCAR5 cells

—■— Binding to T cells

OVCAR5 cells                    T cells cx4910

Anti-CD3

2° only cx4910

—●— Binding to OVCAR5 cells
—■— Binding to T cells cx3547: 5T4xCD3 cx3497: 5T4xCD3x41BB secondary antibody only

5T4 -/+ 41BB Binding

T cells cx3547: 5T4xCD3 cx3497: 5T4xCD3x41BB anti-CD3 secondary antibody only

APC-A :: APC - Area

Binding to T Cells

-●- cx3547: 5T4xCD3

-■- cx3497: 5T4xCD3x41BB

FIG. 13A                          5T4 -/+ 41BB cytotox
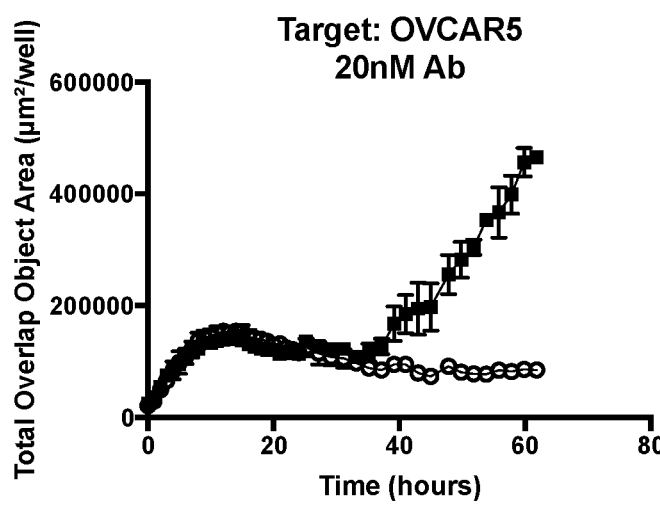
-o- cx3547: 5T4xCD3
-■- cx3497: 5T4xCD3x41BB
FIG. 13B
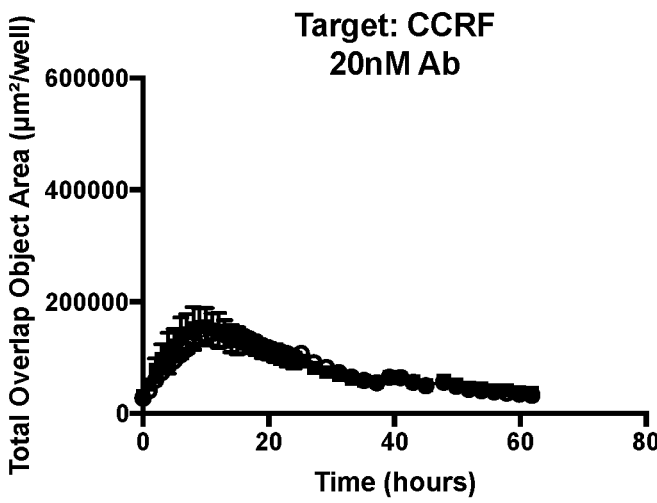
-o- cx3547: 5T4xCD3
-■- cx3497: 5T4xCD3x41BB

5T4 -/+ 41BB INF ELISA

CD4+ T cell proliferation
Target cell: A375

CD4+ T cell proliferation
Target cell: SHP-77

CD4+ T cell proliferation
Target cell: OVCAR5

CD8+ T cells: MitoTracker staining
Target cell: A375

CD8+ T cells: MitoTracker staining
Target cell: SHP-77

CD8+ T cells: MitoTracker staining
Target cell: OVCAR5

- Knob-VH; Hole-VL
- Knob-VL; Hole-VH

SEQUENCE LISTING

<160> NUMBER OF SEQ ID NOS: 412

<210> SEQ ID NO 1
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 1

Gly Gly Ser Gly Gly Ser
1               5

<210> SEQ ID NO 2
<211> LENGTH: 9
<212> TYPE: PRT
<213> ORGANISM: Artificial Sequence
<220> FEATURE:
<223> OTHER INFORMATION: (GGS)3  linker

<400> SEQUENCE: 2

Gly Gly Ser Gly Gly Ser Gly Gly Ser
1               5

<210> SEQ ID NO 3
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 3

Gly Gly Ser Gly Gly Ser Gly Gly Ser Gly Gly Ser
1               5                   10

-continued

```
<210> SEQ ID NO 4
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 4

Gly Gly Ser Gly Gly Ser Gly Gly Ser Gly Gly Ser Gly Gly Ser
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: glycine linker

<400> SEQUENCE: 5

Gly Gly Gly Gly
1

<210> SEQ ID NO 6
<211> LENGTH: 5
<212> TYPE: PRT
<213> ORGANISM: Artificial Sequence
<220> FEATURE:
<223> OTHER INFORMATION: glycine linker

<400> SEQUENCE: 6

Gly Gly Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Glycine linker

<400> SEQUENCE: 7

Gly Gly Gly Gly Gly Gly
1               5

<210> SEQ ID NO 8
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(218)
<223> OTHER INFORMATION: human IgG1 Fc

<400> SEQUENCE: 8

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60
```

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
            195                 200                 205

Gln Lys Ser Leu Ser Leu Ser Pro Gly Lys
    210                 215

<210> SEQ ID NO 9
<211> LENGTH: 215
<212> TYPE: PRT
<213> ORGANISM: Artificial Sequence
<220> FEATURE:
<223> OTHER INFORMATION: Fc xELL

<400> SEQUENCE: 9

Pro Ala Pro Gly Gly Pro Ser Val Phe Leu Phe Pro Pro Lys Pro Lys
1                   5                   10                  15

Asp Thr Leu Met Ile Ser Arg Thr Pro Glu Val Thr Cys Val Val Val
                20                  25                  30

Asp Val Ser His Glu Asp Pro Glu Val Lys Phe Asn Trp Tyr Val Asp
            35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
            85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
            195                 200                 205

-continued

```
Leu Ser Leu Ser Pro Gly Lys
    210                 215

<210> SEQ ID NO 10
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(217)
<223> OTHER INFORMATION: human IgG2 Fc

<400> SEQUENCE: 10

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 11
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(218)
<223> OTHER INFORMATION: human IgG3 Fc

<400> SEQUENCE: 11

Pro Ala Pro Glu Leu Leu Gly Gly Pro Ser Val Phe Leu Phe Pro Pro
1               5                   10                  15
```

-continued

```
Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
            35                  40                  45

Tyr Val Asp Gly Val Glu Val His Asn Ala Lys Thr Lys Pro Arg Glu
            50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
            130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
                180                 185                 190

Ile Phe Ser Cys Ser Val Met His Glu Ala Leu His Asn Arg Phe Thr
                195                 200                 205

Gln Lys Ser Leu Ser Leu Ser Pro Gly Lys
            210                 215
```

```
<210> SEQ ID NO 12
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(218)
<223> OTHER INFORMATION: human IgG4 Fc

<400> SEQUENCE: 12
```

```
Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
            50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
```

-continued

```
           130                135                140

Pro Ser Asp Ile Ala Val Glu Trp Glu Ser Asn Gly Gln Pro Glu Asn
145                150                155                160

Asn Tyr Lys Thr Thr Pro Pro Val Leu Asp Ser Asp Gly Ser Phe Phe
               165                170                175

Leu Tyr Ser Arg Leu Thr Val Asp Lys Ser Arg Trp Gln Glu Gly Asn
               180                185                190

Val Phe Ser Cys Ser Val Met His Glu Ala Leu His Asn His Tyr Thr
               195                200                205

Gln Lys Ser Leu Ser Leu Ser Leu Gly Lys
       210                215
```

```
<210> SEQ ID NO 13
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(218)
<223> OTHER INFORMATION: human IgG4 Fc

<400> SEQUENCE: 13

Pro Ala Pro Glu Leu Leu Gly Gly Pro Ser Val Phe Leu Phe Pro Pro
1                5                10                15

Lys Pro Lys Asp Thr Leu Met Ile Ser Arg Thr Pro Glu Val Thr Cys
               20                25                30

Val Val Val Asp Val Ser Gln Glu Asp Pro Glu Val Gln Phe Asn Trp
               35                40                45

Tyr Val Asp Gly Val Glu Val His Asn Ala Lys Thr Lys Pro Arg Glu
       50                55                60

Glu Gln Phe Asn Ser Thr Tyr Arg Val Val Ser Val Leu Thr Val Leu
65                70                75                80

His Gln Asp Trp Leu Asn Gly Lys Glu Tyr Lys Cys Lys Val Ser Asn
               85                90                95

Lys Gly Leu Pro Ser Ser Ile Glu Lys Thr Ile Ser Lys Ala Lys Gly
               100                105                110

Gln Pro Arg Glu Pro Gln Val Tyr Thr Leu Pro Pro Ser Gln Glu Glu
               115                120                125

Met Thr Lys Asn Gln Val Ser Leu Thr Cys Leu Val Lys Gly Phe Tyr
       130                135                140

Pro Ser Asp Ile Ala Val Glu Trp Glu Ser Asn Gly Gln Pro Glu Asn
145                150                155                160

Asn Tyr Lys Thr Thr Pro Pro Val Leu Asp Ser Asp Gly Ser Phe Phe
               165                170                175

Leu Tyr Ser Arg Leu Thr Val Asp Lys Ser Arg Trp Gln Glu Gly Asn
               180                185                190

Val Phe Ser Cys Ser Val Met His Glu Ala Leu His Asn His Tyr Thr
               195                200                205

Gln Lys Ser Leu Ser Leu Ser Leu Gly Lys
       210                215

<210> SEQ ID NO 14
<211> LENGTH: 14
<212> TYPE: PRT
<213> ORGANISM: Artificial Sequence
```

```
<220> FEATURE:
<223> OTHER INFORMATION: modified IgG1 hinge

<400> SEQUENCE: 14

Glu Pro Lys Ser Ser Asp Lys Thr His Thr Cys Pro Pro Cys
1               5                   10

<210> SEQ ID NO 15
<211> LENGTH: 9
<212> TYPE: PRT
<213> ORGANISM: Artificial Sequence
<220> FEATURE:
<223> OTHER INFORMATION: truncated IgG1 hinge

<400> SEQUENCE: 15

Asp Lys Thr His Thr Cys Pro Pro Cys
1               5

<210> SEQ ID NO 16
<211> LENGTH: 11
<212> TYPE: PRT
<213> ORGANISM: Artificial Sequence
<220> FEATURE:
<223> OTHER INFORMATION: modified IgG4 hinge

<400> SEQUENCE: 16

Glu Ser Lys Tyr Gly Pro Pro Cys Pro Pro Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 17

Gly Gln Gly Thr Leu Val Thr Val Lys Pro Gly Gly
1               5                   10

<210> SEQ ID NO 18
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 18

Gly Gln Gly Thr Leu Val Thr Val Glu Pro Gly Gly
1               5                   10

<210> SEQ ID NO 19
<211> LENGTH: 119
<212> TYPE: PRT
<213> ORGANISM: Artificial Sequence
<220> FEATURE:
<223> OTHER INFORMATION: OKT3 VH

<400> SEQUENCE: 19

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45
```

-continued

```
Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: OKT3 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 21
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 21

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115
```

<210> SEQ ID NO 22
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 22

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 23

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 24
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 24

-continued

Gln Ile Val Leu Thr Gln Ser Pro Ala Ile Met Ser Ala Ser Pro Gly
1                   5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 25
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 25

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Val Ser Tyr Met
                20                  25                  30

Asn Trp Tyr Gln Gln Lys Pro Gly Lys Ala Pro Lys Arg Trp Ile Tyr
            35                  40                  45

Asp Thr Ser Lys Val Ala Ser Gly Val Pro Ala Arg Phe Ser Gly Ser
        50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 26
<211> LENGTH: 108
<212> TYPE: PRT
<213> ORGANISM: Artificial Sequence
<220> FEATURE:
<223> OTHER INFORMATION: OKT3 humanized VL

<400> SEQUENCE: 26

Asp Ile Gln Leu Thr Gln Ser Pro Ser Ile Leu Ser Ala Ser Val Gly
1                   5                   10                  15

Asp Arg Val Thr Ile Thr Cys Arg Ala Ser Ser Ser Val Ser Tyr Met
                20                  25                  30

Asn Trp Tyr Gln Gln Lys Pro Gly Lys Ala Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Glu Tyr Thr Leu Thr Ile Ser Ser Met Gln Pro Glu
65                  70                  75                  80

Asp Phe Ala Thr Tyr Tyr Cys Gln Gln Trp Ser Ser Asn Pro Leu Thr
                85                  90                  95

-continued

Phe Gly Cys Gly Thr Lys Val Glu Ile Lys Arg Thr
            100                 105

<210> SEQ ID NO 27
<211> LENGTH: 125
<212> TYPE: PRT
<213> ORGANISM: Artificial Sequence
<220> FEATURE:
<223> OTHER INFORMATION: anti-CD3 Hv

<400> SEQUENCE: 27

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 28
<211> LENGTH: 109
<212> TYPE: PRT
<213> ORGANISM: Artificial Sequence
<220> FEATURE:
<223> OTHER INFORMATION: anti-CD3 Lv

<400> SEQUENCE: 28

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 29
<211> LENGTH: 5
<212> TYPE: PRT
<213> ORGANISM: Artificial Sequence
<220> FEATURE:
<223> OTHER INFORMATION: anti-CD3 VH CDR1

<400> SEQUENCE: 29

-continued

```
Thr Tyr Ala Met Asn
1               5

<210> SEQ ID NO 30
<211> LENGTH: 19
<212> TYPE: PRT
<213> ORGANISM: Artificial Sequence
<220> FEATURE:
<223> OTHER INFORMATION: anti-CD3 VH CDR2

<400> SEQUENCE: 30

Arg Ile Arg Ser Lys Tyr Asn Asn Tyr Ala Thr Tyr Tyr Ala Asp Ser
1               5                   10                  15

Val Lys Asp

<210> SEQ ID NO 31
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 31

His Gly Asn Phe Gly Asn Ser Tyr Val Ser Trp Phe Ala Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 32

Arg Ser Ser Thr Gly Ala Val Thr Thr Ser Asn Tyr Ala Asn
1               5                   10

<210> SEQ ID NO 33
<211> LENGTH: 7
<212> TYPE: PRT
<213> ORGANISM: Artificial Sequence
<220> FEATURE:
<223> OTHER INFORMATION: anti-CD3 VL CDR2

<400> SEQUENCE: 33

Gly Thr Asn Lys Arg Ala Pro
1               5

<210> SEQ ID NO 34
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 34

Ala Leu Trp Tyr Ser Asn Leu Trp Val
1               5

<210> SEQ ID NO 35
<211> LENGTH: 125
<212> TYPE: PRT
<213> ORGANISM: Artificial Sequence
<220> FEATURE:
<223> OTHER INFORMATION: anti-CD3 VH1

<400> SEQUENCE: 35
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 36
<211> LENGTH: 125
<212> TYPE: PRT
<213> ORGANISM: Artificial Sequence
<220> FEATURE:
<223> OTHER INFORMATION: anti-CD3 VH2

<400> SEQUENCE: 36

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 37
<211> LENGTH: 125
<212> TYPE: PRT
<213> ORGANISM: Artificial Sequence
<220> FEATURE:
<223> OTHER INFORMATION: anti-CD3 VH3

<400> SEQUENCE: 37

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
```

-continued

```
        50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: anti-CD3 VH4

<400> SEQUENCE: 38

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 39
<211> LENGTH: 125
<212> TYPE: PRT
<213> ORGANISM: Artificial Sequence
<220> FEATURE:
<223> OTHER INFORMATION: anti-CD3 VH5

<400> SEQUENCE: 39

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110
```

-continued

```
Ala Tyr Trp Gly Gln Gly Thr Leu Val Thr Val Ser Ser
        115                 120                 125

<210> SEQ ID NO 40
<211> LENGTH: 125
<212> TYPE: PRT
<213> ORGANISM: Artificial Sequence
<220> FEATURE:
<223> OTHER INFORMATION: anti-CD3 VH6

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 41
<211> LENGTH: 125
<212> TYPE: PRT
<213> ORGANISM: Artificial Sequence
<220> FEATURE:
<223> OTHER INFORMATION: anti-CD3 VH7

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 42
<211> LENGTH: 124
<212> TYPE: PRT
<213> ORGANISM: Artificial Sequence
<220> FEATURE:
<223> OTHER INFORMATION: anti-CD3 VH8
```

```
<400> SEQUENCE: 42

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
            115                 120

<210> SEQ ID NO 43
<211> LENGTH: 125
<212> TYPE: PRT
<213> ORGANISM: Artificial Sequence
<220> FEATURE:
<223> OTHER INFORMATION: anti-CD3 VH9

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
            115                 120                 125

<210> SEQ ID NO 44
<211> LENGTH: 125
<212> TYPE: PRT
<213> ORGANISM: Artificial Sequence
<220> FEATURE:
<223> OTHER INFORMATION: anti-CD3 VH10

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45
```

```
Ala Arg Ile Arg Ser Lys Tyr Asn Asn Tyr Ala Thr Tyr Tyr Ala Asp
    50                  55                  60
```

```
Ser Val Lys Gly Arg Phe Thr Ile Ser Arg Asp Asp Ser Lys Asn Thr
65                  70                  75                  80
```

```
Leu Tyr Leu Gln Met Asn Ser Leu Arg Ala Glu Asp Thr Ala Val Tyr
                85                  90                  95
```

```
Tyr Cys Val Arg His Gly Asn Phe Gly Asn Ser Tyr Val Ser Tyr Phe
            100                 105                 110
```

```
Ala Tyr Trp Gly Gln Gly Thr Thr Val Thr Val Ser Ser
        115                 120                 125
```

```
<210> SEQ ID NO 45
<211> LENGTH: 125
<212> TYPE: PRT
<213> ORGANISM: Artificial Sequence
<220> FEATURE:
<223> OTHER INFORMATION: anti-CD3 VH11
```

```
<400> SEQUENCE: 45
```

```
Glu Val Gln Leu Val Glu Ser Gly Gly Gly Leu Val Gln Pro Lys Gly
1               5                   10                  15
```

```
Ser Leu Lys Leu Ser Cys Ala Ala Ser Gly Phe Thr Phe Asn Thr Tyr
                20                  25                  30
```

```
Ala Met Asn Trp Val Arg Gln Ala Pro Gly Lys Gly Leu Glu Trp Val
            35                  40                  45
```

```
Ala Arg Ile Arg Ser Lys Tyr Asn Asn Tyr Ala Thr Tyr Tyr Ala Asp
    50                  55                  60
```

```
Ser Val Lys Asp Arg Phe Thr Ile Ser Arg Asp Asp Ser Gln Ser Ile
65                  70                  75                  80
```

```
Leu Tyr Leu Gln Met Asn Asn Leu Lys Thr Glu Asp Thr Ala Met Tyr
                85                  90                  95
```

```
Tyr Cys Val Arg His Gly Asn Phe Gly Asn Ser Tyr Val Ser Trp Phe
            100                 105                 110
```

```
Ala Tyr Trp Gly Gln Gly Thr Leu Val Thr Val Ser Ser
        115                 120                 125
```

```
<210> SEQ ID NO 46
<211> LENGTH: 125
<212> TYPE: PRT
<213> ORGANISM: Artificial Sequence
<220> FEATURE:
<223> OTHER INFORMATION: anti-CD3 VH12
```

```
<400> SEQUENCE: 46
```

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
                20                  25                  30
```

```
Ala Met Asn Trp Val Arg Gln Ala Pro Gly Lys Gly Leu Glu Trp Val
            35                  40                  45
```

```
Ala Arg Ile Arg Ser Lys Tyr Asn Asn Tyr Ala Thr Tyr Tyr Ala Asp
    50                  55                  60
```

```
Ser Val Lys Gly Arg Phe Thr Ile Ser Arg Asp Asp Ala Lys Asn Thr
65                  70                  75                  80
```

```
Leu Tyr Leu Gln Met Ser Ser Leu Arg Ala Glu Asp Thr Ala Val Tyr
                85                  90                  95
```

```
Tyr Cys Val Arg His Gly Asn Phe Gly Asn Ser Tyr Val Ser Trp Phe
            100                 105                 110
```

-continued

```
Ala Tyr Trp Gly Gln Gly Thr Leu Val Thr Val Lys Pro
        115                 120                 125

<210> SEQ ID NO 47
<211> LENGTH: 125
<212> TYPE: PRT
<213> ORGANISM: Artificial Sequence
<220> FEATURE:
<223> OTHER INFORMATION: anti-CD3 VH13

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125

<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH14

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Cys Gly Thr Leu Val Thr Val Lys Pro
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH15
```

-continued

```
<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 50
<211> LENGTH: 125
<212> TYPE: PRT
<213> ORGANISM: Artificial Sequence
<220> FEATURE:
<223> OTHER INFORMATION: anti-CD3 VH16

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH17

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45
```

-continued

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH18

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH19

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Cys Leu Glu Trp Val
            35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe

-continued

```
              100              105              110

Ala Tyr Trp Gly Gln Gly Thr Leu Val Thr Val Ser Ser
        115              120              125

<210> SEQ ID NO 54
<211> LENGTH: 125
<212> TYPE: PRT
<213> ORGANISM: Artificial Sequence
<220> FEATURE:
<223> OTHER INFORMATION: anti-CD3 VH20

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH21

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 56
<211> LENGTH: 125
<212> TYPE: PRT
<213> ORGANISM: Artificial Sequence
<220> FEATURE:
```

<223> OTHER INFORMATION: anti-CD3 VH22

<400> SEQUENCE: 56

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 57
<211> LENGTH: 125
<212> TYPE: PRT
<213> ORGANISM: Artificial Sequence
<220> FEATURE:
<223> OTHER INFORMATION: anti-CD3 VH23

<400> SEQUENCE: 57

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 58
<211> LENGTH: 125
<212> TYPE: PRT
<213> ORGANISM: Artificial Sequence
<220> FEATURE:
<223> OTHER INFORMATION: anti-CD3 VH24

<400> SEQUENCE: 58

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
```

-continued

```
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125
```

<210> SEQ ID NO 59
<211> LENGTH: 125
<212> TYPE: PRT
<213> ORGANISM: Artificial Sequence
<220> FEATURE:
<223> OTHER INFORMATION: anti-CD3 VH25

<400> SEQUENCE: 59

```
Glu Val Lys Leu Val Glu Ser Gly Gly Gly Leu Val Lys Pro Gly Arg
1                   5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Cys Leu Glu Trp Val
                35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125
```

<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH26

<400> SEQUENCE: 60

```
Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Cys Leu Glu Trp Val
                35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

-continued

```
Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 61
<211> LENGTH: 125
<212> TYPE: PRT
<213> ORGANISM: Artificial Sequence
<220> FEATURE:
<223> OTHER INFORMATION: anti-CD3 VH27

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 62
<211> LENGTH: 124
<212> TYPE: PRT
<213> ORGANISM: Artificial Sequence
<220> FEATURE:
<223> OTHER INFORMATION: anti-CD3 VH28

<400> SEQUENCE: 62

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
        115                 120

<210> SEQ ID NO 63
<211> LENGTH: 125
<212> TYPE: PRT
<213> ORGANISM: Artificial Sequence
```

-continued

<220> FEATURE:
<223> OTHER INFORMATION: anti-CD3 VH29

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125

<210> SEQ ID NO 64
<211> LENGTH: 125
<212> TYPE: PRT
<213> ORGANISM: Artificial Sequence
<220> FEATURE:
<223> OTHER INFORMATION: anti-CD3 VH30

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 65
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 65

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

```
Ala Met Asn Trp Val Arg Gln Ala Pro Gly Lys Cys Leu Glu Trp Val
        35                  40              45

Ala Arg Ile Arg Ser Lys Tyr Asn Asn Tyr Ala Thr Tyr Tyr Ala Asp
    50                  55              60

Ser Val Lys Asp Arg Phe Thr Ile Ser Arg Asp Asp Ser Gln Ser Ile
65                  70              75                  80

Leu Tyr Leu Gln Met Asn Asn Leu Lys Thr Glu Asp Thr Ala Met Tyr
                85                  90              95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 66
<211> LENGTH: 109
<212> TYPE: PRT
<213> ORGANISM: Artificial Sequence
<220> FEATURE:
<223> OTHER INFORMATION: anti-CD3 VL1

<400> SEQUENCE: 66

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 67
<211> LENGTH: 109
<212> TYPE: PRT
<213> ORGANISM: Artificial Sequence
<220> FEATURE:
<223> OTHER INFORMATION: anti-CD3 VL2

<400> SEQUENCE: 67

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105
```

-continued

```
<210> SEQ ID NO 68
<211> LENGTH: 109
<212> TYPE: PRT
<213> ORGANISM: Artificial Sequence
<220> FEATURE:
<223> OTHER INFORMATION: anti-CD3 VL3

<400> SEQUENCE: 68

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 69
<211> LENGTH: 109
<212> TYPE: PRT
<213> ORGANISM: Artificial Sequence
<220> FEATURE:
<223> OTHER INFORMATION: anti-CD3 VL4

<400> SEQUENCE: 69

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 70
<211> LENGTH: 109
<212> TYPE: PRT
<213> ORGANISM: Artificial Sequence
<220> FEATURE:
<223> OTHER INFORMATION: anti-CD3 VL5

<400> SEQUENCE: 70

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30
```

-continued

Asn Tyr Ala Asn Trp Val Gln Gln Thr Pro Gly Gln Ala Phe Arg Gly
            35              40              45

Leu Ile Gly Gly Thr Asn Lys Arg Ala Pro Gly Val Pro Ala Arg Phe
        50              55              60

Ser Gly Ser Ile Leu Gly Asn Lys Ala Ala Leu Thr Ile Thr Gly Ala
65              70              75              80

Gln Ala Asp Asp Glu Ser Ile Tyr Phe Cys Ala Leu Trp Tyr Ser Asn
                85              90              95

Leu Trp Val Phe Gly Gly Gly Thr Lys Leu Thr Val Leu
            100             105

<210> SEQ ID NO 71
<211> LENGTH: 109
<212> TYPE: PRT
<213> ORGANISM: Artificial Sequence
<220> FEATURE:
<223> OTHER INFORMATION: anti-CD3 VL6

<400> SEQUENCE: 71

Gln Ala Val Val Thr Gln Glu Pro Ser Phe Ser Val Ser Pro Gly Gly
1               5               10              15

Thr Val Thr Leu Thr Cys Arg Ser Ser Thr Gly Ala Val Thr Thr Ser
            20              25              30

Asn Tyr Ala Asn Trp Val Gln Gln Thr Pro Gly Gln Ala Phe Arg Gly
            35              40              45

Leu Ile Gly Gly Thr Asn Lys Arg Ala Pro Gly Val Pro Ala Arg Phe
        50              55              60

Ser Gly Ser Ile Leu Gly Asn Lys Ala Ala Leu Thr Ile Thr Gly Ala
65              70              75              80

Gln Ala Asp Asp Glu Ser Asp Tyr Tyr Cys Ala Leu Trp Tyr Ser Asn
                85              90              95

Leu Trp Val Phe Gly Gly Gly Thr Lys Leu Thr Val Leu
            100             105

<210> SEQ ID NO 72
<211> LENGTH: 109
<212> TYPE: PRT
<213> ORGANISM: Artificial Sequence
<220> FEATURE:
<223> OTHER INFORMATION: anti-CD3 VL7

<400> SEQUENCE: 72

Gln Ala Val Val Thr Gln Glu Pro Ser Leu Thr Val Ser Pro Gly Gly
1               5               10              15

Thr Val Thr Leu Thr Cys Gly Ser Ser Thr Gly Ala Val Thr Thr Ser
            20              25              30

Asn Tyr Ala Asn Trp Val Gln Glu Lys Pro Gly Gln Ala Phe Arg Gly
            35              40              45

Leu Ile Gly Gly Thr Asn Lys Arg Ala Pro Gly Thr Pro Ala Arg Phe
        50              55              60

Ser Gly Ser Leu Leu Gly Gly Lys Ala Ala Leu Thr Leu Ser Gly Ala
65              70              75              80

Gln Pro Glu Asp Glu Ala Glu Tyr Tyr Cys Ala Leu Trp Tyr Ser Asn
                85              90              95

Leu Trp Val Phe Gly Gly Gly Thr Lys Leu Thr Val Leu
            100             105

<210> SEQ ID NO 73

```
<211> LENGTH: 109
<212> TYPE: PRT
<213> ORGANISM: Artificial Sequence
<220> FEATURE:
<223> OTHER INFORMATION: anti-CD3 VL8

<400> SEQUENCE: 73

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 74
<211> LENGTH: 109
<212> TYPE: PRT
<213> ORGANISM: Artificial Sequence
<220> FEATURE:
<223> OTHER INFORMATION: anti-CD3 VL9

<400> SEQUENCE: 74

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
            100                 105

<210> SEQ ID NO 75
<211> LENGTH: 109
<212> TYPE: PRT
<213> ORGANISM: Artificial Sequence
<220> FEATURE:
<223> OTHER INFORMATION: anti-CD3 VL10

<400> SEQUENCE: 75

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45
```

-continued

```
Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105

<210> SEQ ID NO 76
<211> LENGTH: 109
<212> TYPE: PRT
<213> ORGANISM: Artificial Sequence
<220> FEATURE:
<223> OTHER INFORMATION: anti-CD3 VL11

<400> SEQUENCE: 76

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Gln Cys Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Glu Gly Thr Lys Leu Glu Ile Lys
            100                 105

<210> SEQ ID NO 77
<211> LENGTH: 109
<212> TYPE: PRT
<213> ORGANISM: Artificial Sequence
<220> FEATURE:
<223> OTHER INFORMATION: anti-CD3 VL12

<400> SEQUENCE: 77

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Cys Gly Thr Lys Leu Thr Val Leu
            100                 105

<210> SEQ ID NO 78
<211> LENGTH: 109
<212> TYPE: PRT
<213> ORGANISM: Artificial Sequence
```

```
<220> FEATURE:
<223> OTHER INFORMATION: anti-CD3 VL13

<400> SEQUENCE: 78

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
            100                 105

<210> SEQ ID NO 79
<211> LENGTH: 109
<212> TYPE: PRT
<213> ORGANISM: Artificial Sequence
<220> FEATURE:
<223> OTHER INFORMATION: anti-CD3 VL14

<400> SEQUENCE: 79

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 80
<211> LENGTH: 109
<212> TYPE: PRT
<213> ORGANISM: Artificial Sequence
<220> FEATURE:
<223> OTHER INFORMATION: anti-CD3 VL15

<400> SEQUENCE: 80

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60
```

-continued

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 81
<211> LENGTH: 109
<212> TYPE: PRT
<213> ORGANISM: Artificial Sequence
<220> FEATURE:
<223> OTHER INFORMATION: anti-CD3 VL16

<400> SEQUENCE: 81

Gln Ala Val Val Thr Gln Glu Pro Ser Phe Ser Val Ser Pro Gly Gly
1                   5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Cys Gly Thr Lys Leu Thr Val Leu
            100                 105

<210> SEQ ID NO 82
<211> LENGTH: 109
<212> TYPE: PRT
<213> ORGANISM: Artificial Sequence
<220> FEATURE:
<223> OTHER INFORMATION: anti-CD3 VL17

<400> SEQUENCE: 82

Gln Ala Val Val Thr Gln Glu Pro Ser Phe Ser Val Ser Pro Gly Gly
1                   5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 83
<211> LENGTH: 109
<212> TYPE: PRT
<213> ORGANISM: Artificial Sequence
<220> FEATURE:
<223> OTHER INFORMATION: anti-CD3 VL18

<400> SEQUENCE: 83

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Cys Gly Thr Lys Leu Thr Val Leu
                100                 105

<210> SEQ ID NO 84
<211> LENGTH: 109
<212> TYPE: PRT
<213> ORGANISM: Artificial Sequence
<220> FEATURE:
<223> OTHER INFORMATION: anti-CD3 VL19

<400> SEQUENCE: 84

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Cys Gly Thr Lys Leu Thr Val Leu
                100                 105

<210> SEQ ID NO 85
<211> LENGTH: 129
<212> TYPE: PRT
<213> ORGANISM: Artificial Sequence
<220> FEATURE:
<223> OTHER INFORMATION: anti-CD3 VHH

<400> SEQUENCE: 85

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

His Met Gly Trp Phe Arg Gln Ala Pro Gly Lys Glu Arg Glu Leu Val
        35                  40                  45

Ala Ala Ile Ser Gly Ser Gly Gly Ser Thr Tyr Tyr Thr Asp Ser Val
    50                  55                  60

Lys Gly Arg Phe Thr Ile Ser Arg Asn Asn Ala Lys Asn Thr Met Ser
65                  70                  75                  80

-continued

```
Leu Gln Met Ser Asn Leu Lys Pro Glu Asp Thr Gly Val Tyr Tyr Cys
              85              90                  95

Thr Thr Pro Thr Glu Lys Gly Ser Ser Ile Asp Tyr Trp Gly Gln Gly
          100             105             110

Thr Gln Val Thr Val Ser Ser Gly Arg Tyr Pro Tyr Asp Val Pro Asp
      115         120             125

Tyr

<210> SEQ ID NO 86
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 86

Gly Arg Pro Phe Ser Ser Tyr Ala Met Gly
1               5                   10

<210> SEQ ID NO 87
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 87

Gly Arg Pro Phe Ser Ser Ser Ala Met Gly
1               5                   10

<210> SEQ ID NO 88
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 88

Ala Val Arg Trp Ile Gly Gly Ala Thr Arg
1               5                   10

<210> SEQ ID NO 89
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 89

Ala Val Ser Arg Asn Gly Gly Ala Ser Gln
1               5                   10

<210> SEQ ID NO 90
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 90

Ala Val Ser Arg Asn Ala Gly Ala Ser Gln
1               5                   10

<210> SEQ ID NO 91
<211> LENGTH: 10
```

```
<212> TYPE: PRT
<213> ORGANISM: Artificial Sequence
<220> FEATURE:
<223> OTHER INFORMATION: 5T4 CDR-H2

<400> SEQUENCE: 91

Ala Val Ser Arg Asn Thr Gly Ala Ser Gln
1               5                   10

<210> SEQ ID NO 92
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 92

Ala Val Ser Arg Gln Gly Gly Ala Ser Gln
1               5                   10

<210> SEQ ID NO 93
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 93

Ala Val Ser Arg Gly Gly Gly Ala Ser Gln
1               5                   10

<210> SEQ ID NO 94
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 94

Ala Val Ser Arg Asn Ala Gly Ala Ser Tyr
1               5                   10

<210> SEQ ID NO 95
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 95

Ala Val Ser Arg Asn Gly Gly Ser Ser Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 96

Ala Val Ser Arg Gln Gly Gly Ser Ser Tyr
1               5                   10

<210> SEQ ID NO 97
<211> LENGTH: 10
<212> TYPE: PRT
```

```
<213> ORGANISM: Artificial Sequence
<220> FEATURE:
<223> OTHER INFORMATION: 5T4 CDR-H2

<400> SEQUENCE: 97

Ala Val Ser Arg Gly Gly Gly Ser Ser Tyr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 98

Ala Val Ser Arg Asn Ala Gly Ser Ser Tyr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 99

Ala Val Ser Arg Asn Thr Gly Ser Ser Tyr
1               5                   10

<210> SEQ ID NO 100
<211> LENGTH: 13
<212> TYPE: PRT
<213> ORGANISM: Artificial Sequence
<220> FEATURE:
<223> OTHER INFORMATION: 5T4 CDR-H3

<400> SEQUENCE: 100

Gly Gln Ala Trp Gly Thr Lys Phe Thr Asp Tyr Ser Asp
1               5                   10

<210> SEQ ID NO 101
<211> LENGTH: 20
<212> TYPE: PRT
<213> ORGANISM: Artificial Sequence
<220> FEATURE:
<223> OTHER INFORMATION: 5T4 CDR-H3

<400> SEQUENCE: 101

Arg Ser Ala Ala Tyr Ser Arg Ser Ser Glu Val Tyr Thr Gly Lys Asp
1               5                   10                  15

Glu Tyr Tyr Tyr
            20

<210> SEQ ID NO 102
<211> LENGTH: 20
<212> TYPE: PRT
<213> ORGANISM: Artificial Sequence
<220> FEATURE:
<223> OTHER INFORMATION: 5T4 CDR-H3

<400> SEQUENCE: 102

Arg Ser Ala Ala Tyr Ser Arg Ser Ser Glu Thr Tyr Thr Glu Lys His
1               5                   10                  15

Asp Tyr Thr Tyr
            20
```

-continued

<210> SEQ ID NO 103
<211> LENGTH: 226
<212> TYPE: PRT
<213> ORGANISM: Artificial Sequence
<220> FEATURE:
<223> OTHER INFORMATION: Knob Fc

<400> SEQUENCE: 103

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Thr
225
```

<210> SEQ ID NO 104
<211> LENGTH: 226
<212> TYPE: PRT
<213> ORGANISM: Artificial Sequence
<220> FEATURE:
<223> OTHER INFORMATION: Hole Fc

<400> SEQUENCE: 104

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
```

-continued

```
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Cys Thr Leu Pro Pro Ser Arg Asp Glu Leu Thr Lys Asn Gln Val Ser
    130             135             140

Leu Ser Cys Ala Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Val Ser Lys Leu Thr Val
            180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro Thr
225
```

```
<210> SEQ ID NO 105
<211> LENGTH: 223
<212> TYPE: PRT
<213> ORGANISM: Artificial Sequence
<220> FEATURE:
<223> OTHER INFORMATION: Knob Fc

<400> SEQUENCE: 105

Asp Lys Thr His Thr Cys Pro Pro Cys Pro Ala Pro Gly Gly Pro Ser
1               5               10              15

Val Phe Leu Phe Pro Pro Lys Pro Lys Asp Thr Leu Met Ile Ser Arg
            20              25              30

Thr Pro Glu Val Thr Cys Val Val Val Asp Val Ser His Glu Asp Pro
        35              40              45

Glu Val Lys Phe Asn Trp Tyr Val Asp Gly Val Glu Val His Asn Ala
    50              55              60

Lys Thr Lys Pro Arg Glu Glu Gln Tyr Asn Ser Thr Tyr Arg Val Val
65              70              75              80

Ser Val Leu Thr Val Leu His Gln Asp Trp Leu Asn Gly Lys Glu Tyr
            85              90              95

Lys Cys Lys Val Ser Asn Lys Ala Leu Pro Ala Pro Ile Glu Lys Thr
            100             105             110

Ile Ser Lys Ala Lys Gly Gln Pro Arg Glu Pro Gln Val Tyr Thr Leu
        115             120             125

Pro Pro Cys Arg Asp Glu Leu Thr Lys Asn Gln Val Ser Leu Trp Cys
    130             135             140

Leu Val Lys Gly Phe Tyr Pro Ser Asp Ile Ala Val Glu Trp Glu Ser
145             150             155             160

Asn Gly Gln Pro Glu Asn Asn Tyr Lys Thr Thr Pro Pro Val Leu Asp
            165             170             175

Ser Asp Gly Ser Phe Phe Leu Tyr Ser Lys Leu Thr Val Asp Lys Ser
            180             185             190

Arg Trp Gln Gln Gly Asn Val Phe Ser Cys Ser Val Met His Glu Ala
```

```
            195              200              205
Leu His Asn His Tyr Thr Gln Lys Ser Leu Ser Leu Ser Pro Thr
    210              215              220

<210> SEQ ID NO 106
<211> LENGTH: 223
<212> TYPE: PRT
<213> ORGANISM: Artificial Sequence
<220> FEATURE:
<223> OTHER INFORMATION: Hole Fc

<400> SEQUENCE: 106

Asp Lys Thr His Thr Cys Pro Pro Cys Pro Ala Pro Gly Gly Pro Ser
1               5               10              15

Val Phe Leu Phe Pro Pro Lys Pro Lys Asp Thr Leu Met Arg Ser Arg
            20              25              30

Thr Pro Glu Val Thr Cys Val Val Val Asp Val Ser His Glu Asp Pro
        35              40              45

Glu Val Lys Phe Asn Trp Tyr Val Asp Gly Val Glu Val His Asn Ala
    50              55              60

Lys Thr Lys Pro Arg Glu Glu Gln Tyr Asn Ser Thr Tyr Arg Val Val
65              70              75              80

Ser Val Leu Thr Val Leu His Gln Asp Trp Leu Asn Gly Lys Glu Tyr
            85              90              95

Lys Cys Lys Val Ser Asn Lys Ala Leu Pro Ala Pro Ile Glu Lys Thr
            100             105             110

Ile Ser Lys Ala Lys Gly Gln Pro Arg Glu Pro Gln Val Cys Thr Leu
        115             120             125

Pro Pro Ser Arg Asp Glu Leu Thr Lys Asn Gln Val Ser Leu Ser Cys
    130             135             140

Ala Val Lys Gly Phe Tyr Pro Ser Asp Ile Ala Val Glu Trp Glu Ser
145             150             155             160

Asn Gly Gln Pro Glu Asn Asn Tyr Lys Thr Thr Pro Pro Val Leu Asp
            165             170             175

Ser Asp Gly Ser Phe Phe Leu Val Ser Lys Leu Thr Val Asp Lys Ser
        180             185             190

Arg Trp Gln Gln Gly Asn Val Phe Ser Cys Ser Val Met His Glu Ala
        195             200             205

Leu His Asn His Tyr Thr Gln Lys Ser Leu Ser Leu Ser Pro Thr
    210             215             220

<210> SEQ ID NO 107
<211> LENGTH: 226
<212> TYPE: PRT
<213> ORGANISM: Artificial Sequence
<220> FEATURE:
<223> OTHER INFORMATION: Knob Fc

<400> SEQUENCE: 107

Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60
```

-continued

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly
225

<210> SEQ ID NO 108
<211> LENGTH: 226
<212> TYPE: PRT
<213> ORGANISM: Artificial Sequence
<220> FEATURE:
<223> OTHER INFORMATION: Hole Fc

<400> SEQUENCE: 108

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Arg Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190
```

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

```
<210> SEQ ID NO 109
<211> LENGTH: 223
<212> TYPE: PRT
<213> ORGANISM: Artificial Sequence
<220> FEATURE:
<223> OTHER INFORMATION: Knob Fc

<400> SEQUENCE: 109
```

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220
```

```
<210> SEQ ID NO 110
<211> LENGTH: 223
<212> TYPE: PRT
<213> ORGANISM: Artificial Sequence
<220> FEATURE:
<223> OTHER INFORMATION: Hole Fc

<400> SEQUENCE: 110
```

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45
```

-continued

```
Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
                115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
                180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220
```

```
<210> SEQ ID NO 111
<211> LENGTH: 226
<212> TYPE: PRT
<213> ORGANISM: Artificial Sequence
<220> FEATURE:
<223> OTHER INFORMATION: Hole Fc

<400> SEQUENCE: 111
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190
```

-continued

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
        210                 215                 220

Pro Thr
225

<210> SEQ ID NO 112
<211> LENGTH: 223
<212> TYPE: PRT
<213> ORGANISM: Artificial Sequence
<220> FEATURE:
<223> OTHER INFORMATION: Hole Fc

<400> SEQUENCE: 112

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
        20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Thr
        210                 215                 220

<210> SEQ ID NO 113
<211> LENGTH: 226
<212> TYPE: PRT
<213> ORGANISM: Artificial Sequence
<220> FEATURE:
<223> OTHER INFORMATION: Hole Fc

<400> SEQUENCE: 113

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

-continued

```
                35                   40                   45

Glu Asp Pro Glu Val Lys Phe Asn Trp Tyr Val Asp Gly Val Glu Val
    50                   55                   60

His Asn Ala Lys Thr Lys Pro Arg Glu Glu Gln Tyr Asn Ser Thr Tyr
65                   70                   75                   80

Arg Val Val Ser Val Leu Thr Val Leu His Gln Asp Trp Leu Asn Gly
                85                   90                   95

Lys Glu Tyr Lys Cys Lys Val Ser Asn Lys Ala Leu Pro Ala Pro Ile
            100                  105                  110

Glu Lys Thr Ile Ser Lys Ala Lys Gly Gln Pro Arg Glu Pro Gln Val
            115                  120                  125

Cys Thr Leu Pro Pro Ser Arg Asp Glu Leu Thr Lys Asn Gln Val Ser
    130                  135                  140

Leu Ser Cys Ala Val Lys Gly Phe Tyr Pro Ser Asp Ile Ala Val Glu
145                  150                  155                  160

Trp Glu Ser Asn Gly Gln Pro Glu Asn Asn Tyr Lys Thr Thr Pro Pro
                165                  170                  175

Val Leu Asp Ser Asp Gly Ser Phe Phe Leu Val Ser Lys Leu Thr Val
            180                  185                  190

Asp Lys Ser Arg Trp Gln Gln Gly Asn Val Phe Ser Cys Ser Val Met
            195                  200                  205

His Glu Ala Leu His Asn Arg Tyr Thr Gln Lys Ser Leu Ser Leu Ser
    210                  215                  220

Pro Gly
225

<210> SEQ ID NO 114
<211> LENGTH: 223
<212> TYPE: PRT
<213> ORGANISM: Artificial Sequence
<220> FEATURE:
<223> OTHER INFORMATION: Hole Fc

<400> SEQUENCE: 114

Asp Lys Thr His Thr Cys Pro Pro Cys Pro Ala Pro Gly Gly Pro Ser
1               5                   10                   15

Val Phe Leu Phe Pro Pro Lys Pro Lys Asp Thr Leu Met Ile Ser Arg
                20                   25                   30

Thr Pro Glu Val Thr Cys Val Val Val Asp Val Ser His Glu Asp Pro
            35                   40                   45

Glu Val Lys Phe Asn Trp Tyr Val Asp Gly Val Glu Val His Asn Ala
    50                   55                   60

Lys Thr Lys Pro Arg Glu Glu Gln Tyr Asn Ser Thr Tyr Arg Val Val
65                   70                   75                   80

Ser Val Leu Thr Val Leu His Gln Asp Trp Leu Asn Gly Lys Glu Tyr
                85                   90                   95

Lys Cys Lys Val Ser Asn Lys Ala Leu Pro Ala Pro Ile Glu Lys Thr
            100                  105                  110

Ile Ser Lys Ala Lys Gly Gln Pro Arg Glu Pro Gln Val Cys Thr Leu
            115                  120                  125

Pro Pro Ser Arg Asp Glu Leu Thr Lys Asn Gln Val Ser Leu Ser Cys
    130                  135                  140

Ala Val Lys Gly Phe Tyr Pro Ser Asp Ile Ala Val Glu Trp Glu Ser
145                  150                  155                  160

Asn Gly Gln Pro Glu Asn Asn Tyr Lys Thr Thr Pro Pro Val Leu Asp
```

```
                  165                 170                 175
Ser Asp Gly Ser Phe Phe Leu Val Ser Lys Leu Thr Val Asp Lys Ser
              180                 185                 190

Arg Trp Gln Gln Gly Asn Val Phe Ser Cys Ser Val Met His Glu Ala
          195                 200                 205

Leu His Asn Arg Tyr Thr Gln Lys Ser Leu Ser Leu Ser Pro Gly
      210                 215                 220
```

<210> SEQ ID NO 115
<211> LENGTH: 226
<212> TYPE: PRT
<213> ORGANISM: Artificial Sequence
<220> FEATURE:
<223> OTHER INFORMATION: Knob Fc

<400> SEQUENCE: 115

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
              20                  25                  30

Ile Ser Arg Thr Pro Glu Val Thr Cys Val Val Val Asp Val Ser His
          35                  40                  45

Glu Asp Pro Glu Val Lys Phe Asn Trp Tyr Val Asp Gly Val Glu Val
      50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
              85                  90                  95

Lys Glu Tyr Lys Cys Lys Val Ser Asn Lys Ala Leu Pro Ala Pro Ile
              100                 105                 110

Glu Lys Thr Ile Ser Lys Ala Lys Gly Gln Pro Arg Glu Pro Gln Val
          115                 120                 125

Tyr Thr Leu Pro Pro Cys Arg Asp Glu Leu Thr Lys Asn Gln Val Ser
      130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
              165                 170                 175

Val Leu Asp Ser Asp Gly Ser Phe Phe Leu Tyr Ser Lys Leu Thr Val
              180                 185                 190

Asp Lys Ser Arg Trp Gln Gln Gly Asn Val Phe Ser Cys Ser Val Val
          195                 200                 205

His Glu Ala Leu His Asn His Tyr Thr Gln Lys Ser Leu Ser Leu Ser
      210                 215                 220

Pro Thr
225
```

<210> SEQ ID NO 116
<211> LENGTH: 223
<212> TYPE: PRT
<213> ORGANISM: Artificial Sequence
<220> FEATURE:
<223> OTHER INFORMATION: Knob Fc

<400> SEQUENCE: 116

```
Asp Lys Thr His Thr Cys Pro Pro Cys Pro Ala Pro Gly Gly Pro Ser
1               5                   10                  15
```

```
Val Phe Leu Phe Pro Pro Lys Pro Lys Asp Thr Leu Tyr Ile Ser Arg
        20              25                  30

Thr Pro Glu Val Thr Cys Val Val Val Asp Val Ser His Glu Asp Pro
        35              40                  45

Glu Val Lys Phe Asn Trp Tyr Val Asp Gly Val Glu Val His Asn Ala
        50              55                  60

Lys Thr Lys Pro Arg Glu Glu Gln Tyr Asn Ser Thr Tyr Arg Val Val
65              70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
        130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Val His Glu Ala
            195                 200                 205

Leu His Asn His Tyr Thr Gln Lys Ser Leu Ser Leu Ser Pro Thr
    210                 215                 220
```

```
<210> SEQ ID NO 117
<211> LENGTH: 226
<212> TYPE: PRT
<213> ORGANISM: Artificial Sequence
<220> FEATURE:
<223> OTHER INFORMATION: Knob Fc

<400> SEQUENCE: 117
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Val
            195             200             205

His Glu Ala Leu His Asn His Tyr Thr Gln Lys Ser Leu Ser Leu Ser
    210             215             220

Pro Gly
225

<210> SEQ ID NO 118
<211> LENGTH: 223
<212> TYPE: PRT
<213> ORGANISM: Artificial Sequence
<220> FEATURE:
<223> OTHER INFORMATION: Hole Fc

<400> SEQUENCE: 118

Asp Lys Thr His Thr Cys Pro Pro Cys Pro Ala Pro Gly Gly Pro Ser
1               5               10              15

Val Phe Leu Phe Pro Pro Lys Pro Lys Asp Thr Leu Tyr Ile Ser Arg
            20              25              30

Thr Pro Glu Val Thr Cys Val Val Val Asp Val Ser His Glu Asp Pro
            35              40              45

Glu Val Lys Phe Asn Trp Tyr Val Asp Gly Val Glu Val His Asn Ala
    50              55              60

Lys Thr Lys Pro Arg Glu Glu Gln Tyr Asn Ser Thr Tyr Arg Val Val
65              70              75              80

Ser Val Leu Thr Val Leu His Gln Asp Trp Leu Asn Gly Lys Glu Tyr
            85              90              95

Lys Cys Lys Val Ser Asn Lys Ala Leu Pro Ala Pro Ile Glu Lys Thr
            100             105             110

Ile Ser Lys Ala Lys Gly Gln Pro Arg Glu Pro Gln Val Tyr Thr Leu
            115             120             125

Pro Pro Cys Arg Asp Glu Leu Thr Lys Asn Gln Val Ser Leu Trp Cys
    130             135             140

Leu Val Lys Gly Phe Tyr Pro Ser Asp Ile Ala Val Glu Trp Glu Ser
145             150             155             160

Asn Gly Gln Pro Glu Asn Asn Tyr Lys Thr Thr Pro Pro Val Leu Asp
            165             170             175

Ser Asp Gly Ser Phe Phe Leu Tyr Ser Lys Leu Thr Val Asp Lys Ser
            180             185             190

Arg Trp Gln Gln Gly Asn Val Phe Ser Cys Ser Val Val His Glu Ala
            195             200             205

Leu His Asn His Tyr Thr Gln Lys Ser Leu Ser Leu Ser Pro Gly
    210             215             220

<210> SEQ ID NO 119
<211> LENGTH: 226
<212> TYPE: PRT
<213> ORGANISM: Artificial Sequence
<220> FEATURE:
<223> OTHER INFORMATION: Hole Fc

<400> SEQUENCE: 119

Asp Lys Thr His Thr Cys Pro Pro Cys Pro Ala Pro Glu Leu Leu Gly
1               5               10              15

```
Gly Pro Ser Val Phe Leu Phe Pro Pro Lys Pro Lys Asp Thr Leu Tyr
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Cys Thr Leu Pro Pro Ser Arg Asp Glu Leu Thr Lys Asn Gln Val Ser
    130             135             140

Leu Ser Cys Ala Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                165             170             175

Val Leu Asp Ser Asp Gly Ser Phe Phe Leu Val Ser Lys Leu Thr Val
            180             185             190

Asp Lys Ser Arg Trp Gln Gln Gly Asn Val Phe Ser Cys Ser Val Val
            195             200             205

His Glu Ala Leu His Asn Arg Tyr Thr Gln Lys Ser Leu Ser Leu Ser
    210             215             220

Pro Thr
225
```

```
<210> SEQ ID NO 120
<211> LENGTH: 223
<212> TYPE: PRT
<213> ORGANISM: Artificial Sequence
<220> FEATURE:
<223> OTHER INFORMATION: Hole Fc

<400> SEQUENCE: 120

Asp Lys Thr His Thr Cys Pro Pro Cys Pro Ala Pro Gly Gly Pro Ser
1               5               10              15

Val Phe Leu Phe Pro Pro Lys Pro Lys Asp Thr Leu Tyr Ile Ser Arg
            20              25              30

Thr Pro Glu Val Thr Cys Val Val Val Asp Val Ser His Glu Asp Pro
        35              40              45

Glu Val Lys Phe Asn Trp Tyr Val Asp Gly Val Glu Val His Asn Ala
    50              55              60

Lys Thr Lys Pro Arg Glu Glu Gln Tyr Asn Ser Thr Tyr Arg Val Val
65              70              75              80

Ser Val Leu Thr Val Leu His Gln Asp Trp Leu Asn Gly Lys Glu Tyr
                85              90              95

Lys Cys Lys Val Ser Asn Lys Ala Leu Pro Ala Pro Ile Glu Lys Thr
            100             105             110

Ile Ser Lys Ala Lys Gly Gln Pro Arg Glu Pro Gln Val Cys Thr Leu
            115             120             125

Pro Pro Ser Arg Asp Glu Leu Thr Lys Asn Gln Val Ser Leu Ser Cys
    130             135             140
```

-continued

```
Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
                180                 185                 190

Arg Trp Gln Gln Gly Asn Val Phe Ser Cys Ser Val Val His Glu Ala
            195                 200                 205

Leu His Asn Arg Tyr Thr Gln Lys Ser Leu Ser Leu Ser Pro Thr
    210                 215                 220
```

```
<210> SEQ ID NO 121
<211> LENGTH: 226
<212> TYPE: PRT
<213> ORGANISM: Artificial Sequence
<220> FEATURE:
<223> OTHER INFORMATION: Hole Fc

<400> SEQUENCE: 121
```

```
Asp Lys Thr His Thr Cys Pro Pro Cys Pro Ala Pro Glu Leu Leu Gly
1               5               10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Val
            195                 200                 205

His Glu Ala Leu His Asn Arg Tyr Thr Gln Lys Ser Leu Ser Leu Ser
    210                 215                 220

Pro Gly
225
```

```
<210> SEQ ID NO 122
<211> LENGTH: 223
<212> TYPE: PRT
<213> ORGANISM: Artificial Sequence
<220> FEATURE:
<223> OTHER INFORMATION: Hole Fc
```

-continued

```
<400> SEQUENCE: 122

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Gly
    210                 215                 220

<210> SEQ ID NO 123
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 1 to 5 times

<400> SEQUENCE: 123

Gly Gly Gly Gly Ser
1               5

<210> SEQ ID NO 124
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(6)
<223> OTHER INFORMATION: Repeated 1 to 4 times

<400> SEQUENCE: 124

Gly Gly Gly Gly Gly Ser
1               5
```

-continued

```
<210> SEQ ID NO 125
<211> LENGTH: 5
<212> TYPE: PRT
<213> ORGANISM: Artificial Sequence
<220> FEATURE:
<223> OTHER INFORMATION: Linker

<400> SEQUENCE: 125

Gly Gly Gly Gly Ser
1               5

<210> SEQ ID NO 126
<211> LENGTH: 6
<212> TYPE: PRT
<213> ORGANISM: Artificial Sequence
<220> FEATURE:
<223> OTHER INFORMATION: Linker

<400> SEQUENCE: 126

Gly Gly Gly Gly Gly Ser
1               5

<210> SEQ ID NO 127
<211> LENGTH: 18
<212> TYPE: PRT
<213> ORGANISM: Artificial Sequence
<220> FEATURE:
<223> OTHER INFORMATION: Linker

<400> SEQUENCE: 127

Gly Gly Gly Gly Gly Ser Gly Gly Gly Gly Gly Ser Gly Gly Gly Gly
1               5                   10                  15

Gly Ser

<210> SEQ ID NO 128
<211> LENGTH: 15
<212> TYPE: PRT
<213> ORGANISM: Artificial Sequence
<220> FEATURE:
<223> OTHER INFORMATION: Linker

<400> SEQUENCE: 128

Gly Gly Gly Gly Ser Gly Gly Gly Gly Ser Gly Gly Gly Gly Ser
1               5                   10                  15

<210> SEQ ID NO 129
<211> LENGTH: 18
<212> TYPE: PRT
<213> ORGANISM: Artificial Sequence
<220> FEATURE:
<223> OTHER INFORMATION: Linker

<400> SEQUENCE: 129

Gly Gly Ser Gly Gly Gly Gly Ser Gly Gly Gly Gly Ser Gly Gly Gly
1               5                   10                  15

Gly Ser

<210> SEQ ID NO 130
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(1)
<223> OTHER INFORMATION: Repeated 1 to 5 times
```

-continued

```
<220> FEATURE:
<221> NAME/KEY: VARIANT
<222> LOCATION: (2)..(2)
<223> OTHER INFORMATION: Xaa is independently selected from A, V, L, I,
      M, F, W, P, G, S, T, C, Y, N, Q, K, R, H, D, or E
<220> FEATURE:
<221> NAME/KEY: REPEAT
<222> LOCATION: (3)..(3)
<223> OTHER INFORMATION: Repeated 1 to 5 times
<220> FEATURE:
<221> NAME/KEY: VARIANT
<222> LOCATION: (4)..(4)
<223> OTHER INFORMATION: Xaa is independently selected from A, V, L, I,
      M, F, W, P, G, S, T, C, Y, N, Q, K, R, H, D, or E
<220> FEATURE:
<221> NAME/KEY: REPEAT
<222> LOCATION: (5)..(5)
<223> OTHER INFORMATION: Repeated 1 to 5 times

<400> SEQUENCE: 130

Gly Xaa Gly Xaa Gly
1               5

<210> SEQ ID NO 131
<211> LENGTH: 11
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (4)..(4)
<223> OTHER INFORMATION: Xaa is independently selected from A, V, L, I,
      M, F, W, P, G, S, T, C, Y, N, Q, K, R, H, D, or E
<220> FEATURE:
<221> NAME/KEY: VARIANT
<222> LOCATION: (8)..(8)
<223> OTHER INFORMATION: Xaa is independently selected from A, V, L, I,
      M, F, W, P, G, S, T, C, Y, N, Q, K, R, H, D, or E

<400> SEQUENCE: 131

Gly Gly Gly Xaa Gly Gly Gly Xaa Gly Gly Gly
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 1 to 19 times

<400> SEQUENCE: 132

Ser Ser Ser Ser Gly
1               5

<210> SEQ ID NO 133
<211> LENGTH: 11
<212> TYPE: PRT
<213> ORGANISM: Artificial Sequence
<220> FEATURE:
<223> OTHER INFORMATION: Linker

<400> SEQUENCE: 133

Gly Gly Gly Gly Gly Cys Gly Gly Gly Gly Gly
1               5                   10

<210> SEQ ID NO 134
```

```
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 20 times

<400> SEQUENCE: 134

Glu Ala Ala Ala Lys
1               5

<210> SEQ ID NO 135
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)..(4)
<223> OTHER INFORMATION: Repeated 2 to 20 times

<400> SEQUENCE: 135

Ala Ser Ala Pro Gly Thr
1               5

<210> SEQ ID NO 136
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)..(7)
<223> OTHER INFORMATION: Repeated 2 to 20 times

<400> SEQUENCE: 136

Ala Ser Glu Ala Ala Ala Lys Gly Thr
1               5

<210> SEQ ID NO 137
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 137

Gly Gly Gly Gly Ala
1               5

<210> SEQ ID NO 138
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 138
```

-continued

```
Pro Gly Gly Gly Ser
1               5

<210> SEQ ID NO 139
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 139

Ala Gly Gly Gly Ser
1               5

<210> SEQ ID NO 140
<211> LENGTH: 20
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)..(17)
<223> OTHER INFORMATION: Repeated 2 to 20 times

<400> SEQUENCE: 140

Gly Gly Ser Glu Gly Lys Ser Ser Gly Ser Gly Ser Glu Ser Lys Ser
1               5                   10                  15

Thr Gly Gly Ser
            20

<210> SEQ ID NO 141
<211> LENGTH: 9
<212> TYPE: PRT
<213> ORGANISM: Artificial Sequence
<220> FEATURE:
<223> OTHER INFORMATION: Linker

<400> SEQUENCE: 141

Ser Ser Ser Ala Ser Ala Ser Ser Ala
1               5

<210> SEQ ID NO 142
<211> LENGTH: 7
<212> TYPE: PRT
<213> ORGANISM: Artificial Sequence
<220> FEATURE:
<223> OTHER INFORMATION: Linker

<400> SEQUENCE: 142

Gly Ser Pro Gly Ser Pro Gly
1               5

<210> SEQ ID NO 143
<211> LENGTH: 11
<212> TYPE: PRT
<213> ORGANISM: Artificial Sequence
<220> FEATURE:
<223> OTHER INFORMATION: Linker

<400> SEQUENCE: 143

Ala Thr Thr Thr Gly Ser Ser Pro Gly Pro Thr
1               5                   10
```

```
<210> SEQ ID NO 144
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: Xaa is I, L, Y, M, F, V, or A
<220> FEATURE:
<221> NAME/KEY: VARIANT
<222> LOCATION: (2)..(2)
<223> OTHER INFORMATION: Xaa is A, G, S, V, E, D, Q, N, or Y
<220> FEATURE:
<221> NAME/KEY: VARIANT
<222> LOCATION: (3)..(3)
<223> OTHER INFORMATION: Xaa is H, P, A, V, G, S, or T
<220> FEATURE:
<221> NAME/KEY: VARIANT
<222> LOCATION: (4)..(4)
<223> OTHER INFORMATION: Xaa is D or E
<220> FEATURE:
<221> NAME/KEY: VARIANT
<222> LOCATION: (5)..(5)
<223> OTHER INFORMATION: Xaa is I, L, Y, M, F, V, T, S, G or A

<400> SEQUENCE: 144

Xaa Xaa Xaa Xaa Xaa
1               5

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: Linker consensus
<220> FEATURE:
<221> NAME/KEY: VARIANT
<222> LOCATION: (1)..(1)
<223> OTHER INFORMATION: Xaa is I or L
<220> FEATURE:
<221> NAME/KEY: VARIANT
<222> LOCATION: (3)..(3)
<223> OTHER INFORMATION: Xaa is P or A
<220> FEATURE:
<221> NAME/KEY: VARIANT
<222> LOCATION: (5)..(5)
<223> OTHER INFORMATION: Xaa is I, V, T, S, or G

<400> SEQUENCE: 145

Xaa Glu Xaa Asp Xaa
1               5

<210> SEQ ID NO 146
<211> LENGTH: 4
<212> TYPE: PRT
<213> ORGANISM: Artificial Sequence
<220> FEATURE:
<223> OTHER INFORMATION: granzyme B substrate

<400> SEQUENCE: 146

Leu Glu Ala Asp
1

<210> SEQ ID NO 147
```

```
<211> LENGTH: 4
<212> TYPE: PRT
<213> ORGANISM: Artificial Sequence
<220> FEATURE:
<223> OTHER INFORMATION: Linker

<400> SEQUENCE: 147

Leu Glu Pro Asp
1

<210> SEQ ID NO 148
<211> LENGTH: 4
<212> TYPE: PRT
<213> ORGANISM: Artificial Sequence
<220> FEATURE:
<223> OTHER INFORMATION: Linker

<400> SEQUENCE: 148

Leu Glu Ala Glu
1

<210> SEQ ID NO 149
<211> LENGTH: 5
<212> TYPE: PRT
<213> ORGANISM: Artificial Sequence
<220> FEATURE:
<223> OTHER INFORMATION: Linker

<400> SEQUENCE: 149

Ile Glu Pro Asp Ile
1               5

<210> SEQ ID NO 150
<211> LENGTH: 5
<212> TYPE: PRT
<213> ORGANISM: Artificial Sequence
<220> FEATURE:
<223> OTHER INFORMATION: Linker

<400> SEQUENCE: 150

Leu Glu Pro Asp Gly
1               5

<210> SEQ ID NO 151
<211> LENGTH: 5
<212> TYPE: PRT
<213> ORGANISM: Artificial Sequence
<220> FEATURE:
<223> OTHER INFORMATION: Linker

<400> SEQUENCE: 151

Leu Glu Ala Asp Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Linker

<400> SEQUENCE: 152

Ile Glu Pro Asp Gly
1               5

<210> SEQ ID NO 153
<211> LENGTH: 5
```

```
<212> TYPE: PRT
<213> ORGANISM: Artificial Sequence
<220> FEATURE:
<223> OTHER INFORMATION: Linker

<400> SEQUENCE: 153

Ile Glu Pro Asp Val
1               5

<210> SEQ ID NO 154
<211> LENGTH: 5
<212> TYPE: PRT
<213> ORGANISM: Artificial Sequence
<220> FEATURE:
<223> OTHER INFORMATION: Linker

<400> SEQUENCE: 154

Ile Glu Pro Asp Ser
1               5

<210> SEQ ID NO 155
<211> LENGTH: 5
<212> TYPE: PRT
<213> ORGANISM: Artificial Sequence
<220> FEATURE:
<223> OTHER INFORMATION: Linker

<400> SEQUENCE: 155

Ile Glu Pro Asp Thr
1               5

<210> SEQ ID NO 156
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is A or V

<400> SEQUENCE: 156

Xaa Gln Ala Arg Xaa
1               5

<210> SEQ ID NO 157
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (5)..(5)
<223> OTHER INFORMATION: Xaa is A or V

<400> SEQUENCE: 157

Arg Gln Ala Arg Xaa
1               5

<210> SEQ ID NO 158
<211> LENGTH: 4
<212> TYPE: PRT
<213> ORGANISM: Artificial Sequence
```

```
<220> FEATURE:
<223> OTHER INFORMATION: matriptase substrate

<400> SEQUENCE: 158

Arg Gln Ala Arg
1

<210> SEQ ID NO 159
<211> LENGTH: 5
<212> TYPE: PRT
<213> ORGANISM: Artificial Sequence
<220> FEATURE:
<223> OTHER INFORMATION: Linker

<400> SEQUENCE: 159

Arg Gln Ala Arg Val
1               5

<210> SEQ ID NO 160
<211> LENGTH: 4
<212> TYPE: PRT
<213> ORGANISM: Artificial Sequence
<220> FEATURE:
<223> OTHER INFORMATION: linker consensus
<220> FEATURE:
<221> NAME/KEY: VARIANT
<222> LOCATION: (1)..(1)
<223> OTHER INFORMATION: Xaa is P, V, or A
<220> FEATURE:
<221> NAME/KEY: VARIANT
<222> LOCATION: (2)..(2)
<223> OTHER INFORMATION: Xaa is Q or D
<220> FEATURE:
<221> NAME/KEY: VARIANT
<222> LOCATION: (3)..(3)
<223> OTHER INFORMATION: Xaa is A or N
<220> FEATURE:
<221> NAME/KEY: VARIANT
<222> LOCATION: (4)..(4)
<223> OTHER INFORMATION: Xaa is L, I, or M

<400> SEQUENCE: 160

Xaa Xaa Xaa Xaa
1

<210> SEQ ID NO 161
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (2)..(2)
<223> OTHER INFORMATION: Xaa is Q or D
<220> FEATURE:
<221> NAME/KEY: VARIANT
<222> LOCATION: (3)..(3)
<223> OTHER INFORMATION: Xaa is A or N
<220> FEATURE:
<221> NAME/KEY: VARIANT
<222> LOCATION: (4)..(4)
<223> OTHER INFORMATION: Xaa is L or I

<400> SEQUENCE: 161

Pro Xaa Xaa Xaa
1

<210> SEQ ID NO 162
<211> LENGTH: 4
<212> TYPE: PRT
```

-continued

```
<213> ORGANISM: Artificial Sequence
<220> FEATURE:
<223> OTHER INFORMATION: MMP substrate

<400> SEQUENCE: 162

Pro Ala Gly Leu
1

<210> SEQ ID NO 163
<211> LENGTH: 19
<212> TYPE: PRT
<213> ORGANISM: Artificial Sequence
<220> FEATURE:
<223> OTHER INFORMATION: Linker

<400> SEQUENCE: 163

Thr Gly Leu Glu Ala Asp Gly Ser Pro Ala Gly Leu Gly Arg Gln Ala
1               5                   10                  15

Arg Val Gly

<210> SEQ ID NO 164
<211> LENGTH: 19
<212> TYPE: PRT
<213> ORGANISM: Artificial Sequence
<220> FEATURE:
<223> OTHER INFORMATION: Linker

<400> SEQUENCE: 164

Thr Gly Leu Glu Ala Asp Gly Ser Arg Gln Ala Arg Val Gly Pro Ala
1               5                   10                  15

Gly Leu Gly

<210> SEQ ID NO 165
<211> LENGTH: 19
<212> TYPE: PRT
<213> ORGANISM: Artificial Sequence
<220> FEATURE:
<223> OTHER INFORMATION: Linker

<400> SEQUENCE: 165

Thr Gly Ser Pro Ala Gly Leu Glu Ala Asp Gly Ser Arg Gln Ala Arg
1               5                   10                  15

Val Gly Ser

<210> SEQ ID NO 166
<211> LENGTH: 19
<212> TYPE: PRT
<213> ORGANISM: Artificial Sequence
<220> FEATURE:
<223> OTHER INFORMATION: Linker

<400> SEQUENCE: 166

Thr Gly Pro Ala Gly Leu Gly Leu Glu Ala Asp Gly Ser Arg Gln Ala
1               5                   10                  15

Arg Val Gly

<210> SEQ ID NO 167
<211> LENGTH: 19
<212> TYPE: PRT
<213> ORGANISM: Artificial Sequence
<220> FEATURE:
<223> OTHER INFORMATION: Linker

<400> SEQUENCE: 167
```

```
Thr Gly Arg Gln Ala Arg Val Gly Leu Glu Ala Asp Gly Ser Pro Ala
1               5                   10                  15

Gly Leu Gly

<210> SEQ ID NO 168
<211> LENGTH: 18
<212> TYPE: PRT
<213> ORGANISM: Artificial Sequence
<220> FEATURE:
<223> OTHER INFORMATION: Linker

<400> SEQUENCE: 168

Thr Gly Ser Arg Gln Ala Arg Val Gly Pro Ala Gly Leu Glu Ala Asp
1               5                   10                  15

Gly Ser

<210> SEQ ID NO 169
<211> LENGTH: 20
<212> TYPE: PRT
<213> ORGANISM: Artificial Sequence
<220> FEATURE:
<223> OTHER INFORMATION: Linker

<400> SEQUENCE: 169

Thr Gly Pro Ala Gly Leu Gly Ser Arg Gln Ala Arg Val Gly Leu Glu
1               5                   10                  15

Ala Asp Gly Ser
            20

<210> SEQ ID NO 170
<211> LENGTH: 18
<212> TYPE: PRT
<213> ORGANISM: Artificial Sequence
<220> FEATURE:
<223> OTHER INFORMATION: Linker

<400> SEQUENCE: 170

Gly Pro Ala Gly Leu Gly Leu Glu Pro Asp Gly Ser Arg Gln Ala Arg
1               5                   10                  15

Val Gly

<210> SEQ ID NO 171
<211> LENGTH: 18
<212> TYPE: PRT
<213> ORGANISM: Artificial Sequence
<220> FEATURE:
<223> OTHER INFORMATION: Linker

<400> SEQUENCE: 171

Gly Gly Ser Gly Gly Gly Gly Ile Glu Pro Asp Ile Gly Gly Ser Gly
1               5                   10                  15

Gly Ser

<210> SEQ ID NO 172
<211> LENGTH: 18
<212> TYPE: PRT
<213> ORGANISM: Artificial Sequence
<220> FEATURE:
<223> OTHER INFORMATION: Linker

<400> SEQUENCE: 172

Gly Gly Ser Gly Gly Gly Gly Leu Glu Ala Asp Thr Gly Gly Ser Gly
1               5                   10                  15
```

Gly Ser

<210> SEQ ID NO 173
<211> LENGTH: 9
<212> TYPE: PRT
<213> ORGANISM: Artificial Sequence
<220> FEATURE:
<223> OTHER INFORMATION: Linker

<400> SEQUENCE: 173

Gly Ser Ile Glu Pro Asp Ile Gly Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Linker

<400> SEQUENCE: 174

Gly Ser Leu Glu Ala Asp Thr Gly Ser
1               5

<210> SEQ ID NO 175
<211> LENGTH: 18
<212> TYPE: PRT
<213> ORGANISM: Artificial Sequence
<220> FEATURE:
<223> OTHER INFORMATION: Linker

<400> SEQUENCE: 175

Gly Gly Ser Gly Gly Gly Gly Ile Glu Pro Asp Gly Gly Gly Ser Gly
1               5                   10                  15

Gly Ser

<210> SEQ ID NO 176
<211> LENGTH: 18
<212> TYPE: PRT
<213> ORGANISM: Artificial Sequence
<220> FEATURE:
<223> OTHER INFORMATION: Linker

<400> SEQUENCE: 176

Gly Gly Ser Gly Gly Gly Gly Ile Glu Pro Asp Val Gly Gly Ser Gly
1               5                   10                  15

Gly Ser

<210> SEQ ID NO 177
<211> LENGTH: 18
<212> TYPE: PRT
<213> ORGANISM: Artificial Sequence
<220> FEATURE:
<223> OTHER INFORMATION: Linker

<400> SEQUENCE: 177

Gly Gly Ser Gly Gly Gly Gly Ile Glu Pro Asp Ser Gly Gly Ser Gly
1               5                   10                  15

Gly Ser

<210> SEQ ID NO 178
<211> LENGTH: 18
<212> TYPE: PRT
<213> ORGANISM: Artificial Sequence
<220> FEATURE:

-continued

<223> OTHER INFORMATION: Linker

<400> SEQUENCE: 178

Gly Gly Ser Gly Gly Gly Gly Ile Glu Pro Asp Thr Gly Gly Ser Gly
1               5                   10                  15

Gly Ser

<210> SEQ ID NO 179
<211> LENGTH: 12
<212> TYPE: PRT
<213> ORGANISM: Artificial Sequence
<220> FEATURE:
<223> OTHER INFORMATION: Linker

<400> SEQUENCE: 179

Gly Gly Gly Ser Leu Glu Pro Asp Gly Ser Gly Ser
1               5                   10

<210> SEQ ID NO 180
<211> LENGTH: 18
<212> TYPE: PRT
<213> ORGANISM: Artificial Sequence
<220> FEATURE:
<223> OTHER INFORMATION: Linker

<400> SEQUENCE: 180

Gly Pro Ala Gly Leu Gly Leu Glu Ala Asp Gly Ser Arg Gln Ala Arg
1               5                   10                  15

Val Gly

<210> SEQ ID NO 181
<211> LENGTH: 15
<212> TYPE: PRT
<213> ORGANISM: Artificial Sequence
<220> FEATURE:
<223> OTHER INFORMATION: Linker

<400> SEQUENCE: 181

Gly Gly Glu Gly Gly Gly Gly Ser Gly Gly Ser Gly Gly Gly Ser
1               5                   10                  15

<210> SEQ ID NO 182
<211> LENGTH: 18
<212> TYPE: PRT
<213> ORGANISM: Artificial Sequence
<220> FEATURE:
<223> OTHER INFORMATION: Linker

<400> SEQUENCE: 182

Gly Ser Ser Ala Gly Ser Glu Ala Gly Gly Ser Gly Gln Ala Gly Val
1               5                   10                  15

Gly Ser

<210> SEQ ID NO 183
<211> LENGTH: 18
<212> TYPE: PRT
<213> ORGANISM: Artificial Sequence
<220> FEATURE:
<223> OTHER INFORMATION: Linker

<400> SEQUENCE: 183

Gly Gly Ser Gly Gly Gly Gly Leu Glu Ala Glu Gly Ser Gly Gly Gly
1               5                   10                  15

Gly Ser

```
<210> SEQ ID NO 184
<211> LENGTH: 18
<212> TYPE: PRT
<213> ORGANISM: Artificial Sequence
<220> FEATURE:
<223> OTHER INFORMATION: Linker

<400> SEQUENCE: 184

Gly Gly Ser Gly Gly Gly Gly Ile Glu Pro Asp Pro Gly Gly Ser Gly
1               5                   10                  15

Gly Ser

<210> SEQ ID NO 185
<211> LENGTH: 19
<212> TYPE: PRT
<213> ORGANISM: Artificial Sequence
<220> FEATURE:
<223> OTHER INFORMATION: Linker

<400> SEQUENCE: 185

Thr Gly Gly Ser Gly Gly Gly Gly Ile Glu Pro Asp Ile Gly Gly Ser
1               5                   10                  15

Gly Gly Ser

<210> SEQ ID NO 186
<211> LENGTH: 204
<212> TYPE: PRT
<213> ORGANISM: Artificial Sequence
<220> FEATURE:
<223> OTHER INFORMATION: 41BBL

<400> SEQUENCE: 186

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
            115                 120                 125

Ala Leu Ala Leu Thr Val Asp Leu Pro Pro Ala Ser Ser Glu Ala Asn
    130                 135                 140

Ser Ala Phe Gly Phe Gln Gly Arg Leu Leu His Leu Ser Ala Gly Gln
145                 150                 155                 160

Arg Leu Gly Val His Leu His Thr Glu Ala Arg Ala Arg His Ala Trp
                165                 170                 175

Gln Leu Thr Gln Gly Ala Thr Val Leu Gly Leu Phe Arg Val Thr Pro
                180                 185                 190

Glu Ile Pro Ala Gly Leu Pro Ser Pro Arg Ser Glu
                195                 200
```

-continued

```
<210> SEQ ID NO 187
<211> LENGTH: 116
<212> TYPE: PRT
<213> ORGANISM: Artificial Sequence
<220> FEATURE:
<223> OTHER INFORMATION: 41BB VH

<400> SEQUENCE: 187

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 188
<211> LENGTH: 108
<212> TYPE: PRT
<213> ORGANISM: Artificial Sequence
<220> FEATURE:
<223> OTHER INFORMATION: 41BB VL

<400> SEQUENCE: 188

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 189
<211> LENGTH: 121
<212> TYPE: PRT
<213> ORGANISM: Artificial Sequence
<220> FEATURE:
<223> OTHER INFORMATION: 41BB VH

<400> SEQUENCE: 189

Gln Val Gln Leu Gln Gln Trp Gly Ala Gly Leu Leu Lys Pro Ser Glu
1               5                   10                  15
```

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120

<210> SEQ ID NO 190
<211> LENGTH: 109
<212> TYPE: PRT
<213> ORGANISM: Artificial Sequence
<220> FEATURE:
<223> OTHER INFORMATION: 41BB VL

<400> SEQUENCE: 190

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 191
<211> LENGTH: 120
<212> TYPE: PRT
<213> ORGANISM: Artificial Sequence
<220> FEATURE:
<223> OTHER INFORMATION: 41BB VH

<400> SEQUENCE: 191

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Tyr Met His Trp Val Arg Gln Ala Pro Gly Gln Gly Leu Glu Trp Met
        35                  40                  45

Gly Trp Val Asn Pro Met Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

-continued

```
Ala Arg Glu Gly Met Ala Met Arg Leu Glu Leu Asp Lys Trp Gly Gln
            100                 105                 110

Gly Thr Leu Val Thr Val Ser Ser
        115                 120

<210> SEQ ID NO 192
<211> LENGTH: 106
<212> TYPE: PRT
<213> ORGANISM: Artificial Sequence
<220> FEATURE:
<223> OTHER INFORMATION: 41BB VL

<400> SEQUENCE: 192

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Val Val
                85                  90                  95

Phe Gly Gly Gly Thr Gln Leu Thr Val Leu
            100                 105

<210> SEQ ID NO 193
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 193

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asn Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

-continued

```
                    165                 170                 175

Asp Gly

<210> SEQ ID NO 194
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 194

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

Ile Lys Met Met Ala Thr Ile Tyr Glu Leu Lys Glu Asp Lys Ser Tyr
            50                  55                  60

Asp Val Thr Met Val Lys Phe Asp Asp Lys Lys Cys Met Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 195
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 195

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

Asn Lys Met Met Ala Thr Ile Tyr Glu Leu Lys Glu Asp Lys Ser Tyr
            50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110
```

-continued

```
Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 196
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 196
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
        20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
        100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 197
<211> LENGTH: 175
<212> TYPE: PRT
<213> ORGANISM: Artificial Sequence
<220> FEATURE:
<223> OTHER INFORMATION: 41BB Anticalin

<400> SEQUENCE: 197
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
        20                  25                  30

Val Val Gly Gln Ala Gly Asn Ile Lys Leu Arg Glu Asp Ser Lys Met
        35                  40                  45
```

-continued

```
Met Ala Thr Ile Tyr Glu Leu Lys Glu Asp Lys Ser Tyr Asp Val Thr
    50              55              60
Gly Val Ser Phe Asp Asp Lys Lys Cys Thr Tyr Ala Ile Met Thr Phe
65              70              75              80
Val Pro Gly Ser Gln Pro Gly Glu Phe Thr Leu Gly Lys Ile Lys Ser
                85              90              95
Phe Pro Gly His Thr Ser Ser Leu Val Arg Val Val Ser Thr Asn Tyr
            100             105             110
Asn Gln His Ala Met Val Phe Phe Lys Phe Val Phe Gln Asn Arg Glu
        115             120             125
Glu Phe Tyr Ile Thr Leu Tyr Gly Arg Thr Lys Glu Leu Thr Ser Glu
    130             135             140
Leu Lys Glu Asn Phe Ile Arg Phe Ser Lys Ser Leu Gly Leu Pro Glu
145             150             155             160
Asn His Ile Val Phe Pro Val Pro Ile Asp Gln Cys Ile Asp Gly
            165             170             175
```

<210> SEQ ID NO 198
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 198

```
Gln Asp Ser Thr Ser Asp Leu Ile Pro Ala Pro Pro Leu Ser Lys Val
1               5               10              15
Pro Leu Gln Gln Asn Phe Gln Asp Asn Gln Phe His Gly Lys Trp Tyr
            20              25              30
Val Val Gly Gln Ala Gly Asn Ile Lys Leu Arg Glu Asp Lys Asp Pro
        35              40              45
Val Lys Met Met Ala Thr Ile Tyr Glu Leu Lys Glu Asp Lys Ser Tyr
    50              55              60
Asp Val Thr Gly Val Thr Phe Asp Asp Lys Lys Cys Arg Tyr Asp Ile
65              70              75              80
Ser Thr Phe Val Pro Gly Ser Gln Pro Gly Glu Phe Thr Phe Gly Lys
                85              90              95
Ile Lys Ser Phe Pro Gly His Thr Ser Ser Leu Val Arg Val Val Ser
            100             105             110
Thr Asn Tyr Asn Gln His Ala Met Val Phe Phe Lys Phe Val Phe Gln
        115             120             125
Asn Arg Glu Glu Phe Tyr Ile Thr Leu Tyr Gly Arg Thr Lys Glu Leu
    130             135             140
Thr Ser Glu Leu Lys Glu Asn Phe Ile Arg Phe Ser Lys Ser Leu Gly
145             150             155             160
Leu Pro Glu Asn His Ile Val Phe Pro Val Pro Ile Asp Gln Cys Ile
            165             170             175
Asp Gly
```

<210> SEQ ID NO 199
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 199

-continued

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

His Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly
```

```
<210> SEQ ID NO 200
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 200
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
            35                  40                  45

Asn Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Leu Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly
```

-continued

<210> SEQ ID NO 201
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 201

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Ser Lys Met Met Ala Thr Ile Tyr Glu Leu Lys Glu Asp Lys Ser Tyr
    50                  55                  60

Asp Val Thr Ala Val Thr Phe Asp Asp Lys Lys Cys Asn Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 202
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(184)
<223> OTHER INFORMATION: 71-254 of human 41BBL

<400> SEQUENCE: 202

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

-continued

```
Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180
```

```
<210> SEQ ID NO 203
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(170)
<223> OTHER INFORMATION: 85-254 of human 41BBL

<400> SEQUENCE: 203

Leu Asp Leu Arg Gln Gly Met Phe Ala Gln Leu Val Ala Gln Asn Val
1                 5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170
```

```
<210> SEQ ID NO 204
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(175)
<223> OTHER INFORMATION: 80-254 of human 41BBL
```

-continued

<400> SEQUENCE: 204

```
Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Lys
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175
```

<210> SEQ ID NO 205
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(203)
<223> OTHER INFORMATION: 52-254 of human 4-1BBL

<400> SEQUENCE: 205

```
Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
            35                  40                  45

Val Leu Leu Ile Asp Gly Pro Leu Ser Trp Tyr Ser Asp Pro Gly Leu
        50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
        130                 135                 140

Ala Phe Gly Phe Gln Gly Arg Leu Leu His Leu Ser Ala Gly Gln Arg
145                 150                 155                 160
```

```
Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
        195                 200

<210> SEQ ID NO 206
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(178)
<223> OTHER INFORMATION: 71-248 of human 41BBL

<400> SEQUENCE: 206

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu

<210> SEQ ID NO 207
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(164)
<223> OTHER INFORMATION: 85-248 of human 41BBL

<400> SEQUENCE: 207

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
```

-continued

```
                 20                  25                  30

Gly Val Ser Leu Thr Gly Gly Leu Ser Tyr Lys Glu Asp Thr Lys Glu
         35                  40                  45

Leu Val Val Ala Lys Ala Gly Val Tyr Tyr Val Phe Phe Gln Leu Glu
     50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                 85                  90                  95

Leu Thr Val Asp Leu Pro Pro Ala Ser Ser Glu Ala Arg Asn Ser Ala
                 100                 105                 110

Phe Gly Phe Gln Gly Arg Leu Leu His Leu Ser Ala Gly Gln Arg Leu
             115                 120                 125

Gly Val His Leu His Thr Glu Ala Arg Ala Arg His Ala Trp Gln Leu
         130                 135                 140

Thr Gln Gly Ala Thr Val Leu Gly Leu Phe Arg Val Thr Pro Glu Ile
145                 150                 155                 160

Pro Ala Gly Leu
```

```
<210> SEQ ID NO 208
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(169)
<223> OTHER INFORMATION: 80-248 of human 41BBL

<400> SEQUENCE: 208
```

```
Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                 20                  25                  30

Asp Pro Gly Leu Ala Gly Val Ser Leu Thr Gly Gly Leu Ser Tyr Lys
         35                  40                  45

Glu Asp Thr Lys Glu Leu Val Val Ala Lys Ala Gly Val Tyr Tyr Val
     50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
             85                  90                  95

Ala Ala Ala Leu Ala Leu Thr Val Asp Leu Pro Pro Ala Ser Ser Glu
             100                 105                 110

Ala Arg Asn Ser Ala Phe Gly Phe Gln Gly Arg Leu Leu His Leu Ser
         115                 120                 125

Ala Gly Gln Arg Leu Gly Val His Leu His Thr Glu Ala Arg Ala Arg
         130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                 165
```

```
<210> SEQ ID NO 209
<211> LENGTH: 197
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(197)
<223> OTHER INFORMATION: 52-248 of human 41BBL

<400> SEQUENCE: 209

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

<210> SEQ ID NO 210
<211> LENGTH: 121
<212> TYPE: PRT
<213> ORGANISM: Artificial Sequence
<220> FEATURE:
<223> OTHER INFORMATION: 41BB sdAb

<400> SEQUENCE: 210

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95
```

-continued

```
Leu Leu Lys Gly Asn Arg Val Val Ser Pro Ser Val Ala Tyr Trp Gly
            100                 105                 110

Gln Gly Thr Leu Val Thr Val Lys Pro
        115                 120
```

```
<210> SEQ ID NO 211
<211> LENGTH: 133
<212> TYPE: PRT
<213> ORGANISM: Artificial Sequence
<220> FEATURE:
<223> OTHER INFORMATION: OX40 ligand

<400> SEQUENCE: 211

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
            85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu
    130
```

```
<210> SEQ ID NO 212
<211> LENGTH: 133
<212> TYPE: PRT
<213> ORGANISM: Artificial Sequence
<220> FEATURE:
<223> OTHER INFORMATION: OX40 ligand

<400> SEQUENCE: 212

Gln Val Ser His Arg Tyr Pro Arg Phe Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
            85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu
    130
```

<210> SEQ ID NO 213
<211> LENGTH: 133
<212> TYPE: PRT
<213> ORGANISM: Artificial Sequence
<220> FEATURE:
<223> OTHER INFORMATION: OX40 ligand

<400> SEQUENCE: 213

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu
    130

<210> SEQ ID NO 214
<211> LENGTH: 133
<212> TYPE: PRT
<213> ORGANISM: Artificial Sequence
<220> FEATURE:
<223> OTHER INFORMATION: OX40 ligand

<400> SEQUENCE: 214

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu
    130

<210> SEQ ID NO 215
<211> LENGTH: 132
<212> TYPE: PRT

<213> ORGANISM: Artificial Sequence
<220> FEATURE:
<223> OTHER INFORMATION: OX40 ligand

<400> SEQUENCE: 215

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
            20                  25                  30

Glu Ile Met Lys Val Gln Asn Asn Ser Val Ile Ile Asn Cys Asp Gly
        35                  40                  45

Phe Tyr Leu Ile Ser Leu Lys Gly Tyr Phe Ser Gln Glu Val Asn Ile
    50                  55                  60

Ser Leu His Tyr Gln Lys Asp Glu Glu Pro Leu Phe Gln Leu Lys Lys
65                  70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130

<210> SEQ ID NO 216
<211> LENGTH: 117
<212> TYPE: PRT
<213> ORGANISM: Artificial Sequence
<220> FEATURE:
<223> OTHER INFORMATION: OX40 VH

<400> SEQUENCE: 216

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 217
<211> LENGTH: 109
<212> TYPE: PRT
<213> ORGANISM: Artificial Sequence
<220> FEATURE:
<223> OTHER INFORMATION: OX40 VL

<400> SEQUENCE: 217

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr
            100                 105
```

<210> SEQ ID NO 218
<211> LENGTH: 121
<212> TYPE: PRT
<213> ORGANISM: Artificial Sequence
<220> FEATURE:
<223> OTHER INFORMATION: OX40 VH

<400> SEQUENCE: 218

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser
            115                 120
```

<210> SEQ ID NO 219
<211> LENGTH: 112
<212> TYPE: PRT
<213> ORGANISM: Artificial Sequence
<220> FEATURE:
<223> OTHER INFORMATION: OX40 VL

<400> SEQUENCE: 219

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

-continued

```
                    85              90              95
Leu Gln Thr Pro Leu Thr Phe Gly Gly Gly Thr Lys Val Glu Ile Lys
            100             105             110
```

```
<210> SEQ ID NO 220
<211> LENGTH: 115
<212> TYPE: PRT
<213> ORGANISM: Artificial Sequence
<220> FEATURE:
<223> OTHER INFORMATION: OX40 sdAb

<400> SEQUENCE: 220

Glu Val Gln Leu Leu Glu Ser Gly Gly Gly Glu Val Gln Pro Gly Gly
1               5               10              15

Ser Leu Arg Leu Ser Cys Ala Ala Ser Gly Phe Thr Phe Ser Asp Ala
            20              25              30

Phe Met Tyr Trp Val Arg Gln Ala Pro Gly Lys Gly Leu Glu Trp Val
            35              40              45

Ser Ser Ile Ser Asn Arg Gly Leu Lys Thr Ala Tyr Ala Glu Ser Val
            50              55              60

Lys Gly Arg Phe Thr Ile Ser Arg Asp Asn Ala Lys Asn Thr Leu Tyr
65              70              75              80

Leu Gln Met Ser Ser Leu Arg Ala Glu Asp Thr Ala Val Tyr Tyr Cys
                85              90              95

Ser Arg Asp Val Asp Gly Asp Phe Arg Gly Gln Gly Thr Leu Val Thr
            100             105             110

Val Lys Pro
        115
```

```
<210> SEQ ID NO 221
<211> LENGTH: 128
<212> TYPE: PRT
<213> ORGANISM: Artificial Sequence
<220> FEATURE:
<223> OTHER INFORMATION: GITR ligand

<400> SEQUENCE: 221

Gln Leu Glu Thr Ala Lys Glu Pro Cys Met Ala Lys Phe Gly Pro Leu
1               5               10              15

Pro Ser Lys Trp Gln Met Ala Ser Ser Glu Pro Pro Cys Val Asn Lys
            20              25              30

Val Ser Asp Trp Lys Leu Glu Ile Leu Gln Asn Gly Leu Tyr Leu Ile
            35              40              45

Tyr Gly Gln Val Ala Pro Asn Ala Asn Tyr Asn Asp Val Ala Pro Phe
    50              55              60

Glu Val Arg Leu Tyr Lys Asn Lys Asp Met Ile Gln Thr Leu Thr Asn
65              70              75              80

Lys Ser Lys Ile Gln Asn Val Gly Gly Thr Tyr Glu Leu His Val Gly
                85              90              95

Asp Thr Ile Asp Leu Ile Phe Asn Ser Glu His Gln Val Leu Lys Asn
            100             105             110

Asn Thr Tyr Trp Gly Ile Ile Leu Leu Ala Asn Pro Gln Phe Ile Ser
            115             120             125
```

```
<210> SEQ ID NO 222
<211> LENGTH: 118
<212> TYPE: PRT
<213> ORGANISM: Artificial Sequence
<220> FEATURE:
```

<223> OTHER INFORMATION: GITR VH

<400> SEQUENCE: 222

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Val Gly Gly Tyr Tyr Asp Ser Met Asp Tyr Trp Gly Gln Gly Thr
            100                 105                 110

Leu Val Thr Val Ser Ser
        115
```

<210> SEQ ID NO 223
<211> LENGTH: 111
<212> TYPE: PRT
<213> ORGANISM: Artificial Sequence
<220> FEATURE:
<223> OTHER INFORMATION: GITR VL

<400> SEQUENCE: 223

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Ala Ala Ser Asn Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Lys
            85                  90                  95

Glu Val Thr Trp Thr Phe Gly Gln Gly Thr Lys Val Glu Ile Lys
            100                 105                 110
```

<210> SEQ ID NO 224
<211> LENGTH: 119
<212> TYPE: PRT
<213> ORGANISM: Artificial Sequence
<220> FEATURE:
<223> OTHER INFORMATION: GITR VH

<400> SEQUENCE: 224

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Gln Pro Ser
```

-continued

```
            50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
                100                 105                 110

Thr Leu Val Thr Val Ser Ser
            115

<210> SEQ ID NO 225
<211> LENGTH: 107
<212> TYPE: PRT
<213> ORGANISM: Artificial Sequence
<220> FEATURE:
<223> OTHER INFORMATION: GITR VL

<400> SEQUENCE: 225

Glu Ile Val Met Thr Gln Ser Pro Ala Thr Leu Ser Val Ser Pro Gly
1                   5                   10                  15

Glu Arg Ala Thr Leu Ser Cys Lys Ala Ser Gln Asn Val Gly Thr Asn
                20                  25                  30

Val Ala Trp Tyr Gln Gln Lys Pro Gly Gln Ala Pro Arg Leu Leu Ile
            35                  40                  45

Tyr Ser Ala Ser Tyr Arg Tyr Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
            100                 105

<210> SEQ ID NO 226
<211> LENGTH: 125
<212> TYPE: PRT
<213> ORGANISM: Artificial Sequence
<220> FEATURE:
<223> OTHER INFORMATION: GITR VH

<400> SEQUENCE: 226

Gln Val Gln Leu Gln Glu Ser Gly Pro Gly Leu Val Lys Pro Ser Glu
1                   5                   10                  15

Thr Leu Ser Leu Thr Cys Thr Val Ser Gly Gly Ser Ile Ser Ser Gly
                20                  25                  30

Gly Tyr Phe Trp Ser Trp Ile Arg Gln Pro Pro Gly Lys Gly Leu Glu
            35                  40                  45

Trp Ile Gly Tyr Ile Tyr Tyr Ser Gly Thr Thr Tyr Tyr Asn Pro Ser
        50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Leu Phe Tyr Tyr Asp Thr Ser Gly Pro Arg Gly Phe
                100                 105                 110

Asp Pro Trp Gly Gln Gly Thr Leu Val Thr Val Ser Ser
            115                 120                 125
```

-continued

<210> SEQ ID NO 227
<211> LENGTH: 108
<212> TYPE: PRT
<213> ORGANISM: Artificial Sequence
<220> FEATURE:
<223> OTHER INFORMATION: GITR VL

<400> SEQUENCE: 227

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Asn
                20                  25                  30

Tyr Leu Ala Trp Tyr Gln Gln Lys Pro Gly Gln Ala Pro Arg Leu Leu
            35                  40                  45

Ile Tyr Gly Ser Ser Thr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Trp Thr Phe Gly Gln Gly Thr Lys Val Glu Ile Lys
            100                 105

<210> SEQ ID NO 228
<211> LENGTH: 123
<212> TYPE: PRT
<213> ORGANISM: Artificial Sequence
<220> FEATURE:
<223> OTHER INFORMATION: GITR VH

<400> SEQUENCE: 228

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Pro Gly Ser Asn Lys Tyr Tyr Ala Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Leu Gly Arg Tyr Tyr Tyr Gly Met Asp Val
            100                 105                 110

Trp Gly Gln Gly Thr Thr Val Thr Val Ser Ser
        115                 120

<210> SEQ ID NO 229
<211> LENGTH: 107
<212> TYPE: PRT
<213> ORGANISM: Artificial Sequence
<220> FEATURE:
<223> OTHER INFORMATION: GITR VL

<400> SEQUENCE: 229

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Gly Ile Arg Asn Asp

-continued

```
                20                25                30

Leu Gly Trp Tyr Gln Gln Lys Pro Gly Lys Ala Pro Lys Arg Leu Ile
        35                40                45

Tyr Ala Ala Ser Ser Leu Gln Ser Gly Val Pro Ser Arg Phe Ser Gly
    50                55                60

Ser Gly Ser Gly Thr Glu Phe Thr Leu Thr Ile Ser Ser Leu Gln Pro
65                70                75                80

Glu Asp Phe Ala Thr Tyr Tyr Cys Leu Gln His Asn Asn Tyr Pro Trp
                85                90                95

Thr Phe Gly Gln Gly Thr Lys Val Asp Ile Lys
            100               105
```

<210> SEQ ID NO 230
<211> LENGTH: 119
<212> TYPE: PRT
<213> ORGANISM: Artificial Sequence
<220> FEATURE:
<223> OTHER INFORMATION: GITR sdAb

<400> SEQUENCE: 230

```
Glu Val Gln Leu Leu Glu Ser Gly Gly Gly Glu Val Gln Pro Gly Gly
1               5                10                15

Ser Leu Arg Leu Ser Cys Ala Ala Ser Gly Ser Val Phe Ser Ile Asp
            20                25                30

Ala Met Gly Trp Tyr Arg Gln Ala Pro Gly Lys Gln Arg Glu Leu Val
            35                40                45

Ala Val Leu Ser Gly Ile Ser Ser Ala Lys Tyr Ala Ala Ser Ala Pro
    50                55                60

Gly Arg Phe Thr Ile Ser Arg Asp Asn Ala Lys Asn Thr Val Tyr Leu
65                70                75                80

Gln Met Ser Ser Leu Arg Ala Glu Asp Thr Ala Val Tyr Tyr Cys Tyr
            85                90                95

Ala Asp Val Ser Thr Gly Trp Gly Arg Asp Ala His Gly Tyr Trp Gly
            100               105               110

Gln Gly Thr Leu Val Thr Val
        115
```

<210> SEQ ID NO 231
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(193)
<223> OTHER INFORMATION: UniProt No. P32970, CD70-ECD

<400> SEQUENCE: 231

```
Met Pro Glu Glu Gly Ser Gly Cys Ser Val Arg Arg Arg Pro Tyr Gly
1               5                10                15

Cys Val Leu Arg Ala Ala Leu Val Pro Leu Val Ala Gly Leu Val Ile
            20                25                30

Cys Leu Val Val Cys Ile Gln Arg Phe Ala Gln Ala Gln Gln Gln Leu
            35                40                45

Pro Leu Glu Ser Leu Gly Trp Asp Val Ala Glu Leu Gln Leu Asn His
    50                55                60

Thr Gly Pro Gln Gln Asp Pro Arg Leu Tyr Trp Gln Gly Gly Pro Ala
```

-continued

```
65              70              75              80

Leu Gly Arg Ser Phe Leu His Gly Pro Glu Leu Asp Lys Gly Gln Leu
                85              90              95

Arg Ile His Arg Asp Gly Ile Tyr Met Val His Ile Gln Val Thr Leu
            100             105             110

Ala Ile Cys Ser Ser Thr Thr Ala Ser Arg His His Pro Thr Thr Leu
            115             120             125

Ala Val Gly Ile Cys Ser Pro Ala Ser Arg Ser Ile Ser Leu Leu Arg
        130             135             140

Leu Ser Phe His Gln Gly Cys Thr Ile Ala Ser Gln Arg Leu Thr Pro
145             150             155             160

Leu Ala Arg Gly Asp Thr Leu Cys Thr Asn Leu Thr Gly Thr Leu Leu
            165             170             175

Pro Ser Arg Asn Thr Asp Glu Thr Phe Phe Gly Val Gln Trp Val Arg
            180             185             190

Pro

<210> SEQ ID NO 232
<211> LENGTH: 119
<212> TYPE: PRT
<213> ORGANISM: Artificial Sequence
<220> FEATURE:
<223> OTHER INFORMATION: CD70 VH

<400> SEQUENCE: 232

Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Asp Met His Trp Val Arg Gln Ala Pro Gly Lys Gly Leu Glu Trp Val
            35              40              45

Ala Val Ile Trp Tyr Asp Gly Ser Asn Lys Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Gly Ser Gly Asn Trp Gly Phe Phe Asp Tyr Trp Gly Gln Gly
            100             105             110

Thr Leu Val Thr Val Ser Ser
        115

<210> SEQ ID NO 233
<211> LENGTH: 107
<212> TYPE: PRT
<213> ORGANISM: Artificial Sequence
<220> FEATURE:
<223> OTHER INFORMATION: CD70 VL

<400> SEQUENCE: 233

Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Arg Trp
            20              25              30

Leu Ala Trp Tyr Gln Gln Lys Pro Glu Lys Ala Pro Lys Ser Leu Ile
        35              40              45

Tyr Ala Ala Ser Ser Leu Gln Ser Gly Val Pro Ser Arg Phe Ser Gly
```

```
       50                 55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
                100                 105
```

```
<210> SEQ ID NO 234
<211> LENGTH: 124
<212> TYPE: PRT
<213> ORGANISM: Artificial Sequence
<220> FEATURE:
<223> OTHER INFORMATION: ICOS sdAb

<400> SEQUENCE: 234

Gln Val Gln Leu Gln Gln Ser Gly Gly Gly Leu Val Gln Pro Gly Gly
1               5                   10                  15

Ser Leu Arg Leu Ser Cys Ala Ala Ser Gly Ser Ile Phe Ser Ile Asn
                20                  25                  30

Gly Met Gly Trp Tyr Arg Gln Ala Pro Gly Lys Glu Arg Glu Leu Val
            35                  40                  45

Ala Gly Leu Thr Ser Gly Gly Ser Val Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Arg Ala Glu Ile Phe Thr Arg Thr Gly Glu Asn Tyr Tyr Gly Met Asp
                100                 105                 110

Tyr Trp Gly Lys Gly Thr Gln Val Thr Val Lys Pro
            115                 120
```

```
<210> SEQ ID NO 235
<211> LENGTH: 124
<212> TYPE: PRT
<213> ORGANISM: Artificial Sequence
<220> FEATURE:
<223> OTHER INFORMATION: CD28 sdAb

<400> SEQUENCE: 235

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
                20                  25                  30

Ala Met Gly Trp Phe Arg Gln Ala Pro Gly Lys Glu Arg Glu Phe Val
            35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
                100                 105                 110

Tyr Trp Gly Gln Gly Thr Leu Val Thr Val Lys Pro
            115                 120
```

-continued

```
<210> SEQ ID NO 236
<211> LENGTH: 112
<212> TYPE: PRT
<213> ORGANISM: Artificial Sequence
<220> FEATURE:
<223> OTHER INFORMATION: CD3zeta signaling domain

<400> SEQUENCE: 236

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 237
<211> LENGTH: 42
<212> TYPE: PRT
<213> ORGANISM: Artificial Sequence
<220> FEATURE:
<223> OTHER INFORMATION: 4-1BB-derived costimulatory domain

<400> SEQUENCE: 237

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 238
<211> LENGTH: 40
<212> TYPE: PRT
<213> ORGANISM: Artificial Sequence
<220> FEATURE:
<223> OTHER INFORMATION: CD28-derived costimulatory domain

<400> SEQUENCE: 238

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
                20                  25                  30

Arg Asp Phe Ala Ala Tyr Arg Ser
        35                  40

<210> SEQ ID NO 239
<211> LENGTH: 41
<212> TYPE: PRT
<213> ORGANISM: Artificial Sequence
<220> FEATURE:
<223> OTHER INFORMATION: CD28-derived costimulatory domain 2

<400> SEQUENCE: 239
```

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 240
<211> LENGTH: 44
<212> TYPE: PRT
<213> ORGANISM: Artificial Sequence
<220> FEATURE:
<223> OTHER INFORMATION: CD28-derived costimulatory domain 3

<400> SEQUENCE: 240

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40

<210> SEQ ID NO 241
<211> LENGTH: 71
<212> TYPE: PRT
<213> ORGANISM: Artificial Sequence
<220> FEATURE:
<223> OTHER INFORMATION: CD8-derived hinge and transmembrane domain

<400> SEQUENCE: 241

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys
65                  70

<210> SEQ ID NO 242
<211> LENGTH: 69
<212> TYPE: PRT
<213> ORGANISM: Artificial Sequence
<220> FEATURE:
<223> OTHER INFORMATION: CD8-derived hinge and transmembrane domain

<400> SEQUENCE: 242

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65
```

<210> SEQ ID NO 243
<211> LENGTH: 68
<212> TYPE: PRT
<213> ORGANISM: Artificial Sequence
<220> FEATURE:
<223> OTHER INFORMATION: CD8 hinge and transmembrane domain

<400> SEQUENCE: 243

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr
65

<210> SEQ ID NO 244
<211> LENGTH: 420
<212> TYPE: PRT
<213> ORGANISM: Artificial Sequence
<220> FEATURE:
<223> OTHER INFORMATION: 5T4

<400> SEQUENCE: 244

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

-continued

```
Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
            275                 280                 285

Val Phe Leu Asp Asn Asn Pro Trp Val Cys Asp Cys His Met Ala Asp
        290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
            355                 360                 365

Ile Phe Leu Leu Val Leu Tyr Leu Asn Arg Lys Gly Ile Lys Lys Trp
        370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420
```

<210> SEQ ID NO 245
<211> LENGTH: 122
<212> TYPE: PRT
<213> ORGANISM: Artificial Sequence
<220> FEATURE:
<223> OTHER INFORMATION: L12E9

<400> SEQUENCE: 245

```
Gln Val Gln Leu Val Gln Ser Gly Gly Gly Leu Val Gln Ala Gly Gly
1               5                   10                  15

Ser Leu Arg Leu Ser Cys Ala Ala Ser Arg Arg Pro Phe Ser Ser Lys
            20                  25                  30

Thr Met Ala Trp Phe Arg Gln Thr Pro Gly Lys Glu Arg Glu Phe Val
            35                  40                  45

Ala Ala Val Arg Trp Ile Gly Gly Ala Thr Arg Tyr Thr Asp Ser Val
        50                  55                  60

Lys Gly Arg Phe Ser Ile Ser Lys Asp Asn Ala Ile Asn Thr Val Tyr
65                  70                  75                  80

Leu Gln Met Asn Ser Leu Lys Ser Glu Asp Thr Ala Val Tyr Tyr Cys
                85                  90                  95

Ala Ala Gly Gln Ala Trp Gly Thr Lys Phe Thr Asp Tyr Ser Asp Trp
            100                 105                 110

Gly Gln Gly Thr Gln Val Thr Val Lys Pro
            115                 120
```

<210> SEQ ID NO 246
<211> LENGTH: 122
<212> TYPE: PRT
<213> ORGANISM: Artificial Sequence
<220> FEATURE:
<223> OTHER INFORMATION: hz12E9v1

<400> SEQUENCE: 246

```
Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
            20                  25                  30

Thr Met Ala Trp Phe Arg Gln Ala Pro Gly Lys Gly Arg Glu Phe Val
        35                  40                  45

Ala Ala Val Arg Trp Ile Gly Gly Ala Thr Arg Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
            100                 105                 110

Gly Gln Gly Thr Leu Val Thr Val Lys Pro
        115                 120
```

<210> SEQ ID NO 247
<211> LENGTH: 122
<212> TYPE: PRT
<213> ORGANISM: Artificial Sequence
<220> FEATURE:
<223> OTHER INFORMATION: hz12E9v2

<400> SEQUENCE: 247

```
Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
            20                  25                  30

Thr Met Ala Trp Phe Arg Gln Ala Pro Gly Lys Glu Arg Glu Phe Val
        35                  40                  45

Ala Ala Val Arg Trp Ile Gly Gly Ala Thr Arg Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
            100                 105                 110

Gly Gln Gly Thr Leu Val Thr Val Lys Pro
        115                 120
```

<210> SEQ ID NO 248
<211> LENGTH: 122
<212> TYPE: PRT
<213> ORGANISM: Artificial Sequence
<220> FEATURE:
<223> OTHER INFORMATION: hz12E9v3

<400> SEQUENCE: 248

```
Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
            20                  25                  30

Thr Met Ala Trp Phe Arg Gln Ala Pro Gly Lys Glu Arg Glu Phe Val
        35                  40                  45

Ala Ala Val Arg Trp Ile Gly Gly Ala Thr Arg Tyr Ala Glu Ser Val
```

```
            50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
                100                 105                 110

Gly Gln Gly Thr Leu Val Thr Val Lys Pro
        115                 120

<210> SEQ ID NO 249
<211> LENGTH: 122
<212> TYPE: PRT
<213> ORGANISM: Artificial Sequence
<220> FEATURE:
<223> OTHER INFORMATION: hz12E9v4

<400> SEQUENCE: 249

Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
                20                  25                  30

Thr Met Ala Trp Phe Arg Gln Ala Pro Gly Lys Glu Arg Glu Phe Val
            35                  40                  45

Ala Ala Val Arg Trp Ile Gly Gly Ala Thr Arg Tyr Thr Glu Ser Val
            50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
                100                 105                 110

Gly Gln Gly Thr Leu Val Thr Val Lys Pro
        115                 120

<210> SEQ ID NO 250
<211> LENGTH: 122
<212> TYPE: PRT
<213> ORGANISM: Artificial Sequence
<220> FEATURE:
<223> OTHER INFORMATION: hz12E9v5

<400> SEQUENCE: 250

Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
                20                  25                  30

Thr Met Ala Trp Phe Arg Gln Ala Pro Gly Lys Glu Arg Glu Phe Val
            35                  40                  45

Ala Ala Val Arg Trp Ile Gly Gly Ala Thr Arg Tyr Thr Glu Ser Val
            50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
                100                 105                 110
```

-continued

```
Gly Gln Gly Thr Leu Val Thr Val Lys Pro
      115                 120

<210> SEQ ID NO 251
<211> LENGTH: 122
<212> TYPE: PRT
<213> ORGANISM: Artificial Sequence
<220> FEATURE:
<223> OTHER INFORMATION: hz12E9v6

<400> SEQUENCE: 251

Glu Val Gln Leu Val Glu Ser Gly Gly Gly Glu Val Gln Ala Gly Gly
1               5                   10                  15

Ser Leu Arg Leu Ser Cys Ala Ala Ser Arg Arg Pro Phe Ser Ser Lys
           20                  25                  30

Thr Met Ala Trp Phe Arg Gln Thr Pro Gly Lys Glu Arg Glu Phe Val
       35                  40                  45

Ala Ala Val Arg Trp Ile Gly Gly Ala Thr Arg Tyr Ala Glu Ser Val
       50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
               85                  90                  95

Ala Ala Gly Gln Ala Trp Gly Thr Lys Phe Thr Asp Tyr Ser Asp Trp
           100                 105                 110

Gly Gln Gly Thr Leu Val Thr Val Lys Pro
      115                 120

<210> SEQ ID NO 252
<211> LENGTH: 122
<212> TYPE: PRT
<213> ORGANISM: Artificial Sequence
<220> FEATURE:
<223> OTHER INFORMATION: hz12E9v7

<400> SEQUENCE: 252

Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
           20                  25                  30

Thr Met Ala Trp Phe Arg Gln Ala Pro Gly Lys Glu Arg Glu Phe Val
       35                  40                  45

Ala Ala Val Arg Trp Ile Gly Gly Ala Thr Arg Tyr Thr Asp Ser Val
       50                  55                  60

Lys Gly Arg Phe Ser Ile Ser Lys Asp Asn Ala Lys Asn Thr Val Tyr
65                  70                  75                  80

Leu Gln Met Ser Ser Leu Arg Ala Glu Asp Thr Ala Val Tyr Tyr Cys
               85                  90                  95

Ala Ala Gly Gln Ala Trp Gly Thr Lys Phe Thr Asp Tyr Ser Asp Trp
           100                 105                 110

Gly Gln Gly Thr Leu Val Thr Val Lys Pro
      115                 120

<210> SEQ ID NO 253
<211> LENGTH: 122
<212> TYPE: PRT
<213> ORGANISM: Artificial Sequence
<220> FEATURE:
<223> OTHER INFORMATION: hz12E9v8
```

-continued

<400> SEQUENCE: 253

Glu Val Gln Leu Val Glu Ser Gly Gly Gly Glu Val Gln Pro Gly Gly
1               5                   10                  15

Ser Leu Arg Leu Ser Cys Ala Ala Ser Arg Arg Pro Phe Ser Ser Lys
            20                  25                  30

Thr Met Ala Trp Phe Arg Gln Ala Pro Gly Lys Glu Arg Glu Phe Val
        35                  40                  45

Ala Ala Val Arg Trp Ile Gly Gly Ala Thr Arg Tyr Ala Glu Ser Val
    50                  55                  60

Lys Gly Arg Phe Thr Ile Ser Arg Asp Asn Ala Ile Asn Thr Val Tyr
65                  70                  75                  80

Leu Gln Met Asn Ser Leu Lys Ser Glu Asp Thr Ala Val Tyr Tyr Cys
                85                  90                  95

Ala Ala Gly Gln Ala Trp Gly Thr Lys Phe Thr Asp Tyr Ser Asp Trp
            100                 105                 110

Gly Gln Gly Thr Leu Val Thr Val Lys Pro
        115                 120

<210> SEQ ID NO 254
<211> LENGTH: 124
<212> TYPE: PRT
<213> ORGANISM: Artificial Sequence
<220> FEATURE:
<223> OTHER INFORMATION: hz12E9v9

<400> SEQUENCE: 254

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Lys
            20                  25                  30

Thr Met Ala Trp Phe Arg Gln Ala Pro Gly Lys Glu Arg Glu Phe Val
        35                  40                  45

Ala Ala Val Arg Trp Ile Gly Gly Ala Thr Arg Tyr Thr Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
            100                 105                 110

Gly Gln Gly Thr Leu Val Thr Val Lys Pro Gly Gly
        115                 120

<210> SEQ ID NO 255
<211> LENGTH: 129
<212> TYPE: PRT
<213> ORGANISM: Artificial Sequence
<220> FEATURE:
<223> OTHER INFORMATION: L14B5

<400> SEQUENCE: 255

Gln Val Gln Leu Val Gln Ser Gly Gly Gly Leu Val Gln Ala Gly Asp
1               5                   10                  15

Ser Leu Thr Leu Ser Cys Ala Val Ser Glu Arg Pro Phe Gly Thr Tyr
            20                  25                  30

Ala Met Gly Trp Phe Arg Gln Ala Pro Gly Arg Glu Arg Asp Leu Val
        35                  40                  45

-continued

```
Ala Ala Val Ser Arg Asn Gly Gly Ala Ser Gln Tyr Gly Asp Ser Val
50                  55                  60

Lys Gly Arg Phe Ser Ile Ser Arg Asp Asn Ile Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Arg Ser Ala Ala Tyr Ser Arg Ser Ser Glu Val Tyr Thr Gly
                100                 105                 110

Lys Asp Glu Tyr Tyr Tyr Trp Gly Gln Gly Thr Gln Val Thr Val Lys
        115                 120                 125

Pro
```

<210> SEQ ID NO 256
<211> LENGTH: 129
<212> TYPE: PRT
<213> ORGANISM: Artificial Sequence
<220> FEATURE:
<223> OTHER INFORMATION: hz14B5v1

<400> SEQUENCE: 256

```
Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
                20                  25                  30

Ala Met Gly Trp Phe Arg Gln Ala Pro Gly Lys Gly Arg Asp Leu Val
                35                  40                  45

Ser Ala Val Ser Arg Asn Gly Gly Ala Ser Gln Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
                100                 105                 110

Lys Asp Glu Tyr Tyr Tyr Trp Gly Gln Gly Thr Leu Val Thr Val Lys
        115                 120                 125

Pro
```

<210> SEQ ID NO 257
<211> LENGTH: 129
<212> TYPE: PRT
<213> ORGANISM: Artificial Sequence
<220> FEATURE:
<223> OTHER INFORMATION: hz14B5v2

<400> SEQUENCE: 257

```
Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
                20                  25                  30

Ala Met Gly Trp Phe Arg Gln Ala Pro Gly Lys Glu Arg Asp Leu Val
                35                  40                  45

Ala Ala Val Ser Arg Asn Gly Gly Ala Ser Gln Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
```

```
                        85                      90                      95

Ala Ala Arg Ser Ala Ala Tyr Ser Arg Ser Ser Glu Val Tyr Thr Gly
            100                     105                     110

Lys Asp Glu Tyr Tyr Tyr Trp Gly Gln Gly Thr Leu Val Thr Val Lys
            115                     120                     125

Pro

<210> SEQ ID NO 258
<211> LENGTH: 129
<212> TYPE: PRT
<213> ORGANISM: Artificial Sequence
<220> FEATURE:
<223> OTHER INFORMATION: hz14B5v3

<400> SEQUENCE: 258

Glu Val Gln Leu Val Glu Ser Gly Gly Gly Glu Val Gln Pro Gly Gly
1               5                       10                      15

Ser Leu Arg Leu Ser Cys Ala Ala Ser Glu Arg Pro Phe Gly Thr Tyr
            20                      25                      30

Ala Met Gly Trp Phe Arg Gln Ala Pro Gly Lys Glu Arg Asp Leu Val
            35                      40                      45

Ala Ala Val Ser Arg Asn Gly Gly Ala Ser Gln Tyr Ala Glu Ser Val
        50                      55                      60

Lys Gly Arg Phe Thr Ile Ser Arg Asp Asn Ala Lys Asn Thr Met Tyr
65                      70                      75                      80

Leu Gln Met Ser Ser Leu Arg Ala Glu Asp Thr Ala Val Tyr Tyr Cys
                85                      90                      95

Ala Ala Arg Ser Ala Ala Tyr Ser Arg Ser Ser Glu Val Tyr Thr Gly
            100                     105                     110

Lys Asp Glu Tyr Tyr Tyr Trp Gly Gln Gly Thr Leu Val Thr Val Lys
        115                     120                     125

Pro

<210> SEQ ID NO 259
<211> LENGTH: 129
<212> TYPE: PRT
<213> ORGANISM: Artificial Sequence
<220> FEATURE:
<223> OTHER INFORMATION: hz14B5v4

<400> SEQUENCE: 259

Glu Val Gln Leu Val Glu Ser Gly Gly Gly Glu Val Gln Pro Gly Gly
1               5                       10                      15

Ser Leu Arg Leu Ser Cys Ala Ala Ser Glu Arg Pro Phe Gly Thr Tyr
            20                      25                      30

Ala Met Gly Trp Phe Arg Gln Ala Pro Gly Lys Glu Arg Asp Leu Val
            35                      40                      45

Ala Ala Val Ser Arg Asn Gly Gly Ala Ser Gln Tyr Ala Glu Ser Val
        50                      55                      60

Lys Gly Arg Phe Thr Ile Ser Arg Asp Asn Ala Lys Asn Thr Val Tyr
65                      70                      75                      80

Leu Gln Met Ser Ser Leu Arg Ala Glu Asp Thr Ala Val Tyr Tyr Cys
                85                      90                      95

Ala Ala Arg Ser Ala Ala Tyr Ser Arg Ser Ser Glu Val Tyr Thr Gly
            100                     105                     110

Lys Asp Glu Tyr Tyr Tyr Trp Gly Gln Gly Thr Leu Val Thr Val Lys
        115                     120                     125
```

Pro

<210> SEQ ID NO 260
<211> LENGTH: 129
<212> TYPE: PRT
<213> ORGANISM: Artificial Sequence
<220> FEATURE:
<223> OTHER INFORMATION: hz14B5v5

<400> SEQUENCE: 260

```
Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
        35                  40                  45

Ala Ala Val Ser Arg Asn Ala Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125
```

Pro

<210> SEQ ID NO 261
<211> LENGTH: 129
<212> TYPE: PRT
<213> ORGANISM: Artificial Sequence
<220> FEATURE:
<223> OTHER INFORMATION: hz14B5v6

<400> SEQUENCE: 261

```
Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
        35                  40                  45

Ala Ala Val Ser Arg Asn Thr Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125
```

Pro

<210> SEQ ID NO 262
<211> LENGTH: 129
<212> TYPE: PRT

-continued

<213> ORGANISM: Artificial Sequence
<220> FEATURE:
<223> OTHER INFORMATION: hz14B5v7

<400> SEQUENCE: 262

```
Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
        35                  40                  45

Ala Ala Val Ser Arg Gln Gly Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro
```

<210> SEQ ID NO 263
<211> LENGTH: 129
<212> TYPE: PRT
<213> ORGANISM: Artificial Sequence
<220> FEATURE:
<223> OTHER INFORMATION: hz14B5v8

<400> SEQUENCE: 263

```
Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
        35                  40                  45

Ala Ala Val Ser Arg Gly Gly Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro
```

<210> SEQ ID NO 264
<211> LENGTH: 129
<212> TYPE: PRT
<213> ORGANISM: Artificial Sequence
<220> FEATURE:
<223> OTHER INFORMATION: hz14B5v9

<400> SEQUENCE: 264

```
Glu Val Gln Leu Val Glu Ser Gly Gly Gly Glu Val Gln Pro Gly Gly
```

-continued

```
1               5               10              15
Ser Leu Arg Leu Ser Cys Ala Ala Ser Glu Arg Pro Phe Gly Thr Tyr
            20              25              30

Ala Met Gly Trp Phe Arg Gln Ala Pro Gly Lys Glu Arg Asp Leu Val
            35              40              45

Ala Ala Val Ser Arg Asn Gly Gly Ala Ser Gln Tyr Gly Asp Ser Val
            50              55              60

Lys Gly Arg Phe Thr Ile Ser Arg Asp Asn Ala Lys Asn Thr Met Tyr
65                  70              75              80

Leu Gln Met Ser Ser Leu Arg Ala Glu Asp Thr Ala Val Tyr Tyr Cys
                85              90              95

Ala Ala Arg Ser Ala Ala Tyr Ser Arg Ser Ser Glu Val Tyr Thr Gly
            100             105             110

Lys Asp Glu Tyr Tyr Tyr Trp Gly Gln Gly Thr Leu Val Thr Val Lys
            115             120             125

Pro
```

<210> SEQ ID NO 265
<211> LENGTH: 129
<212> TYPE: PRT
<213> ORGANISM: Artificial Sequence
<220> FEATURE:
<223> OTHER INFORMATION: hz14B5v10

<400> SEQUENCE: 265

```
Glu Val Gln Leu Val Glu Ser Gly Gly Gly Glu Val Gln Pro Gly Gly
1               5               10              15

Ser Leu Arg Leu Ser Cys Ala Ala Ser Glu Arg Pro Phe Gly Thr Tyr
            20              25              30

Ala Met Gly Trp Phe Arg Gln Ala Pro Gly Lys Glu Arg Asp Leu Val
            35              40              45

Ala Ala Val Ser Arg Asn Gly Gly Ala Ser Gln Tyr Gly Glu Ser Val
            50              55              60

Lys Gly Arg Phe Thr Ile Ser Arg Asp Asn Ala Lys Asn Thr Met Tyr
65                  70              75              80

Leu Gln Met Ser Ser Leu Arg Ala Glu Asp Thr Ala Val Tyr Tyr Cys
                85              90              95

Ala Ala Arg Ser Ala Ala Tyr Ser Arg Ser Ser Glu Val Tyr Thr Gly
            100             105             110

Lys Asp Glu Tyr Tyr Tyr Trp Gly Gln Gly Thr Leu Val Thr Val Lys
            115             120             125

Pro
```

<210> SEQ ID NO 266
<211> LENGTH: 129
<212> TYPE: PRT
<213> ORGANISM: Artificial Sequence
<220> FEATURE:
<223> OTHER INFORMATION: hz14B5v11

<400> SEQUENCE: 266

```
Glu Val Gln Leu Val Glu Ser Gly Gly Gly Glu Val Gln Ala Gly Asp
1               5               10              15

Ser Leu Thr Leu Ser Cys Ala Val Ser Glu Arg Pro Phe Gly Thr Tyr
            20              25              30

Ala Met Gly Trp Phe Arg Gln Ala Pro Gly Arg Glu Arg Asp Leu Val
            35              40              45
```

```
Ala Ala Val Ser Arg Asn Ala Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro

<210> SEQ ID NO 267
<211> LENGTH: 129
<212> TYPE: PRT
<213> ORGANISM: Artificial Sequence
<220> FEATURE:
<223> OTHER INFORMATION: hz14B5v12

<400> SEQUENCE: 267

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
        35                  40                  45

Ala Ala Val Ser Arg Asn Ala Gly Ala Ser Gln Tyr Gly Glu Ser Val
    50                  55                  60

Lys Gly Arg Phe Ser Ile Ser Arg Asp Asn Ile Lys Asn Thr Met Tyr
65                  70                  75                  80

Leu Gln Met Ser Ser Leu Lys Pro Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro

<210> SEQ ID NO 268
<211> LENGTH: 129
<212> TYPE: PRT
<213> ORGANISM: Artificial Sequence
<220> FEATURE:
<223> OTHER INFORMATION: hz14B5v13

<400> SEQUENCE: 268

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Glu Thr Val
        35                  40                  45

Ala Ala Val Ser Arg Asn Ala Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80
```

-continued

```
Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro

<210> SEQ ID NO 269
<211> LENGTH: 129
<212> TYPE: PRT
<213> ORGANISM: Artificial Sequence
<220> FEATURE:
<223> OTHER INFORMATION: hz14B5v14

<400> SEQUENCE: 269

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Glu Phe Val
        35                  40                  45

Ala Ala Val Ser Arg Asn Ala Gly Ala Ser Gln Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro

<210> SEQ ID NO 270
<211> LENGTH: 129
<212> TYPE: PRT
<213> ORGANISM: Artificial Sequence
<220> FEATURE:
<223> OTHER INFORMATION: hz14B5v15

<400> SEQUENCE: 270

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
        35                  40                  45

Ala Ala Val Ser Arg Asn Ala Gly Ala Ser Tyr Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
```

```
          115                 120                 125

Pro

<210> SEQ ID NO 271
<211> LENGTH: 129
<212> TYPE: PRT
<213> ORGANISM: Artificial Sequence
<220> FEATURE:
<223> OTHER INFORMATION: hz14B5v16

<400> SEQUENCE: 271

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
            35                  40                  45

Ala Ala Val Ser Arg Asn Ala Gly Ala Ser Gln Tyr Gly Glu Phe Val
            50                  55                  60

Lys Gly Arg Phe Thr Ile Ser Arg Asp Asn Ala Lys Asn Thr Met Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
            115                 120                 125

Pro

<210> SEQ ID NO 272
<211> LENGTH: 129
<212> TYPE: PRT
<213> ORGANISM: Artificial Sequence
<220> FEATURE:
<223> OTHER INFORMATION: hz14B5v17

<400> SEQUENCE: 272

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Gly Thr Tyr
            20                  25                  30

Ala Met Gly Trp Phe Arg Gln Ala Pro Gly Lys Glu Arg Asp Leu Val
            35                  40                  45

Ala Ala Val Ser Arg Asn Ala Gly Ala Ser Tyr Tyr Ala Glu Ser Val
            50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
            115                 120                 125

Pro

<210> SEQ ID NO 273
<211> LENGTH: 129
```

-continued

```
<212> TYPE: PRT
<213> ORGANISM: Artificial Sequence
<220> FEATURE:
<223> OTHER INFORMATION: hz14B5v18

<400> SEQUENCE: 273

Glu Val Gln Leu Val Glu Ser Gly Gly Gly Glu Val Gln Pro Gly Gly
1               5                   10                  15

Ser Leu Arg Leu Ser Cys Ala Ala Ser Glu Arg Pro Phe Ser Ser Tyr
            20                  25                  30

Ala Met Gly Trp Phe Arg Gln Ala Pro Gly Lys Glu Arg Asp Leu Val
            35                  40                  45

Ala Ala Val Ser Arg Asn Ala Gly Ala Ser Tyr Tyr Ala Glu Ser Val
            50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
                100                 105                 110

Lys Asp Glu Tyr Tyr Tyr Trp Gly Gln Gly Thr Leu Val Thr Val Lys
            115                 120                 125

Pro

<210> SEQ ID NO 274
<211> LENGTH: 129
<212> TYPE: PRT
<213> ORGANISM: Artificial Sequence
<220> FEATURE:
<223> OTHER INFORMATION: hz14B5v19

<400> SEQUENCE: 274

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Gly Thr Tyr
            20                  25                  30

Ala Met Gly Trp Phe Arg Gln Ala Pro Gly Lys Glu Arg Asp Leu Val
            35                  40                  45

Ala Ala Val Ser Arg Asn Ala Gly Ala Ser Tyr Tyr Ala Glu Ser Val
            50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
                100                 105                 110

Lys Asp Glu Tyr Tyr Tyr Trp Gly Gln Gly Thr Leu Val Thr Val Lys
            115                 120                 125

Pro

<210> SEQ ID NO 275
<211> LENGTH: 129
<212> TYPE: PRT
<213> ORGANISM: Artificial Sequence
<220> FEATURE:
<223> OTHER INFORMATION: hz14B5v20

<400> SEQUENCE: 275
```

-continued

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Tyr
            20                  25                  30

Ala Met Gly Trp Phe Arg Gln Ala Pro Gly Lys Glu Arg Asp Leu Val
            35                  40                  45

Ala Ala Val Ser Arg Asn Ala Gly Ala Ser Tyr Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Val Tyr Thr Gly
            100                 105                 110

Lys Asp Glu Tyr Tyr Tyr Trp Gly Gln Gly Thr Leu Val Thr Val Lys
        115                 120                 125

Pro
```

```
<210> SEQ ID NO 276
<211> LENGTH: 129
<212> TYPE: PRT
<213> ORGANISM: Artificial Sequence
<220> FEATURE:
<223> OTHER INFORMATION: L16G10

<400> SEQUENCE: 276
```

```
Gln Val Gln Leu Leu Gln Ser Gly Gly Gly Leu Val Gln Ala Gly Gly
1               5                   10                  15

Ser Leu Ile Leu Ser Cys Ala Val Ser Gly Arg Pro Phe Ser Ser Ser
            20                  25                  30

Ala Met Gly Trp Phe Arg Gln Ala Pro Gly Lys Glu Arg Glu Thr Val
            35                  40                  45

Ala Ala Val Ser Arg Asn Gly Gly Ser Ser Tyr Tyr Ala Asp Phe Val
        50                  55                  60

Lys Gly Arg Phe Thr Ile Ser Arg Asp Asn Asp Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Gln Val Thr Val Lys
        115                 120                 125

Pro
```

```
<210> SEQ ID NO 277
<211> LENGTH: 129
<212> TYPE: PRT
<213> ORGANISM: Artificial Sequence
<220> FEATURE:
<223> OTHER INFORMATION: hz16G10v1

<400> SEQUENCE: 277
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Gly Arg Glu Thr Val
```

-continued

```
                 35                  40                  45

Ser Ala Val Ser Arg Asn Gly Gly Ser Ser Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
               100                 105                 110

Lys His Asp Tyr Thr Tyr Trp Gly Gln Gly Thr Leu Val Thr Val Lys
           115                 120                 125

Pro

<210> SEQ ID NO 278
<211> LENGTH: 129
<212> TYPE: PRT
<213> ORGANISM: Artificial Sequence
<220> FEATURE:
<223> OTHER INFORMATION: hz16G10v2

<400> SEQUENCE: 278

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
                20                  25                  30

Ala Met Gly Trp Phe Arg Gln Ala Pro Gly Lys Glu Arg Glu Thr Val
            35                  40                  45

Ala Ala Val Ser Arg Asn Gly Gly Ser Ser Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
               100                 105                 110

Lys His Asp Tyr Thr Tyr Trp Gly Gln Gly Thr Leu Val Thr Val Lys
           115                 120                 125

Pro

<210> SEQ ID NO 279
<211> LENGTH: 129
<212> TYPE: PRT
<213> ORGANISM: Artificial Sequence
<220> FEATURE:
<223> OTHER INFORMATION: hz16G10v3

<400> SEQUENCE: 279

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
                20                  25                  30

Ala Met Gly Trp Phe Arg Gln Ala Pro Gly Lys Glu Arg Glu Thr Val
            35                  40                  45

Ala Ala Val Ser Arg Asn Gly Gly Ser Ser Tyr Tyr Ala Glu Ser Val
    50                  55                  60

Lys Gly Arg Phe Thr Ile Ser Arg Asp Asn Ala Lys Asn Thr Val Tyr
65                  70                  75                  80
```

```
Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro
```

```
<210> SEQ ID NO 280
<211> LENGTH: 129
<212> TYPE: PRT
<213> ORGANISM: Artificial Sequence
<220> FEATURE:
<223> OTHER INFORMATION: hz16G10v4

<400> SEQUENCE: 280
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
        35                  40                  45

Ala Ala Val Ser Arg Gln Gly Gly Ser Ser Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro
```

```
<210> SEQ ID NO 281
<211> LENGTH: 129
<212> TYPE: PRT
<213> ORGANISM: Artificial Sequence
<220> FEATURE:
<223> OTHER INFORMATION: hz16G10v5

<400> SEQUENCE: 281
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
        35                  40                  45

Ala Ala Val Ser Arg Gly Gly Gly Ser Ser Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110
```

```
Lys His Asp Tyr Thr Tyr Trp Gly Gln Gly Thr Leu Val Thr Val Lys
        115                 120                 125

Pro

<210> SEQ ID NO 282
<211> LENGTH: 129
<212> TYPE: PRT
<213> ORGANISM: Artificial Sequence
<220> FEATURE:
<223> OTHER INFORMATION: hz16G10v6

<400> SEQUENCE: 282

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
            35                  40                  45

Ala Ala Val Ser Arg Asn Ala Gly Ser Ser Tyr Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro

<210> SEQ ID NO 283
<211> LENGTH: 129
<212> TYPE: PRT
<213> ORGANISM: Artificial Sequence
<220> FEATURE:
<223> OTHER INFORMATION: hz16G10v7

<400> SEQUENCE: 283

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
            35                  40                  45

Ala Ala Val Ser Arg Asn Thr Gly Ser Ser Tyr Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro

<210> SEQ ID NO 284
```

<211> LENGTH: 129
<212> TYPE: PRT
<213> ORGANISM: Artificial Sequence
<220> FEATURE:
<223> OTHER INFORMATION: hz16G10v8

<400> SEQUENCE: 284

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
            35                  40                  45

Ala Ala Val Ser Arg Asn Gly Gly Ser Ser Tyr Tyr Ala Asp Phe Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
            115                 120                 125

Pro

<210> SEQ ID NO 285
<211> LENGTH: 129
<212> TYPE: PRT
<213> ORGANISM: Artificial Sequence
<220> FEATURE:
<223> OTHER INFORMATION: hz16G10v9

<400> SEQUENCE: 285

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
            35                  40                  45

Ala Ala Val Ser Arg Asn Gly Gly Ser Ser Tyr Tyr Ala Glu Ser Val
        50                  55                  60

Lys Gly Arg Phe Thr Ile Ser Arg Asp Asn Asp Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
            115                 120                 125

Pro

<210> SEQ ID NO 286
<211> LENGTH: 129
<212> TYPE: PRT
<213> ORGANISM: Artificial Sequence
<220> FEATURE:
<223> OTHER INFORMATION: hz16G10v10

<400> SEQUENCE: 286

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Ser
            20                  25                  30

Ala Met Gly Trp Phe Arg Gln Ala Pro Gly Lys Glu Arg Glu Thr Val
        35                  40                  45

Ala Ala Val Ser Arg Asn Ala Gly Ser Ser Tyr Tyr Ala Asp Phe Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro
```

<210> SEQ ID NO 287
<211> LENGTH: 129
<212> TYPE: PRT
<213> ORGANISM: Artificial Sequence
<220> FEATURE:
<223> OTHER INFORMATION: hz16G10v11

<400> SEQUENCE: 287

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Tyr
            20                  25                  30

Ala Met Gly Trp Phe Arg Gln Ala Pro Gly Lys Glu Arg Glu Thr Val
        35                  40                  45

Ala Ala Val Ser Arg Asn Ala Gly Ser Ser Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro
```

<210> SEQ ID NO 288
<211> LENGTH: 10
<212> TYPE: PRT
<213> ORGANISM: Artificial Sequence
<220> FEATURE:
<223> OTHER INFORMATION: 5T4CDR-H1

<400> SEQUENCE: 288

```
Arg Arg Pro Phe Ser Ser Lys Thr Met Ala
1               5                   10
```

<210> SEQ ID NO 289
<211> LENGTH: 10

```
<212> TYPE: PRT
<213> ORGANISM: Artificial Sequence
<220> FEATURE:
<223> OTHER INFORMATION: 5T4 CDR-H1

<400> SEQUENCE: 289

Gly Arg Pro Phe Ser Ser Lys Thr Met Ala
1               5                   10

<210> SEQ ID NO 290
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 290

Glu Arg Pro Phe Gly Thr Tyr Ala Met Gly
1               5                   10

<210> SEQ ID NO 291
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 291

Glu Arg Pro Phe Ser Ser Tyr Ala Met Gly
1               5                   10

<210> SEQ ID NO 292
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 292

Gly Arg Pro Phe Gly Thr Tyr Ala Met Gly
1               5                   10

<210> SEQ ID NO 293
<211> LENGTH: 109
<212> TYPE: PRT
<213> ORGANISM: Artificial Sequence
<220> FEATURE:
<223> OTHER INFORMATION: anti-CD3 VL

<400> SEQUENCE: 293

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
            100                 105
```

-continued

<210> SEQ ID NO 294
<211> LENGTH: 123
<212> TYPE: PRT
<213> ORGANISM: Artificial Sequence
<220> FEATURE:
<223> OTHER INFORMATION: 7E1

<400> SEQUENCE: 294

Gln Val Gln Leu Val Gln Ser Gly Gly Gly Leu Val Gln Ala Gly Ala
1                   5                   10                  15

Ser Leu Arg Leu Ser Cys Val Ala Ser Gly Arg Thr Arg Ser Leu Arg
                20                  25                  30

Thr Met Ala Trp Phe Arg Gln Ala Pro Gly Lys Glu Arg Ile Phe Val
            35                  40                  45

Ala Ala Ile Ser Trp Arg Ser Asp Ser Thr Tyr Tyr Ala Asp Ser Val
        50                  55                  60

Lys Gly Arg Phe Thr Ile Ser Arg Asp Asn Ala Lys Asn Thr Ala Tyr
65                  70                  75                  80

Leu Gln Met Asn Thr Leu Lys Pro Glu Asp Thr Ala Val Tyr Tyr Cys
                85                  90                  95

Ala Ala Gly Gly Gly Trp Leu Ala Thr Thr Pro Asp Glu Tyr Thr Tyr
            100                 105                 110

Trp Gly Gln Gly Thr Leu Val Thr Val Lys Pro
        115                 120

<210> SEQ ID NO 295
<211> LENGTH: 119
<212> TYPE: PRT
<213> ORGANISM: Artificial Sequence
<220> FEATURE:
<223> OTHER INFORMATION: 14F4

<400> SEQUENCE: 295

Gln Val Gln Leu Gln Glu Ser Gly Gly Gly Leu Met Gln Ala Gly Asp
1                   5                   10                  15

Ser Leu Arg Leu Ser Cys Val Val Ser Gly Val Thr Trp Asn Ser Tyr
                20                  25                  30

Thr Met Ala Trp Phe Arg Gln Ala Pro Gly Lys Glu Arg Glu Phe Val
            35                  40                  45

Ala Ala Ile Arg Trp Thr Val Asp Thr Thr Tyr Tyr Ala Asp Phe Val
        50                  55                  60

Lys Gly Arg Phe Thr Ile Ser Arg Asp Tyr Ala Lys Lys Thr Met Tyr
65                  70                  75                  80

Leu Gln Met Asn Asn Leu Lys Pro Glu Asp Ala Ala Val Tyr Tyr Cys
                85                  90                  95

Ala Val Gly Arg Lys Trp Pro Lys Ala Asp Asp Tyr Trp Gly Gln Gly
            100                 105                 110

Thr Leu Val Thr Val Lys Pro
        115

<210> SEQ ID NO 296
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 296

-continued

```
Gly Arg Thr Arg Ser Leu Arg Thr Met Ala
1               5                   10

<210> SEQ ID NO 297
<211> LENGTH: 10
<212> TYPE: PRT
<213> ORGANISM: Artificial Sequence
<220> FEATURE:
<223> OTHER INFORMATION: 5T4 CDR-H1

<400> SEQUENCE: 297

Gly Val Thr Trp Asn Ser Tyr Thr Met Ala
1               5                   10

<210> SEQ ID NO 298
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 298

Ala Ile Ser Trp Arg Ser Asp Ser Thr Tyr
1               5                   10

<210> SEQ ID NO 299
<211> LENGTH: 10
<212> TYPE: PRT
<213> ORGANISM: Artificial Sequence
<220> FEATURE:
<223> OTHER INFORMATION: 5T4 CDR-H2

<400> SEQUENCE: 299

Ala Ile Arg Trp Thr Val Asp Thr Thr Tyr
1               5                   10

<210> SEQ ID NO 300
<211> LENGTH: 14
<212> TYPE: PRT
<213> ORGANISM: Artificial Sequence
<220> FEATURE:
<223> OTHER INFORMATION: 5T4 CDR-H3

<400> SEQUENCE: 300

Gly Gly Gly Trp Leu Ala Thr Thr Pro Asp Glu Tyr Thr Tyr
1               5                   10

<210> SEQ ID NO 301
<211> LENGTH: 10
<212> TYPE: PRT
<213> ORGANISM: Artificial Sequence
<220> FEATURE:
<223> OTHER INFORMATION: 5T4 CDR-H3

<400> SEQUENCE: 301

Gly Arg Lys Trp Pro Lys Ala Asp Asp Tyr
1               5                   10

<210> SEQ ID NO 302
<211> LENGTH: 122
<212> TYPE: PRT
<213> ORGANISM: Artificial Sequence
<220> FEATURE:
<223> OTHER INFORMATION: 4D3

<400> SEQUENCE: 302

Gln Val Gln Leu Gln Glu Ser Gly Gly Gly Leu Val Gln Ala Gly Gly
```

-continued

```
1               5                   10                  15

Ser Leu Arg Leu Ser Cys Ala Ala Ser Arg Arg Pro Phe Ser Ser Lys
            20                  25                  30

Thr Met Ala Trp Phe Arg Gln Thr Pro Gly Lys Glu Arg Glu Phe Val
        35                  40                  45

Ala Ala Val Arg Trp Ile Gly Gly Ala Thr Arg Tyr Thr Asp Ser Val
    50                  55                  60

Lys Gly Arg Phe Ser Ile Ser Lys Asp Asn Ala Ile Asn Thr Val Tyr
65                  70                  75                  80

Leu Gln Thr Asn Ser Leu Lys Ser Glu Asp Thr Ala Val Tyr Tyr Cys
                85                  90                  95

Ala Ala Gly Gln Thr Trp Gly Thr Lys Phe Thr Asp Tyr Ser Asp Trp
            100                 105                 110

Gly Gln Gly Thr Leu Val Thr Val Lys Pro
        115                 120
```

```
<210> SEQ ID NO 303
<211> LENGTH: 13
<212> TYPE: PRT
<213> ORGANISM: Artificial Sequence
<220> FEATURE:
<223> OTHER INFORMATION: 5T4 CDR-H3

<400> SEQUENCE: 303

Gly Gln Thr Trp Gly Thr Lys Phe Thr Asp Tyr Ser Asp
1               5                   10
```

```
<210> SEQ ID NO 304
<211> LENGTH: 117
<212> TYPE: PRT
<213> ORGANISM: Artificial Sequence
<220> FEATURE:
<223> OTHER INFORMATION: hz18H10v1

<400> SEQUENCE: 304

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gly Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115
```

```
<210> SEQ ID NO 305
<211> LENGTH: 117
<212> TYPE: PRT
<213> ORGANISM: Artificial Sequence
<220> FEATURE:
<223> OTHER INFORMATION: hz18H10v2

<400> SEQUENCE: 305
```

-continued

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
            85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 306
<211> LENGTH: 117
<212> TYPE: PRT
<213> ORGANISM: Artificial Sequence
<220> FEATURE:
<223> OTHER INFORMATION: hz18H10v3

<400> SEQUENCE: 306

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
            85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 307
<211> LENGTH: 117
<212> TYPE: PRT
<213> ORGANISM: Artificial Sequence
<220> FEATURE:
<223> OTHER INFORMATION: hz18H10v4

<400> SEQUENCE: 307

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
```

-continued

```
            50              55              60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
        115

<210> SEQ ID NO 308
<211> LENGTH: 117
<212> TYPE: PRT
<213> ORGANISM: Artificial Sequence
<220> FEATURE:
<223> OTHER INFORMATION: hz18H10v5

<400> SEQUENCE: 308

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
        115

<210> SEQ ID NO 309
<211> LENGTH: 117
<212> TYPE: PRT
<213> ORGANISM: Artificial Sequence
<220> FEATURE:
<223> OTHER INFORMATION: hz18H10v6

<400> SEQUENCE: 309

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110
```

-continued

```
Val Lys Pro Gly Gly
        115

<210> SEQ ID NO 310
<211> LENGTH: 117
<212> TYPE: PRT
<213> ORGANISM: Artificial Sequence
<220> FEATURE:
<223> OTHER INFORMATION: hz18H10v7

<400> SEQUENCE: 310

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 311
<211> LENGTH: 117
<212> TYPE: PRT
<213> ORGANISM: Artificial Sequence
<220> FEATURE:
<223> OTHER INFORMATION: hz18H10v8

<400> SEQUENCE: 311

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 312
<211> LENGTH: 117
<212> TYPE: PRT
<213> ORGANISM: Artificial Sequence
<220> FEATURE:
<223> OTHER INFORMATION: hz18H10v9
```

-continued

```
<400> SEQUENCE: 312

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
            85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 313
<211> LENGTH: 117
<212> TYPE: PRT
<213> ORGANISM: Artificial Sequence
<220> FEATURE:
<223> OTHER INFORMATION: hz18H10v10

<400> SEQUENCE: 313

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
            85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 314
<211> LENGTH: 117
<212> TYPE: PRT
<213> ORGANISM: Artificial Sequence
<220> FEATURE:
<223> OTHER INFORMATION: hz18H10v11

<400> SEQUENCE: 314

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45
```

-continued

```
Ser Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
        115

<210> SEQ ID NO 315
<211> LENGTH: 117
<212> TYPE: PRT
<213> ORGANISM: Artificial Sequence
<220> FEATURE:
<223> OTHER INFORMATION: hz18H10v12

<400> SEQUENCE: 315

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
        115

<210> SEQ ID NO 316
<211> LENGTH: 117
<212> TYPE: PRT
<213> ORGANISM: Artificial Sequence
<220> FEATURE:
<223> OTHER INFORMATION: hz18H10v13

<400> SEQUENCE: 316

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
                20                  25                  30

Thr Met Gly Trp Tyr Arg Gln Ala Pro Gly Lys Gln Arg Glu Leu Val
            35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110
```

-continued

```
Val Lys Pro Gly Gly
        115

<210> SEQ ID NO 317
<211> LENGTH: 117
<212> TYPE: PRT
<213> ORGANISM: Artificial Sequence
<220> FEATURE:
<223> OTHER INFORMATION: hz18H10v14

<400> SEQUENCE: 317

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 318
<211> LENGTH: 117
<212> TYPE: PRT
<213> ORGANISM: Artificial Sequence
<220> FEATURE:
<223> OTHER INFORMATION: hz18H10v15

<400> SEQUENCE: 318

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 319
<211> LENGTH: 117
<212> TYPE: PRT
<213> ORGANISM: Artificial Sequence
<220> FEATURE:
<223> OTHER INFORMATION: hz18H10v16
```

<400> SEQUENCE: 319

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
            115
```

<210> SEQ ID NO 320
<211> LENGTH: 117
<212> TYPE: PRT
<213> ORGANISM: Artificial Sequence
<220> FEATURE:
<223> OTHER INFORMATION: hz18H10v17

<400> SEQUENCE: 320

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Asn Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
            115
```

<210> SEQ ID NO 321
<211> LENGTH: 10
<212> TYPE: PRT
<213> ORGANISM: Artificial Sequence
<220> FEATURE:
<223> OTHER INFORMATION: CDR1

<400> SEQUENCE: 321

```
Gly Ser Met Thr Gly Ala Asn Thr Met Gly
1               5                   10
```

<210> SEQ ID NO 322
<211> LENGTH: 10
<212> TYPE: PRT
<213> ORGANISM: Artificial Sequence

<220> FEATURE:
<223> OTHER INFORMATION: CDR1

<400> SEQUENCE: 322

Gly Ser Val Thr Gly Ala Asn Thr Met Gly
1               5                   10

<210> SEQ ID NO 323
<211> LENGTH: 10
<212> TYPE: PRT
<213> ORGANISM: Artificial Sequence
<220> FEATURE:
<223> OTHER INFORMATION: CDR1

<400> SEQUENCE: 323

Gly Ser Ile Thr Gly Ala Asn Thr Met Gly
1               5                   10

<210> SEQ ID NO 324
<211> LENGTH: 8
<212> TYPE: PRT
<213> ORGANISM: Artificial Sequence
<220> FEATURE:
<223> OTHER INFORMATION: CDR2

<400> SEQUENCE: 324

Leu Ile Gly Asn Tyr Val Thr His
1               5

<210> SEQ ID NO 325
<211> LENGTH: 8
<212> TYPE: PRT
<213> ORGANISM: Artificial Sequence
<220> FEATURE:
<223> OTHER INFORMATION: CDR3

<400> SEQUENCE: 325

Tyr Thr Asp Asn Leu Gly Thr Ser
1               5

<210> SEQ ID NO 326
<211> LENGTH: 115
<212> TYPE: PRT
<213> ORGANISM: Artificial Sequence
<220> FEATURE:
<223> OTHER INFORMATION: 18H10

<400> SEQUENCE: 326

Gln Val Gln Leu Val Gln Ser Gly Gly Gly Leu Val Gln Pro Gly Gly
1               5                   10                  15

Ser Leu Arg Leu Ser Cys Val Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr His Tyr Ala Asp Ser Val Lys Gly Arg Phe
    50                  55                  60

Thr Ile Ser Arg Glu Asn Ala Lys Asn Thr Val Ile Leu Gln Met Asn
65                  70                  75                  80

Ser Leu Asn Pro Glu Asp Thr Ala Val Tyr Tyr Cys Tyr Leu Tyr Thr
                85                  90                  95

Asp Asn Leu Gly Thr Ser Trp Gly Gln Gly Thr Leu Val Thr Val Lys
            100                 105                 110

Pro Gly Gly

```
      115

<210> SEQ ID NO 327
<211> LENGTH: 5
<212> TYPE: PRT
<213> ORGANISM: Artificial Sequence
<220> FEATURE:
<223> OTHER INFORMATION: Linker

<400> SEQUENCE: 327

Pro Gly Gly Gly Gly
1               5

<210> SEQ ID NO 328
<211> LENGTH: 225
<212> TYPE: PRT
<213> ORGANISM: Artificial Sequence
<220> FEATURE:
<223> OTHER INFORMATION: Knob Fc

<400> SEQUENCE: 328

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 329
<211> LENGTH: 225
<212> TYPE: PRT
<213> ORGANISM: Artificial Sequence
<220> FEATURE:
<223> OTHER INFORMATION: Hole Fc

<400> SEQUENCE: 329
```

-continued

```
Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Arg Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Cys Thr Leu Pro Pro Ser Arg Asp Glu Leu Thr Lys Asn Gln Val Ser
    130             135             140

Leu Ser Cys Ala Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Val Ser Lys Leu Thr Val
            180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
    210             215             220

Pro
225
```

```
<210> SEQ ID NO 330
<211> LENGTH: 222
<212> TYPE: PRT
<213> ORGANISM: Artificial Sequence
<220> FEATURE:
<223> OTHER INFORMATION: Knob Fc

<400> SEQUENCE: 330
```

```
Asp Lys Thr His Thr Cys Pro Pro Cys Pro Ala Pro Gly Gly Pro Ser
1               5               10              15

Val Phe Leu Phe Pro Pro Lys Pro Lys Asp Thr Leu Met Ile Ser Arg
            20              25              30

Thr Pro Glu Val Thr Cys Val Val Val Asp Val Ser His Glu Asp Pro
        35              40              45

Glu Val Lys Phe Asn Trp Tyr Val Asp Gly Val Glu Val His Asn Ala
    50              55              60

Lys Thr Lys Pro Arg Glu Glu Gln Tyr Asn Ser Thr Tyr Arg Val Val
65              70              75              80

Ser Val Leu Thr Val Leu His Gln Asp Trp Leu Asn Gly Lys Glu Tyr
            85              90              95

Lys Cys Lys Val Ser Asn Lys Ala Leu Pro Ala Pro Ile Glu Lys Thr
            100             105             110

Ile Ser Lys Ala Lys Gly Gln Pro Arg Glu Pro Gln Val Tyr Thr Leu
            115             120             125
```

```
Pro Pro Cys Arg Asp Glu Leu Thr Lys Asn Gln Val Ser Leu Trp Cys
    130             135             140
```

```
Leu Val Lys Gly Phe Tyr Pro Ser Asp Ile Ala Val Glu Trp Glu Ser
145             150             155             160
```

```
Asn Gly Gln Pro Glu Asn Asn Tyr Lys Thr Thr Pro Pro Val Leu Asp
                165             170             175
```

```
Ser Asp Gly Ser Phe Phe Leu Tyr Ser Lys Leu Thr Val Asp Lys Ser
            180             185             190
```

```
Arg Trp Gln Gln Gly Asn Val Phe Ser Cys Ser Val Met His Glu Ala
            195             200             205
```

```
Leu His Asn His Tyr Thr Gln Lys Ser Leu Ser Leu Ser Pro
    210             215             220
```

```
<210> SEQ ID NO 331
<211> LENGTH: 222
<212> TYPE: PRT
<213> ORGANISM: Artificial Sequence
<220> FEATURE:
<223> OTHER INFORMATION: Hole Fc

<400> SEQUENCE: 331
```

```
Asp Lys Thr His Thr Cys Pro Pro Cys Pro Ala Pro Gly Gly Pro Ser
1               5               10              15
```

```
Val Phe Leu Phe Pro Pro Lys Pro Lys Asp Thr Leu Met Arg Ser Arg
            20              25              30
```

```
Thr Pro Glu Val Thr Cys Val Val Val Asp Val Ser His Glu Asp Pro
            35              40              45
```

```
Glu Val Lys Phe Asn Trp Tyr Val Asp Gly Val Glu Val His Asn Ala
    50              55              60
```

```
Lys Thr Lys Pro Arg Glu Glu Gln Tyr Asn Ser Thr Tyr Arg Val Val
65              70              75              80
```

```
Ser Val Leu Thr Val Leu His Gln Asp Trp Leu Asn Gly Lys Glu Tyr
            85              90              95
```

```
Lys Cys Lys Val Ser Asn Lys Ala Leu Pro Ala Pro Ile Glu Lys Thr
            100             105             110
```

```
Ile Ser Lys Ala Lys Gly Gln Pro Arg Glu Pro Gln Val Cys Thr Leu
            115             120             125
```

```
Pro Pro Ser Arg Asp Glu Leu Thr Lys Asn Gln Val Ser Leu Ser Cys
    130             135             140
```

```
Ala Val Lys Gly Phe Tyr Pro Ser Asp Ile Ala Val Glu Trp Glu Ser
145             150             155             160
```

```
Asn Gly Gln Pro Glu Asn Asn Tyr Lys Thr Thr Pro Pro Val Leu Asp
                165             170             175
```

```
Ser Asp Gly Ser Phe Phe Leu Val Ser Lys Leu Thr Val Asp Lys Ser
            180             185             190
```

```
Arg Trp Gln Gln Gly Asn Val Phe Ser Cys Ser Val Met His Glu Ala
            195             200             205
```

```
Leu His Asn His Tyr Thr Gln Lys Ser Leu Ser Leu Ser Pro
    210             215             220
```

```
<210> SEQ ID NO 332
<211> LENGTH: 225
<212> TYPE: PRT
<213> ORGANISM: Artificial Sequence
<220> FEATURE:
<223> OTHER INFORMATION: Hole Fc
```

```
<400> SEQUENCE: 332

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn Arg Tyr Thr Gln Lys Ser Leu Ser Leu Ser
    210                 215                 220

Pro
225

<210> SEQ ID NO 333
<211> LENGTH: 222
<212> TYPE: PRT
<213> ORGANISM: Artificial Sequence
<220> FEATURE:
<223> OTHER INFORMATION: Hole Fc

<400> SEQUENCE: 333

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
```

-continued

```
            115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
                180                 185                 190

Arg Trp Gln Gln Gly Asn Val Phe Ser Cys Ser Val Met His Glu Ala
            195                 200                 205

Leu His Asn Arg Tyr Thr Gln Lys Ser Leu Ser Leu Ser Pro
    210                 215                 220

<210> SEQ ID NO 334
<211> LENGTH: 225
<212> TYPE: PRT
<213> ORGANISM: Artificial Sequence
<220> FEATURE:
<223> OTHER INFORMATION: Knob Fc

<400> SEQUENCE: 334

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
            195                 200                 205

His Glu Ala Leu His Asn His Tyr Thr Gln Lys Ser Leu Ser Leu Ser
    210                 215                 220

Pro
225

<210> SEQ ID NO 335
<211> LENGTH: 222
<212> TYPE: PRT
```

```
<213> ORGANISM: Artificial Sequence
<220> FEATURE:
<223> OTHER INFORMATION: Knob Fc

<400> SEQUENCE: 335

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
                20                  25                  30

Thr Pro Glu Val Thr Cys Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
                115                 120                 125

Pro Pro Cys Arg Asp Glu Leu Thr Lys Asn Gln Val Ser Leu Trp Cys
            130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Val His Glu Ala
            195                 200                 205

Leu His Asn His Tyr Thr Gln Lys Ser Leu Ser Leu Ser Pro
    210                 215                 220

<210> SEQ ID NO 336
<211> LENGTH: 225
<212> TYPE: PRT
<213> ORGANISM: Artificial Sequence
<220> FEATURE:
<223> OTHER INFORMATION: Hole Fc

<400> SEQUENCE: 336

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110
```

```
Glu Lys Thr Ile Ser Lys Ala Lys Gly Gln Pro Arg Glu Pro Gln Val
    115                 120             125
```

```
Cys Thr Leu Pro Pro Ser Arg Asp Glu Leu Thr Lys Asn Gln Val Ser
    130             135             140
```

```
Leu Ser Cys Ala Val Lys Gly Phe Tyr Pro Ser Asp Ile Ala Val Glu
145                 150             155             160
```

```
Trp Glu Ser Asn Gly Gln Pro Glu Asn Asn Tyr Lys Thr Thr Pro Pro
            165             170             175
```

```
Val Leu Asp Ser Asp Gly Ser Phe Phe Leu Val Ser Lys Leu Thr Val
            180             185             190
```

```
Asp Lys Ser Arg Trp Gln Gln Gly Asn Val Phe Ser Cys Ser Val Val
            195             200             205
```

```
His Glu Ala Leu His Asn Arg Tyr Thr Gln Lys Ser Leu Ser Leu Ser
    210             215             220
```

```
Pro
225
```

```
<210> SEQ ID NO 337
<211> LENGTH: 222
<212> TYPE: PRT
<213> ORGANISM: Artificial Sequence
<220> FEATURE:
<223> OTHER INFORMATION: Hole Fc
```

```
<400> SEQUENCE: 337
```

```
Asp Lys Thr His Thr Cys Pro Pro Cys Pro Ala Pro Gly Gly Pro Ser
1               5               10              15
```

```
Val Phe Leu Phe Pro Pro Lys Pro Lys Asp Thr Leu Tyr Ile Ser Arg
            20              25              30
```

```
Thr Pro Glu Val Thr Cys Val Val Val Asp Val Ser His Glu Asp Pro
        35              40              45
```

```
Glu Val Lys Phe Asn Trp Tyr Val Asp Gly Val Glu Val His Asn Ala
    50              55              60
```

```
Lys Thr Lys Pro Arg Glu Glu Gln Tyr Asn Ser Thr Tyr Arg Val Val
65              70              75              80
```

```
Ser Val Leu Thr Val Leu His Gln Asp Trp Leu Asn Gly Lys Glu Tyr
            85              90              95
```

```
Lys Cys Lys Val Ser Asn Lys Ala Leu Pro Ala Pro Ile Glu Lys Thr
            100             105             110
```

```
Ile Ser Lys Ala Lys Gly Gln Pro Arg Glu Pro Gln Val Cys Thr Leu
    115             120             125
```

```
Pro Pro Ser Arg Asp Glu Leu Thr Lys Asn Gln Val Ser Leu Ser Cys
    130             135             140
```

```
Ala Val Lys Gly Phe Tyr Pro Ser Asp Ile Ala Val Glu Trp Glu Ser
145                 150             155             160
```

```
Asn Gly Gln Pro Glu Asn Asn Tyr Lys Thr Thr Pro Pro Val Leu Asp
            165             170             175
```

```
Ser Asp Gly Ser Phe Phe Leu Val Ser Lys Leu Thr Val Asp Lys Ser
            180             185             190
```

```
Arg Trp Gln Gln Gly Asn Val Phe Ser Cys Ser Val Val His Glu Ala
            195             200             205
```

```
Leu His Asn Arg Tyr Thr Gln Lys Ser Leu Ser Leu Ser Pro
    210             215             220
```

```
<210> SEQ ID NO 338
<211> LENGTH: 226
```

-continued

```
<212> TYPE: PRT
<213> ORGANISM: Artificial Sequence
<220> FEATURE:
<223> OTHER INFORMATION: Fc-Het-1

<400> SEQUENCE: 338

Asp Lys Thr His Thr Cys Pro Pro Cys Pro Ala Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
            35                  40                  45

Asp Pro Glu Val Lys Phe Asn Trp Tyr Val Asp Gly Val Glu Val His
    50                  55                  60

Asn Ala Lys Thr Lys Pro Arg Glu Glu Glu Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
            115                 120                 125

Thr Leu Pro Pro Ser Arg Glu Glu Met Thr Lys Asn Gln Val Ser Leu
    130                 135                 140

Thr Cys Asp Val Ser Gly Phe Tyr Pro Ser Asp Ile Ala Val Glu Trp
145                 150                 155                 160

Glu Ser Asp Gly Gln Pro Glu Asn Asn Tyr Lys Thr Thr Pro Pro Val
            165                 170                 175

Leu Asp Ser Asp Gly Ser Phe Phe Leu Tyr Ser Lys Leu Thr Val Asp
            180                 185                 190

Lys Ser Arg Trp Glu Gln Gly Asp Val Phe Ser Cys Ser Val Met His
            195                 200                 205

Glu Ala Leu His Asn His Tyr Thr Gln Lys Ser Leu Ser Leu Ser Pro
    210                 215                 220

Gly Lys
225

<210> SEQ ID NO 339
<211> LENGTH: 226
<212> TYPE: PRT
<213> ORGANISM: Artificial Sequence
<220> FEATURE:
<223> OTHER INFORMATION: Fc-Het-2

<400> SEQUENCE: 339

Asp Lys Thr His Thr Cys Pro Pro Cys Pro Ala Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
            35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95
```

-continued

```
Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
            115                 120                 125

Thr Leu Pro Pro Ser Arg Glu Gln Met Thr Lys Asn Gln Val Lys Leu
        130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225
```

```
<210> SEQ ID NO 340
<211> LENGTH: 109
<212> TYPE: PRT
<213> ORGANISM: Artificial Sequence
<220> FEATURE:
<223> OTHER INFORMATION: anti-CD3 VL21

<400> SEQUENCE: 340

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
            100                 105
```

```
<210> SEQ ID NO 341
<211> LENGTH: 125
<212> TYPE: PRT
<213> ORGANISM: Artificial Sequence
<220> FEATURE:
<223> OTHER INFORMATION: anti-CD3 VH32

<400> SEQUENCE: 341

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
```

```
            50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser
        115                 120                 125

<210> SEQ ID NO 342
<211> LENGTH: 109
<212> TYPE: PRT
<213> ORGANISM: Artificial Sequence
<220> FEATURE:
<223> OTHER INFORMATION: anti-CD3 VL20

<400> SEQUENCE: 342

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
                100                 105

<210> SEQ ID NO 343
<211> LENGTH: 123
<212> TYPE: PRT
<213> ORGANISM: Artificial Sequence
<220> FEATURE:
<223> OTHER INFORMATION: anti-CD3 VH34

<400> SEQUENCE: 343

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Thr Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val
        115                 120
```

```
<210> SEQ ID NO 344
<211> LENGTH: 225
<212> TYPE: PRT
<213> ORGANISM: Artificial Sequence
<220> FEATURE:
<223> OTHER INFORMATION: IgG1 Knob

<400> SEQUENCE: 344

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro
225

<210> SEQ ID NO 345
<211> LENGTH: 225
<212> TYPE: PRT
<213> ORGANISM: Artificial Sequence
<220> FEATURE:
<223> OTHER INFORMATION: IgG1 Knob

<400> SEQUENCE: 345

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

-continued

```
Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Cys Thr Leu Pro Pro Ser Arg Asp Glu Leu Thr Lys Asn Gln Val Ser
    130             135             140

Leu Ser Cys Ala Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                165             170             175

Val Leu Asp Ser Asp Gly Ser Phe Phe Leu Val Ser Lys Leu Thr Val
            180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro
225
```

```
<210> SEQ ID NO 346
<211> LENGTH: 15
<212> TYPE: PRT
<213> ORGANISM: Artificial Sequence
<220> FEATURE:
<223> OTHER INFORMATION: Linker

<400> SEQUENCE: 346

Gly Gly Gly Gly Ser Gly Gly Gly Gly Ser Gly Gly Gly Gly Ser
1               5               10              15
```

```
<210> SEQ ID NO 347
<211> LENGTH: 10
<212> TYPE: PRT
<213> ORGANISM: Artificial Sequence
<220> FEATURE:
<223> OTHER INFORMATION: 41BB CDR1

<400> SEQUENCE: 347

Gly Phe Ser Phe Ser Ile Asn Ala Met Gly
1               5               10
```

```
<210> SEQ ID NO 348
<211> LENGTH: 9
<212> TYPE: PRT
<213> ORGANISM: Artificial Sequence
<220> FEATURE:
<223> OTHER INFORMATION: 41BB CDR2

<400> SEQUENCE: 348

Ala Ile Glu Ser Gly Arg Asn Thr Val
1               5
```

```
<210> SEQ ID NO 349
<211> LENGTH: 13
<212> TYPE: PRT
<213> ORGANISM: Artificial Sequence
<220> FEATURE:
<223> OTHER INFORMATION: 41BB CDR3

<400> SEQUENCE: 349
```

-continued

```
Leu Lys Gly Asn Arg Val Val Ser Pro Ser Val Ala Tyr
1               5                   10

<210> SEQ ID NO 350
<211> LENGTH: 10
<212> TYPE: PRT
<213> ORGANISM: Artificial Sequence
<220> FEATURE:
<223> OTHER INFORMATION: anti-CD3 VH CDR1

<400> SEQUENCE: 350

Gly Phe Thr Phe Asn Thr Tyr Ala Met Asn
1               5                   10

<210> SEQ ID NO 351
<211> LENGTH: 12
<212> TYPE: PRT
<213> ORGANISM: Artificial Sequence
<220> FEATURE:
<223> OTHER INFORMATION: anti-CD3 VH CDR2

<400> SEQUENCE: 351

Arg Ile Arg Ser Lys Tyr Asn Asn Tyr Ala Thr Tyr
1               5                   10

<210> SEQ ID NO 352
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 352

His Gly Asn Phe Gly Asp Ser Tyr Val Ser Trp Phe Ala Tyr
1               5                   10

<210> SEQ ID NO 353
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 353

Ala Leu Trp Tyr Ser Asn His Trp Val
1               5

<210> SEQ ID NO 354
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 354

Val Leu Trp Tyr Ser Asn Arg Trp Val
1               5

<210> SEQ ID NO 355
<211> LENGTH: 10
<212> TYPE: PRT
<213> ORGANISM: Artificial Sequence
<220> FEATURE:
<223> OTHER INFORMATION: anti-CD3 VH CDR1

<400> SEQUENCE: 355
```

```
Gly Phe Thr Phe Ser Thr Tyr Ala Met Asn
1               5                   10

<210> SEQ ID NO 356
<211> LENGTH: 12
<212> TYPE: PRT
<213> ORGANISM: Artificial Sequence
<220> FEATURE:
<223> OTHER INFORMATION: anti-CD3 VH CDR2

<400> SEQUENCE: 356

Arg Ile Arg Ser Lys Tyr Asn Asn Tyr Ala Thr Tyr
1               5                   10

<210> SEQ ID NO 357
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 357

Gly Ser Ser Thr Gly Ala Val Thr Thr Ser Asn Tyr Ala Asn
1               5                   10

<210> SEQ ID NO 358
<211> LENGTH: 125
<212> TYPE: PRT
<213> ORGANISM: Artificial Sequence
<220> FEATURE:
<223> OTHER INFORMATION: anti-CD3 VH33

<400> SEQUENCE: 358

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
            35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 359
<211> LENGTH: 121
<212> TYPE: PRT
<213> ORGANISM: Artificial Sequence
<220> FEATURE:
<223> OTHER INFORMATION: 41BB sdAb

<400> SEQUENCE: 359

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30
```

-continued

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
                100                 105                 110

Gln Gly Thr Leu Val Thr Val Lys Pro
        115                 120

<210> SEQ ID NO 360
<211> LENGTH: 122
<212> TYPE: PRT
<213> ORGANISM: Artificial Sequence
<220> FEATURE:
<223> OTHER INFORMATION: hz12E9v9

<400> SEQUENCE: 360

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Pro Phe Ser Ser Lys
                20                  25                  30

Thr Met Ala Trp Phe Arg Gln Ala Pro Gly Lys Glu Arg Glu Phe Val
        35                  40                  45

Ala Ala Val Arg Trp Ile Gly Gly Ala Thr Arg Tyr Thr Glu Ser Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
                100                 105                 110

Gly Gln Gly Thr Leu Val Thr Val Lys Pro
        115                 120

<210> SEQ ID NO 361
<211> LENGTH: 5
<212> TYPE: PRT
<213> ORGANISM: Artificial Sequence
<220> FEATURE:
<223> OTHER INFORMATION: Linker

<400> SEQUENCE: 361

Ile Glu Pro Asp Pro
1               5

<210> SEQ ID NO 362
<211> LENGTH: 324
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MISC_FEATURE
<222> LOCATION: (1)..(324)
<223> OTHER INFORMATION: 5T4 ECD, amino acids 32-355 of human 5T4
     (UniProt No. Q13641)

```
<400> SEQUENCE: 362

Ser Ser Pro Thr Ser Ser Ala Ser Ser Phe Ser Ser Ser Ala Pro Phe
1               5                   10                  15

Leu Ala Ser Ala Val Ser Ala Gln Pro Pro Leu Pro Asp Gln Cys Pro
                20                  25                  30

Ala Leu Cys Glu Cys Ser Glu Ala Ala Arg Thr Val Lys Cys Val Asn
            35                  40                  45

Arg Asn Leu Thr Glu Val Pro Thr Asp Leu Pro Ala Tyr Val Arg Asn
        50                  55                  60

Leu Phe Leu Thr Gly Asn Gln Leu Ala Val Leu Pro Ala Gly Ala Phe
65                  70                  75                  80

Ala Arg Arg Pro Pro Leu Ala Glu Leu Ala Ala Leu Asn Leu Ser Gly
                85                  90                  95

Ser Arg Leu Asp Glu Val Arg Ala Gly Ala Phe Glu His Leu Pro Ser
            100                 105                 110

Leu Arg Gln Leu Asp Leu Ser His Asn Pro Leu Ala Asp Leu Ser Pro
        115                 120                 125

Phe Ala Phe Ser Gly Ser Asn Ala Ser Val Ser Ala Pro Ser Pro Leu
    130                 135                 140

Val Glu Leu Ile Leu Asn His Ile Val Pro Pro Glu Asp Glu Arg Gln
145                 150                 155                 160

Asn Arg Ser Phe Glu Gly Met Val Val Ala Ala Leu Leu Ala Gly Arg
                165                 170                 175

Ala Leu Gln Gly Leu Arg Arg Leu Glu Leu Ala Ser Asn His Phe Leu
            180                 185                 190

Tyr Leu Pro Arg Asp Val Leu Ala Gln Leu Pro Ser Leu Arg His Leu
        195                 200                 205

Asp Leu Ser Asn Asn Ser Leu Val Ser Leu Thr Tyr Val Ser Phe Arg
    210                 215                 220

Asn Leu Thr His Leu Glu Ser Leu His Leu Glu Asp Asn Ala Leu Lys
225                 230                 235                 240

Val Leu His Asn Gly Thr Leu Ala Glu Leu Gln Gly Leu Pro His Ile
                245                 250                 255

Arg Val Phe Leu Asp Asn Asn Pro Trp Val Cys Asp Cys His Met Ala
                260                 265                 270

Asp Met Val Thr Trp Leu Lys Glu Thr Glu Val Val Gln Gly Lys Asp
            275                 280                 285

Arg Leu Thr Cys Ala Tyr Pro Glu Lys Met Arg Asn Arg Val Leu Leu
        290                 295                 300

Glu Leu Asn Ser Ala Asp Leu Asp Cys Asp Pro Ile Leu Pro Pro Ser
305                 310                 315                 320

Leu Gln Thr Ser

<210> SEQ ID NO 363
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)..(6)
<223> OTHER INFORMATION: Repeated 0 to 10 times

<400> SEQUENCE: 363

Gly Gly Ser Gly Gly Ser
```

-continued

```
1               5

<210> SEQ ID NO 364
<211> LENGTH: 113
<212> TYPE: PRT
<213> ORGANISM: Artificial Sequence
<220> FEATURE:
<223> OTHER INFORMATION: 18H10

<400> SEQUENCE: 364

Gln Val Gln Leu Val Gln Ser Gly Gly Gly Leu Val Gln Pro Gly Gly
1               5                   10                  15

Ser Leu Arg Leu Ser Cys Val Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr His Tyr Ala Asp Ser Val Lys Gly Arg Phe
    50                  55                  60

Thr Ile Ser Arg Glu Asn Ala Lys Asn Thr Val Ile Leu Gln Met Asn
65                  70                  75                  80

Ser Leu Asn Pro Glu Asp Thr Ala Val Tyr Tyr Cys Tyr Leu Tyr Thr
                85                  90                  95

Asp Asn Leu Gly Thr Ser Trp Gly Gln Gly Thr Leu Val Thr Val Lys
            100                 105                 110

Pro

<210> SEQ ID NO 365
<211> LENGTH: 115
<212> TYPE: PRT
<213> ORGANISM: Artificial Sequence
<220> FEATURE:
<223> OTHER INFORMATION: hz18H10v1

<400> SEQUENCE: 365

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gly Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 366
<211> LENGTH: 115
<212> TYPE: PRT
<213> ORGANISM: Artificial Sequence
<220> FEATURE:
<223> OTHER INFORMATION: hz18H10v2

<400> SEQUENCE: 366
```

-continued

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

```
<210> SEQ ID NO 367
<211> LENGTH: 115
<212> TYPE: PRT
<213> ORGANISM: Artificial Sequence
<220> FEATURE:
<223> OTHER INFORMATION: hz18H10v3

<400> SEQUENCE: 367
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

```
<210> SEQ ID NO 368
<211> LENGTH: 115
<212> TYPE: PRT
<213> ORGANISM: Artificial Sequence
<220> FEATURE:
<223> OTHER INFORMATION: hz18H10v4

<400> SEQUENCE: 368
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60
```

-continued

```
Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 369
<211> LENGTH: 115
<212> TYPE: PRT
<213> ORGANISM: Artificial Sequence
<220> FEATURE:
<223> OTHER INFORMATION: hz18H10v5

<400> SEQUENCE: 369

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 370
<211> LENGTH: 115
<212> TYPE: PRT
<213> ORGANISM: Artificial Sequence
<220> FEATURE:
<223> OTHER INFORMATION: hz18H10v6

<400> SEQUENCE: 370

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
```

-continued

```
                                    115

<210> SEQ ID NO 371
<211> LENGTH: 115
<212> TYPE: PRT
<213> ORGANISM: Artificial Sequence
<220> FEATURE:
<223> OTHER INFORMATION: hz18H10v7

<400> SEQUENCE: 371

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 372
<211> LENGTH: 115
<212> TYPE: PRT
<213> ORGANISM: Artificial Sequence
<220> FEATURE:
<223> OTHER INFORMATION: hz18H10v8

<400> SEQUENCE: 372

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 373
<211> LENGTH: 115
<212> TYPE: PRT
<213> ORGANISM: Artificial Sequence
<220> FEATURE:
<223> OTHER INFORMATION: hz18H10v9

<400> SEQUENCE: 373
```

-continued

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

```
<210> SEQ ID NO 374
<211> LENGTH: 115
<212> TYPE: PRT
<213> ORGANISM: Artificial Sequence
<220> FEATURE:
<223> OTHER INFORMATION: hz18H10v10

<400> SEQUENCE: 374
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

```
<210> SEQ ID NO 375
<211> LENGTH: 115
<212> TYPE: PRT
<213> ORGANISM: Artificial Sequence
<220> FEATURE:
<223> OTHER INFORMATION: hz18H10v11

<400> SEQUENCE: 375
```

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
```

-continued

```
          50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
               100                 105                 110

Val Lys Pro
        115

<210> SEQ ID NO 376
<211> LENGTH: 115
<212> TYPE: PRT
<213> ORGANISM: Artificial Sequence
<220> FEATURE:
<223> OTHER INFORMATION: hz18H10v12

<400> SEQUENCE: 376

Glu Val Gln Leu Val Glu Ser Gly Gly Gly Glu Val Gln Pro Gly Gly
1                   5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
            50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
               100                 105                 110

Val Lys Pro
        115

<210> SEQ ID NO 377
<211> LENGTH: 115
<212> TYPE: PRT
<213> ORGANISM: Artificial Sequence
<220> FEATURE:
<223> OTHER INFORMATION: hz18H10v13

<400> SEQUENCE: 377

Glu Val Gln Leu Val Glu Ser Gly Gly Gly Glu Val Gln Pro Gly Gly
1                   5                   10                  15

Ser Leu Arg Leu Ser Cys Ala Ala Ser Gly Ser Met Thr Gly Ala Asn
                20                  25                  30

Thr Met Gly Trp Tyr Arg Gln Ala Pro Gly Lys Gln Arg Glu Leu Val
            35                  40                  45

Ala Leu Ile Gly Asn Tyr Val Thr His Tyr Ala Glu Ser Val Lys Gly
            50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
               100                 105                 110
```

```
Val Lys Pro
        115

<210> SEQ ID NO 378
<211> LENGTH: 115
<212> TYPE: PRT
<213> ORGANISM: Artificial Sequence
<220> FEATURE:
<223> OTHER INFORMATION: hz18H10v14

<400> SEQUENCE: 378

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 379
<211> LENGTH: 115
<212> TYPE: PRT
<213> ORGANISM: Artificial Sequence
<220> FEATURE:
<223> OTHER INFORMATION: hz18H10v15

<400> SEQUENCE: 379

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 380
<211> LENGTH: 115
<212> TYPE: PRT
<213> ORGANISM: Artificial Sequence
<220> FEATURE:
<223> OTHER INFORMATION: hz18H10v16
```

<400> SEQUENCE: 380

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

<210> SEQ ID NO 381
<211> LENGTH: 115
<212> TYPE: PRT
<213> ORGANISM: Artificial Sequence
<220> FEATURE:
<223> OTHER INFORMATION: hz18H10v17

<400> SEQUENCE: 381

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Asn Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

<210> SEQ ID NO 382
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(389)
<223> OTHER INFORMATION: human 5T4 construct

<400> SEQUENCE: 382

```
Ser Ser Pro Thr Ser Ser Ala Ser Ser Phe Ser Ser Ser Ala Pro Phe
1               5                   10                  15

Leu Ala Ser Ala Val Ser Ala Gln Pro Pro Leu Pro Asp Gln Cys Pro
```

-continued

```
                20                25                30

Ala Leu Cys Glu Cys Ser Glu Ala Ala Arg Thr Val Lys Cys Val Asn
            35                40                45

Arg Asn Leu Thr Glu Val Pro Thr Asp Leu Pro Ala Tyr Val Arg Asn
        50                55                60

Leu Phe Leu Thr Gly Asn Gln Leu Ala Val Leu Pro Ala Gly Ala Phe
65                70                75                80

Ala Arg Arg Pro Pro Leu Ala Glu Leu Ala Ala Leu Asn Leu Ser Gly
                85                90                95

Ser Arg Leu Asp Glu Val Arg Ala Gly Ala Phe Glu His Leu Pro Ser
            100                105                110

Leu Arg Gln Leu Asp Leu Ser His Asn Pro Leu Ala Asp Leu Ser Pro
        115                120                125

Phe Ala Phe Ser Gly Ser Asn Ala Ser Val Ser Ala Pro Ser Pro Leu
    130                135                140

Val Glu Leu Ile Leu Asn His Ile Val Pro Pro Glu Asp Glu Arg Gln
145                150                155                160

Asn Arg Ser Phe Glu Gly Met Val Val Ala Ala Leu Leu Ala Gly Arg
            165                170                175

Ala Leu Gln Gly Leu Arg Arg Leu Glu Leu Ala Ser Asn His Phe Leu
            180                185                190

Tyr Leu Pro Arg Asp Val Leu Ala Gln Leu Pro Ser Leu Arg His Leu
            195                200                205

Asp Leu Ser Asn Asn Ser Leu Val Ser Leu Thr Tyr Val Ser Phe Arg
        210                215                220

Asn Leu Thr His Leu Glu Ser Leu His Leu Glu Asp Asn Ala Leu Lys
225                230                235                240

Val Leu His Asn Gly Thr Leu Ala Glu Leu Gln Gly Leu Pro His Ile
            245                250                255

Arg Val Phe Leu Asp Asn Asn Pro Trp Val Cys Asp Cys His Met Ala
            260                265                270

Asp Met Val Thr Trp Leu Lys Glu Thr Glu Val Val Gln Gly Lys Asp
        275                280                285

Arg Leu Thr Cys Ala Tyr Pro Glu Lys Met Arg Asn Arg Val Leu Leu
        290                295                300

Glu Leu Asn Ser Ala Asp Leu Asp Cys Asp Pro Ile Leu Pro Pro Ser
305                310                315                320

Leu Gln Thr Ser Tyr Val Phe Leu Gly Ile Val Leu Ala Leu Ile Gly
            325                330                335

Ala Ile Phe Leu Leu Val Leu Tyr Leu Asn Arg Lys Gly Ile Lys Lys
            340                345                350

Trp Met His Asn Ile Arg Asp Ala Cys Arg Asp His Met Glu Gly Tyr
            355                360                365

His Tyr Arg Tyr Glu Ile Asn Ala Asp Pro Arg Leu Thr Asn Leu Ser
        370                375                380

Ser Asn Ser Asp Val
385
```

```
<210> SEQ ID NO 383
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MISC_FEATURE
<222> LOCATION: (1)..(395)
<223> OTHER INFORMATION: murine 5T4 construct

<400> SEQUENCE: 383

Ser Ala Pro Ser Ser Ser Val Pro Ser Ser Ser Thr Ser Pro Ala Ala
1               5                   10                  15

Phe Leu Ala Ser Gly Ser Ala Gln Pro Pro Pro Ala Glu Arg Cys Pro
                20                  25                  30

Ala Ala Cys Glu Cys Ser Glu Ala Ala Arg Thr Val Lys Cys Val Asn
            35                  40                  45

Arg Asn Leu Leu Glu Val Pro Ala Asp Leu Pro Pro Tyr Val Arg Asn
        50                  55                  60

Leu Phe Leu Thr Gly Asn Gln Met Thr Val Leu Pro Ala Gly Ala Phe
65              70                  75                  80

Ala Arg Gln Pro Pro Leu Ala Asp Leu Glu Ala Leu Asn Leu Ser Gly
                85                  90                  95

Asn His Leu Lys Glu Val Cys Ala Gly Ala Phe Glu His Leu Pro Gly
            100                 105                 110

Leu Arg Arg Leu Asp Leu Ser His Asn Pro Leu Thr Asn Leu Ser Ala
        115                 120                 125

Phe Ala Phe Ala Gly Ser Asn Ala Ser Val Ser Ala Pro Ser Pro Leu
        130                 135                 140

Glu Glu Leu Ile Leu Asn His Ile Val Pro Pro Glu Asp Gln Arg Gln
145             150                 155                 160

Asn Gly Ser Phe Glu Gly Met Val Ala Phe Glu Gly Met Val Ala Ala
            165                 170                 175

Ala Leu Arg Ser Gly Leu Ala Leu Arg Gly Leu Thr Arg Leu Glu Leu
            180                 185                 190

Ala Ser Asn His Phe Leu Phe Leu Pro Arg Asp Leu Leu Ala Gln Leu
        195                 200                 205

Pro Ser Leu Arg Tyr Leu Asp Leu Arg Asn Asn Ser Leu Val Ser Leu
    210                 215                 220

Thr Tyr Ala Ser Phe Arg Asn Leu Thr His Leu Glu Ser Leu His Leu
225             230                 235                 240

Glu Asp Asn Ala Leu Lys Val Leu His Asn Ser Thr Leu Ala Glu Trp
            245                 250                 255

His Gly Leu Ala His Val Lys Val Phe Leu Asp Asn Asn Pro Trp Val
            260                 265                 270

Cys Asp Cys Tyr Met Ala Asp Met Val Ala Trp Leu Lys Glu Thr Glu
        275                 280                 285

Val Val Pro Asp Lys Ala Arg Leu Thr Cys Ala Phe Pro Glu Lys Met
    290                 295                 300

Arg Asn Arg Gly Leu Leu Asp Leu Asn Ser Ser Asp Leu Asp Cys Asp
305                 310                 315                 320

Ala Val Leu Pro Gln Ser Leu Gln Thr Ser Tyr Val Phe Leu Gly Ile
                325                 330                 335

Val Leu Ala Leu Ile Gly Ala Ile Phe Leu Leu Val Leu Tyr Leu Asn
            340                 345                 350

Arg Lys Gly Ile Lys Lys Trp Met His Asn Ile Arg Asp Ala Cys Arg
            355                 360                 365

Asp His Met Glu Gly Tyr His Tyr Arg Tyr Glu Ile Asn Ala Asp Pro
        370                 375                 380
```

-continued

```
Arg Leu Thr Asn Leu Ser Ser Asn Ser Asp Val
385                 390             395

<210> SEQ ID NO 384
<211> LENGTH: 389
<212> TYPE: PRT
<213> ORGANISM: Artificial Sequence
<220> FEATURE:
<223> OTHER INFORMATION: hmc5T4.1 (human residues underlined)

<400> SEQUENCE: 384

Ser Ser Pro Thr Ser Ser Ala Ser Ser Phe Ser Ser Ser Ala Pro Phe
1               5                   10                  15

Leu Ala Ser Ala Val Ser Ala Gln Pro Pro Leu Pro Asp Gln Cys Pro
            20                  25                  30

Ala Leu Cys Glu Cys Ser Glu Ala Ala Arg Thr Val Lys Cys Val Asn
        35                  40                  45

Arg Asn Leu Thr Glu Val Pro Thr Asp Leu Pro Ala Tyr Val Arg Asn
    50                  55                  60

Leu Phe Leu Thr Gly Asn Gln Leu Ala Val Leu Pro Ala Gly Ala Phe
65                  70                  75                  80

Ala Arg Arg Pro Pro Leu Ala Glu Leu Ala Ala Leu Asn Leu Ser Gly
                85                  90                  95

Ser Arg Leu Asp Glu Val Arg Ala Gly Ala Phe Glu His Leu Pro Ser
            100                 105                 110

Leu Arg Gln Leu Asp Leu Ser His Asn Pro Leu Ala Asp Leu Ser Pro
        115                 120                 125

Phe Ala Phe Ser Gly Ser Asn Ala Ser Val Ser Ala Pro Ser Pro Leu
    130                 135                 140

Val Glu Leu Ile Leu Asn His Ile Val Pro Pro Glu Asp Glu Arg Gln
145                 150                 155                 160

Asn Arg Ser Phe Glu Gly Met Val Val Ala Ala Leu Leu Ser Gly Leu
                165                 170                 175

Ala Leu Arg Gly Leu Thr Arg Leu Glu Leu Ala Ser Asn His Phe Leu
            180                 185                 190

Phe Leu Pro Arg Asp Leu Leu Ala Gln Leu Pro Ser Leu Arg Tyr Leu
        195                 200                 205

Asp Leu Arg Asn Asn Ser Leu Val Ser Leu Thr Tyr Ala Ser Phe Arg
    210                 215                 220

Asn Leu Thr His Leu Glu Ser Leu His Leu Glu Asp Asn Ala Leu Lys
225                 230                 235                 240

Val Leu His Asn Ser Thr Leu Ala Glu Trp His Gly Leu Ala His Val
                245                 250                 255

Lys Val Phe Leu Asp Asn Asn Pro Trp Val Cys Asp Cys Tyr Met Ala
            260                 265                 270

Asp Met Val Ala Trp Leu Lys Glu Thr Glu Val Val Pro Asp Lys Ala
        275                 280                 285

Arg Leu Thr Cys Ala Phe Pro Glu Lys Met Arg Asn Arg Gly Leu Leu
    290                 295                 300

Asp Leu Asn Ser Ser Asp Leu Asp Cys Asp Ala Val Leu Pro Gln Ser
305                 310                 315                 320

Leu Gln Thr Ser Tyr Val Phe Leu Gly Ile Val Leu Ala Leu Ile Gly
                325                 330                 335

Ala Ile Phe Leu Leu Val Leu Tyr Leu Asn Arg Lys Gly Ile Lys Lys
            340                 345                 350
```

-continued

```
Trp Met His Asn Ile Arg Asp Ala Cys Arg Asp His Met Glu Gly Tyr
    355                 360                 365

His Tyr Arg Tyr Glu Ile Asn Ala Asp Pro Arg Leu Thr Asn Leu Ser
    370                 375                 380

Ser Asn Ser Asp Val
385

<210> SEQ ID NO 385
<211> LENGTH: 389
<212> TYPE: PRT
<213> ORGANISM: Artificial Sequence
<220> FEATURE:
<223> OTHER INFORMATION: hmc5T4.2 (human residues underlined)

<400> SEQUENCE: 385

Ser Ala Pro Ser Ser Ser Val Pro Ser Ser Ser Thr Ser Pro Ala Ala
1               5                   10                  15

Phe Leu Ala Ser Gly Ser Ala Gln Pro Pro Ala Glu Arg Cys Pro
            20                  25                  30

Ala Ala Cys Glu Cys Ser Glu Ala Ala Arg Thr Val Lys Cys Val Asn
        35                  40                  45

Arg Asn Leu Leu Glu Val Pro Ala Asp Leu Pro Pro Tyr Val Arg Asn
    50                  55                  60

Leu Phe Leu Thr Gly Asn Gln Met Thr Val Leu Pro Ala Gly Ala Phe
65                  70                  75                  80

Ala Arg Gln Pro Pro Leu Ala Asp Leu Glu Ala Leu Asn Leu Ser Gly
            85                  90                  95

Asn His Leu Lys Glu Val Cys Ala Gly Ala Phe Glu His Leu Pro Ser
            100                 105                 110

Leu Arg Gln Leu Asp Leu Ser His Asn Pro Leu Ala Asp Leu Ser Pro
            115                 120                 125

Phe Ala Phe Ser Gly Ser Asn Ala Ser Val Ser Ala Pro Ser Pro Leu
    130                 135                 140

Val Glu Leu Ile Leu Asn His Ile Val Pro Pro Glu Asp Glu Arg Gln
145                 150                 155                 160

Asn Arg Ser Phe Glu Gly Met Val Val Ala Ala Leu Leu Ala Gly Arg
            165                 170                 175

Ala Leu Gln Gly Leu Arg Arg Leu Glu Leu Ala Ser Asn His Phe Leu
            180                 185                 190

Tyr Leu Pro Arg Asp Val Leu Ala Gln Leu Pro Ser Leu Arg His Leu
            195                 200                 205

Asp Leu Ser Asn Asn Ser Leu Val Ser Leu Thr Tyr Val Ser Phe Arg
    210                 215                 220

Asn Leu Thr His Leu Glu Ser Leu His Leu Glu Asp Asn Ala Leu Lys
225                 230                 235                 240

Val Leu His Asn Ser Thr Leu Ala Glu Trp His Gly Leu Ala His Val
            245                 250                 255

Lys Val Phe Leu Asp Asn Asn Pro Trp Val Cys Asp Cys Tyr Met Ala
            260                 265                 270

Asp Met Val Ala Trp Leu Lys Glu Thr Glu Val Val Pro Asp Lys Ala
            275                 280                 285

Arg Leu Thr Cys Ala Phe Pro Glu Lys Met Arg Asn Arg Gly Leu Leu
    290                 295                 300

Asp Leu Asn Ser Ser Asp Leu Asp Cys Asp Ala Val Leu Pro Gln Ser
305                 310                 315                 320
```

-continued

```
Leu Gln Thr Ser Tyr Val Phe Leu Gly Ile Val Leu Ala Leu Ile Gly
            325                 330                 335

Ala Ile Phe Leu Leu Val Leu Tyr Leu Asn Arg Lys Gly Ile Lys Lys
            340                 345                 350

Trp Met His Asn Ile Arg Asp Ala Cys Arg Asp His Met Glu Gly Tyr
            355                 360                 365

His Tyr Arg Tyr Glu Ile Asn Ala Asp Pro Arg Leu Thr Asn Leu Ser
        370                 375                 380

Ser Asn Ser Asp Val
385

<210> SEQ ID NO 386
<211> LENGTH: 395
<212> TYPE: PRT
<213> ORGANISM: Artificial Sequence
<220> FEATURE:
<223> OTHER INFORMATION: hmc5T4.3 (human residues underlined)

<400> SEQUENCE: 386

Ser Ser Pro Thr Ser Ser Ala Ser Ser Phe Ser Ser Ser Ala Pro Phe
1               5                   10                  15

Leu Ala Ser Ala Val Ser Ala Gln Pro Pro Leu Pro Asp Gln Cys Pro
            20                  25                  30

Ala Leu Cys Glu Cys Ser Glu Ala Ala Arg Thr Val Lys Cys Val Asn
            35                  40                  45

Arg Asn Leu Thr Glu Val Pro Thr Asp Leu Pro Ala Tyr Val Arg Asn
        50                  55                  60

Leu Phe Leu Thr Gly Asn Gln Met Thr Val Leu Pro Ala Gly Ala Phe
65                  70                  75                  80

Ala Arg Gln Pro Pro Leu Ala Asp Leu Glu Ala Leu Asn Leu Ser Gly
            85                  90                  95

Asn His Leu Lys Glu Val Cys Ala Gly Ala Phe Glu His Leu Pro Gly
            100                 105                 110

Leu Arg Arg Leu Asp Leu Ser His Asn Pro Leu Thr Asn Leu Ser Ala
        115                 120                 125

Phe Ala Phe Ala Gly Ser Asn Ala Ser Val Ser Ala Pro Ser Pro Leu
        130                 135                 140

Glu Glu Leu Ile Leu Asn His Ile Val Pro Pro Glu Asp Gln Arg Gln
145                 150                 155                 160

Asn Gly Ser Phe Glu Gly Met Val Ala Phe Glu Gly Met Val Ala Ala
            165                 170                 175

Ala Leu Arg Ser Gly Leu Ala Leu Arg Gly Leu Thr Arg Leu Glu Leu
            180                 185                 190

Ala Ser Asn His Phe Leu Phe Leu Pro Arg Asp Leu Leu Ala Gln Leu
        195                 200                 205

Pro Ser Leu Arg Tyr Leu Asp Leu Arg Asn Asn Ser Leu Val Ser Leu
        210                 215                 220

Thr Tyr Ala Ser Phe Arg Asn Leu Thr His Leu Glu Ser Leu His Leu
225                 230                 235                 240

Glu Asp Asn Ala Leu Lys Val Leu His Asn Ser Thr Leu Ala Glu Trp
            245                 250                 255

His Gly Leu Ala His Val Lys Val Phe Leu Asp Asn Asn Pro Trp Val
            260                 265                 270

Cys Asp Cys Tyr Met Ala Asp Met Val Ala Trp Leu Lys Glu Thr Glu
        275                 280                 285
```

-continued

```
Val Val Pro Asp Lys Ala Arg Leu Thr Cys Ala Phe Pro Glu Lys Met
    290                 295             300
```

```
Arg Asn Arg Gly Leu Leu Asp Leu Asn Ser Ser Asp Leu Asp Cys Asp
305                 310                 315                 320
```

```
Ala Val Leu Pro Gln Ser Leu Gln Thr Ser Tyr Val Phe Leu Gly Ile
                325                 330                 335
```

```
Val Leu Ala Leu Ile Gly Ala Ile Phe Leu Leu Val Leu Tyr Leu Asn
            340                 345                 350
```

```
Arg Lys Gly Ile Lys Lys Trp Met His Asn Ile Arg Asp Ala Cys Arg
            355                 360                 365
```

```
Asp His Met Glu Gly Tyr His Tyr Arg Tyr Glu Ile Asn Ala Asp Pro
    370                 375                 380
```

```
Arg Leu Thr Asn Leu Ser Ser Asn Ser Asp Val
385                 390                 395
```

```
<210> SEQ ID NO 387
<211> LENGTH: 395
<212> TYPE: PRT
<213> ORGANISM: Artificial Sequence
<220> FEATURE:
<223> OTHER INFORMATION: hmc5T4.4 (human residues underlined)

<400> SEQUENCE: 387
```

```
Ser Ala Pro Ser Ser Ser Val Pro Ser Ser Ser Thr Ser Pro Ala Ala
1               5                   10                  15
```

```
Phe Leu Ala Ser Gly Ser Ala Gln Pro Pro Ala Glu Arg Cys Pro
            20                  25                  30
```

```
Ala Ala Cys Glu Cys Ser Glu Ala Ala Arg Thr Val Lys Cys Val Asn
            35                  40                  45
```

```
Arg Asn Leu Leu Glu Val Pro Ala Asp Leu Pro Pro Tyr Val Arg Asn
    50                  55                  60
```

```
Leu Phe Leu Thr Gly Asn Gln Met Thr Val Leu Pro Ala Gly Ala Phe
65                  70                  75                  80
```

```
Ala Arg Gln Pro Pro Leu Ala Asp Leu Glu Ala Leu Asn Leu Ser Gly
                85                  90                  95
```

```
Asn His Leu Lys Glu Val Cys Ala Gly Ala Phe Glu His Leu Pro Gly
            100                 105                 110
```

```
Leu Arg Arg Leu Asp Leu Ser His Asn Pro Leu Thr Asn Leu Ser Ala
            115                 120                 125
```

```
Phe Ala Phe Ala Gly Ser Asn Ala Ser Val Ser Ala Pro Ser Pro Leu
    130                 135                 140
```

```
Glu Glu Leu Ile Leu Asn His Ile Val Pro Pro Glu Asp Gln Arg Gln
145                 150                 155                 160
```

```
Asn Gly Ser Phe Glu Gly Met Val Ala Phe Glu Gly Met Val Ala Ala
                165                 170                 175
```

```
Ala Leu Arg Ser Gly Leu Ala Leu Arg Gly Leu Thr Arg Leu Glu Leu
            180                 185                 190
```

```
Ala Ser Asn His Phe Leu Phe Leu Pro Arg Asp Leu Leu Ala Gln Leu
            195                 200                 205
```

```
Pro Ser Leu Arg Tyr Leu Asp Leu Arg Asn Asn Ser Leu Val Ser Leu
    210                 215                 220
```

```
Thr Tyr Ala Ser Phe Arg Asn Leu Thr His Leu Glu Ser Leu His Leu
225                 230                 235                 240
```

```
Glu Asp Asn Ala Leu Lys Val Leu His Asn Ser Thr Leu Ala Glu Trp
                245                 250                 255
```

-continued

```
His Gly Leu Ala His Val Lys Val Phe Leu Asp Asn Asn Pro Trp Val
            260             265                 270

Cys Asp Cys Tyr Met Ala Asp Met Val Thr Trp Leu Lys Glu Thr Glu
            275             280                 285

Val Val Gln Gly Lys Asp Arg Leu Thr Cys Ala Tyr Pro Glu Lys Met
    290             295             300

Arg Asn Arg Val Leu Leu Glu Leu Asn Ser Ala Asp Leu Asp Cys Asp
305             310             315                 320

Pro Ile Leu Pro Pro Ser Leu Gln Thr Ser Tyr Val Phe Leu Gly Ile
            325             330                 335

Val Leu Ala Leu Ile Gly Ala Ile Phe Leu Leu Val Leu Tyr Leu Asn
            340             345             350

Arg Lys Gly Ile Lys Lys Trp Met His Asn Ile Arg Asp Ala Cys Arg
            355             360             365

Asp His Met Glu Gly Tyr His Tyr Arg Tyr Glu Ile Asn Ala Asp Pro
    370             375             380

Arg Leu Thr Asn Leu Ser Ser Asn Ser Asp Val
385             390             395
```

```
<210> SEQ ID NO 388
<211> LENGTH: 122
<212> TYPE: PRT
<213> ORGANISM: Artificial Sequence
<220> FEATURE:
<223> OTHER INFORMATION: Anti CD3 VH 312557

<400> SEQUENCE: 388

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20              25              30

Ala Met His Trp Val Arg Gln Ala Pro Gly Lys Gly Leu Glu Trp Val
            35              40              45

Ser Gly Ile Ser Trp Asn Ser Gly Ser Ile Gly Tyr Ala Asp Ser Val
    50              55              60

Lys Gly Phe Thr Ile Ser Arg Asp Asn Ala Lys Asn Ser Leu Tyr Leu
65              70              75                  80

Gln Met Asn Ser Leu Arg Ala Glu Asp Thr Ala Leu Tyr Tyr Cys Ala
            85              90              95

Lys Asp Ser Arg Gly Tyr Gly Asp Tyr Arg Leu Gly Gly Ala Tyr Trp
            100             105             110

Gly Gln Gly Thr Leu Val Thr Val Ser Ser
            115             120
```

```
<210> SEQ ID NO 389
<211> LENGTH: 122
<212> TYPE: PRT
<213> ORGANISM: Artificial Sequence
<220> FEATURE:
<223> OTHER INFORMATION: Anti-CD3 VH 312557 G44C

<400> SEQUENCE: 389

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20              25              30

Ala Met His Trp Val Arg Gln Ala Pro Gly Lys Cys Leu Glu Trp Val
            35              40              45
```

-continued

```
Ser Gly Ile Ser Trp Asn Ser Gly Ser Ile Gly Tyr Ala Asp Ser Val
    50                  55                  60

Lys Gly Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr Tyr Cys Ala
                85                  90                  95

Lys Asp Ser Arg Gly Tyr Gly Asp Tyr Arg Leu Gly Gly Ala Tyr Trp
                100                 105                 110

Gly Gln Gly Thr Leu Val Thr Val Ser Ser
            115                 120

<210> SEQ ID NO 390
<211> LENGTH: 107
<212> TYPE: PRT
<213> ORGANISM: Artificial Sequence
<220> FEATURE:
<223> OTHER INFORMATION: Anti-CD3 VL 312557

<400> SEQUENCE: 390

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 391
<211> LENGTH: 107
<212> TYPE: PRT
<213> ORGANISM: Artificial Sequence
<220> FEATURE:
<223> OTHER INFORMATION: Anti-CD3 VL 312557 Q100C

<400> SEQUENCE: 391

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Cys Gly Thr Lys Val Glu Ile Lys
            100                 105
```

-continued

```
<210> SEQ ID NO 392
<211> LENGTH: 124
<212> TYPE: PRT
<213> ORGANISM: Artificial Sequence
<220> FEATURE:
<223> OTHER INFORMATION: CD3-VH-G

<400> SEQUENCE: 392

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 393
<211> LENGTH: 124
<212> TYPE: PRT
<213> ORGANISM: Artificial Sequence
<220> FEATURE:
<223> OTHER INFORMATION: CD3-VH-G

<400> SEQUENCE: 393

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Cys Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 394
<211> LENGTH: 108
<212> TYPE: PRT
<213> ORGANISM: Artificial Sequence
<220> FEATURE:
<223> OTHER INFORMATION: VK1-39Jk5

<400> SEQUENCE: 394

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Ser Ile Ser Ser Tyr
        20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

```
<210> SEQ ID NO 395
<211> LENGTH: 108
<212> TYPE: PRT
<213> ORGANISM: Artificial Sequence
<220> FEATURE:
<223> OTHER INFORMATION: VK1-39Jk5 Q100C

<400> SEQUENCE: 395

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
        20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Cys Gly Thr Arg Leu Glu Ile Lys
            100                 105
```

```
<210> SEQ ID NO 396
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 396

Ala Asp Ala Ala Pro
1               5
```

```
<210> SEQ ID NO 397
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times
```

-continued

```
<400> SEQUENCE: 397

Ala Asp Ala Ala Pro Gly
1               5

<210> SEQ ID NO 398
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 398

Gly Glu Pro Gln Gly
1               5

<210> SEQ ID NO 399
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 399

Gly Glu Pro Gln Gly Gly
1               5

<210> SEQ ID NO 400
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 400

Ala Gly Gly Glu Pro
1               5

<210> SEQ ID NO 401
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 401

Ala Gly Gly Glu Pro Gly
1               5

<210> SEQ ID NO 402
<211> LENGTH: 5
<212> TYPE: PRT
<213> ORGANISM: Artificial Sequence
<220> FEATURE:
```

```
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 402

Ala Gly Ser Glu Pro
1               5

<210> SEQ ID NO 403
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20

<400> SEQUENCE: 403

Ala Gly Ser Glu Pro Gly
1               5

<210> SEQ ID NO 404
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 404

Gly Gly Gly Glu Gln
1               5

<210> SEQ ID NO 405
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 405

Gly Gly Gly Glu Gln Gly
1               5

<210> SEQ ID NO 406
<211> LENGTH: 11
<212> TYPE: PRT
<213> ORGANISM: Artificial Sequence
<220> FEATURE:
<223> OTHER INFORMATION: Linker

<400> SEQUENCE: 406

Ala Asp Ala Ala Pro Ala Asp Ala Ala Pro Gly
1               5                   10

<210> SEQ ID NO 407
<211> LENGTH: 11
<212> TYPE: PRT
```

<213> ORGANISM: Artificial Sequence
<220> FEATURE:
<223> OTHER INFORMATION: Linker

<400> SEQUENCE: 407

Gly Glu Pro Gln Gly Gly Glu Pro Gln Gly Gly
1               5                   10

<210> SEQ ID NO 408
<211> LENGTH: 11
<212> TYPE: PRT
<213> ORGANISM: Artificial Sequence
<220> FEATURE:
<223> OTHER INFORMATION: Linker

<400> SEQUENCE: 408

Ala Gly Gly Glu Pro Ala Gly Gly Glu Pro Gly
1               5                   10

<210> SEQ ID NO 409
<211> LENGTH: 11
<212> TYPE: PRT
<213> ORGANISM: Artificial Sequence
<220> FEATURE:
<223> OTHER INFORMATION: Linker

<400> SEQUENCE: 409

Ala Gly Ser Glu Pro Ala Gly Ser Glu Pro Gly
1               5                   10

<210> SEQ ID NO 410
<211> LENGTH: 11
<212> TYPE: PRT
<213> ORGANISM: Artificial Sequence
<220> FEATURE:
<223> OTHER INFORMATION: Linker

<400> SEQUENCE: 410

Gly Gly Gly Glu Gln Gly Gly Gly Glu Gln Gly
1               5                   10

<210> SEQ ID NO 411
<211> LENGTH: 53
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MISC_FEATURE
<222> LOCATION: (1)..(53)
<223> OTHER INFORMATION: Amino acids 60-112 of human 5T4 ECD

<400> SEQUENCE: 411

Ala Tyr Val Arg Asn Leu Phe Leu Thr Gly Asn Gln Leu Ala Val Leu
1               5                   10                  15

Pro Ala Gly Ala Phe Ala Arg Arg Pro Pro Leu Ala Glu Leu Ala Ala
            20                  25                  30

Leu Asn Leu Ser Gly Ser Arg Leu Asp Glu Val Arg Ala Gly Ala Phe
        35                  40                  45

Glu His Leu Pro Ser
    50

<210> SEQ ID NO 412
<211> LENGTH: 52
<212> TYPE: PRT

-continued

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(52)
<223> OTHER INFORMATION: Amino acids 173-224 of human 5T4 ECD

<400> SEQUENCE: 412

Leu Ala Gly Arg Ala Leu Gln Gly Leu Arg Arg Leu Glu Leu Ala Ser
1               5                   10                  15

Asn His Phe Leu Tyr Leu Pro Arg Asp Val Leu Ala Gln Leu Pro Ser
            20                  25                  30

Leu Arg His Leu Asp Leu Ser Asn Asn Ser Leu Val Ser Leu Thr Tyr
        35                  40                  45

Val Ser Phe Arg
    50
```

5T4 SINGLE DOMAIN ANTIBODIES AND THERAPEUTIC COMPOSITIONS THEREOF

CROSS-REFERENCE TO RELATED APPLICATIONS

This application is a National Stage application under 35 U.S.C. § 371 of International Application No. PCT/US2019/055454, filed on Oct. 9, 2019, which claims priority to U.S. provisional applications 62/744,631, filed Oct. 11, 2018, entitled "5T4 SINGLE DOMAIN ANTIBODIES AND THERAPEUTIC COMPOSITIONS THEREOF'; and 62/877,824, filed Jul. 23, 2019, entitled "5T4 SINGLE DOMAIN ANTIBODIES AND THERAPEUTIC COMPOSITIONS THEREOF" the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 69601-708.831_ST25.txt, created Aug. 8, 2025, which is 395,156 bytes in size. The information in the electronic format of the Sequence Listing is incorporated by reference in its entirety.

FIELD

This disclosure generally provides binding polypeptides that specifically bind 5T4. More specifically, the disclosure relates to fusion proteins, including multivalent and/or multispecific constructs and chimeric antigen receptors, that bind at least 5T4. The disclosure also provides nucleic acid molecules encoding the polypeptides and vectors and cells thereof, and methods of use and uses of the provided 5T4 binding polypeptides for treating diseases and conditions, such as cancer.

BACKGROUND

5T4, also known as trophoblast glycoprotein (TPBG), is a transmembrane glycoprotein expressed on the surface of a wide variety of tumor cells, and its expression has been associated with poor prognosis in a number of cancers. The expression of 5T4 on a variety of cancers in humans, combined with its rare expression in normal adult tissues, makes 5T4 a desirable therapeutic target. Improved therapeutic molecules and agents targeting 5T4 are needed. Provided herein are embodiments that meet such needs.

SUMMARY

Provided herein is a 5T4-binding polypeptide construct, comprising at least one heavy chain only variable domain (5T4 VHH domain) that specifically binds 5T4 and one or more additional binding domain that binds to a target other than 5T4. In some embodiments, the at least one 5T4 VHH domain comprises a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303.

Provided herein is a 5T4-binding construct, comprising at least one heavy chain only variable domain (5T4 VHH domain) comprising a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303.

In some of any of the provided embodiments, the 5T4 is a human 5T4. In some embodiments, the at least one 5T4 VHH domain is humanized. In some embodiments, the 5T4 has the sequence set forth in SEQ ID NO: 244 or a mature form thereof lacking the signal sequence.

In some of any of the provided embodiments, the one or more additional binding domains binds to an activating receptor on an immune cell. In some of any of the provided embodiments, the immune cell is a T cell. In some of any of the provided embodiments, the activating receptor is CD3 (CD3ε). In some examples, the 5T4-binding polypeptide construct is bispecific for 5T4 and CD3. In some embodiments, the immune cell is a Natural Killer (NK) cell.

In some of any of the provided embodiments, the activating receptor is CD16 (CD16a). In some examples, the 5T4-binding polypeptide construct is bispecific for 5T4 and CD16a.

In some of any of the provided embodiments, the one or more additional binding domain binds to a cytokine receptor.

In some of any of the provided embodiments, the one or more additional binding domain comprises an antibody or antigen-binding fragment thereof. In some embodiments, the one or more additional binding domain is monovalent. In some embodiments, the antibody or antigen-binding fragment thereof is an Fv, a disulfide-stabilized Fv (dsFv), scFv, a Fab, a single domain antibody (sdAb), a VNAR, or a VHH. In some embodiments, the single domain antibody (sdAb) is a VNAR, or a VHH. In some embodiments, a single domain antibody (sdAb) is a camelid VHH. In some embodiments, a single domain antibody (sdAb) is a humanized form of a camelid VHH.

In some of any of the provided embodiments, the one or more additional binding domain is a cytokine or is a truncated fragment or variant thereof capable of binding to the cytokine receptor. In some aspects, the cytokine is an interferon, or is a truncated fragment or variant of an interferon. In some examples, the interferon is a type I interferon or a type II interferon, is a truncated fragment or variant of a type I interferon or is a truncated fragment or variant of a type II interferon. In some embodiments, the type I interferon is an IFN-alpha or an IFN-beta or is a truncated fragment or variant thereof; or the type II interferon is an IFN-gamma or is a truncated fragment or variant thereof.

In some of any of the provided embodiments, the polypeptide comprises an immunoglobulin Fc region. In some of any of the provided embodiments, the polypeptide comprises an immunoglobulin Fc region that links the at least one single domain antibody and the one or more additional binding domain. In some of any of the provided embodiments, the 5T4-binding polypeptide construct is a dimer. In some of any of the provided embodiments, the Fc region is a homodimeric Fc region. In some of any of the provided embodiments, the Fc region comprises the sequence of amino acids set forth in any of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 or 13 and binds 5T4. In some of any of the provided embodiments, the Fc region is a human IgG1. In some of any of the provided embodiments, the Fc region comprises the sequence of amino acids set forth in SEQ ID NO:8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8. In some of any of the provided embodiments, the Fc region is a heterodimeric Fc region.

In some embodiments, the Fc region exhibits effector function. In some of any of the provided embodiments, the Fc region comprises a polypeptide comprising one or more amino acid modification that reduces effector function and/ or reduces binding to an effector molecule selected from an Fc gamma receptor or C1q. In some examples, the one or more amino acid modification is deletion of one or more of Glu233, Leu234 or Leu235. In some cases, the Fc region comprises the sequence of amino acids set forth in SEQ ID NO:9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

In some of any of the provided embodiments, the at least one 5T4 VHH domain comprises the VHH domain sequence set forth in any of SEQ ID NOS: 245-287, 294, 295, 302, 360 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-287, 294, 295, 302, 360 and binds 5T4.

In some of any of the provided embodiments, the at least one 5T4 VHH domain binds to an epitope in human 5T4 but does not exhibit crossreactive binding to mouse 5T4.

In some of any of the provided embodiments, the at least one 5T4 VHH domain binds to amino acid residues between amino acids 60 and 112 of SEQ ID NO:382.

In some of any of the provided embodiments, the at least one 5T4 VHH domain binds to amino acid residues between amino acids 173 and 224 of SEQ ID NO:382.

In some of any of the provided embodiments, the at least one 5T4 VHH domain comprises the sequence set forth in (i) SEQ ID NO:245, (ii) a humanized variant of SEQ ID NO:245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:245 and binds 5T4. In some of any of the provided embodiments, the at least one 5T4 VHH domain comprises a CDR1 comprising an amino acid sequence selected from the group consisting of SEQ ID NO: 288 and 289; a CDR2 comprising an amino acid sequence set forth in SEQ ID NO: 88; and a CDR3 comprising an amino acid sequence set forth in SEQ ID NO: 100. In some examples, the at least one 5T4 VHH domain comprises a CDR1, CDR2 and CDR3 set forth in SEQ ID NOS: 288, 88, and 100, respectively; or SEQ ID NOS: 289, 88, and 100, respectively.

In some of any of the provided embodiments, a 5T4 VHH domain comprises the VHH domain sequence set forth in SEQ ID NO:245. In some of any of the provided embodiments, a 5T4 VHH domain comprises the VHH domain sequence set forth in SEQ ID NO:249. In some of any of the provided embodiments, a 5T4 VHH domain comprises the VHH domain sequence set forth in SEQ ID NO: 254. In some of any of the provided embodiments, a 5T4 VHH domain comprises the VHH domain sequence set forth in SEQ ID NO:255. In some of any of the provided embodiments, a 5T4 VHH domain comprises the VHH domain sequence set forth in SEQ ID NO:270. In some of any of the provided embodiments, a 5T4 VHH domain comprises the VHH domain sequence set forth in SEQ ID NO:276. In some of any of the provided embodiments, a 5T4 VHH domain comprises the VHH domain sequence set forth in SEQ ID NO:287. In some of any of the provided embodiments, a 5T4 VHH domain comprises the VHH domain sequence set forth in SEQ ID NO:294. In some of any of the provided embodiments, a 5T4 VHH domain comprises the VHH domain sequence set forth in SEQ ID NO:302. In some of any of the provided embodiments, a 5T4 VHH domain comprises the VHH domain sequence set forth in SEQ ID NO: 360.

In some of any of the provided embodiments, the at least one 5T4 VHH domain comprises the sequence of amino acids set forth in any one of SEQ ID NOs: 246-254 or 360 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 246-254 or 360 and binds 5T4. In some of any of the provided embodiments, the at least one 5T4 VHH domain comprises the sequence of amino acids set forth in any one of SEQ ID NOS: 246-254 or 360. In some of any of the provided embodiments, the at least one 5T4 VHH domain comprises the sequence set forth in (i) SEQ ID NO:255, (ii) a humanized variant of SEQ ID NO: 255, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255 and binds 5T4. In some of any of the provided embodiments, the at least one 5T4 VHH domain comprises a CDR1 comprising an amino acid sequence selected from the group consisting of SEQ ID NOS: 86, 290-292; a CDR2 comprising an amino acid sequence selected from the group consisting of SEQ ID NO: 89-94; and a CDR3 comprising an amino acid sequence set forth in SEQ ID NO: 101. In some examples, the at least one 5T4 VHH domain comprises a CDR1, CDR2 and CDR3 set forth in SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively, the at least one 5T4 VHH domain comprises the sequence of amino acids set forth in any one of SEQ ID NOs: 256-275 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256-275 and binds 5T4. In some of any of the provided embodiments, the at least one 5T4 VHH domain comprises the sequence of amino acids set forth in any one of SEQ ID NOS: 256-275. In some of any of the provided embodiments, the at least one 5T4 VHH domain comprises the sequence set forth in (i) SEQ ID NO:276 (ii) a humanized variant of SEQ ID NO: 276, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 276 and binds 5T4. In some of any of the provided embodiments, the at least one 5T4 VHH domain comprises a CDR1 comprising an amino acid sequence selected from the group consisting of SEQ ID NOS: 86 and 87; a CDR2 comprising an amino acid sequence selected from the group consisting of SEQ ID NOS: 95-99; and a CDR3 comprising an amino acid sequence set forth in SEQ ID NO: 102. In some examples, the at least one 5T4 VHH domain comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

In some of any of the provided embodiments, the at least one 5T4 VHH domain comprises the sequence of amino acids set forth in any one of SEQ ID NOs: 277-287 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 277-287 and binds 5T4. In some of any of the provided embodiments, the at least one 5T4 VHH domain comprises the sequence of amino acids set forth in any one of SEQ ID NOS: 277-287. In some of any of the provided embodiments, the at least one 5T4 VHH domain comprises the sequence set forth in (i) SEQ ID NO:294 (ii) a humanized variant of SEQ ID NO: 294, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:294 and binds 5T4. In some of any of the provided embodiments, the at least one 5T4 VHH domain comprises a CDR1 comprising an amino acid sequence set forth in SEQ ID NO: 296; a CDR2 comprising an amino acid sequence set forth in SEQ ID NO: 298; and a CDR3 comprising an amino acid sequence set forth in SEQ ID NO: 300. In some examples, the at least one 5T4 VHH domain comprises a CDR3 comprising an amino acid sequence selected from the group consisting of SEQ ID NOS: 300, 301, and 303.

In some of any of the provided embodiments, the at least one 5T4 VHH domain comprises a CDR1 comprising an amino acid sequence selected from the group consisting of SEQ ID NOS: 288, 296, and 297; and/or a CDR2 comprising an amino acid sequence selected from the group consisting of SEQ ID NOS: 88, 298, and 299.

In some of any of the provided embodiments, the at least one 5T4 VHH domain comprises the sequence set forth in (i) SEQ ID NO:295 (ii) a humanized variant of SEQ ID NO:295, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:295 and binds 5T4. In some of any of the provided embodiments, the at least one 5T4 VHH domain comprises a CDR1 comprising an amino acid sequence set forth in SEQ ID NO: 297; a CDR2 comprising an amino acid sequence set forth in SEQ ID NO: 299; and a CDR3 comprising an amino acid sequence set forth in SEQ ID NO: 301.

In some of any of the provided embodiments, the at least one 5T4 VHH domain comprises the sequence set forth in (i) SEQ ID NO:302 (ii) a humanized variant of SEQ ID NO: 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 302 and binds 5T4. In some of any of the provided embodiments, the at least one 5T4 VHH domain comprises a CDR1 comprising an amino acid sequence set forth in SEQ ID NO: 288; a CDR2 comprising an amino acid sequence set forth in SEQ ID NO: 88; and a CDR3 comprising an amino acid sequence set forth in SEQ ID NO: 303.

In some of any of the provided embodiments, the at least one 5T4 VHH domain comprises the sequence set forth in (i) SEQ ID NO:294, 295, or 302 (ii) a humanized variant of SEQ ID NO: 294, 295, or 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, 295, or 302 and binds 5T4. In some of any of the provided embodiments, the at least one 5T4 VHH domain comprises a CDR1, CDR2 and CDR3 set forth in SEQ ID NOS: 296, 298, and 300, respectively; SEQ ID NOS: 297, 299, and 301, respectively; or SEQ ID NOS: 288, 88, and 303, respectively.

In some of any of the provided embodiments, a 5T4 VHH domain binds to an epitope located between amino acid residues 60 and 112 of the 5T4 extracellular domain set forth in SEQ ID NO:411. In some of any of the provided embodiments, a 5T4 VHH domain binds to an epitope located between amino acid residues 173 and 224 of the 5T4 extracellular domain set forth in SEQ ID NO:412.

In some embodiments, a 5T4 VHH does not cross react with the mouse 5T4 antigen. In some embodiments, a 5T4 VHH comprising the amino acid sequence set forth in SEQ ID NO:245, or humanized variants thereof, do not cross react with the mouse 5T4 antigen. In some embodiments, a 5T4 VHH comprising the amino acid sequence set forth in SEQ ID NO:255, or humanized variants thereof, do not cross react with the mouse 5T4 antigen. In some embodiments, a 5T4 VHH comprising the amino acid sequence set forth in SEQ ID NO:276, or humanized variants thereof, do not cross react with the mouse 5T4 antigen.

In some of any of the provided embodiments, the at least one 5T4 VHH domain is set forth in SEQ ID NO:245, 249, 255, 270, 276, 294, 295 or 302. In some of any of the provided embodiments, the at least one 5T4 VHH domain is set forth in SEQ ID NO:254 or 360. In some of any of the provided embodiments, the at least one 5T4 VHH domain is set forth in SEQ ID NO:360.

In some of any of the provided embodiments, a 5T4 VHH domain may comprise additional amino acids at its N- and/or C-terminal, such as for linkage to another amino acid sequence, such as another polypeptide. In some of any of the provided embodiments, a 5T4 VHH domain may comprise a flexible linker, such as a glycine linker or a linker composed predominately of the amino acids Glycine and Serine, denoted as GS-linkers herein. Such linkers of the present disclosure can be of various lengths, for example, 5, 6, 7, 8, 9, 10, 11, 12, 13, 14, 15, 16, 17, 18, 19, 20 amino acids in length. In some embodiments, the linker comprises an amino acid sequence selected from the group consisting of GGSGGS, i.e., (GGS)₂ (SEQ ID NO: 1); GGSGGGSGGS, i.e., (GGS)₃ (SEQ ID NO: 2); GGSGGSGGSGGS, i.e., (GGS)₄ (SEQ ID NO: 3); and GGSGGSGGSGGSGGS, i.e., (GGS)₅ (SEQ ID NO: 4), Gly-Gly (GG), GGG, GGGG (SEQ ID NO: 5), GGGGG (SEQ ID NO: 6), and GGGGGG (SEQ ID NO: 7). In some embodiments, the linker is (GGGGS)n, wherein n is 1 to 5 (SEQ ID NO:123); (GGGGGS)n, wherein n is 1 to 4 (SEQ ID NO:124); GGGGS (SEQ ID NO:125); GGGGGS (SEQ ID NO: 126); GGGGGSGGGGGSGGGGGS (SEQ ID NO:127); GGGGSGGGGSGGGGS (SEQ ID NO: 128); GGSGGGGSGGGGSGGGGS (SEQ ID NO:129); or PGGGG (SEQ ID NO:327). In some embodiments, the linker is a GG linker. In some embodiments, the 5T4-binding polypeptide includes a combination of a GS-linker and a Glycine linker. In some embodiments, a 5T4 VHH domain may comprise the additional linker at its C-terminus, such as for linkage to another amino acid sequence, such as another polypeptide. In some of any of the provided embodiments, a 5T4 VHH domain may comprise the linker at its N-terminus, such as for linkage to another amino acid sequence, such as another polypeptide.

Provided herein is a multispecific polypeptide construct, comprising a first component comprising a heterodimeric Fc region comprising a first Fc polypeptide and a second Fc polypeptide and a second component comprising an anti-CD3 antibody or antigen-binding fragment comprising a variable heavy chain region (VH) and a variable light chain region (VL), wherein the VH and VL that comprise the anti-CD3 antibody or antigen binding fragment are linked to opposite polypeptides of the heterodimeric Fc; the first and second components are coupled by a linker, wherein the heterodimeric Fc region is positioned N-terminal to the anti-CD3 antibody; and one or both of the first and second components comprises at least one antigen binding domain comprising a heavy chain only variable domain that specifically binds 5T4 (5T4 VHH domain). In some embodiments, the multispecific polypeptide construct comprises at least a first polypeptide comprising the first Fc polypeptide of the heterodimeric Fc region, the linker and the VH or VL domain of the anti-CD3 antibody or antigen binding fragment; and a second polypeptide comprising the second Fc polypeptide of the heterodimeric Fc region, the linker, optionally the same linker as present in the first polypeptide, and the other of the VH or VL domain of the anti-CD3 antibody or antigen binding fragment, wherein one or both of the first and second polypeptide comprise the at least one 5T4 VHH domain.

In some of any of the provided embodiments, one or both of the first and second Fc polypeptides of the heterodimeric Fc region comprises at least one modification to induce heterodimerization compared to a polypeptide of a homodimeric Fc region, optionally compared to the Fc polypeptide set forth in SEQ ID NO: 8 or an immunologically active fragment thereof. In some embodiments, each of the first and second Fc polypeptides of the heterodimeric Fc independently comprise at least one amino acid modification. In some embodiments, each of the first and second Fc polypeptides of the heterodimeric Fc comprise a knob-into-hole modification or comprise a charge mutation to increase electrostatic complementarity of the polypeptides. In some examples, the amino acid modification is a knob-into-hole modification.

In some of any of the provided embodiments, the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification Thr366Trp. In some of any of the provided embodiments, the first and second Fc polypeptides further comprises a modification of a non-cysteine residue to a cysteine residue, wherein the modification of the first polypeptide is at one of the position Ser354 and Tyr349 and the modification of the second Fc polypeptide is at the other of the position Ser354 and Tyr349. In some of any of the provided embodiments, the VL domain of the anti-CD3 antibody or antigen binding fragment is linked to the first Fc polypeptide of the heterodimeric Fc and the VH domain of the anti-CD3 antibody or antigen binding fragment is linked to the second Fc polypeptide of the heterodimeric Fc.

In some of any of the provided embodiments, the amino acid modification is a charge mutation to increase electrostatic complementarity of the polypeptides. In some of any of the provided embodiments, the first and/or second Fc polypeptides or each of the first and second Fc polypeptide comprise a modification in complementary positions, wherein the modification is replacement with an amino acid having an opposite charge to the complementary amino acid of the other polypeptide.

In some of any of the provided embodiments, one of the first or second Fc polypeptide of the heterodimeric Fc further comprises a modification at residue Ile253. In some examples, the modification is Ile253Arg. In some of any of the provided embodiments, one of the first or second Fc polypeptide of the heterodimeric Fc further comprises a modification at residue His435. In some examples, the modification is His435Arg. In some of any of the provided embodiments, the Fc region comprises a polypeptide that lacks Lys447.

In some of any of the provided embodiments, the Fc region comprises a polypeptide comprising at least one modification to enhance FcRn binding. In some embodiments, the modification is at a position selected from the group consisting of Met252, Ser254, Thr256, Met428, Asn434, and combinations thereof. In some cases, the modification is at a position selected from the group consisting of Met252Y, Ser254T, Thr256E, Met428L, Met428V, Asn434S, and combinations thereof. In some examples, the modification is at position Met252 and at position Met428. In some embodiments, the modification is Met252Y and Met428L. In some cases, the modification is Met252Y and Met428V.

In some of any of the provided embodiments, the first polypeptide of the heterodimeric Fc comprises the sequence of amino acids set forth in any of SEQ ID NOS: 103, 107, 115 or 117, and the second polypeptide of the heterodimeric Fc comprises the sequence of amino acids set forth in any of SEQ ID NOS: 104, 108, 111, 113, 119 or 121.

In some embodiments, the first Fc polypeptide of the heterodimeric Fc region comprises the sequence of amino acids set forth in any of SEQ ID NOS: 103, 107, 115, 117, 328, or 334 and the second Fc polypeptide of the heterodimeric Fc region comprises the sequence of amino acids set forth in any of SEQ ID NOS: 104, 108, 111, 113, 119, 121, 329, 332, or 336.

In some of any of the provided embodiments, the Fc region comprises a polypeptide comprising at least one amino acid modification that reduces effector function and/or reduces binding to an effector molecule selected from an Fc gamma receptor or C1q. In some examples, the one or more amino acid modification is deletion of one or more of Glu233, Leu234 or Leu235.

In some of any of the provided embodiments, the first polypeptide of the heterodimeric Fc comprises the sequence of amino acids set forth in any of SEQ ID NOS: 105, 109, 116 or 118 and the second polypeptide of the heterodimeric Fc comprises the sequence of amino acids set forth in any of SEQ ID NOS: 106, 110, 112, 114, 120 or 122.

In some of any of the provided embodiments, the first Fc polypeptide of the heterodimeric Fc region comprises the sequence of amino acids set forth in any of SEQ ID NOS: 105, 109, 116, 118, 330, or 335 and the second Fc polypeptide of the heterodimeric Fc region comprises the sequence of amino acids set forth in any of SEQ ID NOS: 106, 110, 112, 114, 120, 122, 331, 333, or 337.

In some of any of the provided embodiments, the anti-CD3 antibody or antigen binding fragment is monovalent. In some of any of the provided embodiments, the anti-CD3 antibody or antigen binding fragment is not a single chain antibody, optionally is not a single chain variable fragment (scFv). In some of any of the provided embodiments, the anti-CD3 antibody or antigen binding fragment is an Fv antibody fragment. In some examples, the Fv antibody fragment comprises a disulfide stabilized anti-CD3 binding Fv fragment (dsFv).

In some of any of the provided embodiments, the anti-CD3 antibody or antigen-binding fragment comprises a VH CDR1 comprising the amino acid sequence TYAMN (SEQ ID NO: 29); a VH CD2 comprising the amino acid sequence RIRSKYNNYATYYADSVKD (SEQ ID NO: 30); a VH CDR3 comprising the amino acid sequence HGNFGN-SYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34). In some of any of the provided embodiments, the anti-CD3 antibody or antigen-binding fragment comprises a VH having the amino acid sequence of any of SEQ ID NOS: 27, 35-65, 341, 343, and 358 or a sequence that exhibits at least 90%, 91%, 92%, 93%, 94%, 95%, 96%, 97%, 98% or 99% sequence identity to any of SEQ ID NOS: 27, 35-65, 341, 343, and 358 and binds CD3; and a VL having the amino acid sequence of any of SEQ ID NOS: 28, 66-84, 293, 340, and 342 or a sequence that exhibits at least 90%, 91%, 92%, 93%, 94%, 95%, 96%, 97%, 98% or 99% sequence identity to any of SEQ ID NOS: 28, 66-84, 293, 340, and 342 and binds CD3. In some of any of the provided embodiments, the anti-CD3 antibody or antigen-binding fragment comprises a VH having the amino acid sequence of any of SEQ ID NOS: 27, 35-65, 341, 343, 358, 388, 389, 392, 393, or a sequence that exhibits at least 90%, 91%, 92%, 93%, 94%, 95%, 96%, 97%, 98% or 99% sequence identity to any of SEQ ID NOS: 27, 35-65, 341, 343, 358, 388, 389, 392, 393, and binds CD3; and a VL having the amino acid sequence of any of SEQ ID NOS: 28, 66-84, 293, 340, 342, 390, 391, 394, 395, or a sequence that exhibits at least 90%, 91%, 92%, 93%, 94%, 95%, 96%, 97%, 98% or 99% sequence identity to any of SEQ ID NOS: 28, 66-84, 293, 340, 342, 390, 391, 394, 395, and binds CD3. Any of the above VH and VL sequences can be combined in any combination in an anti-CD3 antibody or antigen-binding fragment in the provided constructs herein.

In some of any of the provided embodiments, the at least one antigen binding domain binds to an epitope in human 5T4 but does not exhibit crossreactive binding to mouse 5T4.

In some of any of the provided embodiments, the at least one antigen binding domain binds to amino acid residues between amino acids 60 and 112 of SEQ ID NO:382.

In some of any of the provided embodiments, the at least one antigen binding domain binds to amino acid residues between amino acids 173 and 224 of SEQ ID NO:382.

In some of any of the provided embodiments, the anti-CD3 antibody or antigen-binding fragment comprises the amino acid sequence of SEQ ID NO: 47 and the amino acid sequence of SEQ ID NO: 75. In some examples, the anti-CD3 antibody or antigen-binding fragment comprises the amino acid sequence of SEQ ID NO: 47 and the amino acid sequence of SEQ ID NO: 293. In some examples, the anti-CD3 antibody or antigen-binding fragment comprises the amino acid sequence of SEQ ID NO: 341 and the amino acid sequence of SEQ ID NO: 342.

In some of any of the provided embodiments, the at least one 5T4 single domain antibody is positioned amino-terminally relative to the Fc region and/or carboxy-terminally relative to the CD3 binding region of the multispecific polypeptide construct. In some of any of the provided embodiments, the multispecific polypeptide construct comprises a first 5T4 VHH domain that specifically bind 5T4 and a second 5T4 VHH domain that specifically binds 5T4. In some of any of the provided embodiments, the first or second 5T4 VHH domain is positioned amino-terminally relative to the Fc region of the multispecific construct and the other of the first or second 5T4 VHH domain is positioned carboxy-terminally relative to the CD3 binding region of the multispecific construct.

In some of any of the provided embodiments, the first polypeptide comprises in order of N-terminus to C-terminus a first 5T4 VHH domain that binds 5T4, a first polypeptide comprising the first Fc polypeptide of the heterodimeric Fc region, the linker, the VH or VL domain of the anti-CD3 antibody or antigen binding fragment and a second 5T4 VHH domain that binds 5T4; and the second polypeptide comprises in order of N-terminus to C-terminus the second Fc polypeptide of the heterodimeric Fc region, the linker, optionally the same linker as present in the first polypeptide, and the other of the VH or VL domain of the anti-CD3 antibody or antigen binding fragment.

In some of any of the provided embodiments, the first and second 5T4 VHH domain are the same. In some of any of the provided embodiments, the first and second 5T4 VHH domain are different. In some of any of the provided embodiments, the first and second 5T4 VHH domain bind a distinct or non-overlapping epitope of 5T4 and/or do not compete for binding to 5T4. In some of any of the provided embodiments, a 5T4 VHH domain binds to an epitope located between amino acid residues 60 and 112 of the 5T4 extracellular domain corresponding to residues set forth in SEQ ID NO:382. In some of any of the provided embodiments, a 5T4 VHH domain binds to an epitope located between amino acid residues 173 and 224 of the 5T4 extracellular domain corresponding to residues set forth in SEQ ID NO: 382.

In some of any of the provided embodiments, the first and second 5T4 VHH domains bind to the same or an overlapping epitope of the 5T4 extracellular domain. In some of any of the provided embodiments, the first and second 5T4 VHH domains both bind an epitope located between amino acid residues 60 and 112 of the 5T4 extracellular domain corresponding to residues set forth in SEQ ID NO: 382. In some of any of the provided embodiments, the first and second 5T4 VHH domains both bind an epitope located between amino acid residues 173 and 224 of the 5T4 extracellular domain corresponding to residues set forth in SEQ ID NO:382.

In some of any of the provided embodiments, the first and second 5T4 VHH domains bind to different epitopes of the 5T4 extracellular domain. In some of any of the provided embodiments, the first 5T4 VHH domain binds an epitope located between amino acid residues 60 and 112 of the 5T4 extracellular domain corresponding to residues set forth in SEQ ID NO:382, and the second 5T4 VHH domain binds an epitope located between amino acid residues 173 and 224 of the 5T4 extracellular domain corresponding to residues set forth in SEQ ID NO:382.

In some of any of the provided embodiments, the first VHH domain or sdAb comprises the amino acid sequence set forth in any one of SEQ ID NOS: 245-254, 295, 302, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-254, 295, 302, and binds 5T4; and the second VHH domain or sdAb comprises the amino acid sequence set forth in any one of SEQ ID NOS: 255-287, 294, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 255-287, 294 and binds 5T4.

In some of any of the provided embodiments, the first VHH domain or sdAb comprises the amino acid sequence set forth in any one of SEQ ID NOS: 245-254, 295, 302, 360, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-254, 295, 302, 360, and binds 5T4; and the second VHH domain or sdAb comprises the amino acid sequence set forth in any one of SEQ ID NOS: 255-287, 294, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 255-287, 294 and binds 5T4.

In some of any of the provided embodiments, the first and second antibody (5T4 VHH domain) are selected from SEQ ID NO: 245 and SEQ ID NO: 294, respectively. In some of any of the provided embodiments, the first and second 5T4 VHH domains are selected from SEQ ID NO: 245 and SEQ ID NO: 276, respectively. In some of any of the provided embodiments, the first and second 5T4 VHH domain are selected from SEQ ID NO: 245 and SEQ ID NO: 255, respectively. In some of any of the provided embodiments, the first and second 5T4 VHH domain are selected from SEQ ID NO: 245 and SEQ ID NO: 294, respectively. In some of any of the provided embodiments, the first and second 5T4 VHH domain are selected from SEQ ID NO: 295 and SEQ ID NO: 294, respectively. In some of any of the provided embodiments, the first and second 5T4 VHH domain are selected from SEQ ID NO: 249 and SEQ ID NO: 270, respectively. In some of any of the provided embodiments, the first and second 5T4 VHH domain are selected from SEQ ID NO: 254 and SEQ ID NO: 287; respectively. In some of any of the provided embodiments, the first and second 5T4 VHH domain are selected from SEQ ID NO: 302 and SEQ ID NO: 302, respectively. In some of any of the provided embodiments, the first and second 5T4 VHH domain are selected from SEQ ID NO: 360 and SEQ ID NO: 287, respectively. In some of any of the provided embodiments, the at least one 5T4 VHH domain, or each of the first and second 5T4 VHH domain, independently comprises the VHH domain sequence set forth in any of SEQ ID NOS: 245-287, 294, 295, 302, or 360, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-287, 294, 295, 302, or 360 and binds 5T4.

In some of any of the provided embodiments, the at least one 5T4 VHH domain, or each of the first and second 5T4 VHH domain, independently comprises the VHH domain sequence set forth in SEQ ID NO: 360, or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 360 and binds 5T4.

In some of any of the provided embodiments, the at least one 5T4 VHH domain, or each of the first and second 5T4 VHH domain, independently comprises the sequence set forth in (i) SEQ ID NO: 245, (ii) a humanized variant of SEQ ID NO: 245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 245, and binds 5T4. In some of any of the provided embodiments, the at least one 5T4 VHH domain, or each of the first and second 5T4 VHH domain, independently comprises a CDR1 comprising an amino acid sequence selected from the group consisting of SEQ ID NO: 86-87 and 288-292, 296, and 297; a CDR2 comprising an amino acid sequence selected from the group consisting of SEQ ID NO: 88-99, 298, and 299; and a CDR3 comprising an amino acid sequence selected from the group consisting of SEQ ID NO: 100-102, 300, 301, and 303. In some of any of the provided embodiments, the at least one 5T4 VHH domain, or each of the first and second 5T4 VHH domain, independently comprises a CDR1, CDR2 and CDR3 set forth in SEQ ID NOS: 288, 88, and 100, respectively; SEQ ID NOS: 289, 88, and 100, respectively; SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; SEQ ID NOS: 86, 94, and 101, respectively; SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; SEQ ID NOS: 86, 98, and 102, respectively; SEQ ID NOS: 296, 298, and 300, respectively; SEQ ID NOS: 297, 299, and 301, respectively; or SEQ ID NOS: 288, 88, and 303, respectively.

In some of any of the provided embodiments, the at least one 5T4 VHH domain, or each of the first and second 5T4 VHH domain, independently comprises the sequence of amino acids set forth in any one of SEQ ID NOS: 246-254 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NOS: 246-254, and binds 5T4. In some of any of the provided embodiments, the at least one 5T4 VHH domain, or each of the first and second 5T4 VHH domain, independently comprises the sequence of amino acids set forth in any one of SEQ ID NOS: 246-254.

In some of any of the provided embodiments, the at least one 5T4 VHH domain, or each of the first and second 5T4 VHH domain, independently comprises the sequence of amino acids set forth in SEQ ID NO: 360 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 360, and binds 5T4. In some of any of the provided embodiments, the at least one 5T4 VHH domain, or each of the first and second 5T4 VHH domain, independently comprises the sequence of amino acids set forth in SEQ ID NO: 360.

In some of any of the provided embodiments, the at least one 5T4 VHH domain, or each of the first and second 5T4 VHH domain, independently comprises the sequence set forth in (i) SEQ ID NO: 255, (ii) a humanized variant of SEQ ID NO: 255, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255, and binds 5T4. In some of any of the provided embodiments, the at least one 5T4 VHH domain, or each of the first and second 5T4 VHH domain, independently comprises a CDR1 comprising an amino acid sequence selected from the group consisting of SEQ ID NOS: 86, 290-292; a CDR2 comprising an amino acid sequence selected from the group consisting of SEQ ID NOS: 89-94; and a CDR3 comprising an amino acid sequence set forth in SEQ ID NO: 101. In some examples, the at least one 5T4 VHH domain, or each of the first and second 5T4 VHH domain, independently comprises a CDR1, CDR2 and CDR3 set forth in SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively.

In some of any of the provided embodiments, the at least one 5T4 VHH domain, or each of the first and second 5T4 VHH domain, independently comprises the sequence of amino acids set forth in any one of SEQ ID NOs: 256-275 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256-275, and binds 5T4. In some of any of the provided embodiments, the at least one 5T4 VHH domain, or each of the first and second 5T4 VHH domain, independently comprises the sequence of amino acids set forth in any one of SEQ ID NOS: 256-275. In some examples, the at least one 5T4 VHH domain, or each of the first and second 5T4 VHH domain, independently comprises the sequence set forth in (i) SEQ ID NO: 276 (ii) a humanized variant of SEQ ID NO: 276, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 276, and binds 5T4. In some of any of the provided embodiments, the at least one 5T4 VHH domain, or each of the first and second sdAb, independently comprises a CDR1 comprising an amino acid sequence selected from the group consisting of SEQ ID NO: 86 and 87; a CDR2 comprising an amino acid sequence selected from the group consisting of SEQ ID NOS: 95-99; and a CDR3 comprising an amino acid sequence set forth in SEQ ID NO: 102. In some of any of the provided embodiments, the at least one 5T4 VHH domain, or each of the first and second 5T4 VHH domain, independently comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

In some of any of the provided embodiments, the at least one 5T4 VHH domain, or each of the first and second 5T4 VHH domain, independently comprises the sequence of amino acids set forth in any one of SEQ ID NOs: 277-287 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 277-287, and binds 5T4. In some of any of the provided embodiments, the at least one 5T4 VHH domain, or each of the first and second 5T4 VHH domain, independently comprises the sequence of amino acids set forth in any one of SEQ ID NOS: 277-287. In some of any of the provided embodiments, the at least one 5T4 VHH domain, or each of the first and second 5T4 VHH domain, independently comprises the sequence set forth in (i) SEQ ID NO: 294 (ii) a humanized variant of SEQ ID NO: 294, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, and binds 5T4. In some of any of the provided embodiments, the at least one 5T4 VHH domain, or each of the first and second 5T4 VHH domain, independently comprises a CDR1 comprising an amino acid sequence set forth in SEQ ID NO: 296; a CDR2 comprising an amino acid sequence set forth in SEQ ID NO: 298; and a CDR3 comprising an amino acid sequence set forth in SEQ ID NO: 300.

In some of any of the provided embodiments, the at least one 5T4 VHH domain, or each of the first and second 5T4

VHH domain, independently comprises the sequence set forth in (i) SEQ ID NO: 295 (ii) a humanized variant of SEQ ID NO: 295, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 295, and binds 5T4. In some of any of the provided embodiments, the at least one 5T4 VHH domain, or each of the first and second 5T4 VHH domain, independently comprises a CDR1 comprising an amino acid sequence set forth in SEQ ID NO: 297; a CDR2 comprising an amino acid sequence set forth in SEQ ID NO: 299; and a CDR3 comprising an amino acid sequence set forth in SEQ ID NO: 301. In some of any of the provided embodiments, the at least one 5T4 VHH domain, or each of the first and second 5T4 VHH domain, independently comprises the sequence set forth in (i) SEQ ID NO: 302 (ii) a humanized variant of SEQ ID NO: 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 302, and binds 5T4. In some of any of the provided embodiments, the at least one 5T4 VHH domain, or each of the first and second 5T4 VHH domain, independently comprises a CDR1 comprising an amino acid sequence set forth in SEQ ID NO: 288; a CDR2 comprising an amino acid sequence set forth in SEQ ID NO: 88; and a CDR3 comprising an amino acid sequence set forth in SEQ ID NO: 303.

In some of any of the provided embodiments, the at least one 5T4 VHH domain, or each of the first and second sdAb, independently comprises the sequence set forth in (i) SEQ ID NO: 294, 295, or 302 (ii) a humanized variant of SEQ ID NO: 294, 295, or 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, 295, or 302, and binds 5T4.

In some of any of the provided embodiments, the at least one 5T4 VHH domain, or each of the first and second 5T4 VHH domain, independently comprises a CDR1, CDR2 and CDR3 set forth in SEQ ID NOS: 296, 298, and 300, respectively; SEQ ID NOS: 297, 299, and 301, respectively; or SEQ ID NOS: 288, 88, and 303, respectively.

In some of any of the provided embodiments, the at least one 5T4 VHH domain, or each of the first and second 5T4 VHH domain, independently is set forth in SEQ ID NO: 245, 249, 255, 270, 276, 294, 295 or 302.

In some of any of the provided embodiments, the at least one 5T4 VHH domain, or each of the first and second 5T4 VHH domain, independently is set forth in SEQ ID NO: 245, 249, 254, 255, 270, 276, 287, 294, 295, 302, or 360.

In some of any of the provided embodiments, one or both of the first and second components comprises at least one co-stimulatory receptor binding region (CRBR) that binds a co-stimulatory receptor. In some of any of the provided embodiments, the at least one co-stimulatory receptor binding region (CRBR) is positioned amino-terminally relative to the Fc region and/or carboxy-terminally relative to the CD3 binding region of the multispecific polypeptide construct. In some embodiments, the multispecific polypeptide construct comprises only one co-stimulatory receptor binding region (CRBR). In some of any of the provided embodiments, the at least one co-stimulatory receptor binding region (CRBR) is positioned amino-terminally relative to the Fc region of the multispecific polypeptide construct. In some of any of the provided embodiments, the at least one co-stimulatory receptor binding region (CRBR) is positioned carboxy-terminally relative to the CD3 binding region of the multispecific polypeptide construct In some of any of the provided embodiments, the first polypeptide comprises in order of N-terminus to C-terminus a first 5T4 VHH domain that binds 5T4, a first polypeptide comprising the first Fc polypeptide of the heterodimeric Fc region, the linker, the VH or VL domain of the anti-CD3 antibody or antigen binding fragment and a second 5T4 VHH domain that binds 5T4; and the second polypeptide comprises the CRBR and comprises in order of N-terminus to C-terminus the second Fc polypeptide of the heterodimeric Fc region, the linker, optionally the same linker as present in the first polypeptide, the other of the VH or VL domain of the anti-CD3 antibody or antigen binding fragment, wherein the CRBR is positioned amino-terminally relative to the Fc region or carboxy-terminally relative to the anti-CD3 antibody or antigen binding fragment of the second polypeptide.

In some of any of the provided embodiments, the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor. In some of any of the provided embodiments, the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some examples, the antibody or antigen-binding fragment thereof is a Fv, a scFv, a Fab, a single domain antibody (sdAb), a VNAR, or a VHH. In some cases, the antibody or antigen-binding fragment is an sdAb. In some embodiments, the sdAb is a human or humanized sdAb. In some embodiments, the sdAb is a VNAR or a VHH.

In some of any of the provided embodiments, the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D. In some of any of the provided embodiments, the at least one co-stimulatory receptor binding region (CRBR) binds a co-stimulatory receptor selected from among 41BB (CD137), OX40 (CD134), and glucocorticoid-induced TNFR-related protein (GITR). In some of any of the provided embodiments, the at least one co-stimulatory receptor binding region (CRBR) comprises the sequence of amino acids set forth in SEQ ID NO:210 or a sequence that has at least 85%, 86%, 87%, 88%, 89%, 90%, 91%, 92%, 93%, 94%, 95%, 96%, 97%, 98%, or 99% sequence identity to the sequence set forth in SEQ ID NO:210 and binds 4-1BB. In some of any of the provided embodiments, the at least one co-stimulatory receptor binding region (CRBR) comprises the sequence of amino acids set forth in SEQ ID NO:210 binds 4-1BB.

In some of any of the provided embodiments, one or both of the first and second components comprises at least one inhibitory receptor binding region (IRBR) that binds an inhibitory receptor. In some of any of the provided embodiments, the at least one inhibitory receptor binding region (IRBR) is positioned amino-terminally relative to the Fc region and/or carboxy-terminally relative to the CD3 binding region of the multispecific polypeptide construct. In some of any of the provided embodiments, the multispecific polypeptide construct comprises only one inhibitory receptor binding region (IRBR).

In some of any of the provided embodiments, the first polypeptide comprises in order of N-terminus to C-terminus a first 5T4 VHH domain that binds 5T4, a first polypeptide comprising the first Fc polypeptide of the heterodimeric Fc region, the linker, the VH or VL domain of the anti-CD3 antibody or antigen binding fragment and a second 5T4 VHH domain that binds 5T4; and the second polypeptide comprises the IRBR and comprises in order of N-terminus to C-terminus the second Fc polypeptide of the heterodimeric Fc region, the linker, optionally the same linker as present in the first polypeptide, the other of the VH or VL domain of the anti-CD3 antibody or antigen binding fragment, wherein the IRBR is positioned amino-terminally relative to the Fc region or carboxy-terminally relative to the anti-CD3 antibody or antigen-binding fragment of the second polypeptide.

In some of any of the provided embodiments, the at least one IRBR is or comprises the extracellular domain or binding fragment thereof of the native cognate binding partner of the inhibitory receptor, or a variant thereof that exhibits binding activity to the inhibitory receptor. In some of any of the provided embodiments, the at least one IRBR is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the antibody or antigen-binding fragment thereof is a Fv, a scFv, a Fab, a single domain antibody (sdAb), a VNAR, or a VHH. In some cases, the antibody or antigen-binding fragment is an sdAb. In some embodiments, the sdAb is a human or humanized sdAb.

In some of any of the provided embodiments, the at least one IRBR binds a inhibitory receptor selected from among PD-1, CTLA-4, TIGIT, VISTA and TIM3. In some examples, the at least one IRBR binds PD-1.

In some of any of the provided embodiments, the first polypeptide comprises in order of N-terminus to C-terminus a first 5T4 VHH domain that binds 5T4, a first polypeptide comprising the first Fc polypeptide of the heterodimeric Fc region, the linker, the VH or VL domain of the anti-CD3 antibody or antigen binding fragment and a second 5T4 VHH domain that binds 5T4; and the second polypeptide comprises in order of N-terminus to C-terminus one of the IRBR or the CRBR, the second Fc polypeptide of the heterodimeric Fc region, the linker, optionally the same linker as present in the first polypeptide, the other of the VH or VL domain of the anti-CD3 antibody or antigen binding fragment, and the other of the CRBR or IRBR.

In some of any of the provided embodiments, the linker is a peptide or polypeptide linker, optionally wherein the linker is 3, 4, 5, 6, 7, 8, 9, 10, 11, 12, 13, 14, 15, 16, 17, 18, 19 or 20 amino acids in length. In some of any of the provided embodiments, the linker is a non-cleavable linker. In some of any of the provided embodiments, the non-cleavable linker is or comprises GG. In some of any of the provided embodiments, the non-cleavable linker comprises GS, GGS, GGGGS (SEQ ID NO:125), GGGGGS (SEQ ID NO:126) and combinations thereof. In some of any of the provided embodiments, the linker is or comprises the sequence GGGGGSGGGGGSGGGGGS (SEQ ID NO:127). In some of any of the provided embodiments, the linker is a cleavable linker. In some of any of the provided embodiments, the cleavable linker is a polypeptide that functions as a substrate for a protease.

In some of any of the provided embodiments, the protease is produced by an immune effector cell, by a tumor, or by cells present in the tumor microenvironment. In some of any of the provided embodiments, the protease is produced by an immune effector cell and the immune effector cell is an activated T cell, a natural killer (NK) cell, or an NK T cell. In some examples, the protease is selected from among matriptase, a matrix metalloprotease (MMP), granzyme B, and combinations thereof. In some cases, the protease is granzyme B.

In some of any of the provided embodiments, the cleavable linker comprises the amino acid sequence GGSGGG-GIEPDIGGSGGS (SEQ ID NO:171).

Provided herein is an isolated single domain antibody that binds 5T4, comprising a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303. In some embodiments, the isolated single domain antibody comprises the amino acid sequence set forth in any of SEQ ID NOS: 245-287, 294, 295, 302, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-287, 294, 295, 302, and binds 5T4.

In some of any of the provided embodiments, the isolated single domain antibody binds to an epitope in human 5T4 but does not exhibit crossreactive binding to mouse 5T4.

In some of any of the provided embodiments, the isolated single domain antibody binds to amino acid residues between amino acids 60 and 112 of SEQ ID NO:382.

In some of any of the provided embodiments, the isolated single domain antibody binds to amino acid residues between amino acids 173 and 224 of SEQ ID NO:382.

Provided herein is an isolated single domain antibody that binds 5T4, comprising a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303. In some embodiments, the isolated single domain antibody comprises the amino acid sequence set forth in any of SEQ ID NOS: 245-287, 294, 295, 302, 360, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-287, 294, 295, 302, 360, and binds 5T4.

In some of any of the provided embodiments, the single domain antibody comprises the sequence set forth in (i) SEQ ID NO: 245, (ii) a humanized variant of SEQ ID NO: 245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 245, and binds 5T4. In some of any of the provided embodiments, the sdAb comprises a CDR1 comprising an amino acid sequence selected from the group consisting of SEQ ID NO: 288 and 289; a CDR2 comprising an amino acid sequence set forth in SEQ ID NO: 88; and a CDR3 comprising an amino acid sequence set forth in SEQ ID NO: 100. In some of any of the provided embodiments, the sdAb comprises a CDR1, CDR2 and CDR3 set forth in SEQ ID NOS: 288, 88, and 100, respectively; or SEQ ID NOS: 289, 88, and 100, respectively. In some of any of the provided embodiments, the sdAb comprises the sequence of amino acids set forth in any one of SEQ ID NOs: 246-254 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 246-254, and binds 5T4. In some of any of the provided embodiments, the sdAb comprises the sequence of amino acids set forth in any one of SEQ ID NOS: 246-254.

In some of any of the provided embodiments, the single domain antibody comprises the sequence set forth in (i) SEQ ID NO: 245, (ii) a humanized variant of SEQ ID NO: 245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 245, and binds 5T4. In some of any of the provided embodiments, the sdAb comprises a CDR1 comprising an amino acid sequence selected from the group consisting of SEQ ID NO: 288 and 289; a CDR2 comprising an amino acid sequence set forth in SEQ ID NO: 88; and a CDR3 comprising an amino acid sequence set forth in SEQ ID NO: 100. In some of any of the provided embodiments, the sdAb comprises a CDR1, CDR2 and CDR3 set forth in SEQ ID NOS: 288, 88, and 100, respectively; or SEQ ID NOS: 289, 88, and 100, respectively. In some of any of the provided embodiments, the sdAb comprises the sequence of amino acids set forth in any one of SEQ ID NOs: 246-254 or 360 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 246-254, and binds 5T4. In some of any of the provided embodiments, the sdAb comprises the sequence of amino acids set forth in any one of SEQ ID NOS: 246-254 or 360.

In some of any of the provided embodiments, the sdAb comprises the sequence set forth in (i) SEQ ID NO: 255, (ii) a humanized variant of SEQ ID NO: 255, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255, and binds 5T4. In some of any of the provided embodiments, the sdAb comprises a CDR1 comprising an amino acid sequence set forth in SEQ ID NO: 86, 290-292; a CDR2 comprising an amino acid sequence selected from the group consisting of SEQ ID NO: 89-94; and a CDR3 comprising an amino acid sequence set forth in SEQ ID NO: 101. In some of any of the provided embodiments, the sdAb comprises a CDR1, CDR2 and CDR3 set forth in SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively.

In some of any of the provided embodiments, the sdAb comprises the sequence of amino acids set forth in any one of SEQ ID NOs: 256-275 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256-275, and binds 5T4. In some of any of the provided embodiments, the sdAb comprises the sequence of amino acids set forth in any one of SEQ ID NOS: 256-275. In some of any of the provided embodiments, the sdAb comprises the sequence set forth in (i) SEQ ID NO: 276 (ii) a humanized variant of SEQ ID NO: 276, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 276, and binds 5T4. In some of any of the provided embodiments, the sdAb comprises a CDR1 comprising an amino acid sequence selected from the group consisting of SEQ ID NO: 86 and 87; a CDR2 comprising an amino acid sequence selected from the group consisting of SEQ ID NOS: 95-99; and a CDR3 comprising an amino acid sequence set forth in SEQ ID NO: 102. In some examples, the sdAb comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

In some of any of the provided embodiments, the sdAb comprises the sequence of amino acids set forth in any one of SEQ ID NOs: 277-287 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 277-287, and binds 5T4. In some of any of the provided embodiments, the at least one 5T4 VHH domain comprises the sequence of amino acids set forth in any one of SEQ ID NOS: 277-287.

In some of any of the provided embodiments, the sdAb comprises the sequence set forth in (i) SEQ ID NO: 294 (ii) a humanized variant of SEQ ID NO: 294, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, and binds 5T4. In some of any of the provided embodiments, the sdAb comprises a CDR1 comprising an amino acid sequence set forth in SEQ ID NO: 296; a CDR2 comprising an amino acid sequence set forth in SEQ ID NO: 298; and a CDR3 comprising an amino acid sequence set forth in SEQ ID NO: 300.

In some of any of the provided embodiments, the sdAb comprises a CDR3 comprising an amino acid sequence selected from the group consisting of SEQ ID NOS: 300, 301, and 303. In some of any of the provided embodiments, the sdAb comprises a CDR1 comprising an amino acid sequence selected from the group consisting of SEQ ID NOS: 288, 296, and 297; and/or a CDR2 comprising an amino acid sequence selected from the group consisting of SEQ ID NOS: 88, 298, and 299.

In some of any of the provided embodiments, the sdAb comprises the sequence set forth in (i) SEQ ID NO:295 (ii) a humanized variant of SEQ ID NO:295, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:295, and binds 5T4. In some of any of the provided embodiments, the sdAb comprises a CDR1 comprising an amino acid sequence set forth in SEQ ID NO: 297; a CDR2 comprising an amino acid sequence set forth in SEQ ID NO: 299; and a CDR3 comprising an amino acid sequence set forth in SEQ ID NO: 301. In some of any of the provided embodiments, the sdAb comprises the sequence set forth in (i) SEQ ID NO:302 (ii) a humanized variant of SEQ ID NO:302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:302, and binds 5T4. In some of any of the provided embodiments, the sdAb comprises a CDR1 comprising an amino acid sequence set forth in SEQ ID NO: 288; a CDR2 comprising an amino acid sequence set forth in SEQ ID NO: 88; and a CDR3 comprising an amino acid sequence set forth in SEQ ID NO: 303.

In some of any of the provided embodiments, the sdAb comprises the sequence set forth in (i) SEQ ID NO: 294, 295, or 302 (ii) a humanized variant of SEQ ID NO: 294, 295, or 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, 295, or 302, and binds 5T4. In some of any of the provided embodiments, the at least one 5T4 VHH domain comprises a CDR1, CDR2 and CDR3 set forth in SEQ ID NOS: 296, 298, and 300, respectively; SEQ ID NOS: 297, 299, and 301, respectively; or SEQ ID NOS: 288, 88, and 303, respectively.

Provided herein is a polynucleotide(s) encoding any of the 5T4-binding polypeptide provided herein.

Provided herein is a polynucleotide(s) encoding any of the multispecific polypeptide constructs provided herein.

Provided herein is a polynucleotide, comprising a first nucleic acid sequence encoding a first polypeptide of any of the multispecific constructs provided herein and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping. In some embodiments, the first nucleic acid sequence and second nucleic acid sequence are operably linked to the same promoter.

In some of any of the provided embodiments, the nucleic acid encoding a self-cleaving peptide or a peptide that causes ribosome skipping is selected from a T2A, a P2A, a E2A or a F2A.

Provided herein is a polynucleotide encoding any of the provided single domain antibodies.

Provided herein is a vector comprising any of the provided polynucleotides. In some of any of the provided embodiments, the vector is an expression vector. In some of any of the provided embodiments, the vector is a viral vector or a eukaryotic vector, optionally wherein the eukaryotic vector is a mammalian vector.

Provided herein is a cell comprising any of the provided polynucleotide or polynucleotides or any of the provided vector or vectors. In some embodiments, the cell is recombinant or isolated. In some embodiments, the cell is a mammalian cell.

Provided herein is a method of producing a polypeptide, the method comprising introducing into a cell any of the provided polynucleotide or polynucleotides or any of the provided vector or vectors of and culturing the cell under conditions to produce the multispecific polypeptide construct. In some of any of the provided embodiments, the method further comprises isolating or purifying the polypeptide from the cell.

Provided herein is a polypeptide produced by any of the provided methods.

Provided herein is an engineered immune cell, comprising a chimeric antigen receptor comprising an extracellular domain comprising any of the provided single domain antibodies, a transmembrane domain; and an intracellular signaling domain. In some embodiments, the cell is a lymphocyte. In some of any of the provided embodiments, the cell is a T cell or a natural killer (NK) cell. In some of any of the provided embodiments, the intracellular signaling domain comprises an immunoreceptor tyrosine-based activation motif (ITAM) signaling domain. In some of any of the provided embodiments, the intracellular signaling domain is or comprises a CD3zeta signaling domain, optionally a human CD3zeta signaling domain. In some of any of the provided embodiments, the intracellular signaling domain further comprises a signaling domain of a costimulatory molecule. In some of any of the provided embodiments, the costimulatory molecule is CD28, ICOS, 41BB or OX40, optionally a human CD28, a human ICOS, a human 41BB or a human OX40.

Provided herein is a pharmaceutical composition comprising any of provided 5T4-binding polypeptides, multispecific polypeptide constructs, single domain antibodies or engineered immune cells. In some of any of the provided embodiments, the pharmaceutical composition includes a pharmaceutically acceptable carrier. In some embodiments, the pharmaceutical composition is sterile.

Provided herein is a method of stimulating or inducing an immune response in a subject, the method comprising administering, to a subject in need thereof, any of the provided 5T4-binding polypeptides, multispecific polypeptide constructs, single domain antibodies or engineered immune cells or a pharmaceutical compositions. In some embodiments, the immune response is increased against a tumor or cancer, optionally a tumor or a cancer that expresses 5T4. In some embodiments, the method treats a disease or condition in the subject.

Provided herein is a method of treating a disease or condition in a subject, the method comprising administering, to a subject in need thereof, a therapeutically effective amount of any of the provided 5T4-binding polypeptides, multispecific polypeptide constructs, single domain antibodies or engineered immune cells or a pharmaceutical compositions. In some of any of the provided embodiments, the disease or condition is a tumor or a cancer. In some of any of the provided embodiments, said subject is a human.

BRIEF DESCRIPTION OF THE DRAWINGS

FIGS. 2A-2C show binding of 12E9 and humanized variants thereof on T47D. FIGS. 2D-2E show binding of 14B5 and humanized variants thereof on T47D. FIG. 2F shows binding of 16G10 and humanized variants thereof on T47D. Herein the 5T4 sdAbs were operably linked to a human Fc.

FIG. 11B depicts relative luminescence units (RLU) of the luciferase reporter in the presence or absence of 5T4+ cells and treated with 50 nM of the indicated sdAb-Fc or hzsdAb-Fc. FIGS. 11C and 11D depict RLU of the luciferase reporter in the presence (FIG.

11C) or absence (FIG. 11D) of 5T4+ cells and treated with a titration of the indicated hzsdAb-Fc.

Figure 12A:
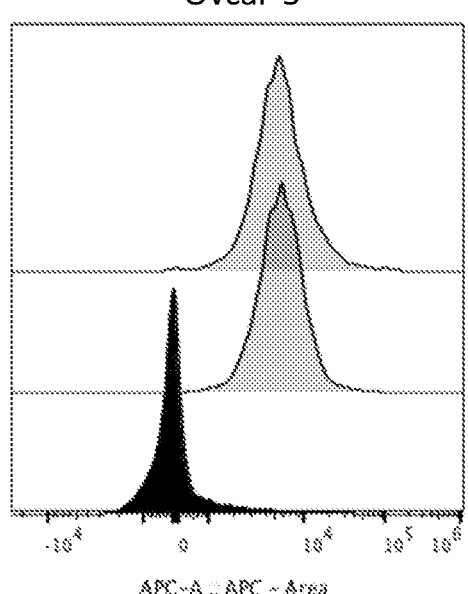
Figure 12B:
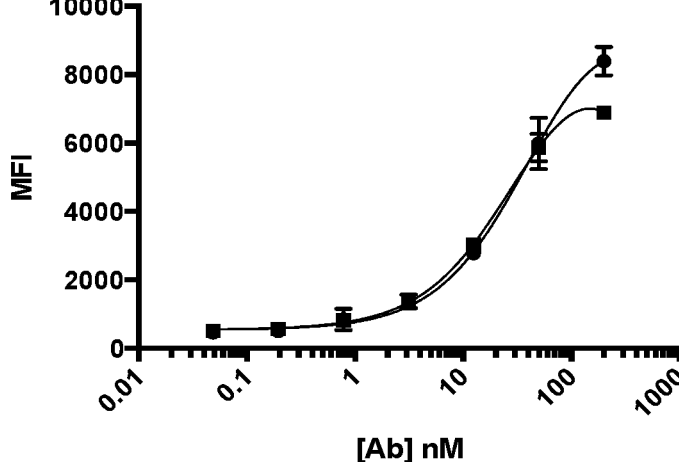
Figure 12C:
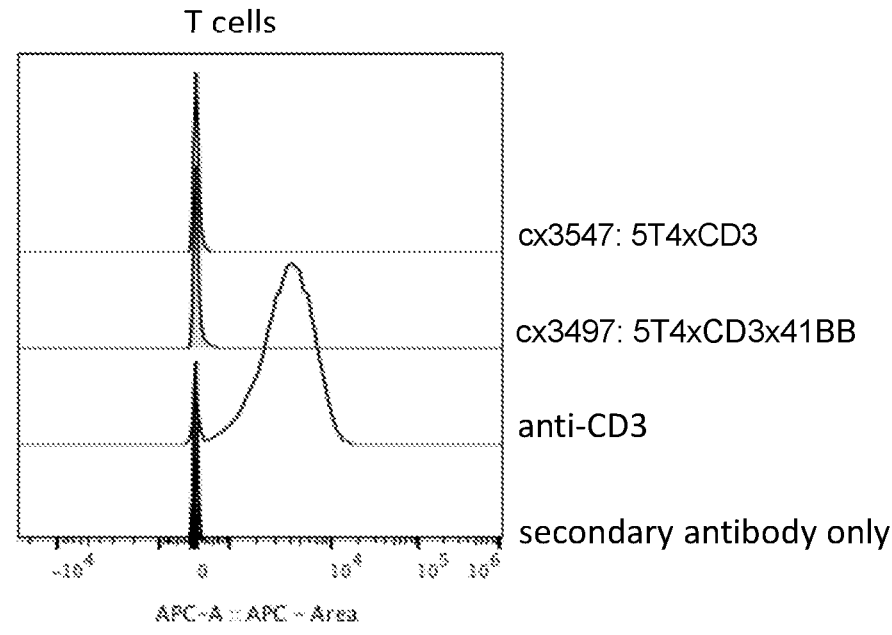
Figure 12D:
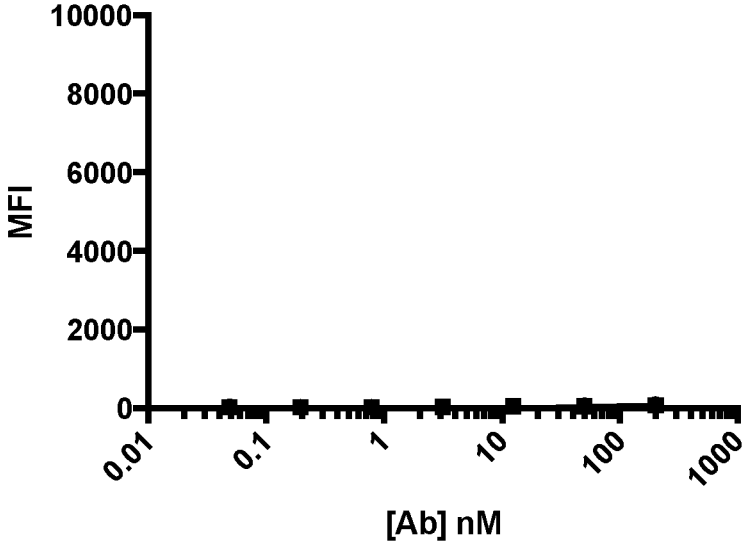

FIGS. 12A-12D depict cellular binding by representative 5T4-targeting constrained CD3 engaging constructs, cx3497 (with a 41BB binding domain) and cx3547 (without a 41BB binding domain). FIG. 12A and FIG. 12B show binding to Ovcar-5 cells (a 5T4 positive melanoma cell line). FIG. 12C and FIG. 12D depict binding to T cells and show the lack of binding to T cells in isolation by the tested constructs. FIG. 12A and FIG. 12C display histograms of the normalized cell counts vs. fluorescence at 200 nM of each construct. The full titration of each construct on the various cell types are shown in FIG. 12B and FIG. 12D. Shown in FIGS. 12A and 12C, the secondary anti-human APC antibody only control is shown in the filled black trace, while the positive control anti-CD3 binding is shown in the open trace, and cx3547 and cx3497 are shown in the gray shaded traces.

FIGS. 13A and 13B depict the kinetics of T-cell cytotoxicity mediated by representative 5T4-targeting constrained CD3 engaging constructs, cx3497 (with a 41BB binding domain) and cx3547 (without a 41BB binding domain) toward a 5T4 positive cell line, Ovcar-5 (FIG. 13A), and a 5T4 negative cell line, CCRF-CEM (FIG. 13B). Total overlap area is representative of double positive: cleaved caspase-3/7 substrate in fluorescently labeled target cells. The initial cytotoxicity observed on the antigen negative cell line is likely mediated by MHC-mismatch between the target cells and the T-cells. Notably only, cx3497 containing a 41BB binding domain was capable of inducing cytotoxicity and the kinetics are consistent with that of 41BB upregulation following TCR-signaling.

Figure 14:
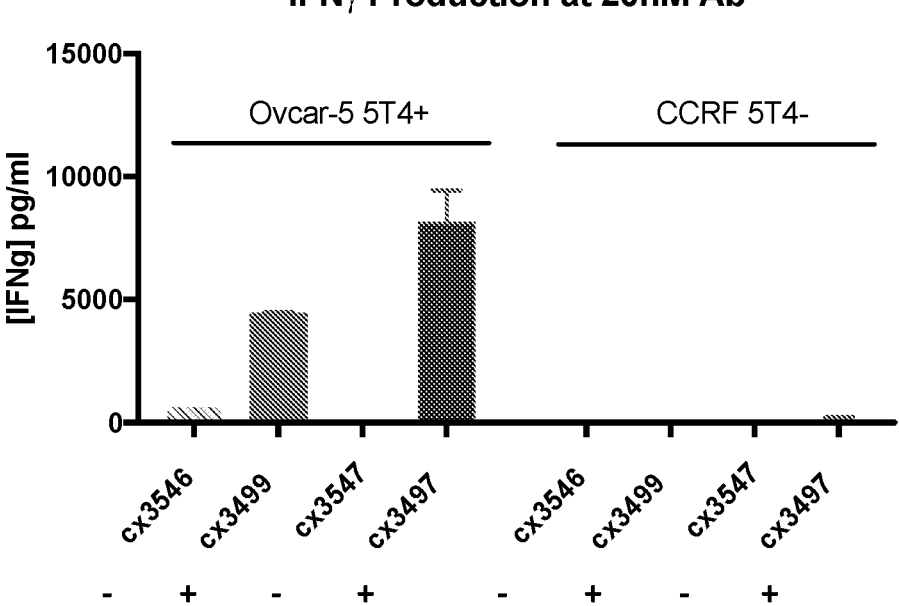

FIG. 14 shows a comparison of IFNγ production by T cells treated with representative 5T4-targeted constrained CD3 engaging constructs with a 41BB binding domain, cx3499 and cx3497, and without a 41BB binding domain, cx3546 and cx3547 in the presence of 5T4-positive Ovcar-5 cells and 5T4-negative CCRF-CEM cells. Cytokine production was monitored by ELISA. cx3546 and cx3499 contain the same 5T4-targeting sdAbs, and cx3547 and cx3497 contain the same 5T4-targeting sdAbs. Thus, the only difference between these sets of constructs is the addition of the 41BB binding domain. 5T4-targeted constrained CD3 engaging constructs incorporating a 41BB binding domain display enhanced capacity to induce IFNγ production from T cells in an antigen-dependent manner.

Figure 15A:
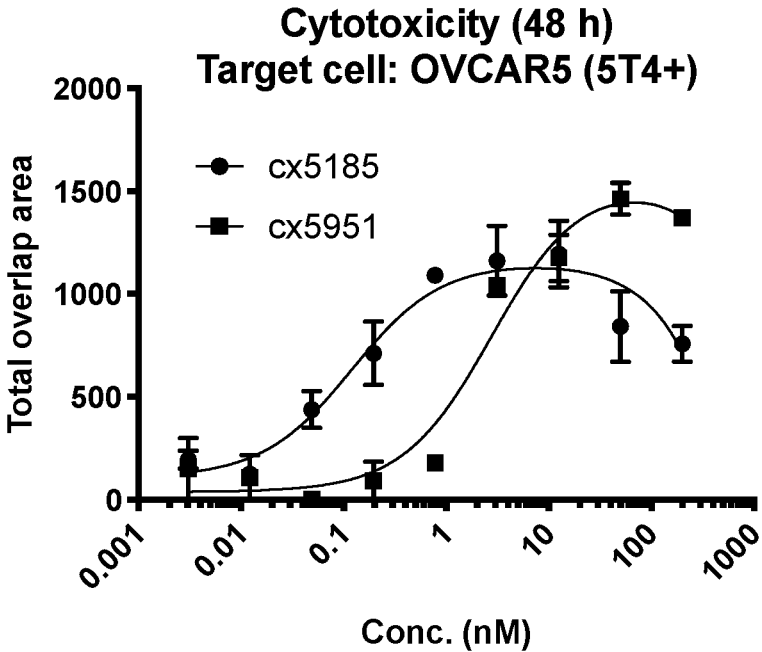
Figure 15B:
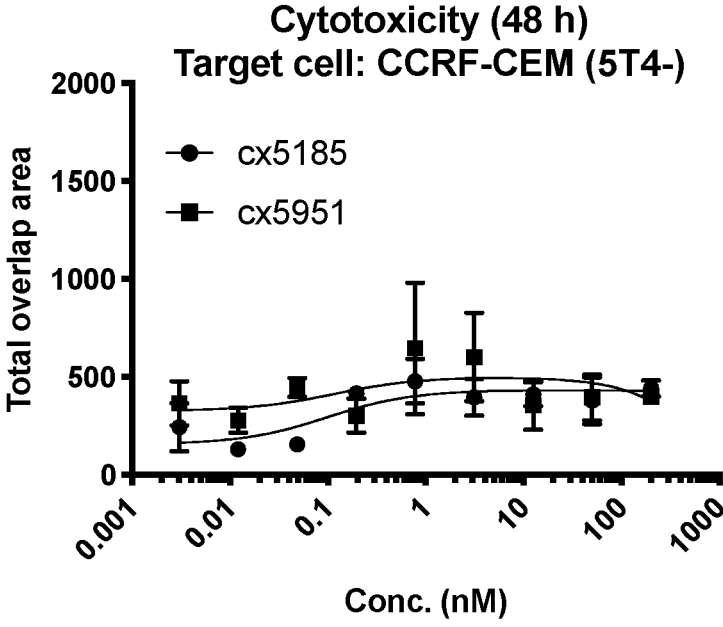

FIGS. 15A and 15B depict the potency of T-cell-mediated cytotoxicity driven by exemplary 5T4-targeted constrained CD3 engaging constructs with a 41BB binding domain, cx5185, and without a 41BB binding domain, cx5951. A titration range of 200 nM to 3.1 pM of the CD3 engaging constructs on the 5T4-positive Ovcar5 cell line is shown in FIG. 15A and the 5T4-negative CCRF-CEM cell line shown in FIG. 15B.

Figure 16A:
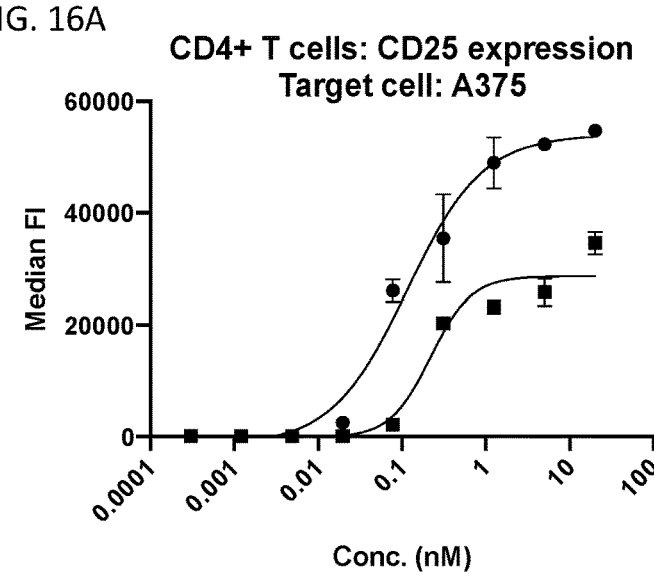
Figure 16A:
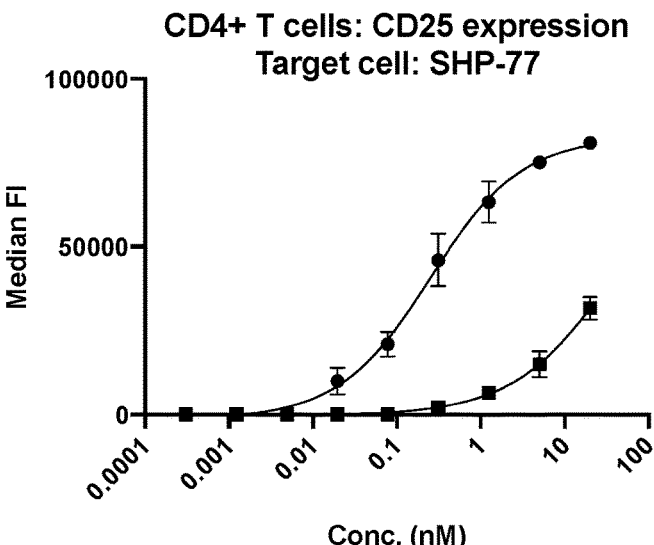
Figure 16A:
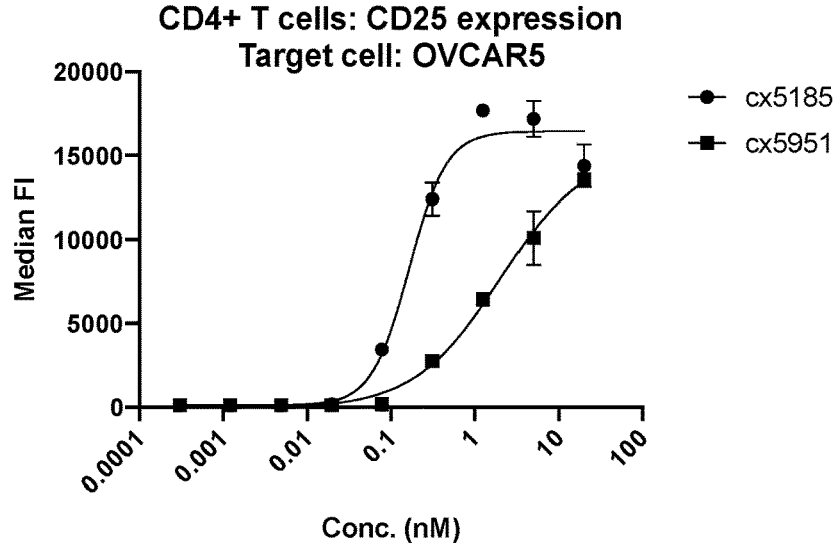
Figure 16B:
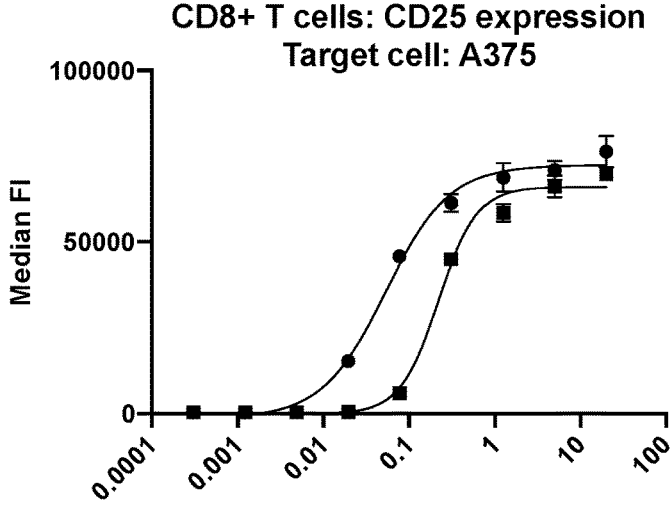
Figure 16B:
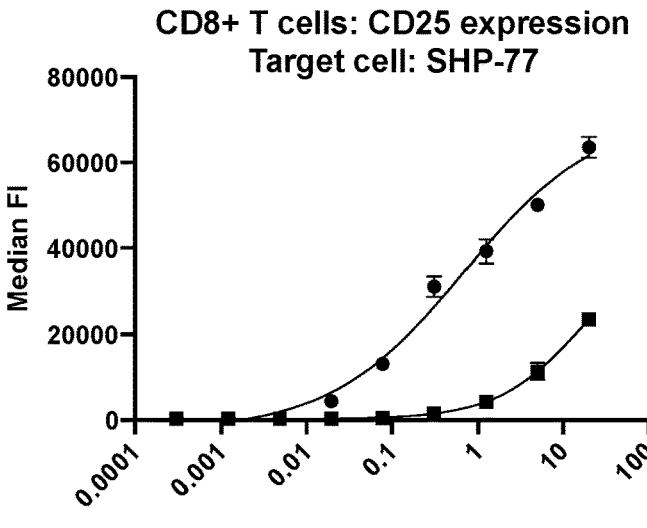
Figure 16B:
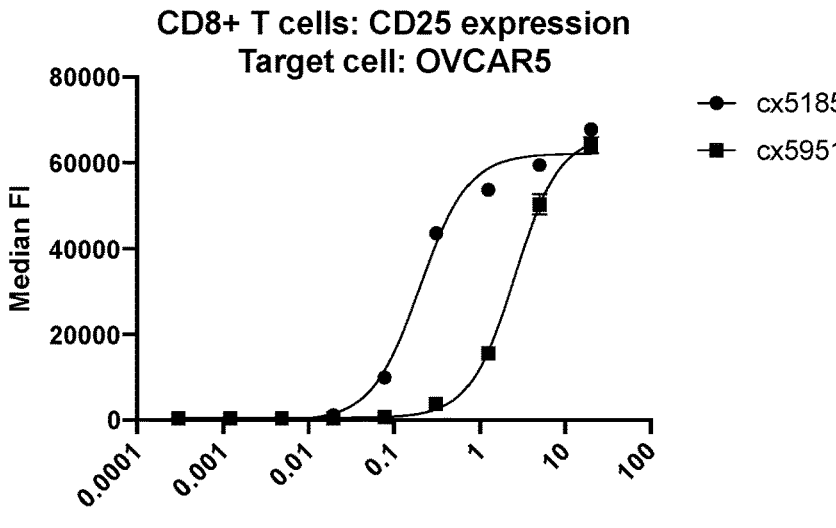

FIG. 16A and FIG. 16B depict T cell activation as assessed by CD25 expression on CD4 (FIG. 16A) and CD8 (FIG. 16B) cells following incubation with representative 5T4-targeted constrained CD3 engaging constructs with a 41BB binding domain, cx5185, and without a 41BB binding domain, cx5951, in the presence of 5T4 positive cells, A375, Ovcar-5, and SHP-77. T-cell activation was assessed by flow cytometery monitoring cell surface expression of CD25.

Figure 17:
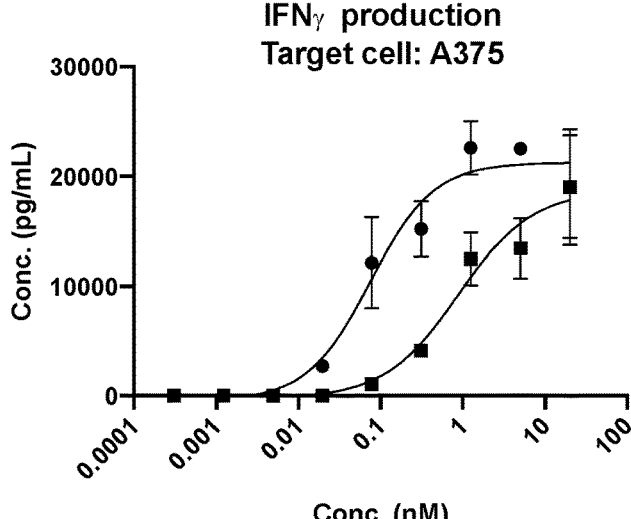
Figure 17:
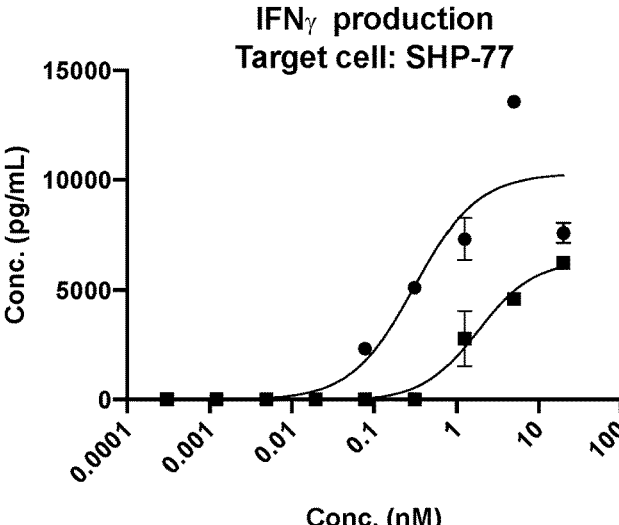
Figure 17:
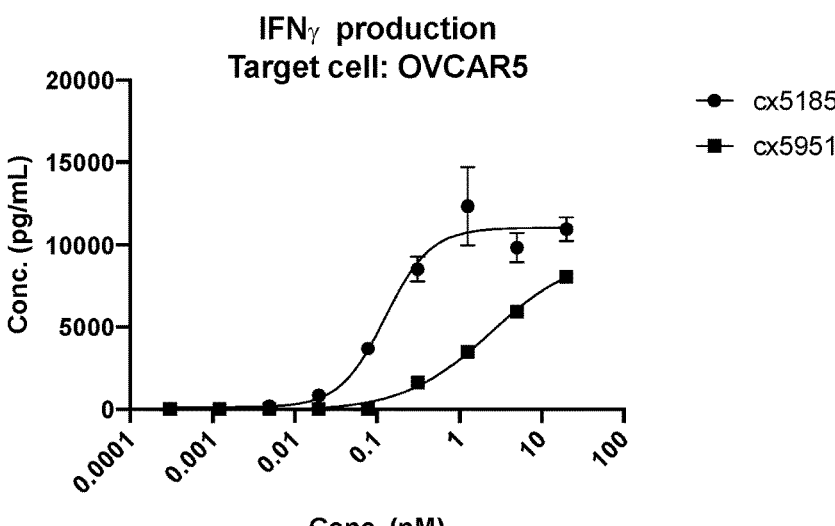

FIG. 17 shows a comparison of IFNγ production by T-cells treated with a titration of representative 5T4-targeted constrained CD3 engaging constructs with a 41BB binding domain, cx5185, and without a 41BB binding domain, cx5951, in the presence of 5T4 positive cell lines, A375, SHP-77, and Ovcar5.

Figure 18:
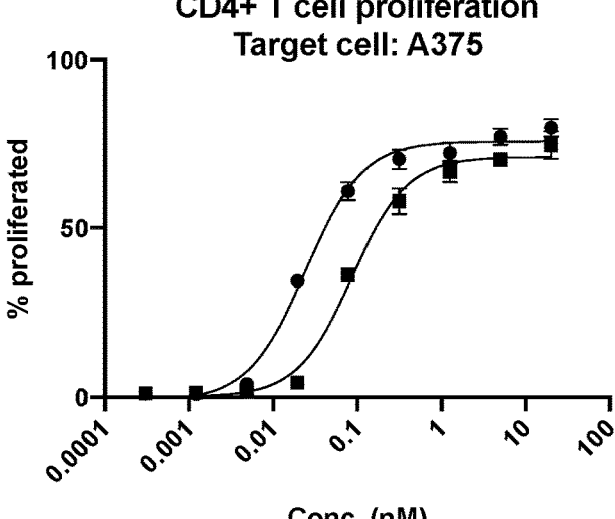
Figure 18:
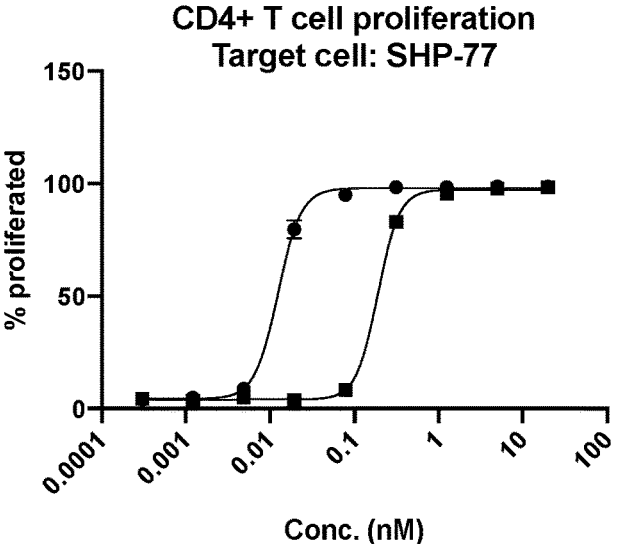
Figure 18:
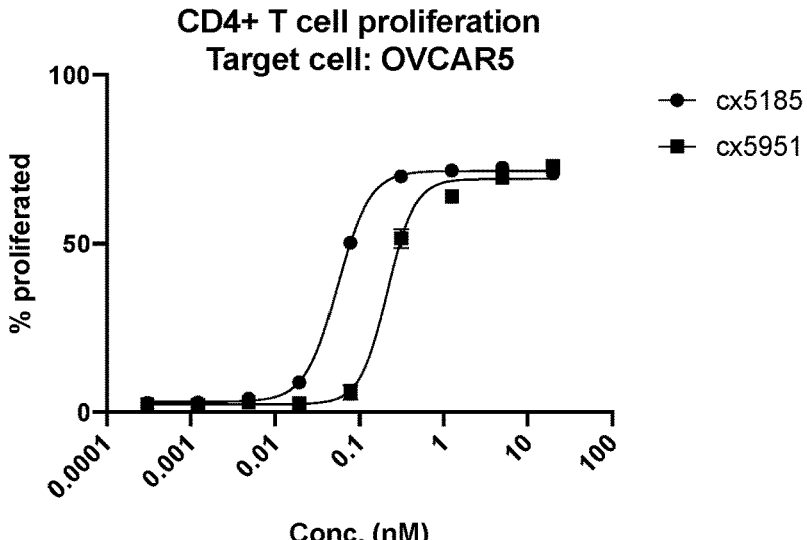

FIG. 18 depicts T cell proliferation on CD4 T cells following incubation with representative 5T4-targeted constrained CD3 engaging constructs with a 41BB binding domain, cx5185, and without a 41BB binding domain, cx5951, in the presence of 5T4 positive cell lines, A375, Ovcar-5, and SHP-77. T-cell proliferation was monitored via dilution of CellTrace™ dye. The results depict the percent of proliferating cells as monitored by dilution of CellTrace™ Violet dye.

Figure 19:
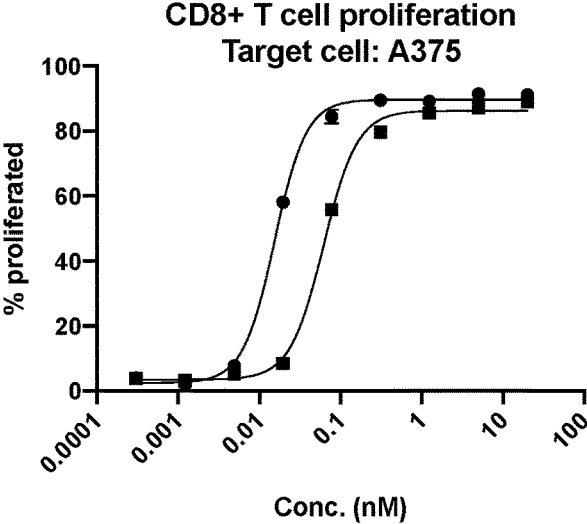
Figure 19:
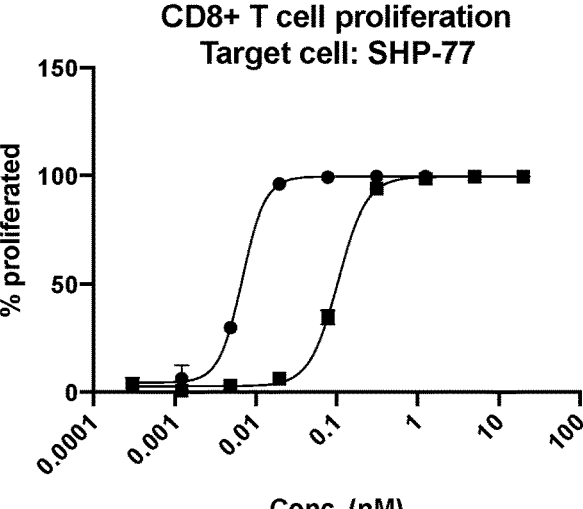
Figure 19:
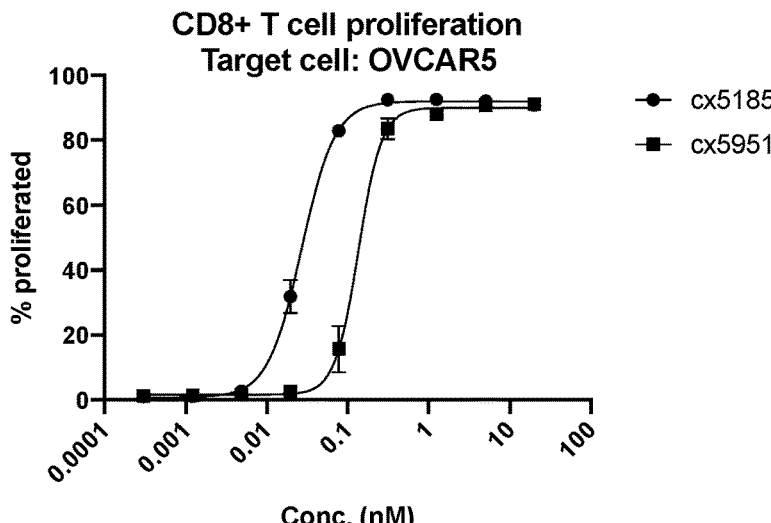

FIG. 19 depicts T cell proliferation on CD8 T cells following incubation with representative 5T4-targeted constrained CD3 engaging constructs with a 41BB binding domain, cx5185, and without a 41BB binding domain, cx5951, in the presence of 5T4 positive cell lines, A375, Ovcar-5, and SHP-77. T-cell proliferation was monitored via dilution of CellTrace™ dye. The results depict the percent of proliferating cells as monitored by dilution of CellTrace™ Violet dye.

Figure 20:
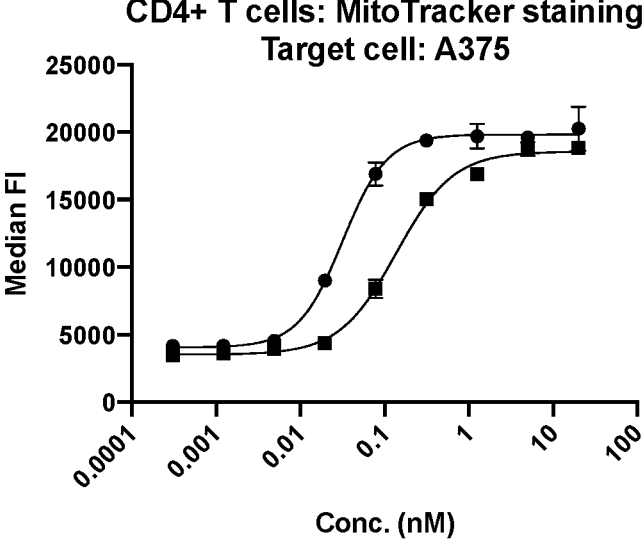
Figure 20:
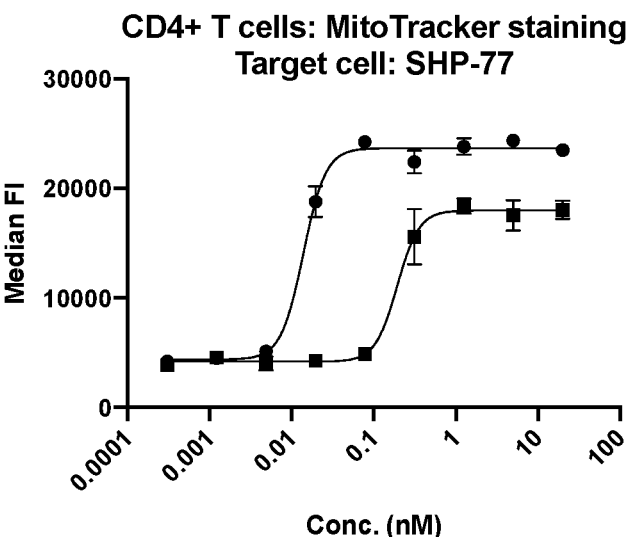
Figure 20:
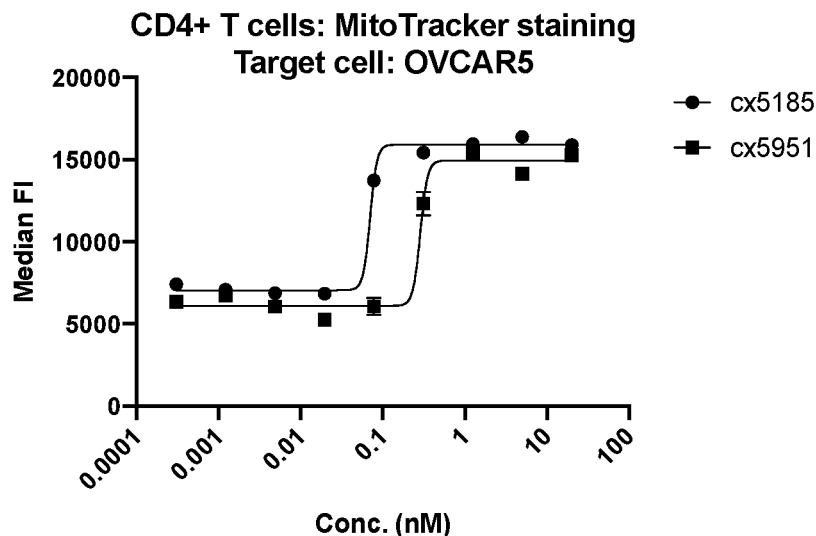

FIG. 20 depicts assessment of mitochondrial function in CD4 T-cells following incubation with representative 5T4-targeted constrained CD3 engaging constructs with a 41BB binding domain, cx5185, and without a 41BB binding domain, cx5951, in the presence of 5T4 positive cells, A375, Ovcar-5, and SHP-77. Mitochondrial function was assessed by flow cytometry using MitoTracker Green, a fluorescent mitochondria-selective probe that accumulates in active mitochondria.

Figure 21:
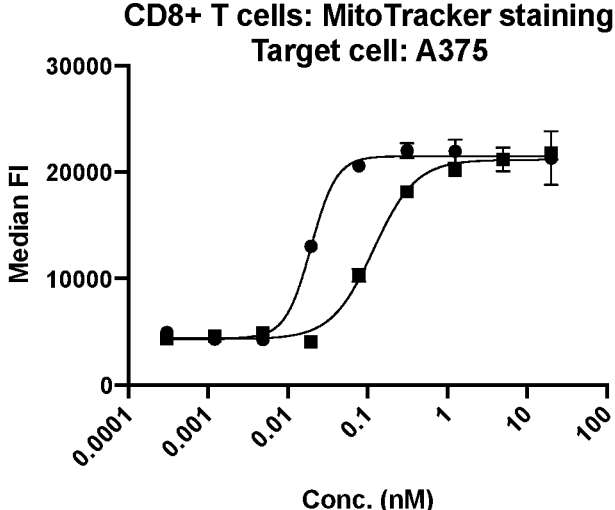
Figure 21:
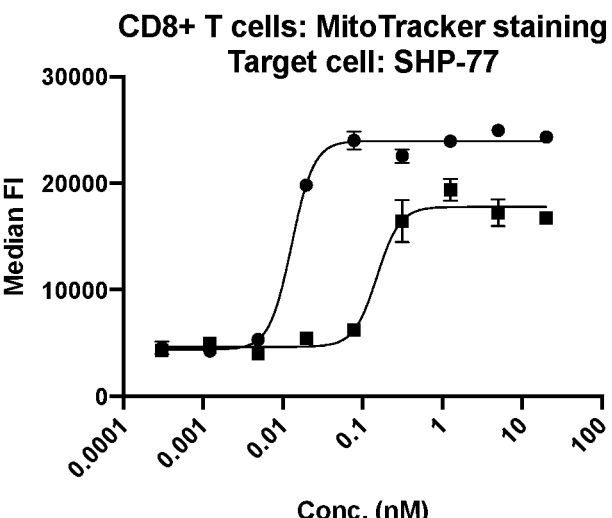
Figure 21:
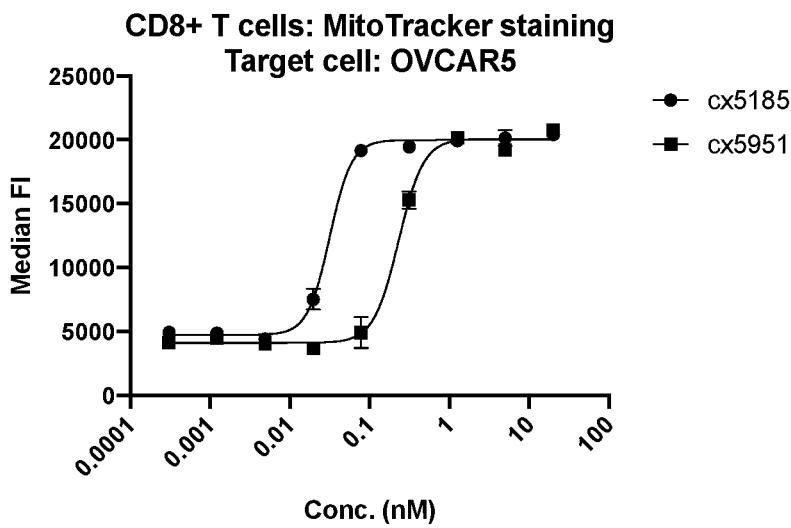

FIG. 21 depicts assessment of mitochondrial function in CD8 T-cells following incubation with representative 5T4-targeted constrained CD3 engaging constructs with a 41BB binding domain, cx5185, and without a 41BB binding domain, cx5951, in the presence of 5T4 positive cells, A375, Ovcar-5, and SHP-77. Mitochondrial function was assessed by flow cytometery using MitoTracker Green, a fluorescent mitochondria-selective probe that accumulates in active mitochondria.

Figure 22:
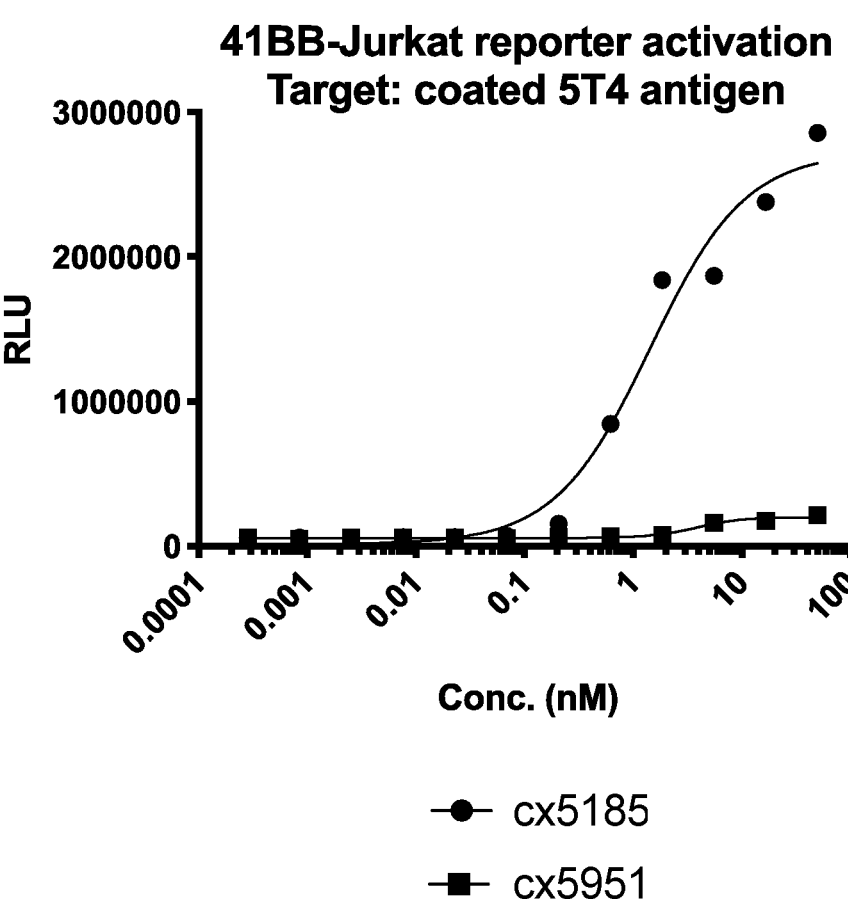

FIG. 22 shows the ability of the 5T4-targeted constrained CD3 engaging construct with a 41BB binding domain, cx5185, but not the same construct lacking a 41BB binding domain, cx5951, to mediate 41BB signaling. 41BB signaling was monitored using a Jurkat 41BB NFkB-luciferase reporter cell and recombinant plate bound 5T4 as the source of the antigen.

Figure 23A:
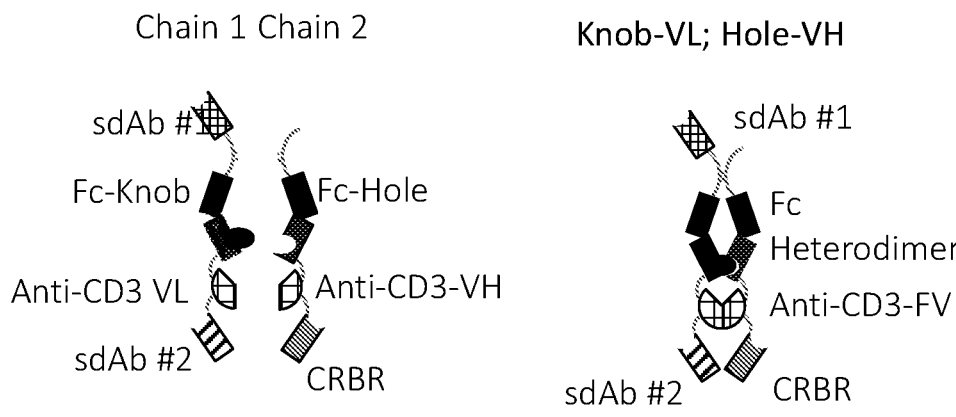
Figure 23B:
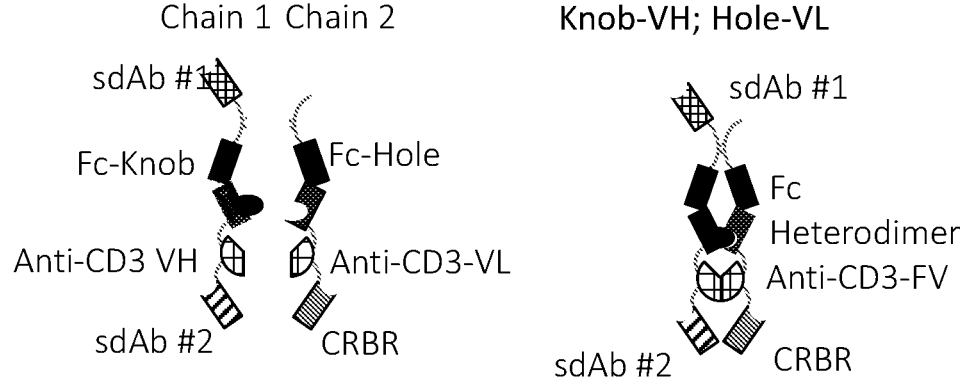

FIG. 23A-B depict exemplary TAA-targeted constrained CD3 engagers with a co-stimulatory receptor binding region (CRBR). The constructs have an antigen-targeting sdAb positioned at the N and C-termini of one chain of the heterodimer, the Fc knob, and have a co-stimulatory receptor binding region (CRBR) positioned at the C-termini of the opposite chain of the heterodimer, the Fc hole, but have the VH and VL of the CD3 binding Fv positioned on opposite sides with respect to each other.

FIG. 24 depict results of T cell reporter assays for exemplary constructs described in FIG. 23A-B. FIGS. 24A and 24B depict mean fluorescence intensity (MFI) of the GFP reporter when the TAA-positive cell line A375 or the TAA-negative cell line CCRF-CEM, respectively, was co-cultured with Jurkat CD3 NFAT-GFP reporter cells. FIGS. 24C and 24D depict relative luminescent units (RLU) of the luciferase reporter when the TAA-positive cell line A375 or the TAA-negative cell line CCRF-CEM, respectively, were co-cultured with Jurkat CD3 NFAT-Luciferase reporter cells.

Figure 25:
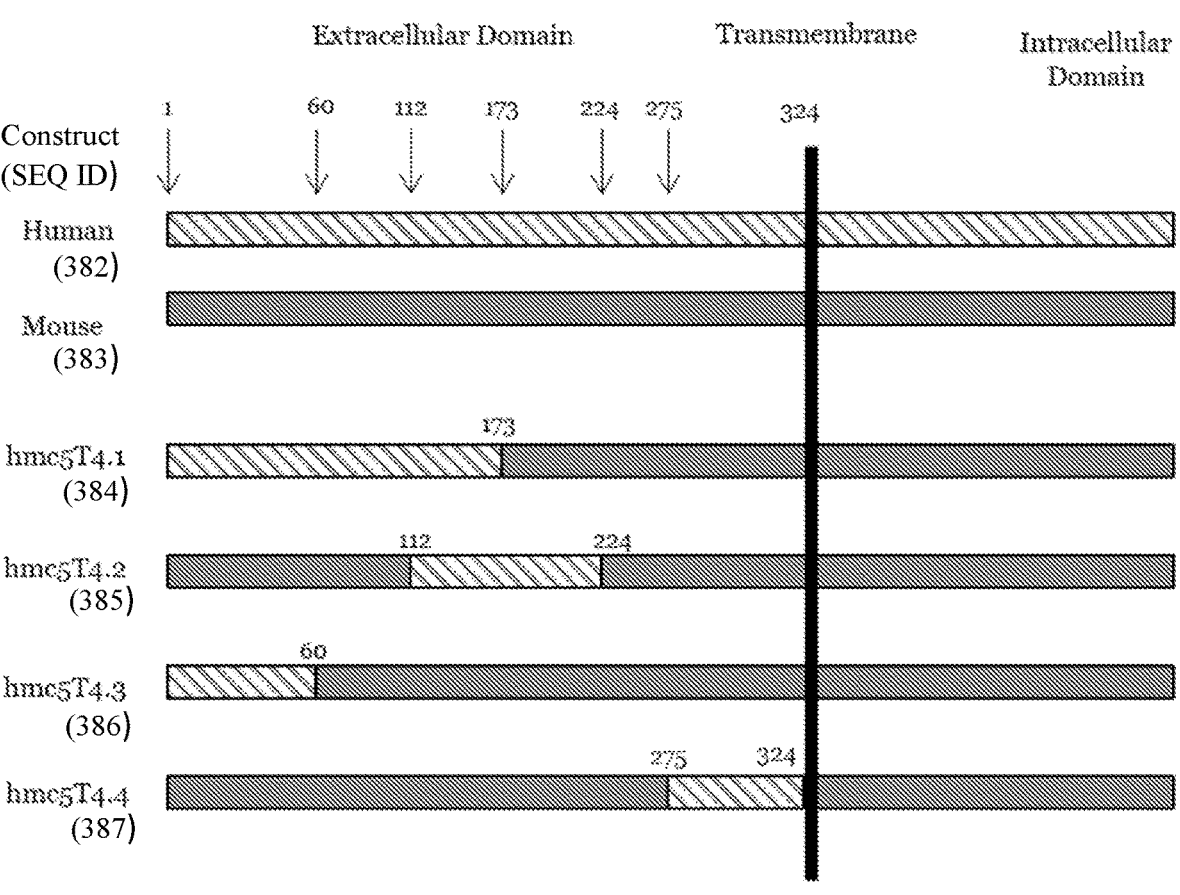

FIG. 25 is a schematic of various hybrid mouse/human 5T4 constructs used for epitope mapping. Regions of the human 5T4 extracellular domain (ECD) were grafted in place of the corresponding regions of the mouse 5T4 full length construct. The sdAbs are able to bind human 5T4 but not mouse 5T4. Binding of a sdAb to a hybrid mouse/human 5T4 indicated that the epitope bound by the sdAb was in the grafted region.

Figure 26A:
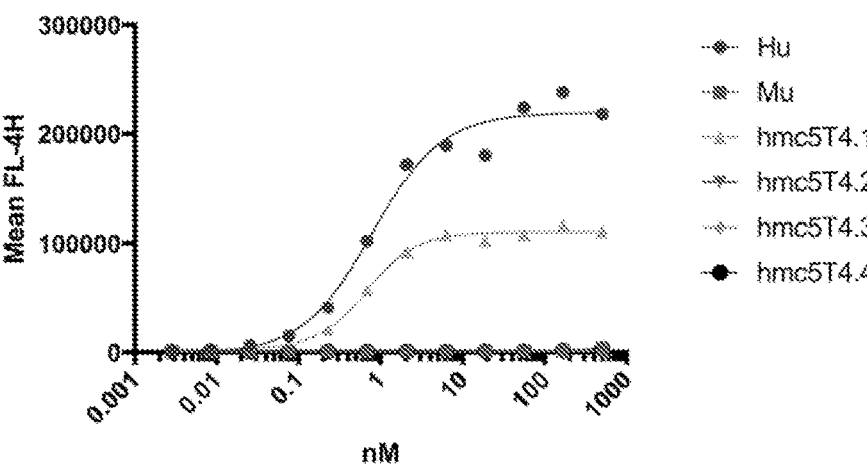
Figure 26B:
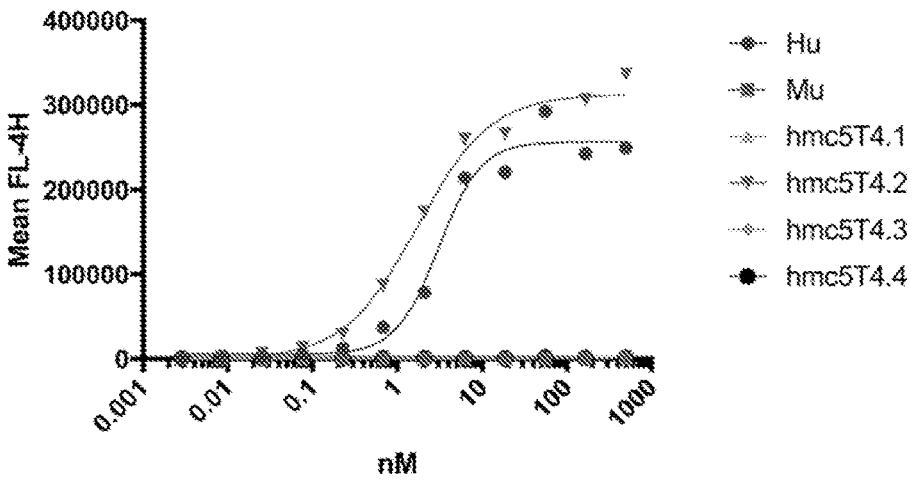
Figure 26C:
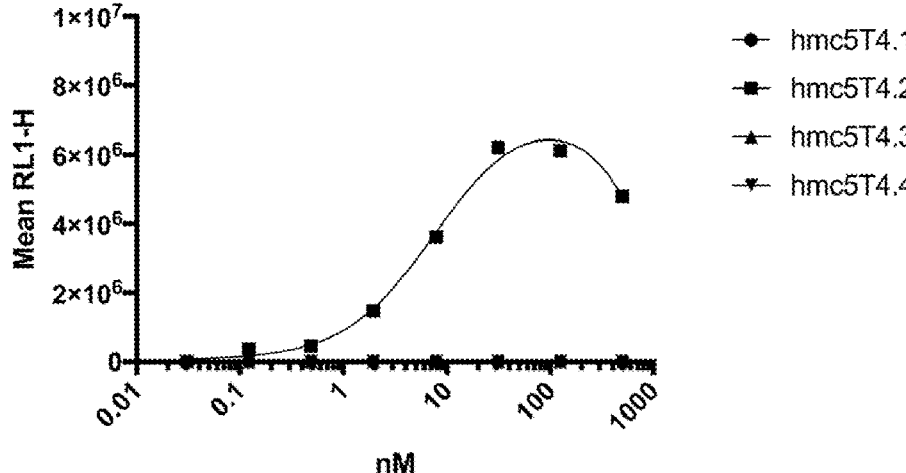

FIG. 26A depicts the binding of 12E9v9 to the various hybrid mouse/human 5T4 constructs, demonstrating the epitope recognized by this sdAb likely resides between amino acid residues 60 and 112 (SEQ ID NO:411). FIG. 26B depicts the binding of 16G10v11 to the various hybrid mouse/human 5T4 constructs, demonstrating the epititope recognized by this sdAb likely resides between amino acid residues 173 and 224 (SEQ ID NO:412). FIG. 26C depicts the binding of 14B5v17 to the various hybrid mouse/human 5T4 constructs, demonstrating the epitope recognized by this sdAb likely resides between amino acid residues 173 and 224 (SEQ ID NO:412). The Hu and Mu denote the full length human and mouse 5T4 extracellular domain constructs, respectively.

Figure 27A:
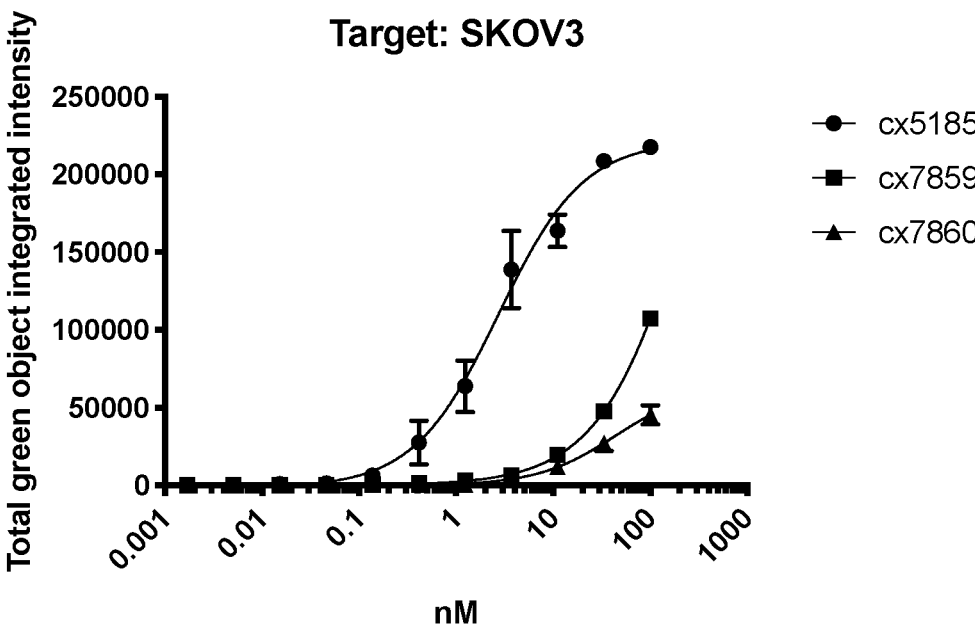
Figure 27B:
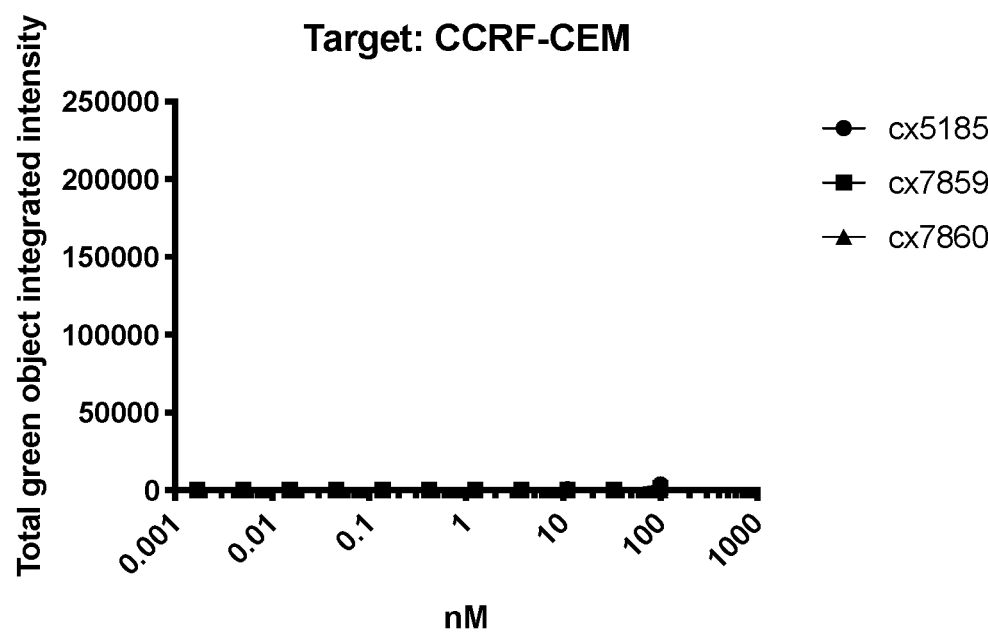

FIGS. 27A-27B depict the ability of 5T4-targeted constrained CD3 engaging constructs to elicit 5T4-dependent T-cell activation. A Jurkat CD3 NFAT-GFP reporter cell line was used to monitor T-cell activation. SKOV-3 (FIG. 27A) cells were used as antigen-positive cells and CCRF-CEM (FIG. 27B) were used as antigen-negative cells.

DETAILED DESCRIPTION

Provided herein are polypeptides that specifically bind to 5T4, hereinafter also called 5T4-binding polypeptides. In some embodiments, the provided binding polypeptides comprise at least one VHH domain that binds 5T4. In some embodiments, a 5T4-binding polypeptide provided herein comprises one, two, three, four, five, six, seven, or eight VHH domains that each individually binds 5T4. In some embodiments, a 5T4-binding polypeptide provided herein comprises one, two, three, or four VHH domains that bind 5T4. In some embodiments, the 5T4-binding polypeptides are monospecific. In some embodiments, the 5T4-binding polypeptides are multispecific. For example, provided 5T4-binding polypeptides include polypeptides that may comprise at least one VHH domain that binds 5T4 and one or more additional binding domains, such as one or more additional VHH domains, that bind one or more target proteins other than 5T4.

In some embodiments, a 5T4-binding polypeptide comprises at least one VHH domain that binds 5T4 and an Fc domain. In some embodiments, a 5T4-binding polypeptide provided herein comprises one, two, three, or four VHH domains that bind 5T4 and an Fc domain. In some embodiments, an Fc domain mediates dimerization of the 5T4-binding polypeptide at physiological conditions such that a dimer is formed that doubles the number of 5T4 binding sites. For example, a 5T4-binding polypeptide comprising three VHH domains that bind 5T4 and an Fc region is trivalent as a monomer, but at physiological conditions, the Fc region may mediate dimerization, such that the 5T4-binding polypeptide exists as a hexavalent dimer under such conditions.

5T4 oncofetal antigen (also known as trophoblast glycoprotein, TPBG; 5T4 oncofetal trophoblast glycoprotein; and Wnt-activated inhibitory factor 1, WAIF1) is a 72 kDa glycoprotein identified by a murine monoclonal antibody produced by a hybridoma from splenocytes of mice immunized with syncytiotrophoblast microvillous membrane glycoproteins. 5T4 is expressed on the surface of a wide variety of tumor cells and tumor vasculature including, but not limited to, renal cell carcinoma, head and heck squamous cell carcinoma, colorectal carcinoma, ovarian carcinoma and gastric carcinoma. Transduction of the 5T4 cDNA into cell lines enhances cell motility and reduces cell-cell contacts suggesting that it may be mechanistically involved in the malignant phenotype (Carsberg et al., 1996, Int J Cancer. 68 1:84-92). In addition, upregulation of 5T4 expression is a marker of loss of pluripotency in the early differentiation of embryonic stem (ES) cells and forms an integrated component of an epithelial-mesenchymal transition, a process important during both embryonic development and metastatic spread of epithelial tumors (Southgate et al., 2010, PLOS One. 5 (4): e9982). 5T4 expression is very limited in normal tissue but is widespread in transformed cell lines as well as malignant tumors throughout their development (Hole & Stern, 1988, Br. J. Cancer, 57, 239-246; Southall et al., 1990, Br. J. Cancer, 61, 89-95.; Jones et al., 1990, Br. J. Cancer, 61, 96-100.; Starzynska et al. 1992, Br. J. Cancer 66:867-869). In addition, a high level of 5T4 expression on tumor tissue correlated with advanced tumor stage and poorer survival in colorectal carcinoma (Starzynska et al., 1992, Br. J. Cancer 66:867-869), gastric carcinoma (Starzynska et al., 1998, Eur J Gastroenterol Hepatol. 10 (6): 479-84), ovarian carcinoma (Wrigley et al., 1995, Int J Gynecol Cancer 5 (4): 269-274), head and neck squamous cell carcinoma (Kerk et al., 2017, Clin Cancer Res. 23 (10): 2516-2527.) and acute lymphoblastic leukemia (McGinn et al., 2017, Haematologica, 102:1075-1084).

An exemplary sequence of human 5T4 is set forth as follows:

```
MPGGCSRGPAAGDGRLRLARLALVLLGWVSSSSPTSSASSFSSSAPFLAS

AVSAQPPLPDQCPALCECSEAARTVKCVNRNLTEVPTDLPAYVRNLFLTG

NQLAVLPAGAFARRPPLAELAALNLSGSRLDEVRAGAFEHLPSLRQLDLS

HNPLADLSPFAFSGSNASVSAPSPLVELILNHIVPPEDERQNRSFEGMVV

AALLAGRALQGLRRLELASNHFLYLPRDVLAQLPSLRHLDLSNNSLVSLT

YVSFRNLTHLESLHLEDNALKVLHNGTLAELQGLPHIRVFLDNNPWVCDC

HMADMVTWLKETEVVQGKDRLTCAYPEKMRNRVLLELNSADLDCDPILPP

SLQTSYVFLGIVLALIGAIFLLVLYLNRKGIKKWMHNIRDACRDHMEGYH

YRYEINADPRLTNLSSNSDV (SEQ ID NO: 244, signal sequence underlined)
```

In some embodiments, a provided 5T4 binding polypeptides bind to the extracellular domain of human 5T4, such as to a region or epitope within the sequence of amino acids set forth in SEQ ID NO: 382. In some aspects, a provided 5T4 binding polypeptide binds to a contiguous sequence of amino acids in the extracellular domain of human 5T4 set forth in SEQ ID NO:382. In some embodiments, the epitope is a linear epitope.

In some embodiments, provided are 5T4 binding polypeptides that contain at least a first 5T4 VHH domain sequence and a second 5T4 VHH domain sequence in which both bind to a region or epitope within the sequence of amino acids set forth in SEQ ID NO:382. In some aspects, each of the first 5T4 VHH domain sequence and a second 5T4 VHH domain sequence binds to a contiguous sequence of amino acids in the extracellular domain of human 5T4 set forth in SEQ ID NO:382. In some embodiments, the epitope is a linear epitope. In some embodiments, the first 5T4 VHH domain sequence and the second 5T4 VHH domain sequence bind to the same or an overlapping epitope in the 5T4 extracellular domain. In some embodiments, the first 5T4 VHH domain sequence and the second 5T4 VHH domain sequence bind to different epitopes in the 5T4 extracellular domain. In some embodiments, the first 5T4 VHH domain binds to an epitope located within amino acids 60-112, inclusive, of the human 5T4 extracellular domain (given by SEQ ID NO:411) and the second 5T4 VHH domain binds to an epitope located within amino acids 173-224, inclusive, of the human 5T4 extracellular domain (given by SEQ ID NO:412). In some embodiments, the first 5T4 VHH domain comprises the amino acid sequence set forth in SEQ ID NO:245 or a humanized variant thereof, and the second 5T4 VHH domain comprises the amino acid sequence set forth in SEQ ID NO:276 or a humanized variant thereof. In some embodiments, the first 5T4 VHH domain comprises the amino acid sequence set forth in SEQ ID NO: 360 and the second 5T4 VHH domain comprises the amino acid sequence set forth in SEQ ID NO: 287.

In some embodiments, a 5T4 VHH does not cross react with the mouse 5T4 antigen. In some embodiments, a 5T4 VHH comprising the amino acid sequence set forth in SEQ ID NO:245, or humanized variants thereof, do not cross react with the mouse 5T4 antigen. In some embodiments, a 5T4 VHH comprising the amino acid sequence set forth in SEQ ID NO:255, or humanized variants thereof, do not cross react with the mouse 5T4 antigen. In some embodiments, a 5T4 VHH comprising the amino acid sequence set forth in SEQ ID NO:276, or humanized variants thereof, do not cross react with the mouse 5T4 antigen.

In some embodiments, provided are multispecific polypeptide constructs that contain at least a first 5T4 VHH domain and a second 5T4 VHH domain. In some embodiments, provided are multispecific polypeptide constructs that contain a first 5T4 VHH domain comprising the amino acid sequence set forth in SEQ ID NO:360, and a second 5T4 VHH domain comprising the amino acid sequence set forth in SEQ ID NO:360. In some embodiments, provided are multispecific polypeptide constructs that contain a first 5T4 VHH domain comprising the amino acid sequence set forth in SEQ ID NO: 287 and a second 5T4 VHH domain comprising the amino acid sequence set forth in SEQ ID NO: 287. In some embodiments, provided are multispecific polypeptide constructs that contain at least a first 5T4 VHH domain comprising the amino acid sequence set forth in SEQ ID NO:360, or a humanized variant thereof, and a second 5T4 VHH domain comprising the amino acid sequence set forth in SEQ ID NO: 287, or a humanized variant thereof.

In some cases, the provided 5T4 binding polypeptides directly block or inhibit activity of 5T4, which, in some aspects, can be used as a therapeutic to inhibit or reduce tumor cell growth or survival.

A variety of 5T4 polypeptide binding formats are provided. In some examples, 5T4 binding polypeptides include 5T4 VHH-Fc polypeptides. In some embodiments, the Fc is an Fc that exhibits immune effector activity, such as one or more effector functions such as antibody-dependent cellular cytotoxicity (ADCC), antibody-dependent cellular phagocytosis (ADCP) and/or complement-dependent cytotoxicity (CDC).

In some embodiments, the provided 5T4-binding polypeptides can be used to stimulate an immune response in a subject, which, in some aspects, treats a disease or disorder, such as a cancer, in the subject. In some aspects, a 5T4-binding polypeptide provided herein, such as a 5T4-Fc, can bind to 5T4-expressing tumor cells and induce an active immune response against the tumor cells expressing 5T4. In some cases, the active immune response can cause the death of the cancerous cells (e.g., antibody binding to cancer cells inducing apoptotic cell death), or inhibit the growth (e.g., block cells cycle progression) of the cancerous cells. In other cases, a 5T4-binding polypeptide provided herein, such as a 5T4 VHH-Fc, can bind to cancerous cells and antibody dependent cellular cytotoxicity (ADCC) can eliminate cancerous cells to which the 5T4-binding polypeptide binds. In some cases, provided 5T4 VHH-binding polypeptides can also activate both cellular and humoral immune responses and recruit more natural killer cells or increased production of cytokines (e.g., IL-2, IFN-gamma, IL-12, TNF-alpha, TNF-beta, etc.) that further activate an individual's immune system to destroy cancerous cells. In yet another embodiment, 5T4 binding polypeptides, such as 5T4 VHH-Fc, can bind to cancerous cells, and macrophages or other phagocytic cell can opsonize the cancerous cells, such as via CDC or ADCP processes.

In other aspects, also provided herein are VHH-binding polypeptides that exhibit multispecific binding. In some cases, the binding polypeptides include polypeptides that exhibit dual affinity for 5T4 and a T cell antigen, such as CD3. In some aspects, such dual affinity molecules are capable of engaging or activating T cells at the site of a tumor upon binding of tumor-expressed 5T4. In particular, among such molecules provided herein are molecules that exhibit constrained CD3 binding. Also provided herein are engineered cells, such as engineered T cells, that express a chimeric antigen receptor containing a 5T4 binding polypeptide.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

The section headings used herein are for organizational purposes only and are not to be construed as limiting the subject matter described.

I. DEFINITIONS

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The term "isolated polynucleotide" as used herein shall mean a polynucleotide of genomic, cDNA, or synthetic origin or some combination thereof, which by virtue of its origin (1) is not associated with all or a portion of a polynucleotide found in nature, (2) is operably linked to a polynucleotide that it is not linked to in nature, or (3) does not occur in nature as part of a larger sequence.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, RNA or other RNA, of may be of synthetic origin, or any combination thereof. In certain embodiments, the isolated protein is substantially pure or substantially free from proteins or polypeptides or other contaminants that are found in its natural environment that would interfere with its use (therapeutic, diagnostic, prophylactic, research or otherwise).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a 5T4 epitope is a sdAb or VHH-containing polypeptide that binds this epitope with greater affinity, avidity, more readily, and/or with greater duration than it binds to other 5T4 epitopes or non-5T4 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The terms "antibody" and "antigen-binding molecule" are used interchangeably in the broadest sense and encompass various polypeptides that comprise antibody-like antigen-binding domains, including but not limited to conventional antibodies (typically comprising at least one heavy chain and at least one light chain), single-domain antibodies (sdAbs, comprising just one chain, which is typically similar to a heavy chain), VHH-containing polypeptides (polypeptides comprising at least one heavy chain only antibody variable domain, or VHH), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc domains (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The term "variable region" or "variable domain" refers to the domain of an antibody heavy or light chain that is involved in binding the antibody to antigen. The variable regions of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity, e.g. a single domain antibody, such as a VHH. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150:880-887 (1993); Clarkson et al., Nature 352:624-628 (1991).

An "antibody fragment" or "antigen-binding fragment" refers to a molecule other than a conventional or intact antibody that comprises a portion of an conventional or intact antibody containing at least a variable region that binds an antigen. Examples of antibody fragments include but are not limited to Fv, single chain Fvs (sdFvs), Fab, Fab', Fab'-SH, F(ab')$_2$; diabodies; linear antibodies; an single-domain antibodies comprising only the $V_H$ region (VHH).

As used herein, "monovalent" with reference to a binding molecule refers to binding molecules that have a single antigen recognition site that is specific for a target antigen. Examples of monovalent binding molecules include, for example, a monovalent antibody fragment, a proteinaceous binding molecule with antibody-like binding properties or an MHC molecule. Examples of monovalent antibody fragments include, but are not limited to, a Fab fragment, an Fv fragment, and a single-chain Fv fragment (scFv).

The terms "single domain antibody", "sdAb", "VHH" are used interchangeably herein to refer to an antibody having a single monomeric domain antigen binding/recognition domain. Such antibodies include a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprise only a partial FR1 and/or FR4, or lacks one or both of those framework regions, so long as the VHH substantially maintains antigen binding and specificity.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc domain. In some such embodiments, the VHH polypeptide may form a dimer. Nonlimiting structures of VHH-containing polypeptides include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains).

As used herein, a 5T4-binding polypeptide is a polypeptide or protein that specifically binds 5T4. Typically, a 5T4-binding polypeptide herein is a VHH-containing polypeptide containing at least one VHH domain that binds 5T4. A 5T4-binding polypeptide includes conjugates, including fusion proteins. A 5T4-binding polypeptide includes fusion proteins, including those containing an Fc domain. In some embodiments, a 5T4-binding polypeptide contains two, three, or four or more VHH domains that each specifically bind to 5T4, wherein each VHH domain may be the same or different. In some embodiments, a 5T4-binidng polypeptide is multivalent. In some embodiments, a 5T4-binding polypeptide is multispecific. In some cases, a 5T4-binding polypeptide may contain one or more additional domains that bind to one or more further or additional antigens other than 5T4.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat.

No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273,927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27 (1): 55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309 (3): 657-70, ("Aho" numbering scheme); and Martin et al., "Modeling antibody hypervariable loops: a combined algorithm," PNAS, 1989, 86 (23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3. Table 1, below, lists exemplary position boundaries of CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-H1 located before CDR-H1, FR-H2 located between CDR-H1 and CDR-H2, FR-H3 located between CDR-H2 and CDR-H3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

| Boundaries of CDRs according to various numbering schemes. | | | | |
|---|---|---|---|---|
| CDR | Kabat | Chothia | AbM | Contact |
| CDR-H1 (Kabat Numbering[1]) | H31 - - - H35B | H26 - - - H32 . . . 34 | H26 - - - H35B | H30 - - - H35B |
| CDR-H1 (Chothia Numbering[2]) | H31 - - - H35 | H26 - - - H32 | H26 - - - H35 | H30 - - - H35 |
| CDR-H2 | H50 - - - H65 | H52 - - - H56 | H50 - - - H58 | H47 - - - H58 |
| CDR-H3 | H95 - - - H102 | H95 - - - H102 | H95 - - - H102 | H93 - - - H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VHH amino acid sequence, it is understood that such a CDR has a sequence of the corresponding CDR (e.g., CDR-H3) within the VHH, as defined by any of the aforementioned schemes. In some embodiments, specific CDR sequences are specified. Exemplary CDR sequences of provided antibodies are described using various numbering schemes (see e.g. Table 1), although it is understood that a provided antibody can include CDRs as described according to any of the other aforementioned numbering schemes or other numbering schemes known to a skilled artisan.

As used herein, "conjugate," "conjugation" or grammatical variations thereof refers the joining or linking together of two or more compounds resulting in the formation of another compound, by any joining or linking methods known in the art. It can also refer to a compound which is generated by the joining or linking together two or more compounds. For example, a VHH domain linked directly or indirectly to one or more chemical moieties or polypeptide is an exemplary conjugate. Such conjugates include fusion proteins, those produced by chemical conjugates and those produced by any other methods.

An immunoglobulin Fc fusion ("Fc-fusion"), such as VHH-Fc, is a molecule comprising one or more VHH domains operably linked to an Fc region of an immunoglobulin. An immunoglobulin Fc region may be linked indirectly or directly to one or more VHH domains. Various linkers are known in the art and can optionally be used to link an Fc to a fusion partner to generate an Fc-fusion. In some such embodiments, the linker comprises 1-20 amino acids, preferably 1-20 amino acids predominantly composed of glycine and, optionally, serine. Fc-fusions of identical species can be dimerized to form Fc-fusion homodimers, or using non-identical species to form Fc-fusion heterodimers. In some embodiments, the Fc is a mammalian Fc such as human Fc.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an ai constant region) and IgA2 (comprising an $α_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

A "functional Fc region" possesses an "effector function" of a native sequence Fc region. Exemplary "effector functions" include Fc receptor binding; C1q binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

In general, the numbering of the residues in an immunoglobulin heavy chain or portion thereof, such as an Fc region, is that of the EU index as in Kabat et al., *Sequences of Proteins of Immunological Interest,* 5th Ed. Public Health Service, National Institutes of Health, Bethesda, Md. (1991). The "EU index as in Kabat" refers to the residue numbering of the human IgG1 EU antibody.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, Annu. Rev. Immunol. 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18 (12): 592-598 (1997); Ghetie et al., *Nature Biotechnology,* 15 (7): 637-640 (1997); Hinton et al., *J. Biol. Chem.* 279 (8): 6213-6216 (2004); WO 2004/92219 (Hinton et al.).

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

As used herein, a "chimeric antigen receptor" or "CAR" refers to an engineered receptor, which introduces an antigen specificity, via an antigen binding domain, onto cells to which it is engineered (for example T cells such as naive T cells, central memory T cells, effector memory T cells or combination thereof) thus combining the antigen binding properties of the antigen binding domain with the T cell activity (e.g. lytic capacity and self renewal) of T cells. A CAR typically includes an extracellular antigen-binding domain (ectodomain), a transmembrane domain and an intracellular signaling domain. The intracellular signaling domain generally contains at least one ITAM signaling domain, e.g. derived from CD3zeta, and optionally at least one costimulatory signaling domain, e.g. derived from CD28 or 4-1BB. In a CAR provided herein, a VHH domain forms the antigen binding domain and is located at the extracellular side when expressed in a cell.

"Affinity" refers to the strength of the sum total of noncovalent interactions between a single binding site of a molecule (for example, an antibody or VHH-containing polypeptide) and its binding partner (for example, an antigen). The affinity or the apparent affinity of a molecule X for its partner Y can generally be represented by the dissociation constant ($K_D$) or the $K_{D-apparent}$, respectively. Affinity can be measured by common methods known in the art (such as, for example, ELISA $K_D$, KinExA, flow cytometry, and/or surface plasmon resonance devices), including those described herein. Such methods include, but are not limited to, methods involving BIAcore®, Octet®, or flow cytometry.

The term "$K_D$", as used herein, refers to the equilibrium dissociation constant of an antigen-binding molecule/antigen interaction. When the term "$K_D$" is used herein, it includes $K_D$ and $K_{D-apparent}$.

In some embodiments, the Kp of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_D$ is $K_{D-apparent}$.

The term "biological activity" refers to any one or more biological properties of a molecule (whether present naturally as found in vivo, or provided or enabled by recombinant means). Biological properties include, but are not limited to, binding a ligand, inducing or increasing cell proliferation (such as T cell proliferation), and inducing or increasing expression of cytokines.

An "affinity matured" VHH-containing polypeptide refers to a VHH-containing polypeptide with one or more alterations in one or more CDRs compared to a parent VHH-containing polypeptide that does not possess such alterations, such alterations resulting in an improvement in the affinity of the VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding nonhuman residues. Furthermore, the humanized VHH can comprise residues that are found neither in the original VHH nor in the human framework sequences, but are included to further refine and optimize VHH or VHH-containing polypeptide performance. In some embodiments, a humanized VHH-containing polypeptide comprises a human Fc region. As will be appreciated, a humanized sequence can be identified by its primary sequence and does not necessarily denote the process by which the antibody was created.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGA-LIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 2. Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |

TABLE 2-continued

| Original Residue | Exemplary Substitutions |
|---|---|
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.
Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example a mammal. The term patient includes human and veterinary subjects. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. The subject can be male or female and can be any suitable age, including infant, juvenile, adolescent, adult, and geriatric subjects. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder. In particular embodiments, the subject is a human, such as a human patient.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Also, included in this definition are cells having abnormal proliferation that is not impeded (e.g. immune evasion and immune escape mechanisms) by the immune system (e.g. virus infected cells). Exemplary cancers include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" as used herein refers to a normal cells or tissue. Exemplary non-tumor cells include, but are not limited to: T-cells, B-cells, natural killer (NK)

cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, the terms "treating," "treatment," or "therapy" of a disease, disorder or condition is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS).

"Ameliorating" means a lessening or improvement of one or more symptoms as compared to not administering a therapeutic agent. "Ameliorating" also includes shortening or reduction in duration of a symptom.

"Preventing," "prophylaxis," or "prevention" of a disease or disorder refers to administration of a pharmaceutical composition, either alone or in combination with another compound, to prevent the occurrence or onset of a disease or disorder or some or all of the symptoms of a disease or disorder or to lessen the likelihood of the onset of a disease or disorder.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" refers to a composition known to not contain an analyte ("negative control") or to contain an analyte ("positive control"). A positive control can comprise a known concentration of analyte.

The terms "effective amount" or "therapeutically effective amount" refer to a quantity and/or concentration of a composition containing an active ingredient (e.g. sdAb or VHH-containing polypeptide) that when administered into a patient either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. A therapeutically effective amount of a composition containing an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

As used herein, a composition refers to any mixture of two or more products, substances, or compounds, including cells. It may be a solution, a suspension, liquid, powder, a paste, aqueous, non-aqueous or any combination thereof.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Hence, it is a composition suitable for pharmaceutical use in a mammalian subject, often a human. A pharmaceutical composition typically comprises an effective amount of an active agent (e.g., sdAb or VHH-containing polypeptide) and a carrier, excipient, or diluent. The carrier, excipient, or diluent is typically a pharmaceutically acceptable carrier, excipient or diluent, respectively. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effect of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contain dications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

II. VHH DOMAINS BINDING 5T4

Provided herein are 5T4-binding polypeptides that are VHH-containing polypeptides containing at least one VHH domain that specifically binds to 5T4. In some embodiments, the VHH domain binds human 5T4. In some of any of the provided embodiments, the VHH domain binds 5T4 having the sequence set forth in SEQ ID NO: 244 or a mature form thereof lacking the signal sequence.

In some embodiments, the VHH-containing polypeptides incorporate multiple copies of a VHH domain provided herein. In such embodiments, the VHH-containing polypeptide may incorporate multiple copies of the same VHH domain. In some embodiments, the VHH-containing polypeptides may incorporate multiple copies of a VHH domain that are different but that recognize the same epitope on 5T4.

In some embodiments, a 5T4 VHH does not cross react with the mouse 5T4 antigen. In some embodiments, a 5T4 VHH comprising the amino acid sequence set forth in SEQ ID NO:245, or humanized variants thereof, do not cross react with the mouse 5T4 antigen. In some embodiments, a 5T4 VHH comprising the amino acid sequence set forth in SEQ ID NO:255, or humanized variants thereof, do not cross react with the mouse 5T4 antigen. In some embodiments, a 5T4 VHH comprising the amino acid sequence set forth in SEQ ID NO:276, or humanized variants thereof, do not cross react with the mouse 5T4 antigen. In some embodiments, a provided 5T4 VHH domain binds to an epitope located between amino acid residues 60 and 112 of the 5T4 extracellular domain corresponding to amino acid residues set forth in SEQ ID NO:382. In some embodiments, a 5T4 VHH domain having the amino acid sequence set forth in SEQ ID NO:360 (12E9v9) binds to an epitope located between amino acid residues 60 and 112 of the 5T4 extracellular domain corresponding to amino acid residues set forth in SEQ ID NO: 382.

In some embodiments, a 5T4 VHH domain binds to an epitope located between amino acid residues 173 and 224 of the 5T4 extracellular domain corresponding to amino acid residues set forth in SEQ ID NO:382. In some embodiments, a 5T4 VHH domain having the amino acid sequence set forth in SEQ ID NOS: 272 or 287 (16G10v11 or 14B5v17) binds to an epitope located between amino acid residues 60 and 112 of the 5T4 extracellular domain corresponding to amino acid residues set forth in SEQ ID NO:382.

The VHH-containing polypeptides can be formatted in a variety of formats, including any as described in Section III below.

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, alpaca, vicuna, guanaco, shark, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca, vicuna and guanaco. Other species besides Camelidae may produce heavy chain antibodies naturally devoid of light chain; such VHHs are within the scope of the disclosure.

A VHH domain is an antibody fragment that is a single monomeric variable antibody domain that is able to bind selectively to a specific antigen. With a molecular weight of only 12-15 kDa, VHH domains (also called single-domain antibodies) are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Methods for the screening of VHH domains, including VHH-binding polypeptides, that possess the desired specificity for 5T4 include, but are not limited to, enzyme linked immunosorbent assay (ELISA), enzymatic assays, flow cytometry, and other immunologically mediated techniques known within the art.

Among the provided VHH domains provided herein are 5T4 VHH (llama-derived) and humanized sequences, such as any described below.

In some embodiments, a VHH domain that binds 5T4 may be humanized. Humanized antibodies (such as VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13:1619-1633, and are further described, for example, in Riechmann et al., (1988) *Nature* 332:323-329; Queen et al., (1989) *Proc. Natl Acad. Sci. USA* 86:10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272:10678-10684 and Rosok et al., (1996) *J. Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

Provided herein is a VHH domain that binds 5T4 in which the VHH domain comprises a CDR1, CDR2 and CDR3 contained in a VHH amino acid sequences selected from any of SEQ ID NO: 245-287, 294, 295, 302, or 360 or an amino acid sequence that has at least 90%, 91%, 92%, 93%, 94%, 95%, 96%, 97%, 98%, or 99% sequence identity to the VHH region amino acid selected from any one of SEQ ID NOs: 245-287, 294, 295, 302, or 360. In some embodiments, a 5T4 VHH domain provided herein contains a CDR1 set forth in any one of SEQ ID NOS: 288-292, 86-87, 296, 297, a CDR2 set forth in any one of SEQ ID NOS: 88-99, 298, 299 and a CDR3 set forth in any one of SEQ ID NOS: 100-102, 300, 301, 303. Among the provided 5T4 VHH domain has the amino acid sequence set forth in any of SEQ ID NOS: 245-287, 294, 295, 302, or 360, or an amino acid sequence that has at least 90%, 91%, 92%, 93%, 94%, 95%, 96%, 97%, 98%, or 99% sequence identity to the VHH region amino acid selected from any one of SEQ ID NOs: 245-287, 294, 295, 302, or 360. In some embodiments, the 5T4 VHH domain has the sequence of amino acids set forth in any one of SEQ ID NOS: 245-287, 294, 295, 302, or 360.

In some embodiments, a 5T4 VHH domain provided herein contains a CDR1, CDR2, CDR3, contained in a VHH domain set forth in SEQ ID NO:245, or an amino acid sequence that has at least 90%, 91%, 92%, 93%, 94%, 95%, 96%, 97%, 98%, or 99% sequence identity to the VHH region amino acid selected set forth in SEQ ID NO: 245. In some embodiments, the 5T4 VHH domain has the amino acid sequence set forth in SEQ ID NO: 245 or an amino acid sequence that has at least 90%, 91%, 92%, 93%, 94%, 95%, 96%, 97%, 98%, or 99% sequence identity to the amino acid selected set forth in SEQ ID NO: 245. In some embodiments, the 5T4 VHH domain is a humanized variant of the amino acid sequence set forth in SEQ ID NO: 245.

In some embodiments, a 5T4 VHH domain provided herein contains a CDR1 set forth in SEQ ID NOS: 288 or 289, a CDR2 set forth in SEQ ID NO: 88 and a CDR3 set forth in SEQ ID NO: 100.

In some embodiments, the 5T4 VHH domain provided herein contains a CDR1, CDR2, and CDR3 set forth in SEQ ID NOs: 288, 88, and 100, respectively. In some embodiments, the 5T4 VHH domain provided herein contains a CDR1, CDR2 and CDR3 set forth in SEQ ID NOs: 289, 88, and 100, respectively.

In some aspects, a VHH domain that binds 5T4 comprises a CDR1, CDR2 and CDR3 contained in a VHH amino acid sequences selected from any of SEQ ID NO:246-254, or an amino acid sequence that has at least 90%, 91%, 92%, 93%, 94%, 95%, 96%, 97%, 98%, or 99% sequence identity to the VHH region amino acid selected from any one of SEQ ID NOs: 246-254.

In some aspects, a VHH domain that binds 5T4 comprises a CDR1, CDR2 and CDR3 contained in a VHH amino acid sequences selected from any of SEQ ID NO:246-254 and 360, or an amino acid sequence that has at least 90%, 91%, 92%, 93%, 94%, 95%, 96%, 97%, 98%, or 99% sequence identity to the VHH region amino acid selected from any one of SEQ ID NOs: 246-254 and 360.

In some cases, the provided 5T4 VHH domain is a humanized variant that has the amino acid sequence set forth in any of SEQ ID NOS: 246-254 and 360 or an amino acid sequence that has at least 90%, 91%, 92%, 93%, 94%, 95%, 96%, 97%, 98%, or 99% sequence identity to the VHH region amino acid selected from any one of SEQ ID NOs: 246-254. In some embodiments, the 5T4 humanized VHH domain has the sequence of amino acids set forth in any one of SEQ ID NOS: 246-254.

In some cases, the provided 5T4 VHH domain is a humanized variant that has the amino acid sequence set forth in any of SEQ ID NOS: 246-254 and 360 or an amino acid sequence that has at least 90%, 91%, 92%, 93%, 94%, 95%, 96%, 97%, 98%, or 99% sequence identity to the VHH region amino acid selected from any one of SEQ ID NOs: 246-254 and 360. In some embodiments, the 5T4 humanized VHH domain has the sequence of amino acids set forth in any one of SEQ ID NOS: 246-254 and 360.

In some embodiments, a 5T4 VHH domain provided herein contains a CDR1, CDR2, CDR3, contained in a VHH domain set forth in SEQ ID NO:255, or an amino acid sequence that has at least 90%, 91%, 92%, 93%, 94%, 95%, 96%, 97%, 98%, or 99% sequence identity to the VHH region amino acid selected set forth in SEQ ID NO: 255. In some embodiments, the 5T4 VHH domain has the amino acid sequence set forth in SEQ ID NO: 255 or an amino acid sequence that has at least 90%, 91%, 92%, 93%, 94%, 95%, 96%, 97%, 98%, or 99% sequence identity to the amino acid selected set forth in SEQ ID NO: 255. In some embodiments, the 5T4 VHH domain is a humanized variant of the amino acid sequence set forth in SEQ ID NO: 255.

In some embodiments, a 5T4 VHH domain provided herein contains a CDR1 set forth in any one of SEQ ID NOs: 86, 290-292, a CDR2 set forth in any one of SEQ ID NOs: 89-94 and a CDR3 set forth in SEQ ID NO: 101.

In some embodiments, the 5T4 VHH domain provided herein contains a CDR1, CDR2, and CDR3 set forth in SEQ ID NOs: 290, 89, and 101, respectively. In some embodiments, the 5T4 VHH domain provided herein contains a CDR1, CDR2, and CDR3 set forth in SEQ ID NOs: 290, 90, and 101, respectively. In some embodiments, the 5T4 VHH domain provided herein contains a CDR1, CDR2, and CDR3 set forth in SEQ ID NOs: 290, 91, and 101, respectively. In some embodiments, the 5T4 VHH domain provided herein contains a CDR1, CDR2, and CDR3 set forth in SEQ ID NOs: 290, 92, and 101, respectively. In some embodiments, the 5T4 VHH domain provided herein contains a CDR1, CDR2, and CDR3 set forth in SEQ ID NOs: 290, 93, and 101, respectively. In some embodiments, the 5T4 VHH domain provided herein contains a CDR1, CDR2, and CDR3 set forth in SEQ ID NOs: 290, 94, and 101, respectively. In some embodiments, the 5T4 VHH domain provided herein contains a CDR1, CDR2, and CDR3 set forth in SEQ ID NOs: 291, 94, and 101, respectively. In some embodiments, the 5T4 VHH domain provided herein contains a CDR1, CDR2, and CDR3 set forth in SEQ ID NOs: 292, 94, and 101, respectively. In some embodiments, the 5T4 VHH domain provided herein contains a CDR1, CDR2, and CDR3 set forth in SEQ ID NOs: 86, 94, and 101, respectively.

In some aspects, a VHH domain that binds 5T4 comprises a CDR1, CDR2 and CDR3 contained in a VHH amino acid sequences selected from any of SEQ ID NO:256-275, or an amino acid sequence that has at least 90%, 91%, 92%, 93%, 94%, 95%, 96%, 97%, 98%, or 99% sequence identity to the VHH region amino acid selected from any one of SEQ ID NOs: 256-275.

In some cases, the provided 5T4 VHH domain is a humanized variant that has the amino acid sequence set forth in any of SEQ ID NOS: 256-275 or an amino acid sequence that has at least 90%, 91%, 92%, 93%, 94%, 95%, 96%, 97%, 98%, or 99% sequence identity to the VHH region amino acid selected from any one of SEQ ID NOs: 256-275. In some embodiments, the 5T4 humanized VHH domain has the sequence of amino acids set forth in any one of SEQ ID NOS: 256-275.

In some embodiments, a 5T4 VHH domain provided herein contains a CDR1, CDR2, CDR3, contained in a VHH domain set forth in SEQ ID NO:276, or an amino acid sequence that has at least 90%, 91%, 92%, 93%, 94%, 95%, 96%, 97%, 98%, or 99% sequence identity to the VHH region amino acid selected set forth in SEQ ID NO: 276. In some embodiments, the 5T4 VHH domain has the amino acid sequence set forth in SEQ ID NO: 276 or an amino acid sequence that has at least 90%, 91%, 92%, 93%, 94%, 95%, 96%, 97%, 98%, or 99% sequence identity to the amino acid selected set forth in SEQ ID NO: 276. In some embodiments, the 5T4 VHH domain is a humanized variant of the amino acid sequence set forth in SEQ ID NO: 276.

In some embodiments, a 5T4 VHH domain provided herein contains a CDR1 set forth in any one of SEQ ID NOs: 86 or 87, a CDR2 set forth in SEQ ID NO: 95-99 and a CDR3 set forth in SEQ ID NO: 102.

In some embodiments, the 5T4 VHH domain provided herein contains a CDR1, CDR2, and CDR3 set forth in SEQ ID NOs: 87, 95, 102, respectively. In some embodiments, the 5T4 VHH domain provided herein contains a CDR1, CDR2, and CDR3 set forth in SEQ ID NOs: 87, 96, 102, respectively. In some embodiments, the 5T4 VHH domain provided herein contains a CDR1, CDR2, and CDR3 set forth in SEQ ID NOs: 87, 97, 102, respectively. In some embodiments, the 5T4 VHH domain provided herein contains a CDR1, CDR2, and CDR3 set forth in SEQ ID NOs: 87, 98, 102, respectively. In some embodiments, the 5T4 VHH domain provided herein contains a CDR1, CDR2, and CDR3 set forth in SEQ ID NOs: 87, 99, 102, respectively. In some embodiments, the 5T4 VHH domain provided herein contains a CDR1, CDR2, and CDR3 set forth in SEQ ID NOs: 86, 98, 102, respectively.

In some aspects, a VHH domain that binds 5T4 comprises a CDR1, CDR2 and CDR3 contained in a VHH amino acid sequences selected from any of SEQ ID NO:277-287, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 277-287.

In some cases, the provided 5T4 VHH domain is a humanized variant that has the amino acid sequence set forth in any of SEQ ID NOS: 277-287 or an amino acid sequence that has at least 90%, 91%, 92%, 93%, 94%, 95%, 96%, 97%, 98%, or 99% sequence identity to the VHH region amino acid selected from any one of SEQ ID NOs: 277-287. In some embodiments, the 5T4 humanized VHH domain has the sequence of amino acids set forth in any one of SEQ ID NOS: 277-287.

In some embodiments, a 5T4 VHH domain provided herein contains a CDR1, CDR2, CDR3 contained in a VHH domain set forth in SEQ ID NO: 294, or an amino acid sequence that has at least 90%, 91%, 92%, 93%, 94%, 95%, 96%, 97%, 98%, or 99% sequence identity to the VHH region amino acid selected set forth in SEQ ID NO: 294. In some embodiments, the 5T4 VHH domain has the amino acid sequence set forth in SEQ ID NO: 294 or an amino acid sequence that has at least 90%, 91%, 92%, 93%, 94%, 95%, 96%, 97%, 98%, or 99% sequence identity to the amino acid selected set forth in SEQ ID NO: 294. In some embodiments, the 5T4 VHH domain is a humanized variant of the amino acid sequence set forth in SEQ ID NO: 294.

In some embodiments, a 5T4 VHH domain provided herein contains a CDR1 set forth in SEQ ID NO: 296, a CDR2 set forth in SEQ ID NO: 298 and a CDR3 set forth in SEQ ID NO: 300.

In some embodiments, the 5T4 VHH domain provided herein contains a CDR1, CDR2, and CDR3 set forth in SEQ ID NO: 296, 298, 300, respectively.

In some embodiments, a 5T4 VHH domain provided herein contains a CDR1, CDR2, CDR3 contained in a VHH domain set forth in SEQ ID NO: 295, or an amino acid sequence that has at least 90%, 91%, 92%, 93%, 94%, 95%, 96%, 97%, 98%, or 99% sequence identity to the VHH region amino acid selected set forth in SEQ ID NO: 295. In some embodiments, the 5T4 VHH domain has the amino acid sequence set forth in SEQ ID NO: 295 or an amino acid sequence that has at least 90%, 91%, 92%, 93%, 94%, 95%, 96%, 97%, 98%, or 99% sequence identity to the amino acid selected set forth in SEQ ID NO: 295. In some embodiments, the 5T4 VHH domain is a humanized variant of the amino acid sequence set forth in SEQ ID NO: 295.

In some embodiments, a 5T4 VHH domain provided herein contains a CDR1 set forth in SEQ ID NO: 297, a CDR2 set forth in SEQ ID NO: 299 and a CDR3 set forth in SEQ ID NO: 301.

In some embodiments, the 5T4 VHH domain provided herein contains a CDR1, CDR2, and CDR3 set forth in SEQ ID NO: 297, 299, 301, respectively.

In some embodiments, a 5T4 VHH domain provided herein contains a CDR1, CDR2, CDR3 contained in a VHH domain set forth in SEQ ID NO: 302, or an amino acid sequence that has at least 90%, 91%, 92%, 93%, 94%, 95%, 96%, 97%, 98%, or 99% sequence identity to the VHH region amino acid selected set forth in SEQ ID NO: 302. In some embodiments, the 5T4 VHH domain has the amino acid sequence set forth in SEQ ID NO: 302 or an amino acid sequence that has at least 90%, 91%, 92%, 93%, 94%, 95%, 96%, 97%, 98%, or 99% sequence identity to the amino acid selected set forth in SEQ ID NO: 302. In some embodiments, the 5T4 VHH domain is a humanized variant of the amino acid sequence set forth in SEQ ID NO: 302.

In some embodiments, a 5T4 VHH domain provided herein contains a CDR1 set forth in SEQ ID NO: 288, a CDR2 set forth in SEQ ID NO: 88 and a CDR3 set forth in SEQ ID NO: 303.

In some embodiments, the 5T4 VHH domain provided herein contains a CDR1, CDR2, and CDR3 set forth in SEQ ID NO: 288, 88, 303, respectively.

III. FUSION PROTEINS AND CONJUGATES CONTAINING 5T4-BINDING POLYPEPTIDES

Provided herein are fusion proteins and conjugates containing 5T4-binding polypeptides containing at least one VHH domain that specifically binds 5T4 linked, directly or indirectly, to one or more additional domains or moieties. In some embodiments, the fusion protein or conjugate of the present disclosure is composed of a single polypeptide. In other embodiments, the fusion protein or conjugate of the present disclosure is composed of more than one polypeptide. In some embodiments, the 5T4-binding polypeptide of the present disclosure incorporates at least one VHH domain that specifically binds 5T4. In some aspects, the 5T4-binding polypeptide is multivalent. In some embodiments, the 5T4-binding polypeptides include two or more copies of a VHH domain that specifically binds 5T4, for example, three or more, four or more, five or more, or six or more copies of a VHH domain that specifically binds 5T4. In certain aspects, the 5T4-binding polypeptide is multispecific. For example, in some cases, the one or more additional domain may be one or more additional binding domain that binds to one or more further antigen or protein.

In some embodiments, the 5T4-binding polypeptides of the present disclosure include two or more polypeptide sequences that are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length. In some embodiments, the GS-linker comprises an amino acid sequence selected from the group consisting of GGSGGS, i.e., $(GGS)_2$ (SEQ ID NO: 1); GGSGGSGGS, i.e., $(GGS)_3$ (SEQ ID NO: 2); GGSGGSGGSGGS, i.e., $(GGS)_4$ (SEQ ID NO: 3); and GGSGGSGGSGGSGGS, i.e., $(GGS)_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the linker is (GGGGS)n, wherein n is 1 to 5 (SEQ ID NO: 123); (GGGGGS)n, wherein n is 1 to 4 (SEQ ID NO:124); GGGGS (SEQ ID NO:125); GGGGGS (SEQ ID NO:126); GGGGGSGGGGGSGGGGGS (SEQ ID NO:127); GGGGSGGGGSGGGGS (SEQ ID NO: 128); GGSGGGGSGGGGSGGGGS (SEQ ID NO:129); or PGGGG (SEQ ID NO:327). In some embodiments, the 5T4-binding polypeptide includes a combination of a GS-linker and a Glycine linker.

A. Fc Fusions

Provided herein is a 5T4-binding polypeptide that is a fusion protein containing at least one VHH domain that binds 5T4 provided herein and an Fc domain. In some embodiments, a 5T4-binding polypeptide provided herein comprises one, two, three, or four VHH domains that bind 5T4 and an Fc domain.

In some embodiments, incorporation of an immunoglobulin Fc region into the fusion protein can, in some aspects, be composed of two polypeptides that together form a dimer. In some embodiments, an Fc domain mediates dimerization of the 5T4-binding polypeptide at physiological conditions, such as when expressed from a cell, such that a dimer is formed that doubles the number of 5T4 binding sites. For example, a 5T4-binding polypeptide comprising three VHH domains that bind 5T4 and an Fc region is trivalent as a monomer, but the Fc region may mediate dimerization, such that the 5T4-binding polypeptide exists as a hexavalent dimer under such conditions. In some embodiments, a 5T4 VHH domain is fused to an IgG Fc region and in these embodiments, the fusion protein is bivalent having two 5T4 VHH domains per molecule. In some embodiments, two 5T4 binding domains (2×) are fused to an IgG Fc region and in these embodiments, the fusion protein is tetravalent having four 5T4 VHH domains per molecule. In some embodiments, three 5T4 VHH domain (3×) are fused to an IgG Fc region and in these embodiments, the fusion protein is hexavalent having six 5T4 VHH domains per molecule.

In some embodiments, the multivalent 5T4-binding polypeptide is bivalent. In some embodiments, the bivalent 5T4-binding polypeptide of the disclosure includes two copies of a 5T4-binding polypeptide having the following structure: (5T4 VHH)-Linker-Fc. In some embodiments, the multivalent 5T4-binding polypeptide is tetravalent. In some embodiments, the tetravalent 5T4-binding polypeptide of the disclosure includes two copies of a 5T4-polypeptide having the following structure: (5T4 VHH)-Linker-(5T4 VHH)-Linker-Fc. In some embodiments, the multivalent 5T4-binding polypeptide is hexavalent. In some embodiments, the hexavalent 5T4-binding polypeptide of the disclosure includes two copies of a 5T4-binding polypeptide having the following structure: (5T4 VHH)-Linker-(5T4 VHH)-Linker-(5T4 VHH)-Linker-Fc.

In some cases, the CH3 domain of the Fc region can be used as homodimerization domain, such that the resulting fusion protein is formed from two identical polypeptides. In other cases, the CH3 dimer interface region of the Fc region can be mutated so as to enable heterodimerization. For example, a heterodimerization domain can be incorporated into the fusion protein such that the construct is an asymmetric fusion protein.

In any of the provided embodiments, a 5T4 VHH domain can be any as described above. In come embodiments, the 5T4 VHH domain is a humanized VHH domain that binds 5T4.

In various embodiments, an Fc domain included in a 5T4-binding polypeptide is a human Fc domain, or is derived from a human Fc domain. In some embodiments, the fusion protein contains an immunoglobulin Fc region. In some embodiments, the immunoglobulin Fc region is an IgG isotype selected from the group consisting of IgG1 isotype, IgG2 isotype, IgG3 isotype, and IgG4 subclass.

In some embodiments, the immunoglobulin Fc region or immunologically active fragment thereof is an IgG isotype. For example, the immunoglobulin Fc region of the fusion protein is of human IgG1 isotype, having an amino acid sequence:

```
                              (SEQ ID NO: 8)
PAPELLGGPS  VFLFPPKPKD  TLMISRTPEV

TCVVVDVSHE  DPEVKFNWYV  DGVEVHNAKT

KPREEQYNST  YRVVSVLTVL  HQDWLNGKEY

KCKVSNKALP  APIEKTISKA  KGQPREPQVY

TLPPSRDELT  KNQVSLTCLV  KGFYPSDIAV

EWESNGQPEN  NYKTTPPVLD  SDGSFFLYSK

LTVDKSRWQQ  GNVFSCSVMH  EALHNHYTQK

SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 8.

In some embodiments where the fusion protein of the disclosure includes an Fc polypeptide, the Fc polypeptide is mutated or modified. In some cases, the mutations include one or more amino acid substitutions to reduce an effector function of the Fc polypeptide. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information System®, www.imgt.org/IMGTScientificChart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, an Fc region that exhibits reduced effector functions may be a desirable candidate for applications in which 5T4 or CD3 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retain FcRn binding ability. The primary cells for mediating ADCC, NK cells, express FcγRIII only, whereas monocytes express FcγRI, FcγRII and FcγRIII. Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the multispecific polypeptide construct or cleaved components thereof is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18 (12): 1759-1769 (2006)).

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68 (10): 3863-72; Idusogie et al., 2001 J Immunol, 166 (4): 2571-5; Moore et al., 2010 mAbs, 2 (2): 181-189; Lazar et al., 2006 PNAS, 103 (11): 4005-4010, Shields et al., 2001 JBC, 276 (9): 6591-6604; Stavenhagen et al., 2007 Cancer Res, 67 (18): 8882-8890; Stavenhagen et al., 2008 Advan. Enzyme Regul., 48:152-164; Alegre et al, 1992 J Immunol, 148:3461-3468; Reviewed in Kaneko and Niwa, 2011 Biodrugs, 25 (1): 1-11.

Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325), Ala327 (A327) or Pro329 (P329). For example, Leu 234Ala (L234A), Leu235Ala (L235A), Leu235Glu (L235E), Asp265Asn (D265N), Asp265Ala (D265A), Asp270Asn (D270N), Ser298Asn (S298N), Asn297Ala (N297A), Pro329Ala (P329A) or Pro239Gly (P329G), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the human IgG1 Fc region is modified at amino acid Asn297 (Kabat Numbering) to prevent glycosylation of the fusion protein, e.g., Asn297Ala (N297A) or Asn297Asp (N297D). In some embodiments, the Fc region of the fusion protein is modified at amino acid Leu235 (Kabat Numbering) to alter Fc receptor interactions, e.g., Leu235Glu (L235E) or Leu235Ala (L235A). In some embodiments, the Fc region of the fusion protein is modified at amino acid Leu234 (Kabat Numbering) to alter Fc receptor interactions, e.g., Leu234Ala (L234A). In some embodiments, the Fc region of the fusion protein is modified at amino acid Leu234 (Kabat Numbering) to alter Fc receptor interactions, e.g., Leu235Glu (L235E). In some embodiments, the Fc region of the fusion protein is altered at both amino acids 234 and 235, e.g., Leu234Ala and Leu235Ala (L234A/L235A) or Leu234Val and Leu235Ala (L234V/L235A). In some embodiments, the Fc region of the fusion protein is altered at amino acids at 234, 235, and 297, e.g., Leu234Ala, Leu235Ala, Asn297Ala (L234A/L235A/N297A). In some embodiments, the Fc region of the fusion protein is altered at amino acids at 234, 235, and 329, e.g., Leu234Ala, Leu235Ala, Pro239Ala (L234A/L235A/P329A). In some embodiments, the Fc region of the fusion protein is modified at amino acid Asp265 (Kabat Numbering) to alter Fc receptor interactions, e.g Asp265Ala (D265A). In some embodiments, the Fc region of the fusion protein is modified at amino acid Pro329 (Kabat Numbering) to alter Fc receptor interactions, e.g Pro329Ala (P329A) or Pro329Gly (P329G). In some embodiments, the Fc region of the fusion protein is altered at both amino acids 265 and 329, e.g., Asp265Ala and Pro329Ala (D265A/P329A) or Asp265Ala and Pro329Gly (D265A/P329G). In some embodiments, the Fc region of the fusion protein is altered at amino acids at 234, 235, and 265, e.g., Leu234Ala, Leu235Ala, Asp265Ala (L234A/L235A/D265A). In some embodiments, the Fc region of the fusion protein is altered at amino acids at 234, 235, and 329, e.g., Leu234Ala, Leu235Ala, Pro329Gly (L234A/L235A/P329G). In some embodiments, the Fc region of the fusion protein is altered at amino acids at 234, 235, 265 and 329, e.g., Leu234Ala, Leu235Ala, Asp265Ala, Pro329Gly (L234A/L235A/D265A/P329G). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A). In some embodiments, the human IgG1 Fc region lacks Lys447 (EU index of Kabat et al 1991 Sequences of Proteins of Immunological Interest).

In some embodiments, the Fc region of the fusion protein is lacking an amino acid at one or more of the following positions to reduce Fc receptor binding: Glu233 (E233), Leu234 (L234), or Leu235 (L235).). In some embodiments, the Fc region of the fusion protein is lacking an amino acid at one or more of the following positions Glu233 (E233), Leu234 (L234), or Leu235 (L235) and is modified at one or more of the Asp265 (D265), Asn297 (N297), or Pro329 (P329) to reduce Fc receptor binding. For example, an Fc region included in a 5T4-binding polypeptide is derived from a human Fc domain, and comprises a three amino acid deletion in the lower hinge corresponding to IgG1 E233, L234, and L235. In some aspects, such Fc polypeptides do not engage FcγRs and thus are referred to as "effector silent" or "effector null." For example, Fc deletion of these three amino acids reduces the complement protein C1q binding. In some embodiments, a polypeptide with an Fc region with Fc deletion of these three amino acids retains binding to FcRn and therefore has extended half-life and transcytosis associated with FcRn mediated recycling. Such a modified Fc region is referred to as "Fc xELL" or "Fc deletion" and has the following amino acid sequence:

```
                                    (SEQ ID NO: 9)
      PAPGGPSVFL FPPKPKDTLM ISRTPEVTCV

VVDVSHEDPE VKFNWYVDGV EVHNAKTKPR

EEQYNSTYRV VSVLTVLHQD WLNGKEYKCK

VSNKALPAPI EKTISKAKGQ PREPQVYTLP

PSRDELTKNQ VSLTCLVKGF YPSDIAVEWE

SNGQPENNYK TTPPVLDSDG SFFLYSKLTV

DKSRWQQGNV FSCSVMHEAL HNHYTQKSLS

LSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 9.

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, J. Biol Chem Vol. 281 (33)23514-23524), Met428Leu and Asn434Ser (M428L, N434S) (Zalevsky et al 2010 Nature Biotech, Vol. 28 (2) 157-159), or Met252Ile, Thr256Asp, Met428Leu (M252I, T256D, M428L, respectively), (EU index of Kabat et al 1991 Sequences of Proteins of Immunological Interest).

In some embodiments, the Fc domain included in a 5T4-binding polypeptide is derived from a human Fc domain and comprises mutations M252Y and M428V, herein referred to as "Fc-YV". In some embodiments, the mutated or modified Fc polypeptide includes the following mutations: M252Y and M428L using the Kabat numbering system. In some embodiments, such mutations enhance binding to FcRn at the acidic pH of the endosome (near 6.5), while losing detectable binding at neutral pH (about 7.2), allowing for enhanced FcRn mediated recycling and extended half-life.

In some embodiments, the Fc domain included in a 5T4-binding polypeptide is derived from a human Fc domain and comprises mutations to induce heterodimerization. In some embodiments, such mutations include those referred to as "knob" and "hole" mutations. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). In some embodiments, the "knob" Fc domain comprises the mutation T366W. In some embodiments, the "hole" Fc domain comprises mutations T366S, L368A, and Y407V. Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248:7-15). In some embodiments, Fc domains used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hole Fc domain comprises the modification H435R or H435K (referred to as "hole-R" in some instances when the modification is H435R), while the knob Fc domain does not. In some instances, the hole-R mutation improves purification of the heterodimer over homodimeric hole Fc domains that may be present.

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the immunoglobulin Fc region or immunologically active fragment of the fusion protein is of human IgG2 isotype, having an amino acid sequence:

```
                               (SEQ ID NO: 10)
PAPPVAGPSV  FLFPPKPKDT  LMISRTPEVT

CVVVDVSHED  PEVQFNWYVD  GVEVHNAKTK

PREEQFNSTF  RVVSVLTVVH  QDWLNGKEYK

CKVSNKGLPA  PIEKTISKTK  GQPREPQVYT

LPPSREEMTK  NQVSLTCLVK  GFYPSDISVE

WESNGQPENN  YKTTPPMLDS  DGSFFLYSKL

TVDKSRWQQG  NVFSCSVMHE  ALHNHYTQKS

LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 10.

In some embodiments, the human IgG2 Fc region is modified at amino acid Asn297 (e.g. to prevent to glycosylation of the antibody, e.g., Asn297Ala (N297A) or Asn297Asp (N297D). In some embodiments, the human IgG2 Fc region is lacks Lys447 (EU index of Kabat et al 1991 Sequences of Proteins of Immunological Interest).

In some embodiments, the immunoglobulin Fc region or immunologically active fragment of the fusion protein is of human IgG3 isotype, having an amino acid sequence:

```
                               (SEQ ID NO: 11)
PAPELLGGPS  VFLFPPKPKD  TLMISRTPEV

TCVVVDVSHE  DPEVQFKWYV  DGVEVHNAKT

KPREEQYNST  FRVVSVLTVL  HQDWLNGKEY

KCKVSNKALP  APIEKTISKT  KGQPREPQVY

TLPPSREEMT  KNQVSLTCLV  KGFYPSDIAV

EWESSGQPEN  NYNTTPPMLD  SDGSFFLYSK

LTVDKSRWQQ  GNIFSCSVMH  EALHNRFTQK

SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 11.

In some embodiments, the human IgG3 Fc region is modified at amino acid Asn297 (Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region is lacks Lys447 (EU index of Kabat et al 1991 Sequences of Proteins of Immunological Interest).

In some embodiments, the immunoglobulin Fc region or immunologically active fragment of the fusion protein is of human IgG4 isotype, having an amino acid sequence:

```
                               (SEQ ID NO: 12)
PAPEFLGGPS  VFLFPPKPKD  TLMISRTPEV

TCVVVDVSQE  DPEVQFNWYV  DGVEVHNAKT

KPREEQFNST  YRVVSVLTVL  HQDWLNGKEY

KCKVSNKGLP  SSIEKTISKA  KGQPREPQVY

TLPPSQEEMT  KNQVSLTCLV  KGFYPSDIAV

EWESNGQPEN  NYKTTPPVLD  SDGSFFLYSR

LTVDKSRWQE  GNVFSCSVMH  EALHNHYTQK

SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 12.

In some embodiments, the immunoglobulin Fc region or immunologically active fragment of the fusion protein is of human IgG4 isotype, having an amino acid sequence:

```
                              (SEQ ID NO: 13)
PAPELLGGPS VFLFPPKPKD TLMISRTPEV

TCVVVDVSQE DPEVQFNWYV DGVEVHNAKT

KPREEQFNST YRVVSVLTVL HQDWLNGKEY

KCKVSNKGLP SSIEKTISKA KGQPREPQVY

TLPPSQEEMT KNQVSLTCLV KGFYPSDIAV

EWESNGQPEN NYKTTPPVLD SDGSFFLYSR

LTVDKSRWQE GNVFSCSVMH EALHNHYTQK

SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 13.

In some embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447 (EU index of Kabat et al 1991 Sequences of Proteins of Immunological Interest).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTH-TCPPC (SEQ ID NO: 14), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 15).

In some embodiments, the fusion protein has a modified hinge from IgG4, which is modified to prevent or reduce strand exchange, e.g., Ser228Pro (S228P), having the sequence ESKYGPPCPPC (SEQ ID NO: 16). In some embodiments, the fusion protein contains linker polypeptides. In other embodiments, the fusion protein contains linker and hinge polypeptides.

In some embodiments, the Fc region lacks or has reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line.

In some embodiments, the Fc region is engineered to eliminate recognition by pre-existing antibodies found in humans. In some embodiments, VHH-containing polypeptides of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence has the sequence GQGTLVTVKPGG (SEQ ID NO: 17) or GQGTLVTVEPGG (SEQ ID NO: 18) or modification thereof. In some embodiments, the VHH-containing polypeptides of the present disclosure are modified by mutation of position 11 and by changes in carboxy-terminal region.

In some embodiments, the one or more polypeptides of the fusion proteins of the present disclosure are operably linked via amino acid linkers. In some embodiments, these linkers are composed predominately of the amino acids Glycine and Serine, denoted as GS-linkers herein. In some embodiments, these linkers are composed predominately of the amino acids Glycine, denoted as glycine linkers herein. The GS-linkers or glycine linkers of the fusion proteins of the present disclosure can be of various lengths, for example, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 1); GGSGGSGGS, i.e., $(GGS)_3$ (SEQ ID NO: 2); GGSGGSGGSGGS, i.e., $(GGS)_4$ (SEQ ID NO: 3); and GGSGGSGGSGGSGGS, i.e., $(GGS)_5$ (SEQ ID NO: 4). In some embodiments, the linker is a flexible linker is a glycine linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the linker is (GGGGS)n, wherein n is 1 to 5 (SEQ ID NO:123); (GGGGGS)n, wherein n is 1 to 4 (SEQ ID NO: 124); GGGGS (SEQ ID NO:125); GGGGGS (SEQ ID NO:126); GGGGGSGGGGGSGGGGGS (SEQ ID NO:127); GGGGSGGGGSGGGGS (SEQ ID NO:128); GGSGGGGSGGGGSGGGGS (SEQ ID NO: 129); or PGGGG (SEQ ID NO:327). In some embodiments, the fusion proteins can include a combination of a GS-linker and a Glycine linker.

B. Conjugates

Provided herein are conjugates containing at least one VHH domain that specifically binds 5T4 provided herein and one or more further moiety. The further moiety can be a therapeutic agent, such as a cytotoxic agent, or can be a detection agent. In some embodiments, the moiety can be a targeting moiety, a small molecule drug (non-polypeptide drug of less than 500 Daltons molar mass), a toxin, a cytostatic agent, a cytotoxic agent, an immunosuppressive agent, a radioactive agent suitable for diagnostic purposes, a radioactive metal ion for therapeutic purposes, a prodrug-activating enzyme, an agent that increases biological half-life, or a diagnostic or detectable agent.

In some embodiments, the conjugate is an antibody drug conjugate (ADC, also called immunoconjugates) containing one or more 5T4 VHH domain provided herein conjugated to a therapeutic agent, which is either cytotoxic, cytostatic or otherwise provides some therapeutic benefit. In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In some embodiments, provided antibody drug conjugates of the present disclosure allow targeted-delivery of the drug moiety to tumors. In some cases, this can result in targeted killing of the tumor cell.

In some embodiments, there is provided a 5T4-binding conjugate comprising at least one 5T4 VHH domain provided herein conjugated with a therapeutic agent. In some embodiments, the therapeutic agent includes, for example, daunomycin, doxorubicin, methotrexate, and vindesine (Rowland et al., Cancer Immunol. Immunother. 21:183-187, 1986). In some embodiments, the therapeutic agent has an intracellular activity. In some embodiments, the 5T4-binding conjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, *Pseudomonas* exotoxin A and variants thereof. In some embodiments, where the therapeutic agent is a cytotoxin comprising a polypeptide having a ribosome-inactivating activity, the 5T4-binding conjugate must be internalized upon binding to the target cell in order for the protein to be cytotoxic to the cells.

In some embodiments, there is provided a 5T4-binding conjugate comprising at least one 5T4 VHH domain provided herein conjugated with a toxin. In some embodiments, the toxin includes, for example, bacterial toxins such as diphtheria toxin, plant toxins such as ricin, small molecule toxins such as geldanamycin (Mandler et al., J. Nat. Cancer Inst. 92 (19): 1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may exert their cytotoxic and cytostatic effects by mechanisms including tubulin binding, DNA binding, or topoisomerase inhibition.

In some embodiments, there is provided a 5T4-binding conjugate comprising at least one 5T4 VHH domain provided herein conjugated with a label, which can generate a detectable signal, indirectly or directly. These 5T4-binding conjugates can be used for research or diagnostic applications, such as for the in vivo detection of cancer. The label is preferably capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example 99Tc or 123I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The 5T4-binding conjugates may be prepared using any methods known in the art. See, e.g., WO 2009/067800, WO 2011/133886, and U.S. Patent Application Publication No. 2014322129, incorporated by reference herein in their entirety.

In some embodiments, the attachment can be covalent or non-covalent, e.g., via a biotin-streptavidin non-covalent interaction. In some embodiments, 1, 2, 3, 4, 5 or more moieties, which can be the same or different, are conjugated, linked or fused to a 5T4 VHH domain to form a 5T4-binding conjugate. In some embodiments, such moieties can be attached to the VHH domain using various molecular biological or chemical conjugation and linkage methods known in the art and described below. In some embodiments, linkers such as peptide linkers, cleavable linkers, non-cleavable linkers or linkers that aid in the conjugation reaction, can be used to link or conjugate the effector moieties to the variant polypeptide or immunomodulatory protein.

In some embodiments, a 5T4 VHH domain is conjugated to one or more moieties, e.g. about 1 to about 20 drug moieties per VHH, through a linker (L). In some embodiments, the 5T4-binding conjugate comprises the following components: (VHH domain), (L) q and (moiety) m, wherein the VHH domain is any of the described VHH domains capable of specifically binding 5T4 as described; L is a linker for linking the protein or polypeptide to the moiety; m is at least 1; q is 0 or more; and the resulting 5T4-binding conjugate binds to 5T4. In particular embodiments, m is 1 to 4 and q is 0 to 8.

The linker may be composed of one or more linker components. For covalent attachment of the antibody and the drug moiety the linker typically has two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

Exemplary linker components include 6-maleimido-caproyl ("MC"), maleimidopropanoyl ("MP"), valine-citrulline ("val-cit"), a alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-I carboxylate ("SMCC"), and N-Succinimidyl (4-iodo-acetyl) aminobenzoate ("SIAB").

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, at a plasmin protease.

Conjugates of a VHH domain and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl substrate), aldehydes (such as glutaraldehyde), bis-azido compounds (such as bis (p-azido-benzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugate can be prepared by a variety of methods, such as organic chemistry reactions, conditions, and reagents known to those skilled in the art. In one embodiments, methods include: (1) reaction of a nucleophilic group of a VHH domain with a bivalent linker reagent, to form VHH-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of a VHH domain.

Nucleophilic groups on antibodies, including VHH domains, include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugates, such as antibody drug conjugates, may also be produced by modification of an antibody, such as a VHH domain, to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may lead with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid. Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBi esters, haloformates, and acid halides; (ii) alkyl and benzyl halides such as haloacetamides; (iii) aldehydes, ketones, carboxyl, and maleimide groups.

Alternatively, a fusion protein containing a VHH domain and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

C. Multispecific Formats

Provided herein are 5T4-binding polypeptides that are multispecific containing at least one VHH domain that binds 5T4 and one or more additional binding domains. Typically, the one or more additional domains bind to a second antigen or protein other than 5T4. In some embodiments, the one or more additional domain is an antibody or antigen-binding fragment specific for the second antigen or protein. In some embodiments, the additional domain is a VHH domain.

In some embodiments, a multispecific 5T4-binding polypeptide comprises at least one VHH domain that binds 5T4 and at least one additional binding domain that binds a second antigen or protein. In some embodiments, this second antigen is a tumor associated antigen (TAA) or tumor microenvironment associated antigen (TMEAA). In some embodiments, this second antigen is an immunomodulatory antigen, wherein said antigen is involved with enhancing or dampening a signaling pathway in an immune cell. In some embodiments, this second antigen is a tumor associated antigen (TAA) or tumor microenvironment associated antigen (TMEAA). In some embodiments, this second antigen is an immunomodulatory antigen, wherein said antigen is involved with enhancing or dampening a signaling pathway in an immune cell.

In some cases, a multispecific 5T4-binding polypeptide can further contain an Fc domain, such as any described above. In some embodiments, a multispecific 5T4-binding polypeptide provided herein at least one VHH domains that bind 5T4, at least one additional binding domain that binds a second antigen or protein, and an Fc domain. In some embodiments, an Fc domain mediates dimerization of the multispecific 5T4-binding polypeptide at physiological conditions such that a dimer is formed that doubles the number of binding sites for 5T4 and for the additional antigen or protein.

Non-limiting exemplary multispecific 5T4-binding polypeptides are described below.

1. Bispecific T Cells Engager

In some embodiments, the 5T4-binding polypeptide is a bispecific construct that is or comprises at least one 5T4 VHH domain provided herein and at least one additional binding molecule capable of binding to a surface molecule expressed on a T cell. In some embodiments, the surface molecule is an activating component of a T cell, such as a component of the T cell receptor complex. In particular aspects, the surface molecule is an activating T cell antigen that is expressed on a T cell and is capable of inducing T cell activation upon interaction with an antigen binding molecule. For example, in some aspects, interaction of an antigen binding molecule with an activating T cell antigen may induce T cell activation by triggering the signaling cascade of the T cell receptor complex. Suitable assays to measure T cell activation are known, and include any assay to measure or assess proliferation, differentiation, cytokine secretion, cytotoxic activity and/or expression of one or more activation marker. In some embodiments, the simultaneous or near simultaneous binding of such a 5T4-binding polypeptide to both of its targets, 5T4 expressed on target cell and a T cell molecule expressed on a T cell, e.g. activating T cell antigen, can result in a temporary interaction between the target cell and T cell, thereby resulting in activation, e.g. cytotoxic activity, of the T cell and subsequent lysis of the target cell.

In some embodiments, the T surface molecule, such as activating T cell antigen, is CD3 or is CD2. Specifically, a provided bispecific 5T4-binding polypeptide is capable of specifically binding an activating T cell antigen expressed on a human T cell, such as human CD3 or human CD3. In particular aspects, the additional binding domain that is specific to the activating T cell antigen (e.g. CD3 or CD2) is an antibody or antigen-binding fragment. In some embodiments, a 5T4-binding polypeptide can be a bispecific antibody T cell-engager containing at least one 5T4 VHH domain that specifically binds to 5T4 and an additional binding molecule that is an antibody or antigen-binding fragment specific for an activating component of a T cell (e.g. a T cell surface molecule, e.g. CD3 or CD2).

Among bispecific antibody T cell-engagers are bispecific T cell engager (BiTE) molecules, which contain tandem scFv molecules fused by a flexible linker (see e.g. Nagorsen and Bauerle, Exp Cell Res 317, 1255-1260 (2011); tandem scFv molecules fused to each other via, e.g. a flexible linker, and that further contain an Fc domain composed of a first and a second subunit capable of stable association (WO2013026837); diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; or triomabs that include whole hybrid mouse/rat IgG molecules (Seimetz et al, Cancer Treat Rev 36, 458-467 (2010). Similar formats of any of the above molecules can be generated using any of the 5T4 VHH domains provided herein.

In some embodiments, the additional binding domain specific to an activating T cell antigen is an antigen-binding fragment selected from a Fab fragment, a F(ab')₂ fragment, an Fv fragment, a scFv, disulfide stabilized Fv fragment (dsFv), a scAb, a dAb, a single domain heavy chain antibody (VHH), or a single domain light chain antibody. In some embodiments, the additional binding domain is monovalent for binding the activating T cell antigen, such as CD2 or CD3.

In some embodiments, the additional binding domain is capable of binding to CD3 or a CD3 complex. A CD3 complex is a complex of at least five membrane-bound polypeptides in mature T-lymphocytes that are non-covalently associated with one another and with the T-cell receptor. The CD3 complex includes the gamma, delta, epsilon, zeta, and eta chains (also referred to as subunits). In some embodiments, the additional binding molecule is an antibody or antigen-binding fragment capable of specifically binding to CD3 or a CD3 complex, also called a CD3-binding domain. In some embodiments, the CD3-binding domain capable of binding CD3 or a CD3 complex includes one or more copies of an anti-CD3 Fab fragment, an anti-CD3 F(ab')₂ fragment, an anti-CD3 Fv fragment, an anti-CD3 scFv, an anti-CD3 dsFv, an anti-CD3 scAb, an anti-CD3 dAb, an anti-CD3 single domain heavy chain antibody (VHH), and an anti-CD3 single domain light chain antibody. In some embodiments, the anti-CD3 binding domain is monovalent for binding CD3.

In some cases, the CD3-binding domain recognizes the CD3ε-chain. In some embodiments, the anti-CD3ε binding domain includes one or more copies of an anti-CD3ε Fab fragment, an anti-CD3ε F(ab')₂ fragment, an anti-CD3ε Fv fragment, an anti-CD3ε scFv, an anti-CD3ε dsFv, an anti-CD3ε scAb, an anti-CD3ε dAb, an anti-CD3ε single domain heavy chain antibody (VHH), and an anti-CD3ε single domain light chain antibody. In some embodiments, the anti-CD3ε binding domain is monovalent for binding CD3ε.

Exemplary monoclonal antibodies against CD3 or a CD3 complex include, but are not limited to, OKT3, SP34, UCHT1 or 64.1, or an antigen-binding fragment thereof (See e.g., June, et al., J. Immunol. 136:3945-3952 (1986); Yang, et al., J. Immunol. 137:1097-1100 (1986); and Hayward, et al., Immunol. 64:87-92 (1988)). In some aspects, clustering of CD3 on T cells, e.g., by immobilized or cell-localized or tethered anti-CD3-antibodies, leads to T cell activation similar to the engagement of the T cell receptor but independent from its clone typical specificity. In one embodiment, the CD3-binding domain monovalently and specifically binds a CD3 antigen, and is derived from OKT3 (ORTHOCLONE-OKT3™ (muromonab-CD3); humanized OKT3 (U.S. Pat. No. 7,635,475 and published international application No. WO2005040220); SP34 (Pessano et ai. The EMBO Journal. 4:337-344, 1985); humanized variant of SP34 (WO2015001085); Teplizumab™ (MGA031, Eli Lilly); an anti-CD3 binding molecule described in US2011/0275787; UCHT1 (Pollard et al. 1987 J Histochem Cytochem. 35 (11): 1329-38; WO2000041474); NI0401 (WO2007/033230); visilizumab (U.S. Pat. No. 5,834,597); BC-3 (Anasetti et al., Transplantation 54:844 (1992); H2C (described in PCT publication no. WO2008/119567); V9 (described in Rodrigues et al., Int J Cancer Suppl 7, 45-50 (1992) and U.S. Pat. No. 6,054,297)). Other anti-CD3 antibodies also can be used in the constructs provided herein, including any described in International published PCT application Nos. WO199404679, WO2008119567, WO2015095392, WO2016204966, WO2019133761; published patent application Nos. US20170369563, US20180194842, US20180355038; U.S. Pat. Nos. 7,728, 114, 7,381,803, 7,994,289.

In some embodiments, the CD3-binding domain contains a variable heavy (VH) chain set forth in SEQ ID NO:19 and/or a variable light chain set forth in SEQ ID NO:20, or VH and/or VL sequences having at least 60%, 70%, 80%, 90%, 95%, 97%, 98%, 99% identity with these sequences and specifically binds CD3. In some embodiments, the CD3-binding domain contains a CDRH1, CDRH2 and CDRH3 of the variable heavy (VH) chain set forth in SEQ ID NO:19 and a CDRL1, CDRL2 and CDRL3 variable light chain set forth in SEQ ID NO:20. In some cases, the CD3-binding region comprises a humanized version of the VH sequence set forth in SEQ ID NO: 19 and a humanized version of the VL sequence set forth in SEQ ID NO:20. In some embodiments a CD3-binding region can contain a humanized OKT3 derived VH domain sequence set forth in any one of SEQ ID NOs 21, 22, 23 and/or a VL domain sequence set forth in any one of SEQ ID NOs 24, 25, 26, or VH and/or VL sequences having at least 60%, 70%, 80%, 90%, 95%, 97%, 98%, 99% identity with these sequences and specifically binds CD3. In some embodiments, the CD3-binding domain is a Fab, scFv, Fv or dsFv, in which is contained any combination of the above VH and VL sequence, particularly any combination of a VH sequence set forth in any of SEQ ID NOS: 21, 22, 23 and a VL sequence set forth in any of SEQ ID NOS: 24, 25, 26. In some embodiments, the anti-CD3ε binding domain includes a VH CDR1 sequence that includes at least the amino acid sequence TYAMN (SEQ ID NO: 29); a VH CD2 sequence that includes at least the amino acid sequence RIRSKYN-NYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34). In some embodiments, the CD3-binding domain is a Fab, scFv, Fv or dsFv, in which is contained a VH CDR1 sequence that includes at least the amino acid sequence TYAMN (SEQ ID NO: 29); a VH CD2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34).

In some embodiments, the CD3-binding domain contains a variable heavy (VH) chain set forth in SEQ ID NO:27 and/or a variable light chain set forth in SEQ ID NO:28, or VH and/or VL sequences having at least 60%, 70%, 80%, 90%, 95%, 97%, 98%, 99% identity with these sequences and specifically binds to CD3. In some embodiments, the CD3-binding domain contains a CDRH1, CDRH2 and CDRH3 of the variable heavy (VH) chain set forth in SEQ ID NO:27 and a CDRL1, CDRL2 and CDRL3 variable light chain set forth in SEQ ID NO:28. In some embodiments, the CD3-binding domain contains a CDRH1, CDRH2 and CDRH3 set forth in SEQ ID NOs: 29, 30 and 31, respectively and a CDRL1, CDRL2 and CDRL3 variable light chain set forth in SEQ ID NO:32, 33, and 34, respectively. In some cases, the CD3-binding region comprises a humanized version of the VH sequence set forth in SEQ ID NO: 27 and a humanized version of the VL sequence set forth in SEQ ID NO:28. In some embodiments a CD3-binding region can contain a humanized VH domain sequence set forth in any one of SEQ ID NOs 27, 35-65, 341, 343, or 358 and/or a VL domain sequence set forth in any one of SEQ ID NOs: 28, 66-84, 293, 340, or 342, or VH and/or VL sequences having at least 60%, 70%, 80%, 90%, 95%, 97%, 98%, 99% identity with these sequences and specifically binds to CD3. In some embodiments a CD3-binding region can contain a humanized VH domain sequence set forth in any one of SEQ ID NOs 27, 35-65, 341, 343, 358, 388, 389, 392, 393 and/or a VL domain sequence set forth in any one of SEQ ID NOs: 28, 66-84, 293, 340, 342, 390, 391, 394, 395, or VH and/or VL sequences having at least 60%, 70%, 80%, 90%, 95%, 97%, 98%, 99% identity with these sequences and specifically binds to CD3. In some embodiments, the anti-CD3ε binding domain thereof includes a variable heavy chain (VH) comprising the amino acid sequence of SEQ ID NO: 47 and a variable light chain (VL) comprising the amino acid sequence of SEQ ID NO: 75.

In some embodiments, the CD3-binding domain is a Fab, scFv, Fv or dsFv, in which is contained any combination of the above VH and VL sequence, particularly any combination of a VH sequence set forth in any of SEQ ID NOS: 27, 35-65, 341, 343, or 358 and a VL sequence set forth in any of SEQ ID NOS: 28, 66-84, 293, 340, or 342. In some embodiments, the anti-CD3 binding domain is a Fab, scFv, Fv or dsFv, in which is contained a variable heavy chain (VH) comprising the amino acid sequence of SEQ ID NO: 47 and a variable light chain (VL) comprising the amino acid sequence of SEQ ID NO: 75.

In some embodiments, the CD3-binding domain contains a variable heavy (VH) chain set forth in any one of SEQ ID NO:388, 389, 392, or 393. In some embodiments, the CD3-binding domain contains a variable light (VL) chain set forth in any one of SEQ ID NO:390, 391, 394, or 395.

The provided bispecific constructs can be formatted in any of a number of formats containing the at least one 5T4 VHH domain and the at least one additional domain specific to an activating T cell antigen, such as a CD3-binding domain.

In one embodiment, the bispecific construct is a bispecific single-domain antibody-linked Fab (S-Fab) containing at least one 5T4 VHH domain as described linked, directly or indirectly to a Fab antigen binding fragment specific to a T cell activating antigen, e.g. CD3, such as an anti-CD3 Fab.

The Fab against a T cell activating antigen, e.g. anti-CD3 Fab, can contain any of the VH and VL sequences as described. In some embodiments, the 5T4 VHH domain is linked to the C-terminus of the VH or VL chain of an anti-CD3 Fab. In some embodiments, the S-Fab can be further modified, such as by conjugation with polyethylene glycol (PEG), N-(2-hydroxypropyl) methacrylamide (HPMA) copolymers, proteins (such as albumin), polyglutamic acid or PASylation (Pan et al. (2018) International Journal of Nanomedicine, 2018:3189-3201).

In another embodiment, the bispecific construct is a scFv-single domain antibody in which the construct contains at least one 5T4 VHH as described linked, directly or indirectly, to an scFv containing a VH and a VL of an antigen binding domain specific to a T cell activating antigen, e.g. CD3. The scFv against a T cell activating antigen, e.g. anti-CD3 scFv, can contain any of the VH and VL sequences as described. In some embodiments, the VHH domain and the scFv are connected by a linker, such as a peptide linker. In some embodiments, the peptide linker can be a peptide linker as described herein. In some embodiments, the VHH domain and the scFv are each connected, optionally through a hinge region or a linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In a further embodiment, the CD3-binding domain is a single domain antibody, such as is a VHH domain that specifically binds to CD3. Single domain antibodies, including VHH domains that bind to CD3 are known, see e.g. published U.S. patent application No. US20160280795. In some embodiments, the CD3-binding domain is an anti-CD3 VHH set forth in SEQ ID NO:85, or a sequence that exhibits at least 60%, 70%, 80%, 90%, 95%, 97%, 98%, 99% identity with SEQ ID NO:85 and specifically binds to CD3. In such aspects, a bispecific construct provided herein can include at least one 5T4 VHH domain and at least one CD3 VHH domain. For formatting the constructs, in some cases, each VHH domain is connected, optionally through a hinge region or linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In the above embodiments, exemplary modifications of an Fc region to promote heterodimerization are known, including any as described below, e.g. Table 3. In some embodiments, one Fc polypeptide of a heterodimeric Fc comprises the sequence of amino acids set forth in any of SEQ ID NOS: 328 (e.g. SEQ ID NO: 103 or 107), 334 (e.g. SEQ ID NO:115 or 117), and the other Fc polypeptide of the heterodimeric Fc contains the sequence of amino acids set forth in any of SEQ ID NOS: 329 (e.g. SEQ ID NO:104 or 108), 332 (e.g. SEQ ID NO: 111 or 113), 336 (e.g. SEQ ID NO:119 or 121). In some embodiments, one Fc polypeptide of a heterodimeric Fc comprises the sequence of amino acids set forth in any of SEQ ID NOS: 330 (e.g. SEQ ID NO: 105 or 109), 335 (e.g. SEQ ID NO: 116 or 118) and the other Fc polypeptide of the heterodimeric Fc comprises the sequence of amino acids set forth in any of SEQ ID NOS: 331 (e.g. SEQ ID NO:106 or 110), 333 (e.g. SEQ ID NO:112 or 114), 337 (e.g. SEQ ID NO:120 or 122).

2. Constrained CD3 Multispecific Construct

In some embodiments, the 5T4-binding polypeptide is a multispecific polypeptide construct that is a constrained T-cell engaging fusion protein. In particular aspects, the constrained multispecific constructs provided herein bind an activating T cell antigen, such as a CD3, and 5T4. The constrained multispecific polypeptide constructs provided herein include at least a first component that includes an immunoglobulin Fc region, a second component that includes one or more copies of at least a binding domain that binds CD3 (referred to herein as an anti-CD3 binding domain or a CD3 binding domain, which are terms that are used interchangeably herein), and a linker, such as a polypeptide linker, that joins the first component and the second component. In the provided multispecific polypeptide constructs, one or both of the first and second components contain at least one 5T4 VHH domain, which, when engaged upon binding to antigen, render the constrained CD3 binding region substantially able to bind CD3. FIGS. 3A-3E depict exemplary formats of a constrained multispecific construct.

In some embodiments, the constrained multispecific polypeptide constructs provided herein exist in two states in terms of capacity to bind CD3 and subsequently activate T-cells: (1) the "inactive" state occurs when there is no binding of any or all of the antigen binding domain(s) to 5T4, such that the CD3 binding is constrained and T-cell interaction is obviated or reduced, and (2) the "active" state occurs upon antigen binding by any or all of the antigen binding domain(s), such that the CD3 binding region is able to bind CD3 and the T-cell interaction is allowed.

In some embodiments, the Fc region is linked to the CD3 binding domain via a linker or linkers. In some embodiments, the Fc region is linked to the CD3 binding region via a non-cleavable linker or linkers. In some embodiments, the Fc region is linked to the CD3 binding region via a cleavable linker or an otherwise labile linker or linkers. In some embodiments, cleavable linker is a linker that can be specifically cleaved in the presence of a protease. In some aspects, enhanced CD3 binding occurs following cleavage of the cleavable linker. In some such aspects, the "active" state can be further amplified via several mechanisms, including via cleavage of the linker joining the CD3 binding region and the Fc region. In some embodiments, the cleavable linker is a linker that contains a substrate recognition site for a protease. In some embodiments, wherein the Fc region and the CD3 binding region are linked by a cleavable linker, enhanced CD3 binding may occur following cleavage within the linker(s).

Further, in aspects wherein the Fc region and the CD3 binding region are operably linked by a cleavable linker, cleavage of the linker(s) between the Fc region and the CD3 binding region may separate the constrained multispecific polypeptide constructs into a first and second component. Depending on the composition of the constrained multispecific polypeptide construct, the first and second component may have distinct functionalities. In some embodiments, the Fc region is a region that exhibits one or more effector functions, such as ADCC, CDC or ADCP functions. In such examples, the constrained multispecific polypeptide constructs of the disclosure can be used to produce a self-amplifying system. For example, in some aspects, the incorporation of a protease cleavable linker between the Fc and the components of the CD3 binding domain enables for amplification of the T-cell activating capacity by allowing full exposure of the CD3 binding domain. Depending on the specific linker included, the amplification step can be mediated by tumor associated proteases or by granzymes released following antigen dependent-T-cell activation. If a tumor protease cleavable linker is included the amplification is mediated by the tumor or tumor-microenvironment. Whereas, if a granzyme B cleavable linker is included the amplification may be self-mediated by T-cells following antigen-dependent activation. Furthermore, in cases wherein an effector enabled Fc is included in the construct, amplification may be mediated by granzymes released from NK cell that occurs through an ADCC mechanism.

The provided constrained multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments, the at least one 5T4 VHH domain is positioned on the amino-terminal (N-term) region of the multispecific polypeptide construct. In some embodiments, the at least one 5T4 VHH domain is positioned on the carboxy-terminal (C-term) region of the multispecific polypeptide construct. In some embodiments, the constrained multispecific polypeptide construct contains at least two 5T4 VHH domains that are positioned on both the N- and C-terminal regions of the multispecific polypeptide construct.

In some embodiments, the constrained multispecific polypeptide construct is a dimer, in which dimerization is formed by covalent or non-covalent interactions between two polypeptide chains. In some embodiments, the two polypeptide chains are covalently bonded to each other by, for example, interchain disulfide bonds. In some embodiments, the Fc region mediates dimerization via interchain disulfide bonds. In particular embodiments, a constrained multispecific polypeptide construct contains a heterodimeric Fc region in which, in some cases, the polypeptide chains of the multispecific polypeptide construct are different (heterodimer). In particular examples of a heterodimeric multispecific polypeptide construct, the CD3-binding region is a two chain polypeptide containing a VH and a VL chain, such as is an Fv antibody fragment containing the VH and VL. In some embodiments, the Fv antibody fragment includes a disulfide stabilized anti-CD3 binding Fv fragment (dsFv).

In particular embodiments, the Fv is a disulfide stabilized Fv fragment (dsFv) in which the the $V_H$-$V_L$ heterodimer is stabilized by an interchain disulfide bond. In some embodiments, the interchain disulfide bond is engineered by mutation of position in framework positions of the VH and/or VL chain. In some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, a constrained multispecific polypeptide construct is formed from or includes two polypeptides, including a first polypeptide comprising a first Fc polypeptide of a heterodimeric Fc region, a linker (e.g. cleavable or non-cleavable linker), a VH domain of an anti-CD3 antibody or antigen binding fragment (e.g. Fv); and a second polypeptide comprising a second Fc polypeptide of the heterodimeric Fc region, the linker (e.g. the cleavable linker or non-cleavable), a VL domain of the anti-CD3 antibody or antigen binding fragment (e.g. Fv). In some embodiments, the first polypeptide contains one or two VHH domains that bind to 5T4. In some embodiments, the second polypeptide contains one or two VHH domains that bind to 5T4. In some embodiments, a constrained multispecific polypeptide construct contains at least two 5T4 VHH domains. In some cases, at least one 5T4 VHH domain is located N-terminally to the Fc polypeptide and at least one 5T4 VHH domain is located C-terminally to the chain of the CD3-binding region.

In some embodiments, the first polypeptide or second polypeptide or both the first and second polypeptide further include a co-stimulatory receptor binding region (CRBR) that binds a co-stimulatory receptor. In some embodiments, the CRBR of the first and/or second polypeptide can be located N-terminally to the Fc polypeptide and/or C-terminally to the chain of the CD3-binding region.

In some embodiments, a constrained multispecific polypeptide construct contains at least two VHH domains that bind 5T4 and at least one co-stimulatory receptor binding region (CRBR) that binds a co-stimulatory receptor. In some embodiments, a constrained multispecific polypeptide construct contains (1) a first polypeptide comprising in order of N-terminus to C-terminus: a first 5T4 VHH domain, the first Fc polypeptide of a heterodimeric Fc region, a linker (e.g. a cleavable or non-cleavable linker), a chain (e.g. VH or VL) of an anti-CD3 antibody or antigen binding fragment (e.g. Fv or dsFv), and a second 5T4 VHH domain; and (2) a second polypeptide comprising in order of N-terminus to C-terminus: the second Fc polypeptide of the heterodimeric Fc region, the same linker (e.g. same cleavable linker), the other chain (other of the VH or VL) of the anti-CD3 antibody or antigen binding fragment, and a co-stimulatory receptor binding region (CRBR) that binds a co-stimulatory receptor.

In some embodiments, the first polypeptide or second polypeptide or both the first and second polypeptide further include an inhibitory receptor binding region (IRBR) that binds an inhibitory receptor. In some embodiments, the IRBR of the first and/or second polypeptide can be located N-terminally to the Fc polypeptide and/or C-terminally to the chain of the CD3-binding region.

In some embodiments, a constrained multispecific polypeptide construct contains at least two VHH domains that bind 5T4 and at least one inhibitory receptor binding region (IRBR) that binds an inhibitory receptor. In some embodiments, a constrained multispecific polypeptide construct contains (1) a first polypeptide comprising in order of N-terminus to C-terminus: a first 5T4 VHH domain, the first Fc polypeptide of a heterodimeric Fc region, a linker (e.g. a cleavable or non-cleavable linker), a chain (e.g. VH or VL) of an anti-CD3 antibody or antigen binding fragment (e.g. Fv or dsFv), and a second 5T4 VHH domain; and (2) a second polypeptide comprising in order of N-terminus to C-terminus: the second Fc polypeptide of the heterodimeric Fc region, the same linker (e.g. same cleavable or non-cleavable linker), the other chain (other of the VH or VL) of the anti-CD3 antibody or antigen binding fragment, and an inhibitory receptor binding region (IRBR) that binds an inhibitory receptor.

In some embodiments, at least one of the first polypeptide or second polypeptide further include a co-stimulatory receptor binding region (CRBR) that binds a co-stimulatory receptor and at least one of the first polypeptide or second polypeptide further includes an inhibitory receptor binding region (IRBR) that binds an inhibitory receptor. In some embodiments, the CRBR of the first and/or second polypeptide can be located N-terminally to the Fc polypeptide and/or C-terminally to the chain of the CD3-binding region. In some embodiments, the IRBR of the first and/or second polypeptide can be located N-terminally to the Fc polypeptide and/or C-terminally to the chain of the CD3-binding region.

In some embodiments, a constrained multispecific polypeptide construct contains at least two VHH domains that bind 5T4, a co-stimulatory receptor binding region (CRBR) that binds a co-stimulatory receptor and an inhibitory receptor binding region (IRBR) that binds an inhibitory receptor. In some embodiments, a constrained multispecific polypeptide construct contains (1) a first polypeptide comprising in order of N-terminus to C-terminus: a first 5T4 VHH domain, the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second 5T4 VHH domain; and (2) a second polypeptide comprising in order of N-terminus to C-terminus: one of an IRBR or CRBR, the second Fc polypeptide of the heterodimeric Fc region, the same linker (e.g. same cleavable linker), the other chain (other of the VH or VL) of the anti-CD3 antibody or antigen binding fragment, and the other of the IRBR or CRBR.

Each of the components of the multispecific polypeptide constructs of the disclosure is described in more detail below.

a. 5T4 VHH Antigen Binding Domain

A constrained multispecific polypeptide construct of the disclosure includes at least one 5T4 VHH domain from among any provided herein. In some embodiments, the 5T4 VHH domain comprises the sequence of amino acids set forth in any of SEQ ID NOS: 245-287, 294-295, 302. In some embodiments, the 5T4 VHH domain comprises the sequence of amino acids set forth in any of SEQ ID NO: 245-287, 294-295, 302, 360. In some embodiments, the 5T4 VHH domain comprises the sequence of amino acids set forth in SEQ ID NO: 360.

In particular embodiments, a constrained multispecific polypeptide construct contains at least two 5T4 domain. In some cases, at least one 5T4 VHH domain is positioned amino terminally relative to an Fc polypeptide of the heterodimeric Fc and at least one 5T4 VHH domain is positioned carboxy-terminally relative to VH or VL chain of the CD3 binding region.

In aspects of a constrained multispecific polypeptide construct containing at least two or containing two 5T4 VHH domains, each of the 5T4 VHH domains can bind to the same or an overlapping epitope on 5T4.

In aspects of a constrained multispecific polypeptide construct containing at least two or containing two 5T4 VHH domains, each of the 5T4 VHH domains can bind to a different or a non-overlapping epitope on 5T4. In some embodiments, the first and second 5T4 sdAb bind a distinct or non-overlapping epitope of 5T4 and/or do not compete for binding to 5T4.

In some embodiments, a 5T4 VHH does not cross react with the mouse 5T4 antigen. In some embodiments, a 5T4 VHH comprising the amino acid sequence set forth in SEQ ID NO:245, or humanized variants thereof, do not cross react with the mouse 5T4 antigen. In some embodiments, a 5T4 VHH comprising the amino acid sequence set forth in SEQ ID NO:255, or humanized variants thereof, do not cross react with the mouse 5T4 antigen. In some embodiments, a 5T4 VHH comprising the amino acid sequence set forth in SEQ ID NO:276, or humanized variants thereof, do not cross react with the mouse 5T4 antigen.

In some examples, the first sdAb comprises the amino acid sequence set forth in any one of SEQ ID NOS: 245-254, 295, 302, 360 a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-254, 295, 302, 360 and binds 5T4; and the second sdAb comprises the amino acid sequence set forth in any one of SEQ ID NOS: 255-287, 294, 302, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 255-287, 294 and binds 5T4.

In some embodiments, the first sdAb (first 5T4 VHH domain) comprises the amino acid sequence set forth in SEQ ID NO: 245 or a humanized variant set forth in any of SEQ ID NOS: 246-254, 295, or 302; and the second sdAb (second 5T4 VHH domain) comprises the amino acid sequence set forth in SEQ ID NO:255 or a humanized variant set forth in any of SEQ ID NOS: 256-275, SEQ ID NO: 276 or a humanized variant thereof set forth in any of SEQ ID NOS: 277-287, 294, or 302.

In some embodiments, the first sdAb (first 5T4 VHH domain) comprises the amino acid sequence set forth in SEQ ID NO: 245 or a humanized variant set forth in any of SEQ ID NOS: 246-254, 295, 302 or 360; and the second sdAb (second 5T4 VHH domain) comprises the amino acid sequence set forth in SEQ ID NO:255 or a humanized variant set forth in any of SEQ ID NOS: 256-275, SEQ ID NO: 276 or a humanized variant thereof set forth in any of SEQ ID NOS: 277-287, 294, or 302.

In some embodiments, the first sdAb (first 5T4 VHH domain) and the second sdAb (second 5T4 VHH domain) have the amino acid sequences set forth in SEQ ID NO: 245 and SEQ ID NO:294. In some embodiments, the first sdAb (first 5T4 VHH domain) and the second sdAb (second 5T4 VHH domain) have the amino acid sequences set forth in SEQ ID NO: 245 and SEQ ID NO:276. In some embodiments, the first sdAb (first 5T4 VHH domain) and the second sdAb (second 5T4 VHH domain) have the amino acid sequences set forth in SEQ ID NO: 245 and SEQ ID NO:255. In some embodiments, the first sdAb (first 5T4 VHH domain) and the second sdAb (second 5T4 VHH domain) have the amino acid sequences set forth in SEQ ID NO:245 and SEQ ID NO: 295. In some embodiments, the first sdAb (first 5T4 VHH domain) and the second sdAb (second 5T4 VHH domain) have the amino acid sequences set forth in SEQ ID NO: 295 and SEQ ID NO:294. In some embodiments, the first sdAb (first 5T4 VHH domain) and the second sdAb (second 5T4 VHH domain) have the amino acid sequences set forth in SEQ ID NO: 249 and SEQ ID NO:270. In some embodiments, the first sdAb (first 5T4 VHH domain) and the second sdAb (second 5T4 VHH domain) have the amino acid sequences set forth in SEQ ID NO: 254 and SEQ ID NO:287. In some embodiments, the first sdAb (first 5T4 VHH domain) and the second sdAb (second 5T4 VHH domain) have the amino acid sequences set forth in SEQ ID NO:302 and SEQ ID NO:302. In some embodiments, the first sdAb (first 5T4 VHH domain) and the second sdAb (second 5T4 VHH domain) have the amino acid sequences set forth in SEQ ID NO: 360 and SEQ ID NO:287.

In some embodiments, a constrained multispecific polypeptide construct contains at least one 5T4 VHH domains, such as any provided herein, and at least one further antigen binding domain specific to another tumor associated antigen (TAA). In some embodiments, the at least one further antigen binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In particular embodiments, the further TAA antigen binding domain is a single chain antibody. In some examples, the single chain is an scFv, a scAb, a single domain heavy chain antibody, or a single domain light chain antibody. For example, in some cases, the further TAA antigen binding domain includes one or more single domain antibody (sdAb) fragments, for example V$_H$H, V$_{NAR}$, engineered V$_H$ Or V$_K$ domains. V$_H$Hs can be generated from natural camelid heavy chain only antibodies, genetically modified rodents that produce heavy chain only antibodies, or naïve/synthetic camelid or humanized camelid single domain antibody libraries. V$_{NAR}$s can be generated from cartilaginous fish heavy chain only antibodies. Various methods have been implemented to generate monomeric sdAbs from conventionally heterodimeric V$_H$ and V$_K$ domains, including interface engineering and selection of specific germline families.

In some embodiments, the further TAA is selected from the group consisting of 1-92-LFA-3, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the antigen binding domain, such as a 5T4 VHH domain, is linked, directly or indirectly via a linker, to the Fc region and/or to the CD3 binding region. In some embodiments, linkage is via a linker. In some embodiments, the linker is a linking peptide (LP), which can include any flexible or rigid linker as described. In some embodiments, the linker is selected from the group consisting of GGSGGS, i.e., (GGS), (SEQ ID NO: 1); GGSGGSGGS, i.e., (GGS), (SEQ ID NO: 2); GGSGGSGGSGGS, i.e., (GGS)₄ (SEQ ID NO: 3); and GGSGGSGGSGGSGGS, i.e., (GGS)₅ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the linker is (GGGGS)n, wherein n is 1 to 5 (SEQ ID NO: 123); (GGGGGS)n, wherein n is 1 to 4 (SEQ ID NO:124); GGGGS (SEQ ID NO:125); GGGGGS (SEQ ID NO:126); GGGGGSGGGGGSGGGGGS (SEQ ID NO:127); GGGGSGGGGSGGGGS (SEQ ID NO: 128); GGSGGGGSGGGGSGGGGS (SEQ ID NO:129); or PGGGG (SEQ ID NO:327). In some embodiments, the linker includes a combination of a GS-linker and a Glycine linker.

b. Fc Region

A constrained multispecific polypeptide construct includes an immunoglobulin Fc region. Generally, the constrained multispecific polypeptide construct is a dimer formed by polypeptides, each containing an Fc. The Fc polypeptide can be any as set forth above. In particular embodiments, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multispecific polypeptide construct are different.

Various methods are known for promoting heterodimerization of complementary Fc polypeptides, see e.g. Ridgway et al, Protein Eng. 9:617-621 (1996); Merchant et al, Nat. Biotechnol. 16 (7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285:19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

Methods and variants for heterodimerization also include those described in published international PCT App. WO2014/145806, including "knobs and holes" mutations (also called "skew" variants), mutations that relate to "electrostatic steering" or "charge pairs," and pI variants. Heterodimeric variants also include any as described in U.S. published Appl. No. US2012/0149876 or US2018/011883.

In some embodiments, to promote heterodimerization both polypeptides of the Fc heterodimer contain paired or complementary amino acid modifications. Exemplary paired amino acid modification of polypeptides of an Fc fusion are set forth in Table 3.

TABLE 3

| Paired amino acids of Heterodimeric Fc | |
| --- | --- |
| First Fc polypeptide | Second Fc Polypeptide |
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (knob) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine(S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9:617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9:617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248:7-15).

In particular embodiments, a multispecific polypeptide construct contains a first and second Fc able to mediate Fc heterodimerization contains a first Fc polypeptide containing mutations T366W and S354C and a second Fc polypeptide containing mutations T366S, L368A, Y407V and Y349C. In some embodiments, the first Fc polypeptide is selected from an Fc polypeptide comprising the sequence set forth in SEQ ID NO: 328 or 334 and the second Fc polypeptide is selected from an Fc polypeptide comprising the sequence set forth in SEQ ID NO: 329, 332 or 336. In some embodiments, the first Fc polypeptide is or comprises the sequence of amino acids set forth in any of SEQ ID NOS: 103, 107, 115 or 117 and the second Fc polypeptide is or comprises the sequence of amino acids set forth in any of SEQ ID NOS: 104, 108, 111, 113, 119 or 121.

In some embodiments, the Fc polypeptide exhibits features providing Fc-mediated effector functions. In particular examples, the first Fc polypeptide is or comprises the sequence set forth in SEQ ID NOs: 328 and a second Fc polypeptide that is or comprises SEQ ID NO: 329 or 332. In some embodiments, the first Fc polypeptide is or comprises the sequence set forth in SEQ ID NO: 103 and the second Fc polypeptide is or comprises the sequence set forth in SEQ ID NO: 104 or 111. In some embodiments, the first Fc polypeptide is or comprises the sequence set forth in SEQ ID NO: 107 and the second Fc polypeptide is or comprises the sequence set forth in SEQ ID NO: 108 or 113. The first and second Fc polypeptide can be formatted on either polypeptide chain of the construct.

In some embodiments, one or both of the first and second Fc polypeptides can further include one or more amino acid mutations to further reduce one or more Fc effector functions, such as reduced Fc receptor binding. Exemplary mutations to reduce Fc effector functions include any as described. In some embodiments, the modification can be a deletion of one or more positions Glu233 (E233), Leu234 (L234), or Leu235 (L235), such as a deletion of amino acids Glu233 (E233), Leu234 (L234), and Leu235 (L235). In some embodiments, the first Fc polypeptide is selected from an Fc polypeptide comprising the sequence set forth in SEQ ID NO: 330 or 335 and the second Fc polypeptide is selected from an Fc polypeptide comprising the sequence set forth in SEQ ID NO: 331,333 or 337. In some embodiments, the first Fc polypeptide is or comprises the sequence of amino acids set forth in any of SEQ ID NOS: 105, 109, 116, or 118 and the second Fc polypeptide is or comprises the sequence of amino acids set forth in any of SEQ ID NOS: 106, 110, 112, 114, 120 or 122.

In particular examples, the first Fc polypeptide is or comprises the sequence set forth in SEQ ID NOs: 330 and a second Fc polypeptide that is or comprises SEQ ID NO: 331 or 333. In some embodiments, the first Fc polypeptide is or comprises the sequence set forth in SEQ ID NO: 105 and the second Fc polypeptide is or comprises the sequence set forth in SEQ ID NO: 106 or 112. In some embodiments, the first Fc polypeptide is or comprises the sequence set forth in SEQ ID NO: 109 and the second Fc polypeptide is or comprises the sequence set forth in SEQ ID NO: 110 or 114. The first and second Fc polypeptide can be formatted on either polypeptide chain of the construct.

In some embodiments, the first Fc polypeptide or second Fc polypeptide further includes mutations M252Y and/or M428V. In particular examples, the first Fc polypeptide is or comprises the sequence set forth in SEQ ID NO:334 and the second Fc polypeptide is or comprises the sequence set forth in SEQ ID NO:336. In some embodiments, the first Fc polypeptide is or comprises the sequence set forth in SEQ ID NO:115 and the second Fc polypeptide is or comprises the sequence set forth in SEQ ID NO: 119. In some embodiments, the first Fc polypeptide is or comprises the sequence set forth in SEQ ID NO: 117 and the second Fc polypeptide is or comprises the sequence set forth in SEQ ID NO: 121. In other examples, the first Fc polypeptide is or comprises the sequence set forth in SEQ ID NO:335 and the second Fc polypeptide is or comprises the sequence set forth in SEQ ID NO:337. In some embodiments, the first Fc polypeptide is or comprises the sequence set forth in SEQ ID NO: 116 and the second Fc polypeptide is or comprises the sequence set forth in SEQ ID NO: 120. In some embodiments, the first Fc polypeptide is or comprises the sequence set forth in SEQ ID NO: 118 and the second Fc polypeptide is or comprises the sequence set forth in SEQ ID NO: 122. The first and second Fc polypeptide can be formatted on either polypeptide chain of the construct.

Additional examples of variants that can facilitate the promotion of heterodimers are any combination or pair of steric variants (e.g. skew variants) of a first Fc polypeptide and a second Fc polypeptide from among: S364K/E357Q and L368D/K370S; L368D/K370S and S364K; L368E/ K370S and S364K; T411T/E360E/Q362E and D401K; L368D/K370S and S364K/E357L, K370S and S364K/ E357Q and T366S/L368A/Y407V and T366W or 366S/ L368A/Y407V/Y349C and T366W/S354C), where each pair represents mutations in the first Fc polypeptide and second Fc polypeptide. In particular embodiments, a provided construct contains a first and second Fc polypeptide containing the pair of mutations L368D/K370S and S364K and E357Q.

An additional mechanism that can be used in the generation of heterodimers is sometimes referred to as "electrostatic steering" as described in Gunasekaran et al., J. Biol. Chem. 285 (25): 19637 (2010). This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". In one embodiments, a first Fc polypeptide can contain mutations D221E/P228E/L368E and a second Fc polypeptide can contain mutations D221R/P228R/K409R. In another embodiments, a first Fc polypeptide can contain mutations C220E/P228E/368E and a second Fc polypeptide can contain mutations C220R/E224R/P228R/K409R.

In some embodiments, heterodimerization can be facilitated by pI variants. In some aspects, a pI variant can include those that increase the pI of the protein (basic changes). In other aspects, the pI variant can include those that decrease the pI of the protein (acidic changes). In some cases, all combinations of these variants can be done, including combinations in which one Fc polypeptide may be wild type, or a variant that does not display a significantly different pI from wild-type, and the other Fc polypeptide can be either more basic or more acidic. Alternatively, each Fc polypeptide can be changed, one to more basic and one to more acidic. In some embodiments, at least one Fc polypeptide is a negative pI variant Fc containing mutations Q295E/N384D/Q418E/N421D.

In some embodiments, a combination of steric heterodimerization variants (e.g. knob and hole) and pI or charge pair variants can be used.

In particular embodiments, the provided constructs contains (a) a first Fc polypeptide comprising the skew variants S364K/E357Q; and b) a second Fc polypeptide containing skew variants L368D/K370S and the pI variants N208D/Q295E/N384D/Q418E/N421D. In some embodiments, one or both of the first and second polypeptide can contain further mutations to reduce Fc effector activity, such as the exemplary mutations E233P/L234V/L235A/G236del/S267K. An example of such a first Fc polypeptide and a second Fc polypeptide able to mediate Fc heterodimerization comprise the sequences set forth in SEQ ID NOs: 338 and 339. The first and second Fc polypeptide can be formatted on either polypeptide chain of the construct.

The resulting constrained multispecific polypeptide constructs can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201 (1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG− amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification maybe combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function. In some embodiments, the Fc region is altered to provide reduced Fc-mediated effector functions, such as via reduced Fc receptor binding, e.g. binding to FcγR binding but generally not FcRn binding.

In some embodiments, the Fc region is mutated in one or more of the following positions to reduce Fc receptor binding: Glu233 (E233), Leu234 (L234), or Leu235 (L235). The one or more mutations can include E233P, L234V and/or L235A.

In particular embodiments, the mutations of the Fc region to reduce Fc effector function, e.g. via reducing Fc receptor binding to FcγR, include mutations from among any of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G, E233P/L234V/L235A/G236del, D265A/P329A, D265A/P329G, D265A/N297A, L234V/L235A/D265A, L234V/L235A/N297A, L234V/L235A/P329A, or L234V/L235A/P329G. In some embodiments, one Fc polypeptide of a heterodimeric Fc comprises the sequence of amino acids set forth in any of SEQ ID NOS: 328 (e.g. SEQ ID NO:103 or 107), 334 (e.g. SEQ ID NO: 115 or 117), and the other Fc polypeptide of the heterodimeric Fc contains the sequence of amino acids set forth in any of SEQ ID NOS: 329 (e.g. SEQ ID NO: 104 or 108), 332 (e.g. SEQ ID NO: 111 or 113), 336 (e.g. SEQ ID NO:119 or 121). In some embodiments, one Fc polypeptide of a heterodimeric Fc comprises the sequence of amino acids set forth in any of SEQ ID NOS: 330 (e.g. SEQ ID NO: 105 or 109), 335 (e.g. SEQ ID NO: 116 or 118) and the other Fc polypeptide of the heterodimeric Fc comprises the sequence of amino acids set forth in any of SEQ ID NOS: 331 (e.g. SEQ ID NO:106 or 110), 333 (e.g. SEQ ID NO:112 or 114), 337 (SEQ ID NO: 120 or 122).

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments in which the multispecific polypeptide constructs contain a cleavable linker, cleavage of the linker can produce two components that each have biological activity: the CD3-binding region that is able to bind and engage CD3 on a T cell, which, in some aspects, also can contain a CRBR for inducing a costimulatory signal on the T cell and/or an IRBR for inducing an inhibitory signal on the T cell; and the Fc region linked to the 5T4 VHH domain that can exhibit target-specific effector function. In particular embodiments provided herein, the multispecific polypeptide constructs contain a non-cleavable linker and may, in some aspects, not exhibit an independent Fc-mediated effector function.

In some embodiments, the Fc region includes an Fc polypeptide that is mutated or modified to alter one or more effector functions. Thus, in some cases, effector functions such as on or more of ADCC, ADCP and/or CDC can be altered, such as reduced or enhanced, in an Fc for use with the provided constrained multispecific polypeptide constructs. Exemplary mutations to reduce effector function include any as described above.

In some embodiments, an IgG1 Fc polypeptide or a variant thereof such as any described below can be made in a G1 m1 or G1 m3 allotype. In some embodiments, the Fc region can contain amino acids of the human G1 ml allotype, such as residues containing Asp (D) and Leu (L) at positions 356 and 358, e.g. as set forth in SEQ ID NO:8. In some cases, an Fc polypeptide can contain amino acid substitutions E356D and M358L to reconstitute residues of allotype G1 m1. In other embodiments, the Fc region can contain amino acids of the human G1 m3 allotype, such as residues Glu (E) and Met (M) at positions 356 and 358 by EU numbering, e.g. as set forth in SEQ ID NOS: 338 and 339. In some cases, an Fc polypeptide can contain amino acid substitutions D356E and L358M to reconstitute residues of allotype G1 m3.

c. CD3 binding Domain

A constrained multispecific polypeptide construct includes one or more copies of an antiCD3 binding domain. The anti-CD3 binding domains of the disclosure activate T cells via engagement of CD3 or a member of the CD3 complex on the T cells. In preferred embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

The CD3 binding domain can be any as described above. In particular embodiments, the CD3 binding domain is an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described. In such embodiments, the variable heavy chain (VH) and variable light chain (VL) of the CD3 binding region are linked on opposite chains of the heterodimeric Fc.

In some embodiments, the CD3 binding region is an Fv or dsFv of SP34 (Pessano et ai. The EMBO Journal. 4:337-344, 1985) or of a humanized variant of SP34 (WO2015001085).

In some embodiments, the anti-CD3ε binding domain thereof is an Fv, such as a dsFv fragment, that includes a combination of heavy chain variable amino acid sequence and a light chain variable amino acid sequence. In some embodiments, the CD3-binding domain is an Fv or dsFv fragment in which is contained a VH CDR1 sequence that includes at least the amino acid sequence TYAMN (SEQ ID NO: 29); a VH CDR2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence TYAMN (SEQ ID NO: 29); a VH CDR2 sequence that is at least 90%, 91%, 92%, 93%, 94%, 95%, 96%, 97%, 98%, 99% or more identical to the amino acid sequence RIRSKYNNYATYYADSVKD (SEQ ID NO: 30); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 31), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 32); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNLWV (SEQ ID NO: 34).

In some embodiments, the anti-CD3ε binding domain includes a VH CDR1 sequence that includes at least the amino acid sequence GFTFNTYAMN (SEQ ID NO: 350); a VH CDR2 sequence that includes at least the amino acid sequence RIRSKYNNYATY (SEQ ID NO: 351); a VH CDR3 sequence that includes at least the amino acid sequence HGNFGNSYVSWFAY (SEQ ID NO:31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO:34).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 350); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 351); a VH CDR3 sequence that is at least 90%, 91%, 92%, 93%, 94%, 95%, 96%, 97%, 98%, 99% or more identical to the amino acid sequence HGNFGN-SYVSWFAY (SEQ ID NO: 31), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 32); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNLWV (SEQ ID NO: 34).

In some embodiments, the anti-CD3ε binding domain includes a VH CDR1 sequence that includes at least the amino acid sequence GFTFNTYAMN (SEQ ID NO:350); a VH CDR2 sequence that includes at least the amino acid sequence RIRSKYNNYATY (SEQ ID NO: 351); a VH CDR3 sequence that includes at least the amino acid sequence HGNFGNSYVSWFAY (SEQ ID NO: 31), a VL CDR1 sequence that includes at least the amino acid sequence GSSTGAVTTSNYAN (SEQ ID NO: 357); a VL CDR2 sequence that includes at least the amino acid sequence GTNKRAP (SEQ ID NO: 33); and a VL CDR3 sequence that includes at least the amino acid sequence ALWYSNHWV (SEQ ID NO: 353).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 350); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 351); a VH CDR3 sequence that is at least 90%, 91%, 92%, 93%, 94%, 95%, 96%, 97%, 98%, 99% or more identical to the amino acid sequence HGNFGN-SYVSWFAY (SEQ ID NO: 31), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 357); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNHWV (SEQ ID NO: 353).

In some embodiments, the anti-CD3ε binding domain includes a VH CDR1 sequence that includes at least the amino acid sequence GFTFSTYAMN (SEQ ID NO: 355); a VH CDR2 sequence that includes at least the amino acid sequence RIRSKYNNYATY (SEQ ID NO: 356); a VH CDR3 sequence that includes at least the amino acid sequence HGNFGDSYVSWFAY (SEQ ID NO: 352), a VL CDR1 sequence that includes at least the amino acid sequence GSSTGAVTTSNYAN (SEQ ID NO: 357); a VL CDR2 sequence that includes at least the amino acid sequence GTNKRAP (SEQ ID NO: 33); and a VL CDR3 sequence that includes at least the amino acid sequence ALWYSNHWV (SEQ ID NO: 353).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFSTYAMN (SEQ ID NO: 355); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 356); a VH CDR3 sequence that is at least 90%, 91%, 92%, 93%, 94%, 95%, 96%, 97%, 98%, 99% or more identical to the amino acid sequence HGNFGDSYVSWFAY (SEQ ID NO: 352), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 357); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNHWV (SEQ ID NO: 353).

In some embodiments, the anti-CD3ε binding domain includes a CDR3 that includes at least amino acids VLWYSNRWV (SEQ ID NO:354). In some embodiments, the anti-CD3ε binding domain includes a CDR3 that is at least 90%, 91%, 92%, 93%, 94%, 95%, 96%, 97%, 98%, 99% or more identical to the amino acids VLWYSNRWV (SEQ ID NO:354).

In some embodiments, the anti-CD3ε binding domain includes one or more copies of an antibody or an antigen-binding fragment thereof selected from the group consisting of a Fab fragment, a F(ab')₂ fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is not a single chain antibody. For example, in some aspects, the CD3 binding region is not a single chain variable fragment (scFv).

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described in Section III.C.2.b. In such embodiments, the variable heavy chain (VH) and variable light chain (VL) of the CD3 binding region are linked on opposite chains of the heterodimeric Fc.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 27-28, 35-84, 293, 340-343, and 358. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 27-28, 35-84, 293, 340-343, and 358.

In some embodiments, the anti-CD3ε binding domain thereof is an Fv fragment that includes a combination of heavy chain variable amino acid sequence selected from the group of SEQ ID NO: 27, 35-65, 341, 343, and 358 and light chain variable amino acid sequence selected from the group consisting of SEQ ID NO: 28, 66-84, 293, 340, and 342. In some embodiments, the anti-CD3ε binding domain thereof is an Fv fragment that includes a combination of heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-65, 341, 343, and 358 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66-84, 293, 340, and 342.

In some embodiments, the anti-CD3ε binding domain thereof includes a combination of a heavy chain variable region amino acid sequence and a light chain variable region amino acid sequence comprising an amino acid sequence selected from the group of SEQ ID NO: 27-28, 35-84, 293, 340-343, and 358. In some embodiments, the anti-CD3ε binding domain thereof includes a combination of a heavy chain variable region amino acid sequence selected from the group of SEQ ID NO: 27, 35-65, 341, 343, and 358 and a light chain variable region amino acid sequence comprising an amino acid sequence selected from the group of SEQ ID NO: 28,66-84, 293, 340, and 342. In some embodiments, the anti-CD3ε Fv antibody fragment includes a combination of a heavy chain variable amino acid sequence selected from the group of SEQ ID NO: 27, 35-65, 341, 343, and 358 and a light chain variable amino acid sequence selected from the group consisting of SEQ ID NO: 28, 66-84, 293, 340, 342. In some embodiments, the anti-CD3ε Fv antibody fragment includes a combination of a heavy chain variable amino acid sequence selected from the group of SEQ ID NO: 27, 35-65, 341, 343, 358, 388, 389, 392, 393 and a light chain variable amino acid sequence selected from the group consisting of SEQ ID NO: 28, 66-84, 293, 340, 342, 390, 391, 394, 395.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO:27. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 27 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising the amino acid sequence of SEQ ID NO: 27. In some embodiments, the anti-CD3ε binding domain includes a variable light chain (VL) comprising the amino acid sequence of SEQ ID NO: 28. In some embodiments, the anti-CD3ε binding domain thereof includes a variable heavy chain (VH) comprising the amino acid sequence of SEQ ID NO: 27 and a variable light chain (VL) comprising the amino acid sequence of SEQ ID NO: 28.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 341. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 342. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 341 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 342. In some embodiments, the anti-CD3ε binding domain thereof includes a variable heavy chain (VH) comprising the amino acid sequence of SEQ ID NO: 341. In some embodiments, the anti-CD3€ binding domain includes a variable light chain (VL) comprising the amino acid sequence of SEQ ID NO: 342. In some embodiments, the anti-CD3ε binding domain thereof includes a variable heavy chain (VH) comprising the amino acid sequence of SEQ ID NO: 341 and a variable light chain (VL) comprising the amino acid sequence of SEQ ID NO: 342.

In particular embodiments, the Fv is a disulfide stabilized Fv fragment (dsFv) in which the the $V_H$-$V_L$ heterodimer is stabilized by an interchain disulfide bond. In some embodiments, the interchain disulfide bond is engineered by mutation of position in framework positions of the VH and/or VL chain. In some embodiments, the disulfide stabilized anti-CD3 Fv comprises an anti-CD3 VH with the mutation 44 to Cys and an anti-CD3 VL with the mutation 100 to Cys by Kabat numbering. For example, in some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3ε binding domain thereof is an Fv, such as a dsFv fragment, that includes a heavy chain variable amino acid sequence selected from the group of SEQ ID NO: 35-65 and a light chain variable amino acid sequence selected from the group consisting of SEQ ID NO: 66-84, 293. In some embodiments, the anti-CD3ε binding domain thereof is an Fv, such as a dsFv fragment, that includes a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 35-65 and an amino acid sequence that is at least 90%, 91%, 92%, 93%, 94%, 95%, 96%, 97%, 98%, 99% or more identical to an amino acid sequence selected from the group consisting of SEQ ID NO: 66-84, 293 an amino acid sequence. In some embodiments, the anti-CD3 binding domain is an Fv or dsFv, in which is contained a variable heavy chain (VH) comprising the amino acid sequence of SEQ ID NO: 47 and a variable light chain (VL) comprising the amino acid sequence of SEQ ID NO: 293.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 27-28, 35-84, 293, 340-343, and 358. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 27-28, 35-84, 293, 340-343, and 358.

In some embodiments, the anti-CD3ε binding domain thereof is an Fv fragment that includes a combination of heavy chain variable amino acid sequence selected from the group of SEQ ID NO: 27, 35-65, 341, 343, and 358 and light chain variable amino acid sequence selected from the group consisting of SEQ ID NO: 28, 66-84, 293, 340, and 342. In some embodiments, the anti-CD3ε binding domain thereof is an Fv fragment that includes a combination of heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-65, 341, 343, and 358 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66-84, 293, 340, and 342.

In some embodiments, the anti-CD3ε binding domain thereof includes a combination of a heavy chain variable region amino acid sequence and a light chain variable region amino acid sequence comprising an amino acid sequence selected from the group of SEQ ID NO: 27-28, 35-84, 293, 340-343, and 358. In some embodiments, the anti-CD3ε binding domain thereof includes a combination of a heavy chain variable region amino acid sequence selected from the group of SEQ ID NO: 27, 35-65, 341, 343, and 358 and a light chain variable region amino acid sequence comprising an amino acid sequence selected from the group of SEQ ID NO: 28,66-84, 293, 340, and 342. In some embodiments, the anti-CD3ε Fv antibody fragment includes a combination of a heavy chain variable amino acid sequence selected from the group of SEQ ID NO: 27, 35-65, 341, 343, and 358 and a light chain variable amino acid sequence selected from the group consisting of SEQ ID NO: 28, 66-84, 293, 340, 342.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO:27. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 27 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising the amino acid sequence of SEQ ID NO: 27. In some embodiments, the anti-CD3ε binding domain includes a variable light chain (VL) comprising the amino acid sequence of SEQ ID NO: 28. In some embodiments, the anti-CD3ε binding domain thereof includes a variable heavy chain (VH) comprising the amino acid sequence of SEQ ID NO: 27 and a variable light chain (VL) comprising the amino acid sequence of SEQ ID NO: 28.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 341. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 342. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 341 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 342. In some embodiments, the anti-CD3ε binding domain thereof includes a variable heavy chain (VH) comprising the amino acid sequence of SEQ ID NO: 341. In some embodiments, the anti-CD3ε binding domain includes a variable light chain (VL) comprising the amino acid sequence of SEQ ID NO: 342. In some embodiments, the anti-CD3ε binding domain thereof includes a variable heavy chain (VH) comprising the amino acid sequence of SEQ ID NO: 341 and a variable light chain (VL) comprising the amino acid sequence of SEQ ID NO: 342.

In particular embodiments, the Fv is a disulfide stabilized Fv fragment (dsFv) in which the the $V_H$-$V_L$ heterodimer is stabilized by an interchain disulfide bond. In some embodiments, the interchain disulfide bond is engineered by mutation of position in framework positions of the VH and/or VL chain. In some embodiments, the disulfide stabilized anti-CD3 Fv comprises an anti-CD3 VH with the mutation 44 to Cys and an anti-CD3 VL with the mutation 100 to Cys by Kabat numbering. For example, in some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3ε binding domain thereof includes a combination of a heavy chain variable region amino acid sequence and a light chain variable region amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NO: 67, 75, 77, 79, 81-84, 293, and 340. In some embodiments, the anti-CD3ε binding domain thereof includes a combination of a heavy chain variable region amino acid sequence and a light chain variable region amino acid sequence comprising an amino acid sequence selected from the group of SEQ ID NO: 47, 52-65, 67, 75, 77, 79, 81-84, 293, 340, 343, and 358. In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to a light chain variable amino acid sequence selected from the group consisting of SEQ ID NO: 47 and 52-65, 343, and 358 and an amino acid sequence that is at least 90%, 91%, 92%, 93%, 94%, 95%, 96%, 97%, 98%, 99% or more identical to an amino acid sequence selected from the group consisting of SEQ ID NO: 67, 75, 77, 79, 81-84, 293, and 340. In some embodiments, the anti-CD3ε Fv antibody fragment includes a combination of a heavy chain variable amino acid sequence selected from the group of SEQ ID NO: 47, 52-65, 343, and 358 and a light chain variable amino acid sequence selected from the group consisting of SEQ ID NO: 67, 75, 77, 79, 81-84, 293, and 340. In some of any such embodiments, the anti-CD3 Fv is a dsFv that has a VH chain containing the mutation G44C and a VL chain containing the mutation G100C, each by kabat numbering.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 47. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 75. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 47 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 75. In some embodiments, the anti-CD3ε binding domain thereof includes a variable heavy chain (VH) comprising the amino acid sequence of SEQ ID NO: 47. In some embodiments, the anti-CD3ε binding domain includes a variable light chain (VL) comprising the amino acid sequence of SEQ ID NO: 75. In some embodiments, the anti-CD3ε binding domain thereof includes a variable heavy chain (VH) comprising the amino acid sequence of SEQ ID NO: 47 and a variable light chain (VL) comprising the amino acid sequence of SEQ ID NO: 75. In some of any such embodiments, the anti-CD3 Fv is a dsFv that has a VH chain containing the mutation G44C and a VL chain containing the mutation G100C, each by kabat numbering.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 343. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 340. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 343 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 340. In some embodiments, the anti-CD3ε binding domain thereof includes a variable heavy chain (VH) comprising the amino acid sequence of SEQ ID NO: 343. In some embodiments, the anti-CD3ε binding domain includes a variable light chain (VL) comprising the amino acid sequence of SEQ ID NO: 340. In some embodiments, the anti-CD3ε binding domain thereof includes a variable heavy chain (VH) comprising the amino acid sequence of SEQ ID NO: 343 and a variable light chain (VL) comprising the amino acid sequence of SEQ ID NO: 340. In some of any such embodiments, the anti-CD3 Fv is a dsFv that has a VH chain containing the mutation G44C and a VL chain containing the mutation G100C, each by kabat numbering.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 358. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 340. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 358 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 340. In some embodiments, the anti-CD3ε binding domain thereof includes a variable heavy chain (VH) comprising the amino acid sequence of SEQ ID NO: 358. In some embodiments, the anti-CD3ε binding domain includes a variable light chain (VL) comprising the amino acid sequence of SEQ ID NO: 340. In some embodiments, the anti-CD3ε binding domain thereof includes a variable heavy chain (VH) comprising the amino acid sequence of SEQ ID NO:358 and a variable light chain (VL) comprising the amino acid sequence of SEQ ID NO: 340. In some of any such embodiments, the anti-CD3 Fv is a dsFv that has a VH chain containing the mutation G44C and a VL chain containing the mutation G100C, each by kabat numbering.

d. Linker

A constrained multispecific polypeptide constructs contain a linker that joins or couples the first component containing the immunoglobulin Fc region and the second component containing the CD3 binding region. In some embodiments, the linker is positioned at the end of the C-terminal region of the Fc region, such that the Fc region is N-terminal to the CD3 binding region. It is understood that because the provided constrained multispecific polypeptide constructs are multimers, such as dimers containing a first and second polypeptide that together form the first and second component, the provided constructs include a linker joining the Fc portion and the CD3 binding region of the first and a linker joining the Fc portion and the CD3 binding region of the second polypeptide. In some embodiments, the first polypeptide includes a first Fc polypeptide of a heterodimeric Fc region, a linker, and a first domain (e.g. VH) of a CD3 binding region, and the second polypeptide includes a second Fc polypeptide of the heterodimeric Fc region, a linker and second domain (e.g. VL) of the CD3 binding region. Typically, the linkers present in the first and second polypeptides of the constrained multispecific polypeptide construct are the same. Thus, in some embodiments, each domain of the CD3 binding domain is linked via a linker, such as the same linker, to opposite polypeptides of the Fc, such as heterodimeric Fc.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491, 6,132,992).

In some embodiments, the linker is chosen so that, when the CD3 binding region is joined to the Fc region of the multispecific polypeptide conjugate, the CD3 binding region is constrained and not able to, or not substantially able to, bind or engage CD3 on the surface of a cell, e.g. T cell, upon contact of the multispecific polypeptide construct with the cell. Various assays can be employed to assess binding or engagement of CD3 by the multispecific polypeptide construct, including assays to assess T cell binding, NFAT activation using a reporter system, cytolytic T cell activity, cytokine production and/or expression of T cell activation markers. Exemplary assays are shown in the provided Examples. Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides. In some embodiments, the linker is a polypeptide linker. The polypeptide linker can be a flexible linker or a rigid linker or a combination of both. In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

In certain aspects, the longer the linker length, the greater the CD3 binding when the multispecific polypeptide conjugate is bounds to its antigen, e.g. TAA. Thus, in some aspects, the linker is greater than 12 amino acids in length, such as greater than 13, 14, 15, 16, 17 or 18 amino acids in length. In some embodiments, the linker is 12 to 40 amino acids in length, 12 to 30 amino acids, 12 to 24 amino acids, 12 to 18 acids, 12 to 15 amino acids, 15 to 40 amino acids, 15 to 30 amino acids, 15 to 24 amino acids, 15 to 18 amino acids, 18 to 40 amino acids, 18 to 30 amino acids, 18 to 24 amino acids, 24 to 40 amino acids, 24 to 30 amino acids or 30 to 40 amino acids.

The linkers can be naturally-occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains (GGS)n, wherein n is 1 to 10, such as 1 to 5, for example 1 to 3, such as GGS (GGS)n (SEQ ID NO:363), wherein n is 0 to 10. In particular embodiments, the linker contains the sequence (GGGGS)n (SEQ ID NO: 123), wherein n is 1 to 10 or n is 1 to 5, such as 1 to 3. In further embodiments, the linker contains (GGGGGS)n (SEQ ID NO:124), wherein n is 1 to 4, such as 1 to 3. The linker can include combinations of any of the above, such as repeats of 2, 3, 4, or 5 GS, GGS, GGGGS, and/or GGGGGS linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS, GGGGS (SEQ ID NO: 125), GGGGGS (SEQ ID NO: 126), or GGGGSGGGGSGGGGS (SEQ ID NO:346). In some embodiments, the GS-linker comprises an amino acid sequence of GGSGGS, i.e., $(GGS)_2$ (SEQ ID NO: 1); GGSGGSGGS, i.e., $(GGS)_3$ (SEQ ID NO: 2); GGSGGSGGSGGS, i.e., $(GGS)_4$ (SEQ ID NO: 3); GGSGGSGGSGGSGGS, i.e., $(GGS)_5$ (SEQ ID NO: 4); GGGGGSGGGGGSGGGGGS, i.e., $(G5S)_3$ (SEQ ID NO: 127), GGSGGGGSGGGGGSGGGGS (SEQ ID NO: 129) and GGGGSGGGGSGGGGS (SEQ ID NO: 128). In some embodiments, the linker is GGGG (SEQ ID NO:5). In some of any of the above examples, serine can be replaced with alanine (e.g., (Gly4Ala) or (Gly3Ala)). In some embodiments, the linker is GGGGG (SEQ ID NO:6). In some embodiments, the linker is PGGGG (SEQ ID NO: 327).

In some embodiments, the linker includes a peptide linker having the amino acid sequence $Gly_x Xaa-Gly_y -Xaa-Gly_z$ (SEQ ID NO:130), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), His-tidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO: 131), wherein each Xaa is selected as above.

In some embodiments, the linker is serine-rich linkers based on the repetition of a (SSSSG)n (SEQ ID NO: 132) motif where n is at least 1, though y can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker com-prises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cys-teine residues, such as glycine residues and cysteine residues only. Typically, only one cysteine residue will be included per peptide linker. One example of a specific linker com-prising a cysteine residue includes a peptide linker having the amino acid sequence $Gly_m$-Cys-$Gly_n$, wherein n and m are each integers from 1-12, e.g., from 3-9, from 4-8, or from 4-7. In a specific variation, such a peptide linker has the amino acid sequence GGGGG-C-GGGGG (SEQ ID NO: 133).

In some embodiments, the linker of the fusion protein is a structured or constrained linker. In particular embodi-ments, the structured linker contains the sequence (AP)n or (EAAAK)n (SEQ ID NO: 134), wherein n is 2 to 20, preferably 4 to 10, including but not limited to, AS-(AP)n-GT (SEQ ID NO: 135) or AS-(EAAAK)n-GT (SEQ ID NO:136), wherein n is 2 to 20, such as 2, 3, 4, 5, 6, 7, 8, 9, 10, 11, 12, 13, 14 or 15. In other embodiments, the linker comprises the sequences (GGGGA)n (SEQ ID NO: 137), (PGGGS)n (SEQ ID NO:138), (AGGGS)n (SEQ ID NO:139) or GGS-(EGKSSGSGSESKST)n-GGS (SEQ ID NO: 140, wherein n is 2 to 20), (ADAAP)n (SEQ ID NO:396, wherein n is 2 to 20), (ADAAP)n-G (SEQ ID NO:397, wherein n is 2 to 20), (GEPQG)n (SEQ ID NO: 398, wherein n is 2 to 20), (GEPQG)n-G (SEQ ID NO:399, wherein n is 2 to 20), (AGGEP)n (SEQ ID NO: 400, wherein n is 2 to 20), (AGGEP)n-G (SEQ ID NO:401, wherein n is 2 to 20), (AGSEP)n (SEQ ID NO:402, wherein n is 2 to 20), (AGSEP)n-G (SEQ ID NO:403, wherein n is 2 to 20), (GGGEQ)n (SEQ ID NO:404, wherein n is 2 to 20), or (GGGEQ)n-G (SEQ ID NO:405, wherein n is 2 to 20). In some embodiments, the linker is SSSASASSA (SEQ ID NO:141), GSPGSPG (SEQ ID NO: 142), ATTTGSSPGPT (SEQ ID NO:143), ADAAPADAAPG (SEQ ID NO:406), GEPQGGEPQGG (SEQ ID NO:407), AGGEPAGGEPG (SEQ ID NO:408), AGSEPAGSEPG (SEQ ID NO:409), or GGGEQGGGEQG (SEQ ID NO:410). In some embodiments, such linkers, by virtue of their structure, may be more resistant to proteolytic degradation, thereby offering an advantage when injected in vivo. In some embodiments, such linkers are negatively charged and may be better suited for dampening the binding of the CD3 binding domain to CD3.

In some embodiments, the linker is not a cleavable linker, also called non-cleavable linker. In some embodiments, the linker is not a cleavable by a protease. In some embodi-ments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker does not contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the linker does not include a P1-P1' scissile bond sequence that is recognized by a protease. In some aspects, a non-cleavable linker or a linker that does not contain a substrate recognition site that is specifically recognized for cleavage by a protease is one whose cleavage by a protease is substantially less than cleavage of a target substrate of the protease.

In some embodiments, the linker is a cleavable linker. In some aspects, a cleavable linker is a linker, such as any described above, that further includes a sequence that is a substrate for a protease due to the presence of at least one bond that can be broken under physiological conditions. In some cases, a cleavable linker is susceptible to or sensitive to cleavage under specific conditions that exist in vivo, such as following exposure to an extracellular protease, including those present in cellular environments in vivo. In some cases, the protease may be present in a particular physi-ological microenvironment, such as the tumor microenvi-ronment, thereby restricting the sites at which cleavage may occur.

A protease typically exhibits specificity or preference for cleavage of a particular target substrate compared to another non-target substrate. Such a degree of specificity can be determined based on the rate constant of cleavage of a sequence, e.g. linker, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By deter-mining the rate of cleavage at different protease concentra-tions the specificity constant for cleavage ($k_{cat}/K_m$) can be determined for a particular protease towards a particular linker. In some embodiments, a cleavable linker is a linker that is capable of being specifically cleaved by a protease at a rate of about at least $1 \times 10^4$ $M^{-1}S^{-1}$, or at least $5 \times 10^4$ $M^{-1}S$, at least $10 \times 10^4$ $M^{-1}S$. at least $10 \times 10^5$ $M^{-1}S$ or more.

In some embodiments, a constrained multispecific polypeptide constructs of the disclosure include a cleavable linker that joins the first and second components. In some embodiments, the cleavable linker includes an amino acid sequence that can serve as a substrate for a protease, usually an extracellular protease. For example, the cleavable linker may include a cleavage sequence containing at least one peptide bond which preferably lies within a cleavable peptide sequence of a protease. Suitable proteases include, for example, matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. In particular embodiments, the protease is a protease that is produced by a tumor, an activated immune effector cell (e.g. a T cell or a NK cell), or a cell in a tumor microenvironment. In some embodiments, the protease is a granzyme B, a matriptase or an MMP, such as MMP-2.

The cleavable linker may be selected based on a protease that is produced by a tumor that is in proximity to cells that express the target and/or produced by a tumor that is co-localized in tissue with the desired target of the multispecific polypeptide constructs. There are reports in the literature of increased levels of proteases having known substrates in a number of cancers, e.g., solid tumors. See, e.g., La Rocca et al, (2004) British J. of Cancer 90 (7): 1414-1421.

In some embodiments, the cleavable linker that joins the first and second component of a constrained multispecific polypeptide construct is cleaved by a protease produced by an immune effector cell that is activated by one of the components. For example, multispecific polypeptide constructs that encompass an effector enabled or enhanced IgG Fc region are capable of eliciting ADCC when engaged with the target antigen. Central to ADCC is the release of granzyme B and perforin from the effector cells, namely NK cells and cytotoxic T-cells. Upon release, granzyme B enters the target cell in a perforin dependent manner wherein it mediates apoptosis. Importantly, granzyme B is active within the extracellular synapse between the effector cell and the target cell. In some embodiments, the cleavable linker that joins the first and second component multispecific polypeptide construct is cleaved by granzyme B. Granzyme B is released during effector cell activation mediated by one of the components of the multispecific polypeptide construct. In some embodiments, granzyme B and other proteases can be produced by immune effector cells, including activated T cells or NK cells. In some embodiments, activation of T cells by CD3 engagement upon binding of a TAA by a multispecific polypeptide construct may release such proteases, which then can cleave a specific cleavable linker thereby potentiating or increasing activity of the CD3 binding molecule to engage CD3. In some embodiments, the cleavage can amplify or increase the activity achieved by the multispecific construct when bound to TAA in an uncleaved state.

Exemplary substrates include but are not limited to substrates cleavable by one or more of the following enzymes or proteases: ADAMS, ADAMTS, e.g. ADAM8; ADAM9; ADAM10; ADAM12; ADAM15; ADAM17/TACE; ADAMDECI; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof.

In some embodiments, the cleavable linker is cleaved by multiple proteases, e.g., 2 or more proteases, 3 or more proteases, 4 or more proteases, and so on.

In some embodiments, the cleavable linker is selected for use with a specific protease, for example a protease that is known to be produced by a tumor that is in proximity to cells that express the target and/or produced by a tumor that is co-localized with the target of the multispecific polypeptide construct.

In some embodiments, the cleavable linker contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the cleavable linker includes a P1-P1' scissile bond sequence that is recognized by a protease. In some aspects, the cleavable linker is engineered to introduce a peptide bond able to be cleaved by a specific protease, for example by introducing a substrate recognition site sequence or cleavage sequence of the protease.

In some embodiments, the cleavable linker includes a combination of two or more substrate sequences. In some embodiments, each substrate sequence is cleaved by the same protease. In some embodiments, at least two of the substrate sequences are cleaved by different proteases. In some embodiments, the cleavable linker comprises an amino acid that is a substrate for granzyme B. In some embodiments, a granzyme B cleavable linker contains an amino acid sequence having the general formula P4 P3 P2 P1 ↓P1' (SEQ ID NO: 144), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, a granzyme B cleavable linker contains an amino acid sequence having the general formula P4 P3 P2 P1 ↓P1' (SEQ ID NO: 145), wherein P4 is amino acid I or L; P3 is amino acid E; P2 is amino acid P or A; P1 is amino acid D; and P1' is amino acid I, V, T, S, or G.

In some embodiments, the substrate for granzyme B comprises the amino acid sequence LEAD (SEQ ID NO: 146), LEPD (SEQ ID NO: 147), or LEAE (SEQ ID NO:148). In some embodiments, the cleavable linker contains the amino acid sequence the cleavable linker comprises the amino acid sequence IEPDI (SEQ ID NO:149), LEPDG (SEQ ID NO:150), LEADT (SEQ ID NO:151), IEPDG (SEQ ID NO:152), IEPDV (SEQ ID NO: 153), IEPDS (SEQ ID NO:154), IEPDT (SEQ ID NO: 155), IEPDP (SEQ ID NO:361), IEPDG (SEQ ID NO:152) or LEADG (e.g., SEQ ID NO:144).

In some embodiments, the cleavable linker comprises an amino acid that is a substrate for matriptase. In some embodiments, the cleavable linker comprises the sequence PIQAR↓(A/V) (SEQ ID NO: 156), wherein P1 is any amino acid. In some embodiments, the cleavable linker comprises the sequence RQAR (A/V) (SEQ ID NO: 157). In some embodiments, the substrate for matriptase comprises the amino acid sequence RQAR (SEQ ID NO: 158). In some embodiments, the cleavable linker comprises the amino acid sequence RQARV (SEQ ID NO: 159).

In some embodiments, the cleavable linker comprises an amino acid that is a substrate for one or more matrix metalloproteases (MMPs). In some embodiments, the MMP is MMP-2. In some embodiments, the cleavable linker contains. the general formula P3 P2 P1 ↓P1' (SEQ ID NO: 160), wherein P3 is P, V or A; P2 is Q or D; P1 is A or N; and P1' is L, I or M. In some embodiments, the cleavable linker contains the general formula P3 P2 P1 ↓P1' (SEQ ID NO: 161), wherein P3 is P; P2 is Q or D; P1 is A or N; and P1' is L or I. In some embodiments, the substrate for MMP comprises the amino acid sequence PAGL (SEQ ID NO: 162).

In some embodiments, the cleavable linker comprises a combination of an amino acid sequence that is a substrate for granzyme B and an amino acid sequence that is a substrate for matriptase. In some embodiments, the cleavable linker comprises a combination of the amino acid sequence LEAD (SEQ ID NO: 146) and the amino acid sequence RQAR (SEQ ID NO: 158).

In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146) and the amino acid sequence PAGL (SEQ ID NO: 162).

In some embodiments, the cleavable linker comprises a combination of an amino acid sequence that is a substrate for matriptase and an amino acid sequence that is a substrate for MMP. In some embodiments, the cleavable linker comprises a combination of the amino acid sequence RQAR (SEQ ID NO: 158) and the amino acid sequence PAGL (SEQ ID NO: 162).

In some embodiments, the cleavable linker comprises a combination of an amino acid sequence that is a substrate for granzyme B, an amino acid sequence that is a substrate for matriptase, and an amino acid sequence that is a substrate for MMP. In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146), the amino acid sequence RQAR (SEQ ID NO: 158), and the amino acid sequence PAGL (SEQ ID NO: 162).

The cleavable linker can include any known linkers. Examples of cleavable linkers are described in Be'liveau et al. (2009) FEBS Journal, 276; U.S. published application Nos. US20160194399; US20150079088; US20170204139; US20160289324; US20160122425; US20150087810; US20170081397; U.S. Pat. No. 9,644,016.

In some embodiments, the cleavable linker comprises an amino acid sequence selected from the group consisting of TGLEADGSPAGLGRQARVG (SEQ ID NO: 163); TGLEADGSRQARVGPAGLG (SEQ ID NO: 164); TGSPAGLEADGSRQARVGS (SEQ ID NO: 162); TGPAGLGLEADGSRQARVG (SEQ ID NO: 166); TGRQARVGLEADGSPAGLG (SEQ ID NO: 167); TGSRQARVGPAGLEADGS (SEQ ID NO: 168); and TGPAGLGSRQARVGLEADGS (SEQ ID NO: 169); GPAGLGLEPDGSRQARVG (SEQ ID NO: 170); GGSGGGGIEPDIGGSGGS (SEQ ID NO: 171); GGSGGGGLEADTGGSGGS (SEQ ID NO: 172); GSIEPDIGS (SEQ ID NO: 173); GSLEADTGS (SEQ ID NO: 174); GGSGGGGIEPDGGGSGGS (SEQ ID NO: 175); GGSGGGGIEPDVGGSGGS (SEQ ID NO: 176); GGSGGGGIEPDSGGSGGS (SEQ ID NO: 177); GGSGGGGIEPDTGGSGGS (SEQ ID NO: 178); GGGSLEPDGSGS (SEQ ID NO: 179); and GPAGLG-LEADGSRQARVG (SEQ ID NO: 180), GGEGGGGSGGSGGGS (SEQ ID NO: 181); GSSAGSEA-GGSGQAGVGS (SEQ ID NO: 182); GGSGGGGLEAE-GSGGGGS (SEQ ID NO: 183); GGSGGG-GIEPDPGGSGGS (SEQ ID NO: 184); TGGSGGGGIEPDIGGSGGS (SEQ ID NO: 185).

e. Costimulatory Binding Domain

The multispecific polypeptide constructs of the present disclosure include one or more co-stimulatory receptor binding region (CRBR) that binds a costimulatory receptor. In some embodiments, the one or more CRBR of the provided multispecific polypeptide constructs binds a co-stimulatory receptor expressed on T cells. In some embodiments, the co-stimulatory receptor is upregulated, induced, or expressed on the surface of an activated T cell. In some aspects, the CRBR binds a co-stimulatory receptor and stimulates the co-stimulatory receptor. In some embodiments, agonistic binding of the co-stimulatory receptor to the CRBR of the multispecific polypeptide induces downstream signaling in the T cell to potentiate or enhance T cell activation or functionalities following engagement of CD3. In some embodiments, the CRBR, or independently each of the CRBRs, is an antibody or antigen binding fragment, a natural cognate binding partner of the co-stimulatory receptor, an Anticalin (engineered lipocalin), a Darpin, a Fynomer, a Centyrin (engineered fibroneticin III domain), a cystine-knot domain, an Affilin, an Affibody, or an engineered CH3 domain.

In some embodiments, the CRBR, or independently each of the CRBRs, such as the first CRBR and the second CRBRs, includes one or more copies of an antibody or an antigen-binding fragment thereof. In some embodiments, the CRBR or independently each of the CRBRs, such as the first antigen-binding domain and the second CRBRs, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

In some embodiments, the CRBR, or independently each of the CRBRs, such as the first CRBR and the second CRBRs, is a single chain antibody. In some examples, the single chain is an scFv, a scAb, a single domain heavy chain antibody, or a single domain light chain antibody.

In some embodiments, the CRBR, or independently each of the CRBRs, such as the first CRBR and the second CRBR, includes one or more single domain antibody (sdAb) fragments, for example V$_H$H, V$_{NAR}$, engineered V$_H$ or V$_K$ domains. V$_H$Hs can be generated from natural camelid heavy chain only antibodies, genetically modified rodents that produce heavy chain only antibodies, or naïve/synthetic camelid or humanized camelid single domain antibody libraries. $V_{NAR}$s can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the CRBR, or independently each of the CRBRs such as the first CRBR and/or the second CRBR, of the multispecific polypeptide constructs contains at least one sdAb or an scFv that binds a costimulatory receptor. In some embodiments, the at least one scFv or sdAb that binds a costimulatory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a costimulatory receptor, which can be positioned either amino-terminally relative to the Fc region and/or carboxy-terminally relative to the CD3 binding region. In some embodiments, the multispecific polypeptide construct contains two scFv or sdAb that bind to a costimulatory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a costimulatory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to a costimulatory receptor. The scFv or sdAb that binds the costimulatory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the CRBR or independently each of the CRBRs, such as the first CRBR and/or the second CRBRs, contains more than one chain. In some embodiments, the CRBR or independently each of the CRBRs, such as the first CRBR and/or the second CRBRs, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds a costimulatory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to a costimulatory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a costimulatory receptor, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a costimulatory receptor; a second polypeptide comprising a second Fc polypeptide of the heterodimeric Fc region, the linker and, optionally, the same VH-CH1 (Fd) or VL-CL of the Fab antibody fragment that binds to a costimulatory receptor, and a third polypeptide comprising the other of the VH-CH1 (Fd) or VL-CL of the Fab antibody fragment that binds to the costimulatory receptor. The first, second and/or third polypeptide of the multispecific polypeptide construct also can include a 5T4 VHH domain, such as any as described.

In some embodiments, the CRBR, or independently each of the CRBRs, is or includes a natural (native) cognate binding partner of the co-stimulatory receptor (e.g. a natural ligand), or a variant thereof that exhibits binding activity to the co-stimulatory receptor.

In some embodiments, the one or more CRBR of the provided multispecific polypeptide constructs bind a co-stimulatory receptor expressed on T cells. In some embodiments, there are more than one CRBR that binds to a costimulatory receptor and each of the CRBRs, such as the first CRBR and the second CRBR, bind the same co-stimulatory receptor. In some embodiments, each of the CRBRs, such as the first CRBR and the CRBRs, bind a different co-stimulatory receptor. In some embodiments, each of the CRBRs, such as the first CRBR and the second CRBR bind a different epitope on the same co-stimulatory receptor. In some embodiments, each of the CRBRs, such as the first antigen-CRBR and the CRBR, bind the same epitope on the same co-stimulatory receptor.

In some embodiments, the CRBR, or independently each of the CRBRs that binds a co-stimulatory receptor results in monovalent, bivalent, trivalent, or tetravalent binding to the co-stimulatory receptor.

In some embodiments, the antigen binding domains results in monovalent, bivalent, trivalent, or tetravalent binding to the TAA. In some embodiments, bivalent binding to the TAA comprises two antigen binding domains that bind the same epitope of the same antigen (e.g. mono-epitopic). In some embodiments, bivalent binding to the TAA comprises two antigen binding domains that bind different epitopes of the same antigen (e.g. bi-epitopic). In some embodiments, monovalent binding to the TAA comprises one antigen binding domain that binds one epitope of the antigen (e.g. mono-epitopic).

In some embodiments, the co-stimulatory receptor is expressed on T cells, such as primary T cells obtained from a subject. In some embodiments, the co-stimulatory receptor is expressed on human T cells, such as primary human T cells obtained from a human subject.

In some embodiments, the co-stimulatory receptor is a member of the tumor necrosis factor (TNF) receptor family. In some embodiments, the costimulatory receptor is a member of the immunoglobulin superfamily (IgSF). In some embodiments, the costimulatory receptor is a member of the B7 family of receptors.

In some embodiments, the co-stimulatory receptor is selected from the group consisting of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D. In some embodiments, the co-stimulatory receptor is selected from 41BB, OX40, GITR, ICOS, or CD28. In some embodiments, the co-stimulatory receptor is selected from 41BB, OX40, or GITR.

In some embodiments, the costimulatory receptor is 41BB. In some embodiments, the costimulatory receptor is OX40. In some embodiments, the costimulatory receptor is GITR. In some embodiments, the costimulatory receptor is ICOS. In some embodiments, the costimulatory receptor is CD28.

In some embodiments, the CRBR of the multispecific polypeptide is or comprises an agonistic binding molecule to the co-stimulatory receptor. The CRBR can bind to the co-stimulatory receptor and initiate, induce, or stimulate a reaction or activity that is similar to or the same as that initiated, induced, or stimulated by the receptor's natural ligand. In some aspects, the binding of the CRBR to the co-stimulatory receptor induces or stimulates a downstream signal that is more than 5%, more than 10%, more than 20%, more than 30%, more than 40%, more than 50%, more than 60%, more than 70%, more than 80%, more than 90%, or more than 100% of the signal that is initiated, induced, or stimulated by the receptor's natural ligand.

In some embodiments, the one or more CRBR is an antibody or fragment thereof that binds to the co-stimulatory receptor 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA). In some embodiments, the one or more CRBR is an antibody or fragment thereof that binds to the co-stimulatory receptor 41BB, OX40, GITR, ICOS, or CD28. In some embodiments, the one or more CRBR is an antibody or fragment thereof that binds to the co-stimulatory receptor 41BB, OX40, or GITR. Exemplary polypeptides for binding 41BB, OX40 and GITR are described in PCT publication. No. WO2017123650, WO2017123673, and WO2017015623, respectively. In some embodiments, the one or more CRBR is a single domain antibody (sdAb) that binds the co-stimulatory receptor, such as those described in PCT publication. No. WO2017123650, WO2017123673, and WO2017015623.

In some examples, the co-stimulatory receptor binding region (CRBR) binds or comprises a natural cognate binding partner of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), NKG2D. In some embodiments, the natural cognate binding partner is selected from 41BB ligand (41BBL), OX40L (CD252), CD70, GITR Ligand/TNFSF18, CD80 (B7-1), CD86 (B7-2), ICOS Ligand (ICOSL), CD154 (CD40L), B-cell activating factor (BAFF), A proliferation-inducing ligand (APRIL), NKG2D ligands, or a functional fragment thereof.

In some embodiments, the co-stimulatory receptor binding region (CRBR) is an antibody or antigen binding fragment that binds 41BB. In particular examples, the CRBR that binds 4-1BB is a single domain antibody. In some embodiments, the sdAb contains a CDR1 GFSFSINAMG (set forth in SEQ ID NO:347), a CDR2 AIESGRNTV (set forth in SEQ ID NO:348) and a CDR3 LKGNRVVSPSVAY (set forth in SEQ ID NO: 349). Examples of sdAb that target 41BB are described in PCT publication. No. WO2017123650.

Exemplary sequences of CRBRs are set forth in Table 4.

In some embodiments, at least one CRBR, or independently each CRBR, binds the co-stimulatory receptor 41BB. In some examples, the CRBR is or contains an antibody or antigen binding fragment specific to or that binds 41BB, such as a sdAb or fragments containing a VH and VL (e.g. scFv). In some embodiments, at least one CRBR, or independently each CRBR, is a natural ligand of 41BB or is a functional binding fragment thereof. In some embodiments, a 41BB-binding CRBR is a functional fragment of 41BB ligand (41BBL) containing the extracellular domain or a truncated portion thereof, such as corresponding to amino acids 50-254 of UniProt No. P41273, e.g. as set forth in SEQ ID NO: 186, or a truncated portion or fragment thereof set forth in any of SEQ ID NOS: 202-209. Exemplary 41BB-binding CRBRs are set forth in any of SEQ ID NOS: 186-210 and 359. In some embodiments, at least one CRBR, or independently each CRBR, is an anticalin set forth in any of SEQ ID NOS: 193-201. In some embodiments, a sdAb, such as a VHH, contains a CDR1, a CDR2, and a CDR3 having a sequence set forth in SEQ ID NO:347, 348, and 349, respectively. A 41BB-binding CRBR, such as a sdAb, can include the sequence set forth in SEQ ID NO:210. A 41BB-binding CRBR, such as a sdAb, can include the sequence set forth in SEQ ID NO:359. In some embodiments, the 4-1BB-binding domain contains an antigen binding antibody fragment containing a VH and a VL, such as a single chain fragment in which the VH and VL are separated by a linker, for example an scFv. In some embodiments, the 41BB binding CRBR contains a VH set forth in any of SEQ ID NOS: 187, 189 and 191, and a VL set forth in any of SEQ ID NO: 188, 190, or 192. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind 41BB.

In some embodiments, at least one CRBR, or independently each CRBR, binds the co-stimulatory receptor OX40. In some examples, the CRBR is or contains an antibody or antigen binding fragment specific to or that binds OX40, such as a sdAb or fragments containing a VH and VL (e.g. scFv). In some embodiments, at least on CRBR, or independently each CRBR, is a natural ligand of OX40 or is a functional binding fragment thereof. Exemplary of such OX40-binding CRBRs are set forth in any of SEQ ID NOS: 211-220. In some embodiments, the OX40-binding CRBR contains an VH set forth in any of SEQ ID NOS: 216 and 218, and a VL set forth in any of SEQ ID NO: 217 and 219. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind OX40.

In some embodiments, at least one CRBR, or independently each CRBR, binds the co-stimulatory receptor GITR. In some examples, the CRBR is or contains an antibody or antigen binding fragment specific to or that binds GITR, such as a sdAb or fragments containing a VH and VL (e.g. scFv). In some embodiments, at least one CRBR, or independently each CRBR, is a natural ligand of GITR or is a functional binding fragment thereof. Exemplary of such GITR-binding CRBRs are set forth in any of SEQ ID NOS: 221-230. In some embodiments, the GITR binding CRBR contains a VH set forth in any of SEQ ID NOS: 222, 224, 226, and 228 and a VL set forth in any of SEQ ID NO: 223, 225, 227, and 229. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind GITR.

In some embodiments, at least one CRBR, or independently each CRBR, binds the co-stimulatory receptor CD27. In some examples, the CRBR is or contains an antibody or antigen binding fragment specific to or that binds CD27, such as a sdAb or fragments containing a VH and VL (e.g. scFv). In some embodiments, at least one CRBR, or independently each CRBR, is a natural ligand of CD27 or is a functional binding fragment thereof. Exemplary of such CD27-binding CRBRs are set forth in any of SEQ ID NOS: 231. In some embodiments, the CD27 binding CRBR contains a VH set forth SEQ ID NO: 232 and a VL set forth in SEQ ID NO: 233. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind CD27.

In some embodiments, at least one CRBR, or independently each CRBR, binds the co-stimulatory receptor ICOS. In some examples, the CRBR is or contains an antibody or antigen binding fragment specific to or that binds ICOS, such as a sdAb or fragments containing a VH and VL (e.g. scFv). In some embodiments, at least one CRBR, or independently each CRBR, is a natural ligand of ICOS or is a functional binding fragment thereof. An exemplary ICOS-binding CRBR sequence is set forth in SEQ ID NO: 234.

In some embodiments, at least one CRBR, or independently each CRBR, binds the co-stimulatory receptor CD28. In some examples, the CRBR is or contains an antibody or antigen binding fragment specific to or that binds CD28, such as a sdAb or fragments containing a VH and VL (e.g. scFv). In some embodiments, at least one CRBR, or independently each CRBR, is a natural ligand of CD28 or is a functional binding fragment thereof. An exemplary CD28-binding CRBR sequence is set forth in SEQ ID NO: 235.

TABLE 4

Exemplary CRBR Sequences

| CRBR | Format | Reference | SEQ ID NO |
|---|---|---|---|
| 41BB binding CRBR Sequences | | | |
| 41BBL | Natural Ligand | UniProt accession no. P41273 | 186 |
| PF-05082566 | VH | US 2012/0237498 (SEQ ID NO: 43) | 187 |
|  | VL | US 2012/0237498 (SEQ ID NO: 45) | 188 |
| BM5663513 | VH | WO 2005/035584 (SEQ ID NO: 9) | 189 |
|  | VL | WO 2005/035584 (SEQ ID NO: 6) | 190 |
| MSB7 | VH | US 2017/0226215 (SEQ ID NO: 138) | 191 |
|  | VL | US 2017/0226215 (SEQ ID NO: 28) | 192 |
| 41BB Anticalin | Anticalin | WO 2016/177762 (SEQ ID NO: 12) | 193 |
| 41BB Anticalin | Anticalin | WO 2016/177762 (SEQ ID NO: 13) | 194 |
| 41BB Anticalin | Anticalin | WO 2016/177762 (SEQ ID NO: 14) | 195 |
| 41BB Anticalin | Anticalin | WO 2016/177762 (SEQ ID NO: 15) | 196 |
| 41BB Anticalin | Anticalin | WO 2016/177762 (SEQ ID NO: 16) | 197 |
| 41BB Anticalin | Anticalin | WO 2016/177762 (SEQ ID NO: 17) | 198 |
| 41BB Anticalin | Anticalin | WO 2016/177762 (SEQ ID NO: 18) | 199 |
| 41BB Anticalin | Anticalin | WO 2016/177762 SEQ ID NO: 19) | 200 |
| 41BB Anticalin | Anticalin | WO 2016/177762 (SEQ ID NO: 20) | 201 |
| 71-254 of human 41BBL | 41BB ligand | WO 2017/167672 (SEQ ID NO: 3) | 202 |
| 85-254 of human 41BBL | 41BB ligand | WO 2017/167672 (SEQ ID NO: 4) | 203 |
| 80-254 of human 41BBL | 41BB ligand | WO 2017/167672 (SEQ ID NO: 5) | 204 |
| 52-254 of human 41BBL | 41BB ligand | WO 2017/167672 (SEQ ID NO: 6) | 205 |
| 71-248 of human 41BBL | 41BB ligand | WO 2017/167672 (SEQ ID NO: 7) | 206 |
| 85-248 of human 41BBL | 41BB ligand | WO 2017/167672 (SEQ ID NO: 8) | 207 |
| 80-248 of human 41BBL | 41BB ligand | WO 2017/167672 (SEQ ID NO: 9) | 208 |
| 52-248 of human 41BBL | 41BB ligand | WO 2017/167672 (SEQ ID NO: 10) | 209 |
| 41BB sdAb | sdAb | US 2017/0198050 | 210 |
| 41BB sdAb | sdAb | | 359 |
| OX40-binding CRBR Sequences | | | |
| OX40 ligand | Natural Ligand | UniProt accession no. P23510 | 211 |
| OX40 ligand | Natural Ligand | U.S. Pat. No. 7,959,925 (SEQ ID NO: 2) | 212 |
| human OX40L: 51-183 | Natural Ligand | WO 2017/167672 (SEQ ID NO: 11) | 213 |

TABLE 4-continued

| Exemplary CRBR Sequences | | | |
|---|---|---|---|
| CRBR | Format | Reference | SEQ ID NO |
| Human Ox40L: 51-183 N90D | Natural Ligand | WO 2017/167672 (SEQ ID NO: 12) | 214 |
| Human OX40L: 52-183 | Natural Ligand | WO 2017/167672 (SEQ ID NO: 13) | 215 |
| 1A07 | VH | US 2015/0307617 (SEQ ID NO: 56) | 216 |
| | VL | US 2015/0307617 (SEQ ID NO: 59) | 217 |
| 1949 | VH | WO 2016/179517 (SEQ ID NO: 16) | 218 |
| | VL | WO 2016/179517 | 219 |
| 1D10v1 | sdAb | U.S. Pat. No. 9,006,399 | 220 |
| GITR-binding CRBR Sequences | | | |
| GITR ligand | Natural Ligand | UniProt no. Q9UNG2 | 221 |
| 36E5 | VH | US 2014/0348841 (SEQ ID NO: 104) | 222 |
| | VL | US 2014/0348841 (SEQ ID NO: 105) | 223 |
| TRX-518 | VH | US 2013/0183321 (SEQ ID NO: 54) | 224 |
| | VL | US 2013/0183321 (SEQ ID NO: 44) | 225 |
| 5H7v2 | VH | US 2015/0064204 (SEQ ID NO: 282) | 226 |
| | VL | US 2015/0064204 (SEQ ID NO: 134) | 227 |
| 41G5v2 | VH | US 2015/0064204 (SEQ ID NO: 312) | 228 |
| | VL | US 2015/0064204 (SEQ ID NO: 124) | 229 |
| C06v3 | sdAb | US 2017/0022284 (SEQ ID NO: 59) | 230 |
| CD27-binding CRBR Sequences | | | |
| CD70-ECD | Natural Ligand | UniProt no. P32970 | 231 |
| 1F5 | VH | US 2011/0274685 | 232 |
| | VL | US 2011/0274685 | 233 |
| CD28-binding CRBR Sequences | | | |
| CD28 sdAb | sdAb | | 235 |
| ICOS-binding CRBR Sequences | | | |
| ICOS sdAb | sdAb | | 234 |

In some embodiments, the one or more CRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described herein, although generally the peptide linking the CRBR or regions is not a cleavable liker.

In some embodiments, the multispecific polypeptide construct comprises a linking peptide (LP) between the CRBR and the Fc region. In some embodiments, the multispecific polypeptide construct comprises a linking peptide (LP) between the CD3 binding region and the CRBR.

f. Inhibitory Receptor Binding Regions (IRBR)

The multispecific polypeptide constructs of the present disclosure include one or more inhibitor receptor binding region (IRBR) that binds an inhibitory receptor. In some embodiments, the one or more IRBR of the provided multispecific polypeptide constructs bind an inhibitory receptor expressed on T cells. In some embodiments, the inhibitory receptor is upregulated, induced, or expressed on the surface of an activated T cell. In some aspects, the IRBR blocks an interaction between the inhibitory receptor and its ligand, thereby reducing, suppressing or decreasing an inhibitory signal in the cell to which the IRBR binds, e.g. T cell. In some embodiments, the IRBR, or independently each of the IRBRs, is an antibody or antigen binding fragment, a natural cognate binding partner of the co-stimulatory receptor, an Anticalin (engineered lipocalin), a Darpin, a Fynomer, a Centyrin (engineered fibronectin III domain), a cystine-knot domain, an Affilin, an Affibody, or an engineered CH3 domain.

In some embodiments, the IRBR, or independently each of the IRBRs, such as the first IRBR and the second IRBR, includes one or more copies of an antibody or an antigen-binding fragment thereof. In some embodiments, the IRBR or independently each of the IRBRs, such as the first IRBR and the second IRBR, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

In some embodiments, the IRBR, or independently each of the IRBRs, such as the first IRBR and the second IRBR, is a single chain antibody. In some examples, the single chain is an scFv, a scAb, a single domain heavy chain antibody, or a single domain light chain antibody.

In some embodiments, the IRBR, or independently each of the IRBRs, such as the first IRBR and the second IRBR, includes one or more single domain antibody (sdAb) fragments, for example V$_H$H, V$_{NAR}$, engineered V$_H$ or V$_K$ domains. V$_H$Hs can be generated from natural camelid heavy chain only antibodies, genetically modified rodents that produce heavy chain only antibodies, or naïve/synthetic camelid or humanized camelid single domain antibody libraries. V$_{NAR}$s can be generated from cartilaginous fish heavy chain only antibodies. Various methods have been implemented to generate monomeric sdAbs from conventionally heterodimeric V$_H$ and V$_K$ domains, including interface engineering and selection of specific germline families.

In some embodiments, the IRBR, or independently each of the IRBRs such as the first IRBR and/or the second IRBR, of the multispecific polypeptide constructs contains at least one sdAb or an scFv that binds an inhibitory receptor. In some embodiments, the at least one scFv or sdAb that binds an inhibitory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to an inhibitory receptor, which can be positioned either amino-terminally relative to the Fc region and/or carboxy-terminally relative to the CD3 binding region. In some embodiments, the multispecific polypeptide construct contains two scFv or sdAb that bind to an inhibitory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to an inhibitory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to an inhibitory receptor. The scFv or sdAb that binds the inhibitory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the multispecific polypeptide construct is formed from or includes two polypeptides, including a first polypeptide comprising in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide containing the IRBR and comprising in order: a second Fc polypeptide of the heterodimeric Fc region, the linker, a VL domain of the anti-CD3 antibody or antigen binding fragment (e.g. Fv), wherein the IRBR is positioned amino terminally to the Fc region and/or C-terminally to the CD3 binding region. In some embodiments, the IRBR is positioned on the second polypeptide carboxy-terminally to the CD3 binding region. In some embodiments, the IRBR is positioned on the second polypeptide amino-terminally to the Fc region. In some embodiments, the IRBR is positioned amino terminally to the Fc region and C-terminally to the CD3 binding region. In some embodiments, the first and second antigen binding domain is specific to a TAA are the same. In some embodiments, the first and second antigen binding domain is specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

In some embodiments, the IRBR or independently each of the IRBRs, such as the first IRBR and/or the second IRBR, contains more than one chain. In some embodiments, the IRBR or independently each of the IRBRs, such as the first IRBR and/or the second IRBR, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds an inhibitory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to an inhibitory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to an inhibitory receptor, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to an inhibitory receptor; a second polypeptide comprising a second Fc polypeptide of the heterodimeric Fc region, the linker and, optionally, the same VH-CH1 (Fd) or VL-CL of the Fab antibody fragment that binds to a inhibitory receptor, and a third polypeptide comprising the other of the VH-CH1 (Fd) or VL-CL of the Fab antibody fragment that binds to the inhibitory receptor. The first, second and/or third polypeptide of the multispecific polypeptide construct also can include an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a fourth polypeptide where at least a first and second polypeptide includes a chain of the Fab that binds TAA (e.g. VH-CH1 or VL-CL of a Fab) and the fourth polypeptide contains the other chain of the Fab that binds TAA (e.g. the other of VH-CH1 or VL-CL of a Fab).

In some embodiments, the IRBR, or independently each of the IRBRs, is or includes a natural (native) cognate binding partner of the inhibitor receptor (e.g. a natural ligand), or a variant thereof that exhibits binding activity to the inhibitory receptor.

In some embodiments, the one or more IRBR of the provided multispecific polypeptide constructs binds a inhibitory receptor expressed on T cells. In some embodiments, there are more than one IRBR that binds to an inhibitory receptor and each of the IRBRs, such as the first IRBR and the second IRBR, bind the same co-stimulatory receptor. In some embodiments, each of the IRBRs, such as the first IRBR and the second IRBR, binds a different inhibitory receptor. In some embodiments, each of the IRBRs, such as the first IRBR and the second IRBR binds a different epitope on the same inhibitory receptor. In some embodiments, each of the IRBRs, such as the first IRBR and the second IRBR, binds the same epitope on the same inhibitory receptor.

In some embodiments, the IRBR, or independently each of the IRBRs that binds a inhibitory receptor results in monovalent, bivalent, trivalent, or tetravalent binding to the inhibitory receptor.

In some embodiments, the inhibitory receptor is expressed on T cells, such as primary T cells of a subject. In some embodiments, the inhibitory receptor is expressed on human T cells, such as primary human T cells of a human subject.

In some embodiments, the inhibitory receptor is a member of the tumor necrosis factor (TNF) receptor family. In some embodiments, the inhibitory receptor is a member of the immunoglobulin superfamily (IgSF).

In some embodiments, the inhibitory receptor is Programmed cell death protein 1 (PD-1), cytotoxic T-lymphocyte associated protein 4 (CTLA-4), T cell immunoreceptor with Ig and ITIM domains (TIGIT), V-domain immunoglobulin suppressor of T cell activation (VISTA), T cell immunoglobulin and mucin-domain containing-3 (TIM3), or lymphocyte activation gene 3 (LAG3). In some embodiments, the one or more IRBR is an antibody or fragment thereof that binds to the inhibitor receptor PD-1, CTLA-4, TIGIT, VISTA, TIM3 or LAG3. In particular embodiments, the antibody or antigen-binding fragment is humanized or is human.

In some examples, the inhibitory receptor binding region (IRBR) binds or comprises a natural cognate binding partner of PD-1, CTLA-4, TIGIT, VISTA, or TIM3. In some embodiments, the natural cognate binding partner is selected from PD-L1, PD-L2, CD80, CD86, CD155, CD112, or VSIG-3/IGSF11, or a functional fragment thereof.

In some examples, the IRBR contains an antibody fragment, such as an scFv, that contains a variable light (VL) chain and a variable heavy (VH) chain of an antibody that that binds an inhibitory receptor, such as PD-1, CTLA-4, TIGIT, VISTA, or TIM3. In some examples, the IRBR contains a single domain antibody or a VHH domain that specifically binds an inhibitory receptor, such as a PD-1, CTLA-4, TIGIT, VISTA, or TIM3, see e.g. described in PCT publication No. WO2018068695 or WO2018068201.

In some embodiments, the inhibitory receptor is PD-1. In some embodiments, the one or more IRBR is an antibody fragment that binds to PD-1.

In some embodiments, the IRBR is or contains a VHH domain that binds PD-1 comprising a CDR1, CDR2 and CDR3 contained in a VHH amino acid sequences selected from any of SEQ ID NO: 304-320, 326, or 364-381 or an amino acid sequence that has at least 90%, 91%, 92%, 93%, 94%, 95%, 96%, 97%, 98%, or 99% sequence identity to the VHH region amino acid selected from any one of SEQ ID NOs: 304-320, 326 or 364-381 and binds PD-1.

In some embodiments, the IRBR is or contains a VHH domain that contains a CDR1, CDR2, CDR3 contained in a VHH domain set forth in SEQ ID NO: 326, or an amino acid sequence that has at least 90%, 91%, 92%, 93%, 94%, 95%, 96%, 97%, 98%, or 99% sequence identity to the VHH region amino acid selected set forth in SEQ ID NO: 326 and that binds PD-1. In some embodiments, the IRBR is or contains a VHH domain that has the amino acid sequence set forth in SEQ ID NO: 326 or an amino acid sequence that has at least 90%, 91%, 92%, 93%, 94%, 95%, 96%, 97%, 98%, or 99% sequence identity to the amino acid selected set forth in SEQ ID NO: 326 and that binds PD-1. In some embodiments, IRBR is or contains a VHH domain that is a humanized variant of the amino acid sequence set forth in SEQ ID NO: 326. In some embodiments, an IRBR that binds PD-1 has a VHH domain that comprises a CDR1 set forth in any one of SEQ ID NOS: 321, 322 or 323, a CDR2 set forth in SEQ ID NO: 324 and a CDR3 set forth in SEQ ID NO: 325.

In some embodiments, an IRBR that binds PD-1 has a VHH domain that contains a CDR1, CDR2, and CDR3 set forth in SEQ ID NOs: 322, 324, and 325, respectively. In some embodiments, an IRBR that binds PD-1 has a VHH domain that contains a CDR1, CDR2 and CDR3 set forth in SEQ ID NOs: 321, 324, and 325, respectively. In some embodiments, the an IRBR that binds PD-1 has a VHH domain that contains a CDR1, CDR2 and CDR3 set forth in SEQ ID NOs: 323, 324, and 325, respectively.

In some aspects, the IRBR is or contains a VHH domain that contains a CDR1, CDR2 and CDR3 contained in a VHH amino acid sequence selected from any of SEQ ID NO:304-320, or an amino acid sequence that has at least 90%, 91%, 92%, 93%, 94%, 95%, 96%, 97%, 98%, or 99% sequence identity to the VHH region amino acid selected from any one of SEQ ID NOs: 304-320 and that binds PD-1.

In some cases, the IRBR contains a VHH domain that is a humanized variant that has the amino acid sequence set forth in any of SEQ ID NOS: 304-320 or an amino acid sequence that has at least 90%, 91%, 92%, 93%, 94%, 95%, 96%, 97%, 98%, or 99% sequence identity to the VHH region amino acid selected from any one of SEQ ID NOs: 304-320 and that binds PD-1. In some embodiments, the IRBR is or contains a VHH domain sequence that is a humanized VHH domain having the sequence of amino acids set forth in any one of SEQ ID NOS: 304-320.

In some embodiments, the IRBR is or contains a VHH domain that contains a CDR1, CDR2, CDR3 contained in a VHH domain set forth in SEQ ID NO: 364, or an amino acid sequence that has at least 90%, 91%, 92%, 93%, 94%, 95%, 96%, 97%, 98%, or 99% sequence identity to the VHH region amino acid selected set forth in SEQ ID NO: 364 and that binds PD-1. In some embodiments, the IRBR is or contains a VHH domain that has the amino acid sequence set forth in SEQ ID NO: 364 or an amino acid sequence that has at least 90%, 91%, 92%, 93%, 94%, 95%, 96%, 97%, 98%, or 99% sequence identity to the amino acid selected set forth in SEQ ID NO: 364 and that binds PD-1. In some embodiments, IRBR is or contains a VHH domain that is a humanized variant of the amino acid sequence set forth in SEQ ID NO: 364.

In some embodiments, an IRBR that binds PD-1 has a VHH domain that comprises a CDR1 set forth in any one of SEQ ID NOS: 321, 322 or 323, a CDR2 set forth in SEQ ID NO: 324 and a CDR3 set forth in SEQ ID NO: 325.

In some embodiments, an IRBR that binds PD-1 has a VHH domain that contains a CDR1, CDR2, and CDR3 set forth in SEQ ID NOs: 322, 324, and 325, respectively. In some embodiments, an IRBR that binds PD-1 has a VHH domain that contains a CDR1, CDR2 and CDR3 set forth in SEQ ID NOs: 321, 324, and 325, respectively. In some embodiments, the an IRBR that binds PD-1 has a VHH domain that contains a CDR1, CDR2 and CDR3 set forth in SEQ ID NOs: 323, 324, and 325, respectively.

In some aspects, the IRBR is or contains a VHH domain that contains a CDR1, CDR2 and CDR3 contained in a VHH amino acid sequence selected from any of SEQ ID NO:365-381, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 365-381 and that binds PD-1.

In some cases, the IRBR contains a VHH domain that is a humanized variant that has the amino acid sequence set forth in any of SEQ ID NOS: 365-381 or an amino acid sequence that has at least 90%, 91%, 92%, 93%, 94%, 95%, 96%, 97%, 98%, or 99% sequence identity to the VHH region amino acid selected from any one of SEQ ID NOs: 365-381 and that binds PD-1. In some embodiments, the IRBR is or contains a VHH domain sequence that is a humanized VHH domain having the sequence of amino acids set forth in any one of SEQ ID NOS: 365-381.

In some embodiments, the one or more IRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described, such as in Section II.3, although generally the peptide linking the IRBR or regions is not a cleavable liker.

In some embodiments, the multispecific polypeptide construct comprises a linking peptide (LP) between the IRBR and the Fc region. In some embodiments, the multispecific polypeptide construct comprises a linking peptide (LP) between the CD3 binding region and the IRBR.

In some embodiments, the multispecific polypeptide construct comprises more than one IRBR. In some embodiments, the multispecific polypeptide construct comprises a first linking peptide (LP1) between the first IRBR and the Fc region. In some embodiments, the multispecific polypeptide construct comprises a second linking peptide (LP2) between the CD3 binding region and the second IRBR. In some embodiments, the multispecific polypeptide construct comprises a first linking peptide (LP1) between the first IRBR and the Fc region and a second linking peptide (LP2) between the CD3 binding region and the second IRBR. In some aspects, the multispecific polypeptide construct has the structural arrangement from N-terminus to C-terminus as follows: IRBR and/or antigen binding domain-LP1-Fc region-linker-CD3 binding region-LP2-IRBR and/or antigen binding domain. In some embodiments, the two linking peptides are not identical to each other.

In some embodiments, the LP (e.g., LP1 or LP2) is independently a peptide of about 1 to 20 amino acids in length. In some embodiments, the LP1 or LP2 is independently a peptide that is or comprises any Gly-Ser linker as set forth in SEQ ID NOs: 1-4, 125-127, 129 or GGS.

In some embodiments, the multispecific polypeptide construct contains both a CRBR and an IRBR. In some embodiments, one of the CRBR or IRBR is positioned amino-terminally relative to the Fc region and the other of the CRBR or IRBR is positioned carboxy-terminally relative to the CD3 binding region of the multispecific polypeptide construct. In some embodiments, the CRBR and IRBR are present on different polypeptide of a heterodimeric multispecific polypeptide construct, in which at least one of the polypeptides also contains the at least one antigen binding domain specific to a TAA. In some embodiments, the CRBR and IRBR are present on the same polypeptide (first polypeptide) of a heterodimeric multispecific polypeptide construct and the at least one antigen binding domain specific to a TAA is on the other (or second) polypeptide of the heterodimeric multispecific polypeptide construct.

In some embodiments, the multispecific polypeptide construct is formed from or includes two polypeptides. In some aspects, the first polypeptide comprises in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide comprising in order: one of the IRBR or CRBR, a second Fc polypeptide of the heterodimeric Fc region, the linker, a VL domain of the anti-CD3 antibody or antigen binding fragment (e.g. Fv), and the other of the IRBR or CRBR. In some embodiments, the IRBR is positioned on the second polypeptide carboxy-terminally to the CD3 binding region and the CRBR is positioned on the second polypeptide amino-terminally to the Fc region. In some embodiments, the IRBR is positioned on the second polypeptide amino-terminally to the Fc region and the CRBR is positioned on the second polypeptide carboxy-terminally to the CD3 binding region. In some embodiments, the first and second antigen binding domain is specific to a TAA are the same. In some embodiments, the first and second antigen binding domain is specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

3. NK Recruitment

In some embodiments, the 5T4-binding polypeptide is a bispecific construct that is or comprises at least one 5T4 VHH domain provided herein and at least one additional binding molecule capable of binding to a surface molecule expressed on a Natural Killer (NK) cells and/or recruiting NK cells. In particular aspects, the multispecific construct is bispecific for 5T4 and the NK cell surface molecule. In some embodiments, the surface molecule is CD16 (FcγRIII). Specifically, a provided bispecific 5T4-binding polypeptide is capable of specifically binding an NK activating receptor expressed on a human NK cells cell, such as human CD16a.

CD16, a low affinity receptor for the Fc portion of some IgGs known to be involved in antibody-dependent cellular cytotoxicity (ADCC), is the best-characterized membrane receptor responsible for triggering of target cell lysis by NK cells (Mandelboim et al., 1999, PNAS 96:5640-5644). Generally, a large majority (approximately 90%) of human NK cells express CD56 at low density (CD56dim) and FcγRIII (CD16) at a high level (Cooper et al., 2001, Trends Immunol. 22:633-640). Human FcγRIII exists as two isoforms, CD16a (FcγRIIIA) and CD16b (FcγRIIIB), that share 96% sequence identity in their extracellular immunoglobulin-binding regions (van de Winkel and Capel, 1993, Immunol. Today 14 (5): 215-221). In particular embodiments, the additional binding molecule is capable of specifically binding CD16a.

CD16a is expressed on macrophages, mast cells, and NK cells as a transmembrane receptor. On NK cells, the alpha chain of CD16a associates with the immunoreceptor tyrosine-based activation motif (ITAM) containing FcεRI γ-chain and/or the T-cell receptor (TCR)/CD3-chain to mediate signaling (Wirthmueller et al., 1992, J. Exp. Med. 175:1381-1390). The interaction of CD16a with different combinations of homo- and hetero-dimers of the γ and ζ chains has been observed in NK cells, indicating the ability to mediate signaling via different signaling pathways via variations of the CD16a complex in NK cells (Anderson et al., 1990, PNAS 87 (6): 2274-2278; Ackerly et al., 1992, Int. J. Cancer Suppl. 7:11-14). FcγR-expressing effector cells have been shown to be involved in destroying tumor cells via ADCC. For example, engagement of CD16a, such as with an agonist binding molecule capable of specifically binding CD16a can result in activating of NK cells expressing CD16a, thereby eliciting a biological response, in particular a signaling response. In some cases, the binding molecule is capable of triggering cell killing, in a manner analogous to antibody-dependent cellular cytotoxicity (ADCC), by virtue of its binding to such cells.

In particular examples, 5T4-binding polypeptides include bispecific molecules that can specifically bind to 5T4 and to CD16a may target NK cells to cells bearing such antigen, so that the cell bearing the antigen may be eradicated via NK cell mediated cell killing. For example, a binding molecule that specifically binds 5T4 expressed on a tumor cell may target NK-cells to the tumor cell. In some cases, activation of the NK cell caused by the binding molecule binding to CD16a can lead to killing of the tumor cells.

In some embodiments, the additional binding domain specific to an activating NK cell receptor, such as CD16a, is an antigen-binding fragment selected from a Fab fragment, a F(ab')$_2$ fragment, an Fv fragment, a scFv, disulfide stabilized Fv fragment (dsFv), a scAb, a dAb, a single domain heavy chain antibody (VHH), or a single domain light chain antibody. In some embodiments, the additional binding domain is monovalent for binding the activating T NK cell receptor, such as CD16a.

In some cases, the additional binding domain recognizes CD3-binding domain recognizes CD16a. In some embodiments, the anti-CD16a binding domain includes one or more copies of an anti-CD16a Fab fragment, an anti-CD16a F(ab')$_2$ fragment, an anti-CD16a Fv fragment, an anti-CD16a scFv, an anti-CD16a dsFv, an anti-CD16a scAb, an anti-CD16a dAb, an anti-CD16a single domain heavy chain antibody (VHH), and an anti-CD16a single domain light chain antibody. In some embodiments, the anti-CD16a binding domain is monovalent for binding CD16a. In some embodiments, the BH73-binding polypeptide is a bispecific construct that binds BH73 and agonizes the activity of CD16a.

Antibodies and antigen-binding fragments thereof specific for CD16a are known and include, for example, NM3E2 (McCall et al. (1999) Mol. Immunol., 36:433-045. Other anti-CD16a antibodies also can be used in the constructs provided herein, including any described in published U.S. patent application No. US10160280795; U.S. Pat. No. 9,701,750; Behar et al. (2008) Protein Eng Des Sel. 21:1-10; Arndt et al., (1999) Blood 94:2562-2568. In particular examples, the anti-CD16a is an anti-CD16a scFv. In some embodiments, the anti-CD16a is an anti-CD16a antibody included in a TandAb molecule (see e.g. Reush et al. (2014) Mabs, 6:727-738). In some aspects, the anti-CD16a is an anti-CD16a or antigen binding fragment, such as an scFv, described in U.S. Pat. No. 9,035,026.

The provided bispecific constructs can be formatted in any of a number of formats containing the at least one 5T4 VHH domain and the at least one additional domain specific to an activating NK cell receptor, such as a CD16a-binding domain.

In one embodiment, the bispecific construct is a bispecific single-domain antibody-linked Fab (S-Fab) containing at least one 5T4 VHH domain as described linked, directly or indirectly to a Fab antigen binding fragment specific to an NK cell activating receptor, e.g. CD16a, such as an anti-CD16a Fab. In some embodiments, the 5T4 VHH domain is linked to the C-terminus of the VH or VL chain of an anti-C16a Fab. In some embodiments, the S-Fab can be further modified, such as by conjugation with polyethylene glycol (PEG), N-(2-hydroxypropyl) methacrylamide (HPMA) copolymers, proteins (such as albumin), polyglutamic acid or PASylation (Pan et al. (2018) International Jounral of Nanomedicine, 2018:3189-3201).

In another embodiment, the bispecific construct is a scFv-single domain antibody in which the construct contains at least one 5T4 VHH as described linked, directly or indirectly, to an scFv containing a VH and a VL of an antigen binding domain specific to an NK cell activating receptor, e.g. CD16a. The scFv against an NK cell activating receptor, e.g. anti-CD16a scFv, can contain any of the VH and VL sequences as described. In some embodiments, the VHH domain and the scFv are connected by a linker, such as a peptide linker. In some embodiments, the peptide linker can be a peptide linker as described herein. In some embodiments, the VHH domain and the scFv are each connected, optionally through a hinge region or a linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In a further embodiment, the antigen binding domain specific to an NK cell activating receptor, e.g. CD16a, is a single domain antibody, such as is a VHH domain that specifically binds to CD16a. Single domain antibodies, including VHH domains that bind to CD16a are known, see e.g. published U.S. patent application No. US20160280795. In such aspects, a bispecific construct provided herein can include at least one 5T4 VHH domain and at least one CD16a VHH domain. For formatting the constructs, in some cases, each VHH domain is connected, optionally through a hinge region or linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In the above embodiments, exemplary modifications of an Fc region to promote heterodimerization are known, including any as described below, e.g. Table 3. In some embodiments, one Fc polypeptide of a heterodimeric Fc comprises the sequence of amino acids set forth in any of SEQ ID NOS: 328 (e.g. SEQ ID NO:103 or 107), 334 (e.g. SEQ ID NO:115 or 117), and the other Fc polypeptide of the heterodimeric Fc contains the sequence of amino acids set forth in any of SEQ ID NOS: 329 (e.g. SEQ ID NO: 104 or 108), 332 (e.g. SEQ ID NO:111 or 113), 336 (e.g. SEQ ID NO:119 or 121). In some embodiments, one Fc polypeptide of a heterodimeric Fc comprises the sequence of amino acids set forth in any of SEQ ID NOS: 330 (e.g. SEQ ID NO: 105 or 109), 335 (e.g. SEQ ID NO:116 or 118) and the other Fc polypeptide of the heterodimeric Fc comprises the sequence of amino acids set forth in any of SEQ ID NOS: 331 (e.g. SEQ ID NO: 106 or 110), 333 (e.g. SEQ ID NO:112 or 114), 337 (e.g. SEQ ID NO:120 or 122).

4. Cytokine Fusion and/or Cytokine Receptor Targeting

In some embodiments, the 5T4-binding polypeptide is a multispecific polypeptide construct that is a cytokine-antibody fusion protein (also called a 5T4 VHH-cytokine fusion). In some aspects, at least one 5T4 VHH domain provided herein is linked, directly or indirectly, to at least one cytokine, such as to an interferon. In particular embodiments, the cytokine is an interferon capable of exhibiting anti-proliferative activity, apoptotic activity and/or anti-viral activity. In some embodiments, the interferon of a 5T4 VHH-cytokine fusion provided herein is capable of binding to a receptor composed of IFNAR1 and/or 2. Any of a variety of assays can be used to assess the effect of such fusion proteins on binding IFNAR1 and/or 2, reducing or decreasing the growth rather and/or proliferation rate of a cancer cell, reducing tumor size, eliminating tumors or inducing the death of a cancer cell (e.g. via apoptosis). Such assays in include in vitro assays with various cancer cell lines known to express 5T4 or in vivo assays employing animal tumor models.

In some embodiments, the interferon is a type I interferon, such as a human type I interferon or a variant thereof. In some aspects, the human type I interferon is a variant that is a truncated human type I interferon or a human mutant type I interferon. In some embodiments, the type I interferon or variant thereof is a wild-type human IFN-alpha (IFN-alpha; alpha2 and natural higher affinity variants such as alpha 14), interferon beta (IFN-beta) as well as mutants and/or truncated forms thereof. In some embodiments, the interferon is a type II interferon, such as a human type II interferon or a variant thereof. In some aspects, the human type II interferon is a variant that is a truncated human type II interferon or a human mutant type II interferon. In some embodiments, the type II interferon or variant thereof is a wild-type human interferon gamma (IFN-gamma) as well as mutants and/or truncated forms thereof. In some embodiments, the provided cytokine-antibody fusion proteins can be used to inhibit the growth and/or proliferation of target cells (e.g. cancer cells) that express or overexpress 5T4.

In some embodiments, the 5T4 VHH-cytokine fusion protein is similar in format to any as described in International PCT published application No. WO2014194100; U.S. Pat. No. 9,803,021; Valedkarimi et al. (2017) Biomed Pharmacother., 95:731-742; or Young et al. (2014) Semin Oncol., 41:623-636.

In particular embodiments, the interferon, e.g. a type I interferon, such as a human type I interferon (e.g. IFN-alpha, IFN-beta, or IFN-gamma) is one that possesses the endogenous binding affinity and/or activity of the native or wild-type interferon, preferably at a level of at least 60%, or of at least or at least about 80%, such as at least 90%, 95%, 98%, 99%, 100%, or a level greater than the native wild-type interferon (in its isolated form).

Interferons and interferon mutants are a well known and well characterized group of cytokines (see e.g., WO 2002/095067; WO 2002/079249; WO 2002/101048; WO 2002/095067; WO 2002/083733; WO 2002/086156; WO 2002/083733; WO 2003/000896; WO 2002/101048; WO 2002/079249; WO 2003/000896; WO 2004/022593; WO2004/022747; WO 2003/023032; WO 2004/022593 and also in Kim et al. (2003) Cancer Lett. 189 (2): 183-188; Hussain et al. (2000) J. Interferon Cytokine Res. 20 (9): 763-768; Hussain et al. (1998) J. Interferon Cytokine Res. 18 (7): 469-477; Nyman et al. (1988) Biochem. J. 329 (Pt 2): 295-302; Golovleva et al. (1997) J. Interferon Cytokine Res. 17 (10): 637-645; Hussain et al. (1997) J. Interferon Cytokine Res. 17 (9): 559-566; Golovleva et al. (1997) Hum. Hered. 47 (4): 185-188; Kita et al. (1991) J. Interferon Cytokine Res. 17 (3): 135-140; Golovleva et al. (1996) Am. J. Hum. Genet. 59 (3): 570-578; Hussain et al. (1996) J. Interferon Cytokine Res. 16 (7): 523-529; Linge et al. (1995) Biochim Biophys Acta. Any of such can be used in the provided cytokine-antibody fusion proteins.

In some embodiments, the interferon is a human type I interferon. Alleles of the human interferon family of genes/ proteins are known, see e.g. Pestka (10983) Arch Biochem Biophys., 221:1-37; Diaz et al. (1994) Genomics, 22:540-52; Pestka (1986) Meth. Enzymol, 199:3-4; and Krause et al. (2000) J. Biol. Chem., 275:22995-3004.

In some embodiments, the interferon is a full-length IFN-alpha (e.g. human IFN-alpha), a full-length IFN-beta (e.g. human IFN-beta) or a full-length IFN-gamma (e.g. human IFN-gamma). In some embodiments, the interferon is a biologically active truncated IFN-alpha (e.g. human IFN-alpha), a biologically active truncated IFN-beta (e.g. human IFN-beta) or a biologically active truncated IFN-gamma (e.g. human IFN-gamma). In some embodiments, a biologically active truncated interferon contains a contiguous sequence of amino acids of a wild-type or native interferon that is truncated at the N- and/or C-terminus and comprises a length that is at least or at least about 50%, 55%, 60%, 65%, 70%, 75%, 80%, 85%, 90% or more the length of the native or wild-type interferon. Any of a variety of standard assays for assessing biological activity of an interferon can be used. For example, IFN-alpha activity can be assayed by measuring antiviral activity against a particular test virus. Kits for assaying for IFN-alpha activity are commercially available (see, e.g., ILITE™ alphabeta kit by Neutekbio, Ireland). In some aspects, the IFN-alpha is an IFN-$\alpha$2a (e.g. Acc. No. CAA23805), IFN-a-c (Acc. No. P01566), IFN-$\alpha$-d (Acc. No. AAB59403); IFNa-5 (Acc. No. CAA26702); IFNa-6 (Acc. No. AA26704); IFNa-4 (Acc. No. NP_066546); IFNa-4b (Acc. No. CAA26701); IFNa-I (Acc. No. AAA52725); IFNa-J (Acc. No. CAA23792); IFNa-H (Acc. No. CAA23794); IFNa-F (Acc. No. AAA52718); IFNa-7 (Acc. No. CAA26903), or is a biologically active fragment thereof. In some aspects, the IFN-beta is IFN-beta set forth in Acc. No. AAC41702 or is a biologically active fragment thereof. In some aspects, the IFN-gamma is IFN-gamma set forth in Acc. No. P01579 or is a biologically active fragment thereof.

In some embodiments, a provided 5T4 VHH-cytokine fusion contains a variant or mutant interferon alpha 2 (IFNa2) is contemplated. Certain mutants include a mutation of the His at position 57, and/or the E at position 58, and/or the Q at position 61. In certain embodiments the mutants include the mutation H57Y, and/or E58N, and/or Q61S. In certain embodiments the mutants include a mutated IFNa2 having the mutations H57Y, E58N, and Q61S (YNS) (see, e.g., Kalie et al. (2007) J. Biol. Chem., 282:11602-11611). In other embodiments mutants include a mutation of the His at position 57, and/or the E at position 58, and/or the Q at position 61 to A (alanine). In certain embodiments the mutants include a mutated IFNa2 having the mutations H57A, E58A, and Q61A (HEQ) (see, e.g., Jaitin et al. (2006) Mol. Cellular Biol, 26 (5): 1888-1897). In certain embodiments the mutant interferon comprises a mutation of His at position 57 to A, Y, or M, and/or a mutation of E at position 58 to A, or N, or D, or L, and/or a mutation of Q at position 61 to A, or S, or L, or D. In certain embodiments mutant include mutants of interferon alpha 8 (IFN-$\alpha$8), such as variants with amino acid replacement corresponding to R145 to V, I, or L, and/or A146 to N, or S, and/or M149 to Y, e.g. R145V/A146N/M149Y), R145L/A146S/M149Y or R145L/A146S/M149Y (see, e.g., Yamamoto et. al., (2009) J. Interferon & cytokine Res, 29:161-170.

In some embodiments, a provided 5T4 VHH-cytokine fusion contains a mutant or variant IFN-beta containing a serine substituted for the naturally occurring cysteine at amino acid 17 (see, e.g., Hawkins et al. (1985) Cancer Res., 45, 5914-5920).

In some embodiments, a provided 5T4 VHH-cytokine fusion contains a truncated interferon. In one embodiment, a truncated interferon includes a human IFN-alpha with deletions of up to the first 15 amino-terminal amino acid residues and/or up to the last 10-13 carboxyl-terminal amino acid residues, which has been shown to retain activity of the native or wild-type human IFN-alpha (see e.g. Ackerman (1984) Proc. Natl. Acad. Sci, USA, 81:1045-1047). In some embodiments, a truncated human IFN-alpha has 1, 2, 3, 4, 5, 6, 7, 8, 9, 10, 11, 12 or 13 carboxyl terminal amino acid residues deleted and/or 1, 2, 3, 4, 5, 6, 7, 8, 9, 10, 11, 12, 13, 14, or 15 amino terminal amino acid residues deleted.

In some embodiments, a provided 5T4 VHH-cytokine fusion contains a truncated interferon, such as described in published U.S. patent appl. No. US2009/0025106. In some embodiments, a provided 5T4 VHH-cytokine fusion contains a truncated IFN-gamma containing N- and/or C-terminal deletions, such as described in Lundell et al. (1991) Protein Neg., 4:335-341; Pan et al. (1987) Eur. J. Biochem., 166:145-149.

In some embodiments, the interferon, e.g. human interferon, is a mutant interferon that is resistant to proteolysis compared to the unmodified, typically wild-type protein, see e.g. U.S. Pat. Nos. 7,998,469; 8,052,964; 4,832,959 U.S. Pat. No. 6,120,762; WO1992/008737; and EP219781.

In aspects of the provided 5T4 VHH-cytokine fusion proteins, the antibody and the cytokine, e.g. interferon, are attached directly or are attached indirectly via a linker, such as a peptide linker. The attachment can be to the N- or C-terminus of the VHH domain, so long as the attachment does not interfere with binding of the antibody to 5T4. Any linker, e.g. peptide linker, described herein can be used. In some embodiments, the linker is a GS-linker that comprises an amino acid sequence selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is (GGGGS)n, wherein n is 1 to 5 (SEQ ID NO: 123); (GGGGGS)n, wherein n is 1 to 4 (SEQ ID NO:124); GGGGS (SEQ ID NO:125); GGGGGS (SEQ ID NO: 126); GGGGGSGGGGGSGGGGGS (SEQ ID NO:127); GGGGSGGGGSGGGGS (SEQ ID NO: 128); GGSGGGGSGGGGSGGGGGS (SEQ ID NO:129). In some embodiments, the linker is a flexible linker comprising Glycine residues, such as, by way of non-limiting example, GG, GGG, GGGG (SEQ ID NO: 5), GGGGG (SEQ ID NO: 6), GGGGGG (SEQ ID NO: 7), and PGGGG (SEQ ID NO: 327). In some embodiments, the fusion proteins can include a combination of a GS-linker and a Glycine linker.

D. Chimeric Receptors and Engineered Cells

Provided herein are chimeric antigen receptors (CARs) having an extracellular domain comprising one or more of the 5T4 VHH domains provided herein, such as any of the sequences of a 5T4 VHH domain provided herein. CAR constructs provided herein include an extracellular domain containing the one or more 5T4 VHH, a transmembrane domain and an intracellular signaling region. The one or more 5T4 VHH domain which form the antigen binding unit of the CAR "binds" or is "capable of binding", i.e. targets, 5T4 with sufficient affinity such the CAR is useful in therapy in targeting a cell or tissue expressing 5T4.

CARs are synthetic receptors typically containing an extracellular targeting/binding moiety that is associated with one or more signaling domains in a single fusion molecule, and that is expressed on the surface of a cell, such as a T cell. Thus, CARs combine antigen-specificity and T cell activating properties in a single fusion molecule. First generation CARs typically included the cytoplasmic region of the CD3zeta or Fc 1 receptor γ chain as their signaling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signalling domains of a costimulatory molecule, such as CD28, and CD3zeta, provide dual signalling to direct combined activating and co-stimulatory signals. Third generation CARs are more complex with three or more signaling domains (reviewed in Sadelain et al., Cancer Discovery (3), 388-398, 2013 and Dotti et al, Immuno. Rev, 257 (1), 1-36, 2014).

In some embodiments, a provided CAR contains at least one antigen binding domain comprising a 5T4 VHH domain that targets or is capable of specifically binding 5T4. In some embodiments, the CAR contains at least two antigen binding domains (where at least one comprises a 5T4 VHH domain) which target one or more antigen. In one embodiment, the antigen binding domain of a CAR comprises two or at least two 5T4 VHH domains that are specific for 5T4, thus providing a bivalent binding molecule. In one embodiment, the antigen binding domain comprises two or at least two 5T4 VHH domains that are specific for 5T4, but bind to different epitopes on said antigen. In such cases, the antigen binding domain comprises a first 5T4 VHH domain that binds to a first epitope of 5T4 and a second VHH domain that binds to a second epitope of 5T4. The epitopes may be overlapping. Thus, in some embodiments, the antigen binding domain is biparatopic and the CAR is a biparatopic CAR. In yet another embodiment, the antigen binding domain comprises two 5T4 VHH domains that are specific for 5T4 and bind to the same epitopes on 5T4.

The transmembrane domain of a CAR provided herein is a domain that typically crosses or is capable of crossing or spanning the plasma membrane and is connected, directly or indirectly (e.g. via a spacer, such as an immunoglobulin hinge sequence) to the extracellular antigen binding domain and the endoplasmic portion containing the intracellular signaling domain. In one embodiment, the transmembrane domain of the CAR is a transmembrane region of a transmembrane protein (for example Type I transmembrane proteins), an artificial hydrophobic sequence or a combination thereof. In one embodiment, the transmembrane domain comprises the CD3zeta domain or CD28 transmembrane domain. Other transmembrane domains will be apparent to those of skill in the art and may be used in connection with embodiments of a CAR provided herein.

The intracellular signaling region of a CAR provided herein contains one or more intracellular signaling domain that transmits a signal to a T cell upon engagement of the antigen binding domain of the CAR, such as upon binding antigen. In some embodiments, the intracellular region contains an intracellular signaling domain that is or contains an ITAM signaling domain. Exemplary intracellular signaling domains include, for example, a signaling domain derived from ζ chain of the T-cell receptor complex or any of its homologs (e.g., n chain, FesRIy and β chains, MB 1 (Iga) chain, B29 (Ig) chain, etc.), human CD3zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5, OX40 and CD28. In particular embodiments, the intracellular signaling region contains an intracellular signaling domain derived from the human CD3 zeta chain.

In some embodiments, the endodomain comprises at CD3-zeta signaling domain. In some embodiments, the CD3-zeta signaling domain comprises the sequence of amino acids set forth in SEQ ID NO: 236 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 236 and retains the activity of T cell signaling.

In some embodiments, the intracellular signaling region of a CAR can further contain an intracellular signaling domain derived from a costimulatory molecule. In such examples, such a signaling domain may enhance CAR-T cell activity, such as via enhancement of proliferation, survival and/or development of memory cells, after antigen specific engagement, for example, compared to a CAR that only contains an ITAM containing signaling domain, e.g. CD3 zeta. In some embodiments, the co-stimulatory domain is a functional signaling domain obtained from a protein selected from: CD28, CD137 (4-IBB), CD134 (OX40), DapIO, CD27, CD2, CD5, ICAM-1, LFA-1 (CD1 la/CD18), Lck, TNFR-I, TNFR-II, Fas, CD30, CD40 or combinations thereof. In particular embodiments, the costimulatory signaling domain is derived or obtained from a human protein. In some aspects, the costimulatory signaling domain is derived or obtained from human CD28 or human CD137 (4-IBB).

In some embodiments, the costimulatory signaling domain is a derived from CD28 or 4-1BB and comprises the sequence of amino acids set forth in any of SEQ ID NOS: 237-240 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 237-240 and retains the activity of T cell costimulatory signaling.

In particular embodiments, the CAR further comprises a hinge or spacer region which connects the extracellular antigen binding domain and the transmembrane domain. This hinge or spacer region can be used to achieve different lengths and flexibility of the resulting CAR. Examples of the hinge or spacer region that can be used include, but are not limited to, Fc fragments of antibodies or fragments or derivatives thereof, hinge regions of antibodies, or fragments or derivatives thereof, $C_H2$ regions of antibodies, $C_H3$ regions of antibodies, artificial spacer sequences, for example peptide sequences, or combinations thereof. Other hinge or spacer region will be apparent to those of skill in the art and may be used. In one embodiment, the hinge is an IgG4 hinge or a CD8A hinge.

In some embodiments, the spacer and transmembrane domain are the hinge and transmembrane domain derived from CD8, such as having an exemplary sequence set forth in SEQ ID NO: 241-243 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 241-243.

Also provided herein is an isolated nucleic acid construct comprising at least one nucleic acid encoding a CAR as provided herein. In some aspects, the construct is an expression vector for expression of the CAR in a cell. The expression vector may be a viral vector. Viral vector technology is well known in the art and is described, for example, in Sambrook et al. (Molecular Cloning: A Laboratory Manual, Cold Spring Harbor Laboratory, New York, 2013). A number of viral based systems have been developed for gene transfer into mammalian cells. For example, retroviruses such as, adenovirus vectors are used. In one embodiment, a lentivirus vector is used.

In a further aspect, also provided is an isolated cell or cell population comprising one or more nucleic acid construct as described above. Also provided is an isolated cell or cell population that has been genetically modified to express a CAR provided herein. Thus, provided herein are genetically engineered cells which comprise, such as stably express, a CAR provided herein. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. In some cases, the cell is a T cell, such as a CD4 and/or CD8 T cell. In some embodiments, the cells are autologous to the subject. For example, in some embodiments, T cells may be isolated from a patient (also called primary T cells) for engineering, e.g. transfection or transduction, with a CAR nucleic acid construct.

In an exemplary example, primary T-cells can be purified ex vivo (CD4 cells or CD8 cells or both) and stimulated with a TCR/CD28 agonists, such as anti-CD3/anti-CD28 coated beads. After a 2 or 3 day activation process, a recombinant expression vector encoding the CAR can be stably introduced into the primary T cells through standard lentiviral or retroviral transduction protocols or plasmid electroporation strategies. Cells can be monitored for CAR expression by, for example, flow cytometry using anti-epitope tag or antibodies that cross-react with native parental molecule. T-cells that express the CAR can be enriched through sorting with anti-epitope tag antibodies or enriched for high or low expression depending on the application.

The CAR engineered T-cells can be assayed for appropriate function by a variety of means. In some cases, in vitro cytotoxicity, proliferation, or cytokine assays (e.g., IFN-gamma expression) can be used to assess the function of engineered T-cells. Exemplary standard endpoints are percent lysis of a tumor line, proliferation of the engineered T-cell, or IFN-gamma protein expression in culture supernatant. In some cases, the ability to stimulate activation of T cells upon stimulation of the CAR, e.g. via antigen, can be assessed, such as by monitoring expression of activation markers such as CD69, CD44, or CD62L, proliferation and/or cytokine production.

Also provided herein are methods for the prevention and/or treatment of a disease or condition in a subject, such as a cancer, that includes administering to a subject engineered cells comprising a CAR provided herein. Generally, the subject is in need of treatment for the disease or condition. pharmaceutically active amount of a cell and/or of a pharmaceutical composition of the invention.

IV. POLYPEPTIDE EXPRESSION AND PRODUCTION

Nucleic acid molecules comprising polynucleotides that encode any of the provided sdAb and 5T4-binding polypeptides are provided. In some embodiments, the provided nucleic acid sequences and particularly DNA sequences encode fusion proteins as provided herein. In any of the foregoing embodiments, the nucleic acid molecule may also encode a leader sequence that directs secretion of the 5T4-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the 5T4-binding polypeptides described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., *Biotechnol. Prog.* 20:880-889 (2004).

In particular, a DNA vector that encodes a desired 5T4-binding polypeptides, such as a fusion protein, can be used to facilitate the methods of preparing the 5T4-binding polypeptides described herein and to obtain significant quantities. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used.

The disclosure also provides methods of producing a 5T4-binding polypeptides by culturing a cell under conditions that lead to expression of the polypeptide, wherein the cell comprises an isolated nucleic acid molecule encoding a 5T4-binding polypeptide described herein, and/or vectors that include these isolated nucleic acid sequences.

In some embodiments, a 5T4-binding polypeptide may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the 5T4-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses a 5T4-binding polypeptide described herein is provided. The 5T4-binding polypeptides expressed in host cells can be purified by any suitable method. Such methods include, but are not limited to, the use of affinity matrices or hydrophobic interaction chromatography. Suitable affinity ligands include the RORI ECD and agents that bind Fc regions. For example, a Protein A, Protein G, Protein A/G, or an antibody affinity column may be used to bind the Fc region and to purify a 5T4-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the 5T4-binding polypeptide is produced in a cell-free system. Nonlimiting exemplary cell-free systems are described, for example, in Sitaraman et al., *Methods Mol. Biol.* 498:229-44 (2009); Spirin, *Trends Biotechnol.* 22:538-45 (2004); Endo et al., *Biotechnol. Adv.* 21:695-713 (2003).

In some embodiments, 5T4-binding polypeptides prepared by the methods described above are provided. In some embodiments, the 5T4-binding polypeptide is prepared in a host cell. In some embodiments, the 5T4-binding polypeptide is prepared in a cell-free system. In some embodiments, the 5T4-binding polypeptide is purified. In some embodiments, a cell culture media comprising a 5T4-binding polypeptide is provided.

In some embodiments, compositions comprising antibodies prepared by the methods described above are provided. In some embodiments, the composition comprises a 5T4-binding polypeptide prepared in a host cell. In some embodiments, the composition comprises a 5T4-binding polypeptide prepared in a cell-free system. In some embodiments, the composition comprises a purified 5T4-binding polypeptide.

V. PHARMACEUTICAL COMPOSITIONS AND FORMULATIONS

Provided herein are pharmaceutical compositions containing any of the 5T4-binding polypeptides provided herein or engineered cells expressing the same. In some embodiments, 5T4-binding polypeptides, such as fusion proteins of the disclosure (also referred to herein as "active compounds"), and derivatives, fragments, analogs and homologs thereof, can be incorporated into pharmaceutical compositions suitable for administration. In some embodiments, engineered cells expressing a chimeric receptor, such as a chimeric antigen receptor, containing a 5T4-binding polypeptide provided herein can be incorporated into pharmaceutical compositions suitable for administration.

Such compositions typically contain a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intratumoral, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration. These pharmaceutical compositions can be included in diagnostic kits with instructions for use.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, the pharmaceutical composition may be administered in an amount in the range of about 50 μg/kg body weight to about 50 mg/kg body weight per dose. In some embodiments, the pharmaceutical composition may be administered in an amount in the range of about 100 μg/kg body weight to about 50 mg/kg body weight per dose. In some embodiments, the pharmaceutical composition may be administered in an amount in the range of about 100 μg/kg body weight to about 20 mg/kg body weight per dose. In some embodiments, the pharmaceutical composition may be administered in an amount in the range of about 0.5 mg/kg body weight to about 20 mg/kg body weight per dose.

In some embodiments, the pharmaceutical composition may be administered in an amount in the range of about 10 mg to about 1,000 mg per dose. In some embodiments, the pharmaceutical composition may be administered in an amount in the range of about 20 mg to about 500 mg per dose. In some embodiments, the pharmaceutical composition may be administered in an amount in the range of about 20 mg to about 300 mg per dose. In some embodiments, the pharmaceutical composition may be administered in an amount in the range of about 20 mg to about 200 mg per dose.

The pharmaceutical composition may be administered as needed to subjects. In some embodiments, an effective dose of the pharmaceutical composition is administered to a subject one or more times. In various embodiments, an effective dose of the pharmaceutical composition is administered to the subject once a month, less than once a month, such as, for example, every two months, every three months, or every six months. In other embodiments, an effective dose of the pharmaceutical composition is administered more than once a month, such as, for example, every two weeks, every week, twice per week, three times per week, daily, or multiple times per day. An effective dose of the pharmaceutical composition is administered to the subject at least once. In some embodiments, the effective dose of the pharmaceutical composition may be administered multiple times, including for periods of at least a month, at least six months, or at least a year. In some embodiments, the pharmaceutical composition is administered to a subject as-needed to alleviate one or more symptoms of a condition.

VI. METHODS OF TREATMENT AND USES

The 5T4-binding polypeptides or engineered cells expressing the same described herein are useful in a variety of therapeutic, diagnostic and prophylactic indications. For example, the 5T4-binding polypeptides or engineered cells are useful in treating a variety of diseases and disorders in a subject. Such methods and uses include therapeutic methods and uses, for example, involving administration of the molecules or engineered cells, or compositions containing the same, to a subject having a disease, condition, or disorder, such as a tumor or cancer. In some embodiments, the molecule ore engineered cell is administered in an effective amount to effect treatment of the disease or disorder. Uses include uses of molecules containing the 5T4-binding polypeptides or engineered cells in such methods and treatments, and in the preparation of a medicament in order to carry out such therapeutic methods. In some embodiments, the methods are carried out by administering the 5T4-binding polypeptides or engineered cells, or compositions comprising the same, to the subject having or suspected of having the disease or condition. In some embodiments, the methods thereby treat the disease or condition or disorder in the subject.

In one embodiment, a 5T4-binding polypeptide or engineered cell of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. In some cases, a subject is selected that is known, suspected or that has been identified as having a tumor expressing 5T4. A 5T4-binding polypeptide or engineered cell is administered to the subject. A 5T4-binding polypeptide or engineered cell is administered to the subject and will generally have an effect due to its binding with the target(s).

In some embodiments, a provided 5T4 polypeptide multispecific polypeptide construct or engineered cell is capable of modulating, e.g. increasing, an immune response when administered to a subject, such as by engagement of CD3 and/or a CD3 signal in a cell. In some embodiments, provided herein is a method of modulating an immune response in a subject by administering a therapeutically effective amount of a provided multispecific construction or engineered cell, or pharmaceutical compositions thereof. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

In some embodiments, administration of a 5T4-binding polypeptide, such as an 5T4-Fc fusion protein or a multispecific construction containing an Fc region, may activate innate immune cells via engagement of FcγRs through the Fc-region of the multispecific polypeptide construct. Administration of such multispecific polypeptide constructs may agonize, stimulate, activate, and/or augment innate immune cell effector functions, including ADCC, cytokine release, degranulation and/or ADCP. In the case of a constrained multispecific polypeptide construct, administration of such multispecific polypeptide constructs may activate T-cells once the linker(s) joining the first and second component is cleaved by a protease and/or upon binding of 5T4 on a target cell (e.g. tumor cell), thereby allowing the anti-CD3 binding portion to bind CD3ε on the T cells. In some cases, administration of the multispecific polypeptide constructs may agonize, stimulate, activate, and/or augment CD3-mediated T cell activation, cytotoxicity, cytokine release and/or proliferation.

In some embodiments, the provided methods are for treating a disease or condition in a subject by administering a therapeutically effective amount of any of the provided 5T4-binding polypeptides or engineered cells or pharmaceutical compositions thereof. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the 5T4-binding polypeptides or engineered cells, or pharmaceutical compositions thereof, can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

In some embodiments, the 5T4-binding polypeptides or engineered cells, or pharmaceutical compositions thereof, or are useful in treating, alleviating a symptom of, ameliorating and/or delaying the progression of a cancer or other neoplastic condition. In some embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In some embodiments, a therapeutically effective amount of a 5T4-binding polypeptide, such as a fusion protein or multispecific polypeptide construct, of the disclosure relates generally to the amount needed to achieve a therapeutic objective. Typically, precise amount of the compositions of the present disclosure to be administered can be determined by a physician with consideration of individual differences in age, weight, tumor size, extent of infection or metastasis, and condition of the patient (subject).

In some embodiments, a therapeutically effective dose may be, by way of nonlimiting example, from about 0.01 µg/kg body weight to about 10 mg/kg body weight. In some embodiments, the therapeutically effective dose may be, by way of nonlimiting example, from about 0.01 mg/kg body weight to about 5-10 mg/kg body weight. Common dosing frequencies may range, for example, from twice daily to once a week.

In some embodiments, a therapeutic amount of an engineered cell composition of the present disclosure is administered. It can generally be stated that a pharmaceutical composition comprising engineered cells, e.g., T cells, as described herein may be administered at a dosage of $10^4$ to $10^9$ cells/kg body weight, such as $10^5$ to $10^6$ cells/kg body weight, including all integer values within those ranges. Engineered cell compositions, such as T cell compositions, may also be administered multiple times at these dosages. The cells can be administered by using infusion techniques that are commonly known in immunotherapy (see, e.g., Rosenberg et al, New Eng. J. of Med. 319:1676, 1988). The optimal dosage and treatment regime for a particular patient can readily be determined by one skilled in the art of medicine by monitoring the patient for signs of disease and adjusting the treatment accordingly.

Efficaciousness of treatment is determined in association with any known method for diagnosing or treating the particular disorder. Methods for the screening of 5T4-binding polypeptides, or engineered cells containing the same, that possess the desired specificity include, but are not limited to, enzyme linked immunosorbent assay (ELISA) and other immunologically mediated techniques known within the art. A variety of means are known for determining if administration of the provided 5T4-binding polypeptides or engineered cells sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The provided 5T4-binding polypeptides are also useful in a variety of diagnostic and prophylactic formulations. In one embodiment, a 5T4-binding polypeptide is administered to patients that are at risk of developing one or more of the aforementioned disorders. A patient's or organ's predisposition to one or more of the disorders can be determined using genotypic, serological or biochemical markers.

In another embodiment of the disclosure, a 5T4-binding polypeptide or engineered cell is administered to human individuals diagnosed with a clinical indication associated with one or more of the aforementioned disorders. Upon diagnosis, such a therapeutic agent is administered to mitigate or reverse the effects of the clinical indication.

Combination Therapy

5T4-binding polypeptides or engineered cells of the present disclosure can be administered alone or in combination with other modes of treatment, such as other anti-cancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, a 5T4-binding polypeptide provided herein is given concurrently with one or more chemotherapeutic agent, CAR-T (chimeric antigen receptor T-cell) therapy, oncolytic virus therapy, cytokine therapy, and/or agents that target other checkpoint molecules, such as VISTA, gpNMB, B7H4, HHLA2, CD73, CTLA4, TIGIT, etc.

In some embodiments, the 5T4-binding polypeptide or engineered cells of the present disclosure is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, a 5T4-binding polypeptide or engineered cell provided herein is given concurrently with a PD-1/PD-L1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, the 5T4-binding polypeptide or engineered cell of the present disclosure may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., *Agnew, Chem Intl. Ed. Engl.,* 33:183-186 (1994)); dynemicin, including dynemicin A; bisphosphonates, such as clodronate; an esperamicin; as well as neocarzinostatin chromophore and related chromoprotein enediyne antiobiotic chromophores), aclacino-mysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubi-cin), epirubicin, esorubicin, idarubicin, marcellomycin, mitomycins such as mitomycin C, mycophenolic acid, nogalamycin, olivomycins, peplomycin, potfiromycin, puro-mycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercap-topurine, thiamiprine, thioguanine; pyrimidine analogs such as ancitabine, azacitidine, 6-azauridine, carmofur, cytara-bine, dideoxyuridine, doxifluridine, enocitabine, floxuri-dine; androgens such as calusterone, dromostanolone pro-pionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; len-tinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenu-azonic acid; triaziquone; 2,2',2''-trichlorotriethylamine; tri-chothecenes (especially T-2 toxin, verracurin A, roridin A and anguidine); urethan; vindesine; dacarbazine; manno-mustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of pacli-taxel (American Pharmaceutical Partners, Schaumberg, Illi-nois), and TAXOTERE® doxetaxel (Rhône-Poulenc Rorer, Antony, France); chloranbucil; GEMZAR® gemcitabine; 6-thioguanine; mercaptopurine; methotrexate; platinum ana-logs such as cisplatin, oxaliplatin and carboplatin; vinblas-tine; platinum; etoposide (VP-16); ifosfamide; mitoxan-trone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; com-bretastatin; leucovorin (LV); oxaliplatin, including the oxa-liplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selec-tive estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adre-nal glands, such as, for example, 4 (5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligo-nucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vac-cine, and VAXID® vaccine; PROLEUKIN® (aldesleukin) rIL-2; LURTOTECAN® topoisomerase 1 inhibitor; ABARELIX® GnRH agoninst; and pharmaceutically acceptable salts, acids or derivatives of any of the above.

In some embodiments, the 5T4-binding polypeptide and the additional agent are formulated into a single therapeutic composition, and the 5T4-binding polypeptide and addi-tional agent are administered simultaneously. Alternatively, the 5T4-binding polypeptide or engineered cell and the additional agent are separate from each other, e.g., each is formulated into a separate therapeutic composition, and the 5T4-binding polypeptide or engineered cell and the addi-tional agent are administered simultaneously, or the 5T4-binding polypeptide or engineered cell and the additional agent are administered at different times during a treatment regimen. For example, the 5T4-binding polypeptide or engi-neered cell is administered prior to the administration of the additional agent, the 5T4-binding polypeptide or engineered cell is administered subsequent to the administration of the additional agent, or the 5T4-binding polypeptide or engi-neered cell and the additional agent are administered in an alternating fashion. The 5T4-binding polypeptide and addi-tional agent may be administered in single doses or in multiple doses.

In some embodiments, the 5T4-binding polypeptide or engineered cell and the additional agent(s) are administered simultaneously. For example, the 5T4-binding polypeptide and the additional agent(s) can be formulated in a single composition or administered as two or more separate com-positions. In some embodiments, the 5T4-binding polypep-tide or engineered cell and the additional agent(s) are administered sequentially, or the 5T4-binding polypeptide or engineered cell and the additional agent are administered at different times during a treatment regimen.

VII. EXEMPLARY EMBODIMENTS

Among the provided embodiments are:

1. A 5T4-binding polypeptide construct, comprising at least one heavy chain only variable domain (5T4 VHH domain) that specifically binds 5T4 and one or more addi-tional binding domain that binds to a target other than 5T4.

2. The 5T4-binding polypeptide construct of embodiment 1, wherein the at least one 5T4 VHH domain comprises a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303.

3. A 5T4-binding polypeptide construct, comprising at least one heavy chain only variable domain (5T4 VHH domain) comprising a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303.

4. The 5T4-binding polypeptide construct of any of embodiments 1-3, wherein the 5T4 is a human 5T4.

5. The 5T4-binding polypeptide construct of any of embodiments 1-4, wherein the at least one 5T4 VHH domain is humanized.

6. The 5T4-binding polypeptide construct of any of embodiments 1, 2, 4 and 5, wherein the one or more additional binding domains binds to an activating receptor on an immune cell.

7. The 5T4-binding polypeptide construct of embodiment 6, wherein the immune cell is a T cell.

8. The 5T4-binding polypeptide construct of embodiment 6 or embodiment 7, wherein the activating receptor is CD3 (CD3ε).

9. The 5T4-binding polypeptide construct of embodiment 8 that is bispecific for 5T4 and CD3.

10. The 5T4-binding polypeptide construct of embodiment 6, wherein the immune cell is a Natural Killer (NK) cell.

11. The 5T4-binding polypeptide construct of embodiment 6 or embodiment 10, wherein the activating receptor is CD16 (CD16a).

12. The 5T4-binding polypeptide construct of embodiment 11 that is bispecific for 5T4 and CD16a.

13. The 5T4-binding polypeptide construct of any of embodiments 1, 2, 4 and 5, wherein the one or more additional binding domain binds to a cytokine receptor.

14. The 5T4-binding polypeptide construct of any of embodiments 1, 2 and 4-13, wherein the one or more additional binding domain comprises an antibody or antigen-binding fragment thereof.

15. The 5T4-binding polypeptide construct of any of embodiments 1, 2 and 4-14, wherein the one or more additional binding domain is monovalent.

16. The 5T4-binding polypeptide construct of embodiment 14 or embodiment 15, wherein the antibody or antigen-binding fragment thereof is an Fv, a disulfide-stabilized Fv (dsFv), scFv, a Fab, a single domain antibody (sdAb).

17. The 5T4-binding polypeptide construct of embodiment 13, wherein the one or more additional binding domain is a cytokine or is a truncated fragment or variant thereof capable of binding to the cytokine receptor.

18. The 5T4-binding polypeptide construct of embodiment 17, wherein the cytokine is an interferon, or is a truncated fragment or variant of thereof.

19. The 5T4-binding polypeptide construct of embodiment 18, wherein the interferon is a type I interferon or a type II interferon, is a truncated fragment or variant of a type I interferon or is a truncated fragment or variant of a type II interferon.

20. The 5T4-binding polypeptide construct of embodiment 19, wherein:
   the type I interferon is an IFN-alpha or an IFN-beta or is a truncated fragment or variant thereof; or
   the type II interferon is an IFN-gamma or is a truncated fragment or variant thereof.

21. The 5T4-binding polypeptide construct of any of embodiments 1-20, wherein the polypeptide construct comprises an immunoglobulin Fc region.

22. The 5T4-binding polypeptide construct of any of embodiments 1, 2 and 4-21, wherein the polypeptide comprises an immunoglobulin Fc region that links the at least one 5T4 VHH domain and the one or more additional binding domain.

23. The 5T4-binding polypeptide construct of any of embodiments 1-22 that is a dimer.

24. The 5T4-binding polypeptide construct of any of embodiments 21-23, wherein the Fc region is a homodimeric Fc region.

25. The 5T4-binding polypeptide construct of any of embodiments 21-24, wherein the Fc region comprises the sequence of amino acids set forth in any of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 or 13.

26. The 5T4-binding polypeptide construct of any of embodiments 21-25, wherein the Fc region is a human IgG1.

27. The 5T4-binding polypeptide construct of embodiment 26, wherein the Fc region comprises the sequence of amino acids set forth in SEQ ID NO:8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

28. The 5T4-binding polypeptide construct of any of embodiments 21-23, wherein the Fc region is a heterodimeric Fc region.

29. The 5T4-binding polypeptide construct of any of embodiments 21-28, wherein the Fc region exhibits effector function.

30. The 5T4-binding polypeptide construct of any of embodiments 21-29, wherein the Fc region comprises a polypeptide comprising one or more amino acid modification that reduces effector function and/or reduces binding to an effector molecule selected from an Fc gamma receptor or C1q.

31. The 5T4-binding polypeptide construct of embodiment 30, wherein the one or more amino acid modification is deletion of one or more of Glu233, Leu234 or Leu235.

32. The 5T4-binding polypeptide construct of embodiment 30 or embodiment 31, wherein the Fc region comprises the sequence of amino acids set forth in SEQ ID NO:9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

33. The 5T4-binding polypeptide construct of any of embodiments 1-32, wherein the at least one 5T4 VHH domain comprises the sequence set forth in any of SEQ ID NOS: 245-253, 255-287, 294, 295, 302, and 360 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-253, 255-287, 294, 295, 302, and 360 and binds 5T4.

34. The 5T4-binding polypeptide construct of any of embodiments 1-33, wherein the at least one 5T4 VHH domain binds to an epitope in human 5T4 but does not exhibit crossreactive binding to mouse 5T4.

35. The 5T4-binding polypeptide construct of any of embodiments 1-34, wherein the at least one 5T4 VHH domain binds to amino acid residues between amino acids 60 and 112 of SEQ ID NO:382.

36. The 5T4-binding polypeptide construct of any of embodiments 1-35, wherein the at least one 5T4 VHH domain binds to amino acid residues between amino acids 173 and 224 of SEQ ID NO: 382.

37. The 5T4-binding polypeptide construct of any of embodiments 1-36, wherein the at least one 5T4 VHH domain comprises the sequence set forth in (i) SEQ ID NO:245, (ii) a humanized variant of SEQ ID NO:245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:245 and binds 5T4.

38. The 5T4-binding polypeptide construct of any of embodiments 1-37, wherein the at least one 5T4 VHH domain comprises a CDR1 comprising an amino acid sequence selected from the group consisting of SEQ ID NO: 288 and 289; a CDR2 comprising an amino acid sequence set forth in SEQ ID NO: 88; and a CDR3 comprising an amino acid sequence set forth in SEQ ID NO: 100.

39. The 5T4-binding polypeptide construct of any of embodiments 1-38, wherein the at least one 5T4 VHH domain comprises a CDR1, CDR2 and CDR3 set forth in SEQ ID NOS: 288, 88, and 100, respectively; or SEQ ID NOS: 289, 88, and 100, respectively.

40. The 5T4-binding polypeptide construct of any of embodiments 1-39, wherein the at least one 5T4 VHH domain comprises the sequence of amino acids set forth in any one of SEQ ID NOs: 246-253 and 360 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 246-253 and 360 and binds 5T4.

41. The 5T4-binding polypeptide construct of embodiments 1-40, wherein the at least one 5T4 VHH domain comprises the sequence of amino acids set forth in any one of SEQ ID NOS: 246-253 and 360.

42. The 5T4-binding polypeptide construct of any of embodiments 1-36, wherein the at least one 5T4 VHH domain comprises the sequence set forth in (i) SEQ ID NO:255, (ii) a humanized variant of SEQ ID NO: 255, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255 and binds 5T4.

43. The 5T4-binding polypeptide construct of any of embodiments 1-36 and 42, wherein the at least one 5T4 VHH domain comprises a CDR1 comprising an amino acid sequence selected from the group consisting of SEQ ID NOS: 86, 290-292; a CDR2 comprising an amino acid sequence selected from the group consisting of SEQ ID NO: 89-94; and a CDR3 comprising an amino acid sequence set forth in SEQ ID NO: 101.

44. The 5T4-binding polypeptide construct of any of embodiments 1-36, 42 and 43, wherein the at least one 5T4 VHH domain comprises a CDR1, CDR2 and CDR3 set forth in SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively.

45. The 5T4-binding polypeptide construct of any of embodiments 1-36 and 42-44, wherein the at least one 5T4 VHH domain comprises the sequence of amino acids set forth in any one of SEQ ID NOs: 256-275 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256-275 and binds 5T4.

46. The 5T4-binding polypeptide construct of embodiments 1-36 and 43-45, wherein the at least one 5T4 VHH domain comprises the sequence of amino acids set forth in any one of SEQ ID NOS: 256-275.

47. The 5T4-binding polypeptide construct of any of embodiments 1-36, wherein the at least one 5T4 VHH domain comprises the sequence set forth in (i) SEQ ID NO:276 (ii) a humanized variant of SEQ ID NO: 276, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 276 and binds 5T4.

48. The 5T4-binding polypeptide construct of any of embodiments 1-33 and 47, wherein the at least one 5T4 VHH domain comprises a CDR1 comprising an amino acid sequence selected from the group consisting of SEQ ID NOS: 86 and 87; a CDR2 comprising an amino acid sequence selected from the group consisting of SEQ ID NOS: 95-99; and a CDR3 comprising an amino acid sequence set forth in SEQ ID NO: 102.

49. The 5T4-binding polypeptide construct of any of embodiments 1-36, 47 and 48, wherein the at least one 5T4 VHH domain comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

50. The 5T4-binding polypeptide construct of any of embodiments 1-36 and 47-49, wherein the at least one 5T4 VHH domain comprises the sequence of amino acids set forth in any one of SEQ ID NOs: 277-287 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 277-287 and binds 5T4.

51. The 5T4-binding polypeptide construct of embodiments 1-36 and 47-50, wherein the at least one 5T4 VHH domain comprises the sequence of amino acids set forth in any one of SEQ ID NOS: 277-287.

52. The 5T4-binding polypeptide construct of any of embodiments 1-36, wherein the at least one 5T4 VHH domain comprises the sequence set forth in (i) SEQ ID NO:294 (ii) a humanized variant of SEQ ID NO:294, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:294 and binds 5T4.

53. The 5T4-binding polypeptide construct of any of embodiments 1-36 and 52, wherein the at least one 5T4 VHH domain comprises a CDR1 comprising an amino acid sequence set forth in SEQ ID NO: 296; a CDR2 comprising an amino acid sequence set forth in SEQ ID NO: 298; and a CDR3 comprising an amino acid sequence set forth in SEQ ID NO: 300.

54. The 5T4-binding polypeptide construct of any of embodiments 1-36 and 52, wherein the at least one 5T4 VHH domain comprises a CDR3 comprising an amino acid sequence selected from the group consisting of SEQ ID NOS: 300, 301, and 303.

55. The 5T4-binding polypeptide construct of any of embodiments 1-36 and 52, wherein the at least one 5T4 VHH domain comprises:

a CDR1 comprising an amino acid sequence selected from the group consisting of SEQ ID NOS: 288, 296, and 297; and/or a CDR2 comprising an amino acid sequence selected from the group consisting of SEQ ID NOS: 88, 298, and 299.

56. The 5T4-binding polypeptide construct of any of embodiments 1-36, wherein the at least one 5T4 VHH domain comprises the sequence set forth in (i) SEQ ID NO:295 (ii) a humanized variant of SEQ ID NO:295, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:295 and binds 5T4.

57. The 5T4-binding polypeptide construct of any of embodiments 1-36 and 56, wherein the at least one 5T4 VHH domain comprises a CDR1 comprising an amino acid sequence set forth in SEQ ID NO: 297; a CDR2 comprising an amino acid sequence set forth in SEQ ID NO: 299; and a CDR3 comprising an amino acid sequence set forth in SEQ ID NO: 301.

58. The 5T4-binding polypeptide construct of any of embodiments 1-36, wherein the at least one 5T4 VHH domain comprises the sequence set forth in (i) SEQ ID NO:302 (ii) a humanized variant of SEQ ID NO: 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 302 and binds 5T4.

59. The 5T4-binding polypeptide construct of any of embodiments 1-36 and 56, wherein the at least one 5T4 VHH domain comprises a CDR1 comprising an amino acid sequence set forth in SEQ ID NO: 288; a CDR2 comprising an amino acid sequence set forth in SEQ ID NO: 88; and a CDR3 comprising an amino acid sequence set forth in SEQ ID NO: 303.

60. The 5T4-binding polypeptide construct of any of embodiments 1-36, wherein the at least one 5T4 VHH domain comprises the sequence set forth in (i) SEQ ID NO:294, 295, or 302 (ii) a humanized variant of SEQ ID NO: 294, 295, or 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, 295, or 302 and binds 5T4.

61. The 5T4-binding polypeptide construct of any of embodiments 1-36 and 60, wherein the at least one 5T4 VHH domain comprises a CDR1, CDR2 and CDR3 set forth in SEQ ID NOS: 296, 298, and 300, respectively; SEQ ID NOS: 297, 299, and 301, respectively; or SEQ ID NOS: 288, 88, and 303, respectively.

62. The 5T4-binding polypeptide construct of any of embodiments 1-36, 60 and 61, wherein the at least one 5T4 VHH domain is set forth in SEQ ID NO:245, 249, 255, 270, 276, 294, 295 or 302.

63. A multispecific polypeptide construct, comprising: (a) a first component comprising a heterodimeric Fc region comprising a first Fc polypeptide and a second Fc polypeptide and (b) a second component comprising an anti-CD3 antibody or antigen-binding fragment comprising a variable heavy chain region (VH) and a variable light chain region (VL), wherein:

the VH and VL that comprise the anti-CD3 antibody or antigen binding fragment are linked to opposite polypeptides of the heterodimeric Fc;

the first and second components are coupled by a linker, wherein the heterodimeric Fc region is positioned N-terminal to the anti-CD3 antibody; and one or both of the first and second components comprises at least one heavy chain only variable domain (5T4 VHH domain).

64. The multispecific polypeptide construct of embodiment 63, wherein the multispecific polypeptide construct comprises at least (i) a first polypeptide comprising the first Fc polypeptide of the heterodimeric Fc region, the linker and the VH or VL domain of the anti-CD3 antibody or antigen binding fragment; and (ii) a second polypeptide comprising the second Fc polypeptide of the heterodimeric Fc region, the linker, optionally the same linker as present in the first polypeptide, and the other of the VH or VL domain of the anti-CD3 antibody or antigen binding fragment, wherein one or both of the first and second polypeptide comprise the at least one 5T4 VHH domain.

65. The multispecific polypeptide construct of embodiment 63 or embodiment 64, wherein one or both of the first and second Fc polypeptides of the heterodimeric Fc region comprises at least one modification to induce heterodimerization compared to a polypeptide of a homodimeric Fc region, optionally compared to the Fc polypeptide set forth in SEQ ID NO: 8 or an immunologically active fragment thereof.

66. The multispecific polypeptide construct of embodiment 65, wherein each of the first and second Fc polypeptides of the heterodimeric Fc region independently comprise at least one amino acid modification.

67. The multispecific polypeptide construct of embodiment 65 or 66, wherein each of the first and second Fc polypeptides of the heterodimeric Fc region comprise a knob-into-hole modification or comprise a charge mutation to increase electrostatic complementarity of the polypeptides.

68. The multispecific polypeptide construct of embodiment 65-67, wherein the amino acid modification is a knob-into-hole modification.

69. The multispecific polypeptide construct of any of embodiments 63-68, wherein the first Fc polypeptide of the heterodimeric Fc region comprises the modification selected from among Thr366Ser, Leu368Ala, Tyr407Val, and combinations thereof and the second Fc polypeptide of the heterodimeric Fc region comprises the modification Thr366Trp.

70. The multispecific polypeptide of embodiment 69, wherein the first and second Fc polypeptides further comprise a modification of a non-cysteine residue to a cysteine residue, wherein the modification of the first Fc polypeptide is at one of the position Ser354 and Tyr349 and the modification of the second Fc polypeptide is at the other of the position Ser354 and Tyr349.

71. The multispecific polypeptide construct of any of embodiments 65-67, wherein the amino acid modification is a charge mutation to increase electrostatic complementarity of the polypeptides.

72. The multispecific polypeptide construct of any of embodiments 63-67 and 71, wherein the first and/or second Fc polypeptides or each of the first and second Fc polypeptide comprise an amino acid modification in complementary positions, wherein the modification is replacement with an amino acid having an opposite charge to the complementary amino acid of the other polypeptide.

73. The multispecific polypeptide construct of any of embodiments 63-72, wherein one of the first or second Fc polypeptide of the heterodimeric Fc region further comprises a modification at residue Ile253.

74. The multispecific polypeptide construct of embodiment 73, wherein the modification is Ile253Arg.

75. The multispecific polypeptide construct of any of embodiments 63-74, wherein one of the first or second Fc polypeptide of the heterodimeric Fc region further comprises a modification at residue His435.

76. The multispecific polypeptide construct of embodiment 75, wherein the modification is His435Arg.

77. The multispecific polypeptide construct of any of embodiments 63-76, wherein the Fc region comprises a polypeptide that lacks Lys447.

78. The multispecific polypeptide construct of any of embodiments 63-77, wherein the Fc region comprises a polypeptide comprising at least one modification to enhance FcRn binding.

79. The multispecific polypeptide construct of embodiment 78, wherein the at least one modification is at a position selected from the group consisting of Met252, Ser254, Thr256, Met428, Asn434, and combinations thereof.

80. The multispecific polypeptide construct of embodiment 78 or embodiment 79, wherein the at least one modification is selected from the group consisting of Met252Y, Ser254T, Thr256E, Met428L, Met428V, Asn434S, and combinations thereof.

81. The multispecific polypeptide construct of any of embodiments 78-80, wherein the at least one modification is at position Met252 and at position Met428.

82. The multispecific polypeptide construct of any of embodiments 78-81, wherein the at least one modification is Met252Y and Met428L.

83. The multispecific polypeptide construct of any of embodiments 78-81, wherein the at least one modification is Met252Y and Met428V.

84. The multispecific polypeptide construct of any of embodiments 63-83, wherein the first Fc polypeptide of the heterodimeric Fc region comprises the sequence of amino acids set forth in any of SEQ ID NOS: 103, 107, 115, 117, 328, or 334 and the second Fc polypeptide of the heterodimeric Fc region comprises the sequence of amino acids set forth in any of SEQ ID NOS: 104, 108, 111, 113, 119, 121, 329, 332, or 336.

85. The polypeptide construct of any of embodiments 21-84, wherein the Fc region comprises a polypeptide comprising at least one amino acid modification that reduces effector function and/or reduces binding to an effector molecule selected from an Fc gamma receptor and C1q.

86. The multispecific polypeptide construct of embodiment 85, wherein the at least one amino acid modification is deletion of one or more of Glu233, Leu234 and Leu235.

87. The multispecific polypeptide construct of any of embodiments 63-86, wherein the first Fc polypeptide of the heterodimeric Fc region comprises the sequence of amino acids set forth in any of SEQ ID NOS: 105, 109, 116, 118, 330, or 335 and the second Fc polypeptide of the heterodimeric Fc region comprises the sequence of amino acids set forth in any of SEQ ID NOS: 106, 110, 112, 114, 120, 122, 331, 333, or 337.

88. The multispecific polypeptide construct of any of embodiment 63-87, wherein the anti-CD3 antibody or antigen binding fragment is monovalent.

89. The multispecific polypeptide construct of any of embodiments 63-88, wherein the anti-CD3 antibody or antigen binding fragment is not a single chain antibody, optionally is not a single chain variable fragment (scFv).

90. The multispecific polypeptide construct of any of embodiments 63-89, wherein the anti-CD3 antibody or antigen binding fragment is an Fv antibody fragment.

91. The multispecific polypeptide construct of embodiment 90, wherein the Fv antibody fragment comprises a disulfide stabilized anti-CD3 binding Fv fragment (dsFv).

92. The multispecific polypeptide construct of 63-91, wherein the anti-CD3 antibody or antigen-binding fragment comprises a VH CDR1 comprising the amino acid sequence TYAMN (SEQ ID NO: 29); a VH CDR2 comprising the amino acid sequence RIRSKYNNYATYYADSVKD (SEQ ID NO: 30); a VH CDR3 comprising the amino acid sequence HGNFGNSYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34).

93. The multispecific polypeptide construct of any of embodiments 63-92, wherein the anti-CD3 antibody or antigen-binding fragment comprises:

a VH having the amino acid sequence of any of SEQ ID NOS: 27, 35-65, 341, 343, and 358 or a sequence that exhibits at least 90%, 91%, 92%, 93%, 94%, 95%, 96%, 97%, 98% or 99% sequence identity to any of SEQ ID NOS: 27, 35-65, 341, 343, and 358 and binds CD3; and a VL having the amino acid sequence of any of SEQ ID NOS: 28, 66-84, 293, 340, and 342 or a sequence that exhibits at least 90%, 91%, 92%, 93%, 94%, 95%, 96%, 97%, 98% or 99% sequence identity to any of SEQ ID NOS: 28, 66-84, 293, 340, and 342 and 293 and binds CD3.

94. The multispecific polypeptide construct of any of embodiments 63-93, wherein the anti-CD3 antibody or antigen-binding fragment comprises the amino acid sequence of SEQ ID NO: 47 and the amino acid sequence of SEQ ID NO: 75.

95. The multispecific polypeptide construct of any of embodiments 63-93, wherein the anti-CD3 antibody or antigen-binding fragment comprises the amino acid sequence of SEQ ID NO: 47 and the amino acid sequence of SEQ ID NO: 293.

96. The multispecific polypeptide construct of any of embodiment 63-92, wherein the at least one 5T4 VHH domain is positioned amino-terminally relative to the Fc region and/or carboxy-terminally relative to the CD3 binding region of the multispecific polypeptide construct.

97. The multispecific polypeptide construct of any of embodiments 63-96, wherein the multispecific polypeptide construct comprises a first 5T4 VHH domain that specifically binds 5T4 and a second 5T4 VHH domain that specifically binds 5T4.

98. The multispecific polypeptide construct of embodiment 97, wherein the first or second 5T4 VHH domain is positioned amino-terminally relative to the Fc region of the multispecific construct and the other of the first or second 5T4 VHH domain is positioned carboxy-terminally relative to the CD3 binding region of the multispecific construct.

99. The multispecific polypeptide construct of embodiment 97 or embodiment 98, wherein the first component comprises in order of N-terminus to C-terminus a first 5T4 VHH domain that binds 5T4, the first Fc polypeptide of the heterodimeric Fc region, the linker, the VH or VL domain of the anti-CD3 antibody or antigen binding fragment and a second 5T4 VHH domain that binds 5T4; and the second component comprises in order of N-terminus to C-terminus the second Fc polypeptide of the heterodimeric Fc region, the linker, optionally the same linker as present in the first component, and the other of the VH or VL domain of the anti-CD3 antibody or antigen binding fragment.

100. The multispecific polypeptide construct of any of embodiments 97-99, wherein the first and second 5T4 VHH domain are the same.

101. The multispecific polypeptide construct of any of embodiments 97-99, wherein the first and second 5T4 VHH domain are different.

102. The multispecific polypeptide construct of embodiment 101, wherein the first and second 5T4 VHH domain bind a distinct or non-overlapping epitope of 5T4 and/or do not compete for binding to 5T4.

103. The multispecific polypeptide construct of embodiment 102, wherein:

the first 5T4 VHH domain comprises the amino acid sequence set forth in any one of SEQ ID NOS: 245-253, 295, 302, and 360 a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-253, 295, 302, and 360 and binds 5T4; and the second 5T4 VHH domain comprises the amino acid sequence set forth in any one of SEQ ID NOS: 255-287, 294, 302, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 255-287, 294, 302, and binds 5T4.

104. The multispecific polypeptide construct of embodiment 102, wherein:

the first and second 5T4 VHH domains are selected from SEQ ID NO: 245 and SEQ ID NO: 294; SEQ ID NO: 245 and SEQ ID NO: 276; SEQ ID NO: 245 and SEQ ID NO: 255; SEQ ID NO:245 and SEQ ID NO:295; SEQ ID NO: 295 and SEQ ID NO: 294; SEQ ID NO: 249 and SEQ ID NO: 270; SEQ ID NO:302 and SEQ ID NO:302; or SEQ ID NO: 360 and SEQ ID NO: 287.

105. The multispecific polypeptide construct of any of embodiments 63-104, wherein the at least one 5T4 VHH domain, or each of the first and second 5T4 VHH domain, independently comprises the VHH domain sequence set forth in any of SEQ ID NOS: 245-253, 255-287, 294, 295, 302, and 360 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-253, 255-287, 294, 295, 302, and 360 and binds 5T4.

106. The multispecific polypeptide construct of any of embodiments 63-105, wherein the at least one 5T4 VHH domain binds to an epitope in human 5T4 but does not exhibit crossreactive binding to mouse 5T4.

107. The multispecific polypeptide construct of any of embodiments 63-106, wherein the at least one 5T4 VHH domain binds to amino acid residues between amino acids 60 and 112 of SEQ ID NO: 382.

108. The multispecific polypeptide construct of any of embodiments 63-107, wherein the at least one 5T4 VHH domain binds to amino acid residues between amino acids 173 and 224 of SEQ ID NO: 382.

109. The multispecific polypeptide construct of any of embodiments 63-108, wherein the at least one 5T4 VHH domain, or each of the first and second 5T4 VHH domain, independently comprises the sequence set forth in (i) SEQ ID NO: 245, (ii) a humanized variant of SEQ ID NO: 245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 245, and binds 5T4.

110. The multispecific polypeptide construct of any of embodiments 63-109, wherein the at least one 5T4 VHH domain, or each of the first and second 5T4 VHH domain, independently comprises a CDR1 comprising an amino acid sequence selected from the group consisting of SEQ ID NO: 86-87 and 288-292, 296, and 297; a CDR2 comprising an amino acid sequence selected from the group consisting of SEQ ID NO: 88-99, 298, and 299; and a CDR3 comprising an amino acid sequence selected from the group consisting of SEQ ID NO: 100-102, 300, 301, and 303.

111. The multispecific construct of any of embodiments 63-110, wherein the at least one 5T4 VHH domain, or each of the first and second 5T4 VHH domain, independently comprises a CDR1, CDR2 and CDR3 set forth in SEQ ID NOS: 288, 88, and 100, respectively; SEQ ID NOS: 289, 88, and 100, respectively; SEQ ID NOS: 290, 89, and 101, respectively; SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; SEQ ID NOS: 86, 94, and 101, respectively; SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; SEQ ID NOS: 86, 98, and 102, respectively; SEQ ID NOS: 296, 298, and 300, respectively; SEQ ID NOS: 297, 299, and 301, respectively; or SEQ ID NOS: 288, 88, and 303, respectively.

112. The multispecific polypeptide construct of any of embodiments 63-111, wherein the at least one 5T4 VHH domain, or each of the first and second 5T4 VHH domain, independently comprises the sequence of amino acids set forth in any one of SEQ ID NOS: 246-253 and 360 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NOS: 246-253 and 360, and binds 5T4.

113. The multispecific polypeptide construct of any of embodiments 63-112, wherein the at least one 5T4 VHH domain, or each of the first and second 5T4 VHH domain, independently comprises the sequence of amino acids set forth in any one of SEQ ID NOS: 246-253 and 360.

114. The multispecific polypeptide construct of any of embodiments 63-108, wherein the at least one 5T4 VHH domain, or each of the first and second 5T4 VHH domain, independently comprises the sequence set forth in (i) SEQ ID NO: 255, (ii) a humanized variant of SEQ ID NO: 255, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255, and binds 5T4.

115. The multispecific polypeptide construct of any of embodiments 63-108 and 114, wherein the at least one 5T4 VHH domain, or each of the first and second 5T4 VHH domain, independently comprises a CDR1 comprising an amino acid sequence selected from the group consisting of SEQ ID NOS: 86, 290-292; a CDR2 comprising an amino acid sequence selected from the group consisting of SEQ ID NOS: 89-94; and a CDR3 comprising an amino acid sequence set forth in SEQ ID NO: 101.

116. The multispecific polypeptide construct of any of embodiments 63-108, 114 and 115, wherein the at least one 5T4 VHH domain, or each of the first and second 5T4 VHH domain, independently comprises a CDR1, CDR2 and CDR3 set forth in SEQ ID NOS: 290, 89, and 101, respectively; SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively.

117. The multispecific polypeptide construct of any of embodiments 63-108 and 114-116, wherein the at least one 5T4 VHH domain, or each of the first and second 5T4 VHH domain, independently comprises the sequence of amino acids set forth in any one of SEQ ID NOs: 256-275 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256-275, and binds 5T4.

118. The multispecific polypeptide construct of embodiments 63-108 and 114-117, wherein the at least one 5T4 VHH domain, or each of the first and second 5T4 VHH domain, independently comprises the sequence of amino acids set forth in any one of SEQ ID NOS: 256-275.

119. The multispecific polypeptide construct of any of embodiments 63-108, wherein the at least one 5T4 VHH domain, or each of the first and second 5T4 VHH domain, independently comprises the sequence set forth in (i) SEQ ID NO: 276 (ii) a humanized variant of SEQ ID NO: 276, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 276, and binds 5T4.

120. The multispecific polypeptide of any of embodiments 63-108 and 119, wherein the at least one 5T4 VHH domain, or each of the first and second 5T4 VHH domain, independently comprises a CDR1 comprising an amino acid sequence selected from the group consisting of SEQ ID NO: 86 and 87; a CDR2 comprising an amino acid sequence selected from the group consisting of SEQ ID NOS: 95-99; and a CDR3 comprising an amino acid sequence set forth in SEQ ID NO: 102.

121. The multispecific polypeptide construct of any of embodiments 63-108, 119 and 120, wherein the at least one 5T4 VHH domain, or each of the first and second 5T4 VHH domain, independently comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

122. The multispecific polypeptide construct of any of embodiments 63-108 and 119-121, wherein the at least one 5T4 VHH domain, or each of the first and second 5T4 VHH domain, independently comprises the sequence of amino acids set forth in any one of SEQ ID NOs: 277-287 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 277-287, and binds 5T4.

123. The multispecific polypeptide construct of embodiments 63-108 and 119-122, wherein the at least one 5T4 VHH domain, or each of the first and second 5T4 VHH domain, independently comprises the sequence of amino acids set forth in any one of SEQ ID NOS: 277-287.

124. The multispecific polypeptide construct of any of embodiments 63-108, wherein the at least one 5T4 VHH domain, or each of the first and second 5T4 VHH domain, independently comprises the sequence set forth in (i) SEQ ID NO: 294 (ii) a humanized variant of SEQ ID NO: 294, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, and binds 5T4.

125. The multispecific polypeptide construct of any of embodiments 63-108 and 124, wherein the at least one 5T4 VHH domain, or each of the first and second 5T4 VHH domain, independently comprises a CDR1 comprising an amino acid sequence set forth in SEQ ID NO: 296; a CDR2 comprising an amino acid sequence set forth in SEQ ID NO: 298; and a CDR3 comprising an amino acid sequence set forth in SEQ ID NO: 300.

126. The multispecific polypeptide construct of any of embodiments 63-106, wherein the at least one 5T4 VHH domain, or each of the first and second 5T4 VHH domain, independently comprises the sequence set forth in (i) SEQ ID NO: 295 (ii) a humanized variant of SEQ ID NO: 295, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 295, and binds 5T4.

127. The multispecific polypeptide construct of any of embodiments 63-106 and 126, wherein the at least one 5T4 VHH domain, or each of the first and second 5T4 VHH domain, independently comprises a CDR1 comprising an amino acid sequence set forth in SEQ ID NO: 297; a CDR2 comprising an amino acid sequence set forth in SEQ ID NO: 299; and a CDR3 comprising an amino acid sequence set forth in SEQ ID NO: 301.

128. The multispecific polypeptide construct of any of embodiments 63-106, wherein the at least one 5T4 VHH domain, or each of the first and second 5T4 VHH domain, independently comprises the sequence set forth in (i) SEQ ID NO: 302 (ii) a humanized variant of SEQ ID NO: 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 302, and binds 5T4.

129. The multispecific polypeptide construct of any of embodiments 63-106 and 126, wherein the at least one 5T4 VHH domain, or each of the first and second 5T4 VHH domain, independently comprises a CDR1 comprising an amino acid sequence set forth in SEQ ID NO: 288; a CDR2 comprising an amino acid sequence set forth in SEQ ID NO: 88; and a CDR3 comprising an amino acid sequence set forth in SEQ ID NO: 303.

130. The multispecific polypeptide construct of any of embodiments 63-106, wherein the at least one 5T4 VHH domain, or each of the first and second 5T4 VHH domain, independently comprises the sequence set forth in (i) SEQ ID NO: 294, 295, or 302 (ii) a humanized variant of SEQ ID NO: 294, 295, or 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, 295, or 302, and binds 5T4.

131. The multispecific polypeptide construct of any of embodiments 63-106 and 130, wherein the at least one 5T4 VHH domain, or each of the first and second 5T4 VHH domain, independently comprises a CDR1, CDR2 and CDR3 set forth in SEQ ID NOS: 296, 298, and 300, respectively; SEQ ID NOS: 297, 299, and 301, respectively; or SEQ ID NOS: 288, 88, and 303, respectively.

132. The multispecific polypeptide construct of any of embodiments 63-106, 130 and 131, wherein the at least one 5T4 VHH domain, or each of the first and second 5T4 VHH domain, independently is set forth in SEQ ID NO: 245, 249, 255, 270, 276, 294, 295, 302, or 360.

133. The multispecific polypeptide construct of any of embodiments 63-132, wherein one or both of the first and second components comprises at least one co-stimulatory receptor binding region (CRBR) that binds a co-stimulatory receptor.

134. The multispecific polypeptide construct of embodiment 133, wherein the at least one co-stimulatory receptor binding region (CRBR) is positioned amino-terminally relative to the Fc region and/or carboxy-terminally relative to the CD3 binding region of the multispecific polypeptide construct.

135. The multispecific polypeptide construct of embodiment 133 or embodiment 134, wherein the multispecific polypeptide construct comprises only one co-stimulatory receptor binding region (CRBR).

136. The multispecific polypeptide construct of any of embodiments 133-135, wherein the multispecific polypeptide construct comprises two co-stimulatory receptor binding region (CRBR), optionally which are the same or different.

137. The multispecific polypeptide construct of any of embodiments 133-136, wherein the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor.

138. The multispecific polypeptide construct of any of embodiments 133-136, wherein the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

139. The multispecific polypeptide construct of embodiment 138, wherein the antibody or antigen-binding fragment thereof is a Fv, a scFv, a Fab, or a single domain antibody (sdAb).

140. The multispecific polypeptide construct of embodiment 138 or embodiment 139, wherein the antibody or antigen-binding fragment is an sdAb.

141. The multispecific polypeptide construct of embodiment 140, wherein the sdAb is a human or humanized sdAb.

142. The multispecific polypeptide construct of any of embodiments 133-141, wherein the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D.

143. The multispecific polypeptide construct of any of embodiments 133-142, wherein the at least one co-stimulatory receptor binding region (CRBR) binds a co-stimulatory receptor selected from among 41BB (CD137), OX40 (CD134), and glucocorticoid-induced TNFR-related protein (GITR).

144. The multispecific polypeptide construct of any of embodiments 133-143, wherein the at least one co-stimulatory receptor binding region (CRBR) comprises the sequence of amino acids set forth in SEQ ID NO:210 or a sequence that has at least 85%, 86%, 87%, 88%, 89%, 90%, 91%, 92%, 93%, 94%, 95%, 96%, 97%, 98%, or 99% sequence identity to the sequence set forth in SEQ ID NO:210 and binds 4-1BB.

145. The multispecific polypeptide construct of any of embodiments 63-144, wherein one or both of the first and second components comprises at least one inhibitory receptor binding region (IRBR) that binds an inhibitory receptor.

146. The multispecific polypeptide construct of embodiment 145, wherein the at least one inhibitory receptor binding region (IRBR) is positioned amino-terminally relative to the Fc region and/or carboxy-terminally relative to the CD3 binding region of the multispecific polypeptide construct.

147. The multispecific polypeptide construct of embodiment 145 or embodiment 146, wherein the multispecific polypeptide construct comprises only one inhibitory receptor binding region (IRBR).

148. The multispecific polypeptide construct of any of embodiments 145-147, wherein:
the first component comprises in order of N-terminus to C-terminus a first 5T4 VHH domain that binds 5T4, the first Fc polypeptide of the heterodimeric Fc region, the linker, the VH or VL domain of the anti-CD3 antibody or antigen binding fragment and a second 5T4 VHH domain that binds 5T4; and
the second component comprises the IRBR and comprises in order of N-terminus to C-terminus the second Fc polypeptide of the heterodimeric Fc region, the linker, optionally the same linker as present in the first component, the other of the VH or VL domain of the anti-CD3 antibody or antigen binding fragment, wherein the IRBR is positioned amino-terminally relative to the Fc region and/or carboxy-terminally relative to the anti-CD3 antibody or antigen-binding fragment of the second component.

149. The multispecific polypeptide construct of any of embodiments 145-148, wherein the at least one IRBR is or comprises the extracellular domain or binding fragment thereof of the native cognate binding partner of the inhibitory receptor, or a variant thereof that exhibits binding activity to the inhibitory receptor.

150. The multispecific polypeptide construct of any of embodiments 139-142, wherein the at least one IRBR is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

151. The multispecific polypeptide construct of embodiment 150, wherein the antibody or antigen-binding fragment thereof is a Fv, a scFv, a Fab, a single domain antibody (sdAb).

152. The multispecific polypeptide construct of embodiment 150 or embodiment 151, wherein the antibody or antigen-binding fragment is an sdAb.

153. The multispecific polypeptide construct of embodiment 152, wherein the sdAb is a human or humanized sdAb.

153. The multispecific polypeptide construct of any of embodiments 145-153, wherein the at least one IRBR binds a inhibitory receptor selected from among PD-1, CTLA-4, TIGIT, VISTA and TIM3.

155. The multispecific polypeptide construct of any of embodiments 145-154, wherein the at least one IRBR binds PD-1.

156. The multispecific polypeptide construct of any of embodiments 145-155, wherein:

the first component comprises in order of N-terminus to C-terminus a first 5T4 VHH domain that binds 5T4, the first Fc polypeptide of the heterodimeric Fc region, the linker, the VH or VL domain of the anti-CD3 antibody or antigen binding fragment and a second 5T4 VHH domain that binds 5T4; and the second polypeptide comprises in order of N-terminus to C-terminus one of the IRBR or the CRBR, the second Fc polypeptide of the heterodimeric Fc region, the linker, optionally the same linker as present in the first component, the other of the VH or VL domain of the anti-CD3 antibody or antigen binding fragment, and the other of the CRBR or IRBR.

157. The multispecific polypeptide construct of any of embodiments 63-156, wherein the linker is a peptide or polypeptide linker, optionally wherein the linker is 3, 4, 5, 6, 7, 8, 9, 10, 11, 12, 13, 14, 15, 16, 17, 18, 19 or 20 amino acids in length 158. The multispecific polypeptide construct of any of embodiments 63-157, wherein the linker is a non-cleavable linker 159. The multispecific polypeptide construct of embodiment 158, wherein the non-cleavable linker is or comprises GG 160. The multispecific polypeptide construct of embodiment 158, wherein the non-cleavable linker comprises GS, GGS, GGGGS (SEQ ID NO:125), GGGGGS (SEQ ID NO: 126) or combinations thereof.

161. The multispecific polypeptide construct of any of embodiments 63-158, wherein the linker is or comprises the sequence GGGGGSGGGGGSGGGGGS (SEQ ID NO:127)

162. The multispecific polypeptide construct of any of embodiments 63-157, wherein the linker is a cleavable linker.

163. The multispecific polypeptide construct of embodiment 162, wherein the cleavable linker is a polypeptide that functions as a substrate for a protease.

164. The multispecific polypeptide construct of embodiment 163, wherein the protease is produced by an immune effector cell, by a tumor cell, or by cells present in the tumor microenvironment.

165. The multispecific polypeptide construct of embodiment 163 or embodiment 164, wherein the protease is produced by an immune effector cell and the immune effector cell is an activated T cell, a natural killer (NK) cell, or an NK T cell.

166. The multispecific polypeptide construct of any of embodiments 163-165, wherein the protease is selected from among matriptase, a matrix metalloprotease (MMP), granzyme B, and combinations thereof.

167. The multispecific polypeptide construct of embodiment 166, wherein the protease is granzyme B.

168. The multispecific polypeptide construct of any of embodiments 163-167, wherein the cleavable linker comprises the amino acid sequence GGSGGGGIEPDIGGSGGS (SEQ ID NO:171).

169. An isolated single domain antibody (sdAb) that binds 5T4, comprising a complementarity determining region 1 (CDR1) comprising an amino acid sequence selected from the group consisting of SEQ ID NO: 86-87 and 288-292, 296, and 297; a complementarity determining region 2 (CDR2) comprising an amino acid sequence selected from the group consisting of SEQ ID NO: 88-99, 298, and 299; and a complementarity determining region 3 (CDR3) comprising an amino acid sequence selected from the group consisting of SEQ ID NO: 100-102, 300, 301, and 303.

170. The isolated single domain antibody (sdAb) of embodiment 169, wherein the at least one 5T4 VHH domain binds to an epitope in human 5T4 but does not exhibit crossreactive binding to mouse 5T4.

171. The isolated single domain antibody (sdAb) of embodiment 169 or 170, wherein the at least one 5T4 VHH domain binds to amino acid residues between amino acids 60 and 112 of SEQ ID NO: 382.

172. The isolated single domain antibody (sdAb) of any of embodiments 169-171, wherein the at least one 5T4 VHH domain binds to amino acid residues between amino acids 173 and 224 of SEQ ID NO: 382

173. The isolated single domain antibody of embodiment 169, comprising the amino acid sequence set forth in any of SEQ ID NOS: 245-253, 255-287, 294, 295, 302, and 360 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 245-253, 255-287, 294, 295, 302, and 360 and binds 5T4.

174. The isolated single domain antibody of any of embodiments 169-173, wherein the single domain antibody comprises the sequence set forth in (i) SEQ ID NO: 245, (ii) a humanized variant of SEQ ID NO: 245, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 245, and binds 5T4.

175. The isolated single domain antibody of any of embodiments 169-174, wherein the sdAb comprises a CDR1 comprising an amino acid sequence selected from the group consisting of SEQ ID NO: 288 and 289; a CDR2 comprising an amino acid sequence set forth in SEQ ID NO: 88; and a CDR3 comprising an amino acid sequence set forth in SEQ ID NO: 100.

176. The isolated single domain antibody of any of embodiments 169-175, wherein the sdAb comprises a CDR1, CDR2 and CDR3 set forth in SEQ ID NOS: 288, 88, and 100, respectively; or SEQ ID NOS: 289, 88, and 100, respectively.

177. The isolated single domain antibody of any of embodiments 169-176, wherein the sdAb comprises the sequence of amino acids set forth in any one of SEQ ID NOs: 246-253 and 360 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 246-253 and 360, and binds 5T4.

178. The isolated single domain antibody of any of embodiments 169-177, wherein the sdAb comprises the sequence of amino acids set forth in any one of SEQ ID NOS: 246-253 and 360.

179. The isolated single domain antibody of any of embodiments 169-173, wherein the sdAb comprises the sequence set forth in (i) SEQ ID NO: 255, (ii) a humanized variant of SEQ ID NO: 255, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 255, and binds 5T4.

180. The isolated single domain antibody of any of embodiments 169-173 and 179, wherein the sdAb comprises a CDR1 comprising an amino acid sequence set forth in SEQ ID NO: 86, 290-292; a CDR2 comprising an amino acid sequence selected from the group consisting of SEQ ID NO: 89-94; and a CDR3 comprising an amino acid sequence set forth in SEQ ID NO: 101.

181. The isolated single domain antibody of any of embodiments 169-173, 179, and 180, wherein the sdAb comprises a CDR1, CDR2 and CDR3 set forth in SEQ ID NOS: 290, 89, and 101, respectively; SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively.

182. The isolated single domain antibody of any of embodiments 169-173 and 179-181, wherein the sdAb comprises the sequence of amino acids set forth in any one of SEQ ID NOs: 256-275 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 256-275, and binds 5T4.

183. The isolated single domain antibody of any of embodiments 169-173 and 179-182, wherein the sdAb comprises the sequence of amino acids set forth in any one of SEQ ID NOS: 256-275.

184. The isolated single domain antibody of any of embodiments 169-173, wherein the sdAb comprises the sequence set forth in (i) SEQ ID NO: 276 (ii) a humanized variant of SEQ ID NO: 276, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 276, and binds 5T4.

185. The isolated single domain antibody of any of embodiments 169-173 or embodiment 184, wherein the sdAb comprises a CDR1 comprising an amino acid sequence selected from the group consisting of SEQ ID NO: 86 and 87; a CDR2 comprising an amino acid sequence selected from the group consisting of SEQ ID NOS: 95-99; and a CDR3 comprising an amino acid sequence set forth in SEQ ID NO: 102.

186. The isolated single domain antibody of any of embodiments 169-173, 184 and 185, wherein the sdAb comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

187. The isolated single domain antibody of any of embodiments 169-173 and 184-186, wherein the sdAb comprises the sequence of amino acids set forth in any one of SEQ ID NOs: 277-287 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 277-287, and binds 5T4.

188. The isolated single domain antibody of any of embodiments 169-173 and 184-187, wherein the sdAb comprises the sequence of amino acids set forth in any one of SEQ ID NOS: 277-287.

189. The isolated single domain antibody of any of embodiments 169-173, wherein the sdAb comprises the sequence set forth in (i) SEQ ID NO: 294 (ii) a humanized variant of SEQ ID NO: 294, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, and binds 5T4.

190. The isolated single domain antibody of embodiment 169-173 or 189, wherein the sdAb comprises a CDR1 comprising an amino acid sequence set forth in SEQ ID NO: 296; a CDR2 comprising an amino acid sequence set forth in SEQ ID NO: 298; and a CDR3 comprising an amino acid sequence set forth in SEQ ID NO: 300.

191. The isolated single domain antibody of embodiment 169-173 or 189, wherein the sdAb comprises a CDR3 comprising an amino acid sequence selected from the group consisting of SEQ ID NOS: 300, 301, and 303.

192. The isolated single domain antibody of embodiment 169-173 or 189, wherein the sdAb comprises:

a CDR1 comprising an amino acid sequence selected from the group consisting of SEQ ID NOS: 288, 296, and 297; and/or a CDR2 comprising an amino acid sequence selected from the group consisting of SEQ ID NOS: 88, 298, and 299.

193. The isolated single domain antibody of any of embodiments 169-173, wherein the sdAb comprises the sequence set forth in (i) SEQ ID NO:295 (ii) a humanized variant of SEQ ID NO:295, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:295, and binds 5T4.

194. The isolated single domain antibody of any of embodiments 169-173 and 193, wherein the sdAb comprises a CDR1 comprising an amino acid sequence set forth in SEQ ID NO: 297; a CDR2 comprising an amino acid sequence set forth in SEQ ID NO: 299; and a CDR3 comprising an amino acid sequence set forth in SEQ ID NO: 301.

195. The isolated single domain antibody of any of embodiments 169-173, wherein the sdAb comprises the sequence set forth in (i) SEQ ID NO:302 (ii) a humanized variant of SEQ ID NO:302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:302, and binds 5T4.

196. The isolated single domain antibody of any of embodiments 169-173 and 193, wherein the sdAb comprises a CDR1 comprising an amino acid sequence set forth in SEQ ID NO: 288; a CDR2 comprising an amino acid sequence set forth in SEQ ID NO: 88; and a CDR3 comprising an amino acid sequence set forth in SEQ ID NO: 303.

197. The isolated single domain antibody of any of embodiments 169-173, wherein the sdAb comprises the sequence set forth in (i) SEQ ID NO: 294, 295, or 302 (ii) a humanized variant of SEQ ID NO: 294, 295, or 302, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 294, 295, or 302, and binds 5T4.

198. The isolated single domain antibody of any of embodiments 169-173 and 197, wherein the sdAb comprises a CDR1, CDR2 and CDR3 set forth in SEQ ID NOS: 296, 298, and 300, respectively; SEQ ID NOS: 297, 299, and 301, respectively; or SEQ ID NOS: 288, 88, and 303, respectively.

199. A polynucleotide(s) encoding the 5T4-binding polypeptide construct of any of embodiments 1-62.

200. A polynucleotide(s) encoding the multispecific polypeptide construct of any of embodiments 63-168.

201. A polynucleotide, comprising a first nucleic acid sequence encoding a first polypeptide of a multispecific construct of any of embodiments 63-168 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

202. The polynucleotide of embodiment 201, wherein the first nucleic acid sequence and second nucleic acid sequence are operably linked to the same promoter.

203. The polynucleotide of embodiment 201 or 202, wherein the nucleic acid encoding a self-cleaving peptide or a peptide that causes ribosome skipping is selected from a T2A, a P2A, a E2A or a F2A.

204. A polynucleotide encoding the single domain antibody of any of embodiments 169-198.

205. A vector, comprising the polynucleotide of any of embodiments 199-204.

206. The vector of embodiment 205 that is an expression vector.

207. The vector of embodiment 205 or embodiment 206 that is a viral vector or a eukaryotic vector, optionally wherein the eukaryotic vector is a mammalian vector.

208. A cell, comprising polynucleotide or polynucleotides of any of embodiments 199-204, or a vector or vectors of any of embodiments 205-207.

209. The cell of embodiment 208, wherein the cell is recombinant or isolated.

210. The cell of embodiment 209, wherein the cell is a mammalian cell.

211. A method of producing a polypeptide, the method comprising introducing into a cell a polynucleotide or polynucleotides of any of embodiments 199-204 or a vector or vectors of any of embodiments 205-207 and culturing the cell under conditions to produce the multispecific polypeptide construct.

212. The method of embodiment 211, further comprising isolating or purifying the polypeptide from the cell.

213. A polypeptide produced by the method of embodiment 211 or embodiment 212.

214. An engineered immune cell, comprising a chimeric antigen receptor comprising:

an extracellular domain comprising the single domain antibody of any of embodiments 169-198;

a transmembrane domain; and an intracellular signaling domain.

215. The engineered immune cell of embodiment 214, wherein the cell is a lymphocyte.

216. The engineered immune cell of embodiment 214 or embodiment 215, wherein the cell is a T cell or a natural killer (NK) cell.

217. The engineered immune cell of any of embodiments 214-216, wherein the intracellular signaling domain comprises an immunoreceptor tyrosine-based activation motif (ITAM) signaling domain.

218. The engineered immune cell of any of embodiments 214-217, wherein the intracellular signaling domain is or comprises a CD3zeta signaling domain, optionally a human CD3zeta signaling domain.

219. The engineered immune cell of embodiment 214-218, wherein the intracellular signaling domain further comprises a signaling domain of a costimulatory molecule.

220. The engineered immune cell of embodiment 219, wherein the costimulatory molecule is CD28, ICOS, 41BB or OX40, optionally a human CD28, a human ICOS, a human 41BB or a human OX40.

221. A pharmaceutical composition comprising the 5T4-binding polypeptide construct of any of embodiments 1-62, the multispecific polypeptide construct of any of embodiments 63-168, the single domain antibody of any of embodiments 169-198 or the engineered immune cell of any of embodiments 214-220.

222. The pharmaceutical composition of embodiment 221, comprising a pharmaceutically acceptable carrier.

223. The pharmaceutical composition of embodiment 221 or embodiment 222 that is sterile.

224. A method of stimulating or inducing an immune response in a subject, the method comprising administering, to a subject in need thereof, the 5T4-binding polypeptide construct of any of embodiments 1-62, the multispecific polypeptide construct of any of embodiments 63-168, the single domain antibody of any of embodiments 169-198 or the engineered immune cell of any of embodiments 214-220 or a pharmaceutical composition of embodiment 221-223.

225. The method of embodiment 224, wherein the immune response is increased against a tumor or cancer, optionally a tumor or a cancer that expresses 5T4.

226. The method of embodiment 224 or embodiment 225, wherein the method treats a disease or condition in the subject.

227. A method of treating a disease or condition in a subject, the method comprising administering, to a subject in need thereof, a therapeutically effective amount of the 5T4-binding polypeptide construct of any of embodiments 1-59, the multispecific polypeptide construct of any of embodiments 60-161, the single domain antibody of any of embodiments 162-188 or the engineered immune cell of any of embodiments 214-220 or a pharmaceutical composition of embodiment 221-223.

228. The method of embodiment 226 or embodiment 227, wherein the disease or condition is a tumor or a cancer.

229. The method of any of embodiments 224-228, wherein said subject is a human.

VIII. EXAMPLES

The following examples are included for illustrative purposes only and are not intended to limit the scope of the invention.

Example 1: Generation of 5T4 sdAb

Single domain antibodies targeting human 5T4 were generated via immunization of llamas and alpaca. Llamas and alpacas were immunized with a recombinant version of the human 5T4 extracellular domain (ECD; amino acids 32-355 of human 5T4, e.g. UniProt No. Q13641) set forth in SEQ ID NO:362 and as follows:

```
SSPTSSASSFSSSAPFLASAVSAQPPLPDQCPALCECSEAARTVKCVNR

NLTEVPTDLPAYVRNLFLTGNQLAVLPAGAFARRPPLAELAALNLSGSR

LDEVRAGAFEHLPSLRQLDLSHNPLADLSPFAFSGSNASVSAPSPLVEL

ILNHIVPPEDERQNRSFEGMVVAALLAGRALQGLRRLELASNHFLYLPR

DVLAQLPSLRHLDLSNNSLVSLTYVSFRNLTHLESLHLEDNALKVLHNG

TLAELQGLPHIRVFLDNNPWVCDCHMADMVTWLKETEVVQGKDRLTCAY

PEKMRNRVLLELNSADLDCDPILPPSLQTS
```

Following the development of specific anti-5T4 antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. Single domain antibody (sdAb; also called VHH) sequences were specifically amplified via PCR using the cDNA as template and cloned into a yeast surface display vector as sdAb-Fc-AGA2 fusion proteins. The Fc was a human IgG1 Fc (set forth in SEQ ID NO:8).

Yeast libraries displaying these sdAbs were enriched using recombinant forms of the 5T4 ECD via magnetic bead isolation followed by fluorescence activated cell sorting (FACS). Sorted yeast were plated out and isolated colonies were picked into 96-well blocks and grown in media that switched the expression from surface displayed sdAb-Fc to secretion into the media. Supernatants from the 96-well yeast secretion cultures were applied to Ovcar-5 (5T4 positive) or CCRF-CEM cells (5T4 negative), washed, treated with fluorophore labelled anti-human Fc secondary antibody, and analyzed by 96-well flow cytometry.

Binders to 5T4 positive cells and not to 5T4 negative cells were cloned into mammalian expression vectors as sdAb-Fcs, expressed by transient transfection in HEK293 freestyle cells (293F cells) or CHO cells using polyethylenimine. Recombinant protein secreted into the supernatant was collected after 3-7 days and purified by protein A chromatography.

Exemplary identified sdAbs are set forth in Table E1A. In some cases, the sdAbs can include a flexible linker (e.g. GG) for linkage to another polypeptide, such as an Fc or another sdAb.

in 96 well plates. Following three wash steps in FACS buffer, an APC-conjugated anti-human Fcγ specific secondary antibody (Jackson ImmunoResearch) was added and incubated for 30 minutes at 4 degrees Celsius. Following three additional wash steps in FACS buffer bound antibody was detected via flow cytometry (IQue Intellicyte).

Figure 1A:
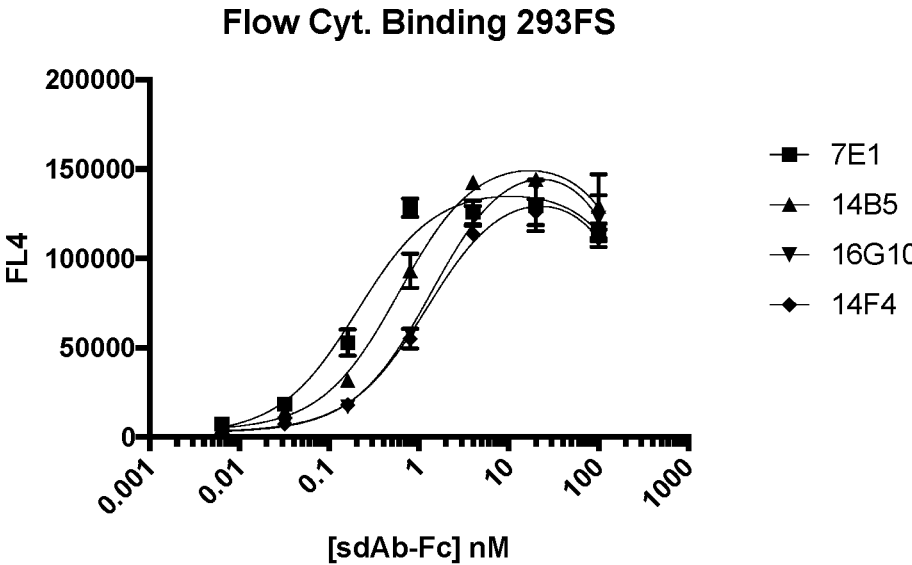
FIGS. 1A-B depict the ability of various single domain antibodies targeting 5T4 to bind cell surface 5T4. Binding was assessed by flow cytometry on HEK-293 freestyle cells endogenously expressing 5T4.
Figure 1B:
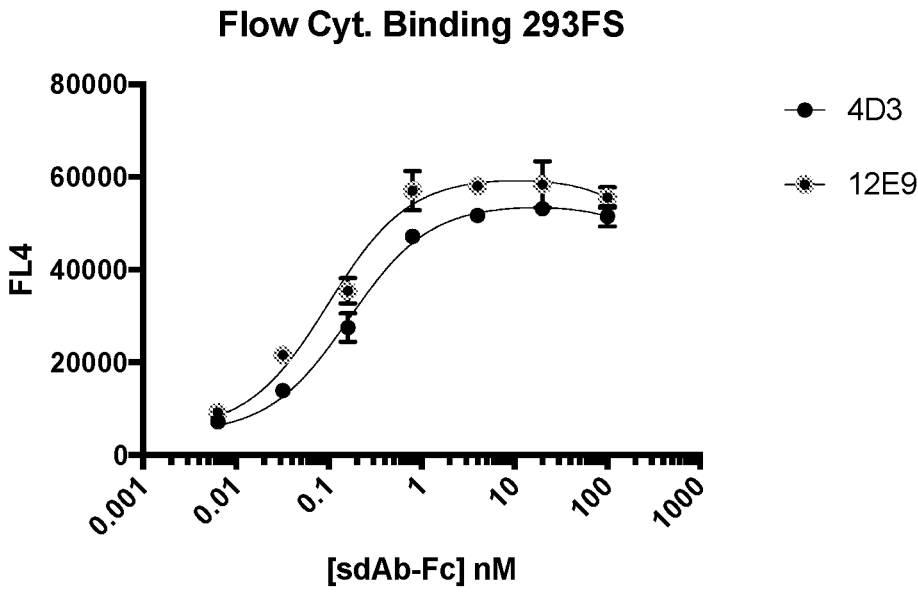
Figure 2A:
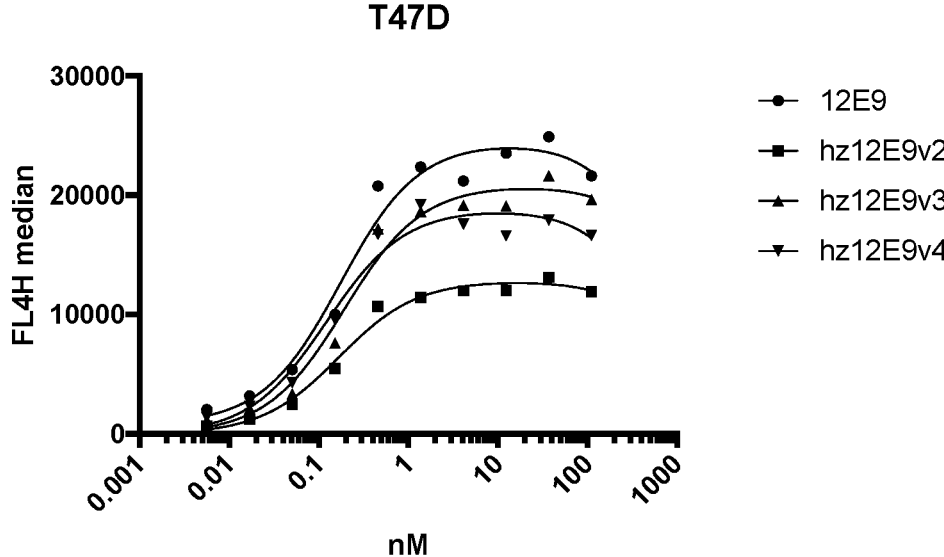
FIGS. 2A-2F depict the ability of sdAbs and humanized variants thereof targeting 5T4 to bind cell surface 5T4 on T47D cells. Binding was assessed by flow cytometry on the 5T4 positive cell line T47D.
Figure 2B:
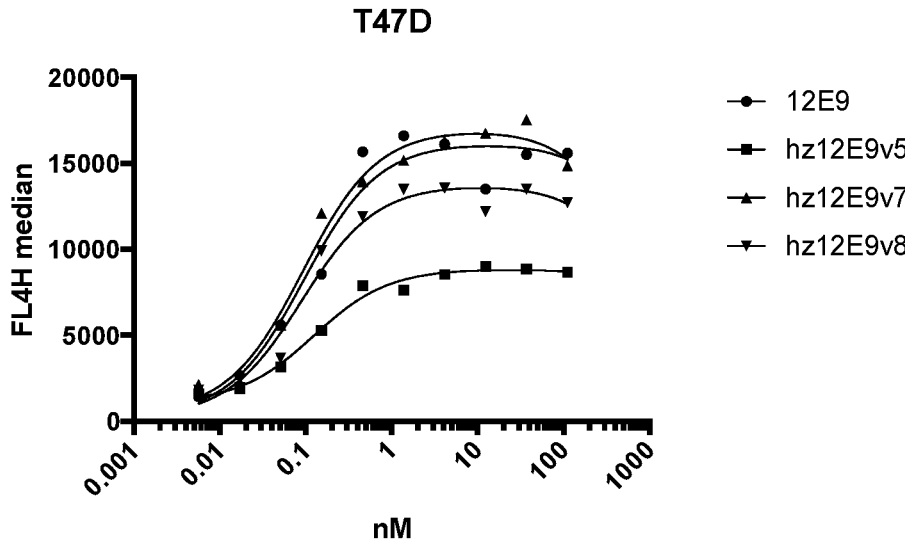
Figure 2C:
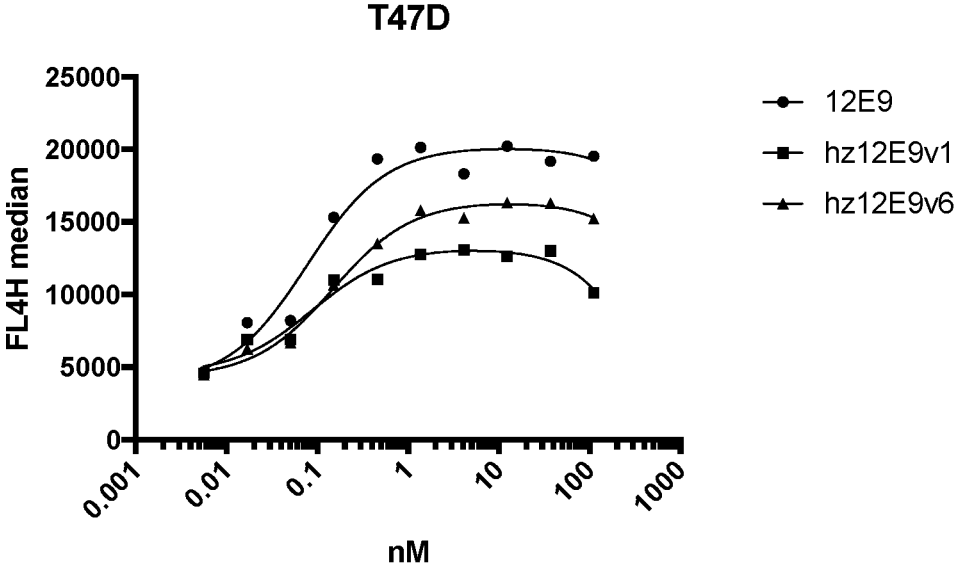
Figure 2D:
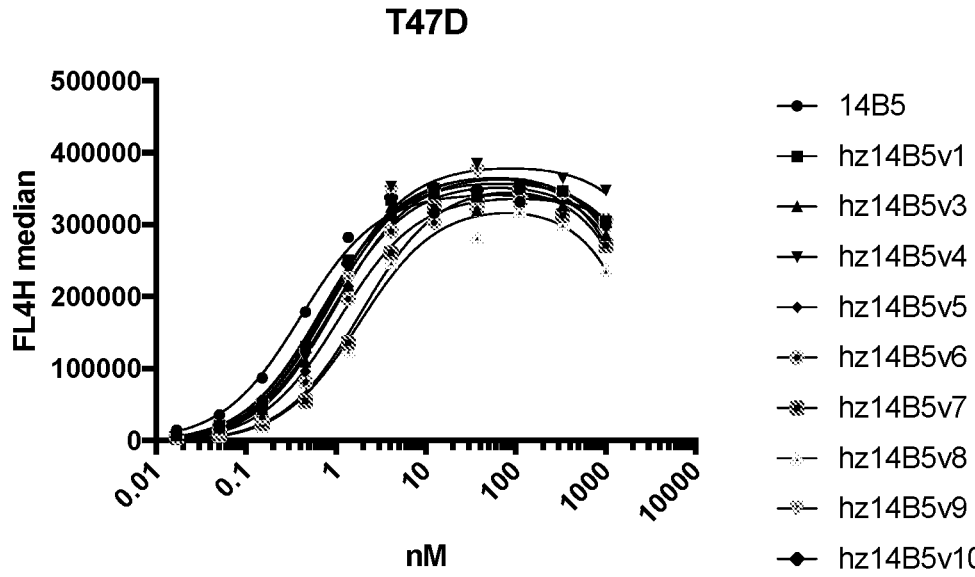
Figure 2E:
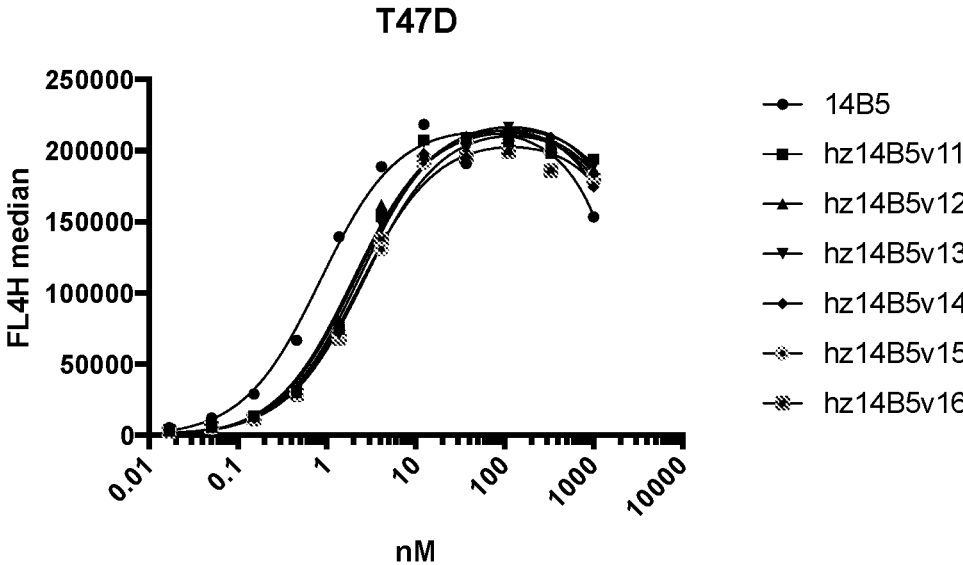
Figure 2F:
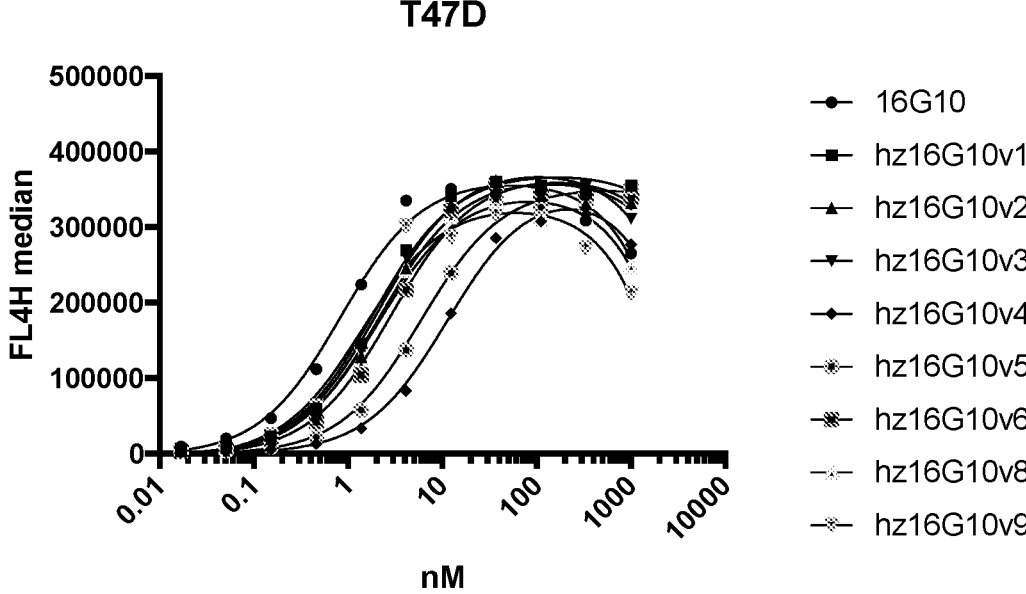
Figure 3A:
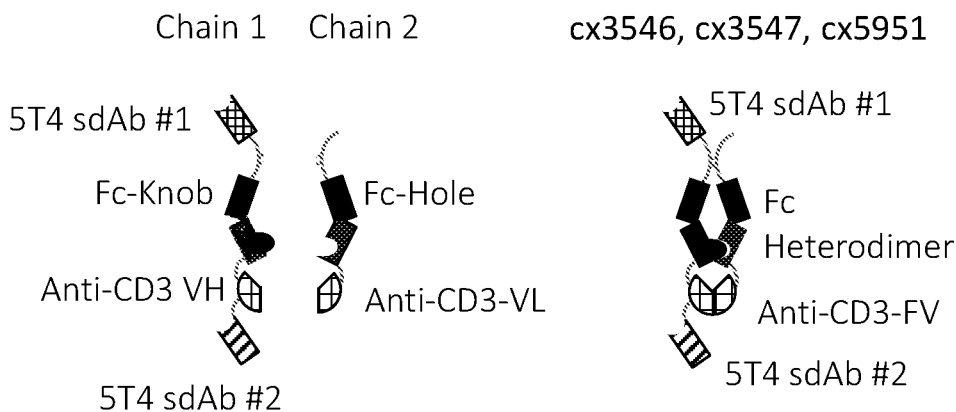
FIGS. 3A-E depict representative 5T4-targeted constrained CD3 engagers without (FIGS. 3A, 3C, 3E) and with a 41BB binding domain (FIGS. 3B, 3D). cx3546 and cx3547 have the same 5T4-targeting sdAb (12E9) positioned at the N-termini of one chain of the heterodimer and distinct 5T4-targeting sdAbs (14B5 or 16G10, respectively) positioned at the C-termini of one chain of the heterodimer. cx3499 and cx3497 are identical to cx3546 and cx3547, respectively, but have a 41BB-targeting sdAb positioned at the C-termini of the opposite chain of the heterodimer. Each of cx3546, cx3547, cx3499 and cx3497 contain a cleavable linker between the Fc region and the CD3 binding region. cx5185 and cx5951 are the same but the former includes a 4-1BB targeting sdAb positioned C-terminally to the CD3 binding region; both contain a non-cleavable linker between the Fc region and the CD3 binding region and contain humanized versions of the 5T4-targeting sdAbs, hz12E9v9 and hz16G10v11, positioned at the N- and C-termini of the Fc heterodimer. These representative 5T4-targeted constrained CD3 engagers display bivalent binding to 5T4, and in constructs containing a 41BB binding domain, display monovalent binding to 41BB.
Figure 3B:
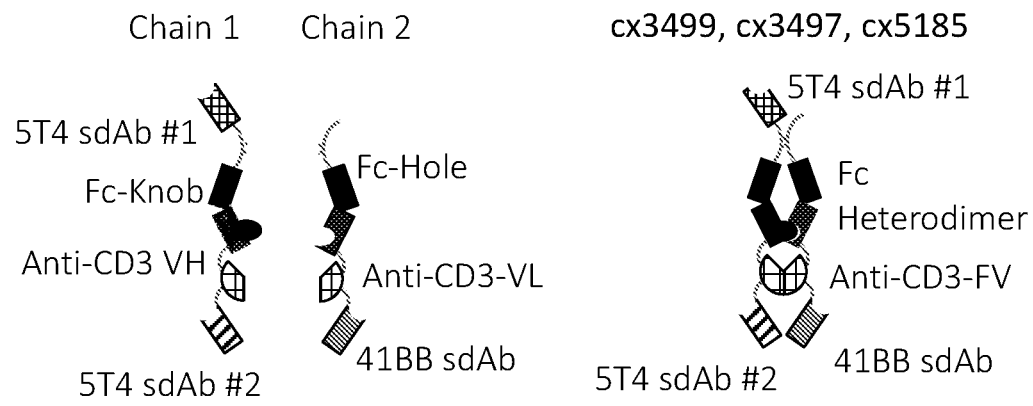
Figure 3C:
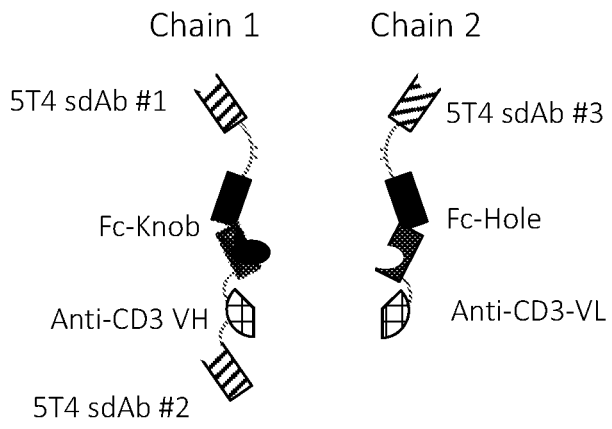
Figure 3C:
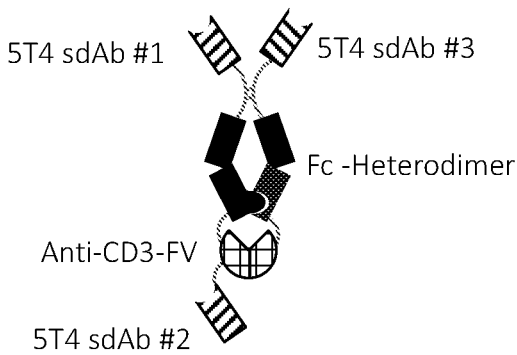
Figure 3D:
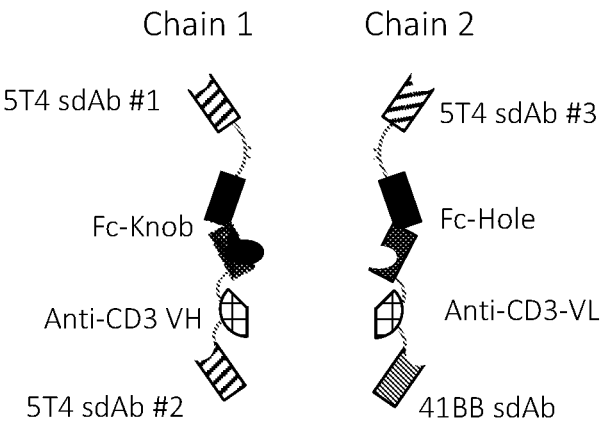
Figure 3D:
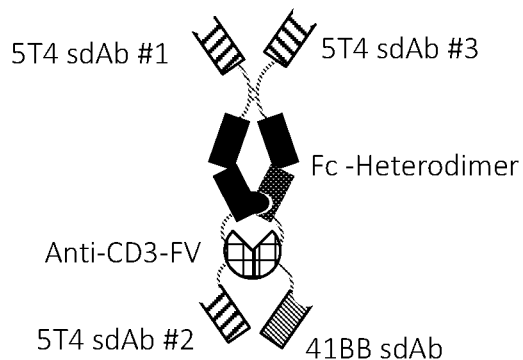
Figure 3E:
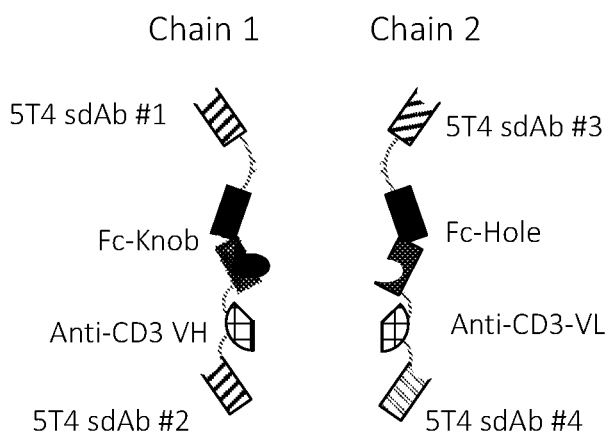
Figure 3E:
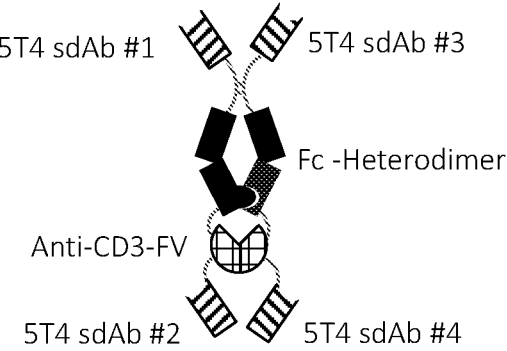

FIGS. 1A-1B set forth results for exemplary 5T4 sdAbs, namely 4D3 (SEQ ID NO: 302), 12E9 (SEQ ID NO: 245), 7E1 (SEQ ID NO: 294), 14B5 (SEQ ID NO: 255), 16G10 (SEQ ID NO: 276), 14F4 (SEQ ID NO: 295).

An epitope binning assay for binding to 5T4 were carried out using exemplary generated sdAbs to test antibodies pairwise for blocking of another's binding to the epitope of an antigen. Results are set forth in Table E1B:

TABLE E1B

| Epitope Binning | |
| --- | --- |
| 12E9 | BIN1 |
| 7E1 | BIN2 |
| 14B5 | BIN2 |
| 16G10 | BIN2 |
| 4D3 | BIN1 |
| 14F4 | BIN1 |

Example 3: Humanization of Camelid Derived 5T4 sdAb

Exemplary camelid derived 5T4 sdAbs, 12E9, 14B5 and 16G10, were humanized using the human VH3-23 germline

TABLE E1A

| | | | | | | | SEQ |
| --- | --- | --- | --- | --- | --- | --- | --- |
| | | SEQ | | SEQ | | SEQ | VHH |
| Clone | | ID | | ID | | ID | ID |
| name | CDR1 | NO | CDR2 | NO | CDR3 | NO | NO |
| L12E9 | RRPFSSKTMA | 288 | AVRWIGGATR | 88 | GQAWGTKFTDYSD | 100 | 245 |
| L14B5 | ERPFGTYAMG | 290 | AVSRNGGASQ | 89 | RSAAYSRSSEVYTGKDEYYY | 101 | 255 |
| L16G10 | GRPFSSSAMG | 87 | AVSRNGGSSY | 95 | RSAAYSRSSETYTEKHDYTY | 102 | 276 |
| 7E1 | GRTRSLRTMA | 296 | AISWRSDSTY | 298 | GGGWLATTPDEYTY | 300 | 294 |
| 14F4 | GVTWNSYTMA | 297 | AIRWTVDTTY | 299 | GRKWPKADDY | 301 | 295 |
| 4D3 | RRPFSSKTMA | 288 | AVRWIGGATR | 88 | GQTWGTKFTDYSD | 303 | 302 |

Example 2: Binding of sdAb to 5T4 Expressing Cells by Flow Cytometry

Specificity and relative affinity were assessed for purified sdAb-Fcs on 5T4-expressing cells. Binding of 5T4-sdAb-Fc fusion proteins was assessed by flow cytometry using 5T4-expressing cells. A titration series of the fusion protein was incubated with the 5T4-expressing cell lines (approximately $2.5 \times 10^4$ to $5 \times 10^4$ cells/well) for 30 minutes at 4 degrees Celsius in FACS Buffer (PBS 1% BSA, 0.1% NaN$_3$ pH 7.4)

as scaffold. Camelid residues that contribute to solubility, specificity, stability and/or affinity remained unmodified. In addition, all humanized variant contained the modification of Leu11Glu (L11E) and the carboxy-terminal modifications of Ser112Lys (S112K) and Ser113Pro (S113P) as these are known prevent or reduce the recognition of pre-existing ADA directed toward sdAbs (as described in US20160207981).

Table E2 sets forth exemplary 5T4 sdAbs humanized variants.

TABLE E2

| | | | | | | | SEQ |
|---|---|---|---|---|---|---|---|

5T4 sdAbs Humanized Variants

| Clone name | CDR1 | SEQ ID NO | CDR2 | SEQ ID NO | CDR3 | SEQ ID NO | SEQ VHH ID NO |
|---|---|---|---|---|---|---|---|
| | | | L12E9 Humanized Variants | | | | |
| hz12E9v1 | RRPFSSKTMA | 288 | AVRWIGGATR | 88 | GQAWGTKFTDYSD | 100 | 246 |
| hz12E9v2 | RRPFSSKTMA | 288 | AVRWIGGATR | 88 | GQAWGTKFTDYSD | 100 | 247 |
| hz12E9v3 | RRPFSSKTMA | 288 | AVRWIGGATR | 88 | GQAWGTKFTDYSD | 100 | 248 |
| hz12E9v4 | RRPFSSKTMA | 288 | AVRWIGGATR | 88 | GQAWGTKFTDYSD | 100 | 249 |
| hz12E9v5 | RRPFSSKTMA | 288 | AVRWIGGATR | 88 | GQAWGTKFTDYSD | 100 | 250 |
| hz12E9v6 | RRPFSSKTMA | 288 | AVRWIGGATR | 88 | GQAWGTKFTDYSD | 100 | 251 |
| hz12E9v7 | RRPFSSKTMA | 288 | AVRWIGGATR | 88 | GQAWGTKFTDYSD | 100 | 252 |
| hz12E9v8 | RRPFSSKTMA | 288 | AVRWIGGATR | 88 | GQAWGTKFTDYSD | 100 | 253 |
| hz12E9v9 | GRPFSSKTMA | 289 | AVRWIGGATR | 88 | GQAWGTKFTDYSD | 100 | 254 360 |
| | | | L14B5 Humanized Variants | | | | |
| hz14B5v1 | ERPFGTYAMG | 290 | AVSRNGGASQ | 89 | RSAAYSRSSEVYTGKDE YYY | 101 | 256 |
| hz14B5v2 | ERPFGTYAMG | 290 | AVSRNGGASQ | 89 | RSAAYSRSSEVYTGKDE YYY | 101 | 257 |
| hz14B5v3 | ERPFGTYAMG | 290 | AVSRNGGASQ | 89 | RSAAYSRSSEVYTGKDE YYY | 101 | 258 |
| hz14B5v4 | ERPFGTYAMG | 290 | AVSRNGGASQ | 89 | RSAAYSRSSEVYTGKDE YYY | 101 | 259 |
| hz14B5v5 | ERPFGTYAMG | 290 | AVSRNAGASQ | 90 | RSAAYSRSSEVYTGKDE YYY | 101 | 260 |
| hz14B5v6 | ERPFGTYAMG | 290 | AVSRNTGASQ | 91 | RSAAYSRSSEVYTGKDE YYY | 101 | 261 |
| hz14B5v7 | ERPFGTYAMG | 290 | AVSRQGGASQ | 92 | RSAAYSRSSEVYTGKDE YYY | 101 | 262 |
| hz14B5v8 | ERPFGTYAMG | 290 | AVSRGGGASQ | 93 | RSAAYSRSSEVYTGKDE YYY | 101 | 263 |
| hz14B5v9 | ERPFGTYAMG | 290 | AVSRNGGASQ | 89 | RSAAYSRSSEVYTGKDE YYY | 101 | 264 |
| hz14B5v10 | ERPFGTYAMG | 290 | AVSRNGGASQ | 89 | RSAAYSRSSEVYTGKDE YYY | 101 | 265 |
| hz14B5v11 | ERPFGTYAMG | 290 | AVSRNAGASQ | 90 | RSAAYSRSSEVYTGKDE YYY | 101 | 266 |
| hz14B5v12 | ERPFGTYAMG | 290 | AVSRNAGASQ | 90 | RSAAYSRSSEVYTGKDE YYY | 101 | 267 |
| hz14B5v13 | ERPFGTYAMG | 290 | AVSRNAGASQ | 90 | RSAAYSRSSEVYTGKDE YYY | 101 | 268 |
| hz14B5v14 | ERPFGTYAMG | 290 | AVSRNAGASQ | 90 | RSAAYSRSSEVYTGKDE YYY | 101 | 269 |
| hz14B5v15 | ERPFGTYAMG | 290 | AVSRNAGASY | 94 | RSAAYSRSSEVYTGKDE YYY | 101 | 270 |
| hz14B5v16 | ERPFGTYAMG | 290 | AVSRNAGASQ | 90 | RSAAYSRSSEVYTGKDE YYY | 101 | 271 |
| hz14B5v17 | ERPFGTYAMG | 290 | AVSRNAGASY | 94 | RSAAYSRSSEVYTGKDE YYY | 101 | 272 |

TABLE E2-continued

5T4 sdAbs Humanized Variants

| Clone name | CDR1 | SEQ ID NO | CDR2 | SEQ ID NO | CDR3 | SEQ ID NO | SEQ VHH ID NO |
|---|---|---|---|---|---|---|---|
| hz14B5v18 | ERPFSSYAMG | 291 | AVSRNAGASY | 94 | RSAAYSRSSEVYTGKDE YYY | 101 | 273 |
| hz14B5v19 | GRPFGTYAM G | 292 | AVSRNAGASY | 94 | RSAAYSRSSEVYTGKDE YYY | 101 | 274 |
| hz14B5v20 | GRPFSSYAMG | 86 | AVSRNAGASY | 94 | RSAAYSRSSEVYTGKDE YYY | 101 | 275 |

L16G10 Humanized Variants

| Clone name | CDR1 | SEQ ID NO | CDR2 | SEQ ID NO | CDR3 | SEQ ID NO | SEQ VHH ID NO |
|---|---|---|---|---|---|---|---|
| hz16G10v1 | GRPFSSSAMG | 87 | AVSRNGGSSY | 95 | RSAAYSRSSETYTEKHD YTY | 102 | 277 |
| hz16G10v2 | GRPFSSSAMG | 87 | AVSRNGGSSY | 95 | RSAAYSRSSETYTEKHD YTY | 102 | 278 |
| hz16G10v3 | GRPFSSSAMG | 87 | AVSRNGGSSY | 95 | RSAAYSRSSETYTEKHD YTY | 102 | 279 |
| hz16G10v4 | GRPFSSSAMG | 87 | AVSRQGGSSY | 96 | RSAAYSRSSETYTEKHD YTY | 102 | 280 |
| hz16G10v5 | GRPFSSSAMG | 87 | AVSRGGGSSY | 97 | RSAAYSRSSETYTEKHD YTY | 102 | 281 |
| hz16G10v6 | GRPFSSSAMG | 87 | AVSRNAGSSY | 98 | RSAAYSRSSETYTEKHD YTY | 102 | 282 |
| hz16G10v7 | GRPFSSSAMG | 87 | AVSRNTGSSY | 99 | RSAAYSRSSETYTEKHD YTY | 102 | 283 |
| hz16G10v8 | GRPFSSSAMG | 87 | AVSRNGGSSY | 95 | RSAAYSRSSETYTEKHD YTY | 102 | 284 |
| hz16G10v9 | GRPFSSSAMG | 87 | AVSRNGGSSY | 95 | RSAAYSRSSETYTEKHD YTY | 102 | 285 |
| hz16G10v10 | GRPFSSSAMG | 87 | AVSRNAGSSY | 98 | RSAAYSRSSETYTEKHD YTY | 102 | 286 |
| hz16G10v11 | GRPFSSYAMG | 86 | AVSRNAGSSY | 98 | RSAAYSRSSETYTEKHD YTY | 102 | 287 |

Humanized variant of the 5T4 sdAbs were tested for their ability to bind 5T4 expressing cells substantially as described in Example 2, and binding was compared to the parental sdAb. 5T4 expressing T47D cells were used in these studies. Results are shown in FIGS. 2A-2F, which confirm binding of the humanized variants. In some cases, binding was increased compared to the parental sdAb.

Example 4: Method of Producing 5T4-Targeted Constrained CD3 Binding Proteins Multispecific polypeptide constructs were generated containing a disulfide stabilized anti-CD3 Fv binding region that exhibits constrained CD3 binding, a heterodimeric Fc domain, and one or more 5T4 sdAb described above positioned amino-terminally relative to the Fc region and/or carboxy-terminally relative to the CD3 binding region. The multispecific constructs were generated in various configurations, as shown in FIG. 3A-3E. In some cases, the constrained CD3 engaging constructs contained at least one co-stimulatory receptor binding region (CRBR) positioned amino-terminally relative to the Fc region and/or carboxy-terminally relative to the CD3 binding region.

In the exemplary constructs, polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, an Fc hole polypeptide (e.g. set forth in SEQ ID NO: 112, or in some cases SEQ ID NO:114); a cleavable or a non-cleavable linker, such as one containing one or more substrate recognition sites for a protease; and a variable light (VL) domain of a dsFv anti-CD3 antibody (e.g. set forth in SEQ ID NO:75). The second polypeptide chain generally included in order, from the N-terminus to C-terminus, an Fc knob polypeptide (e.g. set forth in SEQ ID NO: 105, or in some cases SEQ ID NO: 109); the same cleavable linker or the same non-cleavable linker as the first polypeptide chain; and a variable heavy domain of a dsFv anti-CD3 antibody (e.g. set forth in SEQ ID NO:47). The constructs were generated with the exemplary non-cleavable linker, GGGGGSGGGGGSGGGGGS (SEQ ID NO: 127), or the exemplary cleavable linker, GGSGGGGIEPDIGGSGGS (SEQ ID NO:171) containing a substrate recognition site for granzyme B. One or both of the polypeptide chains additionally encoded one or more 5T4 sdAb amino terminal to the Fc domain and/or carboxy terminal to the CD3 binding region, and/or a co-stimulatory receptor binding domain amino terminal to the Fc domain and/or carboxy terminal to the CD3 binding region, in various configurations.

Separate plasmids encoding each chain of a heterodimeric constrained CD3 binding protein were transiently transfected at an equimolar ratio into mammalian cells (either HEK293 or CHO) using polyethylenimine. Recombinant protein secreted into the supernatant was collected after 3-7 days, and purified by protein A chromatography, followed by either preparative size exclusion chromatography (SEC) or flow-through hydrophobic interaction chromatography The method favored production of heterodimeric multi-specific polypeptide constructs, containing properly paired species of heterodimeric Fc and the disulfide stabilized anti-CD3 Fv as described (e.g. anti-CD3 VH with the mutation G44C as set forth in SEQ ID NO: 47 and VL with the mutation G100C as set forth in SEQ ID NO: 293). Purified heterodimeric constrained CD3 binding protein was stable and did not accumulate cross-paired species upon prolonged incubation at 4° C. or increased protein concentration.

Table E3 sets forth exemplary generated constrained multispecific constructs. The 5T4 binding domains of cx3315 are FAB positioned N and C-terminally within the constrained CD3 engaging construct.

TABLE E3

| 5T4 VHH Constrained Multispecific Constructs | | | | | | |
|---|---|---|---|---|---|---|
| Construt # | Chain | N-term sdAb (Target) (SEQ ID NO) | Fc | Linker | CD3 Binding Domain | C-term sdAb (Target) (SEQ ID NO) |
| cx3253 | 1 | 12E9 (5T4) (245) | hFc-Knob | IEPDI | Con1 VH | 7E1 (5T4) (294) |
|  | 2 | — | hFc-Hole | IEPDI | Con1 VL | RH3v5-1 (41BB) (210) |
| cx3497 | 1 | 12E9 (5T4) (245) | hFc-Knob | IEPDI | Con1 VH | 16G10 (5T4) (276) |
|  | 2 | — | hFc-Hole | IEPDI | Con1 VL | RH3v5-1 (41BB) (210) |
| cx3499 | 1 | 12E9 (5T4) (245) | hFc-Knob | IEPDI | Con1 VH | 14B5 (5T4) (255) |
|  | 2 | — | hFc-Hole | IEPDI | Con1 VL | RH3v5-1 (41BB) (210) |
| cx4224 | 1 | 14F4 (5T4) (245) | hFc-Knob | IEPDI | Con1 VH | 7E1 (5T4) (294) |
|  | 2 | — | hFc-Hole | IEPDI | Con1 VL | RH3v5-1 (41BB) (210) |
| cx3262 | 1 | 12E9 (5T4) (245) | hFc-Knob | IEPDI | Con1 VH | 7E1 (5T4) (294) |
|  | 2 | — | hFc-Hole | IEPDI | Con1 VL | — |
| cx4910 | 1 | hz12E9v4 (5T4) (249) | xELL-Knob | (G5S)3 | Con1 VH | hz14B5v15 (5T4) (270) |
|  | 2 | — | xELL-Hole | (G5S)3 | Con1 VL | RH3v5-1 (41BB) (210) |
| cx4912 | 1 | hz14B5v15 (5T4) (270) | xELL-Knob | (G5S)3 | Con1 VH | hz12E9v4 (5T4) (249) |
|  | 2 | — | xELL-Hole | (G5S)3 | Con1 VL | RH3v5-1 (41BB) (210) |
| cx4911 | 1 | hz12E9v4 (5T4) (249) | xELL-Knob | (G5S)3 | Con1 VH | hz14B5v15 (5T4) (270) |
|  | 2 | — | xELL-Hole | (G5S)3 | Con1 VL | — |
| cx4913 | 1 | hz14B5v15 (5T4) (270) | xELL-Knob | (G5S)3 | Con1 VH | hz12E9v4 (5T4) (249) |
|  | 2 | — | xELL-Hole | (G5S)3 | Con1 VL | — |
| cx3546 | 1 | 12E9 (5T4) (245) | hFc-Knob | IEPDI | Con1 VH | 14B5 (5T4) (255) |
|  | 2 | — | hFc-Hole | IEPDI | Con1 VL | — |
| cx3547 | 1 | 12E9 (5T4) (245) | hFc-Knob | IEPDI | Con1 VH | 16G10 (5T4) (276) |
|  | 2 | — | hFc-Hole | IEPDI | Con1 VL | — |
| cx3264 | 1 | 4D3 (5T4) (302) | hFc-Knob | IEPDI | Con1 VH | 4D3 (5T4) (302) |
|  | 2 | — | hFc-Hole | IEPDI | Con2 VL | RH3v5-1 (41BB) (210) |

(HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

Example 5: Comparison of Binding to Isolated Primary T-Cells Vs. 5T4-Expressing Cancer Cells Binding of exemplary 5T4-targeting constrained CD3 engaging constructs set forth in Table E3 to CD3 on the surface of primary T cells and 5T4 expressing cells (Ovcar-5) was assessed by flow cytometry. The T cells were primary T-cells that were negatively enriched from PBMCs isolated from healthy human donor leukopaks. Bound construct was detected with fluorophore-conjugated secondary antibodies specific for the human Fc (anti-human IgG APC secondary antibody) and binding was measured by flow cytometry. Cells incubated with secondary antibody only served as negative controls. Cells incubated with secondary antibody only served as negative controls.

Figure 4A:
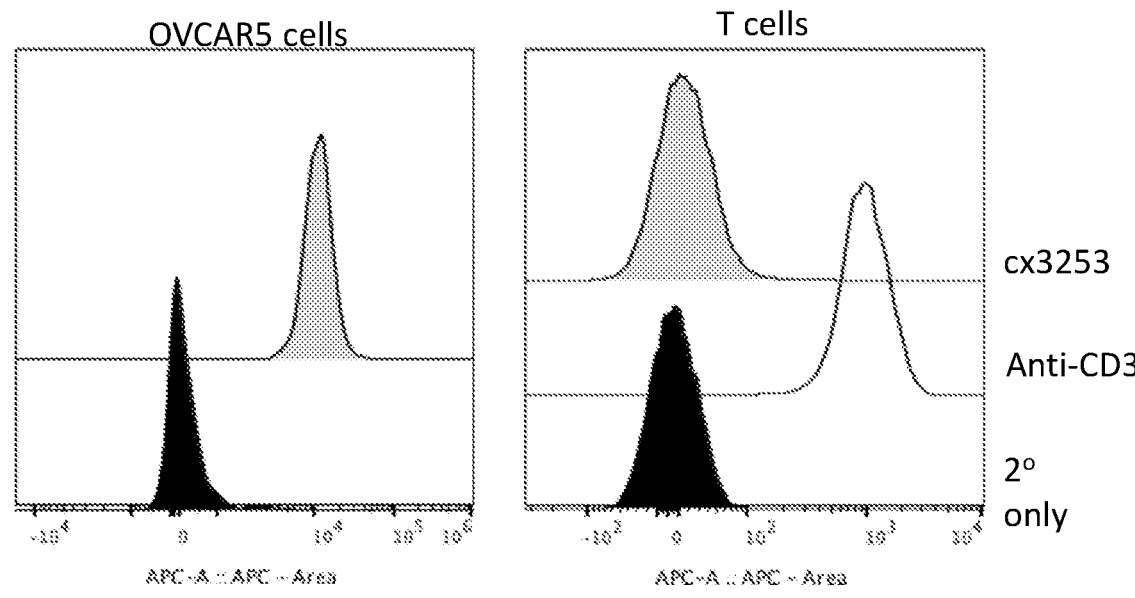
FIGS. 4A-4M depict the binding of various 5T4-target constrained CD3 engaging constructs to the 5T4 positive Ovcar-5 cell line (top left) and the lack of binding to primary human T-cells (top right). The bottom panel shows a titration of the 5T4-target constrained CD3 engaging constructs to compare binding to Ovcar-5 and primary human T-cells. Binding was assessed by flow cytometry using an anti-human IgG APC secondary antibody. The histograms display the normalized cell counts vs fluorescence at 200 nM of each construct.
Figure 4A:
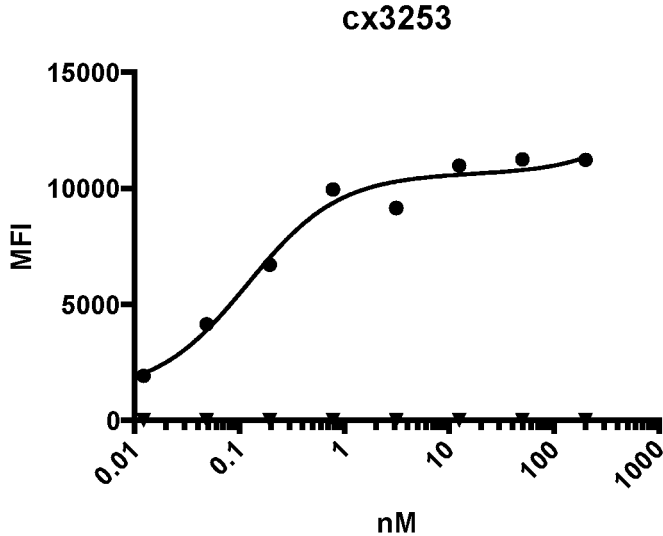
Figure 4B:
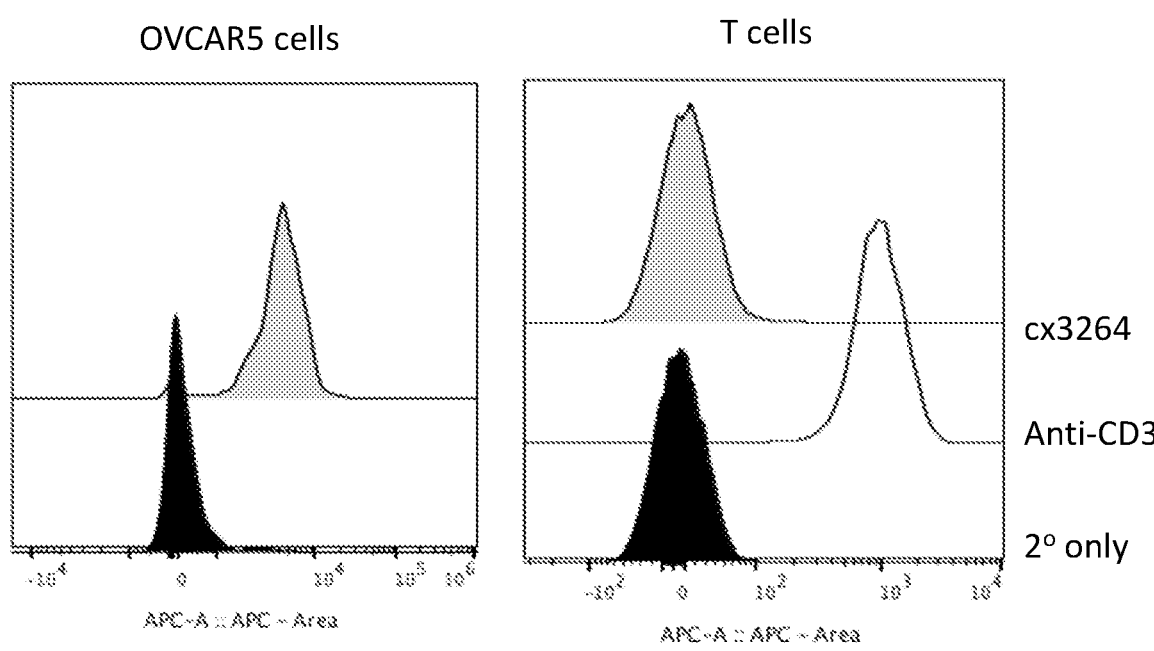
Figure 4B:
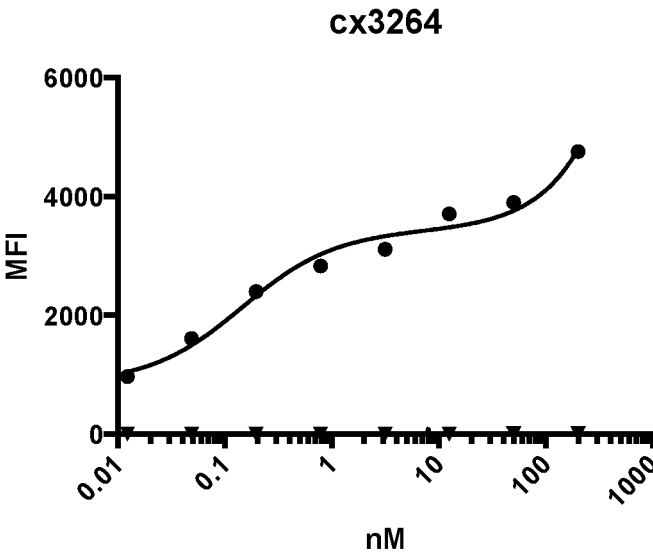
Figure 4C:
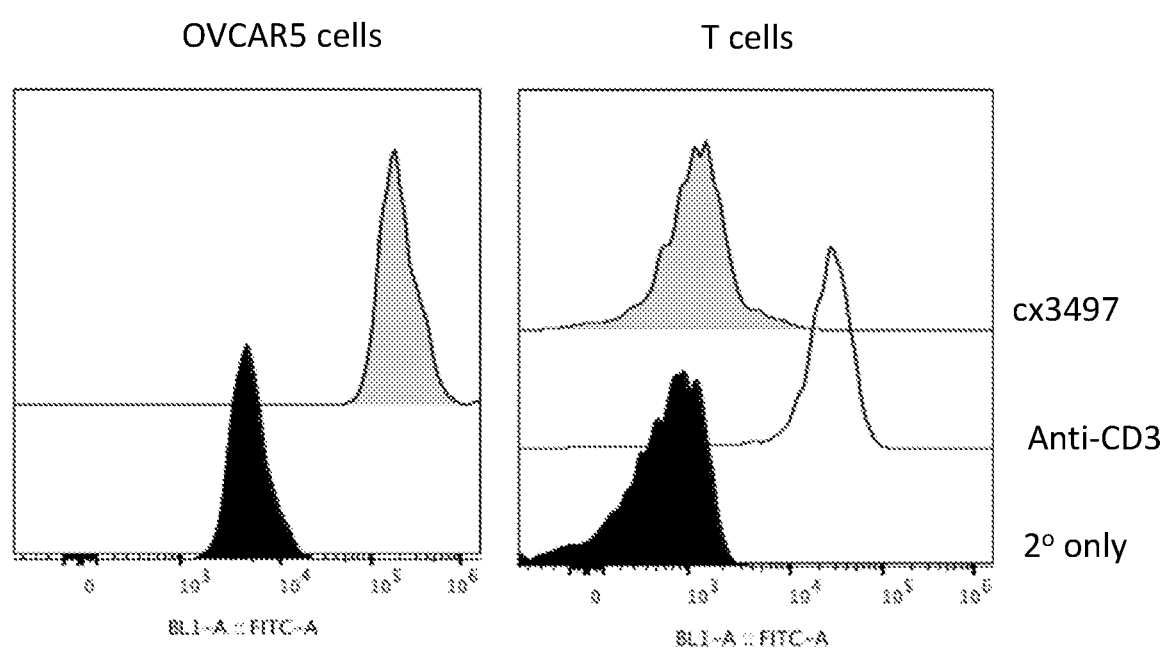
Figure 4C:
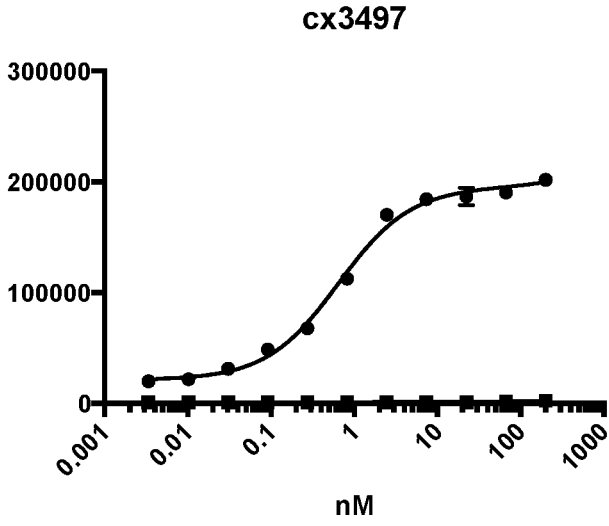
Figure 4D:
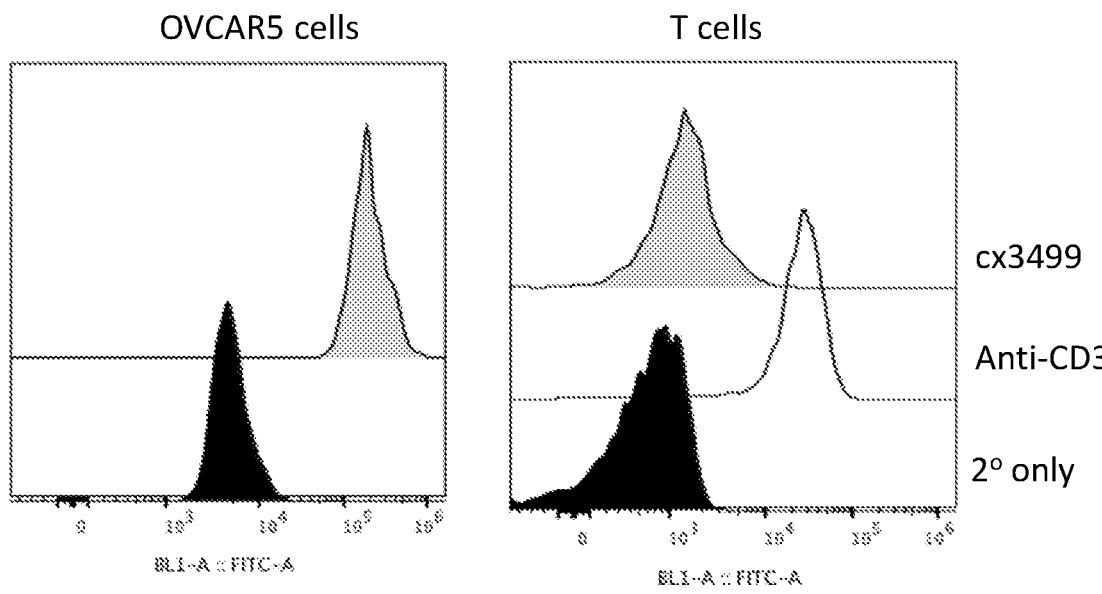
Figure 4D:
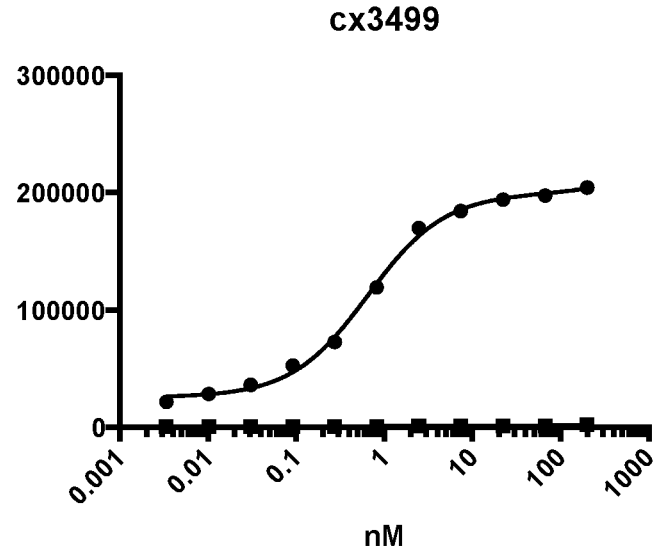
Figure 4E:
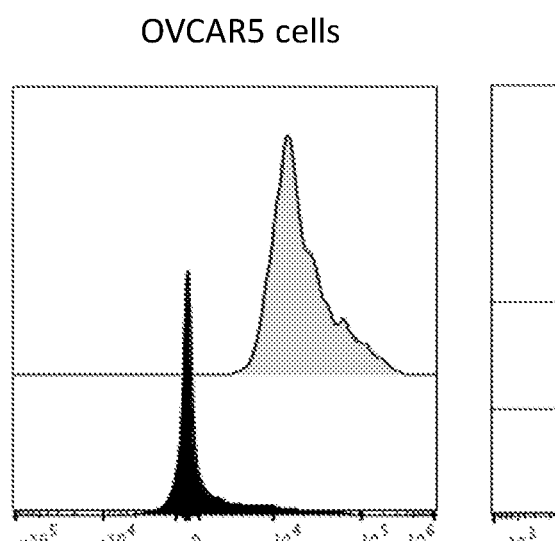
Figure 4E:
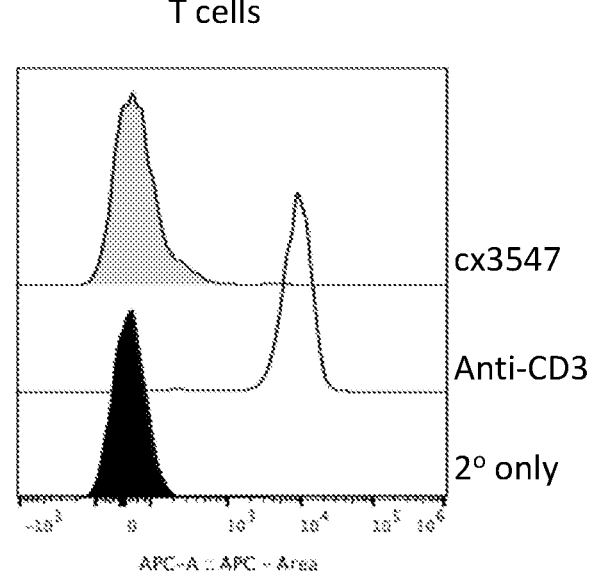
Figure 4E:
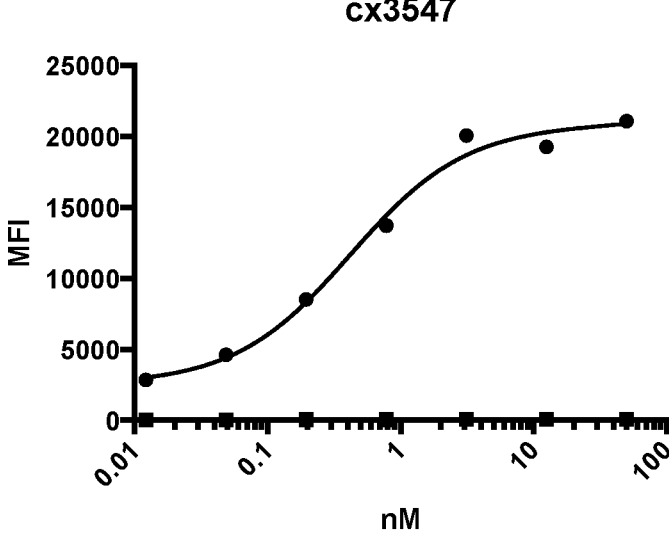
Figure 4F:
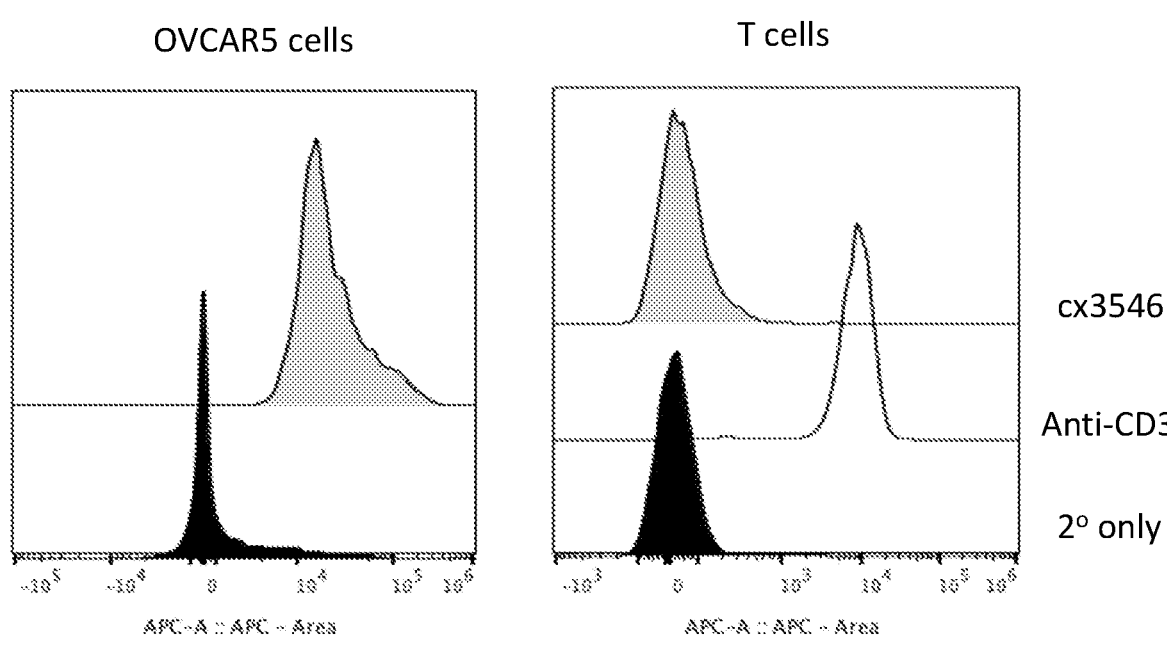
Figure 4F:
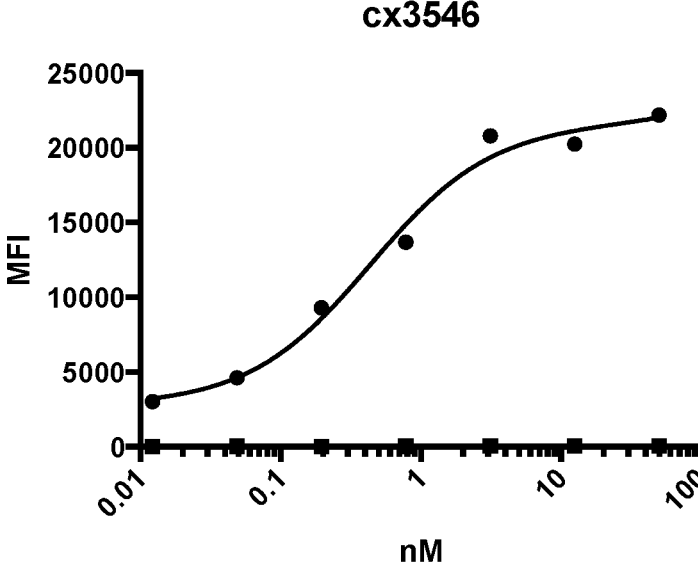
Figure 4G:
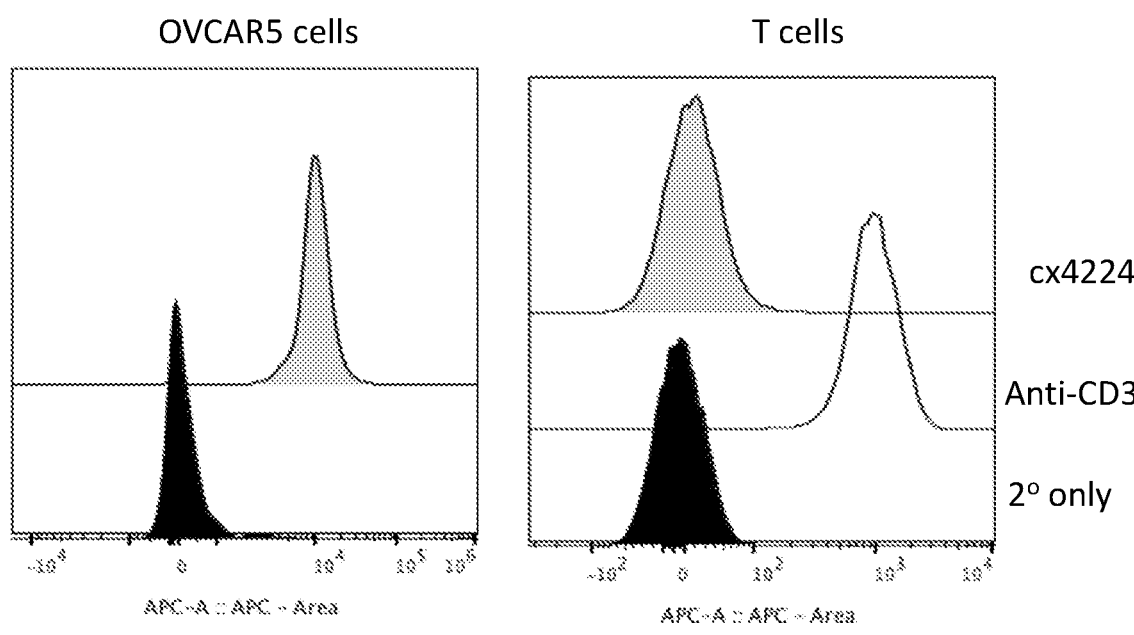
Figure 4G:
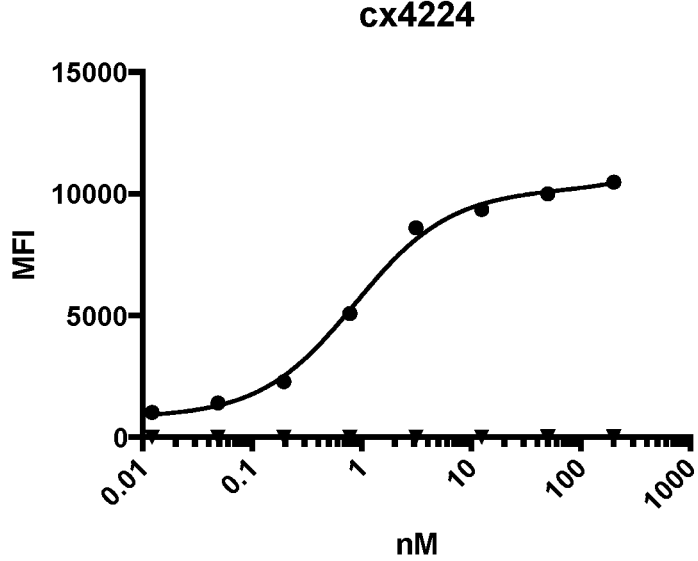
Figure 4H:
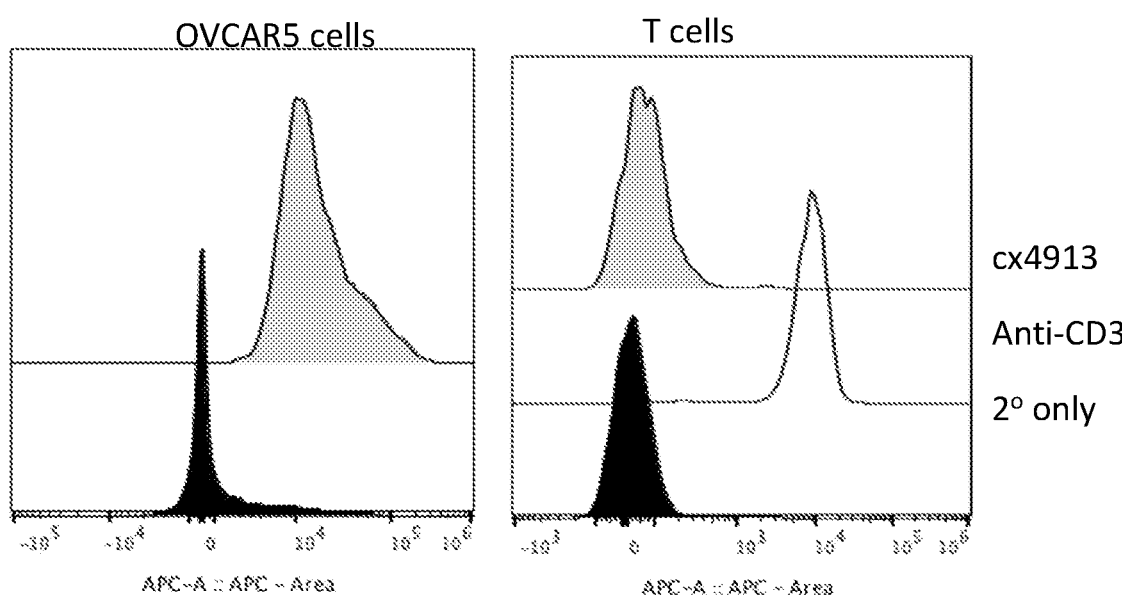
Figure 4H:
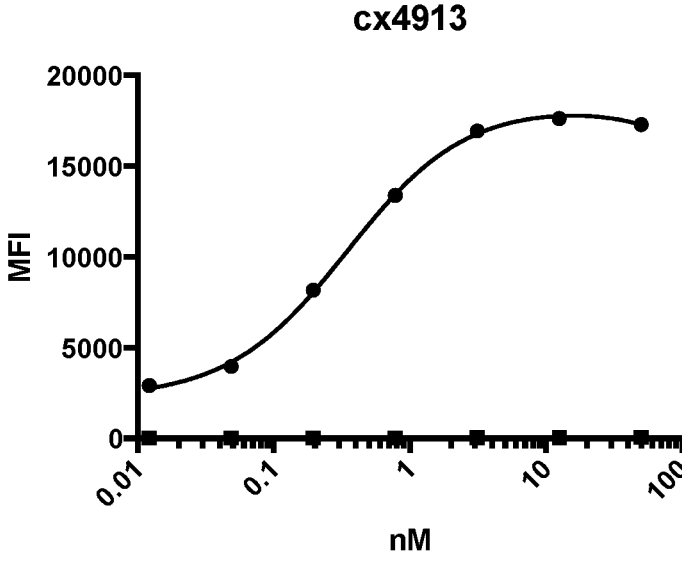
Figure 4I:
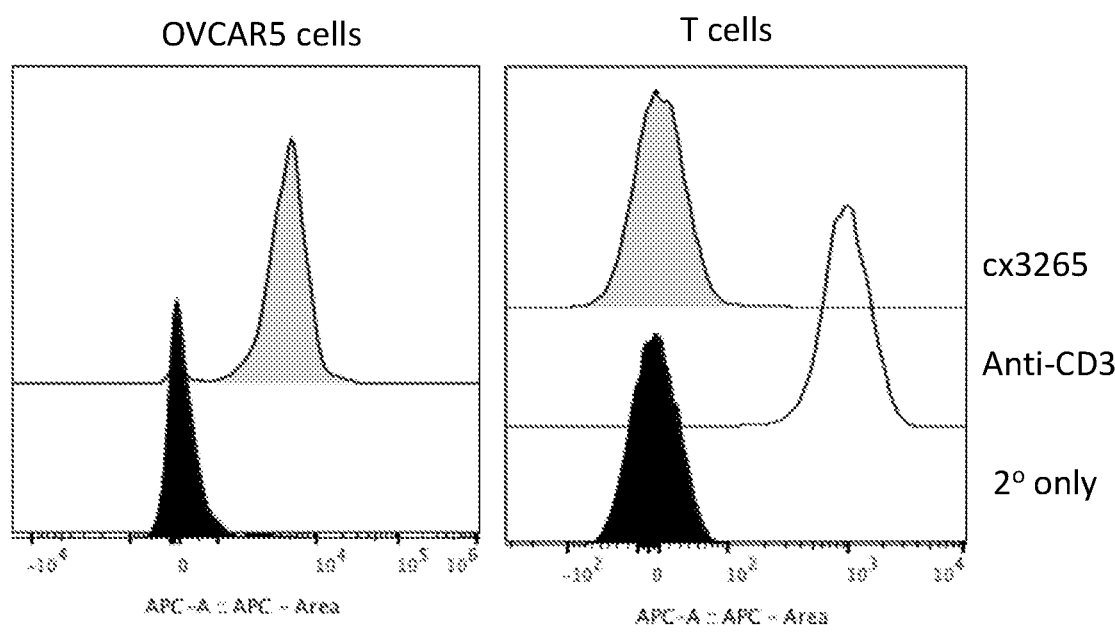
Figure 4I:
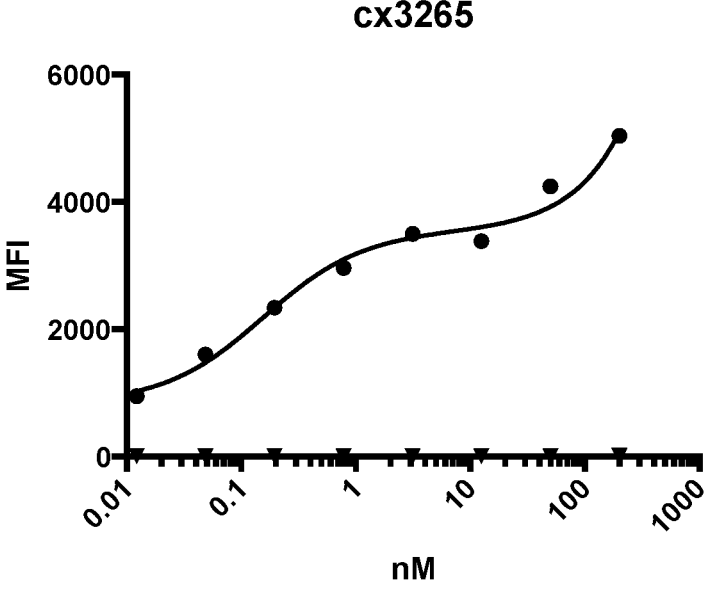
Figure 4J:
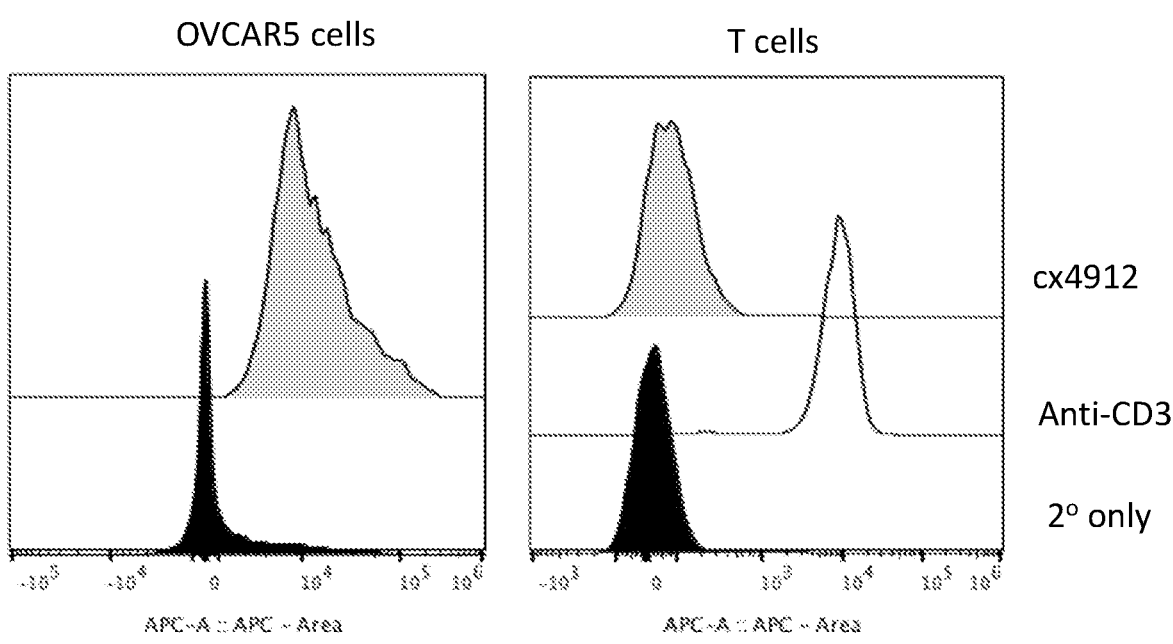
Figure 4J:
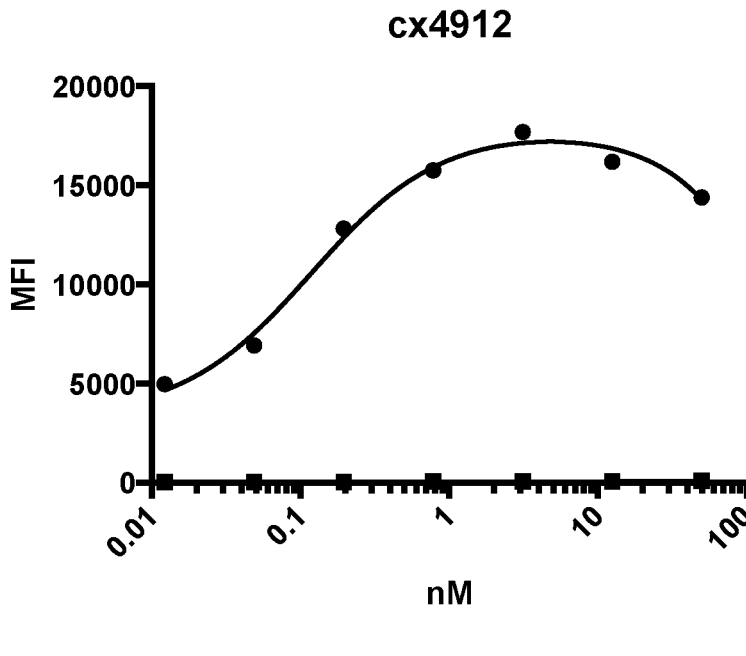
Figure 4K:
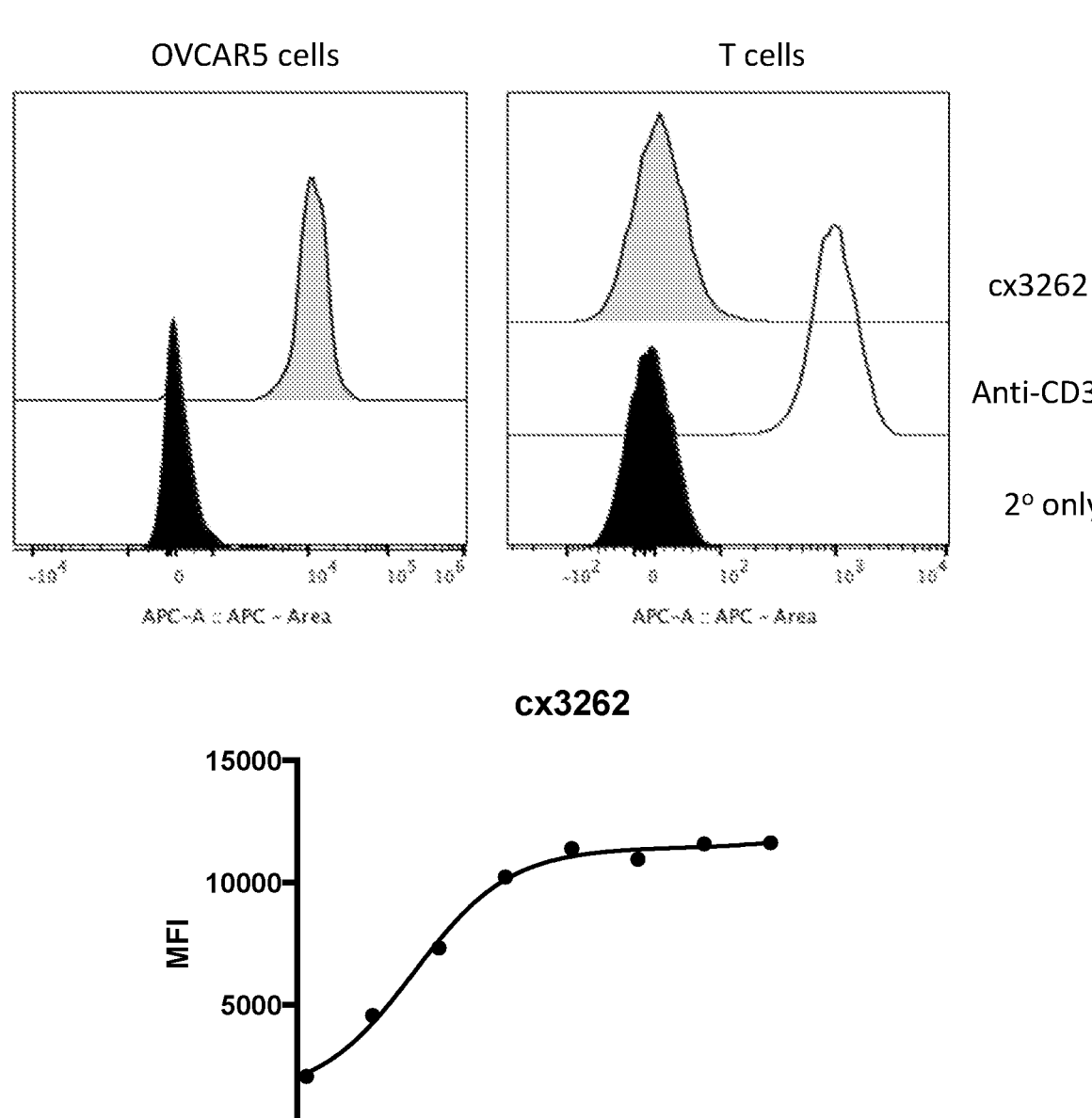
Figure 4L:
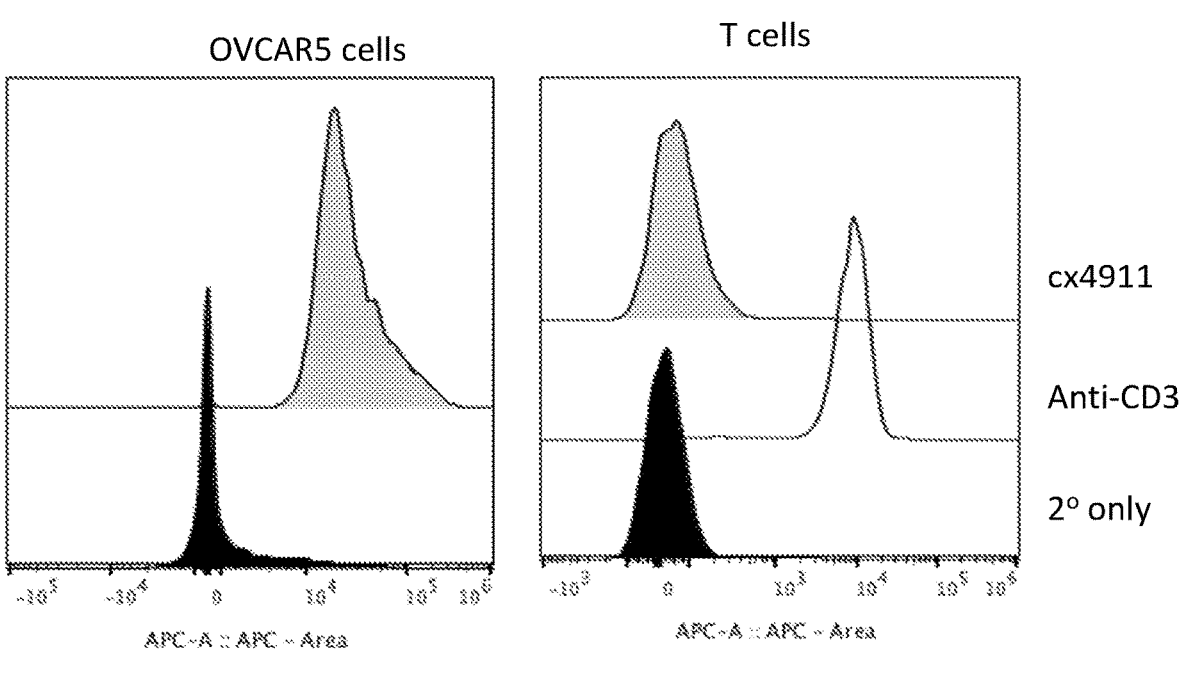
Figure 4L:
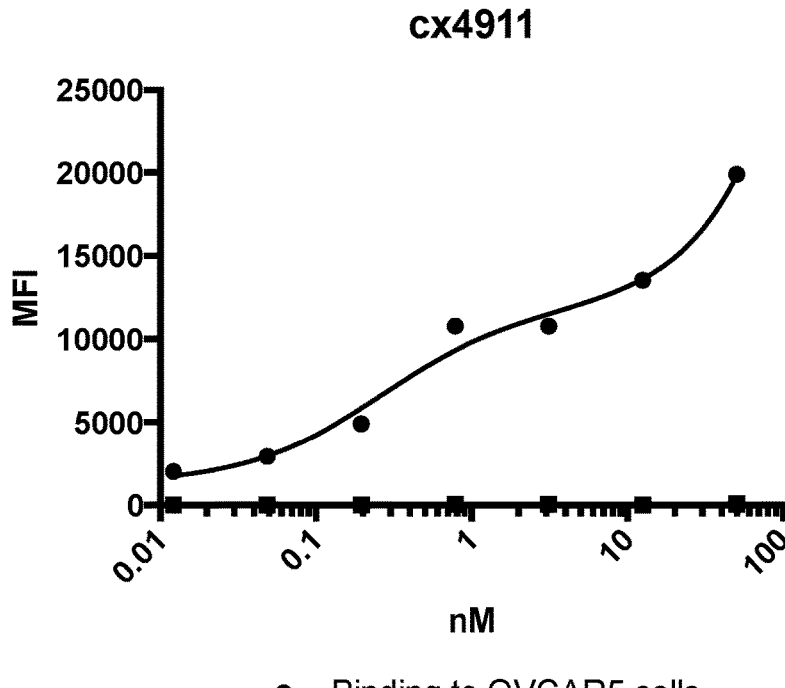
Figure 4M:
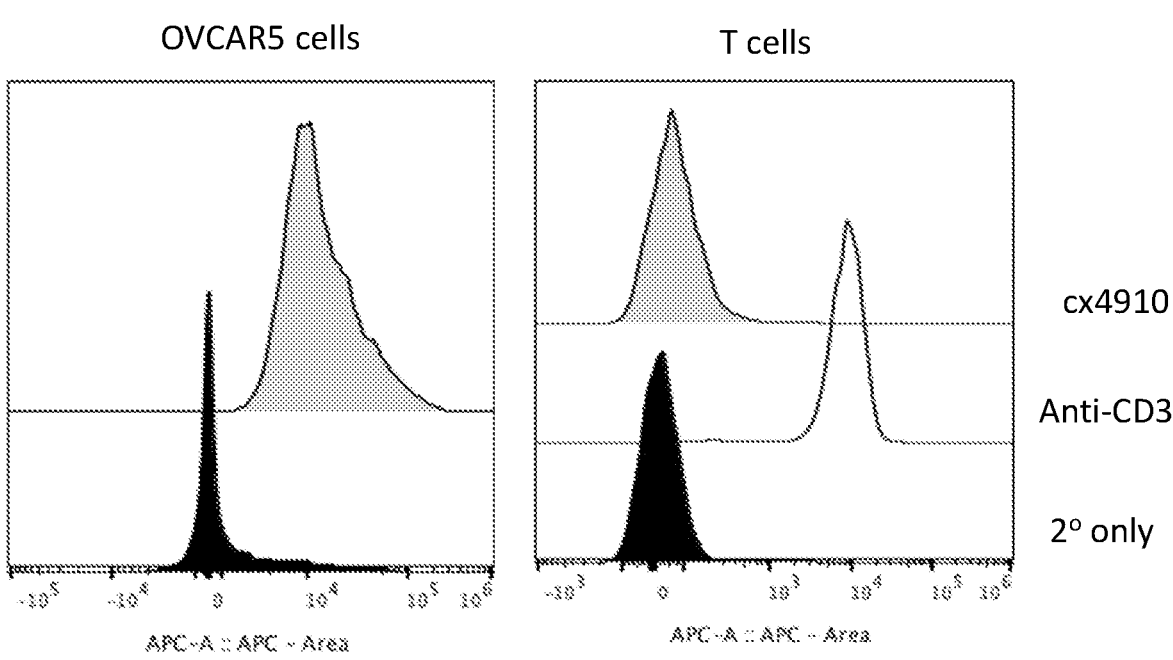
Figure 4M:
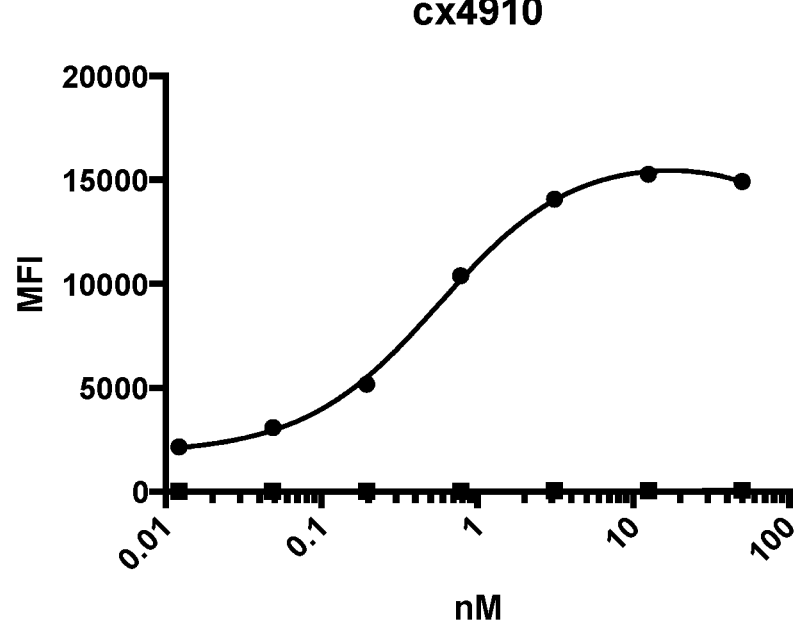

The results, from flow cytometry histograms displaying normalized cell counts versus fluorescence at 200 nM of each construct, are shown in FIG. 4A (cx3253), FIG. 4B (cx3264), FIG. 4C (cx3497), FIG. 4D (cx3499), FIG. 4E (cx3547), FIG. 4F (cx3546), FIG. 4G (cx4224), FIG. 4H (cx4913), FIG. 4I (cx3265), FIG. 4J (cx4912), FIG. 4K (cx3262), FIG. 4L (cx4911), and FIG. 4M (cx4910). As shown, the representative 5T4-targeting constrained CD3 engagers were found to bind Ovcar-5cells expressing 5T4 (top left and bottom panels of each of the figures). However, as shown in the top right and bottom panels of each of the figures, the same constructs were not able to bind to T cells in isolation.

Table E4 summarizes the affinity of exemplary molecules for 5T4 or CD3, as determined from flow cytometry, in these studies.

TABLE E4

| Construct Binding Affinity | | |
| --- | --- | --- |
| Construct # | Affinity 5T4 | Affinity CD3 |
| cx3253 | 0.120 nM | >200 nM |
| cx3497 | 0.646 nM | >200 nM |
| cx3499 | 0.653 nM | >200 nM |
| cx4224 | 0.871 nM | >200 nM |
| cx3262 | 0.116 nM | >200 nM |
| cx4910 | 0.575 nM | >200 nM |
| cx4912 | 0.119 nM | >200 nM |
| cx4911 | 0.259 nM | >200 nM |
| cx4913 | 0.348 nM | >200 nM |
| cx3546 | 0.436 nM | >200 nM |
| cx3547 | 0.419 nM | >200 nM |
| cx3264 | 0.145 nM | >200 nM |
| cx3265 | 0.156 nM | >200 nM |

Example 6: Assessment of 5T4-Dependent CD3 Reporter T Cell Activation Using a Reporter Assay This example describes assessment of the ability of various representative 5T4-targeting constrained CD3 engaging constructs to activate a CD3 NFAT reporter Jurkat cell line in co-culture with 5T4-expressing Ovcar-5 cells or a 5T4 negative cell line, CCFR-CEM. In the reporter assay, engagement of CD3 in the Jurkat cells results in NFAT signaling and production of green fluorescence. These assays were used to demonstrate that while T-cell binding via the CD3-binding domain is restricted or inhibited on isolated T-cells (as shown in Example 5), once the 5T4-targeted constrained CD3 engaging constructs provided herein are bound to a cognate antigen they are capable of engaging T-cells and mediating T-cell activation.

Figure 5A:
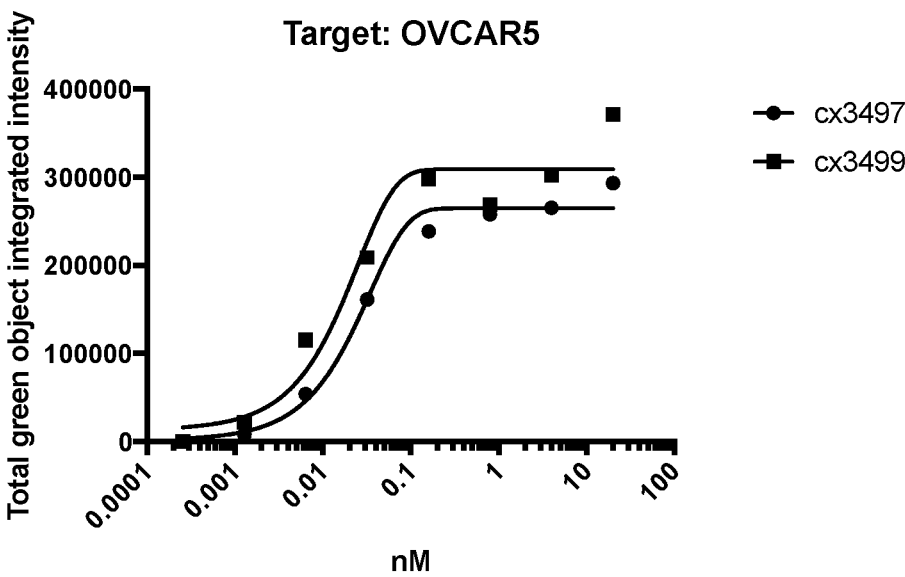
FIGS. 5A-5F depict the ability of 5T4-targeted constrained CD3 engaging constructs to elicit 5T4-dependent T-cell activation. A Jurkat CD3 NFAT-GFP reporter cell line was used to monitor T-cell activation. Ovcar-5 cells (FIGS. 5A, 5C, 5E) were used as antigen-positive cells and CCRF-CEM cells (FIGS. 5B, 5D, 5F) were used as antigen-negative cells.
Figure 5B:
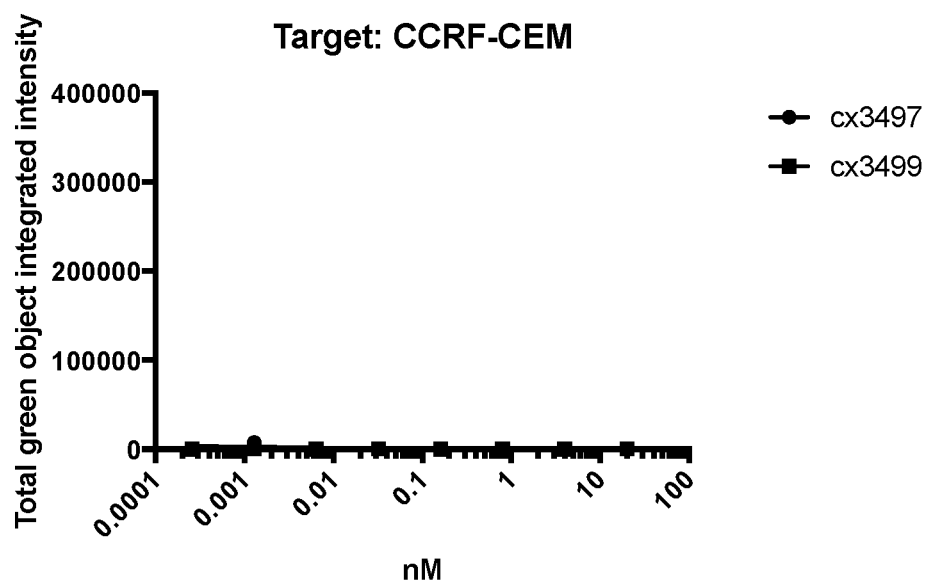
Figure 5C:
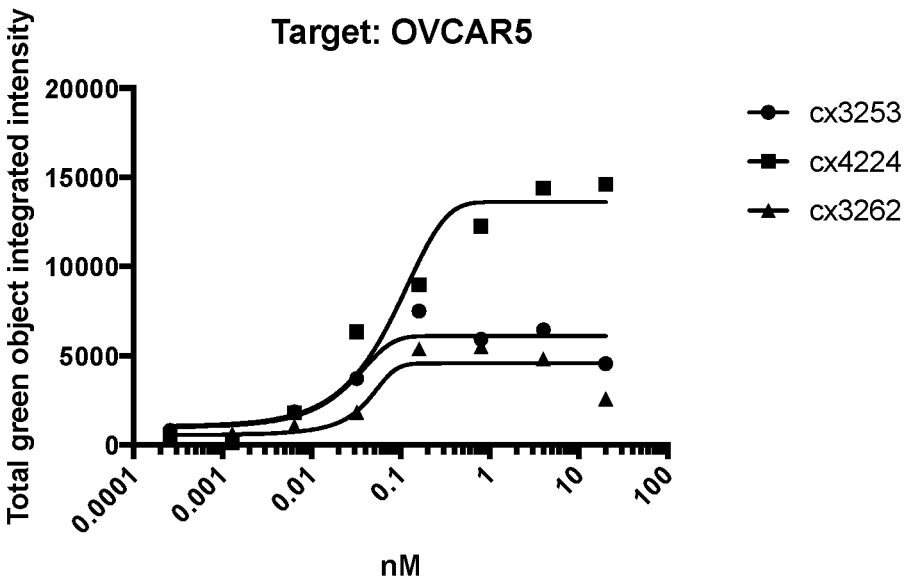
Figure 5D:
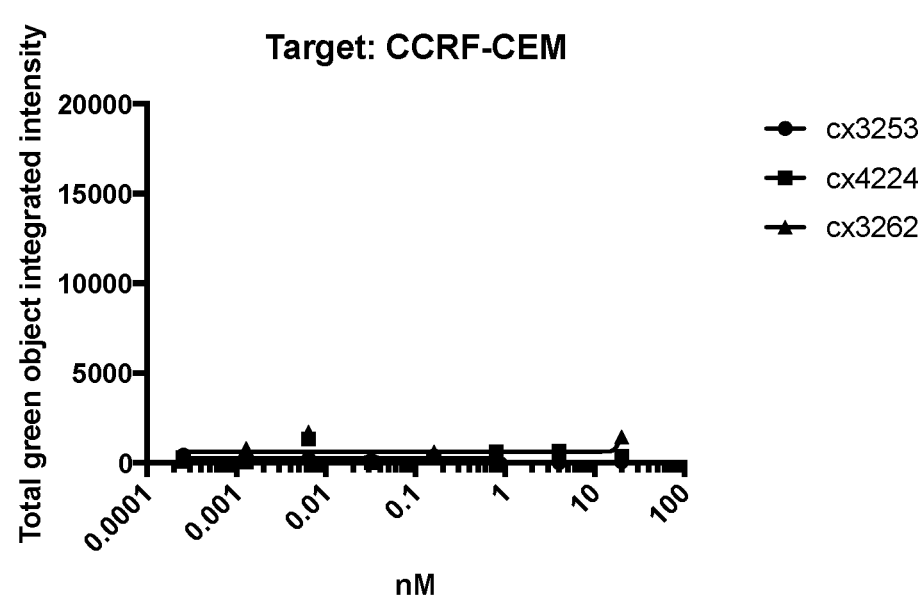
Figure 5E:
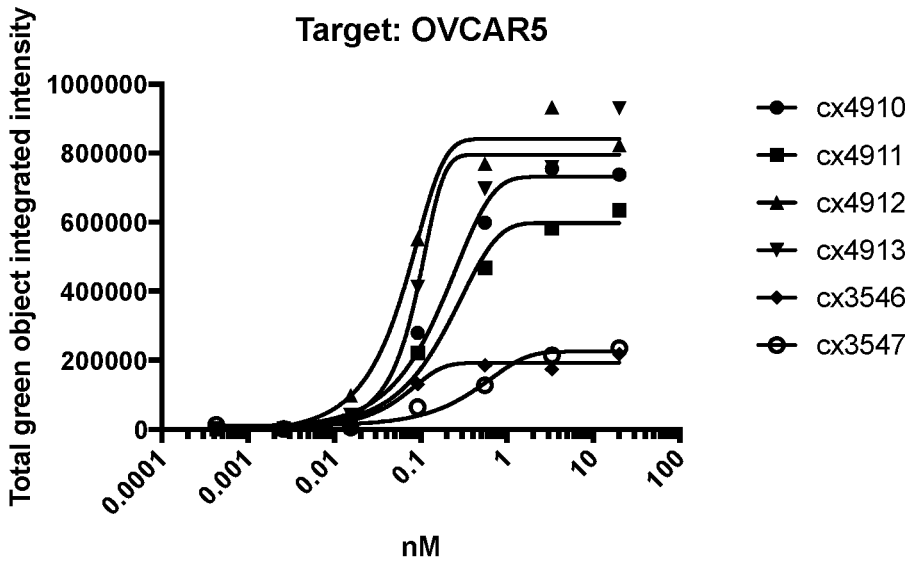
Figure 5F:
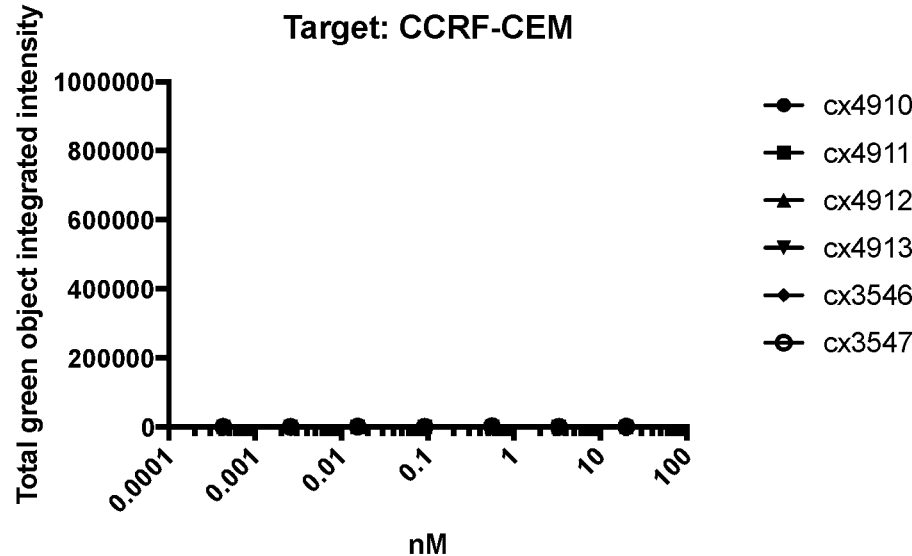

Antigen targeting constrained CD3 engaging constructs were titrated onto co-cultures of 5T4-expressing target cells, Ovcar-5, and engineered Jurkat cells that expressed NFAT-driven green fluorescence protein (GFP). For reporter assays utilizing adherent target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte ZOOM system and CD3 reporter cell activation was determined by measuring total green object integrated intensity. As shown, assessed 5T4-targeted constrained CD3 engaging constructs induced reporter activity in cultures containing 5T4 positive cells (FIGS. 5A, 5C, and 5E), but no measurable reporter activity was observed when T cells were cultured with 5T4 negative cell lines (CCRF-CEMs) (FIGS. 5B, 5D, and 5F).

Example 7: Assessment of Functional Activity

This Example describes the assessment and characterization of exemplary generated 5T4-target constrained CD3 engaging constructs in human primary T cell in vitro assays.
A. T Cell-Mediated Cytotoxicity Target cells were fluorescently labeled with CytoID red. For cytotoxicity assays utilizing adherent target cells Ovcar-5 or CCRF-CEM, target cells were seeded, allowed to settle at room temperature for uniform distribution, and incubated for several hours at 37° C. to permit adherence prior to addition of other assay components. Primary T cells were negatively enriched from PBMCs isolated from healthy human donor leukopaks and added at a 10:1-40:1 T cell-to-target cell ratio. Green caspase-3/7 reagent was added, which fluorescently labeled nuclear DNA of cells undergoing apoptosis. Antibodies were titrated onto the co-culture and assay plates were serially imaged using an IncuCyte ZOOM system. Target cell death was determined by measuring total red/green overlap object area.

Figure 6A:
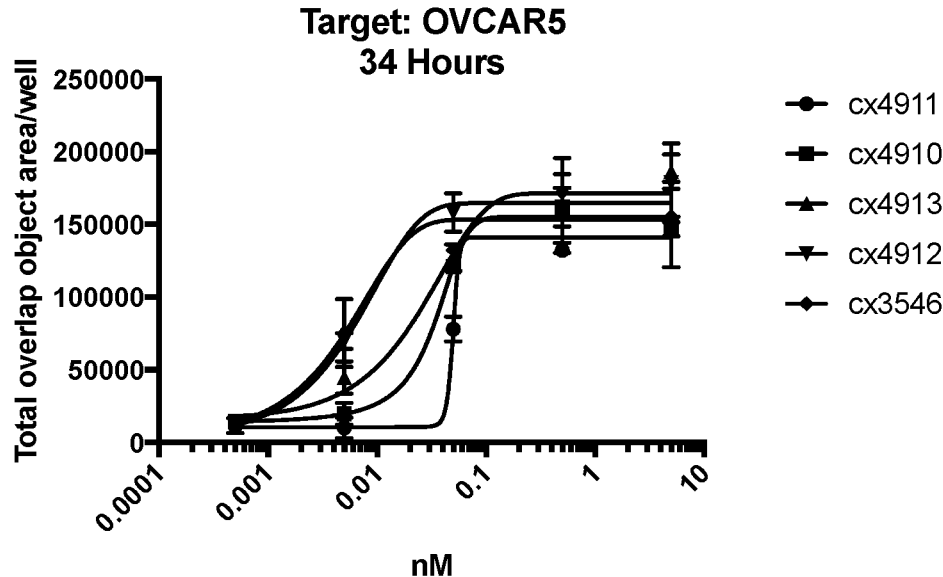
FIGS. 6A and 6B depict the ability of 5T4-targeted constrained CD3 engaging constructs to mediate antigen specific T-cell cytotoxicity on a 5T4 positive cell line, Ovcar-5 (FIG. 6A), and the lack of cytotoxicity directed toward a 5T4 negative cell line, CCRF-CEM (FIG. 6B).
Figure 6B:
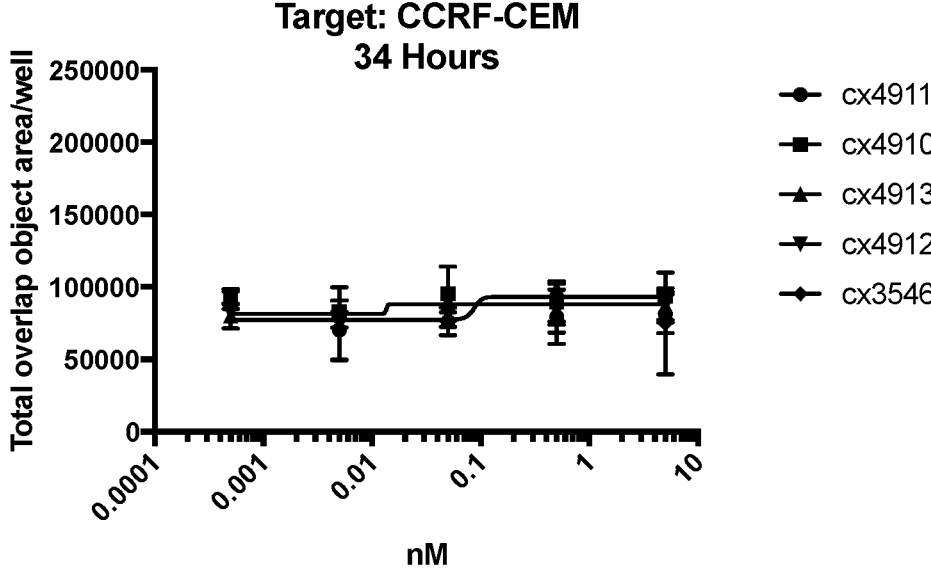
Figure 7A:
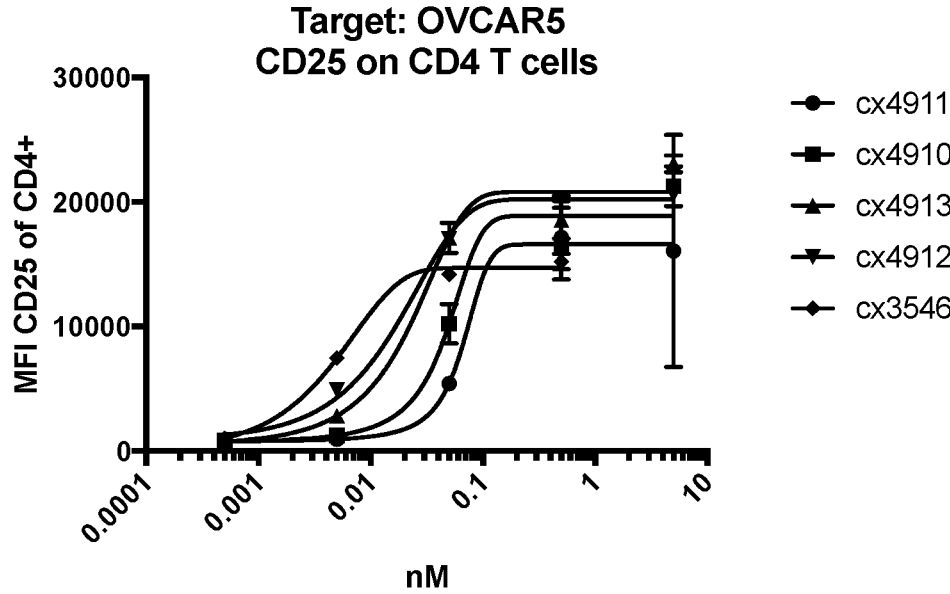
FIGS. 7A-7D depict the ability of 5T4-targeted constrained CD3 engaging constructs to mediate antigen specific T-cell activation on CD4 T cells (FIG. 7A-7B) and CD8 T cells (FIG. 7C-7D) as assessed by flow cytometry by analyzing the activation marker CD25. A 5T4 positive cell line, Ovcar-5, or a 5T4 negative cell line, CCRF-CEM, was used to assess cell activation mediated by exemplary 5T4-targeted constrained CD3 engaging constructs.
Figure 7B:
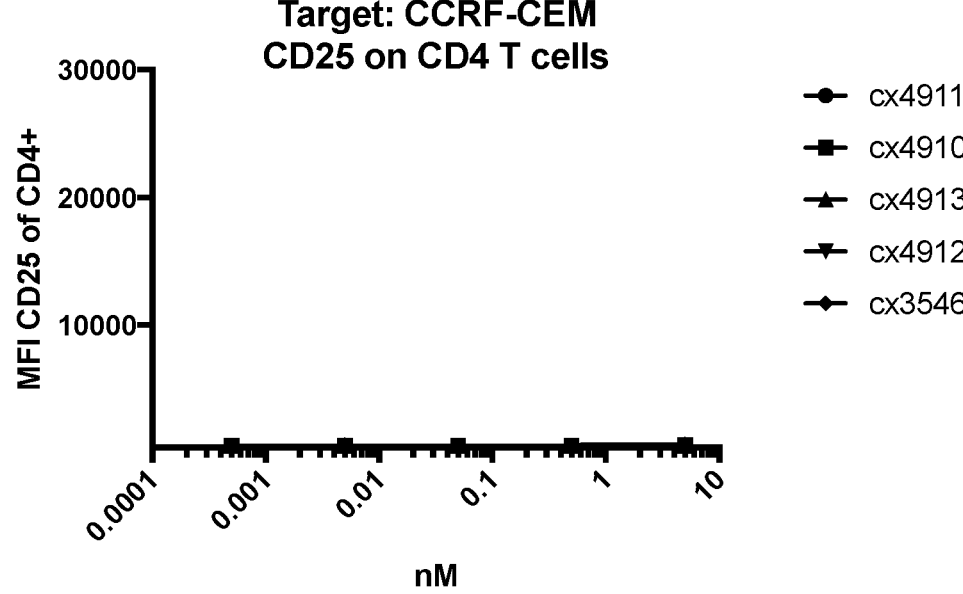
Figure 7C:
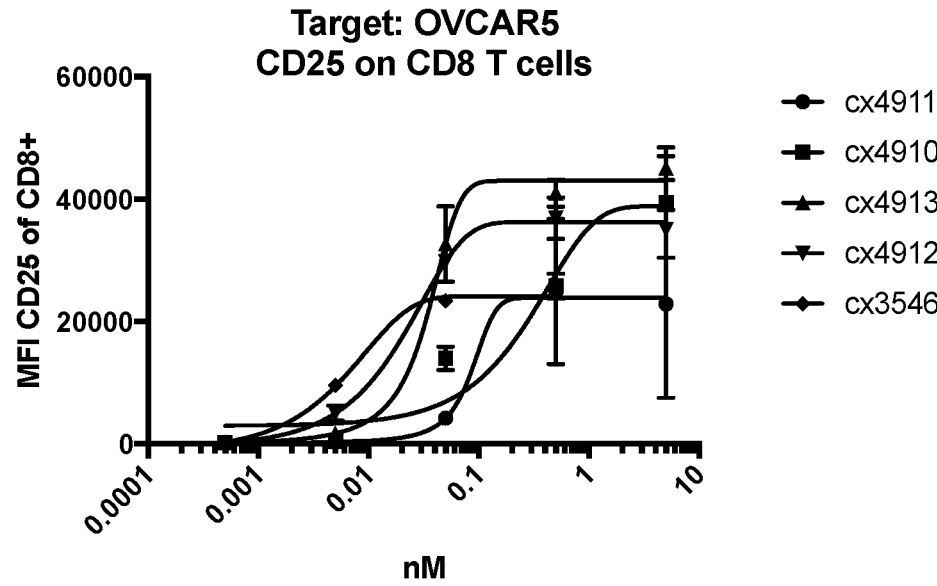
Figure 7D:
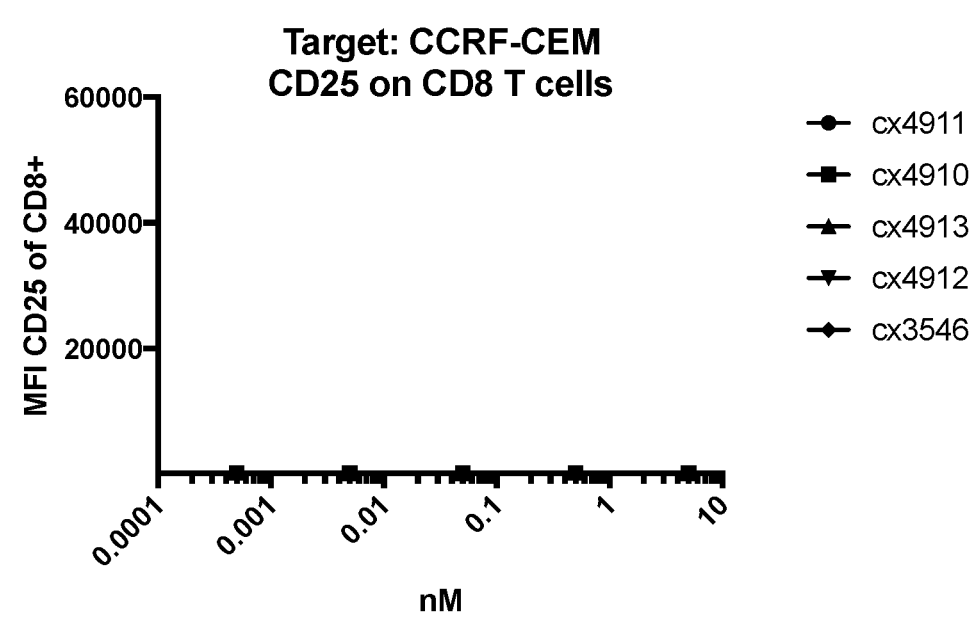
Figure 8A:
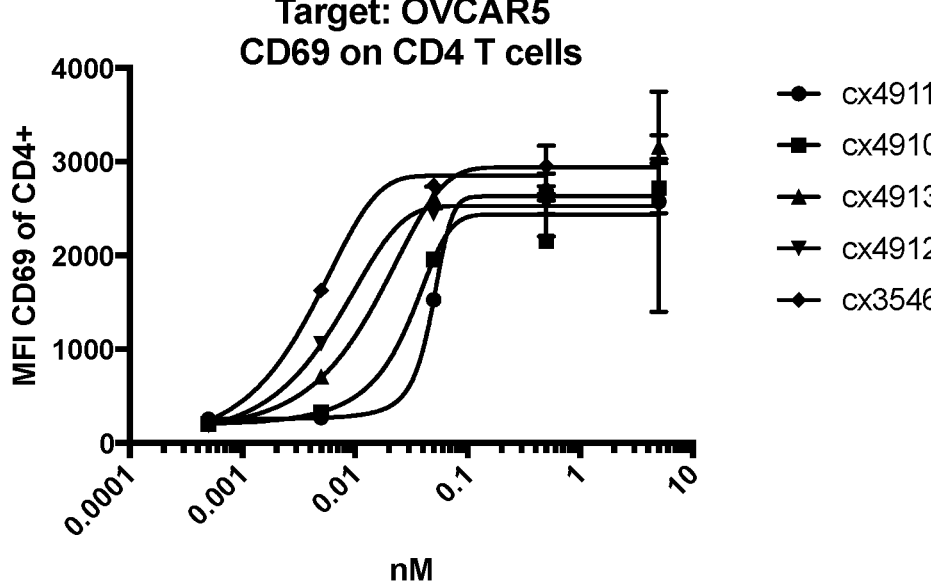
FIGS. 8A-8D depict the ability of 5T4-targeted constrained CD3 engaging constructs to mediate antigen specific T-cell activation on CD4 T cells (FIG. 8A-8B) and CD8 T cells (FIG. 8C-8D) as assessed by flow cytometry by analyzing the activation marker CD69. A 5T4 positive cell line, Ovcar-5, or a 5T4 negative cell line, CCRF-CEM, was used to assess cell activation mediated by exemplary 5T4-targeted constrained CD3 engaging constructs.
Figure 8B:
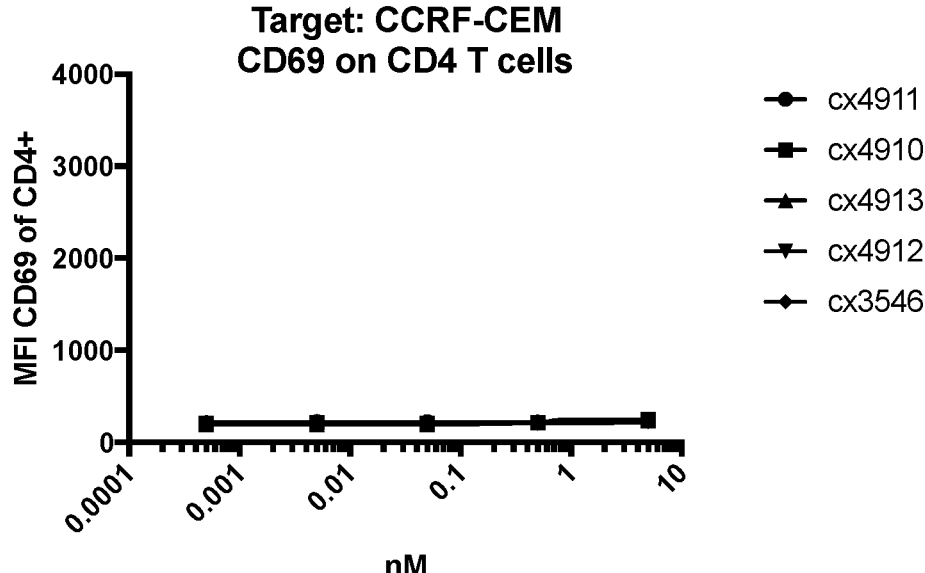
Figure 8C:
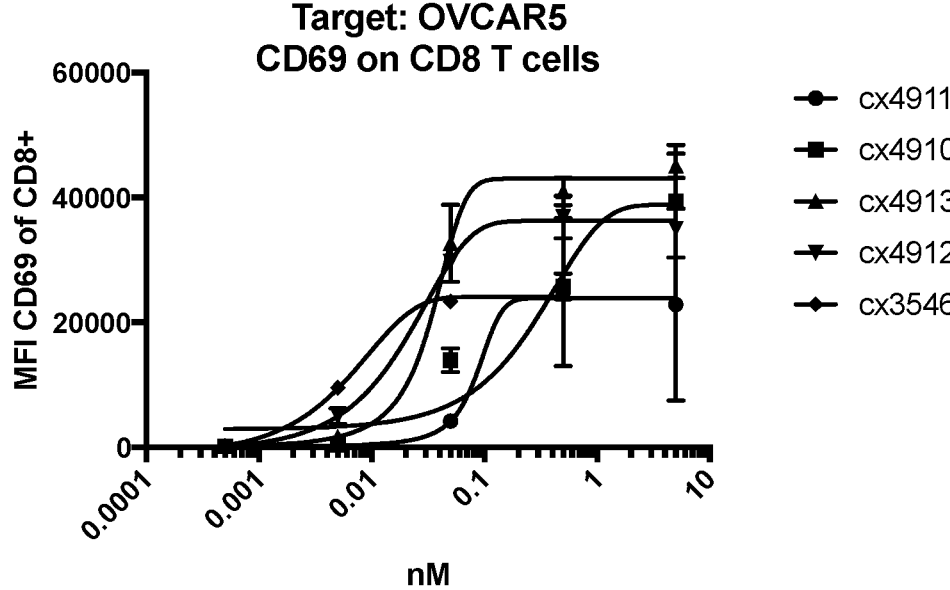
Figure 8D:
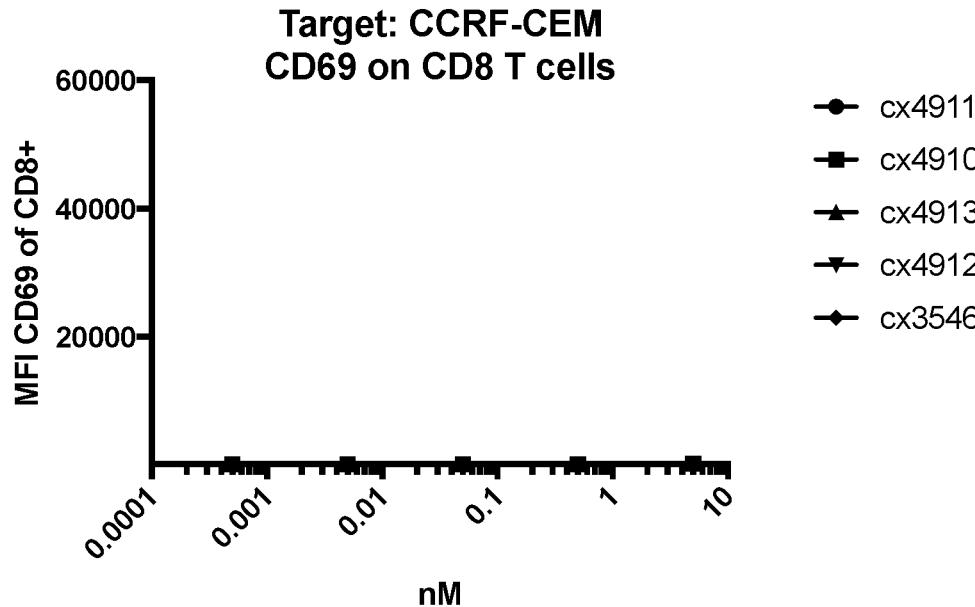
Figure 9A:
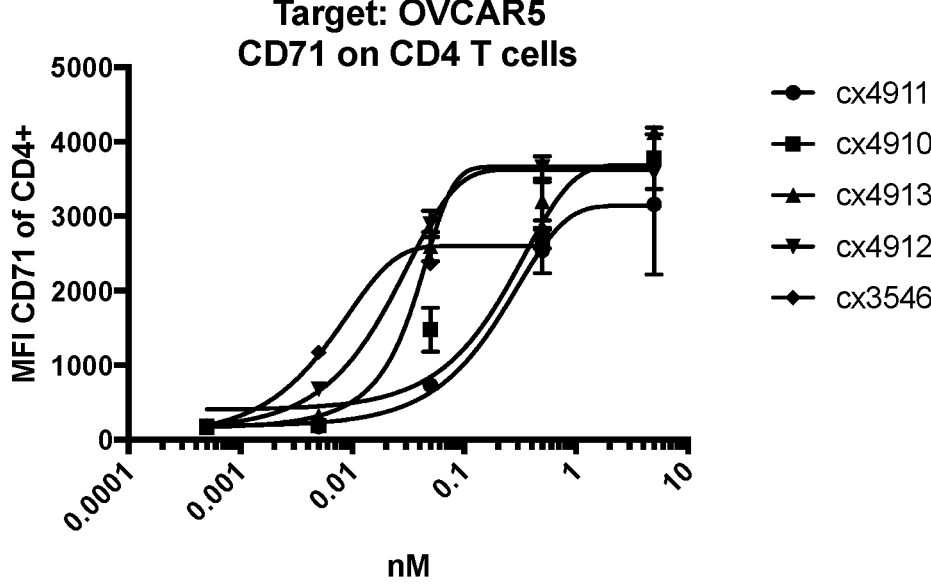
FIGS. 9A-9D depict the ability of 5T4-targeted constrained CD3 engaging constructs to mediate antigen specific T-cell activation on CD4 T cells (FIG. 9A-9B) and CD8 T cells (FIG. 9C-9D) as assessed by flow cytometry by analyzing the activation marker CD71. A 5T4 positive cell line, Ovcar-5, or a 5T4 negative cell line, CCRF-CEM, was used to assess cell activation mediated by exemplary 5T4-targeted constrained CD3 engaging constructs.
Figure 9B:
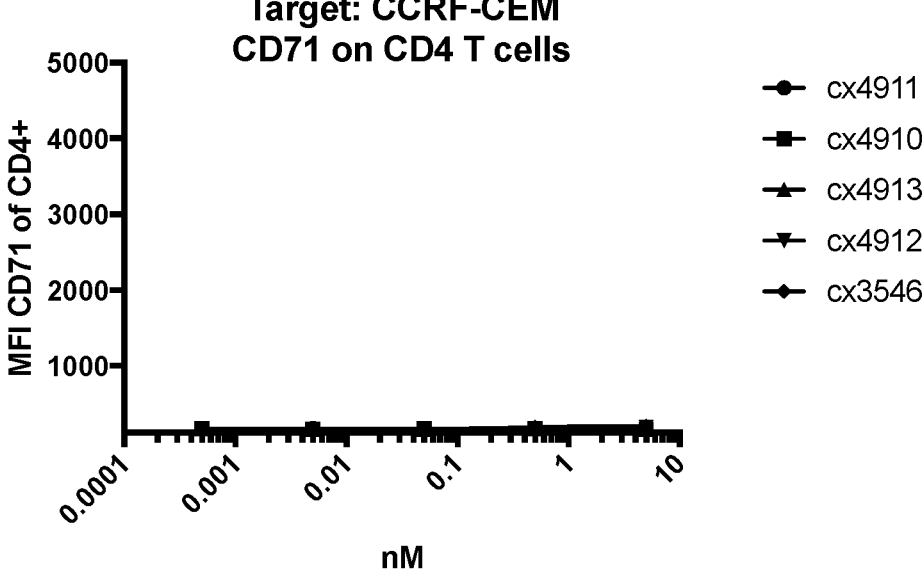
Figure 9C:
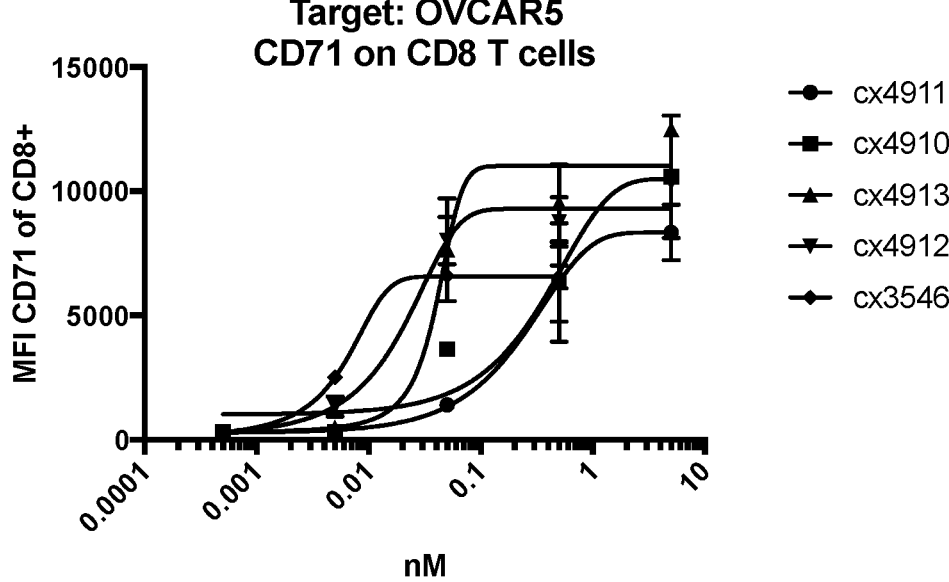
Figure 9D:
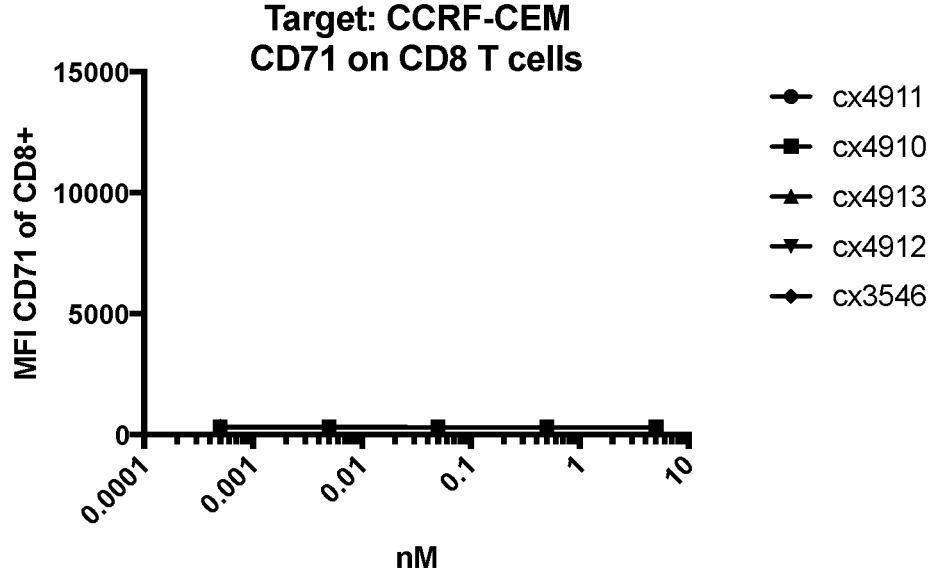

As shown in FIG. 6A, assessed 5T4-targeted constrained CD3 engaging constructs induced potent T-cell-mediated cytotoxicity of 5T4 positive (Ovcar-5) cell line. As shown in FIG. 6B, no measurable T cell cytotoxicity was observed against a 5T4 negative cell line (CCRF-CEM), consistent with the capacity to potently induce antigen-dependent T-cell activation. These observations support that the antigen-targeted constrained CD3 format provided herein compared to other CD3 engaging formats, lack or exhibit reduced T-cell binding in isolation while maintaining potent 5T4-dependent T-cell cytotoxicity inducing capacities.
B. T Cell Activation To assess T cell activation, suspension cells from T cell-mediated cytotoxicity assays were collected and stained with a live/dead stain and fluorophore-conjugated anti-CD4, anti-CD8, anti-CD25, anti-CD69, and/or anti-CD71 antibodies. Cells were analyzed using a SONY SA3800 spectral analyzer and CD4+ or CD8+ T cell activation was determined by measuring expression levels of CD25, CD69 or CD71 or percent CD25-, CD69- or CD71-positive.

FIGS. 7A-7B and FIGS. 7C-7D depict results for CD25 expression on CD4 T cells and CD8 T cells, respectively, upon culture of T cells with 5T4 positive (Ovcar-5) or 5T4 negative (CCRF-CEM) cell lines in the presence of exemplary constructs. FIGS. 8A-8B and FIGS. 8C-8D depict results for CD69 expression on CD4 cells and CD8 T cells, respectively, upon culture of T cells with a 5T4 positive (Ovcar-5) or a 5T4 negative (CCRF-CEM) cell line in the presence of exemplary constructs. FIGS. 9A-9B and FIGS. 9C-9D depict results for CD71 expression on CD4 T cells and CD8 T cells, respectively, upon culture of T cells with a 5T4 positive (Ovcar-5) or a 5T4 negative (CCRF-CEM) cell line in the presence of exemplary constructs. The results showed that the exemplary assessed 5T4-targeting constrained CD3 engaging constructs mediated a dose-dependent 5T4-dependent T-cell activation via CD3 binding, as evidenced by increased expression of CD25, CD69 and CD71 in CD4+ and CD8+ T cells.

Thus, the results demonstrated that the 5T4-targeting constrained CD3 engaging constructs of the present invention induced potent antigen-dependent activation of both CD4 and CD8 T-cells.

C. T Cell Cytokine Production (ELISA)

Figure 10A:
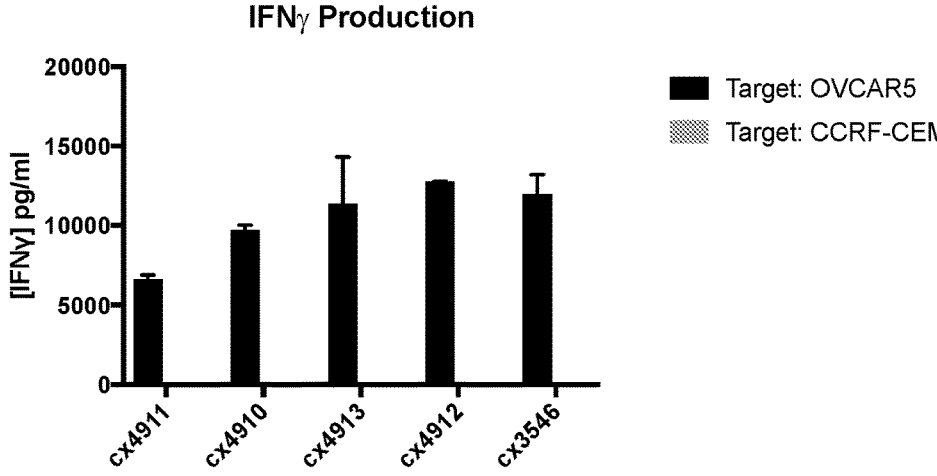
FIGS. 10A-10C show the ability of 5T4-targeted constrained CD3 engaging constructs to elicit IFNgamma (FIGS. 10A and 10B) or TNFalpha (FIG. 10C) production from T cells in an antigen-dependent manner. Cytokine production was monitored using an ELISA method (FIG. 10A) or FluoroSpot assay (FIGS. 10B and 10C).

Supernatants from T cell-mediated cytotoxicity assays were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration. As shown in FIG. 10A, exemplary assessed 5T4-targeting constrained CD3 engaging constructs elicited IFNγ production by T-cells with 5T4 positive (Ovcar-5) and no measurable IFNγ production was observed with a 5T4 negative cell line (CCRF-CEM).

D. T Cell Cytokine Production (FluoroSpot)

Figure 10B:
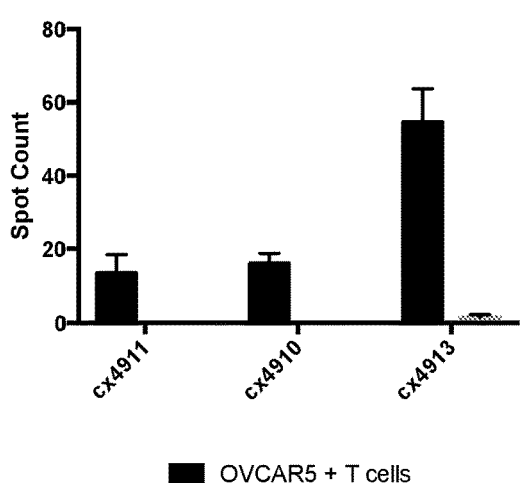
Figure 10C:
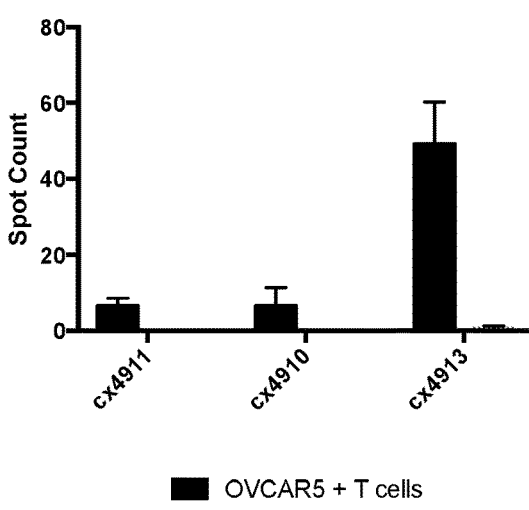

FluoroSpot membranes were coated with IFNγ and TNFα capture antibodies overnight at 4° C. Membranes were washed with PBS and antibody titrations, target cells, and PBMCs or purified T cells negatively enriched from PBMCs were added. Cells were seeded at a 1:10 ratio of target cell to effector cell. Assay plates were incubated for ~24 h at 37° C. and membranes were prepared according to the manufacturer's (C.T.L.) instructions. Membranes were imaged using a CTL-ImmunoSpot S6 Universal Analyzer. Cytokine spot count was measured using uniform exposure time and intensity settings among assay wells. FIG. 10B (IFNγ) and FIG. 10C (TNFα) depict the ability of exemplary 5T4-targeted constrained CD3 engaging constructs to elicit cytokine production from PBMCs or T cells in 5T4-dependent manner.

Example 8: Assessment of NK Cell Activation

A. Activation of Primary NK Cells

To assess the ability of sdAb-IgG1-Fc to activate NK cells in the presence of 5T4-positive cells, co-cultures of A549 cells ($2.5 \times 10^3$ cells/well) and PBMCs ($1.55 \times 10^6$ cells/well; $2.5 \times 10^4$ NK cells/well) were treated with antibody titrations for 4 hours at 37 degrees Celsius. Cells were stained with FITC-anti-CD56 and APC-anti-CD107a. NK activation was determined by measuring CD107a levels on CD56+ cells by flow cytometry. As shown in FIG. 11A, 12E9 and 4D3 formatted as sdAb-Fcs are capable of eliciting target dependent NK cell activation.

B. ADCC Reporter Activation

Figure 11A:
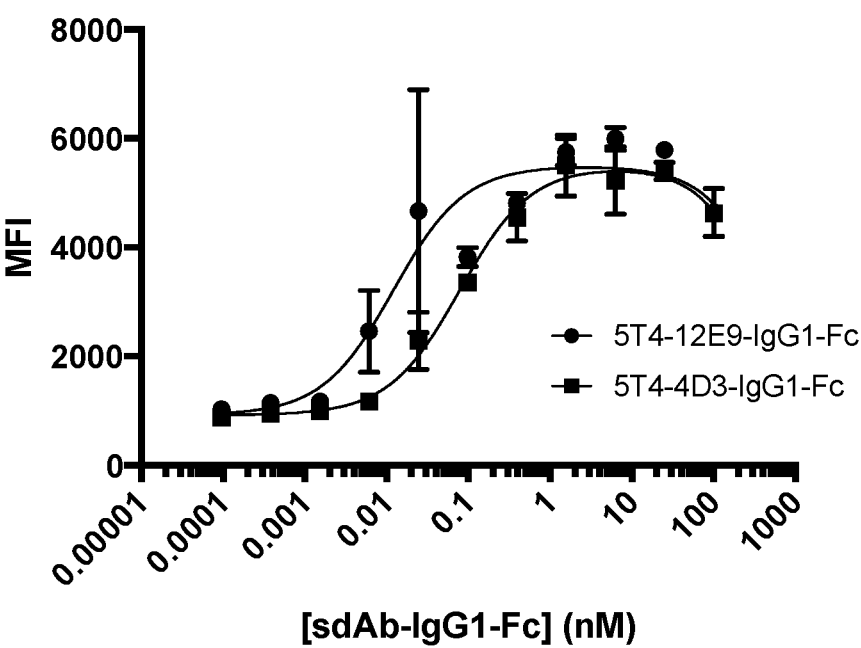
FIG. 11A shows the ability of 5T4 sdAbs, 12E9 and 4D3, formatted as sdAb-Fcs, to mediate NK cell activation as assessed by CD107a expression by flow cytometry.
Figure 11B:
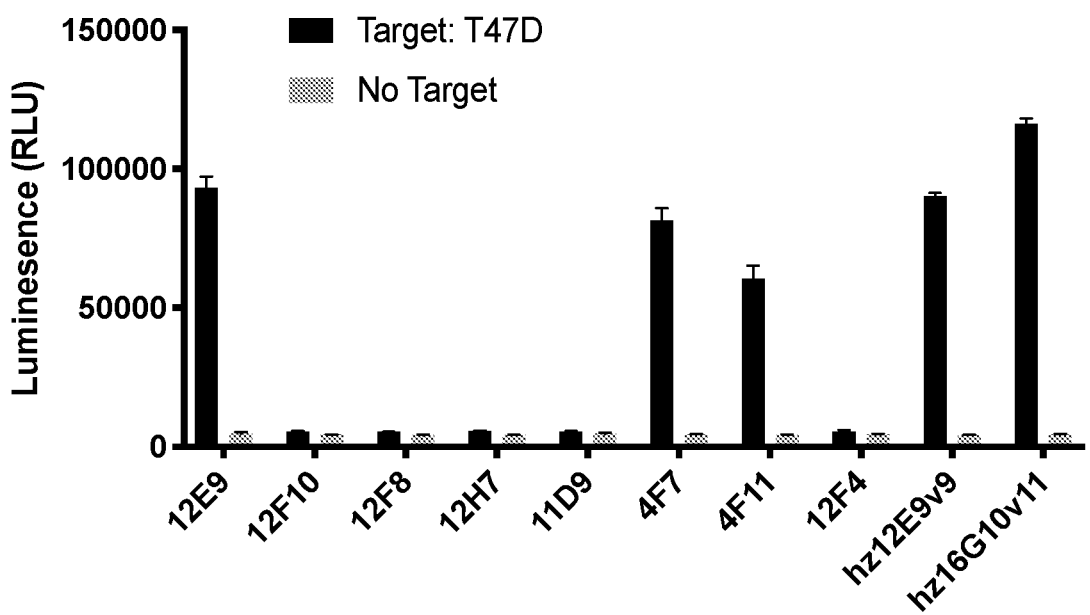
FIGS. 11B to 11D depict results of a CD16 reporter activation assay, a surrogate for ADCC activity, using a Jurkat reporter cell line engineered to stably express CD16a with an NFAT-driven luciferase reporter gene.
Figure 11C:
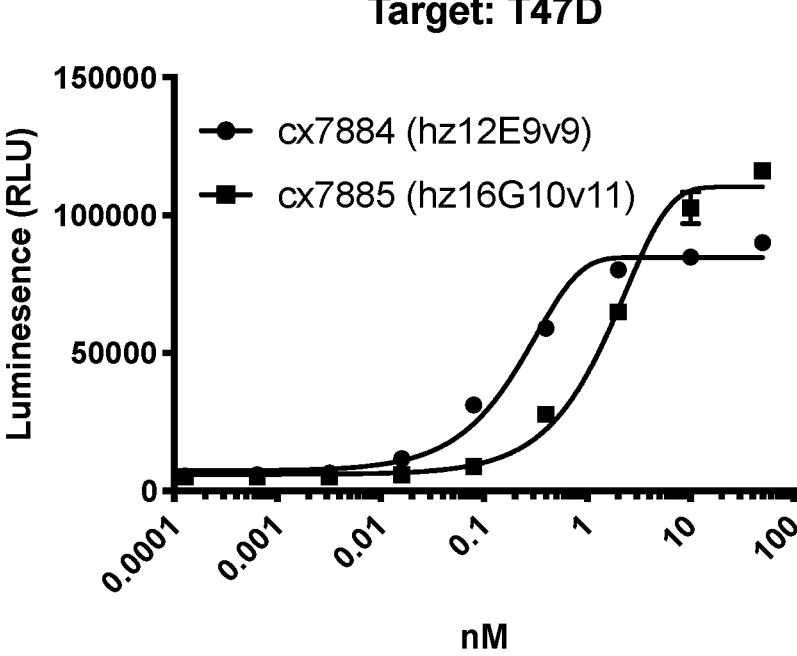
Figure 11D:
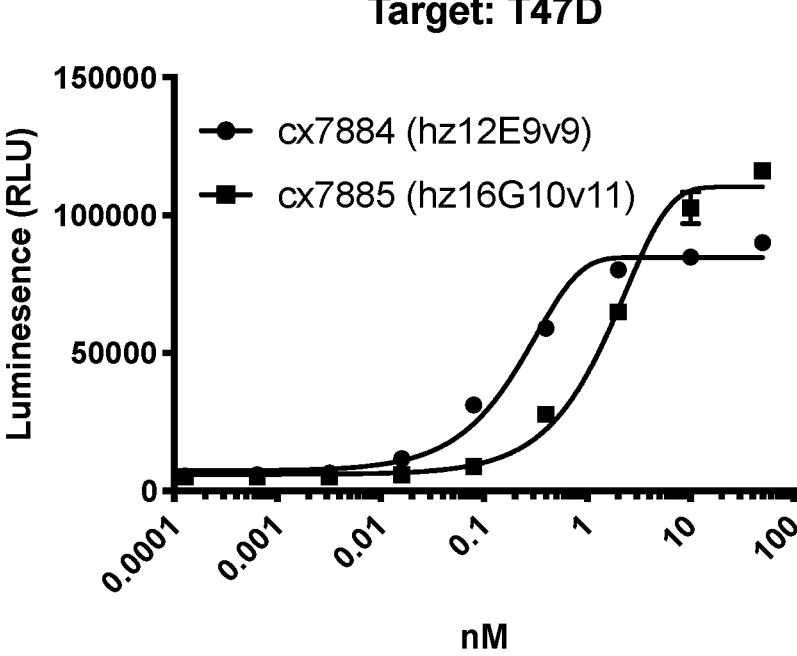

To assess the Fc effector function of exemplary 5T4-targeted sdAbs, a Jurkat reporter cell line engineered to stably express CD16a with an NFAT-driven luciferase reporter gene was used. Jurkat reporter cells were seeded (approximately $6 \times 10^4$ cells/well) in the presence or absence of 5T4-expressing cells (T47D; approximately $3 \times 10^4$ cells/well). 50 nanomolar of antibody was added to the cells and assay plates were incubated at 37 degrees Celsius for six hours, with a final assay volume 75 microliters. Assay plates were equilibrated to room temperature, 75 microliters of Bio-Glo was added to sample wells, and assay plates were incubated at room temperature for 10 minutes. 100 microliter aliquots were transferred to white 96-well plates and luminescence was measured using a Clariostar microplate reader. FIG. 11B depicts the ability of 12E9-Fc, 4F7-Fc, 4F11-Fc, hz12E9v9-Fc, and hz16G10v11-Fc to activate CD16 reporter cells in an antigen-dependent manner. FIGS. 11C and 11D depict the ability of cx7884 (hz12E9v9-Fc)

and cx7885 (hz16G10v11-Fc) to activate CD16 reporter cells in an antigen- and dose-dependent manner.

Example 9: Comparison of 5T4-Targeting CD3 Engaging Constructs

A. Binding to Cancer Cells and Primary T Cells

This Example describes studies assessing binding of exemplary constructs to T cells or to cancer cells. These studies were carried out in single cultures containing either only the T cells or only the cancer cells in isolation from each other.

Binding of exemplary CD3 engaging constructs of the disclosure to CD3 on the surface of primary T cells and to 5T4-expressing Ovcar5 cells was assessed. Primary T cells were negatively enriched from PBMCs isolated from healthy human donor leukopaks. Bound constructs were detected with fluorophore-conjugated secondary antibodies and binding was measured by flow cytometry. Cells incubated with secondary antibody only served as negative controls.

Exemplary 5T4-targeting constrained CD3 engaging constructs were assessed. As shown in Table E3, cx3497 incorporates a 41BB binding domain as a co-stimulatory receptor binding region (CRBR), whereas cx3547 did not incorporate a CRBR. The exemplary cx3497 construct contained a sdAb (containing a CDR1, a CDR2, and a CDR3 set forth in SEQ ID NOS: 347, 348, and 349, respectively; e.g. set forth in SEQ ID NO:210) targeting a 41BB co-stimulatory receptor as a CRBR. Single domain antibodies were incorporated as the 5T4 binding domains of both constructs as well as the 41BB binding domain of cx3497. As shown in FIGS. 12A and 12B, both constructs displayed binding to a 5T4 expressing cell, Ovcar-5. The constructs, however, were unable to bind T-cells in isolation (FIGS. 12C and 12D).

B. T Cell-Mediated Cytotoxicity

This Example describes the assessment and characterization of the tested constrained CD3 engaging constructs in human primary T cell in vitro assays.

Target cells were fluorescently labeled with CytoID red. For adherent target cells, target cells were seeded, allowed to settle at room temperature for uniform distribution, and incubated for several hours at 37° C. to permit adherence prior to addition of other assay components. Primary T cells were negatively enriched from PBMCs isolated from healthy human donor leukopaks and added at a 10:1-40:1 T cell-to-target cell ratio. Green caspase-3/7 reagent was added, which fluorescently labeled nuclear DNA of cells undergoing apoptosis. Antibodies were titrated onto the co-culture and assay plates were serially imaged using an IncuCyte ZOOM system. Target cell death was determined by measuring total red/green overlap object area (as shown in FIGS. 13A and 13B). Herein target cells are labeled as red with the CytoID red, while apoptosis was monitored with the green fluorescent caspase-3/7 substrate, thus apoptotic target cells those that are dual labeled red and green.

In an exemplary assay, the multispecifc construct that were tested included the 5T4-targeted constrained CD3 construct with a 41BB-binding costimulatory receptor binding region (cx3497). As a control, a corresponding 5T4-targeted constrained CD3 construct without the costimulatory receptor binding region also was tested (cx3547). The target cells were 5T4-positive Ovcar5 cells or 5T4-negative CCRF cells. As shown in FIGS. 13A and 13B, a representative 5T4-targeted constrained CD3 engaging construct, cx3547, lacked the capacity to mediate antigen specific cytotoxicity, whereas the addition of a 41BB binding domain induced specific T-cell cytotoxicity toward a 5T4 expressing cell line, Ovcar-5, but not toward a 5T4 negative cell line, CCRF-CEM. Notably, T-cell mediated cytotoxicity mediated by cx3497 was not observed until approximately 40 hrs, which is consistent with the kinetics of 41BB upregulation following TCR signaling.

These results show that the addition of the co-stimulatory receptor binding region targeting a costimulatory receptor, such as 41BB, enhanced the potency of T-cell mediated cytotoxicity over the construct that lacked a 41BB binding domain. These observations support that the antigen-targeted constrained CD3 format with additional co-stimulatory capacity provided herein compared to other CD3 engaging formats, display enhanced potency of mediated cytotoxicity, without substantially binding T cells absent antigen engagement.

C. T Cell Cytokine Production (ELISA)

Supernatants from T cell-mediated cytotoxicity assays, described above, were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration.

FIG. 14 shows that a representative 5T4-targeted constrained CD3 engaging constructs were observed to elicit enhanced IFNγ production by T cells in an antigen dependent manner when a 41BB binding domain was incorporated into the constructs (cx3499 and cx3497 vs. cx3546 and cx3547).

without a 4-1BB targeting sdAb as a CRBR and T cell activity was compared in various assays.

A. Design and Generation of Constructs

Exemplary multispecific constructs were generated with formats as depicted in FIG. 3A-E. Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; and a variable light (VL) domain of an anti-CD3 antibody. The second polypeptide chain generally included in order, from the N-terminus to C-terminus, a second Fc polypeptide (e.g. an Fc knob polypeptide); the same non-cleavable linker as the first polypeptide chain; and a variable heavy (VH) domain of an anti-CD3 antibody. The anti-CD3 antibody included a disulfide-stabilized (dsFv) antibody (anti-CD3 VH with the mutation G44C and VL with the mutation G100C), as set forth in Table E5. One of the polypeptide chains additionally encoded two 5T4 antigen binding domains, one amino-terminal to the Fc domain and one carboxy-terminal to the CD3 binding region. The exemplary construct cx5951 was generated without a CRBR, whereas the construct cx5185 contained a 4-1BB antigen binding domain (e.g. sdAb) as a CRBR positioned carboxy-terminally relative to the CD3 binding region, e.g. a sdAb (containing a CDR1, a CDR2 and a CDR3 set forth in SEQ ID NO: 347, 348, and 349, respectively; e.g. set forth in SEQ ID NO: 210).

Components of the exemplary constrained CD3 binding constructs having 5T4-targeting sdAb domains is given below in Table E5. The constructs were expressed and purified substantially as described in Example 4.

TABLE E5

| | | | | | | | | |
|---|---|---|---|---|---|---|---|---|
| 5T4 VHH Constrained Multispecific Constructs | | | | | | | | |
| Construct | Chain | N-term sdAb (Target) | Fc | Linker | CD3 Binding Domain | C-term sdAb (Target) | Disulfide Stabilized | |
| cx5951 | 1 | 5T4 sdAb hz12E9v09 (360) | xELL-Knob (105) | GGGGGSGGGGGSGGGGGS (127) | VH13 (47) | 5T4 sdAb hz16G10v11 (287) | yes | |
| | 2 | None | hxELL-Hole (106) | GGGGGSGGGGGSGGGGGS (127) | VL10 (75) | None | | |
| cx5185 | 1 | 5T4 sdAb hz12E9v09 (360) | xELL-Knob (105) | GGGGGSGGGGGSGGGGGS (127) | VH13 (47) | 5T4 sdAb hz16G10v11 (287) | yes | |
| | 2 | None | xELL-Hole (112) | GGGGGSGGGGGSGGGGGS (127) | VL10 (75) | 4-1BB sdAb RH3v5-1 (210) | | |

Example 10: Generation and Assessment of CD3-Constrained Multispecific Constructs Containing Antigen-Binding 5T4-Targeting Domain with or without a Costimulatory Binding Region Additional multispecific constructs were generated to contain a heterodimeric Fc region of an immunoglobulin coupled by a linker (e.g. a non-cleavable linker) to the CD3 binding region, and antigen binding domains that binds the 5T4 tumor associated antigen (TAA) positioned amino-terminally relative to the Fc region and carboxy-terminally relative to the CD3 binding region of the multispecific polypeptide construct. Constructs were generated with or B. T Cell Activity Activity of the constructs described above to engage CD3 in various assays was compared.

1. Cytotoxic Activity

Cytotoxic activity towards target cells was assessed in the presence of exemplary 5T4-targeted constructs with a 41BB-binding costimulatory receptor binding region (cx5185) or without the CRBR (cx5951). For cytotoxicity assays, Ovcar-5 cells expressing 5T4 or control CCRF-CEM cells that do not express 5T4 were used as target cells and were seeded, allowed to settle at room temperature for uniform distribution, and incubated for several hours at 37 degrees Celsius to permit adherence prior to addition of other assay components. Primary T cells were negatively enriched from PBMCs isolated from healthy human donor leukopaks and added at a 10:1-40:1 T cell-to-target cell ratio. Herein target cells were labeled as red with the CytoID red, while apoptosis was monitored with the green fluorescent caspase-3/7 substrate; thus apoptotic target cells are those that are dual labeled red and green. Assay plates were serially imaged using an IncuCyte ZOOM system. Target cell death was determined by measuring total red/green overlap object area.

As shown in FIG. 15A, after 48 hours, a marked difference in potency of T-cell mediated target cell cytotoxicity against 5T4-expressing target cells was observed with the 5T4-targeted constrained CD3 engaging construct with a 41BB-binding costimulatory receptor binding region, cx5185, compared to a the same construct lacking the 41BB-binding costimulatory receptor binding region, cx5951. Cytotoxic activity against non-target cells was not observed (FIG. 15B).

These observations support that the antigen-dependent constrained CD3 format with the additional co-stimulatory capacity provided herein, display enhanced potency of mediated cytotoxicity compared to other CD3 engaging formats.

2. T Cell Activation

To assess T cell activation mediated by exemplary 5T4-targeted constrained CD3 engaging constructs, cx5185 and cx5951 were incubated in a co-culture of T-cells and 5T4-expressing target cells, either A375 cells, Ovcar-5 cells, or SHP-77 cells. To assess T cell activation, cells were collected and stained with a live/dead stain and fluorophore-conjugated anti-CD4, anti-CD8, and/or anti-CD25 antibodies. Cells were analyzed using a SONY SA3800 spectral analyzer and CD4+ or CD8+ T cell activation was determined by measuring expression levels of CD25. T-cell activation was assessed by CD25 expression on CD4 and CD8 populations. T cell activation, as measured by expression of CD25, was evident in CD4 (FIG. 16A) and CD8 (FIG. 16B) T cells that had been incubated with 5T4-expressing target cells in the presence of the exemplary constructs. As shown in FIGS. 16A-B, the 5T4-targeted constrained CD3 engaging construct incorporating the 41BB binding domain (cx5185) displayed enhanced activating capacity toward both CD4 and CD8 T-cells compared to the similar construct lacking the 41BB binding domain, cx5951.

3. T Cell Cytokine Production (ELISA)

The impact of the incorporation of the 41BB binding domain into an exemplary 5T4-targeted constrained CD3 engaging construct on T-cell mediated IFNγ production was assessed using various 5T4-expressing cell lines, A375, SHP-77, and Ovcar5. After co-culture of T cells and 5T4-expressing target cells, supernatants were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration. As shown in FIG. 17, the 5T4-targeted constrained CD3 engaging construct incorporating the 41BB binding domain, cx5185, displayed enhanced IFNγ production compared to the similar construct lacking the 41BB binding domain, cx5951.

4. T Cell Proliferation

T-cell proliferation was assessed by measuring the dilution of CellTrace™ Violet dye (Thermo Fisher Scientific) in labeled CD4+ or CD8+ T cells by flow cytometry. T cells were negatively enriched from PBMCs and labeled with CellTrace™ Violet according to the manufacturer's protocol. 5T4-targeted constrained CD3 engaging constructs were titrated onto co-cultures of labeled T cells and 5T4-expressing cells A375, Ovcar-5, and SHP-77, and assay plates were incubated at 37 degrees C. for five days. Cells were stained with the viability dye propidium iodide as well as fluorophore-conjugated anti-CD4 and anti-CD8 antibodies and analyzed using a SONY SA3800 spectral analyzer. Percent proliferated CD4+ or CD8+ T cells was determined by gating on the appropriate viable T cell subpopulation and measuring the percentage of cells with CellTrace™ Violet intensities lower than that of T cells from untreated co-cultures.

The 5T4-targeted constrained CD3 engaging construct incorporating the 41BB binding domain, cx5185, enhanced the proliferation of both CD4 (FIG. 18) and CD8 (FIG. 19) T-cells compared to the similar construct lacking the 41BB binding domain, cx5951.

5. T Cell Mitochondrial Assessment

41BB signaling has been suggested to enhance mitochondrial function. Mitochondrial function can be monitored using the mitochondrial-selective fluorescent probe MitoTracker Green (Thermo Fisher Scientific), which accumulates in active mitochondria. To assess mitochondrial function of T cells, T cells were co-cultured for five days with 5T4-expressing cell lines A375, Ovcar-5, and SHP-77, in the presence of exemplary 5T4-targeted constrained CD3 engaging constructs. MitoTracker Green was added at a final cell staining concentration of 100 nM as well as the viability dye propidium iodide and fluorophore-conjugated anti-CD4 and anti-CD8 antibodies, and cells were analyzed using a SONY SA3800 spectral analyzer. Median MitoTracker Green fluorescent intensity of CD4+ or CD8+ T cells was determined by gating on the appropriate viable T cell subpopulation. The 5T4-targeted constrained CD3 engaging construct incorporating the 41BB binding domain, cx5185, enhanced mitochondrial function of both CD4 (FIG. 20) and CD8 (FIG. 21) T-cells compared to the similar construct lacking the 41BB binding domain, cx5951.

6. T Cell Reporter Assay

The capacity of constrained CD3 engaging constructs containing 5T4-targeted sdAbs to mediate specific agonism of the 41BB co-stimulatory signaling pathway was also assessed. A Jurkat 41BB NFκB-Luciferase reporter cell line was used to test exemplary 5T4-targeting constrained CD3 engaging constructs with either no co-stimulatory receptor binding domain (cx5951) or a 41BB binding domain (cx5185). Recombinant plate bound 5T4 was used as the source of the antigen As shown in FIG. 22, cx5185 incorporating the 41BB binding domain was found to induce specific agonism of the targeted co-stimulatory receptor.

C. Summary

Together, these results demonstrate that CD3 engaging constructs containing 5T4-targeting sdAb domains, with and without a CRBR, are capable of antigen-dependent activation of T cells. Notably, the 5T4-targeted constrained CD3 engaging construct incorporating a 41BB binding domain displayed superior antigen-dependent and activity than the 5T4-targeted constrained CD3 engaging construct without a 41BB binding domain.

Example 11: Comparison of Orientation of CD3 Binding Region in CD3-Constrained Multispecific Constructs Containing Antigen-Targeting Domains A. Design and Generation of Constructs Multispecific polypeptide constructs were generated as shown in FIGS. 23A-B, to contain a heterodimeric Fc region of an immunoglobulin coupled by a linker (e.g. a non-cleavable linker) to the CD3 binding region, an antigen binding domain (e.g. sdAb) as a CRBR positioned carboxy-terminally relative to the CD3 binding region, and dual antigen binding domains that bind a tumor associated antigen (TAA) positioned amino-terminally relative to the Fc region and carboxy-terminally relative to the CD3 binding region of the multispecific polypeptide construct.

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; a variable light (VL; FIG. 23B) or variable heavy (VH; FIG. 23A) domain of an anti-CD3 antibody; and an antigen-binding domain (e.g. sdAb) as a CRBR. The second polypeptide chain generally included in order, from the N-terminus to C-terminus, a first antigen-binding domain (e.g. sdAb #1), a second Fc polypeptide (e.g. an Fc knob polypeptide); the same linker as the first polypeptide chain; the other of the variable heavy (VH) or variable light (VL) domain of an anti-CD3 antibody; and a second antigen-binding domain (e.g. sdAb #2). The anti-CD3 antibody included a disulfide-stabilized (dsFv) antibody (anti-CD3 VH with the mutation G44C and VL with the mutation G100C).

Notably, as shown in FIGS. 23A-B, the orientation of the anti-CD3 VH and anti-CD3 VL of the CD3 Fv were positioned differently relative to the Fc knob or Fc hole of the heterodimeric Fc region. As shown in FIG. 23A, the construct was generated in which the first polypeptide of the heterodimeric construct had the VL of CD3 Fv positioned C-terminal to the Fc knob and antigen-binding domains on the extreme N and C-termini and the second polypeptide of the heterodimeric construct had the VH of CD3 Fv positioned C-terminal to the Fc Hole and a CRBR sdAb on the extreme C-termini. In contrast, FIG. 23B depicts an exemplary construct in which the first polypeptide of the heterodimeric construct had the VH of CD3 Fv positioned C-terminal to the Fc knob and antigen-binding domains on the extreme N and C-termini and the second polypeptide of the heterodimeric construct had the VL of CD3 Fv positioned C-terminal to the Fc Hole and a CRBR sdAb on the extreme C-termini. Some exemplary constructs generated contained a sdAb (containing a CDR1, a CDR2, and a CDR3 set forth in SEQ ID NOS: 347, 348, and 349, respectively; e.g. set forth in SEQ ID NO:210) targeting a 41BB co-stimulatory receptor as a CRBR.

The constructs were expressed as purified substantially as described in Example 4.

B. T Cell Reporter Activity

To compare CD3 engagement, the exemplary constructs were tested in an antigen-dependent CD3 reporter assay by assessing their ability to activate a CD3 NFAT reporter Jurkat cell line in a co-culture with target antigen-expressing cells. Activation was assessed by monitoring either green fluorescent or luciferase reporter signal in Jurkat reporter cells.

Antigen targeting constrained CD3 engaging constructs were titrated onto co-cultures of either A375 cells expressing the target antigen or control CCRF-CEM cells not expressing the target antigen, and engineered Jurkat cells that express NFAT-driven green fluorescence protein (GFP). Engagement of CD3 results in NFAT signaling and production of green fluorescence. For reporter assays utilizing adherent target cells, target cells were seeded, allowed to settle at room temperature for uniform distribution, and incubated for several hours at 37 degrees Celsius to permit adherence prior to addition of reporter cells and antigen targeting constrained CD3 engaging constructs. Assay plates were serially imaged using an IncuCyte ZOOM system and CD3 reporter cell activation was determined by measuring total green object integrated intensity.

Figure 24A:
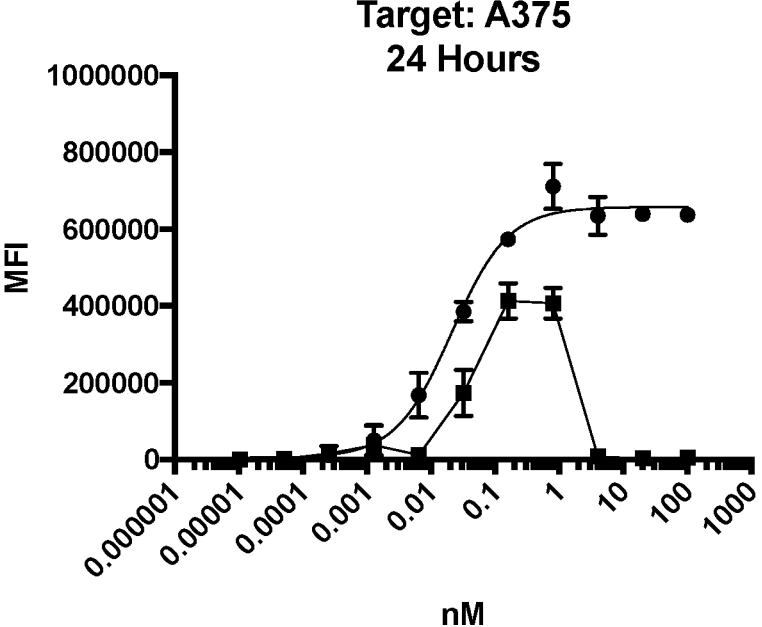
Figure 24B:
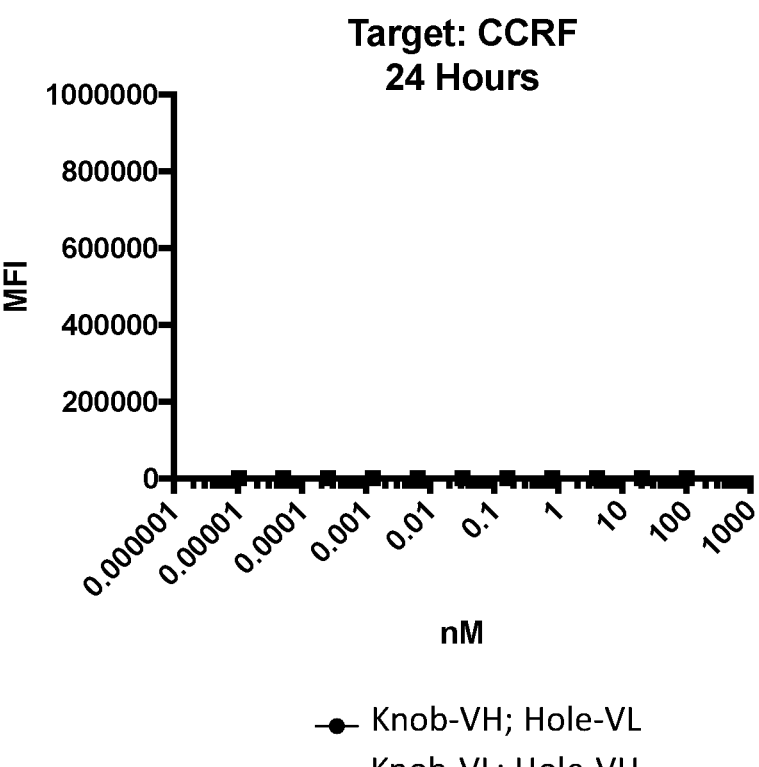

As shown in FIG. 24A, the exemplary antigen-targeted constrained CD3 engaging constructs exhibited capacity to mediate target antigen specific T-cell activation when incubated in reporter T cell co-cultures in the presence of antigen-expressing target cells. Reporter activity, however, was not observed in co-cultures with cells not expressing target antigen (FIG. 24B). Notably, the construct with the Knob-VH; Hole-VL format displayed enhanced T cell activation compared to the construct with the Knob-VL; Hole-VH format.

Figure 24C:
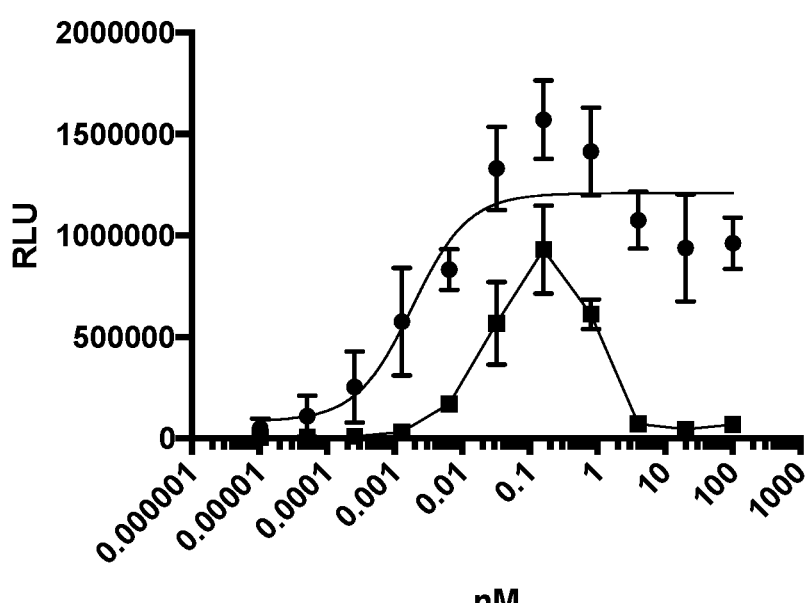
Figure 24D:
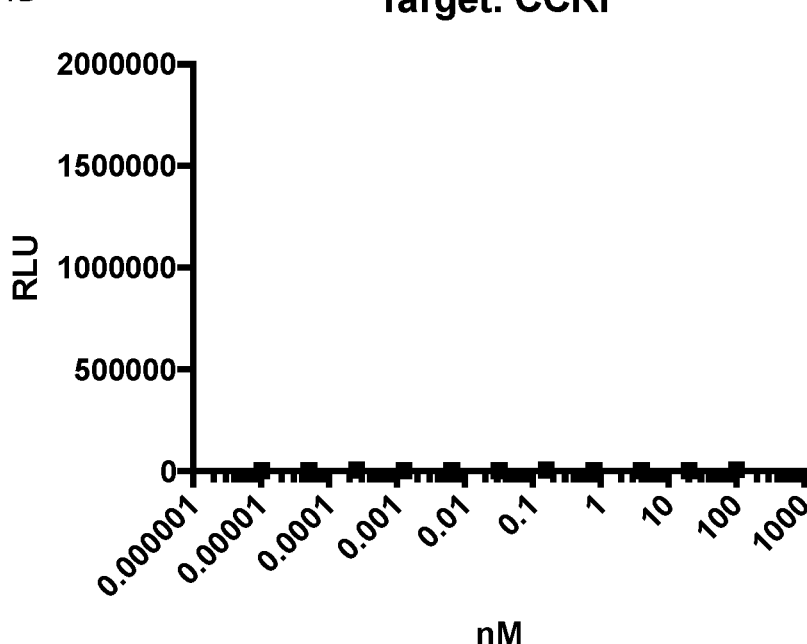

In a similar assay, the same antigen targeting constrained CD3 engaging constructs were titrated onto co-cultures of either A375 cells expressing target antigen or control CCRF-CEM cells not expressing target antigen, and engineered Jurkat cells that express NFAT-driven luciferase. As shown in FIG. 24C, the exemplary antigen-targeted constrained CD3 engaging constructs exhibited capacity to mediate target antigen specific T-cell activation when incubated in reporter T cell co-cultures in the presence of antigen-expressing target cells. Again, reporter activity, was not observed in co-cultures with cells not expressing target antigen (FIG. 24D). As in the GFP reporter assay, the construct with the Knob-VH; Hole-VL format displayed enhanced T cell activation compared to the construct with the Knob-VL; Hole-VH format.

These results are consistent with an observation that enhanced CD3 engagement and activity is observed when the components of the CD3 Fv are oriented so that the VH and VL are positioned C-terminally to the Fc Knob and Fc Hole regions, respectively.

Example 12: 5T4 sdAb Epitope Determination

A. Epitope Determination

The 5T4 targeting sdAbs, 12E9 (SEQ ID NO:245), 16G10 (SEQ ID NO:276) and 14B5 (SEQ ID NO:255) and humanized variants thereof do not cross react with the mouse 5T4 antigen. In order to determine the location of the epitope recognized by these sdAbs, various mouse: human chimeric 5T4 constructs were generated, wherein various portions of the murine extracellular domain of 5T4 were replaced with that of human 5T4. The constructs were generated by grafting a nucleic acid sequence encoding the specific region of human 5T4 into the cognate region of mouse 5T4 in a mammalian expression plasmid encoding the full 5T4 coding region (extracellular domain, transmembrane domain, intracellular domain) fused to an intracellular Citrine tag. The constructs tested included a fully human construct ("Hu"; SEQ ID NO:382), a fully murine construct ("Mu"; SEQ ID NO:383), chimeric hmc5T4.1 (SEQ ID NO:384); chimeric hmc5T4.2 (SEQ ID NO:385), chimeric hmc5T4.3 (SEQ ID NO: 386), and chimeric hmc5T4.4 (SEQ ID NO:387) (FIG. 25). CHO cells were transiently transfected with these constructs to enable cell surface expression, and binding was monitored by flow cytometry. As shown in FIGS. 26A-26C, 12E9v9 (SEQ ID NO:360) recognized an epitope that resides between amino acid residues 60 and 112 (SEQ ID NO:411), while 16G10v11 (SEQ ID NO:287) and 14B5v17 (SEQ ID NO:272) both recognized epitope(s) that reside between amino acid residues 173 and 224 (SEQ ID NO:412).

B. Binding to 5T4 Expressing Cells

Exemplary generated 5T4-targeting constrained CD3 engaging constructs were assessed for their ability to activate a CD3 NFAT reporter Jurkat cell line in co-cultures with 5T4-expressing SKOV3 cells, or 5T4 negative CCFR-CEM cells. All three of the constructs tested contained two 5T4-targeted sdAbs. One of the constructs (cx5185) contained two 5T4-targeted sdAbs (hz12E9v9 and hz16G10v11) that bound distinct epitopes, while the other two constructs (cx7859 and cx7860) each contained two 5T4-targeting sdAbs (either hz12E9v9 or hz16G10v11, respectively) against the same epitope.

In the reporter assay, engagement of CD3 in the Jurkat cells results in NFAT signaling and production of green fluorescence. Antigen targeting constrained CD3 engaging constructs were titrated onto co-cultures of 5T4-expressing SKOV 3 target cells and engineered Jurkat cells that expressed NFAT-driven green fluorescence protein (GFP). Target cells were seeded, allowed to settle at room temperature for uniform distribution, and incubated for several hours at 37° C. to permit adherence prior to addition of reporter cells and antigen targeting constrained CD3 engaging constructs. CD3 reporter cell activation was determined as described in Example 6.

As shown, assessed 5T4-targeted constrained CD3 engaging constructs induced reporter activity in cultures containing 5T4 positive cells (FIG. 27A), but no measurable reporter activity was observed when T cells were cultured with 5T4 negative cells (CCRF-CEMs) (FIG. 27B). As shown in FIG. 27A, the construct containing two 5T4-targeted sdAbs that bound distinct epitopes (cx5185) induced greater activation of the reporter cells than constructs that were also bivalent for 5T4, but only bound one of the two epitopes (cx7859 and cx7860).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| Sequences | | |
|---|---|---|
| # | SEQUENCE | ANNOTATION |
| 1 | GGSGGS | (GGS)2 linker |
| 2 | GGSGGSGGS | (GGS)3 linker |
| 3 | GGSGGSGGSGGS | (GGS)4 linker |
| 4 | GGSGGSGGSGGSGGS | (GGS)5 linker |
| 5 | GGGG | glycine linker |
| 6 | GGGGG | glycine linker |
| 7 | GGGGGG | glycine linker |
| 8 | PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK | human IgG1 Fc |
| 9 | PAPGGPSVFLFPPKPKDTLMISRTPEVTCVVVDVSHEDPEVKF NWYVDGVEVHNAKTKPREEQYNSTYRVVSVLTVLHQDWLN GKEYKCKVSNKALPAPIEKTISKAKGQPREPQVYTLPPSRDEL TKNQVSLTCLVKGFYPSDIAVEWESNGQPENNYKTTPPVLDS DGSFFLYSKLTVDKSRWQQGNVFSCSVMHEALHNHYTQKSLS LSPGK | Fc xELL |
| 10 | PAPPVAGPSV FLFPPKPKDT LMISRTPEVT CVVVDVSHED PEVQFNWYVD GVEVHNAKTK PREEQFNSTF RVVSVLTVVH QDWLNGKEYK CKVSNKGLPA PIEKTISKTK GQPREPQVYT LPPSREEMTK NQVSLTCLVK GFYPSDISVE WESNGQPENN YKTTPPMLDS DGSFFLYSKL TVDKSRWQQG NVFSCSVMHE ALHNHYTQKS LSLSPGK | human IgG2 Fc |
| 11 | PAPELLGGPS VFLFPPKPKD TLMISRTPEV TCVVVDVSHE DPEVQFKWYV DGVEVHNAKT KPREEQYNST FRVVSVLTVL HQDWLNGKEY KCKVSNKALP APIEKTISKT KGQPREPQVY TLPPSREEMT KNQVSLTCLV KGFYPSDIAV EWESSGQPEN NYNTTPPMLD SDGSFFLYSK LTVDKSRWQQ GNIFSCSVMH EALHNRFTQK SLSLSPGK | human IgG3 Fc |
| 12 | PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY | human IgG4 Fc |

-continued

| # | SEQUENCE | ANNOTATION |
|---|---|---|
| | TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | |
| 13 | PAPELLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | human IgG4 Fc |
| 14 | EPKSSDKTHTCPPC | modified IgG1 hinge |
| 15 | DKTHTCPPC | truncated IgG1 hinge |
| 16 | ESKYGPPCPPC | modified IgG4 hinge |
| 17 | GQGTLVTVKPGG | carboxy-terminal sequence |
| 18 | GQGTLVTVEPGG | carboxy-terminal sequence |
| 19 | VQLVQSGGG VVQPGRSLRL SCKASGYTFT RYTMHWVRQA PGKGLEWIGYINPSRGYTNY NQKVKDRFTI SRDNSKNTAF LQMDSLRPED TGVYFCARYYDDHYCLDYWG QGTPVTVSS | OKT3 VH |
| 20 | DIQMTQSPSS LSASVGDRVT ITCSASSSVS YMNWYQQTPG KAPKRWIYDTSKLASGVPSR FSGSGSGTDY TFTISSLQPE DIATYYCQQW SSNPFTFGQGTKLQIT | OKT3 VL |
| 21 | QVQLVQSGGG VVQPGRSLRL SCKASGYTFT RYTMHWVRQA PGKGLEWIGYINPSRGYTNY NQKVKDRFTI SRDNSKNTAF LQMDSLRPED TGVYFCARYYDDHYSLDYWG QGTPVTVSS | OKT3 humanized VH |
| 22 | DVQLVQSGAE VKKPGASVKV SCKASGYTFT RYTMHWVRQA PGQGLEWIGYINPSRGYTNY ADSVKGRFTI TTDKSTSTAY MELSSLRSED TATYYCARYYDDHYCLDWG QGTTVTVSS | OKT3 humanized VH |
| 23 | QVQLVQSGAE LKKPGASVKV SCKASGYTFT RYTMHWVRQA PGQCLEWMGYINPSRGYTNY NQKFKDKATL TADKSTSTAY MELRSLRSDD TAVYYCARYYDDHYSLDYWG QGTLVTVSS | OKT3 humanized VH |
| 24 | QIVLTQSPAI MSASPGEKVT MTCSASSSVS YMNWYQQKSG TSPKRWIYDTSKLASGVPAH FRGSGSGTSY SLTISGMEAE DAATYYCQQW SSNPFTFGSGTKLEIN | OKT3 humanized VL |
| 25 | DIQMTQSPSS LSASVGDRVT ITCRASQSVS YMNWYQQKPG KAPKRWIYDTSKVASGVPAR FSGSGSGTDY SLTINSLEAE DAATYYCQQW SSNPLTFGGGTKVEIK | OKT3 humanized VL |
| 26 | DIQLTQSPSI LSASVGDRVT ITCRASSSVS YMNWYQQKPG KAPKRWIYDTSKVASGVPYR FSGSGSGTEY TLTISSMQPE DFATYYCQQW SSNPLTFGCGTKVEIKRT | OKT3 humanized VL |
| 27 | EVQLVESGGGLVQPGKSLKLSCAASGFTFNTYAMNWVRQAP GKGLEWVARIRSKYNNYATYYADSVKDRFTISRDDSQSILYL QMNNLKTEDTAMYYCVRHGNFGNSYVSWFAWGQGTLVTV SA | anti-CD3 Hv |
| 28 | QAVVTQESALTTSPGETVTLTCRSSTGAVTTSNYANWVQEKP DHLFTGLIGGTNKRAPGVPARFSGSLIGDKAALTITGAQTEDE AIYFCALWYSNLWVFGGGTKLTVL | anti-CD3 Lv |
| 29 | TYAMN | anti-CD3 VH CDR1 |
| 30 | RIRSKYNNYATYYADSVKD | anti-CD3 VH CDR2 |

-continued

| # | SEQUENCE | ANNOTATION |
|---|----------|------------|
| 31 | HGNFGNSYVSWFAY | anti-CD3 VH CDR3 |
| 32 | RSSTGAVTTSNYAN | anti-CD3 VL CDR1 |
| 33 | GTNKRAP | anti-CD3 VL CDR2 |
| 34 | ALWYSNLWV | anti-CD3 VL CDR3 |
| 35 | EVQLVESGGGLVQPGGSLRLSCAASGFTFSTYAMNWVRQAPG KGLEWVGRIRSKYNNYATYYADSVKDRFTISRDDSKNSLYLQ MNSLKTEDTAVYYCVRHGNFGNSYVSWFAWGQGTLVTVSS | anti-CD3 VH1 |
| 36 | EVKLVESGGGLVQPGGSLRLSCAASGFTFNTYAMNWVRQAP GKGLEWVARIRSKYNNYATYYADSVKDRFTISRDDSKSSLYL QMNNLKTEDTAMYYCVRHGNFGNSYVSWFAWGQGTLVTV SS | anti-CD3 VH2 |
| 37 | EVKLVESGGGLVKPGRSLRLSCAASGFTFNTYAMNWVRQAP GKGLEWVARIRSKYNNYATYYADSVKDRFTISRDDSKSILYL QMNNLKTEDTAMYYCVRHGNFGNSYVSWFAWGQGTLVTV SS | anti-CD3 VH3 |
| 38 | EVKLVESGGGLVKPGRSLRLSCAASGFTFNTYAMNWVRQAP GKGLEWVARIRSKYNNYATYYADSVKDRFTISRDDSKSILYL QMNSLKTEDTAMYYCVRHGNFGNSYVSWFAWGQGTLVTV SS | anti-CD3 VH4 |
| 39 | EVKLVESGGGLVKPGRSLRLSCAASGFTFNTYAMNWVRQAP GKGLEWVARIRSKYNNYATYYADSVKDRFTISRDDSKSILYL QMNSLKTEDTAMYYCVRHGNFGNSYVSWFAWGQGTLVTV SS | anti-CD3 VH5 |
| 40 | EVQLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAWGQGTLVTVS S | anti-CD3 VH6 |
| 41 | EVQLVESGGGLVQPGGSLRLSCAASGFTFSTYAMSWVRQAPG KGLEWVGRIRSKYNNYATYYADSVKGRFTISRDDSKNTLYLQ MNSLRAEDTAVYYCVRHGNFGDSYVSWFAWGQGTLVTVS S | anti-CD3 VH7 |
| 42 | EVQLVESGGGLVQPGGSLKLSCAASGFTFNKYAMNWVRQAP GKGLEWVARIRSKYNNYATYYADSVKDRFTISRDDSKNTAYL QMNNLKTEDTAVYYCVRHGNFGNSYISYWAWGQGTLVTV S | anti-CD3 VH8 |
| 43 | EVQLVESGGGLVQPGGSLRLSCAASGFTFNTYAMNWVRQAP GKGLEWVARIRSKYNNYATYYADSVKGRFTISRDDSKNTLYL QMNSLRAEDTAVYYCVRHGNFGNSYVSWFAYWGQGTTVTV SS | anti-CD3 VH9 |
| 44 | EVQLVESGGGLVQPGGSLRLSCAASGFTFNTYAMNWVRQAP GKGLEWVARIRSKYNNYATYYADSVKGRFTISRDDSKNTLYL QMNSLRAEDTAVYYCVRHGNFGNSYVSYFAWGQGTTVTVS S | anti-CD3 VH10 |
| 45 | EVQLVESGGGLVQPKGSLKLSCAASGFTFNTYAMNWVRQAP GKGLEWVARIRSKYNNYATYYADSVKDRFTISRDDSQSILYL QMNNLKTEDTAMYYCVRHGNFGNSYVSWFAWGQGTLVTV SS | anti-CD3 VH11 |
| 46 | EVQLVESGGGLVQPGGSLRLSCAASGFTFNTYAMNWVRQAP GKGLEWVARIRSKYNNYATYYADSVKGRFTISRDDAKNTLYL QMSSLRAEDTAVYYCVRHGNFGNSYVSWFAWGQGTLVTV KP | anti-CD3 VH12 |
| 47 | EVQLVESGGGLVQPGGSLRLSCAASGFTFNTYAMNWVRQAP GKCLEWVARIRSKYNNYATYYADSVKGRFTISRDDAKNTLYL QMSSLRAEDTAVYYCVRHGNFGNSYVSWFAWGQGTLVTV KP | anti-CD3 VH13 |

-continued

| | Sequences | |
|---|---|---|
| # | SEQUENCE | ANNOTATION |
| 48 | EVQLVESGGGLVQPGGSLRLSCAASGFTFNTYAMNWVRQAP<br>GKGLEWVARIRSKYNNYATYYADSVKGRFTISRDDAKNTLYL<br>QMSSLRAEDTAVYYCVRHGNFGNSYVSWFAWGCGTLVTV<br>KP | anti-CD3 VH14 |
| 49 | EVQLVESGGGLVQPGGSLRLSCAASGFTFSTYAMNWVRQAPG<br>KGLEWVARIRSKYNNYATYYADSVKGRFTISRDDAKNTLYLQ<br>MSSLRAEDTAVYYCVRHGNFGNSYVSWFAWGQGTLVTVSS | anti-CD3 VH15 |
| 50 | EVQLVESGGGLVQPGGSLRLSCAASGFTFNTYAMNWVRQAP<br>GKGLEWVSRIRSKYNNYATYYADSVKGRFTISRDDAKNTLYL<br>QMSSLRAEDTAVYYCVRHGNFGNSYVSWFAWGQGTLVTV<br>SS | anti-CD3 VH16 |
| 51 | EVQLVESGGGLVQPGGSLRLSCAASGFTFSTYAMNWVRQAPG<br>KGLEWVSRIRSKYNNYATYYADSVKGRFTISRDDAKNTLYLQ<br>MSSLRAEDTAVYYCVRHGNFGNSYVSWFAWGQGTLVTVSS | anti-CD3 VH17 |
| 52 | EVQLVESGGGLVQPGGSLRLSCAASGFTFSTYAMNWVRQAPG<br>KCLEWVARIRSKYNNYATYYADSVKGRFTISRDDAKNTLYLQ<br>MSSLRAEDTAVYYCVRHGNFGNSYVSWFAWGQGTLVTVSS | anti-CD3 VH18 |
| 53 | EVQLVESGGGLVQPGGSLRLSCAASGFTFNTYAMNWVRQAP<br>GKCLEWVSRIRSKYNNYATYYADSVKGRFTISRDDAKNTLYL<br>QMSSLRAEDTAVYYCVRHGNFGNSYVSWFAWGQGTLVTV<br>SS | anti-CD3 VH19 |
| 54 | EVQLVESGGGLVQPGGSLRLSCAASGFTFSTYAMNWVRQAPG<br>KCLEWVSRIRSKYNNYATYYADSVKGRFTISRDDAKNTLYLQ<br>MSSLRAEDTAVYYCVRHGNFGNSYVSWFAWGQGTLVTVSS | anti-CD3 VH20 |
| 55 | EVQLVESGGGLVQPGGSLRLSCAASGFTFSTYAMNWVRQAPG<br>KCLEWVGRIRSKYNNYATYYADSVKDRFTISRDDSKNSLYLQ<br>MNSLKTEDTAVYYCVRHGNFGNSYVSWFAWGQGTLVTVSS | anti-CD3 VH21 |
| 56 | EVKLVESGGGLVQPGGSLRLSCAASGFTFNTYAMNWVRQAP<br>GKCLEWVARIRSKYNNYATYYADSVKDRFTISRDDSKSSLYL<br>QMNNLKTEDTAMYYCVRHGNFGNSYVSWFAWGQGTLVTV<br>SS | anti-CD3 VH22 |
| 57 | EVKLVESGGGLVKPGRSLRLSCAASGFTFNTYAMNWVRQAP<br>GKCLEWVARIRSKYNNYATYYADSVKDRFTISRDDSKSILYLQ<br>MNNLKTEDTAMYYCVRHGNFGNSYVSWFAYWGQGTLVTVS<br>S | anti-CD3 VH23 |
| 58 | EVKLVESGGGLVKPGRSLRLSCAASGFTFNTYAMNWVRQAP<br>GKCLEWVARIRSKYNNYATYYADSVKDRFTISRDDSKSILYLQ<br>MNSLKTEDTAMYYCVRHGNFGNSYVSWFAYWGQGTLVTVS<br>S | anti-CD3 VH24 |
| 59 | EVKLVESGGGLVKPGRSLRLSCAASGFTFNTYAMNWVRQAP<br>GKCLEWVARIRSKYNNYATYYADSVKDRFTISRDDSKSILYLQ<br>MNSLKTEDTAMYYCVRHGNFGNSYVSWFAYWGQGTLVTVS<br>S | anti-CD3 VH25 |
| 60 | EVQLLESGGGLVQPGGSLRLSCAASGFTFSTYAMNWVRQAPG<br>KCLEWVSRIRSKYNNYATYYADSVKGRFTISRDDSKNTLYLQ<br>MNSLRAEDTAVYYCVRHGNFGNSYVSWFAWGQGTLVTVS<br>S | anti-CD3 VH26 |
| 61 | EVQLVESGGGLVQPGGSLRLSCAASGFTFSTYAMSWVRQAPG<br>KCLEWVGRIRSKYNNYATYYADSVKGRFTISRDDSKNTLYLQ<br>MNSLRAEDTAVYYCVRHGNFGDSYVSWFAWGQGTLVTVS<br>S | anti-CD3 VH27 |
| 62 | EVQLVESGGGLVQPGGSLKLSCAASGFTFNKYAMNWVRQAP<br>GKCLEWVARIRSKYNNYATYYADSVKDRFTISRDDSKNTAYL<br>QMNNLKTEDTAVYYCVRHGNFGNSYISYWAWGQGTLVTV<br>S | anti-CD3 VH28 |
| 63 | EVQLVESGGGLVQPGGSLRLSCAASGFTFNTYAMNWVRQAP<br>GKCLEWVARIRSKYNNYATYYADSVKGRFTISRDDSKNTLYL<br>QMNSLRAEDTAVYYCVRHGNFGNSYVSWFAYWGQGTTVTV<br>SS | anti-CD3 VH29 |

-continued

| | Sequences | |
|---|---|---|
| # | SEQUENCE | ANNOTATION |
| 64 | EVQLVESGGGLVQPGGSLRLSCAASGFTFNTYAMNWVRQAP GKCLEWVARIRSKYNNYATYYADSVKGRFTISRDDSKNTLYL QMNSLRAEDTAVYYCVRHGNFGNSYVSYFAWGQGTTVTVS S | anti-CD3 VH30 |
| 65 | EVQLVESGGGLVQPKGSLKLSCAASGFTFNTYAMNWVRQAP GKCLEWVARIRSKYNNYATYYADSVKDRFTISRDDSQSILYLQ MNNLKTEDTAMYYCVRHGNFGNSYVSWFAYWGQGTLVTVS S | anti-CD3 VH31 |
| 66 | QAVVTQESALTTSPGETVTLTCRSSTGAVTTSNYANWVQEKP DHLFTGLIGGTNKRAPGVPARFSGSLIGDKAALTITGAQTEDE AIYFCALWYSNLWVFGGGTKLTVL | anti-CD3 VL1 |
| 67 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGCGTKLEIK | anti-CD3 VL2 |
| 68 | QAVVTQEPSLTVSPGGTVTLTCRSSTGAVTTSNYANWVQQKP GQAPRGLIGGTNKRAPWTPARFSGSLLGGKAALTITGAQAED EADYYCALWYSNLWVFGGGTKLTVL | anti-CD3 VL3 |
| 69 | QAVVTQEPSFSVSPGGTVTLTCRSSTGAVTTSNYANWVQQTP GQAFRGLIGGTNKRAPGVPARFSGSLIGDKAALTITGAQADDE SIYFCALWYSNLWVFGGGTKLTVL | anti-CD3 VL4 |
| 70 | QAVVTQEPSFSVSPGGTVTLTCRSSTGAVTTSNYANWVQQTP GQAFRGLIGGTNKRAPGVPARFSGSILGNKAALTITGAQADDE SIYFCALWYSNLWVFGGGTKLTVL | anti-CD3 VL5 |
| 71 | QAVVTQEPSFSVSPGGTVTLTCRSSTGAVTTSNYANWVQQTP GQAFRGLIGGTNKRAPGVPARFSGSILGNKAALTITGAQADDE SDYYCALWYSNLWVFGGGTKLTVL | anti-CD3 VL6 |
| 72 | QAVVTQEPSLTVSPGGTVTLTCGSSTGAVTTSNYANWVQEKP GQAFRGLIGGTNKRAPGTPARFSGSLLGGKAALTLSGAQPEDE AEYYCALWYSNLWVFGGGTKLTVL | anti-CD3 VL7 |
| 73 | QTVVTQEPSLTVSPGGTVTLTCGSSTGAVTSGNYPNWVQQKP GQAPRGLIGGTKFLAPGTPARFSGSLLGGKAALTLSGVQPEDE AEYYCVLWYSNRWVFGGGTKLTVL | anti-CD3 VL8 |
| 74 | QAVVTQEPSLTVSPGGTVTLTCGSSTGAVTTSNYANWVQQKP GQAFRGLIGGTNKRAPGVPARFSGSLLGGKAALTISGAQPEDE ADYYCALWYSNHWVFGGGTKLEIK | anti-CD3 VL9 |
| 75 | QAVVTQEPSLTVSPGGTVTLTCGSSTGAVTTSNYANWVQQKP GQAFRGLIGGTNKRAPGVPARFSGSLLGGKAALTISGAQPEDE ADYYCALWYSNHWVFGCGTKLEIK | anti-CD3 VL10 |
| 76 | QAVVTQEPSLTVSPGGTVTLTCGSSTGAVTTSNYANWVQQKP GQCFRGLIGGTNKRAPGVPARFSGSLLGGKAALTISGAQPEDE ADYYCALWYSNHWVFGEGTKLEIK | anti-CD3 VL11 |
| 77 | QAVVTQESALTTSPGETVTLTCRSSTGAVTTSNYANWVQEKP DHLFTGLIGGTNKRAPGVPARFSGSLIGDKAALTITGAQTEDE AIYFCALWYSNLWVFGCGTKLTVL | anti-CD3 VL12 |
| 78 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGGGTKLEIK | anti-CD3 VL13 |
| 79 | QAVVTQEPSLTVSPGGTVTLTCRSSTGAVTTSNYANWVQQKP GQAPRGLIGGTNKRAPWTPARFSGSLLGGKAALTITGAQAED EADYYCALWYSNLWVFGCGTKLTVL | anti-CD3 VL14 |
| 80 | QAVVTQEPSFSVSPGGTVTLTCRSSTGAVTTSNYANWVQQTP GQAFRGLIGGTNKRAPGVPARFSGSLIGDKAALTITGAQADDE SIYFCALWYSNLWVFGGGTKLTVL | anti-CD3 VL15 |
| 81 | QAVVTQEPSFSVSPGGTVTLTCRSSTGAVTTSNYANWVQQTP GQAFRGLIGGTNKRAPGVPARFSGSILGNKAALTITGAQADDE SIYFCALWYSNLWVFGCGTKLTVL | anti-CD3 VL16 |

| | Sequences | |
|---|---|---|
| # | SEQUENCE | ANNOTATION |
| 82 | QAVVTQEPSFSVSPGGTVTLTCRSSTGAVTTSNYANWVQQTP GQAFRGLIGGTNKRAPGVPARFSGSILGNKAALTITGAQADDE SDYYCALWYSNLWVFGCGTKLTVL | anti-CD3 VL17 |
| 83 | QAVVTQEPSLTVSPGGTVTLTCGSSTGAVTTSNYANWVQEKP GQAFRGLIGGTNKRAPGTPARFSGSLLGGKAALTLSGAQPEDE AEYYCALWYSNLWVFGCGTKLTVL | anti-CD3 VL18 |
| 84 | QTVVTQEPSLTVSPGGTVTLTCGSSTGAVTSGNYPNWVQQKP GQAFRGLIGGTKFLAPGTPARFSGSLLGGKAALTLSGVQPEDE AEYYCVLWYSNRWVFGCGTKLTVL | anti-CD3 VL19 |
| 85 | QVQLQESGGGLVQAGGSLRLSCAASGRTFSNYHMGWFRQAP GKERELVAAISGSGGSTYYTDSVKGRFTISRNNAKNTMSLQM SNLKPEDTGVYYCTTPTEKGSSIDWGQGTQVTVSSGRYPYD VPDY | anti-CD3 VHH |
| 86 | GRPFSSYAMG | 5T4 CDR-H1 |
| 87 | GRPFSSSAMG | 5T4 CDR-H1 |
| 88 | AVRWIGGATR | 5T4 CDR-H2 |
| 89 | AVSRNGGASQ | 5T4 CDR-H2 |
| 90 | AVSRNAGASQ | 5T4 CDR-H2 |
| 91 | AVSRNTGASQ | 5T4 CDR-H2 |
| 92 | AVSRQGGASQ | 5T4 CDR-H2 |
| 93 | AVSRGGGASQ | 5T4 CDR-H2 |
| 94 | AVSRNAGASY | 5T4 CDR-H2 |
| 95 | AVSRNGGSSY | 5T4 CDR-H2 |
| 96 | AVSRQGGSSY | 5T4 CDR-H2 |
| 97 | AVSRGGGSSY | 5T4 CDR-H2 |
| 98 | AVSRNAGSSY | 5T4 CDR-H2 |
| 99 | AVSRNTGSSY | 5T4 CDR-H2 |
| 100 | GQAWGTKFTDYSD | 5T4 CDR-H3 |
| 101 | RSAAYSRSSEVYTGKDEYYY | 5T4 CDR-H3 |
| 102 | RSAAYSRSSETYTEKHDYTY | 5T4 CDR-H3 |
| 103 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VYTLPPCRDELTKNQVSLWCLVKGFYPSDIAVEWESNGQPEN NYKTTPPVLDSDGSFFLYSKLTVDKSRWQQGNVFSCSVMHEA LHNHYTQKSLSLSPT | Knob Fc |
| 104 | DKTHTCPPCPAPELLGGPSVFLFPPKPKDTLMRSRTPEVTCVV VDVSHEDPEVKFNWYVDGVEVHNAKTKPREEQYNSTYRVVS VLTVLHQDWLNGKEYKCKVSNKALPAPIEKTISKAKGQPREP QVCTLPPSRDELTKNQVSLSCAVKGFYPSDIAVEWESNGQPEN NYKTTPPVLDSDGSFFLVSKLTVDKSRWQQGNVFSCSVMHEA LHNHYTQKSLSLSPT | Hole Fc |
| 105 | DKTHTCPPCPAPGGPSVFLFPPKPKDTLMISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVYT LPPCRDELTKNQVSLWCLVKGFYPSDIAVEWESNGQPENNYK TTPPVLDSDGSFFLYSKLTVDKSRWQQGNVFSCSVMHEALHN HYTQKSLSLSPT | Knob Fc |
| 106 | DKTHTCPPCPAPGGPSVFLFPPKPKDTLMRSRTPEVTCVVVDV SHEDPEVKFNWYVDGVEVHNAKTKPREEQYNSTYRVVSVLT VLHQDWLNGKEYKCKVSNKALPAPIEKTISKAKGQPREPQVC | Hole Fc |

| | Sequences | |
|---|---|---|
| # | SEQUENCE | ANNOTATION |
| | TLPPSRDELTKNQVSLSCAVKGFYPSDIAVEWESNGQPENNYK<br>TTPPVLDSDGSFFLVSKLTVDKSRWQQGNVFSCSVMHEALHN<br>HYTQKSLSLSPT | |
| 107 | DKTHTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQ<br>VYTLPPCRDELTKNQVSLWCLVKGFYPSDIAVEWESNGQPEN<br>NYKTTPPVLDSDGSFFLYSKLTVDKSRWQQGNVFSCSVMHEA<br>LHNHYTQKSLSLSPG | Knob Fc |
| 108 | DKTHTCPPCPAPELLGGPSVFLFPPKPKDTLMRSRTPEVTCVV<br>VDVSHEDPEVKFNWYVDGVEVHNAKTKPREEQYNSTYRVVS<br>VLTVLHQDWLNGKEYKCKVSNKALPAPIEKTISKAKGQPREP<br>QVCTLPPSRDELTKNQVSLSCAVKGFYPSDIAVEWESNGQPEN<br>NYKTTPPVLDSDGSFFLVSKLTVDKSRWQQGNVFSCSVMHEA<br>LHNHYTQKSLSLSPG | Hole Fc |
| 109 | DKTHTCPPCPAPGGPSVFLFPPKPKDTLMISRTPEVTCVVVDVS<br>HEDPEVKFNWYVDGVEVHNAKTKPREEQYNSTYRVVSVLTV<br>LHQDWLNGKEYKCKVSNKALPAPIEKTISKAKGQPREPQVYT<br>LPPCRDELTKNQVSLWCLVKGFYPSDIAVEWESNGQPENNYK<br>TTPPVLDSDGSFFLYSKLTVDKSRWQQGNVFSCSVMHEALHN<br>HYTQKSLSLSPG | Knob Fc |
| 110 | DKTHTCPPCPAPGGPSVFLFPPKPKDTLMRSRTPEVTCVVVDV<br>SHEDPEVKFNWYVDGVEVHNAKTKPREEQYNSTYRVVSVLT<br>VLHQDWLNGKEYKCKVSNKALPAPIEKTISKAKGQPREPQVC<br>TLPPSRDELTKNQVSLSCAVKGFYPSDIAVEWESNGQPENNYK<br>TTPPVLDSDGSFFLVSKLTVDKSRWQQGNVFSCSVMHEALHN<br>HYTQKSLSLSPG | Hole Fc |
| 111 | DKTHTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQ<br>VCTLPPSRDELTKNQVSLSCAVKGFYPSDIAVEWESNGQPENN<br>YKTTPPVLDSDGSFFLVSKLTVDKSRWQQGNVFSCSVMHEAL<br>HNRYTQKSLSLSPT | Hole Fc |
| 112 | DKTHTCPPCPAPGGPSVFLFPPKPKDTLMISRTPEVTCVVVDVS<br>HEDPEVKFNWYVDGVEVHNAKTKPREEQYNSTYRVVSVLTV<br>LHQDWLNGKEYKCKVSNKALPAPIEKTISKAKGQPREPQVCT<br>LPPSRDELTKNQVSLSCAVKGFYPSDIAVEWESNGQPENNYKT<br>TPPVLDSDGSFFLVSKLTVDKSRWQQGNVFSCSVMHEALHNR<br>YTQKSLSLSPT | Hole Fc |
| 113 | DKTHTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQ<br>VCTLPPSRDELTKNQVSLSCAVKGFYPSDIAVEWESNGQPENN<br>YKTTPPVLDSDGSFFLVSKLTVDKSRWQQGNVFSCSVMHEAL<br>HNRYTQKSLSLSPG | Hole Fc |
| 114 | DKTHTCPPCPAPGGPSVFLFPPKPKDTLMISRTPEVTCVVVDVS<br>HEDPEVKFNWYVDGVEVHNAKTKPREEQYNSTYRVVSVLTV<br>LHQDWLNGKEYKCKVSNKALPAPIEKTISKAKGQPREPQVCT<br>LPPSRDELTKNQVSLSCAVKGFYPSDIAVEWESNGQPENNYKT<br>TPPVLDSDGSFFLVSKLTVDKSRWQQGNVFSCSVMHEALHNR<br>YTQKSLSLSPG | Hole Fc |
| 115 | DKTHTCPPCPAPELLGGPSVFLFPPKPKDTLYISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQ<br>VYTLPPCRDELTKNQVSLWCLVKGFYPSDIAVEWESNGQPEN<br>NYKTTPPVLDSDGSFFLYSKLTVDKSRWQQGNVFSCSVVHEA<br>LHNHYTQKSLSLSPT | Knob Fc |
| 116 | DKTHTCPPCPAPGGPSVFLFPPKPKDTLYISRTPEVTCVVVDVS<br>HEDPEVKFNWYVDGVEVHNAKTKPREEQYNSTYRVVSVLTV<br>LHQDWLNGKEYKCKVSNKALPAPIEKTISKAKGQPREPQVYT<br>LPPCRDELTKNQVSLWCLVKGFYPSDIAVEWESNGQPENNYK<br>TTPPVLDSDGSFFLYSKLTVDKSRWQQGNVFSCSVVHEALHN<br>HYTQKSLSLSPT | Knob Fc |

-continued

| # | SEQUENCE | ANNOTATION |
|---|---|---|
| 117 | DKTHTCPPCPAPELLGGPSVFLFPPKPKDTLYISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VYTLPPCRDELTKNQVSLWCLVKGFYPSDIAVEWESNGQPEN NYKTTPPVLDSDGSFFLYSKLTVDKSRWQQGNVFSCSVVHEA LHNHYTQKSLSLSPG | Knob Fc |
| 118 | DKTHTCPPCPAPGGPSVFLFPPKPKDTLYISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVYT LPPCRDELTKNQVSLWCLVKGFYPSDIAVEWESNGQPENNYK TTPPVLDSDGSFFLYSKLTVDKSRWQQGNVFSCSVVHEALHN HYTQKSLSLSPG | Knob Fc |
| 119 | DKTHTCPPCPAPELLGGPSVFLFPPKPKDTLYISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VCTLPPSRDELTKNQVSLSCAVKGFYPSDIAVEWESNGQPENN YKTTPPVLDSDGSFFLVSKLTVDKSRWQQGNVFSCSVVHEAL HNRYTQKSLSLSPT | Hole Fc |
| 120 | DKTHTCPPCPAPGGPSVFLFPPKPKDTLYISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVVHEALHNR YTQKSLSLSPT | Hole Fc |
| 121 | DKTHTCPPCPAPELLGGPSVFLFPPKPKDTLYISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VCTLPPSRDELTKNQVSLSCAVKGFYPSDIAVEWESNGQPENN YKTTPPVLDSDGSFFLVSKLTVDKSRWQQGNVFSCSVVHEAL HNRYTQKSLSLSPG | Hole Fc |
| 122 | DKTHTCPPCPAPGGPSVFLFPPKPKDTLYISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVVHEALHNR YTQKSLSLSPG | Hole Fc |
| 123 | (GGGGS)n, wherein n is 1 to 5 | Linker |
| 124 | (GGGGGS)n, wherein n is 1 to 4 | linker |
| 125 | GGGGS | Linker |
| 126 | GGGGGS | Linker |
| 127 | GGGGGSGGGGGSGGGGGS | Linker |
| 128 | GGGGSGGGGSGGGGS | Linker |
| 129 | GGSGGGGSGGGGSGGGGS | Linker |
| 130 | GlyxXaa-Glyy-Xaa-Glyz<br>Xaa is independently selected from A, V, L, I, M, F, W, P, G, S, T, C, Y, N, Q, K, R, H, D, or E<br>x, y, and z are each integers in the range from 1-5 | Linker |
| 131 | Gly-Gly-Gly-Xaa-Gly-Gly-Gly-Xaa-Gly-Gly-Gly<br>Xaa is independently selected from A, V, L, I, M, F, W, P, G, S, T, C, Y, N, Q, K, R, H, D, or E | Linker |
| 132 | (SSSSG)n<br>n = 1-9 | Linker |
| 133 | GGGGG-C-GGGGG | Linker |
| 134 | (EAAAK)n<br>n = 2-20 | Linker |

-continued

| # | SEQUENCE | ANNOTATION |
|---|----------|------------|
| 135 | AS-(AP)n-GT<br>n = 2-20 | Linker |
| 136 | AS-(EAAAK)n-GT<br>n = 2-20 | Linker |
| 137 | (GGGGA)n<br>n = 2-20 | Linker |
| 138 | (PGGGS)n<br>n = 2-20 | Linker |
| 139 | (AGGGS)n<br>n = 2-20 | Linker |
| 140 | GGS-(EGKSSGSGSESKST)n-GGS<br>n = 2-20 | Linker |
| 141 | SSSASASSA | Linker |
| 142 | GSPGSPG | Linker |
| 143 | ATTTGSSPGPT | Linker |
| 144 | X1 X2 X3 X4 X5 (P4 P3 P2 P1 ↓ P1')<br>X1 = I, L, Y, M, F, V, or A; (P4 = I, L, Y, M, F, V, or A)<br>X2 = A, G, S, V, E, D, Q, N, or Y; (P3 = A, G, S, V, E, D, Q, N, or Y)<br>X3 = H, P, A, V, G, S, or T; (P2 = H, P, A, V, G, S, or T)<br>X4 = D or E; (P1 = D or E)<br>X5 = I, L, Y, M, F, V, T, S, G or A (P1' = I, L, Y, M, F, V, T, S, G or A) | Linker consensus |
| 145 | X1 E X3 D X5 (P4 P3 P2 P1 ↓ P1')<br>X1 = I or L; (P4 = I or L)<br>(P3 = E)<br>X3 = P or A; (P2 = P or A)<br>X5 = I, V, T, S, or G (P1' = I, V, T, S, or G) | Linker consensus |
| 146 | LEAD | granzyme B substrate |
| 147 | LEPD | Linker |
| 148 | LEAE | Linker |
| 149 | IEPDI | Linker |
| 150 | LEPDG | Linker |
| 151 | LEADT | Linker |
| 152 | IEPDG | Linker |
| 153 | IEPDV | Linker |
| 154 | IEPDS | Linker |
| 155 | IEPDT | Linker |
| 156 | X1QARX5 (P1QAR↓(A/V))<br>X1 = any amino acid; (P1 is any amino acid)<br>X5 = A or V | Linker consensus |
| 157 | RQARX5(RQAR(A/V))<br>X5 = A or V | Linker |
| 158 | RQAR | matriptase substrate |
| 159 | RQARV | linker |
| 160 | X1X2 X3 X4 (P3 P2 P1 ↓ P1')<br>X1 = P, V or A; (P3 = P, V or A)<br>X2 = Q or D; (P2 = Q or D) | Linker consensus |

-continued

| Sequences | | |
|---|---|---|
| # | SEQUENCE | ANNOTATION |
| | X3 = A or N; (P1 = A or N)<br>X4 = L, I or M (P1' = L, I or M) | |
| 161 | PX2X3X4(P3 P2 P1 ↓ P1')<br>(P3 = P)<br>X2 = Q or D; (P2 = Q or D)<br>X3 = A or N; (P1 is A or N)<br>X4 = L or I (P1' is L or I) | Linker consensus |
| 162 | PAGL | MMP substrate |
| 163 | TGLEADGSPAGLGRQARVG | Linker |
| 164 | TGLEADGSRQARVGPAGLG | Linker |
| 165 | TGSPAGLEADGSRQARVGS | Linker |
| 166 | TGPAGLGLEADGSRQARVG | Linker |
| 167 | TGRQARVGLEADGSPAGLG | Linker |
| 168 | TGSRQARVGPAGLEADGS | Linker |
| 169 | TGPAGLGSRQARVGLEADGS | Linker |
| 170 | GPAGLGLEPDGSRQARVG | Linker |
| 171 | GGSGGGGIEPDIGGSGGS | Linker |
| 172 | GGSGGGGLEADTGGSGGS | Linker |
| 173 | GSIEPDIGS | Linker |
| 174 | GSLEADTGS | Linker |
| 175 | GGSGGGGIEPDGGGSGGS | Linker |
| 176 | GGSGGGGIEPDVGGSGGS | Linker |
| 177 | GGSGGGGIEPDSGGSGGS | Linker |
| 178 | GGSGGGGIEPDTGGSGGS | Linker |
| 179 | GGGSLEPDGSGS | Linker |
| 180 | GPAGLGLEADGSRQARVG | Linker |
| 181 | GGEGGGGSGGSGGGS | Linker |
| 182 | GSSAGSEAGGSGQAGVGS | Linker |
| 183 | GGSGGGGLEAEGSGGGGS | Linker |
| 184 | GGSGGGGIEPDPGGSGGS | Linker |
| 185 | TGGSGGGGIEPDIGGSGGS | Linker |
| 186 | ACPWAVSGARASPGSAASPRLREGPELSPDDPAGLLDLRQGM<br>FAQLVAQNVLLIDGPLSWYSDPGLAGVSLTGGLSYKEDTKEL<br>VVAKAGVYYVFFQLELRRVVAGEGSGSVSLALHLQPLRSAAG<br>AAALALTVDLPPASSEANSAFGFQGRLLHLSAGQRLGVHLHT<br>EARARHAWQLTQGATVLGLFRVTPEIPAGLPSPRSE | 41BBL |
| 187 | EVQLVQSGAEVKKPGESLRISCKGSGYSFSTYWISWVRQMPG<br>KGLEWMGKIYPGDSYTNYSPSFQGQVTISADKSISTAYLQWSS<br>LKASDTAMYYCARGYGIFDYWGQGTLVTVSS | 41BB VH |
| 188 | SYELTQPPSVSVSPGQTASITCSGDNIGDQYAHWYQQKPGQSP<br>VLVIYQDKNRPSGIPERFSGSNSGNTATLTISGTQAMDEADYY<br>CATYTGFGSLAVFGGGTKLTVL | 41BB VL |
| 189 | QVQLQQWGAGLLKPSETLSLTCAVYGGSFSGYWSWIRQSPE<br>KGLEWIGEINHGGYVTYNPSLESRVTISVDTSKNQFSLKLSSVT<br>AADTAVYYCARDYGPGNYDWYFDLWGRGTLVTVSS | 41BB VH |

-continued

| | Sequences | |
|---|---|---|
| # | SEQUENCE | ANNOTATION |
| 190 | EIVLTQSPATLSLSPGERATLSCRASQSVSSYLAWYQQKPGQA<br>PRLLIYDASNRATGIPARFSGSGSGTDFTLTISSLEPEDFAVYYC<br>QQRSNWPPALTFGGGTKVEIK | 41BB VL |
| 191 | QMQLVQSGAEVKKPGASVKVSCKASGYSFSGYYMHWVRQA<br>PGQGLEWMGWVNPMSGGTNYAQKFQGRVTITRDTSASTAY<br>MELSSLRSEDTAVYYCAREGMAMRLELDKWGQGTLVTVSS | 41BB VH |
| 192 | SYELTQPPSVSVAPGKTARITCGGNNIGSKSVHWYQQKPGQAP<br>VLVIYYDSDRPSGIPERFSGSNSGNTATLTISRVEAGDEADYYC<br>QVWDSSSVVFGGGTQLTVL | 41BB VL |
| 193 | QDSTSDLIPAPPLSKVPLQQNFQDNQFHGKWYVVGQAGNIKL<br>REDKDPNKMMATIYELKEDKSYNVTGVTFDDKKCTYAISTFV<br>PGSQPGEFTLGKIKSFPGHTSSLVRVVSTNYNQHAMVFFKFVF<br>QNREEFYITLYGRTKELTSELKENFIRFSKSLGLPENHIVFPVPI<br>DQCIDG | 41BB Anticalin |
| 194 | QDSTSDLIPAPPLSKVPLQQNFQDNQFHGKWYVVGQAGNIRL<br>REDKDPIKMMATIYELKEDKSYDVTMVKFDDKKCMYDIWTF<br>VPGSQPGEFTLGKIKSFPGHTSSLVRVVSTNYNQHAMVFFKFV<br>FQNREEFYITLYGRTKELTSELKENFIRFSKSLGLPENHIVFPVPI<br>DQCIDG | 41BB Anticalin |
| 195 | QDSTSDLIPAPPLSKVPLQQNFQDNQFHGKWYVVGQAGNIRL<br>REDKDPNKMMATIYELKEDKSYDVTAVAFDDKKCTYDIWTF<br>VPGSQPGEFTLGKIKSFPGHTSSLVRVVSTNYNQHAMVFFKFV<br>FQNREEFYITLYGRTKELTSELKENFIRFSKSLGLPENHIVFPVPI<br>DQCIDG | 41BB Anticalin |
| 196 | QDSTSDLIPAPPLSKVPLQQNFQDNQFHGKWYVVGQAGNIKL<br>REDKDPNKMMATIYELKEDKSYDVTAVAFDDKKCTYDIWTF<br>VPGSQPGEFTLGKIKSFPGHTSSLVRVVSTNYNQHAMVFFKFV<br>FQNREEFYITLYGRTKELTSELKENFIRFSKSLGLPENHIVFPVPI<br>DQCIDG | 41BB Anticalin |
| 197 | QDSTSDLIPA PPLSKVPLQQ NFQDNQFHGK WYVVGQAGNI<br>KLREDSKMMA TIYELKEDKS YDVTGVSFDD KKCTYAIMTF<br>VPGSQPGEFT LGKIKSFPGH TSSLVRVVST NYNQHAMVFF<br>KFVFQNREEF YITLYGRTKE LTSELKENFI RFSKSLGLPE<br>NHIVFPVPID QCIDG | 41BB Anticalin |
| 198 | QDSTSDLIPA PPLSKVPLQQ NFQDNQFHGK WYVVGQAGNI<br>KLREDKDPVK MMATIYELKE DKSYDVTGVT FDDKKCRYDI<br>STFVPGSQPG EFTFGKIKSF PGHTSSLVRV VSTNYNQHAM<br>VFFKFVFQNR EEFYITLYGR TKELTSELKE NFIRFSKSLG<br>LPENHIVFPV PIDQCIDG | 41BB Anticalin |
| 199 | QDSTSDLIPAPPLSKVPLQQNFQDNQFHGKWYVVGQAGNIRL<br>REDKDPHKMMATIYELKEDKSYDVTGVTFDDKKCTYAISTFV<br>PGSQPGEFTLGKIKSFPGHTSSLVRVVSTNYNQHAMVFFKFV<br>QNREEFYITLYGRTKELTSELKENFIRFSKSLGLPENHIVFPVPI<br>DQCIDG | 41BB Anticalin |
| 200 | QDSTSDLIPAPPLSKVPLQQNFQDNQFHGKWYVVGQAGNIKL<br>REDKDPNKMMATIYELKEDKSYDVTGVTFDDKKCTYAISTLV<br>PGSQPGEFTFGKIKSFPGHTSSLVRVVSTNYNQHAMVFFKFVF<br>QNREEFYITLYGRTKELTSELKENFIRFSKSLGLPENHIVFPVPI<br>DQCIDG | 41BB Anticalin |
| 201 | QDSTSDLIPAPPLSKVPLQQNFQDNQFHGKWYVVGQAGNIRL<br>REDKDPSKMMATIYELKEDKSYDVTAVTFDDKKCNYAISTFV<br>PGSQPGEFTLGKIKSFPGHTSSLVRVVSTNYNQHAMVFFKFVF<br>QNREEFYITLYGRTKELTSELKENFIRFSKSLGLPENHIVFPVPI<br>DQCIDG | 41BB Anticalin |
| 202 | REGPELSPDDPAGLLDLRQGMFAQLVAQNVLLIDGPLSWYSD<br>PGLAGVSLTGGLSYKEDTKELVVAKAGVYYVFFQLELRRVVA<br>GEGSGSVSLALHLQPLRSAAGAAALALTVDLPPASSEARNSAF<br>GFQGRLLHLSAGQRLGVHLTEARARHAWQLTQGATVLGLF<br>RVTPEIPAGLPSPRSE | 71-254 of human<br>41BBL |

-continued

| # | SEQUENCE | ANNOTATION |
|---|----------|------------|
| 203 | LDLRQGMFAQLVAQNVLLIDGPLSWYSDPGLAGVSLTGGLSY<br>KEDTKELVVAKAGVYYVFFQLELRRVVAGEGSGSVSLALHLQ<br>PLRSAAGAAALALTVDLPPASSEARNSAFGFQGRLLHLSAGQR<br>LGVHLHTEARARHAWQLTQGATVLGLFRVTPEIPAGLPSPRSE | 85-254 of human<br>41BBL |
| 204 | DPAGLLDLRQGMFAQLVAQNVLLIDGPLSWYSDPGLAGVSLT<br>GGLSYKEDTKELVVAKAGVYYVFFQLELRRVVAGEGSGSVSL<br>ALHLQPLRSAAGAAALALTVDLPPASSEARNSAFGFQGRLLHL<br>SAGQRLGVHLHTEARARHAWQLTQGATVLGLFRVTPEIPAGL<br>PSPRSE | 80-254 of human<br>41BBL |
| 205 | PWAVSGARASPGSAASPRLREGPELSPDDPAGLLDLRQGMFA<br>QLVAQNVLLIDGPLSWYSDPGLAGVSLTGGLSYKEDTKELVV<br>AKAGVYYVFFQLELRRVVAGEGSGSVSLALHLQPLRSAAGAA<br>ALALTVDLPPASSEARNSAFGFQGRLLHLSAGQRLGVHLHTE<br>ARARHAWQLTQGATVLGLFRVTPEIPAGLPSPRSE | 52-254 of human<br>4-1BBL |
| 206 | REGPELSPDDPAGLLDLRQGMFAQLVAQNVLLIDGPLSWYSD<br>PGLAGVSLTGGLSYKEDTKELVVAKAGVYYVFFQLELRRVVA<br>GEGSGSVSLALHLQPLRSAAGAAALALTVDLPPASSEARNSAF<br>GFQGRLLHLSAGQRLGVHLHTEARARHAWQLTQGATVLGLF<br>RVTPEIPAGL | 71-248 of human<br>41BBL |
| 207 | LDLRQGMFAQLVAQNVLLIDGPLSWYSDPGLAGVSLTGGLSY<br>KEDTKELVVAKAGVYYVFFQLELRRVVAGEGSGSVSLALHLQ<br>PLRSAAGAAALALTVDLPPASSEARNSAFGFQGRLLHLSAGQR<br>LGVHLHTEARARHAWQLTQGATVLGLFRVTPEIPAGL | 85-248 of human<br>41BBL |
| 208 | DPAGLLDLRQGMFAQLVAQNVLLIDGPLSWYSDPGLAGVSLT<br>GGLSYKEDTKELVVAKAGVYYVFFQLELRRVVAGEGSGSVSL<br>ALHLQPLRSAAGAAALALTVDLPPASSEARNSAFGFQGRLLHL<br>SAGQRLGVHLHTEARARHAWQLTQGATVLGLFRVTPEIPAGL | 80-248 of human<br>41BBL |
| 209 | PWAVSGARASPGSAASPRLREGPELSPDDPAGLLDLRQGMFA<br>QLVAQNVLLIDGPLSWYSDPGLAGVSLTGGLSYKEDTKELVV<br>AKAGVYYVFFQLELRRVVAGEGSGSVSLALHLQPLRSAAGAA<br>ALALTVDLPPASSEARNSAFGFQGRLLHLSAGQRLGVHLHTE<br>ARARHAWQLTQGATVLGLFRVTPEIPAGL | 52-248 of human<br>41BBL |
| 210 | EVQLLESGGGEVQPGGSLRLSCAASGFSFSINAMGWYRQAPG<br>KRREFVAAIESGRNTVYAESVKGRFTISRDNAKNTVYLQMSSL<br>RAEDTAVYYCGLLKGNRVVSPSVAWGQGTLVTVKP | 41BB sdAb |
| 211 | QVSHRYPRIQSIKVQFTEYKKEKGFILTSQKEDEIMKVQNNSVI<br>INCDGFYLISLKGYFSQEVNISLHYQKDEEPLFQLKKVRSVNSL<br>MVASLTYKDKVYLNVTTDNTSLDDFHVNGGELILIHQNPGEF<br>CVL | OX40 ligand |
| 212 | QVSHRYPRFQ SIKVQFTEYK KEKGFILTSQ KEDEIMKVQN<br>NSVIINCDGF YLISLKGYFS QEVNISLHYQ KDEEPLFQLK<br>KVRSVNSLMV ASLTYKDKVY LNVTTDNTSL DDFHVNGGEL<br>ILIHQNPGEFCVL | OX40 ligand |
| 213 | QVSHRYPRIQSIKVQFTEYKKEKGFILTSQKEDEIMKVQNNSVI<br>INCDGFYLISLKGYFSQEVNISLHYQKDEEPLFQLKKVRSVNSL<br>MVASLTYKDKVYLNVTTDNTSLDDFHVNGGELILIHQNPGEF<br>CVL | OX40 ligand |
| 214 | QVSHRYPRIQ SIKVQFTEYK KEKGFILTSQ KEDEIMKVQN<br>NSVIINCDGF YLISLKGYFS QEVNISLHYQ KDEEPLFQLK<br>KVRSVNSLMV ASLTYKDKVY LNVTTDNTSL DDFHVNGGEL<br>ILIHQNPGEF CVL | OX40 ligand |
| 215 | VSHRYPRIQSIKVQFTEYKKEKGFILTSQKEDEIMKVQNNSVII<br>NCDGFYLISLKGYFSQEVNISLHYQKDEEPLFQLKKVRSVNSL<br>MVASLTYKDKVYLNVTTDNTSLDDFHVNGGELILIHQNPGEF<br>CVL | OX40 ligand |
| 216 | EVQLVQSGAEVKKPGASVKVSCKASGYTFTDSYMSWVRQAP<br>GQGLEWIGDMYPDNGDSSYNQKFRERVTITRDTSTSTAYLELS<br>SLRSEDTAVYYCVLAPRWYFSVWGQGTLVTVSS | OX40 VH |
| 217 | DIQMTQSPSSLSASVGDRVTITCRASQDISNYLNWYQQKPGKA<br>PKLLIYYTSRLRSGVPSRFSGSGSGTDFTLTISSLQPEDFATYYC<br>QQGHTLPPTFGQGTKVEIKRT | OX40 VL |

-continued

| | | |
|---|---|---|
| | Sequences | |
| # | SEQUENCE | ANNOTATION |
| 218 | EVQLVESGGGLVQPGGSLKLSCAASGFTFSGSAMHWVRQASG KGLEWVGRIRSKANSYATAYAASVKGRFTISRDDSKNTAYLQ MNSLKTEDTAVYYCTSGIYDSSGYDYWGQGTLVTVSS | OX40 VH |
| 219 | DIVMTQSPLSLPVTPGEPASISCRSSQSLLHSNGYNYLDWYLQ KPGQSPQLLIYLGSNRASGVPDRFSGSGSGTDFTLKISRVEAED VGVYYCMQALQTPLTFGGGTKVEIK | OX40 VL |
| 220 | EVQLLESGGGEVQPGGSLRLSCAASGFTFSDAFMWVRQAPG KGLEWVSSISNRGLKTAYAESVKGRFTISRDNAKNTLYLQMSS LRAEDTAVYYCSRDVDGDFRGQGTLVTVKP | OX40 sdAb |
| 221 | QLETAKEPCMAKFGPLPSKWQMASSEPPCVNKVSDWKLEILQ NGLYLIYGQVAPNANYNDVAPFEVRLYKNKDMIQTLTNKSKI QNVGGTYELHVGDTIDLIFNSEHQVLKNNTYWGIILLANPQFIS | GITR ligand |
| 222 | QVQLVESGGGVVQPGRSLRLSCAASGFTFSSYAMSWVRQAPG KGLEWVASISSGGTTYYPDSVKGRFTISRDNSKNTLYLQMNSL RAEDTAVYYCARVGGYYDSMDYWGQGTLVTVSS | GITR VH |
| 223 | EIVLTQSPGTLSLSPGERATLSCRASESVDNYGVSFMNWYQQK PGQAPRLLIYAASNQGSGIPDRFSGSGSGTDFTLTISRLEPEDFA VYYCQQTKEVTWTFGQGTKVEIK | GITR VL |
| 224 | QVTLRESGPALVKPTQTLTLTCTFSGFSLSTSGMGVGWIRQPP GKALEWLAHIWWDDDKYYQPSLKSRLTISKDTSKNQVVLTM TNMDPVDTATYYCARTRRYFPFAWGQGTLVTVSS | GITR VH |
| 225 | EIVMTQSPATLSVSPGERATLSCKASQNVGTNVAWYQQKPGQ APRLLIYSASYRYSGIPARFSGSGSGTEFTLTISSLQSEDFAVYY CQQYNTDPLTFGGGTKVEIK | GITR VL |
| 226 | QVQLQESGPGLVKPSETLSLTCTVSGGSISSGGYFWSWIRQPPG KGLEWIGYIYYSGTTYYNPSLKSRVTISIDTSKNQFSLKLSSVT AADTAVYYCARDLFYYDTSGPRGFDPWGQGTLVTVSS | GITR VH |
| 227 | EIVLTQSPGTLSLSPGERATLSCRASQTVSSNYLAWYQQKPGQ APRLLIYGSSTRATGIPDRFSGSGSGTDFTLTISRLEPEDFAVYY CQQYDSSPWTFGQGTKVEIK | GITR VL |
| 228 | QVQLVESGGGVVQPGRSLRLSCAASGFTFSSYGMHWVRQAP GKGLEWVAVIWYPGSNKYYAESVKGRFTISRDNSKNTLYLQ MNSLRAEDTAVYYCARGGELGRYYYYGMDVWGQGTTVTVS S | GITR VH |
| 229 | DIQMTQSPSSLSASVGDRVTVTCRASQGIRNDLGWYQQKPGK APKRLIYAASSLQSGVPSRFSGSGSGTEFTLTISSLQPEDFATYY CLQHNNYPWTFGQGTKVDIK | GITR VL |
| 230 | EVQLLESGGGEVQPGGSLRLSCAASGSVFSIDAMGWYRQAPG KQRELVAVLSGISSAKYAASAPGRFTISRDNAKNTVYLQMSSL RAEDTAVYYCYADVSTGWGRDAHGYWGQGTLVTV | GITR sdAb |
| 231 | MPEEGSGCSVRRRPYGCVLRAALVPLVAGLVICLVVCI<u>QRFAQ AQQQLPLESLGWDVAELQLNHTGPQQDPRLWQGGPALGRS FLHGPELDKGQLRIHRDGIYMVHIQVTLAICSSTTASRHHPTTL AVGICSPASRSISLLRLSFHQGCTIASQRLTPLARGDTLCTNLTG TLLPSRNTDETFFGVQWVRP</u> | UniProt No. P32970, CD70- ECD residues 39- 193 (underline) |
| 232 | QVQLVESGGGVVQPGRSLRLSCAASGFTFSSYDMHWVRQAP GKGLEWVAVIWYDGSNKYYADSVKGRFTISRDNSKNTLYLQ MNSLRAEDTAVYYCARGSGNWGFFDYWGQGTLVTVSS | CD70 VH |
| 233 | DIQMTQSPSSLSASVGDRVTITCRASQGISRWLAWYQQKPEKA PKSLIYAASSLQSGVPSRFSGSGSGTDFTLTISSLQPEDFATYYC QQYNTYPRTFGQGTKVEIK | CD70 VL |
| 234 | QVQLQQSGGGLVQPGGSLRLSCAASGSIFSINGMGWYRQAPG KERELVAGLTSGGSVTNYADSVKGRFTISRDNAKNTVYLQMN SLKPEDTAVYYCRAEIFTRTGENYYGMDYWGKGTQVTVKP | ICOS sdAb |

-continued

| # | SEQUENCE | ANNOTATION |
|---|----------|------------|
| 235 | EVQLVESGGGEVQPGGSLRLSCAASGRMFSNYAMGWFRQAP GKEREFVAAINYRRDAADYAESVKGRFTISRDNAKNTVYLQM NSLRAEDTAVYYCGFTYAGWASSRRDDYNWGQGTLVTVK P | CD28 sdAb |
| 236 | RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR | CD3zeta signaling domain |
| 237 | KRGRKKLLYIFKQPFMRPVQTTQEEDGCSCRFPEEEEGGCEL | 4-1BB -derived costimulatory domain |
| 238 | SKRSRLLHSDYMNMTPRRPGPTRKHYQPYAPPRDFAAYRS | CD28-derived costimulatory domain |
| 239 | RSKRSRLLHSDYMNMTPRRPGPTRKHYQPYAPPRDFAAYRS | CD28-derived costimulatory domain 2 |
| 240 | FWVRSKRSRLLHSDYMNMTPRRPGPTRKHYQPYAPPRDFAA YRS | CD28-derived costimulatory domain 3 |
| 241 | KPTTTPAPRPPTPAPTIASQPLSLRPEASRPAAGGAVHTRGLDF ASDIYIWAPLAGTCGVLLLSLVITLYC | CD8-derived hinge and transmembrane domain |
| 242 | AKPTTTPAPRPPTPAPTIASQPLSLRPEACRPAAGGAVHTRGLD FACDIYIWAPLAGTCGVLLLSLVIT | CD8-derived hinge and transmembrane domain |
| 243 | KPTTTPAPRPPTPAPTIASQPLSLRPEACRPAAGGAVHTRGLDF ACDIYIWAPLAGTCGVLLLSLVIT | CD8 hinge and transmembrane domain |
| 244 | MPGGCSRGPAAGDGRLRLARLALVLLGWVSSSSPTSSASSFSS SAPFLASAVSAQPPLPDQCPALCECSEAARTVKCVNRNLTEVP TDLPAYVRNLFLTGNQLAVLPAGAFARRPPLAELAALNLSGSR LDEVRAGAFEHLPSLRQLDLSHNPLADLSPFAFSGSNASVSAPS PLVELILNHIVPPEDERQNRSFEGMVVAALLAGRALQGLRRLE LASNHFLYLPRDVLAQLPSLRHLDLSNNSLVSLTYVSFRNLTH LESLHLEDNALKVLHNGTLAELQGLPHIRVFLDNNPWVCDCH MADMVTWLKETEVVQGKDRLTCAYPEKMRNRVLLELNSAD LDCDPILPPSLQTSYVFLGIVLALIGAIFLLVLYLNRKGIKKWM HNIRDACRDHMEGYHYRYEINADPRLTNLSSNSDV | 5T4 |
| 245 | QVQLVQSGGGLVQAGGSLRLSCAASRRPFSSKTMAWFRQTPG KEREFVAAVRWIGGATRYTDSVKGRFSISKDNAINTVYLQMN SLKSEDTAVYYCAAGQAWGTKFTDYSDWGQGTQVTVKP | L12E9 |
| 246 | EVQLVESGGGEVQPGGSLRLSCAASRRPFSSKTMAWFRQAPG KGREFVAAVRWIGGATRYAESVKGRFTISRDNAKNTLYLQMS SLRAEDTAVYYCAAGQAWGTKFTDYSDWGQGTLVTVKP | hz12E9v1 |
| 247 | EVQLVESGGGEVQPGGSLRLSCAASRRPFSSKTMAWFRQAPG KEREFVAAVRWIGGATRYAESVKGRFTISRDNAKNTLYLQMS SLRAEDTAVYYCAAGQAWGTKFTDYSDWGQGTLVTVKP | hz12E9v2 |
| 248 | EVQLVESGGGEVQPGGSLRLSCAASRRPFSSKTMAWFRQAPG KEREFVAAVRWIGGATRYAESVKGRFTISRDNAKNTVYLQMS SLRAEDTAVYYCAAGQAWGTKFTDYSDWGQGTLVTVKP | hz12E9v3 |
| 249 | EVQLVESGGGEVQPGGSLRLSCAASRRPFSSKTMAWFRQAPG KEREFVAAVRWIGGATRYTESVKGRFTISRDNAKNTVYLQMS SLRAEDTAVYYCAAGQAWGTKFTDYSDWGQGTLVTVKP | hz12E9v4 |
| 250 | EVQLVESGGGEVQPGGSLRLSCAASRRPFSSKTMAWFRQAPG KEREFVAAVRWIGGATRYTESVKGRFTISRDNAKNTLYLQMS SLRAEDTAVYYCAAGQAWGTKFTDYSDWGQGTLVTVKP | hz12E9v5 |

-continued

| # | SEQUENCE | ANNOTATION |
|---|----------|------------|
| 251 | EVQLVESGGGEVQAGGSLRLSCAASRRPFSSKTMAWFRQTPG KEREFVAAVRWIGGATRYAESVKGRFTISRDNAKNTVYLQMS SLRAEDTAVYYCAAGQAWGTKFTDYSDWGQGTLVTVKP | hz12E9v6 |
| 252 | EVQLVESGGGEVQPGGSLRLSCAASRRPFSSKTMAWFRQAPG KEREFVAAVRWIGGATRYTDSVKGRFSISKDNAKNTVYLQMS SLRAEDTAVYYCAAGQAWGTKFTDYSDWGQGTLVTVKP | hz12E9v7 |
| 253 | EVQLVESGGGEVQPGGSLRLSCAASRRPFSSKTMAWFRQAPG KEREFVAAVRWIGGATRYAESVKGRFTISRDNAINTVYLQMN SLKSEDTAVYYCAAGQAWGTKFTDYSDWGQGTLVTVKP | hz12E9v8 |
| 254 | EVQLVESGGGEVQPGGSLRLSCAASGRPFSSKTMAWFRQAPG KEREFVAAVRWIGGATRYTESVKGRFTISRDNAKNTVYLQMS SLRAEDTAVYYCAAGQAWGTKFTDYSDWGQGTLVTVKPGG | hz12E9v9 |
| 255 | QVQLVQSGGGLVQAGDSLTLSCAVSERPFGTYAMGWFRQAP GRERDLVAAVSRNGGASQYGDSVKGRFSISRDNIKNTMYLQ NSLKPEDTAVYYCAARSAAYSRSSEVYTGKDEYYYWGQGTQ VTVKP | L14B5 |
| 256 | EVQLVESGGGEVQPGGSLRLSCAASERPFGTYAMGWFRQAPG KGRDLVSAVSRNGGASQYAESVKGRFTISRDNAKNTLYLQMS SLRAEDTAVYYCAARSAAYSRSSEVYTGKDEYYYWGQGTLV TVKP | hz14B5v1 |
| 257 | EVQLVESGGGEVQPGGSLRLSCAASERPFGTYAMGWFRQAPG KERDLVAAVSRNGGASQYAESVKGRFTISRDNAKNTLYLQMS SLRAEDTAVYYCAARSAAYSRSSEVYTGKDEYYYWGQGTLV TVKP | hz14B5v2 |
| 258 | EVQLVESGGGEVQPGGSLRLSCAASERPFGTYAMGWFRQAPG KERDLVAAVSRNGGASQYAESVKGRFTISRDNAKNTMYLQM SSLRAEDTAVYYCAARSAAYSRSSEVYTGKDEYYWGQGTL VTVKP | hz14B5v3 |
| 259 | EVQLVESGGGEVQPGGSLRLSCAASERPFGTYAMGWFRQAPG KERDLVAAVSRNGGASQYAESVKGRFTISRDNAKNTVYLQM SSLRAEDTAVYYCAARSAAYSRSSEVYTGKDEYYWGQGTL VTVKP | hz14B5v4 |
| 260 | EVQLVESGGGEVQPGGSLRLSCAASERPFGTYAMGWFRQAPG KERDLVAAVSRNAGASQYAESVKGRFTISRDNAKNTMYLQM SSLRAEDTAVYYCAARSAAYSRSSEVYTGKDEYYWGQGTL VTVKP | hz14B5v5 |
| 261 | EVQLVESGGGEVQPGGSLRLSCAASERPFGTYAMGWFRQAPG KERDLVAAVSRNTGASQYAESVKGRFTISRDNAKNTMYLQM SSLRAEDTAVYYCAARSAAYSRSSEVYTGKDEYYWGQGTL VTVKP | hz14B5v6 |
| 262 | EVQLVESGGGEVQPGGSLRLSCAASERPFGTYAMGWFRQAPG KERDLVAAVSRQGGASQYAESVKGRFTISRDNAKNTMYLQM SSLRAEDTAVYYCAARSAAYSRSSEVYTGKDEYYWGQGTL VTVKP | hz14B5v7 |
| 263 | EVQLVESGGGEVQPGGSLRLSCAASERPFGTYAMGWFRQAPG KERDLVAAVSRGGGASQYAESVKGRFTISRDNAKNTMYLQM SSLRAEDTAVYYCAARSAAYSRSSEVYTGKDEYYWGQGTL VTVKP | hz14B5v8 |
| 264 | EVQLVESGGGEVQPGGSLRLSCAASERPFGTYAMGWFRQAPG KERDLVAAVSRNGGASQYGDSVKGRFTISRDNAKNTMYLQM SSLRAEDTAVYYCAARSAAYSRSSEVYTGKDEYYWGQGTL VTVKP | hz14B5v9 |
| 265 | EVQLVESGGGEVQPGGSLRLSCAASERPFGTYAMGWFRQAPG KERDLVAAVSRNGGASQYGESVKGRFTISRDNAKNTMYLQM SSLRAEDTAVYYCAARSAAYSRSSEVYTGKDEYYWGQGTL VTVKP | hz14B5v10 |
| 266 | EVQLVESGGGEVQAGDSLTLSCAVSERPFGTYAMGWFRQAP GRERDLVAAVSRNAGASQYAESVKGRFTISRDNAKNTMYLQ MSSLRAEDTAVYYCAARSAAYSRSSEVYTGKDEYYWGQGT LVTVKP | hz14B5v11 |

-continued

| | Sequences | |
|---|---|---|
| # | SEQUENCE | ANNOTATION |
| 267 | EVQLVESGGGEVQPGGSLRLSCAASERPFGTYAMGWFRQAPG<br>KERDLVAAVSRNAGASQYGESVKGRFSISRDNIKNTMYLQMS<br>SLKPEDTAVYYCAARSAAYSRSSEVYTGKDEYYWGQGTLV<br>TVKP | hz14B5v12 |
| 268 | EVQLVESGGGEVQPGGSLRLSCAASERPFGTYAMGWFRQAPG<br>KERETVAAVSRNAGASQYAESVKGRFTISRDNAKNTMYLQM<br>SSLRAEDTAVYYCAARSAAYSRSSEVYTGKDEYYWGQGTL<br>VTVKP | hz14B5v13 |
| 269 | EVQLVESGGGEVQPGGSLRLSCAASERPFGTYAMGWFRQAPG<br>KEREFVAAVSRNAGASQYAESVKGRFTISRDNAKNTMYLQM<br>SSLRAEDTAVYYCAARSAAYSRSSEVYTGKDEYYWGQGTL<br>VTVKP | hz14B5v14 |
| 270 | EVQLVESGGGEVQPGGSLRLSCAASERPFGTYAMGWFRQAPG<br>KERDLVAAVSRNAGASYYAESVKGRFTISRDNAKNTMYLQM<br>SSLRAEDTAVYYCAARSAAYSRSSEVYTGKDEYYWGQGTL<br>VTVKP | hz14B5v15 |
| 271 | EVQLVESGGGEVQPGGSLRLSCAASERPFGTYAMGWFRQAPG<br>KERDLVAAVSRNAGASQYGEFVKGRFTISRDNAKNTMYLQM<br>SSLRAEDTAVYYCAARSAAYSRSSEVYTGKDEYYWGQGTL<br>VTVKP | hz14B5v16 |
| 272 | EVQLVESGGGEVQPGGSLRLSCAASERPFGTYAMGWFRQAPG<br>KERDLVAAVSRNAGASYYAESVKGRFTISRDNAKNTVYLQM<br>SSLRAEDTAVYYCAARSAAYSRSSEVYTGKDEYYWGQGTL<br>VTVKP | hz14B5v17 |
| 273 | EVQLVESGGGEVQPGGSLRLSCAASERPFSSYAMGWFRQAPG<br>KERDLVAAVSRNAGASYYAESVKGRFTISRDNAKNTVYLQM<br>SSLRAEDTAVYYCAARSAAYSRSSEVYTGKDEYYWGQGTL<br>VTVKP | hz14B5v18 |
| 274 | EVQLVESGGGEVQPGGSLRLSCAASGRPFGTYAMGWFRQAP<br>GKERDLVAAVSRNAGASYYAESVKGRFTISRDNAKNTVYLQ<br>MSSLRAEDTAVYYCAARSAAYSRSSEVYTGKDEYYWGQGT<br>LVTVKP | hz14B5v19 |
| 275 | EVQLVESGGGEVQPGGSLRLSCAASGRPFSSYAMGWFRQAPG<br>KERDLVAAVSRNAGASYYAESVKGRFTISRDNAKNTVYLQM<br>SSLRAEDTAVYYCAARSAAYSRSSEVYTGKDEYYWGQGTL<br>VTVKP | hz14B5v20 |
| 276 | QVQLLQSGGGLVQAGGSLILSCAVSGRPFSSSAMGWFRQAPG<br>KERETVAAVSRNGGSSYYADFVKGRFTISRDNDKNTVYLQM<br>NSLKPEDTAVYYCAARSAAYSRSSETYTEKHDYTWGQGTQ<br>VTVKP | L16G10 |
| 277 | EVQLVESGGGEVQPGGSLRLSCAASGRPFSSSAMGWFRQAPG<br>KGRETVSAVSRNGGSSYYAESVKGRFTISRDNAKNTLYLQMS<br>SLRAEDTAVYYCAARSAAYSRSSETYTEKHDYTWGQGTLV<br>TVKP | hz16G10v1 |
| 278 | EVQLVESGGGEVQPGGSLRLSCAASGRPFSSSAMGWFRQAPG<br>KERETVAAVSRNGGSSYYAESVKGRFTISRDNAKNTLYLQMS<br>SLRAEDTAVYYCAARSAAYSRSSETYTEKHDYTWGQGTLV<br>TVKP | hz16G10v2 |
| 279 | EVQLVESGGGEVQPGGSLRLSCAASGRPFSSSAMGWFRQAPG<br>KERETVAAVSRNGGSSYYAESVKGRFTISRDNAKNTVYLQMS<br>SLRAEDTAVYYCAARSAAYSRSSETYTEKHDYTWGQGTLV<br>TVKP | hz16G10v3 |
| 280 | EVQLVESGGGEVQPGGSLRLSCAASGRPFSSSAMGWFRQAPG<br>KERETVAAVSRQGGSSYYAESVKGRFTISRDNAKNTVYLQMS<br>SLRAEDTAVYYCAARSAAYSRSSETYTEKHDYTWGQGTLV<br>TVKP | hz16G10v4 |
| 281 | EVQLVESGGGEVQPGGSLRLSCAASGRPFSSSAMGWFRQAPG<br>KERETVAAVSRGGGSSYYAESVKGRFTISRDNAKNTVYLQMS<br>SLRAEDTAVYYCAARSAAYSRSSETYTEKHDYTWGQGTLV<br>TVKP | hz16G10v5 |

-continued

| # | SEQUENCE | ANNOTATION |
|---|----------|-----------|
| 282 | EVQLVESGGGEVQPGGSLRLSCAASGRPFSSSAMGWFRQAPG<br>KERETVAAVSRNAGSSYYAESVKGRFTISRDNAKNTVYLQMS<br>SLRAEDTAVYYCAARSAAYSRSSETYTEKHDYTYWGQGTLV<br>TVKP | hz16G10v6 |
| 283 | EVQLVESGGGEVQPGGSLRLSCAASGRPFSSSAMGWFRQAPG<br>KERETVAAVSRNTGSSYYAESVKGRFTISRDNAKNTVYLQMS<br>SLRAEDTAVYYCAARSAAYSRSSETYTEKHDYTYWGQGTLV<br>TVKP | hz16G10v7 |
| 284 | EVQLVESGGGEVQPGGSLRLSCAASGRPFSSSAMGWFRQAPG<br>KERETVAAVSRNGGSSYYADFVKGRFTISRDNAKNTVYLQMS<br>SLRAEDTAVYYCAARSAAYSRSSETYTEKHDYTYWGQGTLV<br>TVKP | hz16G10v8 |
| 285 | EVQLVESGGGEVQPGGSLRLSCAASGRPFSSSAMGWFRQAPG<br>KERETVAAVSRNGGSSYYAESVKGRFTISRDNDKNTVYLQMS<br>SLRAEDTAVYYCAARSAAYSRSSETYTEKHDYTYWGQGTLV<br>TVKP | hz16G10v9 |
| 286 | EVQLVESGGGEVQPGGSLRLSCAASGRPFSSSAMGWFRQAPG<br>KERETVAAVSRNAGSSYYADFVKGRFTISRDNAKNTVYLQMS<br>SLRAEDTAVYYCAARSAAYSRSSETYTEKHDYTYWGQGTLV<br>TVKP | hz16G10v10 |
| 287 | EVQLVESGGGEVQPGGSLRLSCAASGRPFSSYAMGWFRQAPG<br>KERETVAAVSRNAGSSYYAESVKGRFTISRDNAKNTVYLQMS<br>SLRAEDTAVYYCAARSAAYSRSSETYTEKHDYTYWGQGTLV<br>TVKP | hz16G10v11 |
| 288 | RRPFSSKTMA | 5T4CDR-H1 |
| 289 | GRPFSSKTMA | 5T4 CDR-H1 |
| 290 | ERPFGTYAMG | 5T4 CDR-H1 |
| 291 | ERPFSSYAMG | 5T4 CDR-H1 |
| 292 | GRPFGTYAMG | 5T4 CDR-H1 |
| 293 | QAVVTQEPSLTVSPGGTVTLTCGSSTGAVTTSNYANWVQQKP<br>GQAFRGLIGGTNKRAPGVPARFSGSLLGGKAALTISGAQPEDE<br>ADYYCALWYSNHWVFGCGTKLTVL | anti-CD3 VL<br>(CON) |
| 294 | QVQLVQSGGGLVQAGASLRLSCVASGRTRSLRTMAWFRQAP<br>GKERIFVAAISWRSDSTYYADSVKGRFTISRDNAKNTAYLQM<br>NTLKPEDTAVYYCAAGGGWLATTPDEYTYWGQGTLVTVKP | 7E1 |
| 295 | QVQLQESGGGLMQAGDSLRLSCVVSGVTWNSYTMAWFRQA<br>PGKEREFVAAIRWTVDTTYYADFVKGRFTISRDYAKKTMYLQ<br>MNNLKPEDAAVYYCAVGRKWPKADDYWGQGTLVTVKP | 14F4 |
| 296 | GRTRSLRTMA | 5T4 CDR-H1 |
| 297 | GVTWNSYTMA | 5T4 CDR-H1 |
| 298 | AISWRSDSTY | 5T4 CDR-H2 |
| 299 | AIRWTVDTTY | 5T4 CDR-H2 |
| 300 | GGGWLATTPDEYTY | 5T4 CDR-H3 |
| 301 | GRKWPKADDY | 5T4 CDR-H3 |
| 302 | QVQLQESGGGLVQAGGSLRLSCAASRRPFSSKTMAWFRQTPG<br>KEREFVAAVRWIGGATRYTDSVKGRFSISKDNAINTVYLQTNS<br>LKSEDTAVYYCAAGQTWGTKFTDYSDWGQGTLVTVKP | 4D3 |
| 303 | GQTWGTKFTDYSD | 5T4 CDR-H3 |
| 304 | EVQLVESGGGEVQPGGSLRLSCAASGSMTGANTMGWYRQAP<br>GKGRDLVSLIGNYVTHYAESVKGRFTISRDNAKNTLYLQMSS<br>LRAEDTAVYYCYLYTDNLGTSWGQGTLVTVKPGG | hz18H10v1 |

-continued

| | Sequences | |
|---|---|---|
| # | SEQUENCE | ANNOTATION |
| 305 | EVQLVESGGGEVQPGGSLRLSCAASGSMTGANTMGWYRQAP GKQRDLVSLIGNYVTHYAESVKGRFTISRDNAKNTLYLQMSS LRAEDTAVYYCYLYTDNLGTSWGQGTLVTVKPGG | hz18H10v2 |
| 306 | EVQLVESGGGEVQPGGSLRLSCAASGSMTGANTMGWYRQAP GKQRDLVSLIGNYVTHYAESVKGRFTISRDNAKNTVYLQMSS LRAEDTAVYYCYLYTDNLGTSWGQGTLVTVKPGG | hz18H10v3 |
| 307 | EVQLVESGGGEVQPGGSLRLSCAASGSMTGANTMGWYRQAP GKQRDLVALIGNYVTHYAESVKGRFTISRDNAKNTVYLQMSS LRAEDTAVYYCYLYTDNLGTSWGQGTLVTVKPGG | hz18H10v4 |
| 308 | EVQLVESGGGEVQPGGSLRLSCAASGSMTGANTMGWYRQAP GKQRDLVALIGNYVTHYAESVKGRFTISRENAKNTVYLQMSS LRAEDTAVYYCYLYTDNLGTSWGQGTLVTVKPGG | hz18H10v5 |
| 309 | EVQLVESGGGEVQPGGSLRLSCAASGSVTGANTMGWYRQAP GKQRDLVALIGNYVTHYAESVKGRFTISRDNAKNTVYLQMSS LRAEDTAVYYCYLYTDNLGTSWGQGTLVTVKPGG | hz18H10v6 |
| 310 | EVQLVESGGGEVQPGGSLRLSCAASGSITGANTMGWYRQAPG KQRDLVALIGNYVTHYAESVKGRFTISRDNAKNTVYLQMSSL RAEDTAVYYCYLYTDNLGTSWGQGTLVTVKPGG | hz18H10v7 |
| 311 | EVQLVESGGGEVQPGGSLRLSCAASGSVTGANTMGWYRQAP GKQRDLVSLIGNYVTHYAESVKGRFTISRDNAKNTLYLQMSS LRAEDTAVYYCYLYTDNLGTSWGQGTLVTVKPGG | hz18H10v8 |
| 312 | EVQLVESGGGEVQPGGSLRLSCAASGSVTGANTMGWYRQAP GKQRDLVSLIGNYVTHYAESVKGRFTISRDNAKNTVYLQMSS LRAEDTAVYYCYLYTDNLGTSWGQGTLVTVKPGG | hz18H10v9 |
| 313 | EVQLVESGGGEVQPGGSLRLSCAASGSMTGANTMGWYRQAP GKQRDLVSLIGNYVTHYAESVKGRFTISRENAKNTVYLQMSS LRAEDTAVYYCYLYTDNLGTSWGQGTLVTVKPGG | hz18H10v10 |
| 314 | EVQLVESGGGEVQPGGSLRLSCAASGSVTGANTMGWYRQAP GKQRDLVSLIGNYVTHYAESVKGRFTISRENAKNTVYLQMSS LRAEDTAVYYCYLYTDNLGTSWGQGTLVTVKPGG | hz18H10v11 |
| 315 | EVQLVESGGGEVQPGGSLRLSCAASGSVTGANTMGWYRQAP GKQRDLVALIGNYVTHYAESVKGRFTISRENAKNTVYLQMSS LRAEDTAVYYCYLYTDNLGTSWGQGTLVTVKPGG | hz18H10v12 |
| 316 | EVQLVESGGGEVQPGGSLRLSCAASGSMTGANTMGWYRQAP GKQRELVALIGNYVTHYAESVKGRFTISRENAKNTVYLQMSS LRAEDTAVYYCYLYTDNLGTSWGQGTLVTVKPGG | hz18H10v13 |
| 317 | EVQLVESGGGEVQPGGSLRLSCAASGSVTGANTMGWYRQAP GKQRDLVALIGNYVTHYAESVKGRFTISRDNAKNTLYLQMSS LRAEDTAVYYCYLYTDNLGTSWGQGTLVTVKPGG | hz18H10v14 |
| 318 | EVQLVESGGGEVQPGGSLRLSCAASGSITGANTMGWYRQAPG KQRDLVALIGNYVTHYAESVKGRFTISRDNAKNTLYLQMSSL RAEDTAVYYCYLYTDNLGTSWGQGTLVTVKPGG | hz18H10v15 |
| 319 | EVQLVESGGGEVQPGGSLRLSCAASGSITGANTMGWYRQAPG KQRDLVALIGNYVTHYAESVKGRFTISRENAKNTVYLQMSSL RAEDTAVYYCYLYTDNLGTSWGQGTLVTVKPGG | hz18H10v16 |
| 320 | EVQLVESGGGEVQPGGSLRLSCAASGSITGANTMGWYRQAPG KQRDLVALIGNYVTHYAESVKGRFTISRDNAKNTVYLQMNSL RAEDTAVYYCYLYTDNLGTSWGQGTLVTVKPGG | hz18H10v17 |
| 321 | GSMTGANTMG | CDR1 |
| 322 | GSVTGANTMG | CDR1 |
| 323 | GSITGANTMG | CDR1 |
| 324 | LIGNYVTH | CDR2 |
| 325 | YTDNLGTS | CDR3 |

| # | SEQUENCE | ANNOTATION |
|---|----------|------------|
| 326 | QVQLVQSGGGLVQPGGSLRLSCVASGSMTGANTMGWYRQAP GKQRDLVALIGNYHYADSVKGRFTISRENAKNTVILQMNSLN PEDTAVYYCYLYTDNLGTSWGQGTLVTVKPGG | 18H10 |
| 327 | PGGGG | Linker |
| 328 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VYTLPPCRDELTKNQVSLWCLVKGFYPSDIAVEWESNGQPEN NYKTTPPVLDSDGSFFLYSKLTVDKSRWQQGNVFSCSVMHEA LHNHYTQKSLSLSP | Knob Fc |
| 329 | DKTHTCPPCPAPELLGGPSVFLFPPKPKDTLMRSRTPEVTCVV VDVSHEDPEVKFNWYVDGVEVHNAKTKPREEQYNSTYRVVS VLTVLHQDWLNGKEYKCKVSNKALPAPIEKTISKAKGQPREP QVCTLPPSRDELTKNQVSLSCAVKGFYPSDIAVEWESNGQPEN NYKTTPPVLDSDGSFFLVSKLTVDKSRWQQGNVFSCSVMHEA LHNHYTQKSLSLSP | Hole Fc |
| 330 | DKTHTCPPCPAPGGPSVFLFPPKPKDTLMISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVYT LPPCRDELTKNQVSLWCLVKGFYPSDIAVEWESNGQPENNYK TTPPVLDSDGSFFLYSKLTVDKSRWQQGNVFSCSVMHEALHN HYTQKSLSLSP | Knob Fc |
| 331 | DKTHTCPPCPAPGGPSVFLFPPKPKDTLMRSRTPEVTCVVVDV SHEDPEVKFNWYVDGVEVHNAKTKPREEQYNSTYRVVSVLT VLHQDWLNGKEYKCKVSNKALPAPIEKTISKAKGQPREPQVC TLPPSRDELTKNQVSLSCAVKGFYPSDIAVEWESNGQPENNYK TTPPVLDSDGSFFLVSKLTVDKSRWQQGNVFSCSVMHEALHN HYTQKSLSLSP | Hole Fc |
| 332 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VCTLPPSRDELTKNQVSLSCAVKGFYPSDIAVEWESNGQPENN YKTTPPVLDSDGSFFLVSKLTVDKSRWQQGNVFSCSVMHEAL HNRYTQKSLSLSP | Hole Fc |
| 333 | DKTHTCPPCPAPGGPSVFLFPPKPKDTLMISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVMHEALHNR YTQKSLSLSP | Hole Fc |
| 334 | DKTHTCPPCPAPELLGGPSVFLFPPKPKDTLYISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VYTLPPCRDELTKNQVSLWCLVKGFYPSDIAVEWESNGQPEN NYKTTPPVLDSDGSFFLYSKLTVDKSRWQQGNVFSCSVVHEA LHNHYTQKSLSLSP | Knob Fc |
| 335 | DKTHTCPPCPAPGGPSVFLFPPKPKDTLYISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVYT LPPCRDELTKNQVSLWCLVKGFYPSDIAVEWESNGQPENNYK TTPPVLDSDGSFFLYSKLTVDKSRWQQGNVFSCSVVHEALHN HYTQKSLSLSP | Knob Fc |
| 336 | DKTHTCPPCPAPELLGGPSVFLFPPKPKDTLYISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VCTLPPSRDELTKNQVSLSCAVKGFYPSDIAVEWESNGQPENN YKTTPPVLDSDGSFFLVSKLTVDKSRWQQGNVFSCSVVHEAL HNRYTQKSLSLSP | Hole Fc |

-continued

| # | SEQUENCE | ANNOTATION |
|---|---|---|
| 337 | DKTHTCPPCPAPGGPSVFLFPPKPKDTLYISRTPEVTCVVVDVS HEDPEVKFNWYVDGVEVHNAKTKPREEQYNSTYRVVSVLTV LHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVVHEALHNR YTQKSLSLSP | Hole Fc |
| 338 | DKTHTCPPCPAPPVAGPSVFLFPPKPKDTLMISRTPEVTCVVVD VKHEDPEVKFNWYVDGVEVHNAKTKPREEEYNSTYRVVSVL TVLHQDWLNGKEYKCKVSNKALPAPIEKTISKAKGQPREPQV YTLPPSREEMTKNQVSLTCDVSGFYPSDIAVEWESDGQPENNY KTTPPVLDSDGSFFLYSKLTVDKSRWEQGDVFSCSVMHEALH NHYTQKSLSLSPGK | Fc-Het-1 |
| 339 | DKTHTCPPCPAPPVAGPSVFLFPPKPKDTLMISRTPEVTCVVVD VKHEDPEVKFNWYVDGVEVHNAKTKPREEQYNSTYRVVSVL TVLHQDWLNGKEYKCKVSNKALPAPIEKTISKAKGQPREPQV YTLPPSREQMTKNQVKLTCLVKGFYPSDIAVEWESNGQPENN YKTTPPVLDSDGSFFLYSKLTVDKSRWQQGNVFSCSVMHEAL HNHYTQKSLSLSPGK | Fc-Het-2 |
| 340 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGCGTKLTVL | anti-CD3 VL21 |
| 341 | EVQLVESGGGLVQPGGSLRLSCAASGFTFSTYAMNWVRQAPG KGLEWVGRIRSKYNNYATYYADSVKGRFTISRDDSKNTLYLQ MNSLRAEDTAVYYCVRHGNFGDSYVSWFAWGQGTLVTVS S | anti-CD3 VH32 |
| 342 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGGGTKLTVL | anti-CD3 VL20 |
| 343 | EVQLVESGGGLVQPGGSLRLSCAASGFTFSTYAMNWVRQAPG KCLEWVARIRSKYNNYATYYADTVKGRFTISRDDAKNTLYLQ MSSLRAEDTAVYYCVRHGNFGDSYVSWFAYWGQGTLVTV | anti-CD3 VH34 |
| 344 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VYTLPPCRDELTKNQVSLWCLVKGFYPSDIAVEWESNGQPEN NYKTTPPVLDSDGSFFLYSKLTVDKSRWQQGNVFSCSVMHEA LHNHYTQKSLSLSP | IgG1 Knob |
| 345 | DKTHTCPPCPAPELLGGPSVFLFPPKPKDTLMRSRTPEVTCVV VDVSHEDPEVKFNWYVDGVEVHNAKTKPREEQYNSTYRVVS VLTVLHQDWLNGKEYKCKVSNKALPAPIEKTISKAKGQPREP QVCTLPPSRDELTKNQVSLSCAVKGFYPSDIAVEWESNGQPEN NYKTTPPVLDSDGSFFLVSKLTVDKSRWQQGNVFSCSVMHEA LHNHYTQKSLSLSP | IgG1 Knob |
| 346 | GGGGSGGGGSGGGGS | Linker |
| 347 | GFSFSINAMG | 41BB CDR1 |
| 348 | AIESGRNTV | 41BB CDR2 |
| 349 | LKGNRVVSPSVAY | 41BB CDR3 |
| 350 | GFTFNTYAMN | anti-CD3 VH CDR1 |
| 351 | RIRSKYNNYATY | anti-CD3 VH CDR2 |
| 352 | HGNFGDSYVSWFAY | anti-CD3 VH CDR3 |
| 353 | ALWYSNHWV | anti-CD3 VL CDR3 |
| 354 | VLWYSNRWV | anti-CD3 VL CDR3 |

-continued

| # | SEQUENCE | ANNOTATION |
|---|----------|------------|
| 355 | GFTFSTYAMN | anti-CD3 VH CDR1 |
| 356 | RIRSKYNNYATY | anti-CD3 VH CDR2 |
| 357 | GSSTGAVTTSNYAN | anti-CD3 VL CDR1 |
| 358 | EVQLVESGGGLVQPGGSLRLSCAASGFTFSTYAMNWVRQAPG<br>KCLEWVGRIRSKYNNYATYYADSVKGRFTISRDDSKNTLYLQ<br>MNSLRAEDTAVYYCVRHGNFGDSYVSWFAWGQGTLVTVS<br>S | anti-CD3 VH33 |
| 359 | EVQLVESGGGEVQPGGSLRLSCAASGFSFSINAMGWYRQAPG<br>KRREFVAAIESGRNTVYAESVKGRFTISRDNAKNTVYLQMSSL<br>RAEDTAVYYCGLLKGNRVVSPSVAWGQGTLVTVKP | 41BB sdAb |
| 360 | EVQLVESGGGEVQPGGSLRLSCAASGRPFSSKTMAWFRQAPG<br>KEREFVAAVRWIGGATRYTESVKGRFTISRDNAKNTVYLQMS<br>SLRAEDTAVYYCAAGQAWGTKFTDYSDWGQGTLVTVKP | hz12E9v09 |
| 361 | IEPDP | Linker |
| 362 | SSPTSSASSFSSSAPFLASAVSAQPPLPDQCPALCECSEAARTVK<br>CVNRNLTEVPTDLPAYVRNLFLTGNQLAVLPAGAFARRPPLA<br>ELAALNLSGSRLDEVRAGAFEHLPSLRQLDLSHNPLADLSPFA<br>FSGSNASVSAPSPLVELILNHIVPPEDERQNRSFEGMVVAALLA<br>GRALQGLRRLELASNHFLYLPRDVLAQLPSLRHLDLSNNSLVS<br>LTYVSFRNLTHLESLHLEDNALKVLHNGTLAELQGLPHIRVFL<br>DNNPWVCDCHMADMVTWLKETEVVQGKDRLTCAYPEKMR<br>NRVLLELNSADLDCDPILPPSLQTS | 5T4 ECD, amino acids 32-355 of human 5T4 (UniProt No. Q13641) |
| 363 | GGS(GGS)n, where n = 0 to 10 | linker |
| 364 | QVQLVQSGGGLVQPGGSLRLSCVASGSMTGANTMGWYRQAP<br>GKQRDLVALIGNYHYADSVKGRFTISRENAKNTVILQMNSLN<br>PEDTAVYYCYLYTDNLGTSWGQGTLVTVKP | 18H10 |
| 365 | EVQLVESGGGEVQPGGSLRLSCAASGSMTGANTMGWYRQAP<br>GKGRDLVSLIGNYVTHYAESVKGRFTISRDNAKNTLYLQMSS<br>LRAEDTAVYYCYLYTDNLGTSWGQGTLVTVKP | hz18H10v1 |
| 366 | EVQLVESGGGEVQPGGSLRLSCAASGSMTGANTMGWYRQAP<br>GKQRDLVSLIGNYVTHYAESVKGRFTISRDNAKNTLYLQMSS<br>LRAEDTAVYYCYLYTDNLGTSWGQGTLVTVKP | hz18H10v2 |
| 367 | EVQLVESGGGEVQPGGSLRLSCAASGSMTGANTMGWYRQAP<br>GKQRDLVSLIGNYVTHYAESVKGRFTISRDNAKNTLYLQMSS<br>LRAEDTAVYYCYLYTDNLGTSWGQGTLVTVKP | hz18H10v3 |
| 368 | EVQLVESGGGEVQPGGSLRLSCAASGSMTGANTMGWYRQAP<br>GKQRDLVALIGNYVTHYAESVKGRFTISRDNAKNTVYLQMSS<br>LRAEDTAVYYCYLYTDNLGTSWGQGTLVTVKP | hz18H10v4 |
| 369 | EVQLVESGGGEVQPGGSLRLSCAASGSMTGANTMGWYRQAP<br>GKQRDLVALIGNYVTHYAESVKGRFTISRENAKNTVYLQMSS<br>LRAEDTAVYYCYLYTDNLGTSWGQGTLVTVKP | hz18H10v5 |
| 370 | EVQLVESGGGEVQPGGSLRLSCAASGSVTGANTMGWYRQAP<br>GKQRDLVALIGNYVTHYAESVKGRFTISRDNAKNTVYLQMSS<br>LRAEDTAVYYCYLYTDNLGTSWGQGTLVTVKP | hz18H10v6 |
| 371 | EVQLVESGGGEVQPGGSLRLSCAASGSITGANTMGWYRQAPG<br>KQRDLVALIGNYVTHYAESVKGRFTISRDNAKNTVYLQMSSL<br>RAEDTAVYYCYLYTDNLGTSWGQGTLVTVKP | hz18H10v7 |
| 372 | EVQLVESGGGEVQPGGSLRLSCAASGSVTGANTMGWYRQAP<br>GKQRDLVSLIGNYVTHYAESVKGRFTISRDNAKNTLYLQMSS<br>LRAEDTAVYYCYLYTDNLGTSWGQGTLVTVKP | hz18H10v8 |
| 373 | EVQLVESGGGEVQPGGSLRLSCAASGSVTGANTMGWYRQAP<br>GKQRDLVSLIGNYVTHYAESVKGRFTISRDNAKNTVYLQMSS<br>LRAEDTAVYYCYLYTDNLGTSWGQGTLVTVKP | hz18H10v9 |

| | Sequences | |
|---|---|---|
| # | SEQUENCE | ANNOTATION |
| 374 | EVQLVESGGGEVQPGGSLRLSCAASGSMTGANTMGWYRQAP GKQRDLVSLIGNYVTHYAESVKGRFTISRENAKNTVYLQMSS LRAEDTAVYYCYLYTDNLGTSWGQGTLVTVKP | hz18H10v10 |
| 375 | EVQLVESGGGEVQPGGSLRLSCAASGSVTGANTMGWYRQAP GKQRDLVSLIGNYVTHYAESVKGRFTISRENAKNTVYLQMSS LRAEDTAVYYCYLYTDNLGTSWGQGTLVTVKP | hz18H10v11 |
| 376 | EVQLVESGGGEVQPGGSLRLSCAASGSVTGANTMGWYRQAP GKQRDLVALIGNYVTHYAESVKGRFTISRENAKNTVYLQMSS LRAEDTAVYYCYLYTDNLGTSWGQGTLVTVKP | hz18H10v12 |
| 377 | EVQLVESGGGEVQPGGSLRLSCAASGSMTGANTMGWYRQAP GKQRELVALIGNYVTHYAESVKGRFTISRENAKNTVYLQMSS LRAEDTAVYYCYLYTDNLGTSWGQGTLVTVKP | hz18H10v13 |
| 378 | EVQLVESGGGEVQPGGSLRLSCAASGSVTGANTMGWYRQAP GKQRDLVALIGNYVTHYAESVKGRFTISRDNAKNTLYLQMSS LRAEDTAVYYCYLYTDNLGTSWGQGTLVTVKP | hz18H10v14 |
| 379 | EVQLVESGGGEVQPGGSLRLSCAASGSITGANTMGWYRQAPG KQRDLVALIGNYVTHYAESVKGRFTISRDNAKNTLYLQMSSL RAEDTAVYYCYLYTDNLGTSWGQGTLVTVKP | hz18H10v15 |
| 380 | EVQLVESGGGEVQPGGSLRLSCAASGSITGANTMGWYRQAPG KQRDLVALIGNYVTHYAESVKGRFTISRENAKNTVYLQMSSL RAEDTAVYYCYLYTDNLGTSWGQGTLVTVKP | hz18H10v16 |
| 381 | EVQLVESGGGEVQPGGSLRLSCAASGSITGANTMGWYRQAPG KQRDLVALIGNYVTHYAESVKGRFTISRDNAKNTLYLQMNSL RAEDTAVYYCYLYTDNLGTSWGQGTLVTVKP | hz18H10v17 |
| 382 | SSPTSSASSFSSSAPFLASAVSAQPPLPDQCPALCECSEAARTVK CVNRNLTEVPTDLPAYVRNLFLTGNQLAVLPAGAFARRPPLA ELAALNLSGSRLDEVRAGAFEHLPSLRQLDLSHNPLADLSPFA FSGSNASVSAPSPLVELILNHIVPPEDERQNRSFEGMVVAALLA GRALQGLRRLELASNHFLYLPRDVLAQLPSLRHLDLSNNSLVS LTYVSFRNLTHLESLHLEDNALKVLHNGTLAELQGLPHIRVFL DNNPWVCDCHMADMVTWLKETEVVQGKDRLTCAYPEKMR NRVLLELNSADLDCDPILPPSLQTSYVFLGIVLALIGAIFLLVLY LNRKGIKKWMHNIRDACRDHMEGYHYRYEINADPRLTNLSS NSDV | human 5T4 construct |
| 383 | SAPSSSVPSSSTSPAAFLASGSAQPPPAERCPAACECSEAARTV KCVNRNLLEVPADLPPYVRNLFLTGNQMTVLPAGAFARQPPL ADLEALNLSGNHLKEVCAGAFEHLPGLRRLDLSHNPLTNLSAF AFAGSNASVSAPSPLEELILNHIVPPEDQRQNGSFEGMVVAFEG MVAAALRSGLALRGLTRLELASNHFLFLPRDLLAQLPSLRYLD LRNNSLVSLTYASFRNLTHLESLHLEDNALKVLHNSTLAEWH GLAHVKVFLDNNPWVCDCYMADMVAWLKETEVVPDKARLT CAFPEKMRNRGLLDLNSSDLDCDAVLPQSLQTSYVFLGIVLAL IGAIFLLVLYLNRKGIKKWMHNIRDACRDHMEGYHYRYEINA DPRLTNLSSNSDV | murine 5T4 construct |
| 384 | SSPTSSASSFSSSAPFLASAVSAQPPLPDQCPALCECSEAARTVK CVNRNLTEVPTDLPAYVRNLFLTGNQLAVLPAGAFARRPPLA ELAALNLSGSRLDEVRAGAFEHLPSLRQLDLSHNPLADLSPFA FSGSNASVSAPSPLVELILNHIVPPEDERQNRSFEGMVVAALLS GLALRGLTRLELASNHFLFLPRDLLAQLPSLRYLDLRNNSLVS LTYASFRNLTHLESLHLEDNALKVLHNSTLAEWHGLAHVKVF LDNNPWVCDCYMADMVAWLKETEVVPDKARLTCAFPEKMR NRGLLDLNSSDLDCDAVLPQSLQTSYVFLGIVLALIGAIFLLVL YLNRKGIKKWMHNIRDACRDHMEGYHYRYEINADPRLTNLS SNSDV | hmc5T4.1 (human residues underlined) |
| 385 | SAPSSSVPSSSTSPAAFLASGSAQPPPAERCPAACECSEAARTV KCVNRNLLEVPADLPPYVRNLFLTGNQMTVLPAGAFARQPPL ADLEALNLSGNHLKEVCAGAFEHLPSLRQLDLSHNPLADLSPF AFSGSNASVSAPSPLVELILNHIVPPEDERQNRSFEGMVVAALL AGRALQGLRRLELASNHFLYLPRDVLAQLPSLRHLDLSNNSLV SLTYVSFRNLTHLESLHLEDNALKVLHNSTLAEWHGLAHVKV FLDNNPWVCDCYMADMVAWLKETEVVPDKARLTCAFPEKM RNRGLLDLNSSDLDCDAVLPQSLQTSYVFLGIVLALIGAIFLLV | hmc5T4.2 (human residues underlined) |

-continued

| | Sequences | |
|---|---|---|
| # | SEQUENCE | ANNOTATION |

LYLNRKGIKKWMHNIRDACRDHMEGYHYRYEINADPRLTNL
SSNSDV

386 <u>SSPTSSASSFSSSAPFLASAVSAQPPLPDQCPALCECSEAARTVK</u>
<u>CVNRNLTEVPTDLPAYVRNLFLTGNQMTVLPAGAFARQPPLA</u>
<u>DLEALNLSGNHLKEVCAGAFEHLPGLRRLDLSHNPLTNLSAFA</u>
FAGSNASVSAPSPLEELILNHIVPPEDQRQNGSFEGMVAFEGM
VAAALRSGLALRGLTRLELASNHFLFLPRDLLAQLPSLRYLDL
RNNSLVSLTYASFRNLTHLESLHLEDNALKVLHNSTLAEWHG
LAHVKVFLDNNPWVCDCYMADMVAWLKETEVVPDKARLTC
AFPEKMRNRGLLDLNSSDLDCDAVLPQSLQTSYVFLGIVLALI
GAIFLLVLYLNRKGIKKWMHNIRDACRDHMEGYHYRYEINA
DPRLTNLSSNSDV
hm.c5T4.3 (human residues underlined)

387 SAPSSSVPSSSTSPAAFLASGSAQPPPAERCPAACECSEAARTV
KCVNRNLLEVPADLPPYVRNLFLTGNQMTVLPAGAFARQPPL
ADLEALNLSGNHLKEVCAGAFEHLPGLRRLDLSHNPLTNLSAF
AFAGSNASVSAPSPLEELILNHIVPPEDQRQNGSFEGMVAFEG
MVAAALRSGLALRGLTRLELASNHFLFLPRDLLAQLPSLRYLD
LRNNSLVSLTYASFRNLTHLESLHLEDNALKVLHNSTLAEWH
GLAHVKVFLDNNPWVCDCYMADMVTWLKETEVVQGKDRLT
CAYPEKMRNRVLLELNSADLDCDPILPPSLQTSYVFLGIVLALI
GAIFLLVLYLNRKGIKKWMHNIRDACRDHMEGYHYRYEINA
DPRLTNLSSNSDV
hm.c5T4.4 (human residues underlined)

388 EVQLVESGGGLVQPGRSLRLSCAASGFTFDDYAMHWVRQAP
GKGLEWVSGISWNSGSIGYADSVKGFTISRDNAKNSLYLQMN
SLRAEDTALYYCAKDSRGYGDYRLGGAWGQGTLVTVSS
Anti-CD3 VH 312557

389 EVQLVESGGGLVQPGRSLRLSCAASGFTFDDYAMHWVRQAP
GKCLEWVSGISWNSGSIGYADSVKGFTISRDNAKNSLYLQMN
SLRAEDTALYYCAKDSRGYGDYRLGGAWGQGTLVTVSS
Anti-CD3 VH 312557 G44C 390 EIVMTQSPATLSVSPGERATLSCRASQSVSSNLAWYQQKPGQA
PRLLIYGASTRATGIPARFSGSGSGTEFTLTISSLQSEDFAVYYC
QQYNNWPWTFGQGTKVEIK
Anti-CD3 VL 312557

391 EIVMTQSPATLSVSPGERATLSCRASQSVSSNLAWYQQKPGQA
PRLLIYGASTRATGIPARFSGSGSGTEFTLTISSLQSEDFAVYYC
QQYNNWPWTFGCGTKVEIK
Anti-CD3 VL 312557 Q100C 392 EVQLVESGGGLVQPGRSLRLSCVASGFTFDDYSMHWVRQAP
GKGLEWVSGISWNSGSKDYADSVKGRFTISRDNAKNSLYLQM
NSLRAEDTALYYCAKYGSGYGKFYHYGLDVWGQGTTVTVSS
CD3-VH-G 393 EVQLVESGGGLVQPGRSLRLSCVASGFTFDDYSMHWVRQAP
GKCLEWVSGISWNSGSKDYADSVKGRFTISRDNAKNSLYLQM
NSLRAEDTALYYCAKYGSGYGKFYHYGLDVWGQGTTVTVSS
CD3-VH-G 394 DIQMTQSPSSLSASVGDRVTITCRASQSISSYLNWYQQKPGKA
PKLLIYAASSLQSGVPSRFSGSGSGTDFTLTISSLQPEDFATYYC
QQSYSTPPITFGQGTRLEIK
$V_{K1}$-39Jκ5

395 DIQMTQSPSSLSASVGDRVTITCRASQSISSYLNWYQQKPGKA
PKLLIYAASSLQSGVPSRFSGSGSGTDFTLTISSLQPEDFATYYC
QQSYSTPPITFGCGTRLEIK
$V_{K1}$-39Jκ5 Q100C 396 (ADAAP)n
    n = 2-20
linker 397 (ADAAP)n-G
    n = 2-20
linker 398 (GEPQG)n
    n = 2-20
linker 399 (GEPQG)n-G
    n = 2-20
linker 400 (AGGEP)n
    n = 2-20
linker 401 (AGGEP)n-G
    n = 2-20
linker -continued

| Sequences | | |
|---|---|---|
| # | SEQUENCE | ANNOTATION |
| 402 | (AGSEP)n<br>n = 2-20 | linker |
| 403 | (AGSEP)n-G<br>n = 2-20 | linker |
| 404 | (GGGEQ)n<br>n = 2-20 | linker |
| 405 | (GGGEQ)n-G<br>n = 2-20 | linker |
| 406 | ADAAPADAAPG | linker |
| 407 | GEPQGGEPQGG | linker |
| 408 | AGGEPAGGEPG | linker |
| 409 | AGSEPAGSEPG | linker |
| 410 | GGGEQGGGEQG | linker |
| 411 | AYVRNLFLTGNQLAVLPAGAFARRPPLAELAALNLSGSRLDE<br>VRAGAFEHLPS | Amino acids 60-<br>112 of human 5T4<br>ECD |
| 412 | LAGRALQGLRRLELASNHFLYLPRDVLAQLPSLRHLDLSNNSL<br>VSLTYVSFR | Amino acids 173-<br>224 of human 5T4<br>ECD |

The invention claimed is:

1. A 5T4-binding polypeptide construct, comprising at least one heavy chain only variable domain (5T4 VHH domain) comprising a complementarity determining region 1 (CDR1) comprising the amino acid sequence selected from the group consisting of SEQ ID NO: 86-87 and 288-292, 296, and 297; a complementarity determining region 2 (CDR2) comprising the amino acid sequence selected from the group consisting of SEQ ID NO: 88-99, 298, and 299; and a complementarity determining region 3 (CDR3) comprising the amino acid sequence selected from the group consisting of SEQ ID NO: 100-102, 300, 301, and 303.

2. The 5T4-binding polypeptide construct of claim 1, wherein the at least one 5T4 VHH domain is humanized.

3. The 5T4-binding polypeptide construct of claim 1, wherein the polypeptide construct comprises an immunoglobulin Fc region.

4. The 5T4-binding polypeptide construct of claim 1 that is a dimer.

5. The 5T4-binding polypeptide construct of claim 3, wherein the Fc region is a heterodimeric Fc region.

6. The 5T4-binding polypeptide construct of claim 1, wherein the at least one 5T4 VHH domain comprises (i) the sequence set forth in SEQ ID NO: 245, (ii) a humanized variant of SEQ ID NO:245, or (iii) a sequence of amino acids that exhibits at least 85% sequence identity to SEQ ID NO:245 and binds 5T4.

7. The 5T4-binding polypeptide construct of claim 1, wherein
the at least one 5T4 VHH domain comprises a CDR1, CDR2 and CDR3 set forth in SEQ ID NOS: 288, 88, and 100, respectively; or SEQ ID NOS: 289, 88, and 100, respectively.

8. The 5T4-binding polypeptide construct of claim 1, wherein the at least one 5T4 VHH domain comprises the sequence of amino acids set forth in any one of SEQ ID NOs: 246-253 and 360 or a sequence of amino acids that exhibits at least 85% sequence identity to any of SEQ ID NO: 246-253 and 360 and binds 5T4.

9. The 5T4-binding polypeptide construct of claim 1, wherein the at least one 5T4 VHH domain comprises (i) the sequence set forth in SEQ ID NO: 255, (ii) a humanized variant of SEQ ID NO: 255, or (iii) a sequence of amino acids that exhibits at least 85% sequence identity to SEQ ID NO: 255 and binds 5T4.

10. The 5T4-binding polypeptide construct of claim 1, wherein
the at least one 5T4 VHH domain comprises a CDR1 comprising the amino acid sequence selected from the group consisting of SEQ ID NOS: 86, 290-292; a CDR2 comprising the amino acid sequence selected from the group consisting of SEQ ID NO: 89-94; and a CDR3 comprising the amino acid sequence set forth in SEQ ID NO: 101.

11. The 5T4-binding polypeptide construct of claim 1, wherein the at least one 5T4 VHH domain comprises the sequence of amino acids set forth in any one of SEQ ID NOs: 256-275 or a sequence of amino acids that exhibits at least 85% sequence identity to any of SEQ ID NO: 256-275 and binds 5T4.

12. The 5T4-binding polypeptide construct of claim 1, wherein the at least one 5T4 VHH domain comprises (i) the sequence set forth in SEQ ID NO: 276, (ii) a humanized variant of SEQ ID NO: 276, or (iii) a sequence of amino acids that exhibits at least 85% sequence identity to SEQ ID NO: 276 and binds 5T4.

13. The 5T4-binding polypeptide construct of claim 1, wherein
the at least one 5T4 VHH domain comprises a CDR1 comprising the amino acid sequence selected from the group consisting of SEQ ID NOS: 86 and 87; a CDR2 comprising the amino acid sequence selected from the group consisting of SEQ ID NOS: 95-99; and a CDR3 comprising the amino acid sequence set forth in SEQ ID NO: 102.

14. The 5T4-binding polypeptide construct of claim 1, wherein the at least one 5T4 VHH domain comprises the sequence of amino acids set forth in any one of SEQ ID NOs: 277-287 or a sequence of amino acids that exhibits at least 85% sequence identity to any one of SEQ ID NO: 277-287 and binds 5T4.

15. The 5T4-binding polypeptide construct of claim 1, wherein
the at least one 5T4 VHH domain comprises (i) the sequence set forth in SEQ ID NO: 294, 295, or 302, (ii) a humanized variant of SEQ ID NO: 294, 295, or 302, or (iii) a sequence of amino acids that exhibits at least 85% sequence identity to SEQ ID NO: 294, 295, or 302 and binds 5T4.

16. The 5T4-binding polypeptide construct of claim 1, wherein the 5T4-binding polypeptide construct comprises a first 5T4 VHH domain that specifically binds 5T4 and a second 5T4 VHH domain that specifically binds 5T4, wherein the first and second 5T4 VHH domains comprise the CDR1 comprising the amino acid sequence selected from the group consisting of SEQ ID NO: 86-87 and 288-292, 296, and 297; the CDR2 comprising the amino acid sequence selected from the group consisting of SEQ ID NO: 88-99, 298, and 299; and the CDR3 comprising the amino acid sequence selected from the group consisting of SEQ ID NO: 100-102, 300, 301, and 303.

17. The 5T4-binding polypeptide construct of claim 16, wherein:

the first 5T4 VHH domain comprises the amino acid sequence set forth in any one of SEQ ID NOS: 245-253, 295, 302, and 360, a humanized variant thereof, or a sequence of amino acids that exhibits at least 85% sequence identity to any of SEQ ID NOS: 245-253, 295, 302, and 360, and binds 5T4; and the second 5T4 VHH domain comprises the amino acid sequence set forth in any one of SEQ ID NOS: 255-287, 294, 302, a humanized variant thereof, or a sequence of amino acids that exhibits at least 85% sequence identity to any of SEQ ID NOS: 255-287, 294, 302, and binds 5T4.

18. The 5T4-binding polypeptide construct of claim 1, wherein the at least one 5T4 VHH domain comprises a CDR1, CDR2 and CDR3 set forth in SEQ ID NOS: 290, 90, and 101, respectively; SEQ ID NOS: 290, 91, and 101, respectively; SEQ ID NOS: 290, 92, and 101, respectively; SEQ ID NOS: 290, 93, and 101, respectively; SEQ ID NOS: 290, 94, and 101, respectively; SEQ ID NOS: 291, 94, and 101, respectively; SEQ ID NOS: 292, 94, and 101, respectively; or SEQ ID NOS: 86, 94, and 101, respectively.

19. The 5T4-binding polypeptide construct of claim 1, wherein the at least one 5T4 VHH domain comprises a CDR1, CDR2 and CDR3 set forth in SEQ ID NOS: 87, 95, and 102, respectively; SEQ ID NOS: 87, 96, and 102, respectively; SEQ ID NOS: 87, 97, and 102, respectively; SEQ ID NOS: 87, 98, and 102, respectively; SEQ ID NOS: 87, 99, and 102, respectively; or SEQ ID NOS: 86, 98, and 102, respectively.

20. The 5T4-binding polypeptide construct of claim 1, wherein the at least one 5T4 VHH domain comprises a CDR1 comprising the amino acid sequence selected from the group consisting of SEQ ID NOS: 288, 296, or 297; a CDR2 comprising the amino acid sequence selected from the group consisting of SEQ ID NOS: 88, 298, or 299; and a CDR3 comprising the amino acid sequence selected from the group consisting of SEQ ID NO:300, 301, or 303.

21. An isolated single domain antibody (sdAb) that binds 5T4, comprising a complementarity determining region 1 (CDR1) comprising the amino acid sequence selected from the group consisting of SEQ ID NO: 86-87 and 288-292, 296, and 297; a complementarity determining region 2 (CDR2) comprising the amino acid sequence selected from the group consisting of SEQ ID NO: 88-99, 298, and 299; and a complementarity determining region 3 (CDR3) comprising the amino acid sequence selected from the group consisting of SEQ ID NO: 100-102, 300, 301, and 303.

22. The isolated single domain antibody of claim 21, comprising the amino acid sequence set forth in any of SEQ ID NOS: 245-253, 255-287, 294, 295, 302, and 360, or a sequence of amino acids that exhibits at least 85% sequence identity to any of SEQ ID NOS: 245-253, 255-287, 294, 295, 302, and 360, and binds 5T4.

23. A pharmaceutical composition comprising the 5T4-binding polypeptide construct of claim 1.

\* \* \* \* \*